(12) United States Patent
Srivastava et al.

(10) Patent No.: US 11,524,959 B1
(45) Date of Patent: Dec. 13, 2022

(54) INDOLE AND AZAINDOLE INHIBITORS OF PAD ENZYMES

(71) Applicant: BRISTOL-MYERS SQUIBB COMPANY, Princeton, NJ (US)

(72) Inventors: Anurag S. Srivastava, Belle Mead, NJ (US); Robert J. Cherney, Newtown, PA (US); Khehyong Ngu, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 24 days.

(21) Appl. No.: 17/265,842

(22) PCT Filed: Aug. 7, 2019

(86) PCT No.: PCT/US2019/045466
§ 371 (c)(1),
(2) Date: Feb. 4, 2021

(87) PCT Pub. No.: WO2020/033520
PCT Pub. Date: Feb. 13, 2020

Related U.S. Application Data

(60) Provisional application No. 62/715,850, filed on Aug. 8, 2018.

(51) Int. Cl.
*C07D 471/04* (2006.01)
*A61K 31/437* (2006.01)
*C07D 471/08* (2006.01)
*A61K 45/06* (2006.01)
*C07D 519/00* (2006.01)

(52) U.S. Cl.
CPC ............ *C07D 471/08* (2013.01); *A61K 45/06* (2013.01); *C07D 519/00* (2013.01)

(58) Field of Classification Search
CPC .. C07D 401/14; C07D 403/14; C07D 471/04; A61K 31/437; A61K 31/454; A61P 35/00; A61P 29/00
USPC .......................... 546/113, 198; 514/300, 322
See application file for complete search history.

(56) References Cited

U.S. PATENT DOCUMENTS

2019/0276440 A1   9/2019   Zhao

FOREIGN PATENT DOCUMENTS

| WO | 2014015905 A1 | 1/2014 |
| WO | 2016185279 A1 | 11/2016 |
| WO | 2017/100601 A1 | 6/2017 |
| WO | 2017108282 A1 | 6/2017 |
| WO | 2017/100594 A1 | 7/2017 |
| WO | 2017147102 A1 | 8/2017 |
| WO | 2018022897 A1 | 2/2018 |
| WO | 2018049296 A1 | 3/2018 |
| WO | 2019077631 A1 | 4/2019 |
| WO | 2020033488 A1 | 2/2020 |
| WO | 2020033490 A1 | 2/2020 |
| WO | 2020033514 A1 | 2/2020 |
| WO | 2020033520 A1 | 2/2020 |

OTHER PUBLICATIONS

Guo, et al., Synthesis of reversible PAD4 inhibitors via copper-catalyzed C—H arylation of benzimidazole; Science China Chemistry; The Frontiers of ChemicalBiology and Synthesis, vol. 62, No. 5, pp. 592-596, 2019.
Lange et al., "Peptidylarginine Deiminases as Mediators ofMicrovesicular Release—Novel Therapeutic Interventions" 2017.

*Primary Examiner* — Charanjit Aulakh
(74) *Attorney, Agent, or Firm* — Hong Liu

(57) ABSTRACT

The present invention provides compounds of Formula (I) useful as inhibitors of PAD4, compositions thereof, and methods of treating PAD4-related disorders, wherein each of Ring A, L, Q, R1, R2, R3, R4, R7, and R8 along with other variables are as defined herein.

(I)

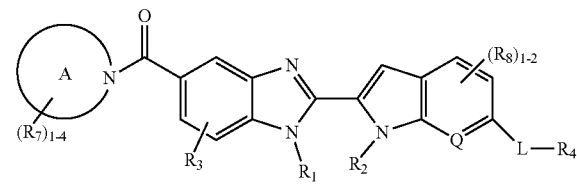

18 Claims, No Drawings

INDOLE AND AZAINDOLE INHIBITORS OF PAD ENZYMES

CROSS REFERENCE

This application is a national phase application under 35 U.S.C. § 371 of International Patent Application No. PCT/US2019/045466 filed on Aug. 7, 2019, which claims the benefit of U.S. Provisional Application Ser. No. 62/715,850 filed Aug. 8, 2018, which is incorporated herein in its entirety.

BACKGROUND OF THE INVENTION

PAD4 is a member of the peptidylarginine deiminase (PAD) family of enzymes capable of catalysing the citrullination of arginine into citrulline within peptide sequences. PAD4 is responsible for the deimination or citrullination of a variety of proteins in vitro and in vivo, with consequences of diverse functional responses in a variety of diseases (Jones J. E. et al, Curr. Opin. Drug Discov. Devel., 12(5), (2009), 616-627). Examples of exemplar diseases include rheumatoid arthritis, diseases with neutrophilic contributions to pathogenesis (for example vasculitis, systemic lupus erythematosus, ulcerative colitis) in addition to oncology indications. PAD4 inhibitors also have wider applicability as tools and therapeutics for human disease through epigenetic mechanisms.

Inhibitors of PAD4 have utility against Rheumatoid Arthritis (RA). RA is an auto-immune disease affecting approximately 1% of the population (Wegner N. et al, Immunol. Rev., 233(1) (2010), 34-54). It is characterised by inflammation of articular joints leading to debilitating destruction of bone and cartilage. A weak genetic association between PAD4 polymorphisms and susceptibility to RA has been suggested, albeit inconsistently, in a number of population studies (Kochi Y. et al, Ann. Rheum. Dis., 70, (2011), 512-515). PAD4 (along with family member PAD2) has been detected in synovial tissue where it is responsible for the deimination of a variety of joint proteins. This process is presumed to lead to a break of tolerance to, and initiation of immune responses to, citrullinated substrates such as fibrinogen, vimentin and collagen in RA joints. These anti-citrullinated protein antibodies (ACPA) contribute to disease pathogenesis and may also be used as a diagnostic test for RA (e.g. the commercially available CCP2 or cyclic citrullinated protein 2 test). In addition, increased citrullination may also offer additional direct contributions to disease pathogenesis through its ability to affect directly the function of several joint and inflammatory mediators (e.g. fibrinogen, anti-thrombin, multiple chemokines). In a smaller subset of RA patients, anti-PAD4 antibodies can be measured and may correlate with a more erosive form of the disease.

PAD4 inhibitors are also useful for the reduction of pathological neutrophil activity in a variety of diseases. Studies suggest that the process of Neutrophil Extracellular Trap (NET) formation, an innate defence mechanism by which neutrophils are able to immobilise and kill pathogens, is associated with histone citrullination and is deficient in PAD4 knockout mice (Neeli I. et al, J. Immunol., 180, (2008), 1895-1902 and Li P. et al, J. Exp. Med., 207(9), (2010), 1853-1862). PAD4 inhibitors may therefore have applicability for diseases where NET formation in tissues contributes to local injury and disease pathology. Such diseases include, but are not limited to, small vessel vasculitis (Kessenbrock K. et al, Nat. Med., 15(6), (2009), 623-625), systemic lupus erythematosus (Hakkim A. et al, Proc. Natl. Acad. Sci. USA, 107(21), (2010), 9813-9818 and Villanueva E. et al, J. Immunol., 187(1), (2011), 538-52), ulcerative colitis (Savchenko A. et al, Pathol. Int., 61(5), (2011), 290-7), cystic fibrosis, asthma (Dworski R et al. J. Allergy Clin. Immunol., 127(5), (2011), 1260-6), deep vein thrombosis (Fuchs T. et al, Proc. Natl. Acad. Sci. USA, 107(36), (2010), 15880-5), periodontitis (Vitkov L. et al, Ultrastructural Pathol., 34(1), (2010), 25-30), sepsis (Clark S. R. et al, Nat. Med., 13(4), (2007), 463-9), appendicitis (Brinkmann V et al, Science, 303, (2004), 1532-5), and stroke. In addition, there is evidence that NETs may contribute to pathology in diseases affecting the skin, e.g., in cutaneous lupus erythematosus (Villanueva E. et al, J. Immunol., 187(1), (2011), 538-52) and psoriasis (Lin A. M. et al., J. Immunol., 187(1), (2011), 490-500), so a PAD4 inhibitor may show benefit to tackle NET skin diseases, when administered by a systemic or cutaneous route. PAD4 inhibitors may affect additional functions within neutrophils and have wider applicability to neutrophilic diseases.

Studies have demonstrated efficacy of tool PAD inhibitors (for example chloro-amidine) in a number of animal models of disease, including collagen-induced arthritis (Willis V. C. et al. J. Immunol., 186(7), (2011), 4396-4404), dextran sulfate sodium (DSS)-induced experimental colitis (Chumanevich A. A. et al, Am. J. Physiol. Gastrointest. Liver Physiol., 300(6), (2011), G929-G938), spinal cord repair (Lange S. et al, Dev. Biol., 355(2), (2011), 205-14), and experimental autoimmune encephalomyelitis (EAE). The DSS colitis report also demonstrates that chloro-amidine drives apoptosis of inflammatory cells both in vitro and in vivo, suggesting that PAD4 inhibitors may be effective more generally in widespread inflammatory diseases.

PAD4 inhibitors are also useful in the treatment of cancers (Slack. J. L. et al, Cell. Mol. Life Sci., 68(4), (2011), 709-720). Over-expression of PAD4 has been demonstrated in numerous cancers (Chang X. et al, BMC Cancer, 9, (2009), 40). An antiproliferative role has been suggested for PAD4 inhibitors from the observation that PAD4 citrullinates arginine residues in histones at the promoters of p53-target genes such as p21, which are involved in cell cycle arrest and induction of apoptosis (Li P. et al, Mol. Cell Biol., 28(15), (2008), 4745-4758).

The aforementioned role of PAD4 in deiminating arginine residues in histones may be indicative of a role for PAD4 in epigenetic regulation of gene expression. PAD4 is the primary PAD family member observed to be resident in the nucleus as well as the cytoplasm. Early evidence that PAD4 may act as a histone demethyliminase as well as a deiminase is inconsistent and unproven. However, it may reduce histone arginine methylation (and hence epigenetic regulation associated with this mark) indirectly via depletion of available arginine residues by conversion to citrulline. PAD4 inhibitors are useful as epigenetic tools or therapeutics for affecting expression of varied target genes in additional disease settings. Through such mechanisms, PAD4 inhibitors may also be effective in controlling citrullination levels in stem cells and may therefore therapeutically affect the pluripotency status and differentiation potential of diverse stem cells including, but not limited to, embryonic stem cells, neural stem cells, haematopoietic stem cells and cancer stem cells. Accordingly, there remains an unmet need to identify and develop PAD4 inhibitors for the treatment of PAD4-mediated disorders.

SUMMARY OF THE INVENTION

It has now been found that compounds of Formula (I) are useful as inhibitors of PAD4:

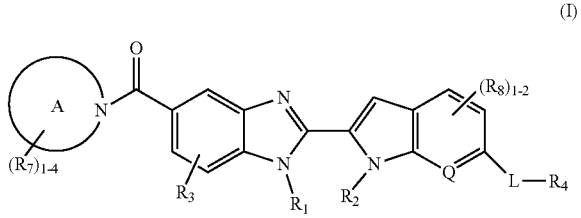

or a pharmaceutically acceptable salt thereof, wherein each of Ring A, L, Q, $R_1$, $R_2$, $R_3$, $R_4$, $R_7$, and $R_8$ along with other variables are as defined herein.

In some embodiments, a provided compound demonstrates selectivity for PAD4 with respect to PAD2. The present invention also provides pharmaceutically acceptable compositions comprising a provided compound. Provided compounds are useful in treatment of various disorders associated with PAD4. Such disorders are described in detail, herein, and include, for example rheumatoid arthritis, vasculitis, systemic lupus erythematosus, ulcerative colitis, cancer, cystic fibrosis, asthma, cutaneous lupus erythematosus, and psoriasis.

DETAILED DESCRIPTION OF THE INVENTION

1. General Description of Certain Aspects of the Invention

In some embodiments, such compounds include those of the formulae described herein, or a pharmaceutically acceptable salt thereof, wherein each variable is as defined herein and described in embodiments. Such compounds have the structure of Formula (I):

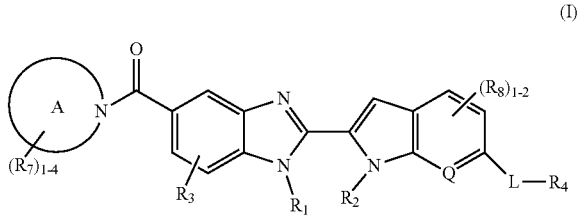

or a pharmaceutically acceptable salt thereof, wherein:

Q is selected from N and CH;
Ring A is 4- to 15-membered heterocyclyl substituted with 1-4 $R_7$;
$R_1$ is selected from $CH_3$ and $CD_3$;
$R_2$ is selected from H, $C_{1-3}$ alkyl substituted with 0-2 $C_{3-6}$ cycloalkyl substituted with 0-4 F, Cl, and $C_{1-3}$ alkyl;
$R_3$ is selected from H, F, Cl, Br, —$OR_b$, and $C_{1-3}$ alkyl substituted with 0-5 $R_e$;
L is absent or selected from —$NR_d$—, —O—, —C(=O)$NR_d$—, and —S(O)$_p$—;
$R_4$ is selected from $C_{1-6}$ alkyl substituted with 1-4 F, OH, and $C_{3-6}$ cycloalkyl, —$(CH_2)_r$-aryl substituted with 1-7 $R_5$, —$(CH_2)_r$—$C_{3-12}$ cycloalkyl substituted with 1-7 $R_5$, —$(CH_2)_r$-heterocyclyl comprising carbon atoms and 1-3 heteroatoms selected from N, $NR_6$, O, and S and substituted with 1-7 $R_5$;
$R_5$, at each occurrence, is independently selected from H, F, Cl, Br, CN, =O, nitro, $C_{1-4}$alkyl substituted with 0-5 $R_e$, $C_{2-4}$alkenyl substituted with 0-5 $R_e$, $C_{2-4}$alkynyl substituted with 0-5 $R_e$, —$(CHR_d)_rOR_b$, —$(CHR_d)_rS(O)_pR_c$, —$(CHR_d)_rS(O)_pNR_aR_a$, —$(CHR_d)_rNR_aS(O)_pR_c$, —$(CHR_d)_rNR_aR_a$, —$(CHR_d)_rNR_aC(=O)R_b$, —$(CHR_d)_rNR_aC(=O)OR_b$, —$(CHR_d)_rC(=O)NR_aR_a$, —$(CHR_d)_rC(=O)R_b$, —$(CHR_d)_rC(=O)OR_b$, —$(CHR_d)_rC(=O)NR_aR_a$, —$(CHR_d)_rOC(=O)R_b$, —$(CHR_d)_rOC(=O)OR_b$, —$(CHR_d)_rO(CH_2)_rC(=O)NR_aR_a$, $C_{3-6}$cycloalkyl substituted with 0-4 $R_e$, aryl substituted with 0-4 $R_e$, and heterocyclyl substituted with 0-4 $R_e$;
$R_6$ is selected from H, $C_{1-3}$alkyl substituted with 0-4 $R_e$, —S(O)$_pR_c$, —$(CH_2)_rC(=O)R_b$, —$(CH_2)_r$ C(=O)$OR_b$, —$(CH_2)_rC(=O)(CH_2)_rNR_aR_a$, —C(=O)$(CH_2)_rNR_aC(=O)R_b$, —S(O)$_pNR_aR_a$, —$(CH_2)_r$—$C_{3-6}$cycloalkyl substituted with 0-4 $R_e$, —$(CH_2)_r$-aryl substituted with 0-4 $R_e$, and —$(CH_2)_r$-heterocyclyl substituted with 0-4 $R_e$;
$R_7$ is selected from H, F, Cl, CN, $C_{1-3}$ alkyl, =N—$OR_b$, —$(CH_2)_rOR_b$, —$(CH_2)_rNR_aR_a$, —$NR_aC$(=NH)$C_{1-3}$alkyl, —$NR_aC$(=O)$OR_b$, carbocyclyle, and heterocyclyle; alternatively, two $R_7$ groups are taken together to form carbocyclyl or heterocyclyl;
$R_8$, at each occurrence, is independently selected from H, F, Cl, Br, and $C_{1-4}$alkyl substituted with 0-5 $R_e$;
$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;
$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;
$R_c$, at each occurrence, is independently selected from $C_{1-6}$ alkyl substituted with 0-5 $R_e$, $C_{2-6}$alkenyl substituted with 0-5 $R_e$, $C_{2-6}$ alkynyl substituted with 0-5 $R_e$, —$(CH_2)_r$—$C_{3-6}$ carbocyclyl substituted with 0-5 $R_e$, and —$(CH_2)_r$-heterocyclyl substituted with 0-5 $R_e$;
$R_d$, at each occurrence, is independently selected from H, $C_{1-6}$ alkyl substituted with 0-5 $R_e$, and OH,
$R_e$, at each occurrence, is independently selected from $C_{1-6}$ alkyl substituted with 0-5 $R_f$, $C_{2-6}$ alkenyl, $C_{2-6}$ alkynyl, —$(CH_2)_rC_{3-6}$ cycloalkyl, —$(CH_2)_r$-aryl, —$(CH_2)_r$-heterocyclyl, Si($C_{1-4}$alkyl)$_3$, F, Cl, Br, CN, $NO_2$, =O, $CO_2$H, —$(CH_2)_rOR_f$, S(O)$_pR_f$, C(=O)$NR_fR_f$, S(O)$_pNR_fR_f$, and —$(CH_2)_rNR_fR_f$;
$R_f$, at each occurrence, is independently selected from H, F, Cl, Br, CN, OH, $C_{1-5}$ alkyl optionally substituted with OH, $C_{2-5}$ alkenyl, $C_{2-5}$ alkynyl, $C_{3-6}$ cycloalkyl, and phenyl, or $R_f$ and $R_f$ together with the nitrogen atom to which they are both attached form a heterocyclic ring optionally substituted with $C_{1-4}$alkyl;
p, at each occurrence, is independently selected from zero, 1, and 2;
r, at each occurrence, is independently selected from zero, 1, 2, 3, and 4;

provided:
(1) when L is absent, $R_4$ is not

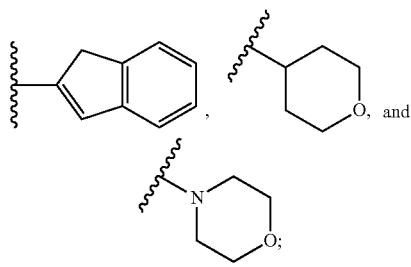

(2) when L is —$NR_d$—, $R_4$ is not

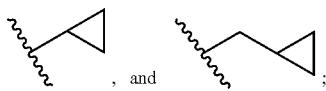

and
(3) when L is —O—, $R_4$ is not $C_{3-6}$ cycloalkyl.

2. Definitions

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For examples, "$C_1$ to $C_{12}$ alkyl" or "$C_{1-12}$ alkyl" (or alkylene), is intended to include $C_1$, $C_2$, $C_3$, $C_4$, $C_5$, $C_6$, $C_7$, $C_8$, $C_9$, $C_{10}$, $C_{11}$ and $C_{12}$ alkyl groups; "$C_4$ to $C18$ alkyl" or "$C_{4-18}$ alkyl" (or alkylene), is intended to include $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, and $C18$ alkyl groups. Additionally, for example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. For example, "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

The term "cycloalkyl" refers to cyclized alkyl groups, including mono-, bi- or poly-cyclic ring systems. For example, "$C_3$ to $C_6$ cycloalkyl" or "$C_{3-6}$ cycloalkyl" is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

As used herein, "carbocycle", "carbocyclyl", or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl." A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or bicyclic aromatic hydrocarbons, including, for example, phenyl, and naphthyl. Aryl moieties are well known and described, for example, in Lewis, R. J., ed., *Hawley's Condensed Chemical Dictionary*, 15th Edition, John Wiley & Sons, Inc., New York (2007). "$C_{6-10}$ aryl" refers to phenyl and naphthyl.

As used herein, the term "heterocycle", "heterocyclyl", or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl. Also included are fused ring and spiro compounds containing, for example, the above heterocycles.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

The term "counter ion" is used to represent a negatively charged species such as chloride, bromide, hydroxide, acetate, and sulfate or a positively charged species such as sodium ($Na^+$), potassium ($K^+$), ammonium ($R_nNH_m+$ where n=0-4 and m=0-4) and the like.

When a dotted ring is used within a ring structure, this indicates that the ring structure may be saturated, partially saturated or unsaturated.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. et al., *Protecting Groups in Organic Synthesis,* 4th Edition, Wiley (2007) and *The Peptides: Analysis, Synthesis, Biology,* Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent.

Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, Jr., L. V., ed., *Remington: The Science and Practice of Pharmacy*, 22nd Edition, Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:
a) Bundgaard, H., ed., *Design of Prodrugs*, Elsevier (1985), and Widder, K. et al., eds., *Methods in Enzymology*, 112:309-396, Academic Press (1985);
b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);
c) Bundgaard, H., Adv. *Drug Deliv. Rev.*, 8:1-38 (1992);
d) Bundgaard, H. et al., *J. Pharm. Sci.*, 77:285 (1988);
e) Kakeya, N. et al., *Chem. Pharm. Bull.*, 32:692 (1984); and
f) Rautio, J., ed., *Prodrugs and Targeted Delivery (Methods and Principles in Medicinal Chemistry)*, Vol. 47, Wiley-VCH (2011).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (2nd Edition, reproduced (2006)); Testa, B. et al., *Hydrolysis in Drug and Prodrug Metabolism. Chemistry, Biochemistry and Ezymology*, VCHA and Wiley-VCH, Zurich, Switzerland (2003); Wermuth, C. G., ed., *The Practice of Medicinal Chemistry*, 3rd Edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium (symbol D or 2H) and tritium (symbol T or 3H). For example, a methyl group may be represented by $CH_3$ or $CD_3$. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

The terms "measurable affinity" and "measurably inhibit," as used herein, means a measurable change in PAD4 activity between a sample comprising a compound of the present invention, or composition thereof, and PAD4, and an equivalent sample comprising PAD4 in the absence of said compound, or composition thereof.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or min, "h" for hour or h, "rt" for room temperature, "RT" for retention time, "atm" for atmosphere, "psi" for pounds per square inch, "conc." for concentrate, "aq" for "aqueous", "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", "Z" and "ee" are stereochemical designations familiar to one skilled in the art. As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio.

AcOH or HOAc acetic acid
ACN acetonitrile
Alk Alkyl
AlMe$_3$ Trimethylaluminum
BBr$_3$ boron tribromide
Bn benzyl
Boc tert-butyloxycarbonyl
BOP reagent benzotriazol-1-yloxytris(dimethylamino)phosphonium hexafluorophosphate
Bu butyl
i-Bu isobutyl
t-Bu tert-butyl
t-BuOH tert-butanol
Cbz carbobenzyloxy
CDCl$_3$ deutero-chloroform
CD$_3$OD deutero-methanol
CH$_2$Cl$_2$ dichloromethane
CH$_3$CN acetonitrile
CHCl$_3$ chloroform
DCM dichloromethane
DIEA, DIPEA or Hunig's base diisopropylethylamine
DMF dimethyl formamide
DMSO dimethyl sulfoxide
Et ethyl
Et$_3$N or TEA triethylamine
Et$_2$O diethyl ether
EtOAc ethyl acetate
EtOH ethanol
HCl hydrochloric acid
HPLC high-performance liquid chromatography
K$_2$CO$_3$ potassium carbonate
K$_2$HPO$_4$ potassium hydrogenphosphate
LCMS liquid chromatography mass spectrometry
LiHMDS lithium bis(trimethylsilyl)amide
LG leaving group
Me methyl
MeOH methanol
MgSO$_4$ magnesium sulfate
MsOH or MSA methylsulfonic acid
NaCl sodium chloride
Na$_2$CO$_3$ sodium carbonate
NaHCO$_3$ sodium bicarbonate
NaOH sodium hydroxide
Na$_2$SO$_4$ sodium sulfate
NH$_3$ ammonia
NH$_4$Cl ammonium chloride
NH$_4$OAc ammonium acetate
Pd(OAc)$_2$ palladium(II) acetate
Pd(dppf)Cl$_2$ [1,1'-Bis(diphenylphosphino)ferrocene]palladium(II) dichloride
Pd(PPh$_3$)$_4$ tetrakis(triphenylphosphine)palladium(0)
PG protecting group
Ph phenyl
Pr propyl
i-Pr isopropyl
i-PrOH or IPA isopropanol
Rt retention time
SiO$_2$ silica oxide
SFC supercritical fluid chromatography
TBAI Tetrabutylammonium iodide
TEA triethylamine
TFA trifluoroacetic acid
TFAA Trifluoroacetic anhydride
THF tetrahydrofuran
TiCl$_4$ titanium tetrachloride
T3P 1-propanephosphonic acid cyclic anhydride 3. Description of Exemplary Compounds In a first aspect, the present invention provides a compound of Formula (I):

or a pharmaceutically acceptable salt thereof, wherein:

Q is selected from N and CH;

Ring A is 4- to 15-membered heterocyclyl substituted with 1-4 $R_7$;

$R_1$ is selected from $CH_3$ and $CD_3$;

$R_2$ is selected from H, $C_{1-3}$ alkyl substituted with 0-5 $R_e$, and $C_{3-6}$ cycloalkyl substituted with 0-5 $R_e$;

$R_3$ is selected from H, F, Cl, Br, —$OR_b$, and $C_{1-3}$ alkyl substituted with 0-5 $R_e$;

L is absent or selected from —$NR_d$—, —O—, —C(=O)$NR_d$—, and —S(O)$_p$—;

$R_4$ is selected from —(CH$_2$)$_r$-aryl substituted with 1-5 $R_5$, —(CH$_2$)$_r$—C$_{3-12}$ cycloalkyl substituted with 1-5 $R_5$, —(CH$_2$)$_r$-heterocyclyl comprising carbon atoms and 1-3 heteroatoms selected from N, $NR_6$, O, and S and substituted with 1-5 $R_5$;

$R_5$, at each occurrence, is independently selected from H, F, Cl, Br, CN, nitro, $C_{1-4}$alkyl substituted with 0-5 $R_e$, $C_{2-4}$alkenyl substituted with 0-5 $R_e$, $C_{2-4}$alkynyl substituted with 0-5 $R_e$, —(CHR$_d$)$_r$OR$_b$, —(CHR$_d$)$_r$S(O)$_p$R$_c$, —(CHR$_d$)$_r$S(O)$_p$NR$_a$R$_a$, —(CHR$_d$)$_r$NR$_a$S(O)$_p$R$_c$, —(CHR$_d$)$_r$NR$_a$R$_a$, —(CHR$_d$)$_r$NR$_a$C(=O)R$_b$, —(CHR$_d$)$_r$NR$_a$C(=O)OR$_b$, —(CHR$_d$)$_r$NR$_a$C(=O)NR$_a$R$_a$, —(CHR$_d$)$_r$C(=O)R$_b$, —(CHR$_d$)$_r$C(=O)OR$_b$, —(CHR$_d$)$_r$C(=O)NR$_a$R$_a$, —(CHR$_d$)$_r$OC(=O)R$_b$, $C_{3-6}$cycloalkyl substituted with 0-4 $R_e$, aryl substituted with 0-4 $R_e$, and heterocyclyl substituted with 0-4 $R_e$;

$R_6$ is selected from H, $C_{1-3}$alkyl substituted with 0-4 $R_e$, —S(O)$_p$R$_c$, —C(=O)R$_b$, —C(=O)OR$_b$, —C(=O)(CH$_2$)$_r$NR$_a$R$_a$, —S(O)$_p$NR$_a$R$_a$, —(CH$_2$)$_r$C$_{3-6}$cycloalkyl substituted with 0-4 $R_e$, —(CH$_2$)$_r$-aryl substituted with 0-4 $R_e$, and —(CH$_2$)$_r$-heterocyclyl substituted with 0-4 $R_e$;

$R_7$ is selected from H, F, Cl, CN, $C_{1-3}$ alkyl, =N—OR$_b$, —(CH$_2$)$_r$OR$_b$, —(CH$_2$)$_r$NR$_a$R$_a$, —NR$_a$C(=NH)C$_{1-3}$alkyl, —NR$_a$C(=O)OR$_b$, a carbocycle, and a heterocycle; alternatively, two $R_7$ groups are taken together to form a carbocycle or heterocyle;

$R_8$, at each occurrence, is independently selected from H, F, Cl, Br, and $C_{1-4}$alkyl substituted with 0-5 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$ alkynyl substituted with 0-5 $R_e$, —(CH$_2$)$_r$—$C_{3-6}$carbocyclyl substituted with 0-5 $R_e$, and —(CH$_2$)$_r$-heterocyclyl substituted with 0-5 $R_e$;

$R_d$, at each occurrence, is independently selected from H and $C_{1-6}$ alkyl substituted with 0-5 $R_e$, $R_e$, at each occurrence, is independently selected from $C_{1-6}$ alkyl substituted with 0-5 $R_f$, $C_{2-6}$ alkenyl, $C_{2-6}$ alkynyl, —(CH$_2$)$_r$C$_{3-6}$ cycloalkyl, —(CH$_2$)$_r$-aryl, Si(C$_{1-4}$alkyl)$_3$, F, Cl, Br, CN, NO$_2$, =O, CO$_2$H, —(CH$_2$)$_r$OR$_f$, S(O)$_p$R$_f$, C(=O)NR$_f$R$_f$, S(O)$_p$NR$_f$R$_f$, and —(CH$_2$)$_r$NR$_f$R$_f$;

$R_f$, at each occurrence, is independently selected from H, F, Cl, Br, CN, OH, $C_{1-5}$ alkyl optionally substituted with OH, $C_{2-5}$ alkenyl, $C_{2-5}$ alkynyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2;

r, at each occurrence, is independently selected from zero, 1, 2, 3, and 4; and provided:

(1) when L is absent, $R_4$ is not

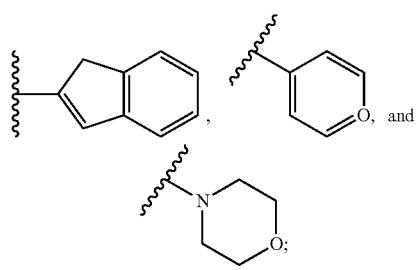

(2) when L is —NR$_d$—, $R_4$ is not

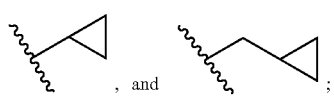

and (3) when L is —O—, $R_4$ is not $C_{3-6}$ cycloalkyl.

In a second aspect, the present invention provides a compound or a pharmaceutically acceptable salt thereof, within the scope of the first aspect, wherein:

Ring A is selected from

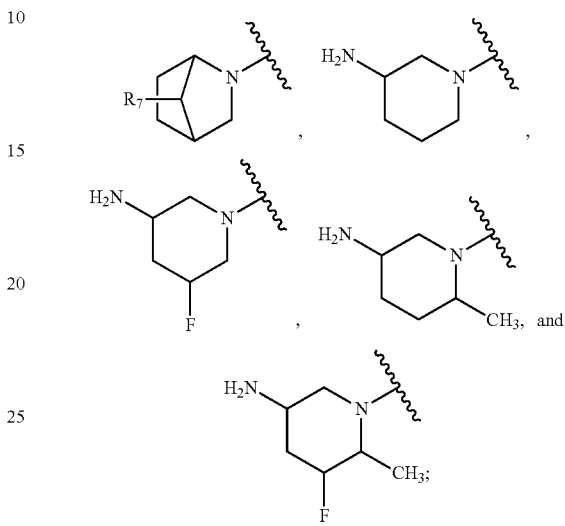

$R_1$ is selected from CH$_3$ and CD$_3$;

$R_2$ is selected from methyl, ethyl, and —CH$_2$-cyclopropyl substituted with 0-3 $R_e$;

$R_3$ is selected from H, F, Cl, Br, and —OC$_{1-4}$ alkyl;

L is absent or selected from —NR$_d$—, —O—, —C(=O) NH—, —S—, and —S(O)$_2$—;

$R_4$ is selected from

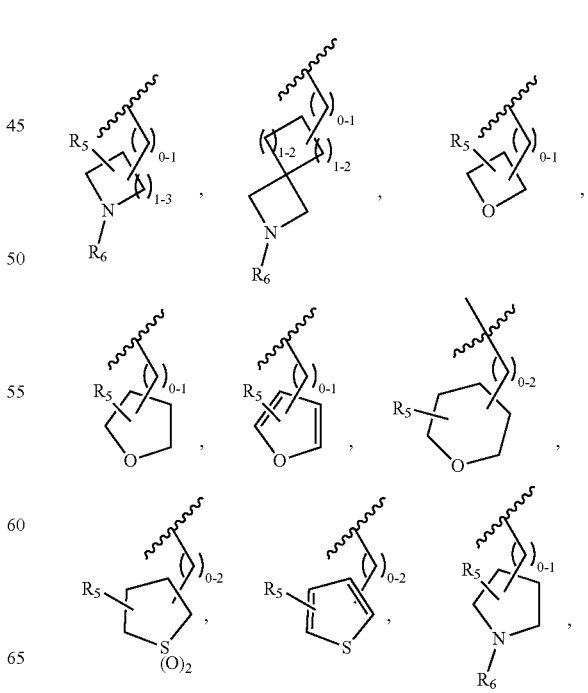

17
-continued
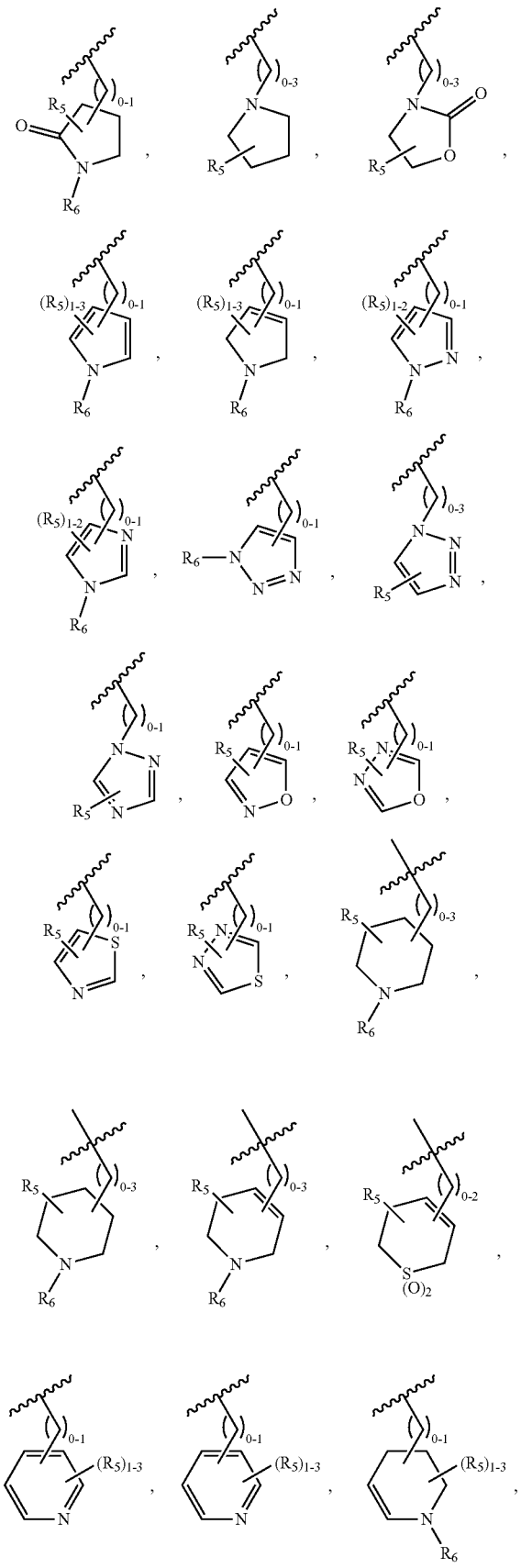
18
-continued
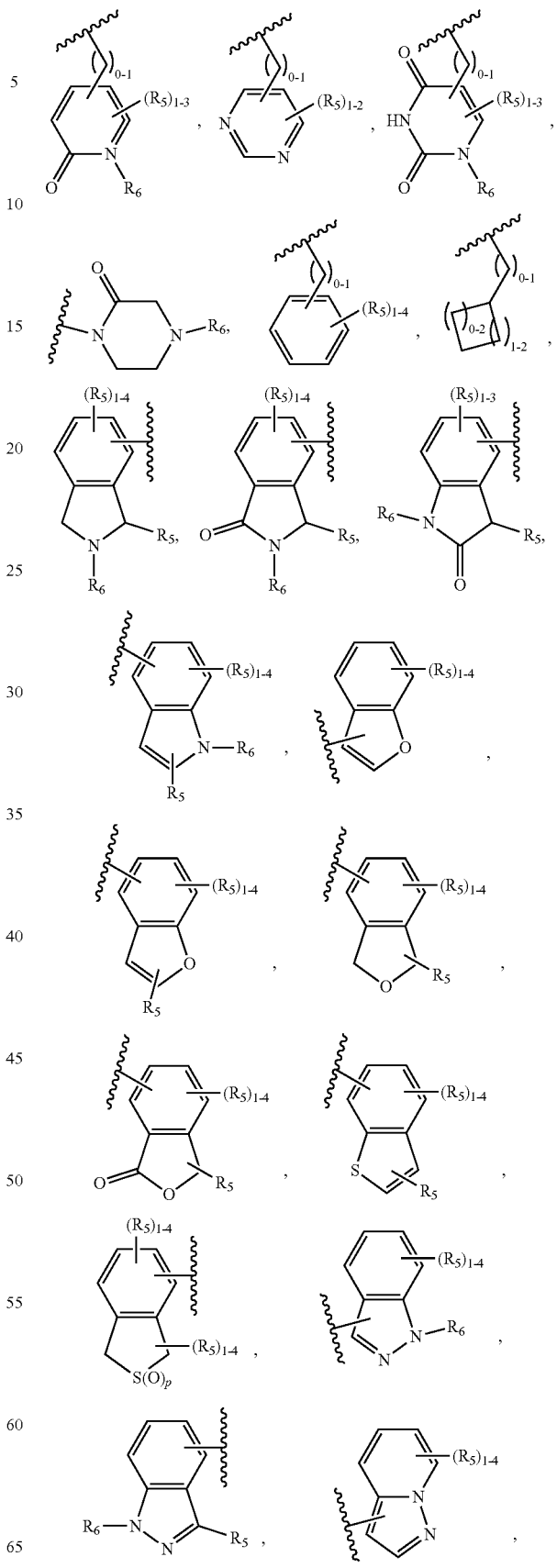

-continued

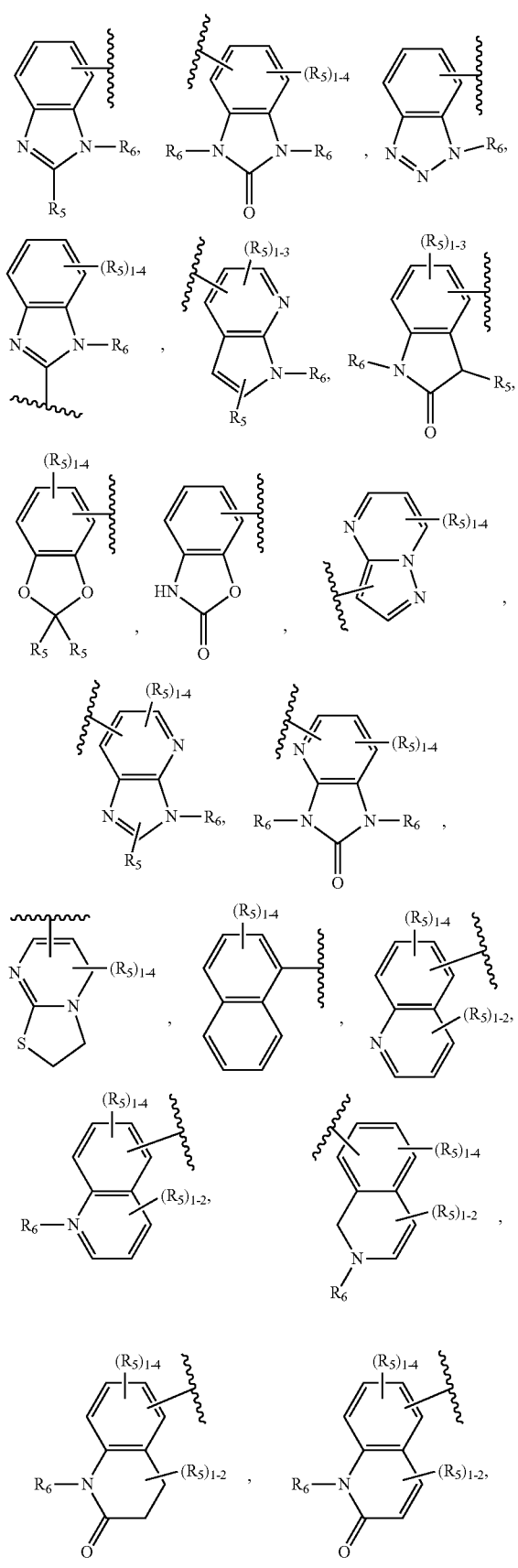
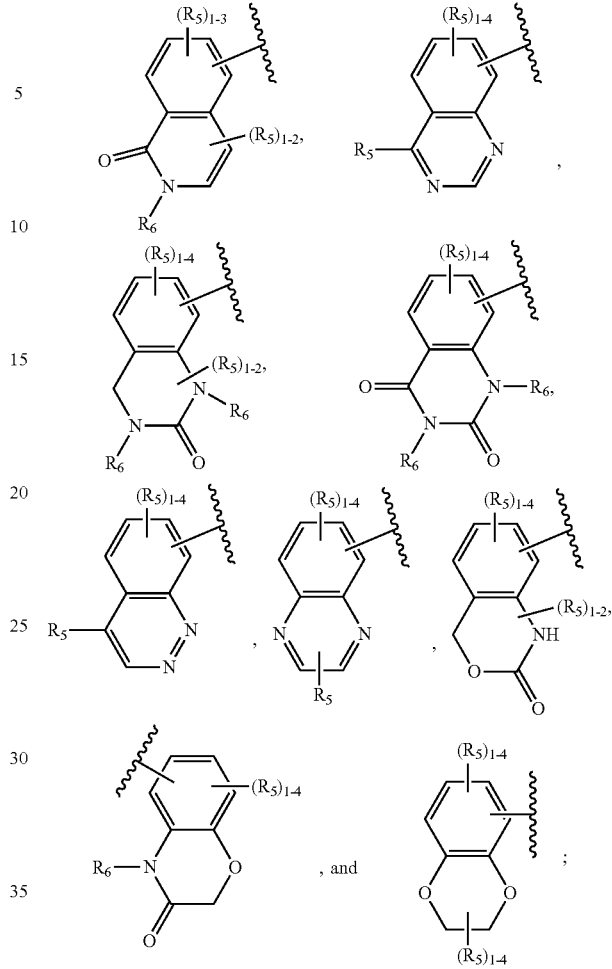

$R_5$, at each occurrence, is independently selected from H, F, Cl, Br, CN, $C_{1-4}$alkyl substituted with 0-5 $R_e$, $C_{2-4}$alkenyl, $C_{2-4}$alkynyl, $-(CHR_d)_rOR_b$, $-(CH_2)_rS(O)_pR_c$, $-(CH_2)_rS(O)_pNR_aR_a$, $-(CH_2)_rNR_aS(O)_pR_c$, $-(CH_2)NR_aR_a$, $-(CH_2)_rNR_aC(=O)R_b$, $-(CH_2)_rNR_aC(=O)OR_b$, $-(CH_2)_rNR_aC(=O)NR_aR_a$, $-(CH_2)_rC(=O)R_b$, $-(CH_2)_rC(=O)OR_b$, $-(CH_2)_rOC(=O)R_b$, $-(CH_2)_rC(=O)NR_aR_a$, $-(CH_2)_rOC(=O)R_b$, $C_{3-6}$cycloalkyl substituted with 0-4 $R_e$, aryl substituted with 0-4 $R_e$, and $-(CH_2)_r$-heterocyclyl substituted with 0-4 $R_e$;

$R_6$, at each occurrence, is independently selected from H, $C_{1-3}$alkyl substituted with 0-4 $R_e$, $-S(O)_pR_c$, $-C(=O)R_b$, $-C(=O)(CH_2)_rNR_aR_a$, $-C(=O)OR_b$, $-S(O)_pNR_aR_a$, $-(CH_2)_r$-aryl substituted with 0-4 $R_e$, and $-(CH_2)_r$-heterocyclyl substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r$—$C_{3-10}$carbocyclyl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r$—$C_{3-10}$carbocyclyl substituted with 0-5 $R_e$, and $-(CH_2)$-heterocyclyl substituted with 0-5 $R_e$;

R_e, at each occurrence, is independently selected from $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-6}$ carbocyclyl substituted with 0-5 $R_e$, and —$(CH_2)_r$-heterocyclyl substituted with 0-5 $R_e$;

$R_d$, at each occurrence, is independently selected from H and $C_{1-6}$ alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$-aryl, F, Cl, Br, CN, $NO_2$, =O, —$NH_2$, —$NHC_{1-4}$alkyl, —$N(C_{1-4}$alkyl$)_2$, —C(=O)OH, —C(=O)O$C_{1-4}$alkyl, —$(CH_2)_r$OH, and —$(CH_2)_r$O$C_{1-4}$alkyl;

$R_f$, at each occurrence, is independently selected from H, F, Cl, Br, CN, OH, $C_{1-5}$ alkyl optionally substituted with OH, $C_{3-6}$ cycloalkyl, and phenyl;

p, at each occurrence, is independently selected from zero, 1, and 2; and r, at each occurrence, is independently selected from zero, 1, 2, 3, and 4.

In a third aspect, the present invention provides a compound of formula (II):

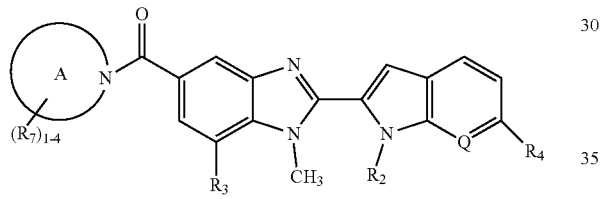

(II)

or a pharmaceutically acceptable salt thereof, wherein:

Ring A is selected from


$R_2$ is selected from methyl and —$CH_2$-cyclopropyl;

$R_3$ is selected from H, F, and —O$C_{1-4}$ alkyl;

$R_4$ is selected from

-continued

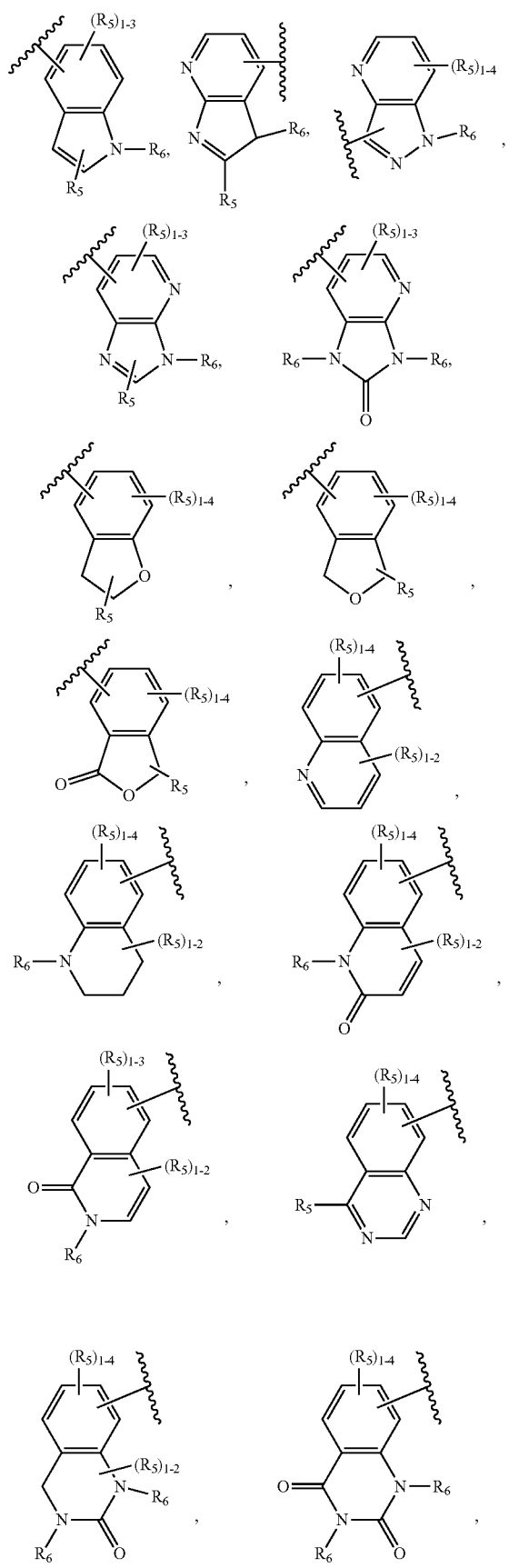

$R_5$, at each occurrence, is independently selected from H, F, Cl, Br, CN, $C_{1-4}$alkyl substituted with 0-4 $R_e$, —(CHR$_d$)$_r$OR$_b$, —S(O)$_p$R$_c$, —S(O)$_p$NR$_a$R$_a$, —(CH$_2$)$_r$N-R$_a$S(O)$_p$R$_c$, —(CH$_2$)$_r$NR$_a$R$_a$, —(CH$_2$)$_r$NR$_a$C(═O)R$_b$, —NR$_a$C(═O)OR$_b$, —NR$_a$C(═O)NR$_a$R$_a$, —(CH$_2$)$_r$C(═O)R$_b$, —(CH$_2$)$_r$C(═O)OR$_b$, —(CH$_2$)$_r$C(═O)NR$_a$R$_a$, —(CH$_2$)$_r$OC(═O)R$_b$, $C_{3-6}$cycloalkyl substituted with 0-4 $R_e$, aryl substituted with 0-4 $R_e$, and heterocyclyl substituted with 0-4 $R_e$;

$R_6$, at each occurrence, is independently selected from H, $C_{1-3}$alkyl substituted with 0-4 $R_e$, —S(O)$_p$R$_c$, —C(═O)R$_b$, —(CH$_2$)$_r$C(═O)NR$_a$R$_a$, —C(═O)(CH$_2$)$_r$NR$_a$C(═O)R$_b$, —C(═O)OR$_b$, —S(O)$_p$NR$_a$R$_a$, aryl substituted with 0-4 $R_e$, and heterocyclyl substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, —(CH$_2$)$_r$C$_{2-6}$ alkynyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$ alkynyl substituted with 0-5 $R_e$, —(CH$_2$)$_r$—$C_{3-6}$ carbocyclyl substituted with 0-5 $R_e$, and —(CH$_2$)$_r$-heterocyclyl substituted with 0-5 $R_e$;

$R_d$, at each occurrence, is independently selected from H and $C_{1-6}$ alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —(CH$_2$)$_r$C$_{3-6}$ cycloalkyl, —(CH$_2$)$_r$-aryl, F, Cl, Br, CN, NO$_2$, ═O, —NH$_2$, —NHC$_{1-4}$alkyl, —N(C$_{1-4}$alkyl)$_2$, —C(═O)OH, —C(═O)OC$_{1-4}$alkyl, —(CH$_2$)$_r$OH, and —(CH$_2$)$_r$OC$_{1-4}$alkyl;

$R_f$, at each occurrence, is independently selected from H, F, Cl, Br, CN, OH, $C_{1-5}$ alkyl optionally substituted with OH, $C_{3-6}$ cycloalkyl, and phenyl;

p, at each occurrence, is independently selected from zero, 1, and 2; and r, at each occurrence, is independently selected from zero, 1, 2, 3, and 4.

In a fourth aspect, the present invention provides a compound of formula (III):

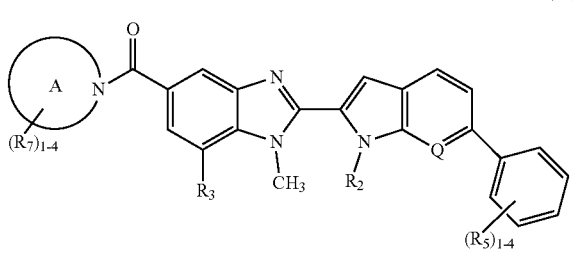

or a pharmaceutically acceptable salt thereof, wherein:
Ring A is

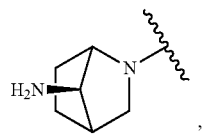 [SMILES: *N1CC2CCC1[C@@H]2N]

, $R_2$ is —$CH_2$-cyclopropyl;
$R_3$ is —$OC_{1-4}$ alkyl;
$R_5$, at each occurrence, is independently selected from H, F, Cl, Br, CN, $C_{1-4}$alkyl substituted with 0-4 $R_e$, —(CHR$_d$)$_r$OR$_b$, —S(O)$_p$R$_c$—(CH$_2$)$_r$NR$_a$R$_a$, —(CH$_2$)$_r$NHC(=O)R$_b$, —NHC(=O)OR$_b$, —(CH$_2$)$_r$NHS(O)$_p$R$_c$, —(CH$_2$)$_r$C(=O)NR$_a$R$_a$, —(CH$_2$)$_r$C(=O)OR$_b$, $C_{3-6}$cycloalkyl substituted with 0-4 $R_e$, aryl substituted with 0-4 $R_e$, and heterocyclyl substituted with 0-4 $R_e$;
$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$; or $R_a$ and $R_a$ together with the nitrogen atom to which they are both attached form a heterocyclic ring substituted with 0-5 $R_e$;
$R_b$, at each occurrence, is independently selected from H, $C_{1-6}$ alkyl substituted with 0-5 $R_e$, $C_{2-6}$ alkenyl substituted with 0-5 $R_e$, —(CH$_2$)$_r$—$C_{2-6}$ alkynyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$;
$R_c$, at each occurrence, is independently selected from $C_{1-6}$ alkyl substituted with 0-5 $R_e$, $C_{2-6}$alkenyl substituted with 0-5 $R_e$, $C_{2-6}$ alkynyl substituted with 0-5 $R_e$, —(CH$_2$)$_r$—$C_{3-6}$ carbocyclyl substituted with 0-5 Re, and —(CH$_2$)$_r$-heterocyclyl substituted with 0-5 $R_e$;
$R_d$, at each occurrence, is independently selected from H and $C_{1-6}$ alkyl;
$R_e$, at each occurrence, is independently selected from $C_{1-6}$ alkyl substituted with 0-5 $R_f$, $C_{2-6}$ alkenyl, $C_{2-6}$ alkynyl, —(CH$_2$)$_r$—$C_{3-6}$ cycloalkyl, —(CH$_2$)$_r$-aryl, F, Cl, Br, CN, NO$_2$, =O, —NH$_2$, —NHC$_{1-4}$alkyl, —N(C$_{1-4}$alkyl)$_2$, —C(=O)OH, —C(=O)OC$_{1-4}$ alkyl, —(CH$_2$)$_r$OH, —(CH$_2$)$_r$OC$_{1-4}$alkyl, and SO$_2$C$_{1-4}$alkyl;
$R_f$, at each occurrence, is independently selected from H, F, Cl, Br, CN, OH, $C_{1-5}$ alkyl optionally substituted with OH, $C_{3-6}$ cycloalkyl, and phenyl;
p, at each occurrence, is independently selected from zero, 1, and 2; and
r, at each occurrence, is independently selected from zero, 1, 2, 3, and 4.

In a fifth aspect, the present invention provides a compound or a pharmaceutically acceptable salt thereof, within the scope of the fourth aspect, wherein:
$R_3$ is —$OCH_3$; and
$R_5$, at each occurrence, is independently selected from H, F, Cl, Br, $C_{1-4}$alkyl, —OH, —OC$_{1-3}$alkyl, and —NHS(O)$_2$C$_{2-4}$alkenyl.

In a sixth aspect, the present invention provides a compound or a pharmaceutically acceptable salt thereof, within the scope of the third aspect, wherein:
Ring A is

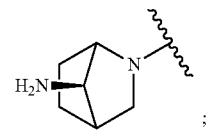

;

$R_2$ is —$CH_2$-cyclopropyl;
$R_3$ is —$OC_{1-4}$ alkyl;
$R_4$ is selected from

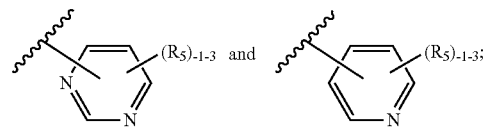

$R_5$, at each occurrence, is independently selected from H, F, Cl, Br, CN, $C_{1-4}$alkyl substituted with 0-4 $R_e$, —(CH$_2$)$_r$OR$_b$, —S(O)$_p$R$_c$, —S(O)$_p$NR$_a$R$_a$, —(CH$_2$)$_r$N-R$_a$S(O)$_p$R$_c$, —(CH$_2$)$_r$NR$_a$R$_a$, —(CH$_2$)$_r$NR$_a$C(=O)R$_b$, —NR$_a$C(=O)OR$_b$, —NR$_a$C(=O)NR$_a$R$_a$, —(CH$_2$)$_r$C(=O)R$_b$, —(CH$_2$)$_r$C(=O)OR$_b$, —(CH$_2$)$_r$C(=O)NR$_a$R$_a$, —(CH$_2$)$_r$OC(=O)R$_b$, $C_{3-6}$cycloalkyl substituted with 0-4 $R_e$, aryl substituted with 0-4 $R_e$, and heterocyclyl substituted with 0-4 $R_e$;
$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$; or $R_a$ and $R_a$ together with the nitrogen atom to which they are both attached form a heterocyclic ring substituted with 0-5 $R_e$;
$R_b$, at each occurrence, is independently selected from H, $C_{1-6}$ alkyl substituted with 0-5 $R_e$, $C_{2-6}$ alkenyl substituted with 0-5 $R_e$, —(CH$_2$)$_r$C$_{2-6}$ alkynyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$;
$R_c$, at each occurrence, is independently selected from $C_{1-6}$ alkyl substituted with 0-5 $R_e$, $C_{2-6}$alkenyl substituted with 0-5 $R_e$, $C_{2-6}$ alkynyl substituted with 0-5 $R_e$, —(CH$_2$)$_r$—$C_{3-6}$ carbocyclyl substituted with 0-5 $R_e$, and —(CH$_2$)$_r$-heterocyclyl substituted with 0-5 $R_e$;
$R_e$, at each occurrence, is independently selected from $C_{1-6}$ alkyl substituted with 0-5 $R_f$, $C_{2-6}$ alkenyl, $C_{2-6}$ alkynyl, —(CH$_2$)$_r$C$_{3-6}$ cycloalkyl, —(CH$_2$)$_r$-aryl, F, Cl, Br, CN, NO$_2$, =O, —NH$_2$, —NHC$_{1-4}$alkyl, —N(C$_{1-4}$alkyl)$_2$, —C(=O)OH, —C(=O)OC$_{1-4}$alkyl, —(CH$_2$)$_r$OH, and —(CH$_2$)$_r$OC$_{1-4}$alkyl;
$R_f$, at each occurrence, is independently selected from H, F, Cl, Br, CN, OH, $C_{1-5}$ alkyl optionally substituted with OH, $C_{3-6}$ cycloalkyl, and phenyl;

p, at each occurrence, is independently selected from zero, 1, and 2; and r, at each occurrence, is independently selected from zero, 1, 2, 3, and 4.

In a seventh aspect, the present invention provides a compound or a pharmaceutically acceptable salt thereof, within the scope of the sixth aspect, wherein:

R$_3$ is —CH$_3$; and

R$_5$, at each occurrence, is independently selected from H, F, Cl, Br, C$_{1-4}$alkyl, —OH, —OC$_{1-3}$alkyl, and —NHS(O)$_2$C$_{2-4}$alkenyl.

In an eighth aspect, the present invention provides a compound or a pharmaceutically acceptable salt thereof, within the scope of the third aspect, wherein:

Ring A is

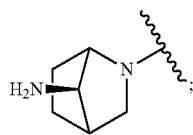

R$_2$ is —CH$_2$-cyclopropyl;

R$_3$ is —OC$_{1-4}$ alkyl;

R$_4$ is selected from

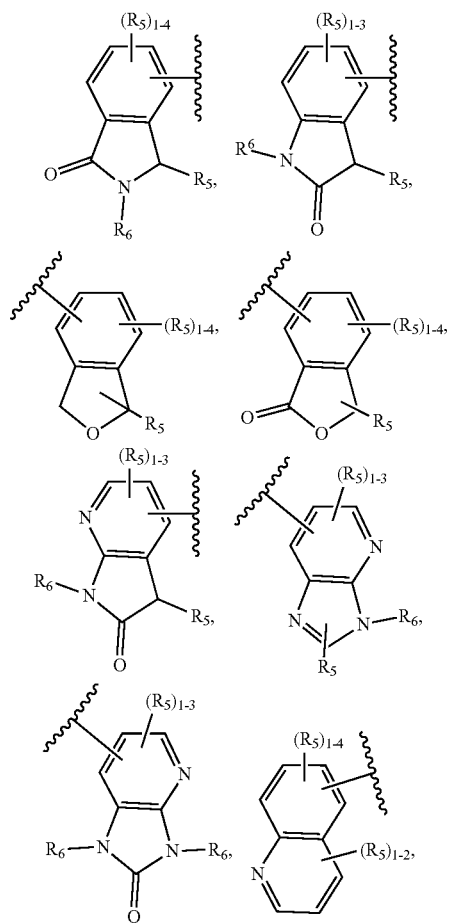

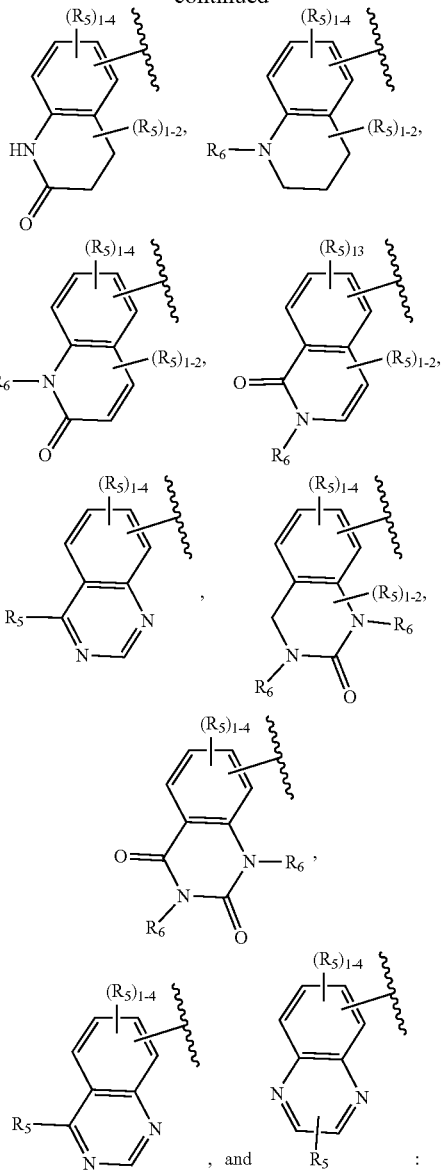

R$_5$, at each occurrence, is independently selected from H, F, Cl, Br, CN C$_{1-4}$alkyl, —OR$_b$, —S(O)$_p$R$_c$, —(CH$_2$)$_r$NR$_a$R$_a$, —(CH$_2$)$_r$NR$_a$C(=O)R$_b$, —NR$_a$C(=O)OR$_b$, —(CH$_2$)$_r$N-R$_a$S(O)$_p$R$_c$, —C(=O)NR$_a$R$_a$, —C(=O)OR$_b$, C$_{3-6}$cycloalkyl substituted with 0-4 R$_e$, aryl substituted with 0-4 R$_e$, and heterocyclyl substituted with 0-4 R$_e$;

R$_6$, at each occurrence, is independently selected from H, C$_{1-3}$alkyl substituted with 0-4 R$_e$, —S(O)$_p$R$_c$, —C(=O)R$_b$, —(CH$_2$)$_r$C(=O)NR$_a$R$_a$, —C(=O)(CH$_2$)$_r$NR$_a$C(=O)R$_b$, —C(=O)OR$_b$, —S(O)$_p$NR$_a$R$_a$, aryl substituted with 0-4 R$_e$, and heterocyclyl substituted with 0-4 R$_e$;

R$_a$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 $R_e$, —$(CH_2)_rC_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$ alkynyl substituted with 0-5 $R_e$, —$(CH_2)_r$—$C_{3-6}$ carbocyclyl substituted with 0-5 $R_e$, and —$(CH_2)_r$-heterocyclyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_rC_{3-6}$ cycloalkyl, —$(CH_2)_r$-aryl, F, Cl, Br, CN, $NO_2$, =O, —$NH_2$, —$NHC_{1-4}$alkyl, —$N(C_{1-4}$alkyl$)_2$, —C(=O)OH, —C(=O)O$C_{1-4}$alkyl, —$(CH_2)_r$OH, and —$(CH_2)_r$O$C_{1-4}$alkyl;

$R_f$, at each occurrence, is independently selected from H, F, Cl, Br, CN, OH, $C_{1-5}$ alkyl optionally substituted with OH, $C_{3-6}$ cycloalkyl, and phenyl;

p, at each occurrence, is independently selected from zero, 1, and 2; and r, at each occurrence, is independently selected from zero, 1, 2, 3, and 4.

In a ninth aspect, the present invention provides a compound or a pharmaceutically acceptable salt thereof, within the scope of the eighth aspect, wherein:

$R_4$ is selected from

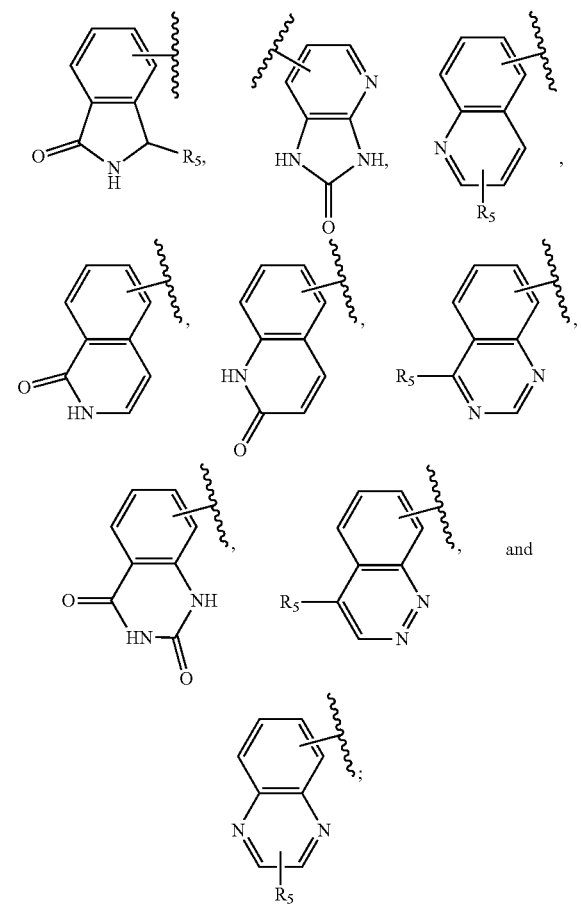

$R_5$, at each occurrence, is independently selected from H, F, Cl, Br, $C_{1-4}$alkyl, and OH.

In a tenth aspect, the present invention provides a compound of formula (IV):

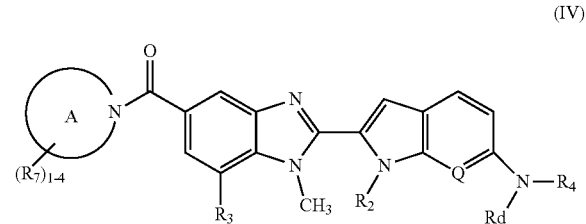

or a pharmaceutically acceptable salt thereof, within the scope of the ninth aspect,
wherein:
Ring A is

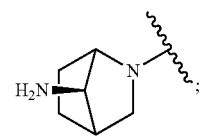

$R_2$ is selected from methyl and —$CH_2$-cyclopropyl;
$R_3$ is selected from H, F, and —$OC_{1-4}$ alkyl;
$R_4$ is selected from

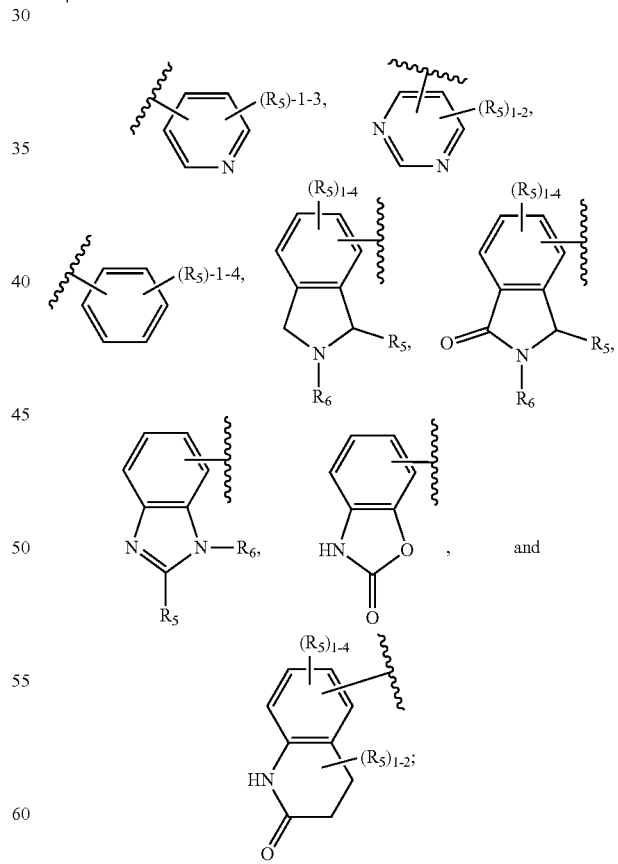

$R_5$, at each occurrence, is independently selected from H, F, Cl, Br, CN, $C_{1-4}$alkyl, —$(CH_2)_rOR_b$, —$NR_aR_a$, —$NR_aC(=O)R_b$, —$NR_aC(=O)OR_b$, —$C(=O)OR_b$, $NR_aS(O)_pR_c$, —$C(=O)NR_aR_a$, —$NR_aC(=O)NR_aR_a$, $C_{3-6}$cycloalkyl substituted with 0-4 $R_e$, aryl substituted with 0-4 $R_e$, and heterocyclyl substituted with 0-4 $R_e$;

$R_6$, at each occurrence, is independently selected from H and $C_{1-3}$alkyl;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$ alkynyl substituted with 0-5 $R_e$, —$(CH_2)_r$—$C_{3-6}$ carbocyclyl substituted with 0-5 $R_e$, and —$(CH_2)_r$-heterocyclyl substituted with 0-5 $R_e$;

$R_d$, at each occurrence, is independently selected from H and $C_{1-3}$ alkyl;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_rC_{3-6}$ cycloalkyl, —$(CH_2)_r$-aryl, F, Cl, Br, CN, $NO_2$, =O, $N(C_{1-4}alkyl)_2$, —C(=O)OH, —C(=O)OC_{1-4}alkyl, —$(CH_2)_r$OH, and —$(CH_2)_rOC_{1-4}$alkyl;

$R_f$, at each occurrence, is independently selected from H, F, Cl, Br, CN, OH, $C_{1-5}$ alkyl optionally substituted with OH, $C_{3-6}$ cycloalkyl, and phenyl;

p, at each occurrence, is independently selected from zero, 1, and 2; and r, at each occurrence, is independently selected from zero, 1, 2, 3, and 4.

In an eleventh aspect, the present invention provides a compound or a pharmaceutically acceptable salt thereof, within the scope of the tenth aspect, wherein:

$R_2$ is $CH_2$-cyclopropyl;
$R_3$ is —$OCH_3$;
$R_4$ is

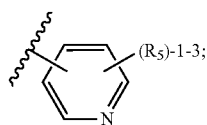

$R_5$, at each occurrence, is independently selected from H, F, Cl, Br, $C_{1-4}$alkyl, and —$(CH_2)_{0-1}$OH; and
$R_d$ is H.

In a twelfth aspect, the present invention provides a compound or a pharmaceutically acceptable salt thereof, within the scope of the second aspect, wherein:
L is —C(=O)NH—;
$R_2$ is —$CH_2$-cyclopropyl;
$R_3$ is —$OC_{1-4}$ alkyl;
$R_4$ is selected from

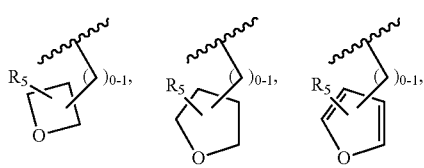

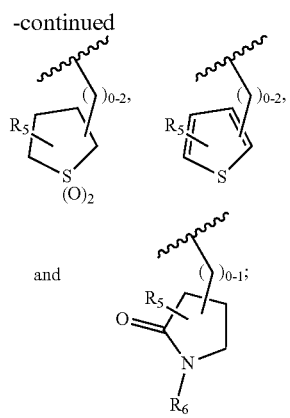

$R_5$, at each occurrence, is independently selected from H, F, Cl, Br, $C_{1-4}$alkyl, —OH, and —CN; and
$R_6$, at each occurrence, is independently selected from H and $C_{1-3}$alkyl.

In a thirteenth aspect, the present invention provides a compound or a pharmaceutically acceptable salt thereof, within the scope of the second aspect, wherein:
L is —O—;
$R_2$ is —$CH_2$-cyclopropyl;
$R_3$ is —$OC_{1-4}$ alkyl;
$R_4$ is selected from

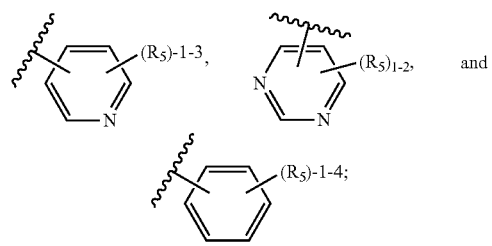

and $R_5$, at each occurrence, is independently selected from H, F, Cl, Br, $C_{1-4}$alkyl, —OH, and —CN.

In a fourteenth aspect, the present invention provides a compound of Formula (I):

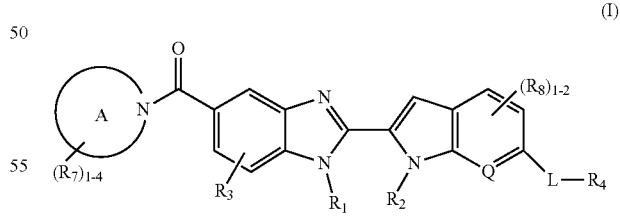

(I)

or a pharmaceutically acceptable salt thereof, wherein:
Q is selected from N and CH;
Ring A is 4- to 15-membered heterocyclyl substituted with 1-4 $R_7$;
$R_1$ is selected from $CH_3$, $CD_3$, and —$CH_2$-5 membered heterocyclyl compring carbon atoms and 1-3 heteroatoms selected from N, $NC_{1-4}$alkyl, O, and S;
$R_2$ is selected from H, $C_{1-3}$ alkyl substituted with 0-5 $R_e$, and —$(CH_2)_r$—$C_{3-6}$ cycloalkyl substituted with 0-5 $R_e$;

R$_3$ is selected from H, F, Cl, Br, —OR$_b$, and C$_{1-3}$ alkyl substituted with 0-5 R$_e$;

L is absent or selected from —NR$_d$—, —O—, —C(=O)NR$_d$—, and —S(O)$_p$—;

R$_4$ is selected from —(CH$_2$)$_r$-aryl substituted with 1-7 R$_5$, —(CH$_2$)$_r$—C$_{3-12}$ cycloalkyl (substituted with 1-2 OR$_b$, C(=O)OR$_b$, —C(=O)NR$_a$R$_a$, —NR$_a$C(=O)R$_b$), —(CH$_2$)$_r$-heterocyclyl comprising carbon atoms and 1-3 heteroatoms selected from N, NR$_6$, O, and S and substituted with 1-7 R$_5$;

R$_5$, at each occurrence, is independently selected from H, F, Cl, Br, CN, =O, nitro, C$_{1-4}$alkyl substituted with 0-5 R$_e$, C$_{2-4}$alkenyl substituted with 0-5 R$_e$, C$_{2-4}$alkynyl substituted with 0-5 R$_e$, —(CHR$_d$)$_r$OR$_b$, —(CHR$_d$)$_r$S(O)$_p$R$_c$, —(CHR$_d$)$_r$S(O)$_p$NR$_a$R$_a$, —(CHR$_d$)$_r$NR$_a$S(O)$_p$R$_c$, (CHR$_d$)NR$_a$R$_a$, —(CHR$_d$)$_r$NR$_a$C(=O)R$_b$, —(CHR$_d$)$_r$N-R$_a$C(=O)OR$_b$, —(CHR$_d$)$_r$C(=O)NR$_a$R$_a$, —(CHR$_d$)$_r$C(=O)R$_b$, —(CHR$_d$)$_r$C(=O)OR$_b$, —(CHR$_d$)$_r$C(=O)NR$_a$R$_a$, —(CHR$_d$)$_r$OC(=O)R$_b$, —(CHR$_d$)$_r$OC(=O)OR$_b$, —(CHR$_d$)$_r$O(CH$_2$)$_r$C(=O)NR$_a$R$_a$, C$_{3-6}$cycloalkyl substituted with 0-4 R$_e$, aryl substituted with 0-4 R$_e$, and heterocyclyl substituted with 0-4 R$_e$;

R$_6$ is selected from H, C$_{1-3}$alkyl substituted with 0-4 R$_e$, —S(O)$_p$R$_c$, —(CH$_2$)$_r$C(=O)R$_b$, —(CH$_2$)$_r$ C(=O)OR$_b$, —(CH$_2$)$_r$C(=O)(CH$_2$)$_r$NR$_a$R$_a$, —C(=O)(CH$_2$)$_r$NR$_a$C(=O)R$_b$, —S(O)$_p$NR$_a$R$_a$, —(CH$_2$)$_r$—C$_{3-6}$cycloalkyl substituted with 0-4 R$_e$, —(CH$_2$)$_r$-aryl substituted with 0-4 R$_e$, and —(CH$_2$)$_r$-heterocyclyl substituted with 0-4 R$_e$;

R$_7$ is selected from H, F, Cl, CN, C$_{1-3}$ alkyl, =N—OR$_b$, —(CH$_2$)$_r$OR$_b$, —(CH$_2$)$_r$NR$_a$R$_a$, —NR$_a$C(=NH)C$_{1-3}$alkyl, —NR$_a$C(=O)OR$_b$, carbocyclyl, and heterocyclyl; alternatively, two R$_7$ groups are taken together to form carbocyclyl or heterocyclyl;

R$_8$, at each occurrence, is independently selected from H, F, Cl, Br, and C$_{1-4}$alkyl substituted with 0-5 R$_e$;

R$_a$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$ alkynyl substituted with 0-5 R$_e$, —(CH$_2$)$_r$—C$_{3-6}$ carbocyclyl substituted with 0-5 R$_e$, and —(CH$_2$)$_r$-heterocyclyl substituted with 0-5 R$_e$;

R$_d$, at each occurrence, is independently selected from H, C$_{1-6}$ alkyl substituted with 0-5 R$_e$, and OH, R$_e$, at each occurrence, is independently selected from C$_{1-6}$ alkyl substituted with 0-5 R$_f$, C$_{2-6}$ alkenyl, C$_{2-6}$ alkynyl, —(CH$_2$)$_r$C$_{3-6}$ cycloalkyl, —(CH$_2$)$_r$-aryl, —(CH$_2$)$_r$-heterocyclyl, Si(C$_{1-4}$alkyl)$_3$, F, Cl, Br, CN, NO$_2$, =O, CO$_2$H, —(CH$_2$)$_r$OR$_f$, S(O)$_p$R$_f$, C(=O)NR$_f$R$_f$, S(O)$_p$NR$_f$R$_f$, and —(CH$_2$)$_r$NR$_f$R$_f$;

R$_f$, at each occurrence, is independently selected from H, F, Cl, Br, CN, OH, C$_{1-5}$ alkyl optionally substituted with OH, C$_{2-5}$ alkenyl, C$_{2-5}$ alkynyl, C$_{3-6}$ cycloalkyl, and phenyl, or R$_f$ and R$_f$ together with the nitrogen atom to which they are both attached form a heterocyclic ring optionally substituted with C$_{1-4}$alkyl;

p, at each occurrence, is independently selected from zero, 1, and 2;

r, at each occurrence, is independently selected from zero, 1, 2, 3, and 4;

provided:

(1) when L is absent, R$_4$ is not

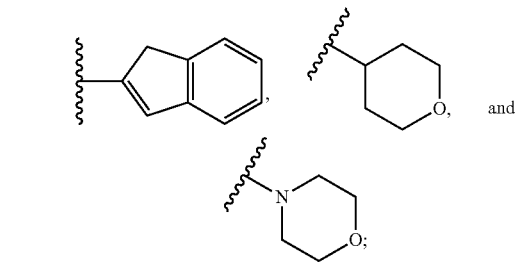

(2) when L is —NR$_d$—, R$_4$ is not

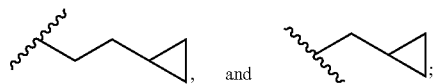 [SMILES: *CCC1CC1 ; *CC1CC1]

and (3) when L is —O—, R$_4$ is not C$_{3-6}$ cycloalkyl.

In a fifteenth aspect, the present invention provides a compound or a pharmaceutically acceptable salt thereof, within the scope of the fourteenth aspect, wherein:

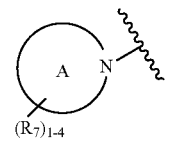

is selected from

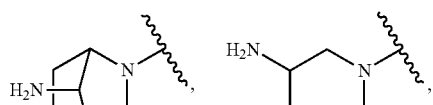

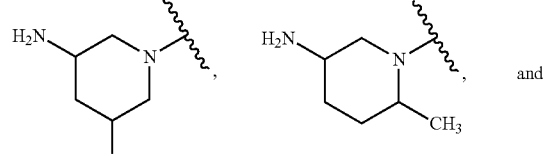

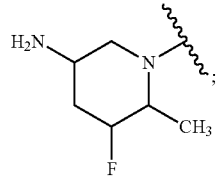

R$_1$ is selected from CH$_3$ and CD$_3$;

R$_2$ is selected from methyl, ethyl and —CH$_2$-cyclopropyl substituted with 0-3 R$_e$;

R₃ is selected from H, F, Cl, Br, and —OC₁₋₄ alkyl;
L is absent or selected from —NR$_a$—, —O—, —C(=O)NH—, —S—, and —S(O)₂—;
R$_a$ is selected from
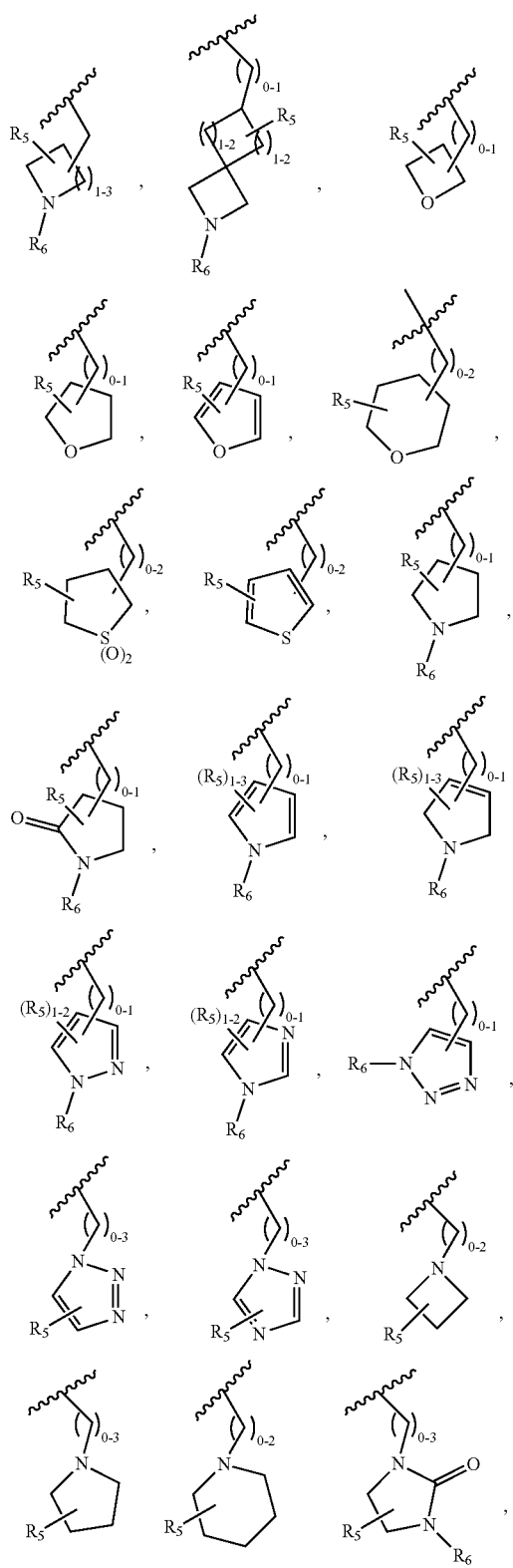
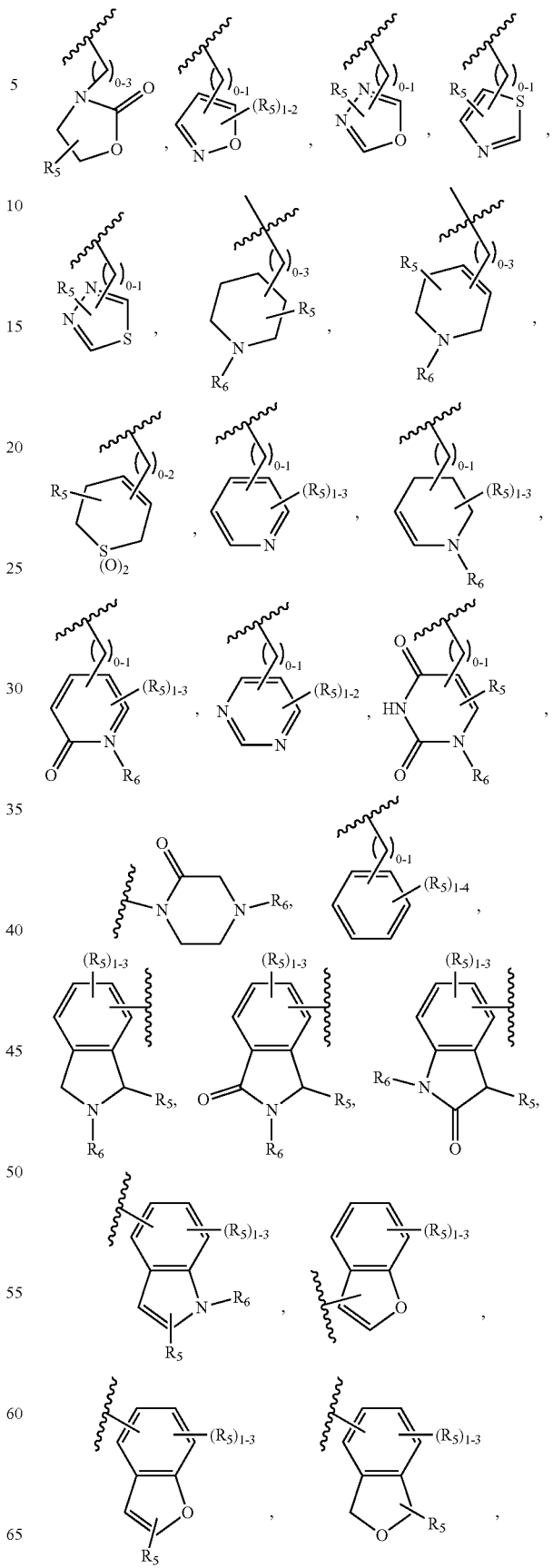

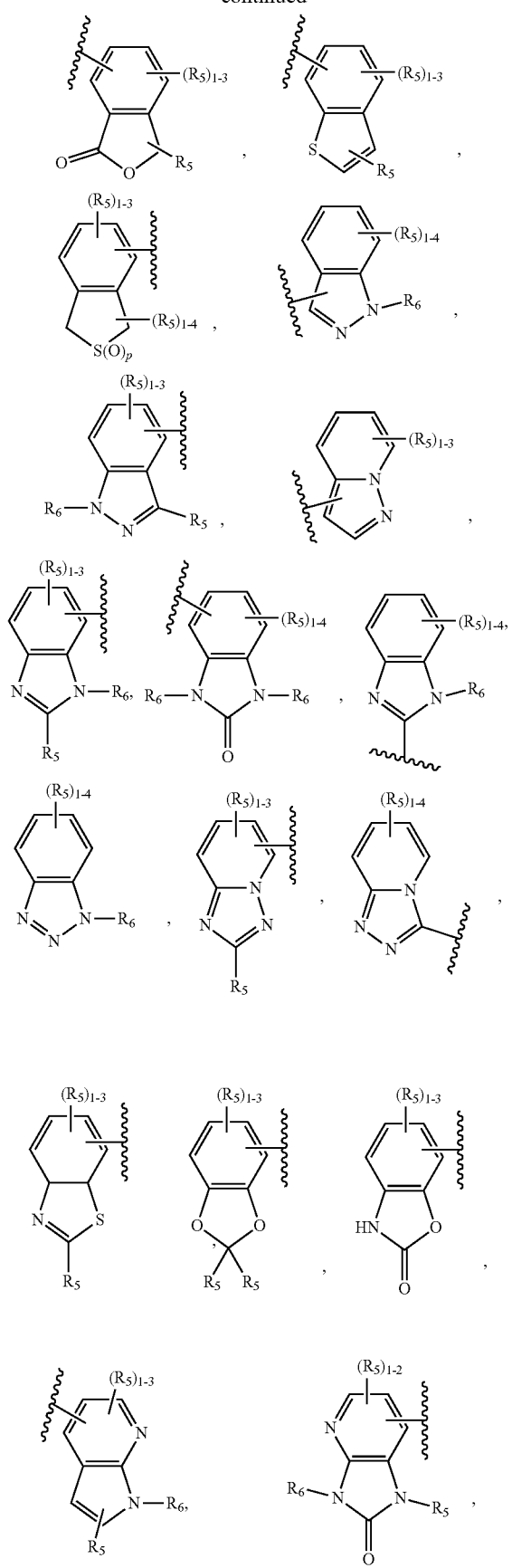
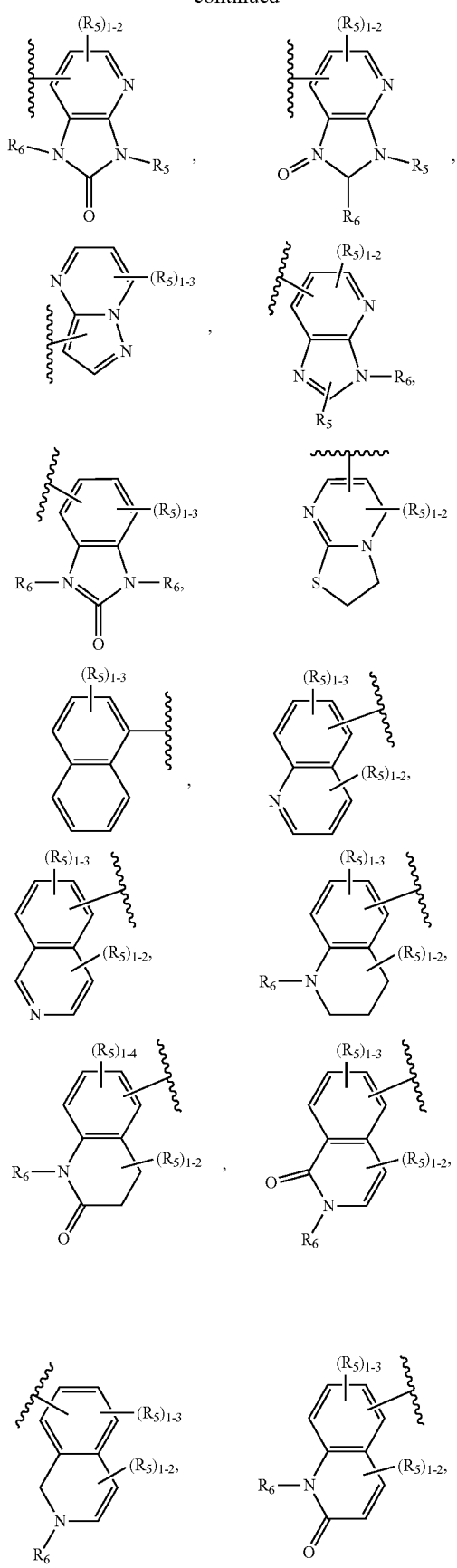

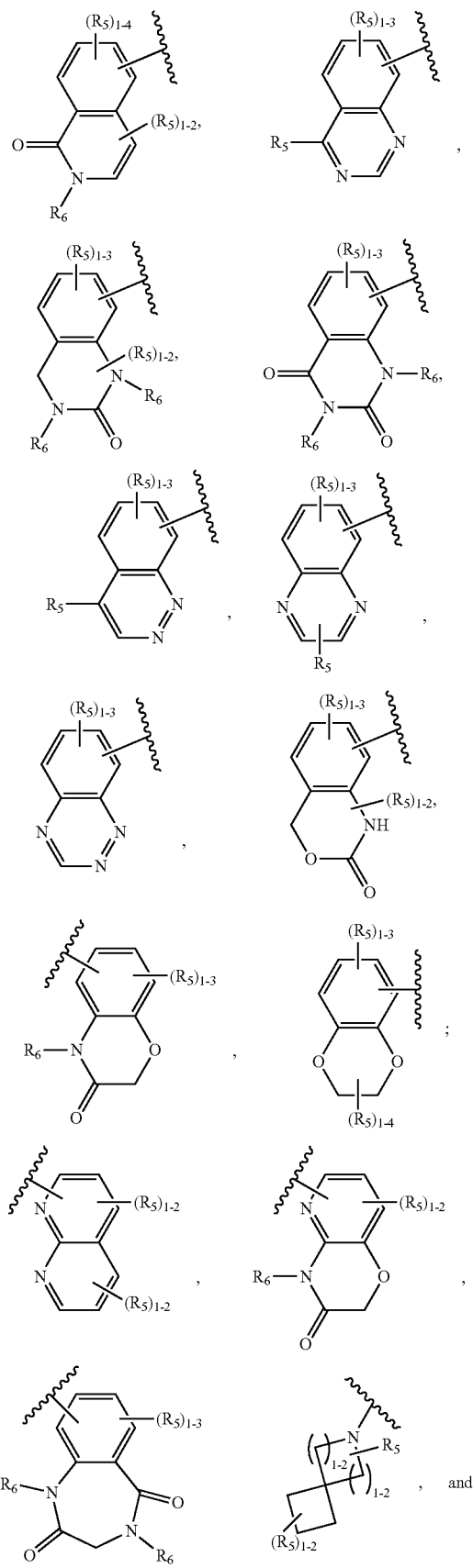

$R_5$, at each occurrence, is independently selected from H, F, Cl, Br, CN, =O, $C_{1-4}$alkyl substituted with 0-5 $R_e$, $C_{2-4}$alkenyl, $C_{2-4}$alkynyl, —$(CHR_d)_rOR_b$, —$(CH_2)_rS(O)_pR_c$, —$(CH_2)_rS(O)_pNR_aR_a$, —$(CH_2)_rNR_aS(O)_pR_c$, —$(CH_2)NR_aR_a$, —$(CH_2)_rNR_aC(=O)R_b$, —$(CH_2)_rNR_aC(=O)OR_b$, —$(CH_2)_rNR_aC(=O)NR_aR_a$, —$(CH_2)_rC(=O)R_b$, —$(CH_2)_rC(=O)OR_b$, —$(CHR_d)_rC(=O)NR_aR_a$, —$(CH_2)_rOC(=O)R_b$, —$(CH_2)_rOC(=O)OR_b$, —$(CH_2)_rO(CH_2)_rC(=O)NR_aR_a$, $C_{3-6}$cycloalkyl substituted with 0-4 $R_e$, aryl substituted with 0-4 $R_e$, and heterocyclyl substituted with 0-4 $R_e$;

$R_6$, at each occurrence, is independently selected from H, $C_{1-3}$alkyl substituted with 0-4 $R_e$, —$S(O)_pR_c$, —$C(=O)R_b$, —$(CH_2)_rC(=O)OR_b$, —$(CH_2)_rC(=O)(CH_2)_rNR_aR_a$, —$C(=O)(CH_2)_rNR_aC(=O)R_b$, —$S(O)_pNR_aR_a$, —$(CH_2)_r$-aryl substituted with 0-4 $R_e$, and —$(CH_2)_r$-heterocyclyl substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_f$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$ alkynyl substituted with 0-5 $R_e$, —$(CH_2)_r$—$C_{3-6}$ carbocyclyl substituted with 0-5 $R_e$, and —$(CH_2)_r$-heterocyclyl substituted with 0-5 $R_e$:

$R_d$, at each occurrence, is independently selected from H, $C_{1-6}$ alkyl substituted with 0-5 $R_e$, and OH;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_rC_{3-6}$ cycloalkyl, —$(CH_2)_r$-aryl, —$(CH_2)_r$-heterocyclyl, F, Cl, Br, CN, $NO_2$, =O, —$NH_2$, —$NHC_{1-4}$alkyl, —$N(C_{1-4}$alkyl$)_2$, —$C(=O)OH$, —$C(=O)OC_{1-4}$alkyl, —$(CH_2)_rOH$, and —$(CH_2)_rOC_{1-4}$alkyl;

$R_f$, at each occurrence, is independently selected from H, F, Cl, Br, CN, OH, $C_{1-5}$ alkyl optionally substituted with OH, $C_{3-6}$ cycloalkyl, and phenyl;

p, at each occurrence, is independently selected from zero, 1, and 2; and r, at each occurrence, is independently selected from zero, 1, 2, 3, and 4.

In a sixteenth aspect, the present invention provides a compound of Formula (II):
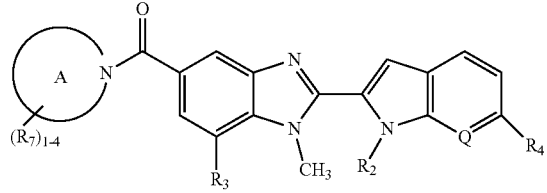
(II)
or a pharmaceutically acceptable salt thereof, within the scope of the fifteenth aspect, wherein:
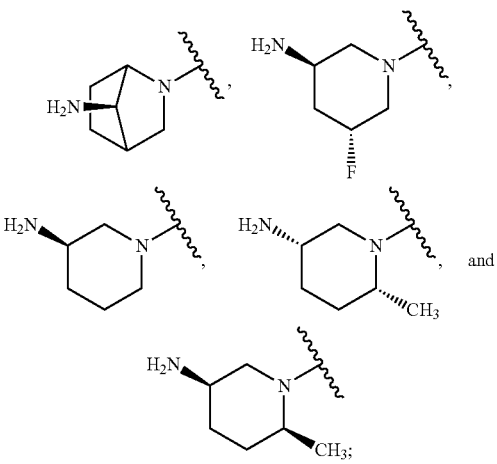
is selected from
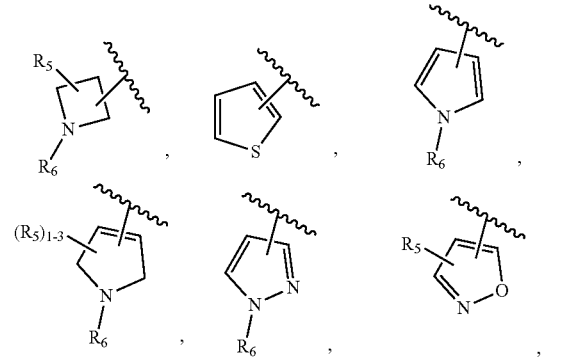
$R_2$ is selected from $CH_3$, $CH_2CH_3$ and —$CH_2$-cyclopropyl substituted with 0-2 F, Cl, and $CH_3$;
$R_3$ is selected from H, F, and —$OC_{1-4}$ alkyl;
$R_4$ is selected from
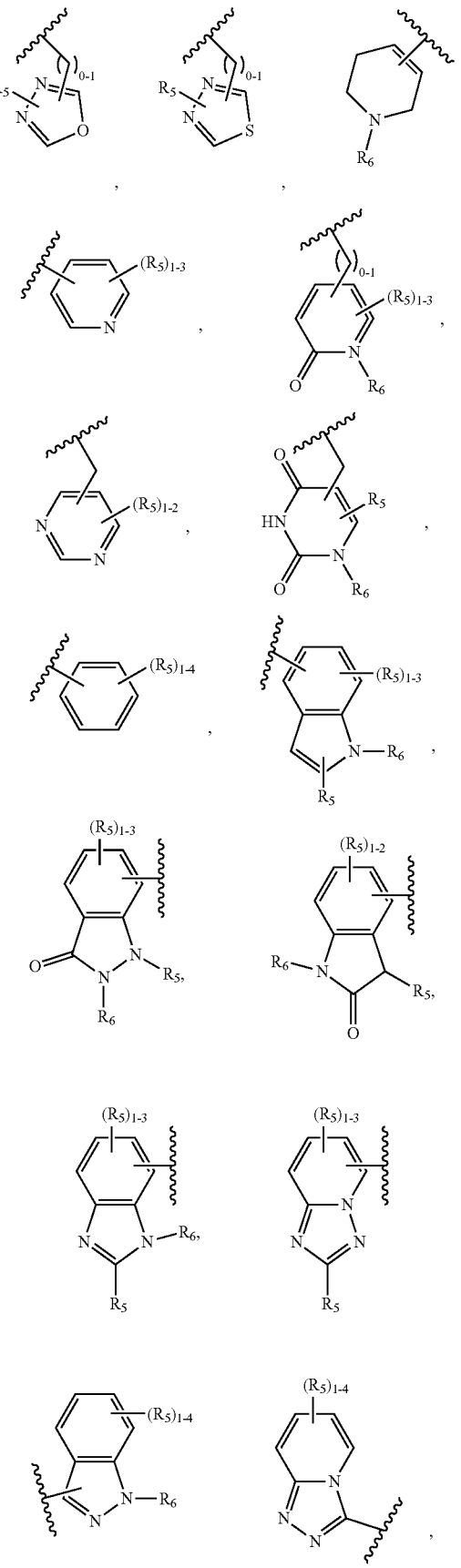

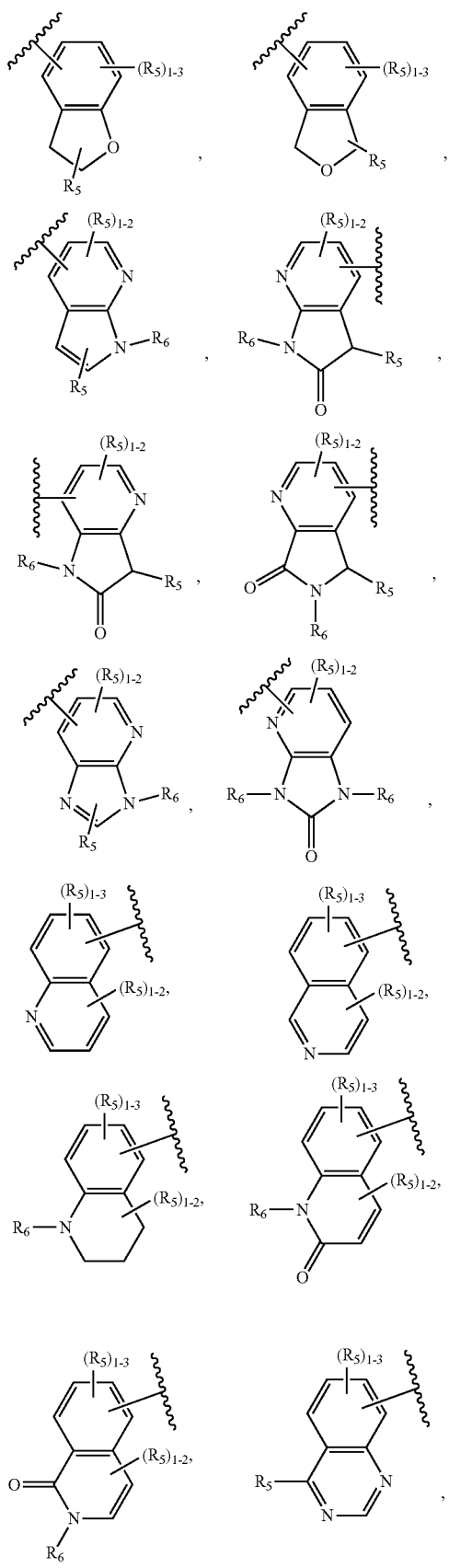
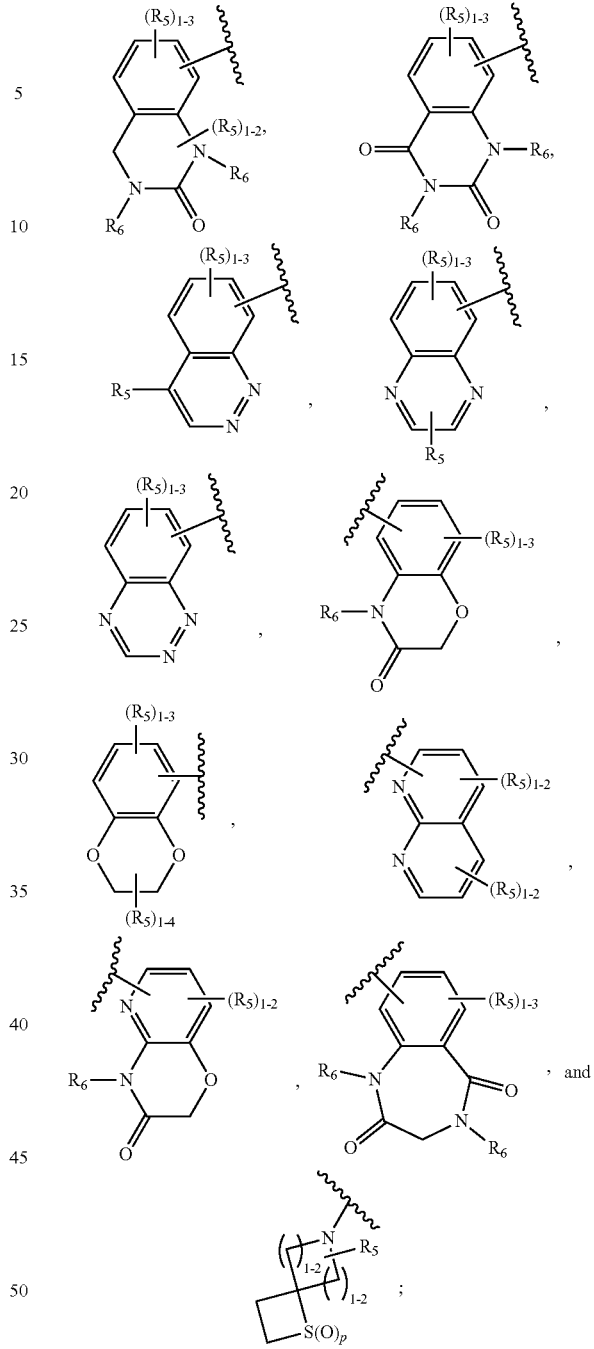

$R_5$, at each occurrence, is independently selected from H, F, Cl, Br, CN, =O, $C_{1-4}$alkyl substituted with 0-4 $R_e$, —(CHR$_d$)$_r$OR$_b$, —(CH$_2$)$_r$S(O)$_p$R$_c$, —S(O)$_p$NR$_a$R$_a$, —(CH$_2$)$_r$NR$_a$S(O)$_p$R$_c$, —(CH$_2$)$_r$NR$_a$R$_a$, —(CH$_2$)$_r$NR$_a$C(=O)R$_b$, —NR$_a$C(=O)OR$_b$, —NR$_a$C(=O)NR$_a$R$_a$, —(CH$_2$)$_r$C(=O)R$_b$, —(CH$_2$)$_r$C(=O)OR$_b$, —(CHR$_d$)$_r$C(=O)NR$_a$R$_a$, —(CH$_2$)$_r$OC(=O)R$_b$, —(CH$_2$)$_r$OC(=O)OR$_b$, —(CH$_2$)O(CH$_2$)$_r$C(=O)NR$_a$R$_a$, $C_{3-6}$cycloalkyl substituted with 0-4 $R_e$, aryl substituted with 0-4 $R_e$, and heterocyclyl substituted with 0-4 $R_e$;

$R_6$, at each occurrence, is independently selected from H, $C_{1-3}$alkyl substituted with 0-4 $R_e$, —S(O)$_p$R$_c$, —C(=O)R$_b$, —(CH$_2$)$_r$C(=O)OR$_b$, —(CH$_2$)$_r$C(=O)NR$_a$R$_a$, —C(=O)(CH$_2$)$_r$NR$_a$C(=O)R$_b$, —S(O)$_p$NR$_a$R$_a$, aryl substituted with 0-4 R$_e$, and heterocyclyl substituted with 0-4 R$_e$;

R$_a$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, —(CH$_2$)$_r$C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$ alkynyl substituted with 0-5 R$_e$, —(CH$_2$)$_r$—C$_{3-6}$ carbocyclyl substituted with 0-5 R$_e$, and —(CH$_2$)$_r$-heterocyclyl substituted with 0-5 R$_e$;

R$_d$, at each occurrence, is independently selected from H and C$_{1-6}$ alkyl substituted with 0-5 R$_e$;

R$_e$, at each occurrence, is independently selected from C$_{1-6}$ alkyl substituted with 0-5 R$_f$, C$_{2-6}$ alkenyl, C$_{2-6}$ alkynyl, —(CH$_2$)$_r$C$_{3-6}$ cycloalkyl, —(CH$_2$)$_r$-aryl, —(CH$_2$)$_r$-heterocyclyl, F, Cl, Br, CN, NO$_2$, =O, —NH$_2$, —NHC$_{1-4}$alkyl, —N(C$_{1-4}$alkyl)$_2$, —C(=O)OH, —C(=O)OC$_{1-4}$alkyl, —(CH$_2$)$_r$OH, and —(CH$_2$)$_r$OC$_{1-4}$alkyl;

R$_f$, at each occurrence, is independently selected from H, F, Cl, Br, CN, OH, C$_{1-5}$ alkyl optionally substituted with OH, C$_{3-6}$ cycloalkyl, and phenyl;

p, at each occurrence, is independently selected from zero, 1, and 2; and r, at each occurrence, is independently selected from zero, 1, 2, 3, and 4.

In a seventeenth aspect, the present invention provides a compound of Formula (III):

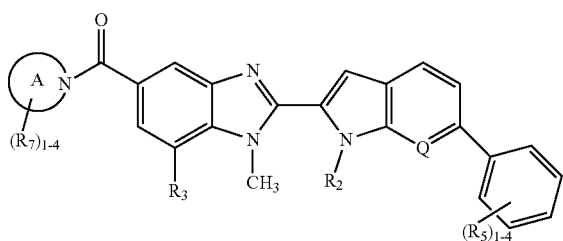

(III)

or a pharmaceutically acceptable salt thereof, within the scope of the sixteenth aspect, wherein:

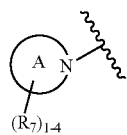

is selected from

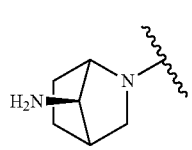 and 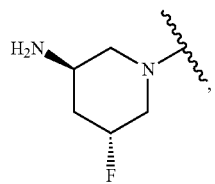,

R$_2$ is —CH$_2$-cyclopropyl;

R$_3$ is —OC$_{1-4}$ alkyl;

R$_5$, at each occurrence, is independently selected from H, F, Cl, Br, CN, C$_{1-4}$alkyl substituted with 0-4 R$_e$, —(CHR$_d$)$_r$OR$_b$, —(CH$_2$)$_r$S(O)$_p$R$_c$, —S(O)$_p$NR$_a$R$_a$, —(CH$_2$)$_r$NHS(O)$_p$R$_c$, —(CH$_2$)$_r$NR$_a$R$_a$, —(CH$_2$)$_r$NHC(=O)R$_b$, —NHC(=O)OR$_b$, —(CHR$_d$)$_r$C(=O)NR$_a$R$_a$, —(CH$_2$)$_r$C(=O)OR$_b$, —OC(=O)OR$_b$, —O(CH$_2$)$_{0-1}$C(=O)NR$_a$R$_a$, C$_{3-6}$cycloalkyl substituted with 0-4 R$_e$, aryl substituted with 0-4 R$_e$, and heterocyclyl substituted with 0-4 R$_e$;

R$_a$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, —(CH$_2$)$_r$C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$ alkynyl substituted with 0-5 R$_e$, —(CH$_2$)$_r$—C$_{3-6}$ carbocyclyl substituted with 0-5 R$_e$, and —(CH$_2$)$_r$-heterocyclyl substituted with 0-5 R$_e$;

R$_d$, at each occurrence, is independently selected from H, C$_{1-4}$ alkyl, and OH;

R$_e$, at each occurrence, is independently selected from C$_{1-6}$ alkyl substituted with 0-5 R$_f$, C$_{2-6}$ alkenyl, C$_{2-6}$ alkynyl, —(CH$_2$)$_r$C$_{3-6}$ cycloalkyl, —(CH$_2$)-aryl, —(CH$_2$)$_r$-heterocyclyl, F, Cl, Br, CN, NO$_2$, =O, —NH$_2$, —NHC$_{1-4}$alkyl, —N(C$_{1-4}$alkyl)$_2$, —C(=O)OH, —C(=O)OC$_{1-4}$alkyl, —(CH$_2$)$_r$OH, —(CH$_2$)$_r$OC$_{1-4}$alkyl, and SO$_2$C$_{1-4}$alkyl;

R$_f$, at each occurrence, is independently selected from H, F, Cl, Br, CN, OH, C$_{1-5}$ alkyl optionally substituted with OH, C$_{3-6}$ cycloalkyl, and phenyl;

p, at each occurrence, is independently selected from zero, 1, and 2; and r, at each occurrence, is independently selected from zero, 1, 2, 3, and 4.

In an eighteenth aspect, the present invention provides a compound or a pharmaceutically acceptable salt thereof, within the scope of the seventeenth aspect, wherein:

R$_3$ is —OCH$_3$;

R$_5$, at each occurrence, is independently selected from H, F, Cl, Br, CN, C$_{1-4}$alkyl, —(CH$_2$)$_{0-1}$OR$_b$, —S(O)$_2$NH$_2$, —NHS(O)$_2$C$_{1-3}$ alkyl, —NHS(O)$_2$C$_{2-4}$alkenyl, —NHC(=O)R$_b$, —C(=O)NH$_2$ and heterocyclyl selected from

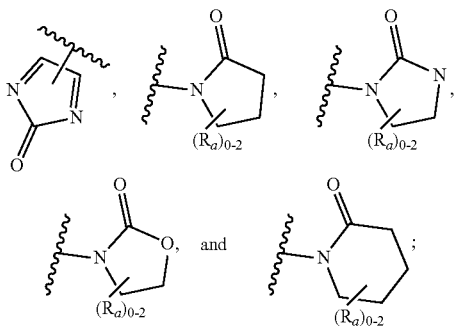

$R_b$, at each occurrence, is independently selected from H and $C_{1-6}$ alkyl substituted with 0-5 $R_e$, $R_e$, at each occurrence, is independently selected from $C_{1-6}$ alkyl, F, Cl, Br, CN, $NO_2$, =O, $-NH_2$, $-NHC_{1-4}$alkyl, $-N(C_{1-4}alkyl)_2$, $-C(=O)OH$, $-C(=O)OC_{1-4}$alkyl, $-(CH_2)_rOH$, $-(CH_2)_rOC_{1-4}$alkyl, and $SO_2C_{1-4}$alkyl;

In a nineteenth aspect, the present invention provides a compound or a pharmaceutically acceptable salt thereof, within the scope of the sixteenth aspect, wherein:

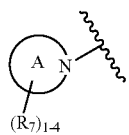

is selected from

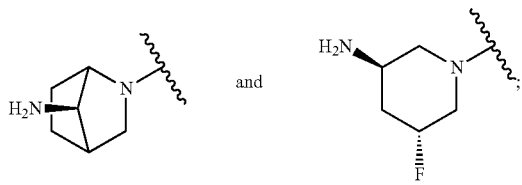 [SMILES: *N1CC2CCC1[C@@H]2N ; *N1C[C@H](N)C[C@@H](F)C1]

$R_2$ is $-CH_2$-cyclopropyl;
$R_3$ is $-OC_{1-4}$ alkyl;
$R_4$ is selected from

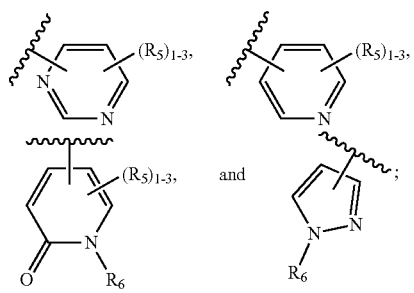

$R_5$, at each occurrence, is independently selected from H, F, Cl, Br, CN, $C_{1-4}$alkyl substituted with 0-4 $R_e$, $-(CH_2)_rOR_b$, $-S(O)_pR_c$, $-S(O)_pNR_aR_a$, $-(CH_2)_r$-$NR_aS(O)_pR_c$, $-(CH_2)_rNR_aR_a$, $-(CH_2)_rNR_aC(=O)R_b$, $-NR_aC(=O)OR_b$, $-NR_aC(=O)NR_aR_a$, $-(CH_2)_rC(=O)R_b$, $-(CH_2)_rC(=O)OR_b$, $-(CH_2)_rC(=O)NR_aR_a$, $-(CH_2)_rOC(=O)R_b$, $C_{3-6}$cycloalkyl substituted with 0-4 $R_e$, aryl substituted with 0-4 $R_e$, and heterocyclyl substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r$-$C_{3-10}$carbocyclyl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $-(CH_2)_r$-$C_{2-6}$ alkynyl substituted with 0-5 $R_e$, $-(CH_2)_r$-$C_{3-10}$carbocyclyl substituted with 0-5 $R_e$, and $-(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$ alkynyl substituted with 0-5 $R_e$, $-(CH_2)_r$-$C_{3-6}$ carbocyclyl substituted with 0-5 $R_e$, and $-(CH_2)_r$-heterocyclyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, $-(CH_2)_r$-$C_{3-6}$ cycloalkyl, $-(CH_2)_r$-aryl, F, Cl, Br, CN, $NO_2$, =O, $-NH_2$, $-NHC_{1-4}$alkyl, $-N(C_{1-4}alkyl)_2$, $-C(=O)OH$, $-C(=O)OC_{1-4}$alkyl, $-(CH_2)_rOH$, and $-(CH_2)_rOC_{1-4}$alkyl, $R_f$, at each occurrence, is independently selected from H, F, Cl, Br, CN, OH, $C_{1-5}$ alkyl optionally substituted with OH, $C_{3-6}$ cycloalkyl, and phenyl;

p, at each occurrence, is independently selected from zero, 1, and 2; and r, at each occurrence, is independently selected from zero, 1, 2, 3, and 4.

In a twentieth aspect, the present invention provides a compound or a pharmaceutically acceptable salt thereof, within the scope of the nineteenth aspect, wherein:

$R_a$ is $-OCH_3$;

$R_5$, at each occurrence, is independently selected from H, F, Cl, Br, $C_{1-4}$alkyl, $-OH$, $-OC_{1-3}$alkyl, $-NHS(O)_2C_{2-4}$alkenyl, $NHC(=O)OC_{1-4}$ alkyl, $C(=O)NH_2$, $C(=O)NHC_{1-4}$alkyl, and heterocyclyl selected from

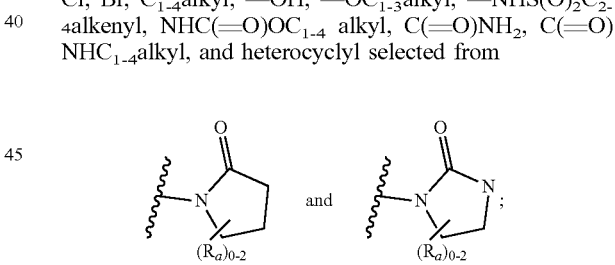

and $R_e$, at each occurrence, is independently selected from $C_{1-6}$ alkyl, F, Cl, Br, CN, $NO_2$, =O, $-NH_2$, $-NHC_{1-4}$alkyl, $-N(C_{1-4}alkyl)_2$, $-C(=O)OH$, $-C(=O)OC_{1-4}$alkyl, $-(CH_2)_rOH$, $-(CH_2)_rOC_{1-4}$alkyl, and $SO_2C_{1-4}$alkyl;

In a twenty first aspect, the present invention provides a compound or a pharmaceutically acceptable salt thereof, within the scope of the sixteenth aspect, wherein:

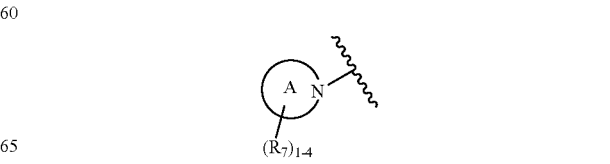

is selected from
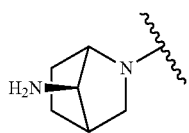 and 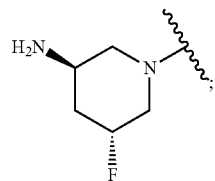;
R$_2$ is —CH$_2$-cyclopropyl;
R$_3$ is —OC$_{1-4}$ alkyl;
R$_4$ is selected from
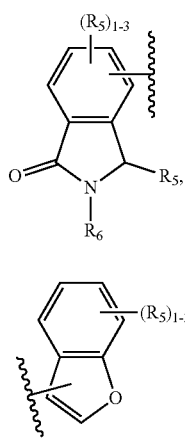
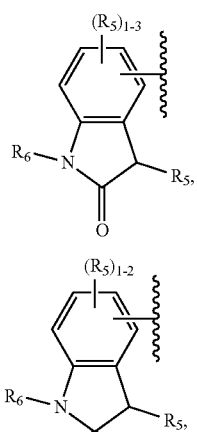
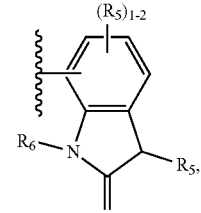
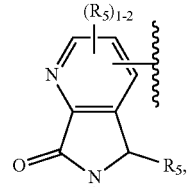
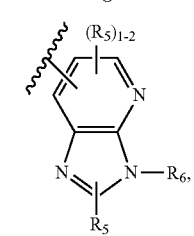
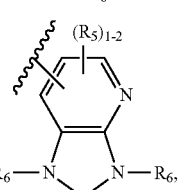
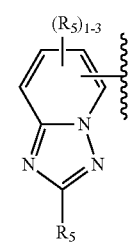
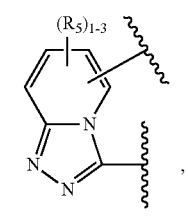
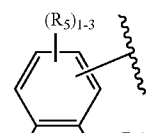 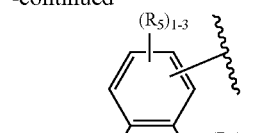
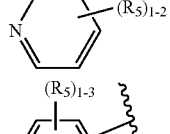
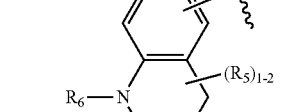
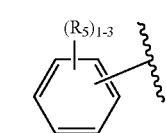 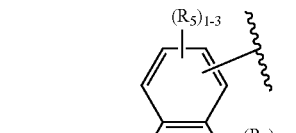
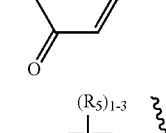
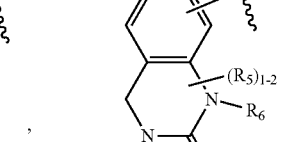
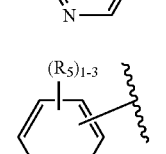 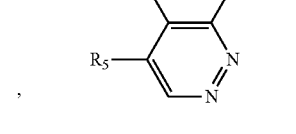
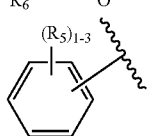 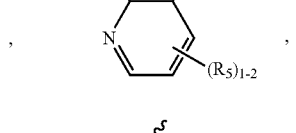
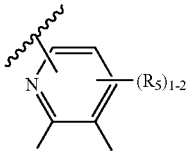 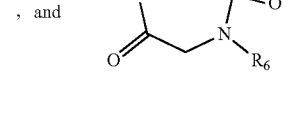, and ;
R$_5$, at each occurrence, is independently selected from H, F, Cl, Br, CN C$_{1-4}$alkyl, —OR$_b$, —S(O)$_p$R$_c$—(CH$_2$)$_r$NR$_a$S —(O)$_p$R$_c$, —(CH$_2$)$_r$NR$_a$R$_a$, —(CH$_2$)$_r$NR$_a$C(=O)R$_b$, —NR$_a$C(=O)OR$_b$, —C(=O)OR$_b$, C(=O)NR$_a$R$_a$, C$_{3-6}$cycloalkyl substituted with 0-4 R$_e$, aryl substituted with 0-4 R$_e$, and heterocyclyl substituted with 0-4 R$_e$;

R$_6$, at each occurrence, is independently selected from H, C$_{1-3}$alkyl substituted with 0-4 R$_e$, —S(O)$_p$R$_c$, —C(=O)R$_b$, —C(=O)OR$_b$, —(CH$_2$)$_r$C(=O)NR$_a$R$_a$, —C(=O)(CH$_2$)$_r$NR$_a$C(=O)R$_b$, —S(O)$_p$NR$_a$R$_a$, aryl substituted with 0-4 R$_e$, and heterocyclyl substituted with 0-4 R$_e$, R$_a$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-5}$ alkyl substituted with 0-5 R$_e$, C$_{2-6}$ alkenyl substituted with 0-5 R$_e$, —(CH$_2$)$_r$C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$ alkynyl substituted with 0-5 R$_e$, —(CH$_2$)$_r$—C$_{3-6}$ carbocyclyl substituted with 0-5 R$_e$, and —(CH$_2$)$_r$-heterocyclyl substituted with 0-5 R$_e$;

R$_e$, at each occurrence, is independently selected from C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, —(CH$_2$)$_r$-aryl, F, Cl, Br, CN, NO$_2$, =O, —NH$_2$, —NHC$_{1-4}$alkyl, —N(C$_{1-4}$alkyl)$_2$, —C(=O)OH, —C(=O)OC$_{1-4}$alkyl, —(CH$_2$)$_r$OH, and —(CH$_2$)$_r$OC$_{1-4}$alkyl:

R$_f$, at each occurrence, is independently selected from H, F, Cl, Br, CN, OH, C$_{1-5}$ alkyl optionally substituted with OH, C$_{3-6}$ cycloalkyl, and phenyl;

p, at each occurrence, is independently selected from zero, 1, and 2; and r, at each occurrence, is independently selected from zero, 1, 2, 3, and 4.

In a twenty second aspect, the present invention provides a compound or a pharmaceutically acceptable salt thereof, within the scope of the twenty first aspect, wherein:

R$_4$ is selected from

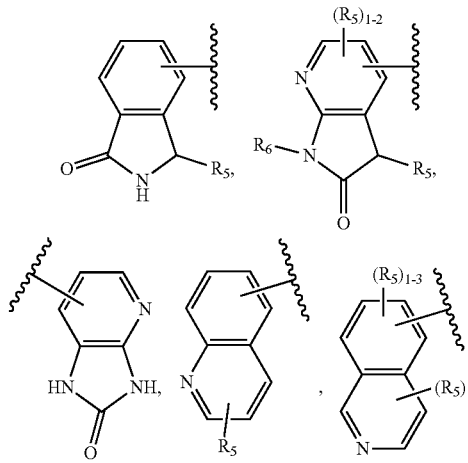

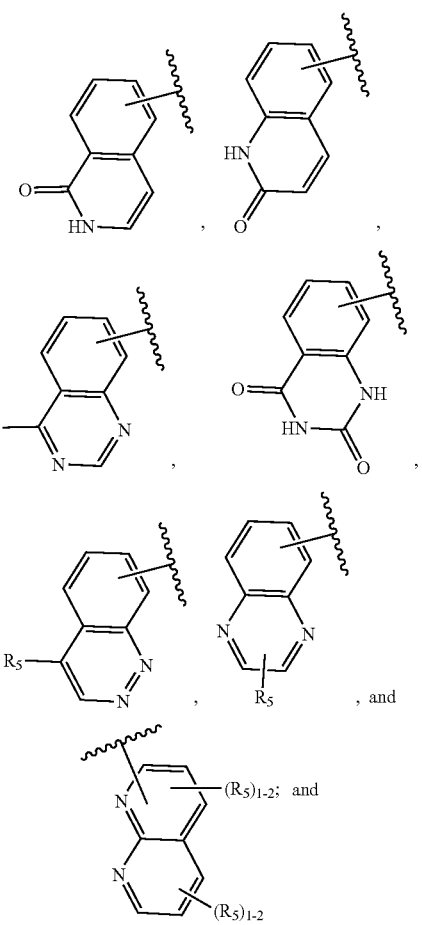

R$_5$, at each occurrence, is independently selected from H, F, Cl, Br, C$_{1-4}$alkyl, OH, and —C(=O)OH.

In a twenty third aspect, the present invention provides a compound of Formula (V):

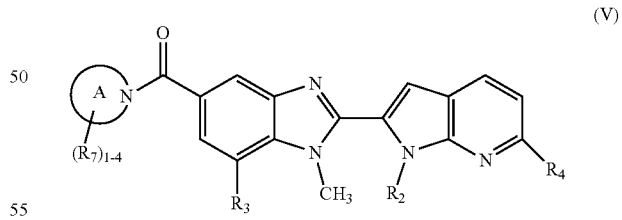

(V)

or a pharmaceutically acceptable salt thereof, wherein:

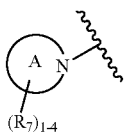

is selected from

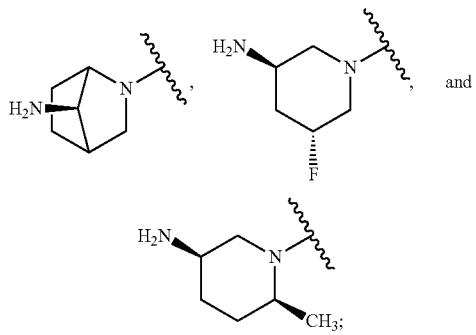

R₂ is —CH₂-cyclopropyl;
R₃ is —OCH₃; and
R₄ is selected from

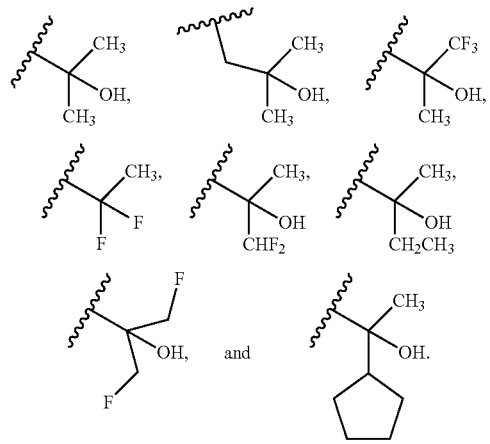

In a twenty fourth aspect, the present invention provides a compound of Formula (VI):

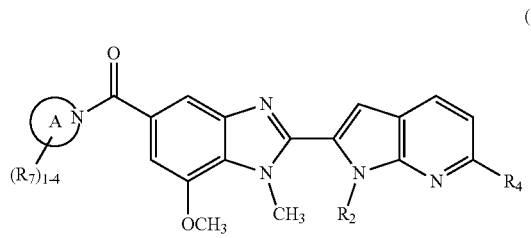

(VI)

or a pharmaceutically acceptable salt thereof, wherein:

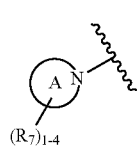

is selected from

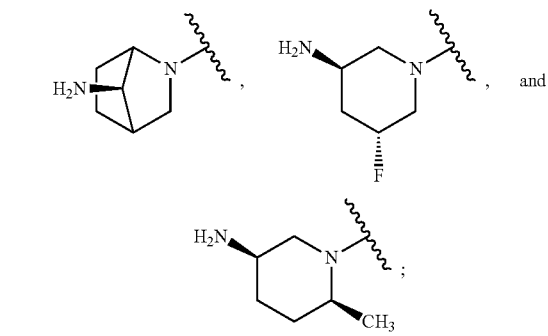

R₂ is —CH₂-cyclopropyl;
R₄ is selected from

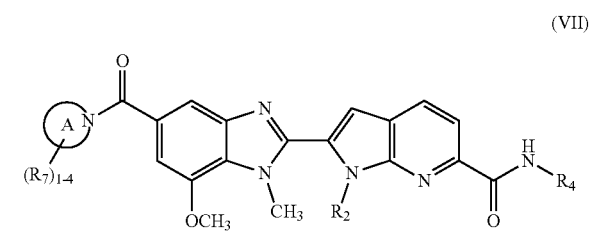

and

R₅ is selected from H, OH, CH₂OH, and —C(CH₃)₂OH.

In a twenty fifth aspect, the present invention provides a compound of Formula (VII):

(VII)

or a pharmaceutically acceptable salt thereof, wherein:

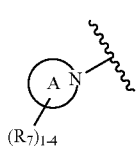

is selected from

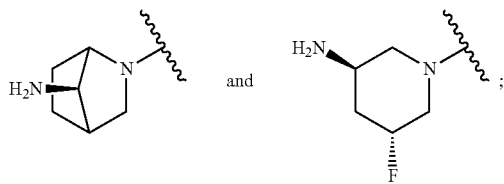 [SMILES: *N1CC2CCC1[C@@H]2N ; *N1C[C@H](N)C[C@@H](F)C1]

$R_2$ is —$CH_2$-cyclopropyl;
$R_4$ is selected from

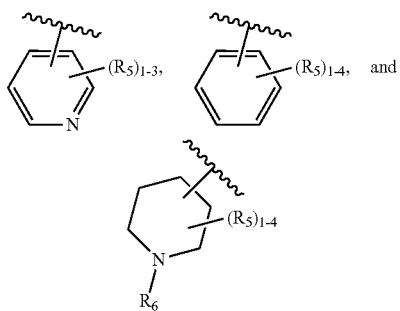

$R_5$, at each occurrence, is independently selected from F, Cl, $C_{1-4}$alkyl, —$(CH_2)_rOR_b$, —$S(O)_2NR_aR_a$, —$NR_aS(O)_2R_c$, and —$C(=O)NR_aR_a$;

$R_6$, at each occurrence, is independently selected from H and $C_{1-3}$alkyl;

$R_a$, at each occurrence, is independently selected from H and $C_{1-4}$ alkyl substituted with 0-5 $R_e$;

$R_b$, at each occurrence, is independently selected from H and $C_{1-4}$ alkyl substituted with 0-5 $R_e$;

$R_c$, at each occurrence, is independently $C_{1-4}$ alkyl substituted with 0-5 $R_e$;

$R_e$, at each occurrence, is independently selected from F, Cl, Br, —OH, and —$OC_{1-4}$alkyl; and r, at each occurrence, is independently selected from zero, 1, and 2.

In one embodiment, the present invention provides compounds with $IC_{50}$ values≤4.000 μM, using the RFMS PAD4 functional assay disclosed herein, preferably, $IC_{50}$ values≤1.000 μM, preferably, $IC_{50}$ values≤0.500 μM, preferably, $IC_{50}$ values≤0.100 μM, more preferably, $IC_{50}$ values≤0.050 μM, more preferably, $IC_{50}$ values≤0.03 μM, more preferably, $IC_{50}$ values≤0.02 μM, even more preferably, $IC_{50}$ values≤0.01 μM.

As defined above and described herein, $R_1$ is selected from $CH_3$ and $CD_3$. In some embodiments, $R_1$ is $CH_3$. In some embodiments, $R_1$ is $CD_3$.

As defined above and described herein, $R_2$ is hydrogen, $C_{1-3}$ alkyl substituted with 0-5 $R_e$, or $C_{3-6}$ cycloalkyl substituted with 0-5 $R_e$. In some embodiments, $R_2$ is hydrogen. In some embodiments, $R_2$ is $C_{1-2}$ alkyl substituted with $C_{3-6}$ cycloalkyl. In some embodiments, $R_2$ is $C_{3-6}$ cycloalkyl. In some embodiments, $R_2$ is methyl. In some embodiments, $R_2$ is ethyl. In some embodiments, $R_2$ is cyclopropyl. In some embodiments, $R_2$ is cyclobutyl. In some embodiments, $R_2$ is cyclopentyl. In some embodiments, $R_2$ is cyclohexyl. In some embodiments, $R_2$ is cyclopropylmethyl. In some embodiments, $R_2$ is cyclobutylmethyl. In some embodiments, $R_2$ is cyclopentylmethyl. In some embodiments, $R_2$ is cyclohexylmethyl. In some embodiments, $R_2$ is cyclopropylethyl. In some embodiments, $R_2$ is cyclobutylethyl. In some embodiments, $R_2$ is cyclopentylethyl. In some embodiments, $R_2$ is cyclohexylethyl. In some embodiments, $R_2$ is —$CH_2$-cyclopropyl or —$CH_2$-cyclobutyl. In some embodiments, $R_2$ is —$CH_2$-cyclobutyl optionally substituted with methyl and —OH. In certain embodiments, $R_2$ is selected from those functional groups depicted in the examples below.

As defined above and described herein, Q is N or CH. In some embodiments, Q is N. In some embodiments, Q is CH. In certain embodiments, Q is selected from those functional groups depicted in the examples below.

As defined above and described herein, $R_3$ is selected from H, F, Cl, Br, —$OR_b$, and $C_{1-3}$ alkyl substituted with 0-5 $R_e$. In some embodiments, $R_3$ is H. In some embodiments, $R_3$ is F, Cl, Br. In some embodiments, $R_3$ is F, In some embodiments, $R^3$ is $C_{1-3}$ alkyl. In some embodiments, $R_3$ is methyl. In some embodiments, $R_3$ is ethyl. In some embodiments, $R_3$ is propyl. In some embodiments, $R_3$ is $OR_b$. In some embodiments, $R_3$ is —$OCH_3$. In some embodiments, $R_3$ is —$OCH_2CH_3$. In some embodiments, $R_3$ is —$OCH_2CH_2CH_3$. In certain embodiments, $R_3$ is —$OCH(F)_2$. In certain embodiments, $R_3$ is selected from those functional groups depicted in the examples below.

As defined above and described herein, L is absent, —$NR_d$—, —O—, —$C(=O)NR_d$—, or —$S(O)_p$—; in some embodiments, L is absent. In some embodiments, L is —$NR_d$—, $R_d$ is H or $C_{1-3}$alkyl. In some embodiments, L is —O—. In some embodiments, L is —$C(=O)NH$—. In some embodiments, L is —$S(O)_2$—. In some embodiments, L is —S—. In certain embodiments, L is selected from those functional groups depicted in the examples below.

As defined above and described herein, each $R_4$ is

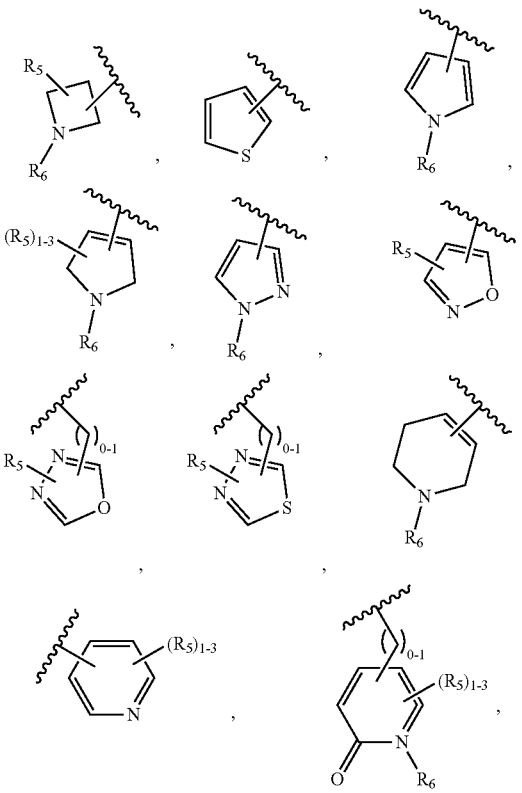

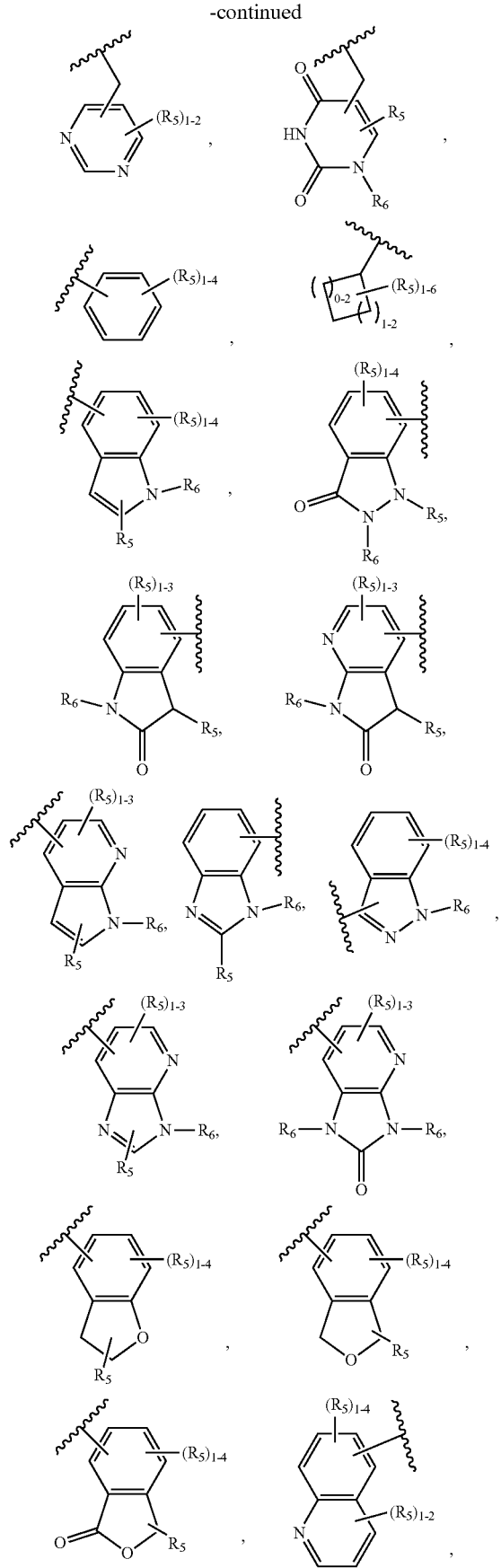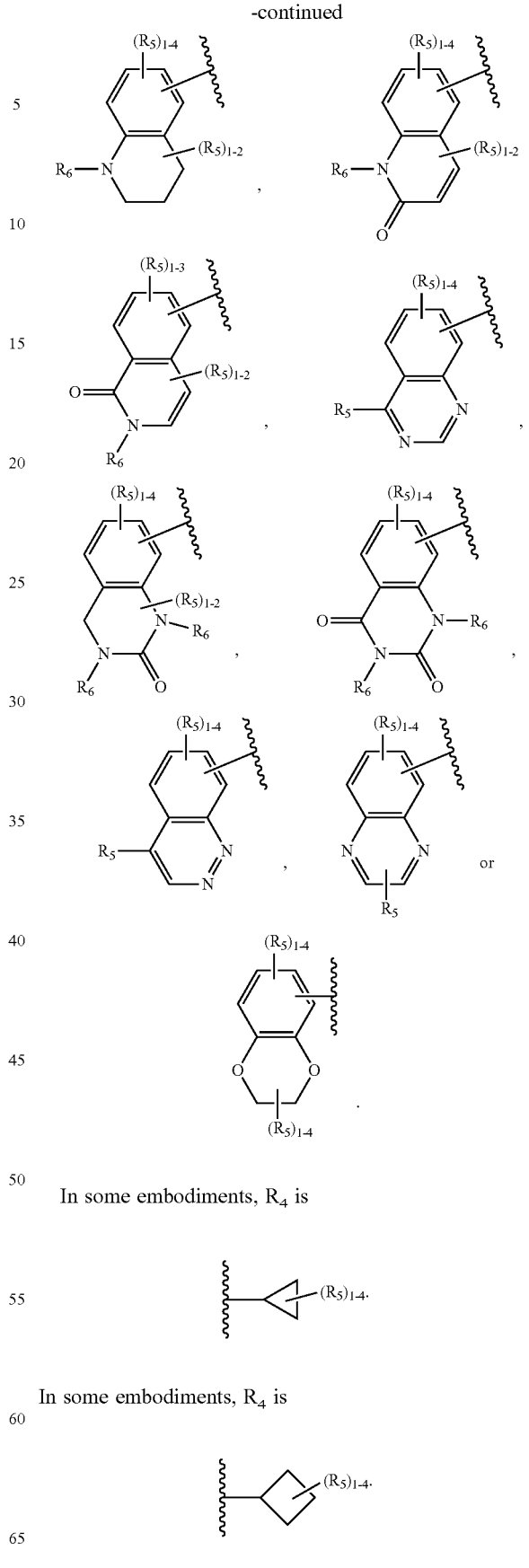
In some embodiments, $R_4$ is
In some embodiments, $R_4$ is In some embodiments, $R_4$ is
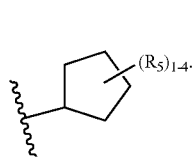
In some embodiments, $R_4$ is
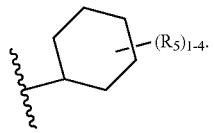
In some embodiments, $R_4$ is
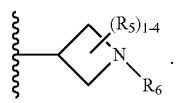
In some embodiments, $R_4$ is
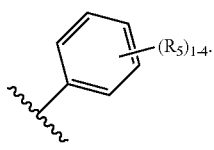
In some embodiments, $R_4$ is
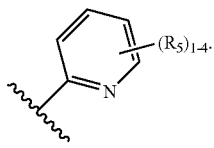
In some embodiments, $R_4$ is
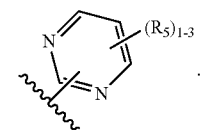
In some embodiments, $R_4$ is
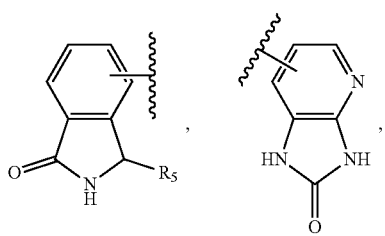
-continued
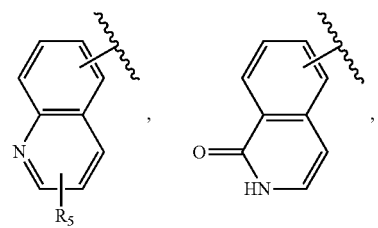
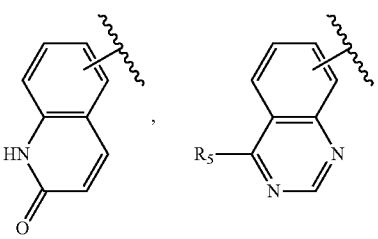
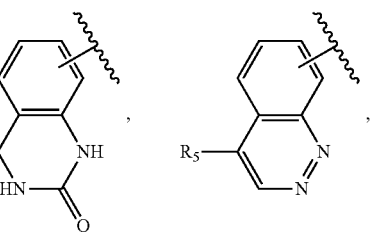
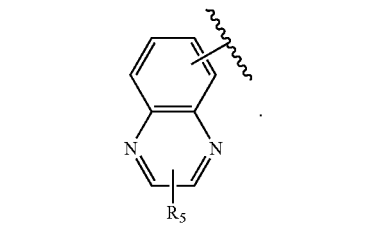
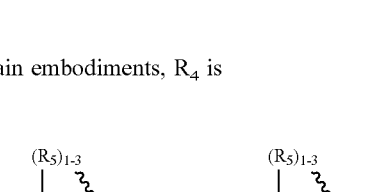
In certain embodiments, $R_4$ is
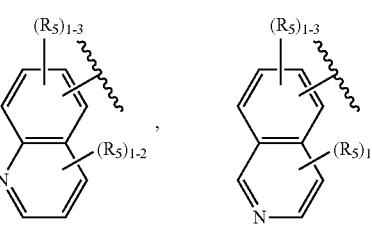
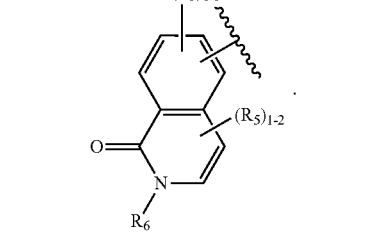

In certain embodiments, R$_4$ is

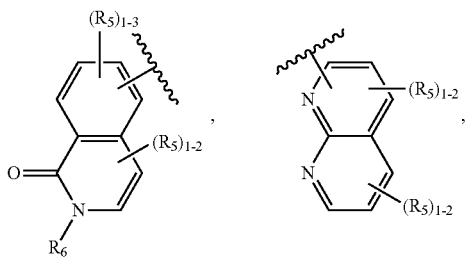

,

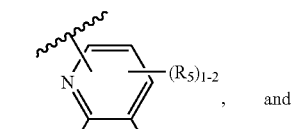

, and

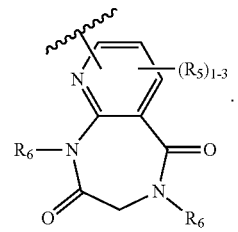

In certain embodiments, R$_4$ is

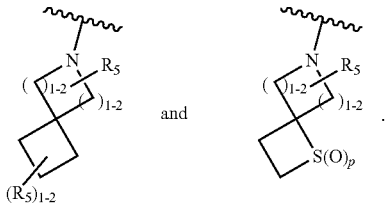

In certain embodiments, R$_4$ is

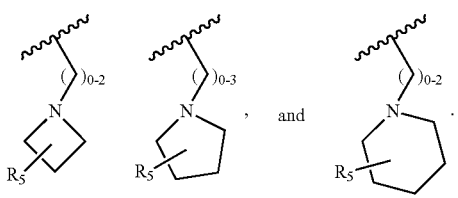

.

In certain embodiments, R$_4$ is

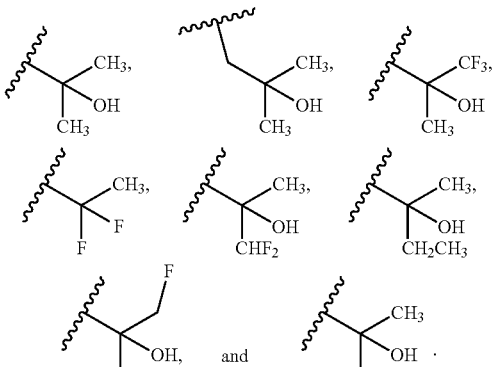

and

In certain embodiments, R$_4$ is C$_{1-5}$ alkyl substituted with 1-4 F, Cl, Br, OH, and C$_{3-6}$ cycloalkyl.

In certain embodiments, R$_4$ is R$_4$ is selected from

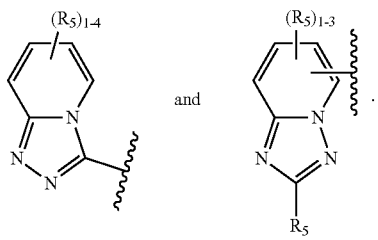

As defined above and described herein, R$_5$ is H, F, Cl, Br, CN, C$_{1-4}$alkyl substituted with 0-5 R$_e$, C$_{2-4}$alkenyl, C$_{2-4}$alkynyl, nitro, —S(O)$_p$R$_c$, —S(O)$_p$NR$_a$R$_a$, —NR$_a$S(O)$_p$R$_c$, —(CH$_2$)$_r$OR$_b$, —(CH$_2$)$_r$NR$_a$R$_a$, —NR$_a$C(=O)R$_b$, NR$_a$C(=O)OR$_b$—NR$_a$C(=O)NR$_a$R$_a$, —C(=O)R$_b$, —C(=O)OR$_b$, C(=O)NR$_a$R$_a$, —OC(=O)R$_b$, C$_{3-6}$cycloalkyl substituted with 0-4 R$_e$, aryl substituted with 0-4 R$_e$, and heterocyclyl substituted with 0-4 R$_e$.

In some embodiments, R$_5$ is H, F, Cl, CN, C$_{1-4}$alkyl, C$_{1-4}$alkyl (substituted with OH, NH$_2$, and COOH), SC$_{1-4}$alkyl, S(O)$_2$C$_{1-4}$alkyl, S(O)$_2$NH-cyclopropyl, —(CH$_2$)$_{0-1}$NHS(O)$_2$C$_{1-4}$alkyl, N(R$_d$)S(O)$_2$C$_{2-4}$alkenyl, —(CH$_2$)$_{0-1}$H, OC$_{1-4}$alkyl, —(CH$_2$)$_{0-1}$NH$_2$, —(CH$_2$)$_{0-1}$NHC(=O)C$_{1-4}$alkyl, —NR$_d$C(=O)C$_{2-4}$alkenyl, —NHC(=O)C$_{2-4}$alkynyl, —(CH$_2$)$_{0-1}$C(=O)OH, —C(=O)OC$_{1-4}$alkyl, —NHC(=O)OC$_{1-4}$alkyl, —NHC(=O)O(CH$_2$)$_2$OC$_{1-4}$alkyl, —NHC(=O)OCH$_2$-cyclopropyl, —NHC(=O)NH$_2$, C(=O)NHC$_{1-4}$alkyl, CONH(CH$_2$)$_{1-2}$C(=O)OH, —(CH$_2$)$_{0-1}$C(=O)NH$_2$, —(CH$_2$)$_{0-1}$C(=O)NHC$_{1-4}$alkyl, C(=O)NH-pyridine, —C(=O)NH(CH$_2$)$_2$N(C$_{1-4}$alkyl)$_2$, —C(=O)NH(CH$_2$)$_2$OH, —C(=O)NH(CH$_2$)$_2$S(O)$_2$C$_{1-4}$alkyl, and —OC(=O)C$_{1-4}$alkyl.

In some embodiments, R$_5$ is

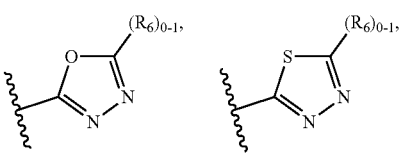

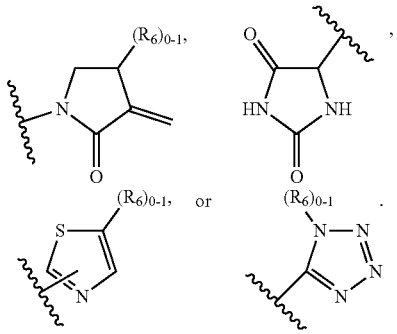

In some embodiments, $R_5$ is

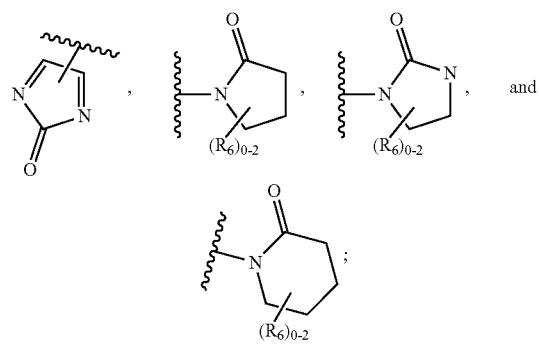

In some embodiments, $R_5$ is F. In some embodiments, $R_5$ is $C_{1-4}$alkyl. In some embodiments, $R_5$ is —OH or —O$C_{1-3}$alkyl. In some embodiments, $R_5$ is —NHS(O)$_2$ $C_{2-4}$alkenyl. In certain embodiments, $R_5$ is selected from those functional groups depicted in the examples below.

As defined above and described herein, $R_6$ is H, $C_{1-3}$alkyl substituted with 0-4 $R_e$, —S(O)$_p$$R_c$, —C(=O)$R_b$, —(CH$_2$)$_r$C(=O)NR$_a$R$_a$, —C(=O)(CH$_2$)$_r$NR$_a$C(=O)$R_b$, —C(=O)O$R_b$, —S(O)$_p$NR$_a$R$_a$, aryl substituted with 0-4 $R_e$, or heterocyclyl substituted with 0-4 $R_e$.

In some embodiments, $R_6$ is H. In some embodiments, $R_6$ is methyl or isopropyl. In some embodiments, $R_6$ is —(CH$_2$)$_2$C(=O)NH$_2$. In some embodiments, $R_6$ is —(CH$_2$)$_2$OH. In some embodiments, $R_6$ is C(=O)$C_{1-4}$alkyl. In certain embodiments, $R_6$ is selected from those functional groups depicted in the examples below.

As defined above and described herein, $R_7$ is H, F, Cl, $C_{1-3}$alkyl, —NR$_a$R$_a$, or —NR$_a$C(=O)O$R_b$. In some embodiments, $R_7$ is NH$_2$. In some embodiments, $R_7$ is F.

As defined above and described herein, $R_8$ is H, F, Cl, Br, or $C_{1-4}$alkyl substituted with 0-5 $R_c$. In some embodiments, $R_8$ is H. In some embodiments, $R_8$ is $C_{1-3}$alkyl.

As defined above, Ring A is

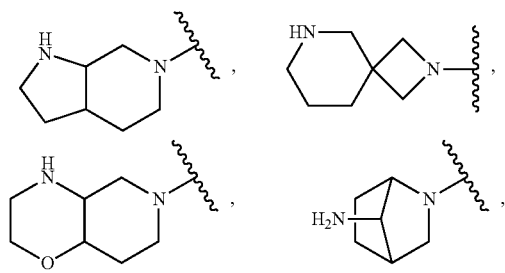

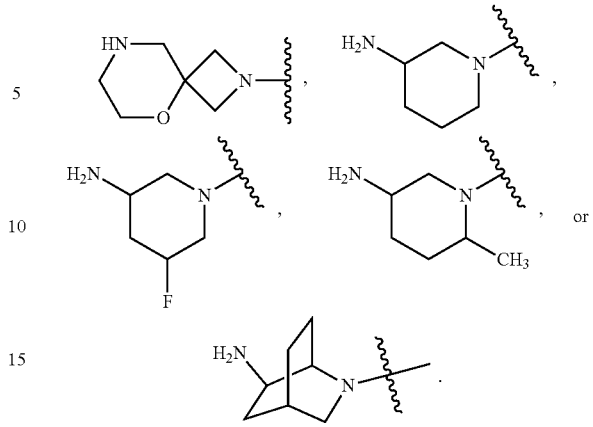

In some embodiments, Ring A is

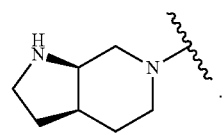 [SMILES: *N1CC[C@H]2CCN[C@H]2C1]

In some embodiments, Ring A is

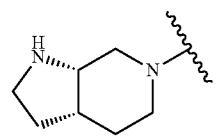

In some embodiments, Ring A is

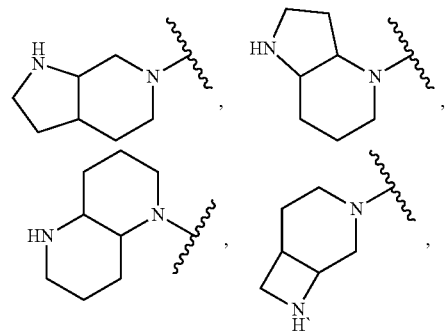

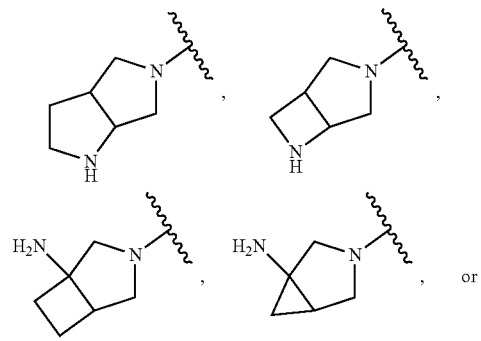

-continued
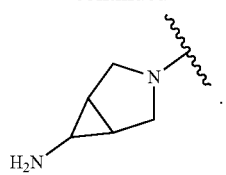
In some embodiments, Ring A is
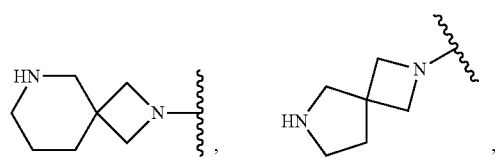
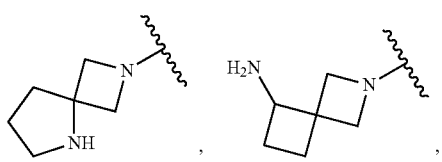
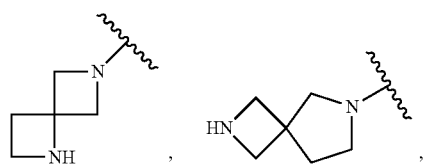
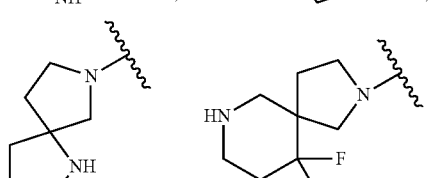
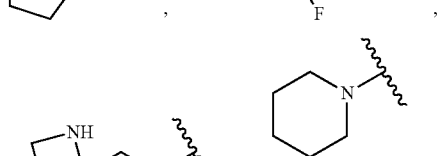
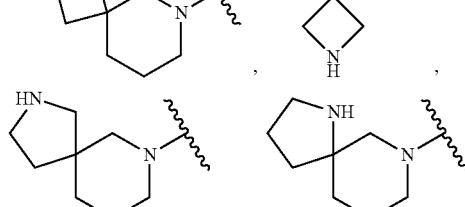
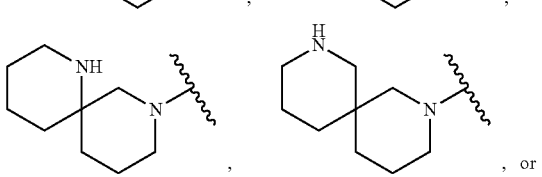, or
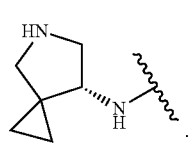.
In some embodiments, Ring A is
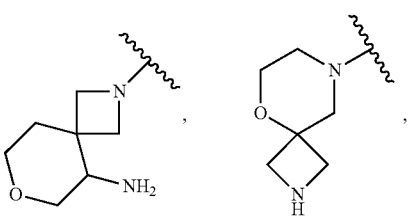
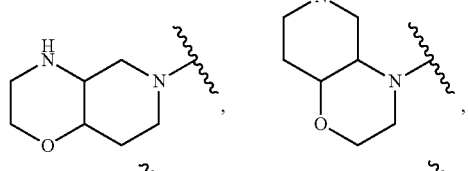
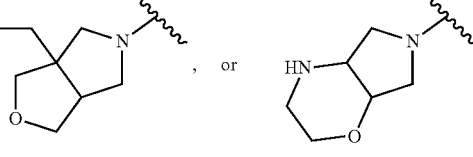, or
In some embodiments, Ring A is
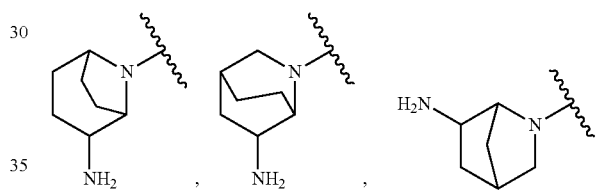
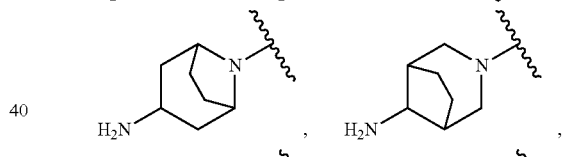
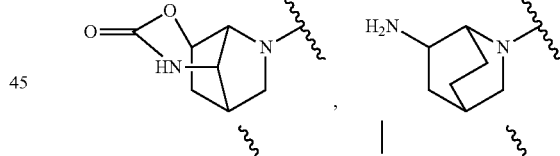
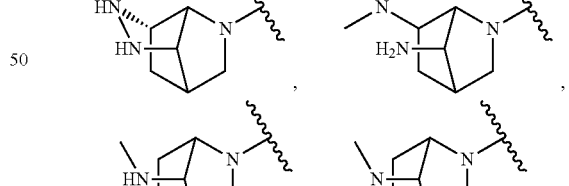
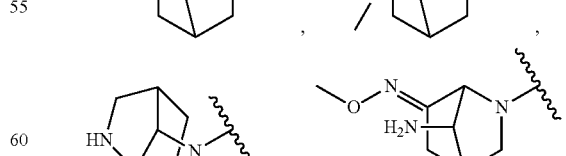
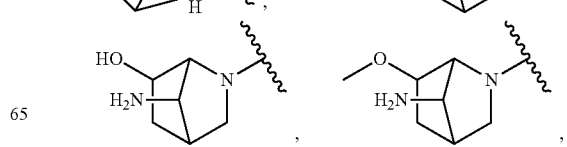

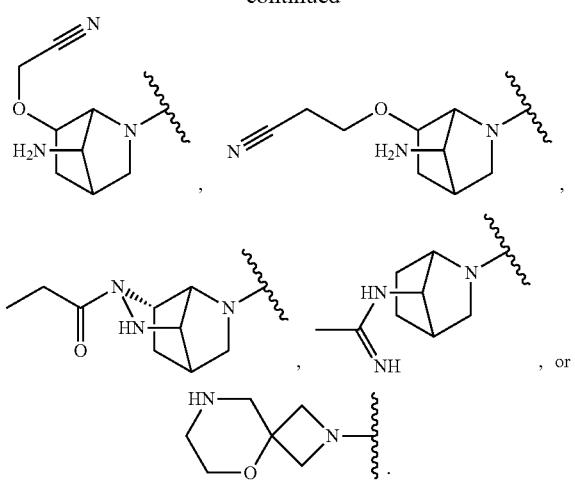
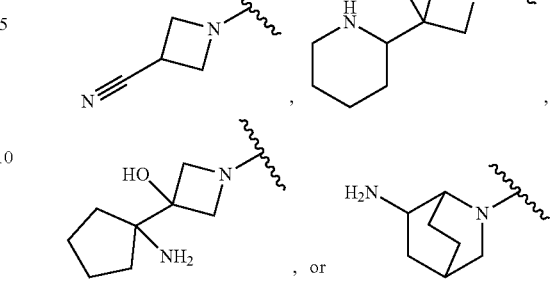
In some embodiments, Ring A is
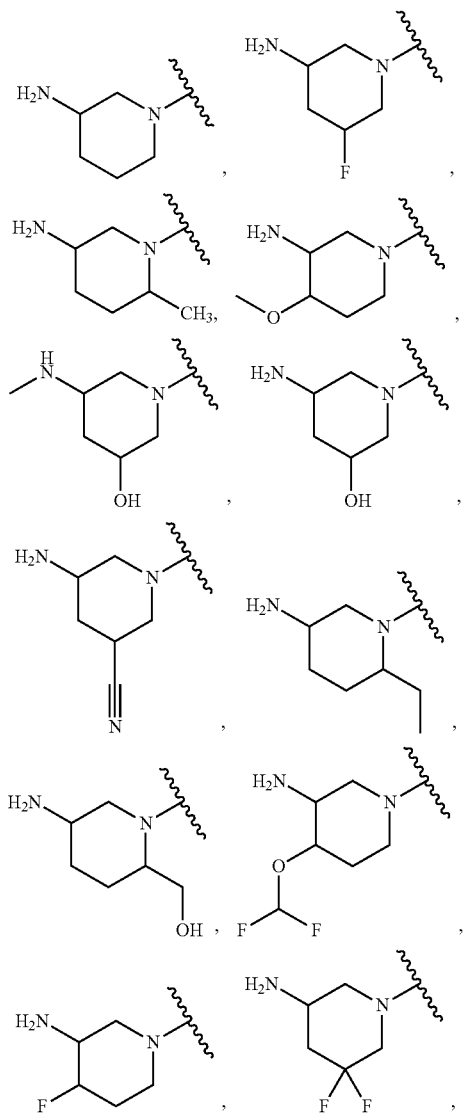
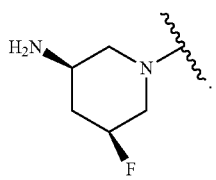 [SMILES: *N1C[C@H](N)C[C@H](F)C1]
In some embodiments, Ring A is
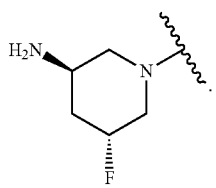 [SMILES: *N1C[C@H](N)C[C@@H](F)C1]
In some embodiments, Ring A is
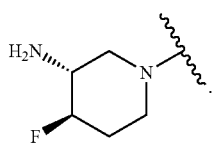 [SMILES: *N1CC[C@@H](F)[C@H](N)C1]
In some embodiments, Ring A is
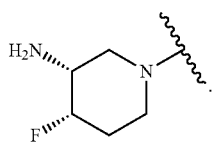
In some embodiments, Ring A is
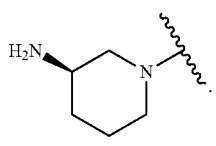 [SMILES: *N1CCC[C@@H](N)C1]

In some embodiments, Ring A is
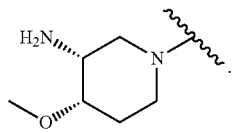
In some embodiments, Ring A is
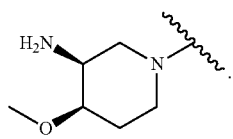 [SMILES: *N1CC[C@@H](OC)[C@@H](N)C1]
In some embodiments, Ring A is
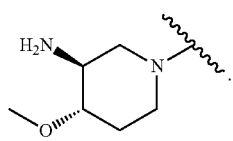 [SMILES: *N1CC[C@H](OC)[C@@H](N)C1]
In some embodiments, Ring A is
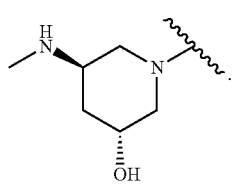 [SMILES: *N1C[C@H](O)C[C@@H](NC)C1]
In some embodiments, Ring A is
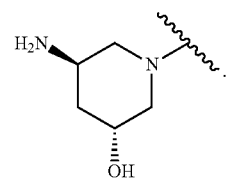
In some embodiments, Ring A is
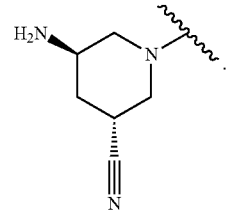 [SMILES: *N1C[C@H](N)C[C@@H](C#N)C1]
In some embodiments, Ring A is
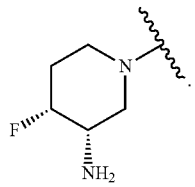
In some embodiments, Ring A is
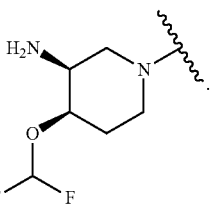
In some embodiments, Ring A is
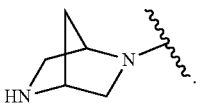
In some embodiments, Ring A is
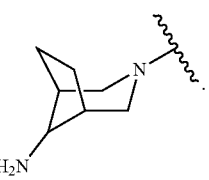
In some embodiments, Ring A is
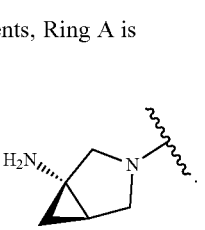
In some embodiments, Ring A is
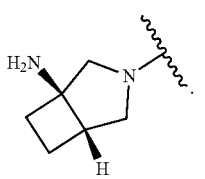 [SMILES: *N1C[C@@H]2CC[C@]2(N)C1]

In some embodiments, Ring A is

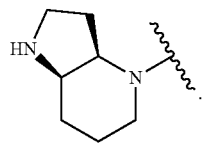

In some embodiments, Ring A is

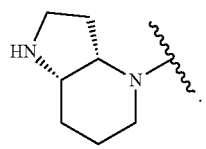

In some embodiments, Ring A is

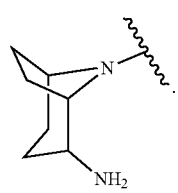

In some embodiments, Ring A is

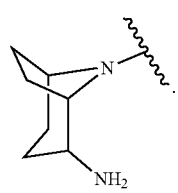

In some embodiments, Ring A is

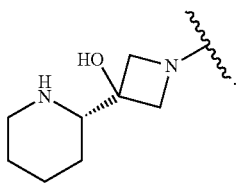 [SMILES: *N1CC(O)([C@@H]2CCCCN2)C1]

In some embodiments, Ring A is

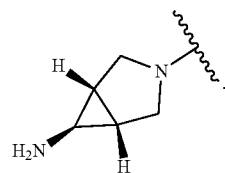 [SMILES: *N1C[C@@H]2[C@@H](N)[C@@H]2C1]

In some embodiments, Ring A is

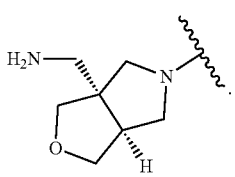

In some embodiments, Ring A is

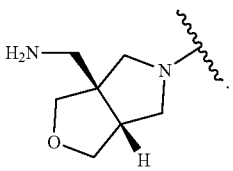 [SMILES: *N1C[C@@H]2COC[C@]2(CN)C1]

In some embodiments, Ring A is

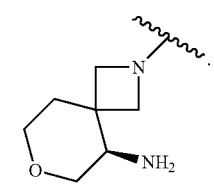 [SMILES: *N1CC2(CCOC[C@@H]2N)C1]

In some embodiments, Ring A is

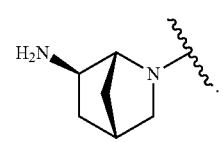 [SMILES: *N1C[C@@H]2C[C@@H](N)[C@H]1C2]

In some embodiments, Ring A is

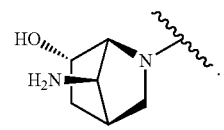

In some embodiments, Ring A is

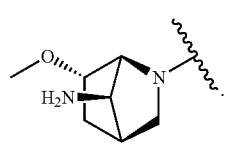 [SMILES: *N1C[C@H]2C[C@H](OC)[C@@H]1[C@@H]2N]

In some embodiments, Ring A is

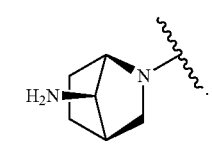

In some embodiments, Ring A is

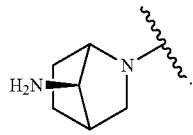

In some embodiments, Ring A is

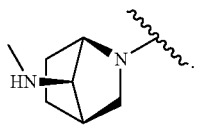 [SMILES: *N1C[C@H]2CC[C@@H]1[C@@H]2NC]

In some embodiments, Ring A is

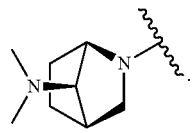 [SMILES: *N1C[C@H]2CC[C@@H]1[C@@H]2N(C)C]

In some embodiments, Ring A is

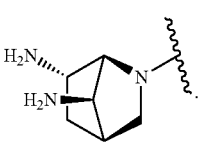 [SMILES: *N1C[C@H]2C[C@H](N)[C@@H]1[C@@H]2N]

In some embodiments, Ring A is

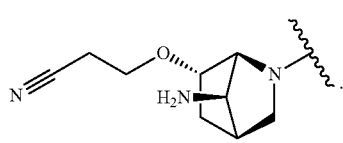 [SMILES: *N1C[C@H]2C[C@H](OCCC#N)[C@@H]1[C@@H]2N]

In some embodiments, Ring A is

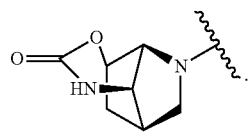 [SMILES: *N1C[C@H]2CC3OC(=O)N[C@H]2[C@@H]31]

In some embodiments, Ring A is

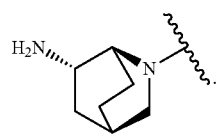

In some embodiments, Ring A is

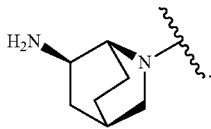

In some embodiments, Ring A is

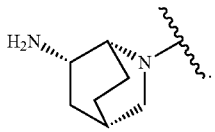

In some embodiments, Ring A is

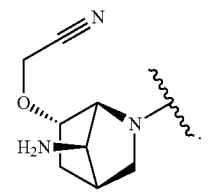 [SMILES: *N1C[C@H]2C[C@H](OCC#N)[C@@H]1[C@@H]2N]

In some embodiments, Ring A is

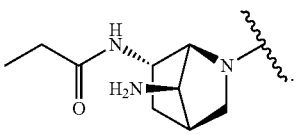 [SMILES: *N1C[C@H]2C[C@H](NC(=O)CC)[C@@H]1[C@@H]2N]

In some embodiments, Ring A is

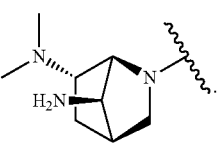 [SMILES: *N1C[C@H]2C[C@H](N(C)C)[C@@H]1[C@@H]2N]

In some embodiments, Ring A is

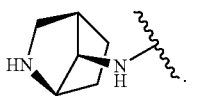

In some embodiments, Ring A is

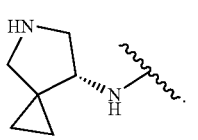

In some embodiments, Ring A is
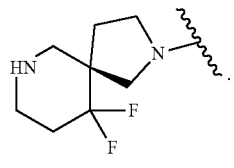 [SMILES: *N1CC[C@]2(CNCCC2(F)F)C1]
In some embodiments, Ring A is
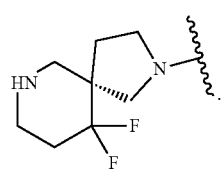
In some embodiments, Ring A is
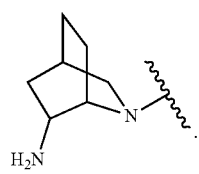
In some embodiments, Ring A is
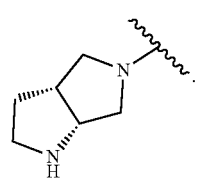 [SMILES: *N1C[C@H]2CCN[C@H]2C1]
In some embodiments, Ring A is
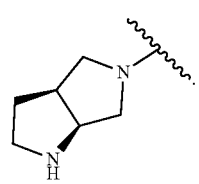 [SMILES: *N1C[C@@H]2CCN[C@@H]2C1]
In some embodiments, Ring A is
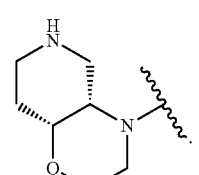
In some embodiments, Ring A is
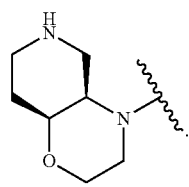 [SMILES: *N1CCO[C@H]2CCNC[C@H]21]
In some embodiments, Ring A is
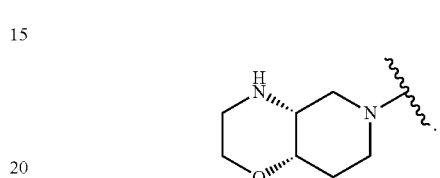
In some embodiments, Ring A is
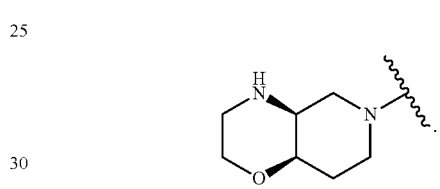
In some embodiments, Ring A is
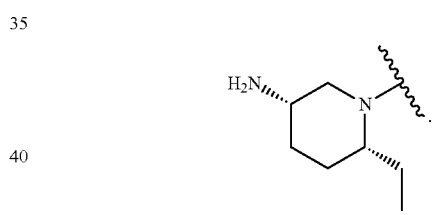
In some embodiments, Ring A is
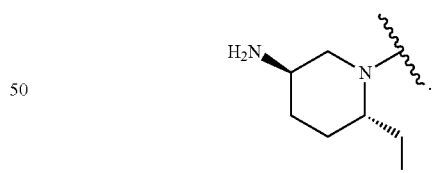
In some embodiments, Ring A is
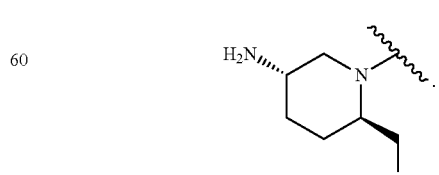

In some embodiments, Ring A is

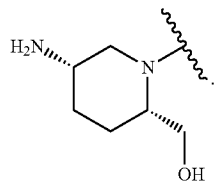

In some embodiments, Ring A is

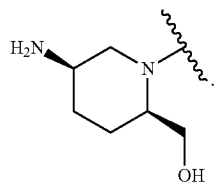

In some embodiments, Ring A is

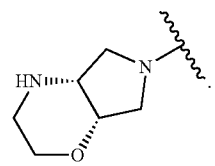

In some embodiments, Ring A is

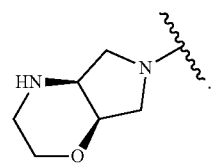 [SMILES: *N1C[C@@H]2NCCO[C@@H]2C1]

In certain embodiments, $R_4$ is selected from those functional groups depicted in the examples below.

As defined above and described herein, r is 0-4. In some embodiments, r is 0. In some embodiments, r is 1. In some embodiments, r is 2. In some embodiments, r is 3. In some embodiments, r is 4. In some embodiments, Ring A is

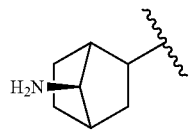 or 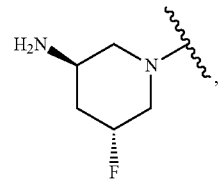

$R_1$ is $CH_3$, $R_2$ is cyclopropylmethyl, Q is N or CH, $R_3$ is H, F, or —$OCH_3$, $R_4$ is

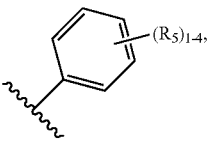

and $R_5$ is H, F, Cl, CN, $C_{1-4}$alkyl, $C_{1-4}$alkyl substituted with OH, $NH_2$, and COOH, $SC_{1-4}$alkyl, $S(O)_2C_{1-4}$alkyl, $S(O)_2NH$-cyclopropyl, —$(CH_2)_{0-1}NHS(O)_2C_{1-4}$alkyl, $N(R_d)S(O)_2C_{2-4}$alkenyl, —$(CH_2)_{0-1}OH$, $OC_{1-4}$alkyl, —$(CH_2)_{0-1}NH_2$, —$(CH_2)_{0-1}NHC(=O)C_{1-4}$alkyl, —$NR_dC(=O)C_{2-4}$alkenyl, —$NHC(=O)C_{2-4}$alkynyl, —$(CH_2)_{0-1}C(=O)OH$, —$C(=O)OC_{1-4}$alkyl, —$NHC(=O)OC_{1-4}$alkyl, —$NHC(=O)O(CH_2)_2OC_{1-4}$alkyl, —$NHC(=O)OCH_2$-cyclopropyl, —$NHC(=O)NH_2$, $C(=O)NHC_{1-4}$alkyl, CONH$(CH_2)_{1-2}C(=O)OH$, —$(CH_2)_{0-1}C(=O)NH_2$, —$(CH_2)_{0-1}C(=O)NHC_{1-4}$alkyl, $C(=O)NH$-pyridine, —$C(=O)NH(CH_2)_2N(C_{1-4}$alkyl$)_2$, —$C(=O)NH(CH_2)_2OH$, —$C(=O)NH(CH_2)_2S(O)_2C_{1-4}$alkyl, and —$OC(=O)C_{1-4}$alkyl,

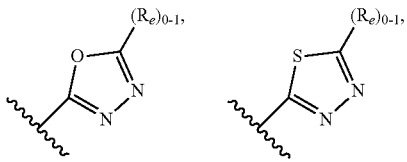

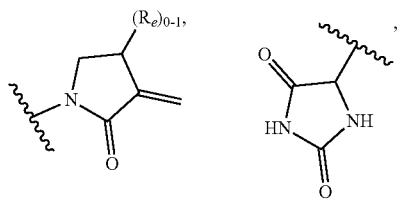

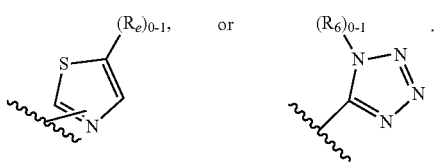

In some embodiments, Ring A is

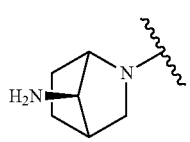 or 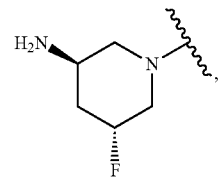

R₁ is CH₃, R₂ is cyclopropylmethyl, Q is N or CH, R₃ is H, F, or —OCH₃, R₅ is

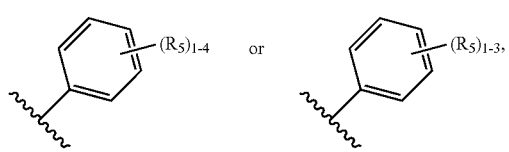 or and R₅ is H, F, Cl, CN, $C_{1-4}$alkyl, $C_{1-4}$alkyl substituted with OH, NH₂, and COOH, $SC_{1-4}$alkyl, $S(O)_2C_{1-4}$alkyl, $S(O)_2$NH-cyclopropyl, —$(CH_2)_{0-1}NHS(O)_2C_{1-4}$alkyl, $N(R_d)S(O)_2C_{2-4}$alkenyl, —$(CH_2)_{0-1}$OH, $OC_{1-4}$alkyl, —$(CH_2)_{0-1}NH_2$, —$(CH_2)_{0-1}NHC(=O)C_{1-4}$alkyl, —$NR_dC(=O)C_{2-4}$alkenyl, —$NHC(=O)C_{2-4}$alkynyl, —$(CH_2)_{0-1}C(=O)OH$, —$C(=O)OC_{1-4}$alkyl, —$NHC(=O)OC_{1-4}$alkyl, —$NHC(=O)O(CH_2)_2OC_{1-4}$alkyl, —$NHC(=O)OCH_2$-cyclopropyl, —$NHC(=O)NH_2$, $C(=O)NHC_{1-4}$alkyl, $CONH(CH_2)_{1-2}C(=O)OH$, —$(CH_2)_{0-1}C(=O)NH_2$, —$(CH_2)_{0-1}C(=O)NHC_{1-4}$alkyl, $C(=O)NH$-pyridine, —$C(=O)NH(CH_2)_2N(C_{1-4}$alkyl$)_2$, —$C(=O)NH(CH_2)_2OH$, —$C(=O)NH(CH_2)_2S(O)_2C_{1-4}$alkyl, and —$OC(=O)C_{1-4}$alkyl,

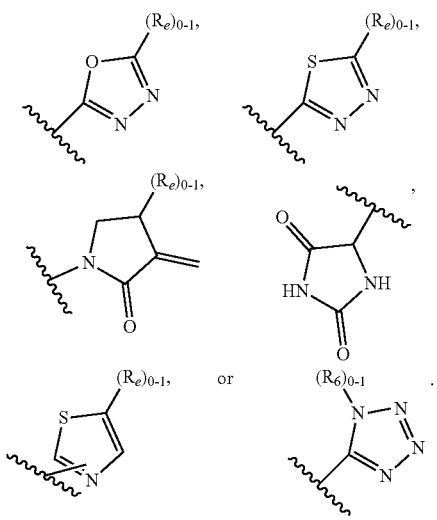

In some embodiments, Ring A is

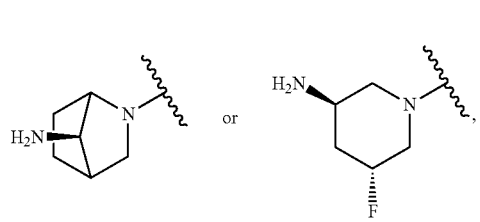 [SMILES: *N1CC2CCC1[C@@H]2N ; *N1C[C@H](N)C[C@@H](F)C1]

R₁ is CH₃, R2 is cyclopropylmethyl, Q is N or CH, R3 is H, F, or —OCH3, R4 is

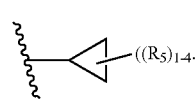

In some embodiments, Ring A is

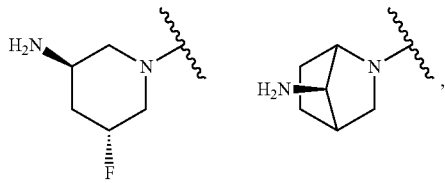 [SMILES: *N1C[C@H](N)C[C@@H](F)C1 ; *N1CC2CCC1[C@@H]2N]

R₁ is CH₃, R₂ is cyclopropylmethyl, Q is N or CH, R₃ is H, F, or —OCH₃, R₄ is

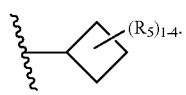

In some embodiments, Ring A is

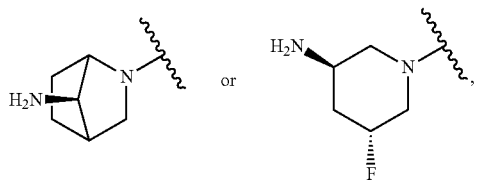 [SMILES: *N1CC2CCC1[C@@H]2N ; *N1C[C@H](N)C[C@@H](F)C1]

R₁ is CH₃, R₂ is cyclopropylmethyl, Q is N or CH, R₃ is H, F, or —OCH₃, R₄ is

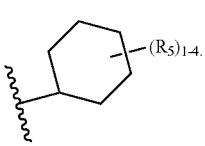

In some embodiments, Ring A is

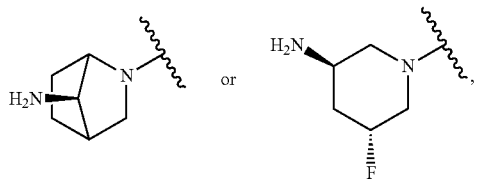 [SMILES: *N1CC2CCC1[C@@H]2N ; *N1C[C@H](N)C[C@@H](F)C1]

R₁ is CH₃, R₂ is cyclopropylmethyl, Q is N or CH, R₃ is H, F, or —OCH₃, R₄ is

In some embodiments, Ring A is or
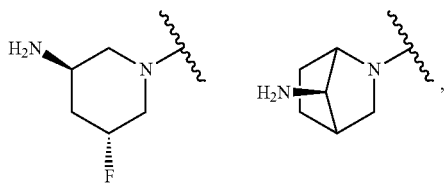
$R_1$ is $CH_3$, $R_2$ is cyclopropylmethyl, Q is N or CH, $R_3$ is H, F, or —$OCH_3$, $R_4$ is
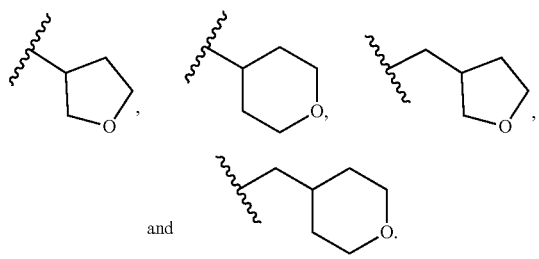
In some embodiments, Ring A is
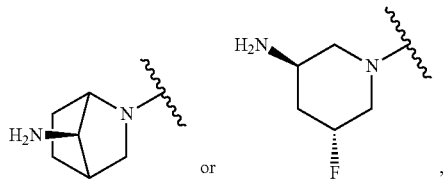 [SMILES: *N1CC2CCC1[C@@H]2N ; *N1C[C@H](N)C[C@@H](F)C1]
$R_1$ is $CH_3$, $R_2$ is cyclopropylmethyl, Q is N or CH, $R_3$ is H, F, or —$OCH_3$, $R_4$ is
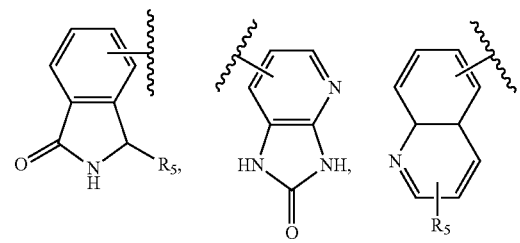
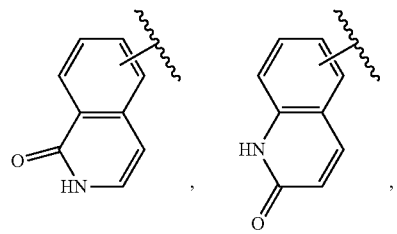
-continued
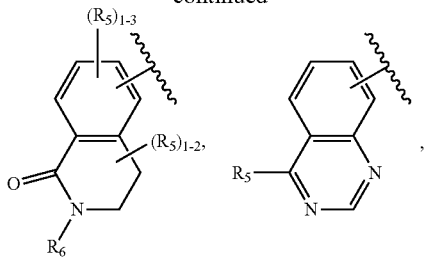
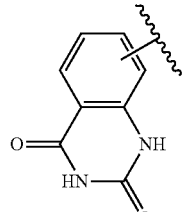
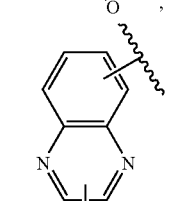, or
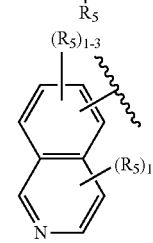
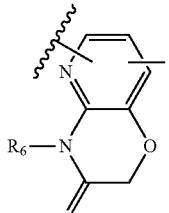
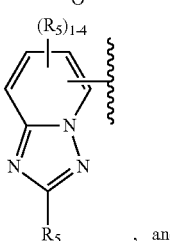
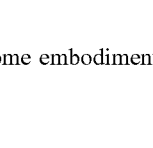, and
In some embodiments, Ring A is
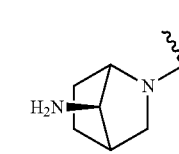

$R_1$ is $CH_3$, $R_2$ is cyclopropylmethyl, Q is N or CH, $R_3$ is H, F, or —$OCH_3$, $R_4$ is

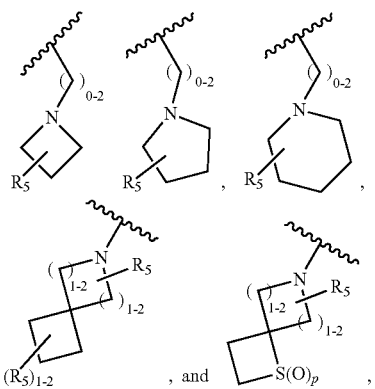

and $R_5$ is H, F, $C_{1-4}$alkyl, —OH, —$OC_{1-3}$alkyl and —NHS$(O)_2C_{2-4}$alkenyl.

In some embodiments, the compound of formula (I) is selected from examples depicted below. In certain embodiments, the present invention provides any compound described above and herein, or a pharmaceutically acceptable salt thereof or a composition for use in therapy. In some embodiments, the present invention provides any compound described above and herein in isolated form. In some embodiments, the present invention provides the compounds according to any one of claims 1 to 16

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit PAD4, in a biological sample or in a patient. In certain embodiments, the amount of compound in compositions of this invention is such that is effective to measurably inhibit PAD4, in a biological sample or in a patient. In certain embodiments, a composition of this invention is formulated for administration to a patient in need of such composition. In some embodiments, a composition of this invention is formulated for oral administration to a patient.

The term "subject," as used herein, is used interchangeably with the term "patient" and means an animal, preferably a mammal. In some embodiments, a subject or patient is a human. In other embodiments, a subject (or patient) is a veterinary subject (or patient). In some embodiments, a veterinary subject (or patient) is a canine, a feline, or an equine subject.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, Prograf); cytotoxic drugs such as azathiprine and cyclophosphamide; TNF-α inhibitors such as tenidap, anti-TNF antibodies or soluble TNF receptor, and rapamycin (sirolimus or Rapamune) or derivatives thereof. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

5. Uses of Compounds and Pharmaceutically Acceptable Compositions

Compounds and compositions described herein are generally useful for the inhibition of PAD4.

The activity of a compound utilized in this invention as an inhibitor of PAD4, may be assayed in vitro, in vivo or in a cell line. In vitro assays include assays that determine the inhibition of PAD4. Detailed conditions for assaying a compound utilized in this invention as an inhibitor of PAD4 are set forth in the Examples below. In some embodiments, a provided compound inhibits PAD4 selectively as compared to PAD2.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of PAD4 and are therefore useful for treating one or more disorders associated with activity of PAD4. Thus, in certain embodiments, the present invention provides a method for treating a PAD4-mediated disorder comprising the step of administering to a patient in need thereof a compound of the present invention, or pharmaceutically acceptable composition thereof.

In one embodiment, a PAD4-mediated disorder is a disease, condition, or disorder mediated by inappropriate PAD4 activity. In some embodiments, a PAD4-mediated disorder is selected from the group consisting of rheumatoid arthritis, vasculitis, systemic lupus erythematosus, ulcerative colitis, cancer, cystic fibrosis, asthma, cutaneous lupus erythematosus, and psoriasis. In a further embodiment, the disorder mediated by inappropriate PAD4 activity is rheumatoid arthritis. In a further embodiment, the disorder mediated by inappropriate PAD4 activity is systemic lupus. In a further embodiment, the disorder mediated by inappropriate PAD4 activity is vasculitis. In a further embodiment, the disorder mediated by inappropriate PAD4 activity is cutaneous lupus erythematosus. In a further embodiment, the disorder mediated by inappropriate PAD4 activity is psoriasis.

In one embodiment there is provided a method of treatment of rheumatoid arthritis, vasculitis, systemic lupus erythematosus, ulcerative colitis, cancer, cystic fibrosis, asthma, cutaneous lupus erythematosus, or psoriasis, which method comprises administering to a human subject in need thereof, a therapeutically effective amount of a provided compound or a pharmaceutically acceptable salt thereof.

In one embodiment there is provided a method of treatment of rheumatoid arthritis, which method comprises administering to a human subject in need thereof, a therapeutically effective amount of a provided compound, or a pharmaceutically acceptable salt thereof. In one embodiment there is provided a method of treatment of systemic lupus, which method comprises administering to a human subject in need thereof, a therapeutically effective amount of a provided compound, or a pharmaceutically acceptable salt thereof. In one embodiment there is provided a method of treatment of vasculitis, which method comprises administering to a human subject in need thereof, a therapeutically effective amount of a provided compound, or a pharmaceutically acceptable salt thereof. In one embodiment there is provided a method of treatment of cutaneous lupus erythematosus, which method comprises administering to a human subject in need thereof, a therapeutically effective amount of a provided compound, or a pharmaceutically acceptable salt thereof. In one embodiment there is provided a method of treatment of psoriasis, which method comprises administering to a human subject in need thereof, a therapeutically effective amount of a provided compound, or a pharmaceutically acceptable salt thereof.

In some embodiments, a PAD4-mediated disorder is selected from the group consisting of acid-induced lung injury, acne (PAPA), acute lymphocytic leukemia, acute, respiratory distress syndrome, Addison's disease, adrenal hyperplasia, adrenocortical insufficiency, ageing, AIDS, alcoholic hepatitis, alcoholic hepatitis, alcoholic liver disease, allergen induced asthma, allergic bronchopulmonary, aspergillosis, allergic conjunctivitis, alopecia, Alzheimer's disease, amyloidosis, amyotropic lateral sclerosis, and weight loss, angina pectoris, angioedema, anhidrotic ecodermal dysplasia-ID, ankylosing spondylitis, anterior segment, inflammation, antiphospholipid syndrome, aphthous stomatitis, appendicitis, arthritis, asthma, atherosclerosis, atopic dermatitis, autoimmune diseases, autoimmune hepatitis, bee sting-induced inflammation, Bechet's disease, Bechet's syndrome, Bells Palsey, berylliosis, Blau syndrome, bone pain, bronchiolitis, burns, bursitis, cancer, cardiac hypertrophy, carpal tunnel syndrome, catabolic disorders, cataracts, cerebral aneurysm, chemical irritant-induced inflammation, chorioretinitis, chronic heart failure, chronic lung disease of prematurity, chronic lymphocytic leukemia, chronic obstructive pulmonary disease, colitis, complex regional pain syndrome, connective tissue disease, corneal ulcer, crohn's disease, cryopyrin-associated periodic syndromes, cyrptococcosis, cystic fibrosis, deficiency of the interleukin-1-receptor antagonist (DIRA), dermatitis, dermatitis endotoxemia, dermatomyositis, diffuse intrinsic pontine glioma, endometriosis, endotoxemia, epicondylitis, erythroblastopenia, familial amyloidotic polyneuropathy, familial cold urticarial, familial Mediterranean fever, fetal growth retardation, glaucoma, glomerular disease, glomerular nephritis, gout, gouty arthritis, graft-versus-host disease, gut diseases, head injury, headache, hearing loss, heart disease, hemolytic anemia, Henoch-Scholein purpura, hepatitis, hereditary periodic fever syndrome, herpes zoster and simplex, HIV-1, Hodgkin's disease, Huntington's disease, hyaline membrane disease, hyperammonemia, hypercalcemia, hypercholesterolemia, hyperimmunoglobulinemia D with recurrent fever (HIDS), hypoplastic and other anemias, hypoplastic anemia, idiopathic thrombocytopenic purpura, incontinentia pigmenti, infectious mononucleosis, inflammatory bowel disease, inflammatory lung disease, inflammatory neuropathy, inflammatory pain, insect bite-induced inflammation, iritis, irritant-induced inflammation, ischemia/reperfusion, juvenile rheumatoid arthritis, keratitis, kidney disease, kidney injury caused by parasitic infections, kidney injury caused by parasitic infections, kidney transplant rejection prophylaxis, leptospiriosis, leukemia, Loeffler's syndrome, lung injury, lung injury, lupus, lupus, lupus nephritis, lymphoma, meningitis, mesothelioma, mixed connective tissue disease, Muckle-Wells syndrome (urticaria deafness amyloidosis), multiple sclerosis, muscle wasting, muscular dystrophy, myasthenia gravis, myocarditis, mycosis fungiodes, mycosis fungoides, myelodysplastic syndrome, myositis, nasal sinusitis, necrotizing enterocolitis, neonatal onset multisystem inflammatory disease (NOMID), nephrotic syndrome, neuritis, neuropathological diseases, non-allergen induced asthma, obesity, ocular allergy, optic neuritis, organ transplant, osteoarthritis, otitis media, Paget's disease, pain, pancreatitis, Parkinson's disease, pemphigus, pericarditis, periodic fever, periodontitis, peritoneal endometriosis, pertussis, pharyngitis and adenitis (PFAPA syndrome), plant irritant-induced inflammation, pneumonia, pneumonitis, pneumosysts infection, poison ivy/urushiol oil-induced inflammation, polyarteritis nodosa, polychondritis, polycystic kidney disease, polymyositis, psoriasis, psoriasis, psoriasis, psoriasis, psychosocial stress diseases, pulmonary disease, pulmonary hypertension, pulmonayr fibrosis, pyoderma gangrenosum, pyogenic sterile arthritis, renal disease, retinal disease, rheumatic carditis, rheumatic disease, rheumatoid arthritis, sarcoidosis, seborrhea, sepsis, severe pain, sickle cell, sickle cell anemia, silica-induced disease, Sjogren's syndrome, skin diseases, sleep apnea, solid tumors, spinal cord injury, Stevens-Johnson syndrome, stroke, subarachnoid hemorrhage, sunburn, temporal arteritis, tenosynovitis, thrombocytopenia, thyroiditis, tissue transplant, TNF receptor associated periodic syndrome (TRAPS), toxoplasmosis, transplant, traumatic brain injury, tuberculosis, type 1 diabetes, type 2 diabetes, ulcerative colitis, urticarial, uveitis, Wegener's granulomatosis, interstitial lung disease, psoriatic arthritis, juvenile idiopathic arthritis, Sjogren's syndrome, antineutrophil cytoplasmic antibody (ANCA)-associated vasculitis, antiphospholipid antibody syndrome, sepsis, deep vein thrombosis, fibrosis, Alzheimer's, scleroderma and CREST syndrome.

In one embodiment, the invention provides a provided compound, or a pharmaceutically acceptable salt thereof, for use in therapy. In another embodiment, the invention provides a provided compound, or a pharmaceutically acceptable salt thereof, for use in the treatment of a disorder mediated by inappropriate PAD4 activity. In another embodiment, the invention provides a provided compound, or a pharmaceutically acceptable salt thereof, for use in the treatment of rheumatoid arthritis, vasculitis, systemic lupus erythematosus, ulcerative colitis, cancer, cystic fibrosis, asthma, cutaneous lupus erythematosus, or psoriasis. In another embodiment, the invention provides a provided compound, or a pharmaceutically acceptable salt thereof, for use in the treatment of rheumatoid arthritis. In another embodiment, the invention provides a provided compound, or a pharmaceutically acceptable salt thereof, for use in the treatment of systemic lupus. In another embodiment, the invention provides a provided compound, or a pharmaceutically acceptable salt thereof, for use in the treatment of vasculitis. In another embodiment, the invention provides a provided compound, or a pharmaceutically acceptable salt thereof, for use in the treatment of cutaneous lupus erythematosus. In another embodiment, the invention provides a provided compound, or a pharmaceutically acceptable salt thereof, for use in the treatment of psoriasis. In another embodiment, the invention provides the use of a provided compound, or a pharmaceutically acceptable salt thereof, in the manufacture of a medicament for use in the treatment of a disorder mediated by inappropriate PAD4 activity. In another embodiment, the invention provides the use of a provided compound, or a pharmaceutically acceptable salt thereof, in the manufacture of a medicament for use in the treatment of rheumatoid arthritis, vasculitis, systemic lupus erythematosus, ulcerative colitis, cancer, cystic fibrosis, asthma, cutaneous lupus erythematosus, or psoriasis. In another embodiment, the invention provides the use of a provided compound, or a pharmaceutically acceptable salt thereof, in the manufacture of a medicament for use in the treatment of rheumatoid arthritis. In another embodiment, the invention provides the use of a provided compound, or a pharmaceutically acceptable salt thereof, in the manufacture of a medicament for use in the treatment of systemic lupus. In another embodiment, the invention provides the use of a provided compound, or a pharmaceutically acceptable salt thereof, in the manufacture of a medicament for use in the treatment of vasculitis. In another embodiment, the invention provides the use of a provided compound, or a pharmaceutically acceptable salt thereof, in the manufacture of a medicament for use in the treatment of cutaneous lupus erythematosus. In another embodiment, the invention provides the use of a provided compound, or a pharmaceutically acceptable salt thereof, in the manufacture of a medicament for use in the treatment of psoriasis. In a further embodiment, the invention provides a pharmaceutical composition for the treatment or prophylaxis of a disorder mediated by inappropriate PAD4 activity comprising a provided compound, or a pharmaceutically acceptable salt thereof. In a further embodiment, the invention provides a pharmaceutical composition for the treatment or prophylaxis of rheumatoid arthritis, vasculitis, systemic lupus erythematosus, ulcerative colitis, cancer, cystic fibrosis, asthma, cutaneous lupus erythematosus, or psoriasis, comprising a provided compound, or a pharmaceutically acceptable salt thereof. In a further embodiment, the invention provides a pharmaceutical composition for the treatment or prophylaxis of rheumatoid arthritis comprising a provided compound, or a pharmaceutically acceptable salt thereof. In a further embodiment, the invention provides a pharmaceutical composition for the treatment or prophylaxis of systemic lupus comprising a provided compound, or a pharmaceutically acceptable salt thereof. In a further embodiment, the invention provides a pharmaceutical composition for the treatment or prophylaxis of vasculitis comprising a provided compound, or a pharmaceutically acceptable salt thereof. In a further embodiment, the invention provides a pharmaceutical composition for the treatment or prophylaxis of cutaneous lupus erythematosus comprising a provided compound, or a pharmaceutically acceptable salt thereof. In a further embodiment, the invention provides a pharmaceutical composition for the treatment or prophylaxis of psoriasis comprising a provided compound, or a pharmaceutically acceptable salt thereof All features of each of the aspects of the invention apply to all other aspects mutatis mutandis.

In order that the invention described herein may be more fully understood, the following examples are set forth. It should be understood that these examples are for illustrative purposes only and are not to be construed as limiting this invention in any manner.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Certain compounds of the present invention were prepared according to Schemes described below.

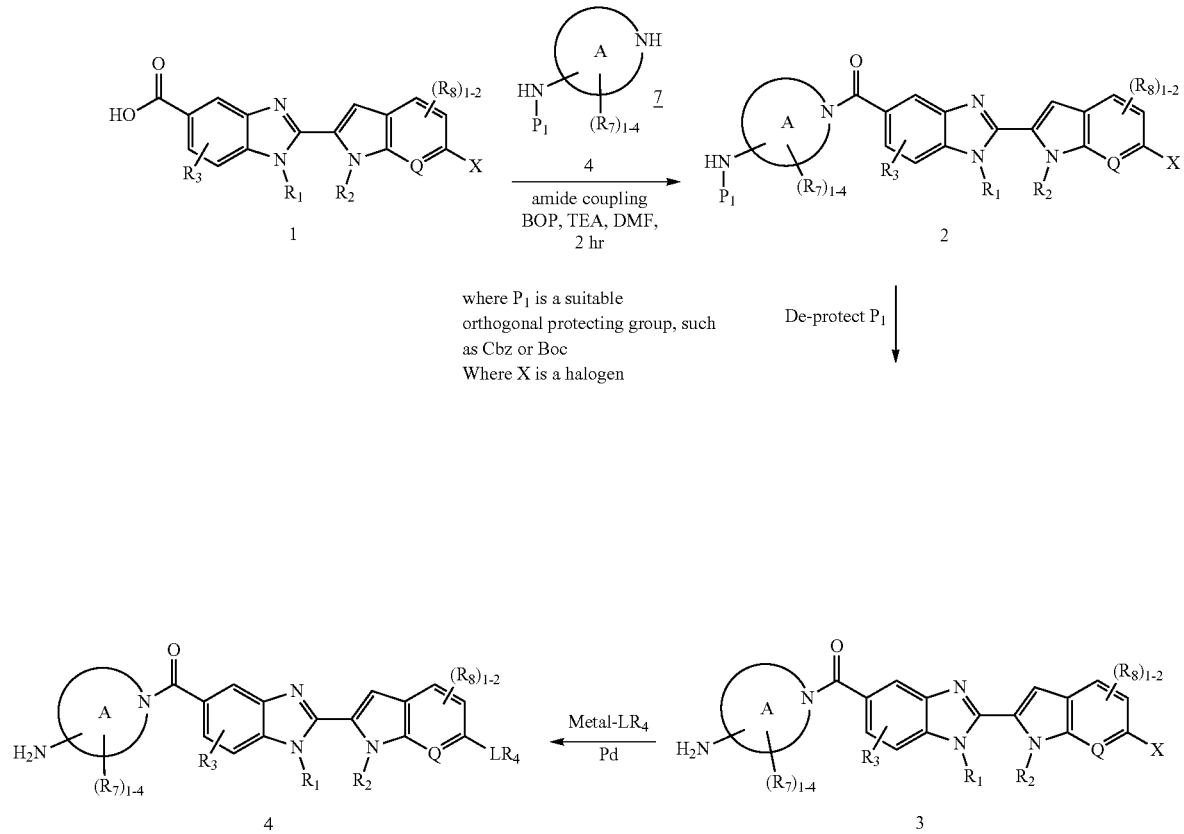

For compounds that involve heteroatom couplings, see Scheme 2.

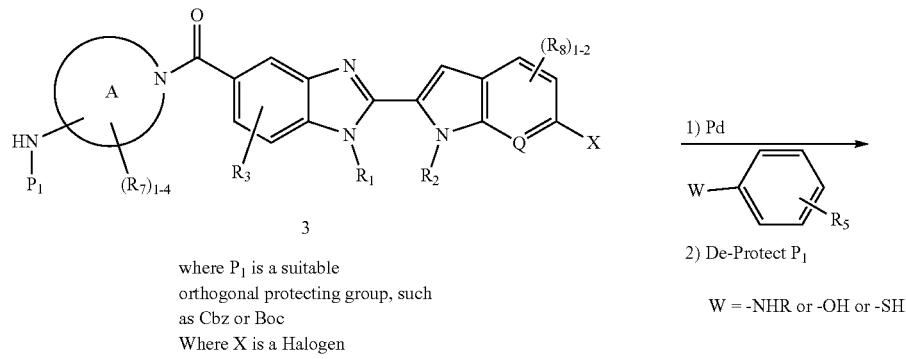

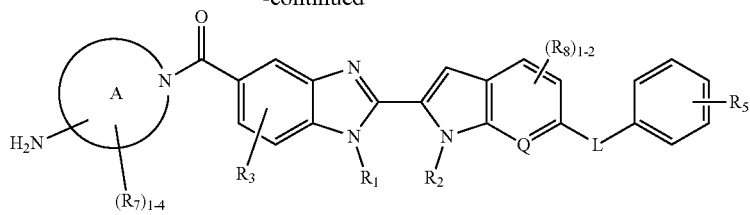
6
L = NR or NH or O or S
For the synthesis of sulfones, see Scheme 3.
Scheme 3
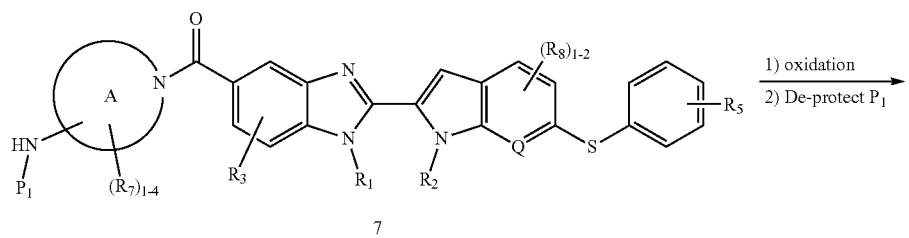
1) oxidation
2) De-protect $P_1$
7
where $P_1$ is suitable
orthogonal protecting group, such
as Cbz or Boc
Where X is a halogen
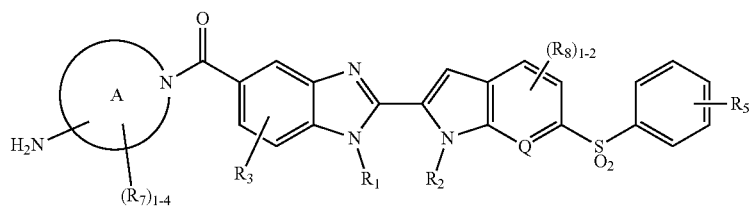
8
For the synthesis of carboxamides, see Scheme 4.
Scheme 4
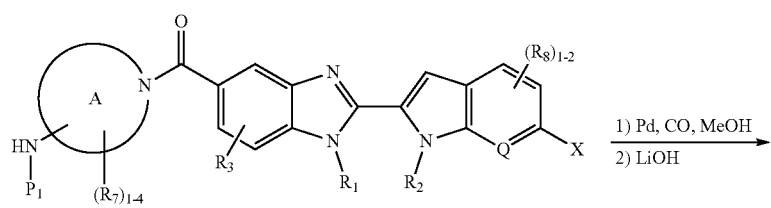
1) Pd, CO, MeOH
2) LiOH
3
where $P_1$ is a suitable
orthogonal protecting group, such
as Cbz or Boc
Where X is a halogen

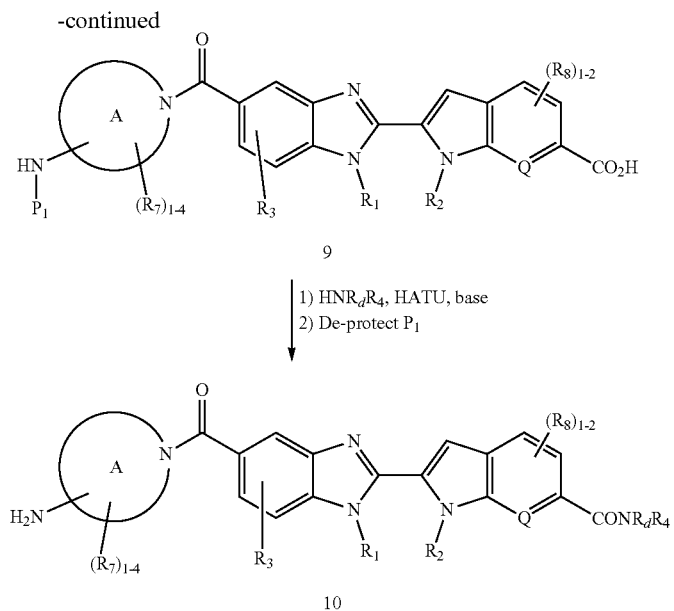

9

1) HNR$_d$R$_4$, HATU, base
2) De-protect P$_1$

10

For the synthesis of compounds involving photoredox chemistry, see Scheme 5.

Scheme 5

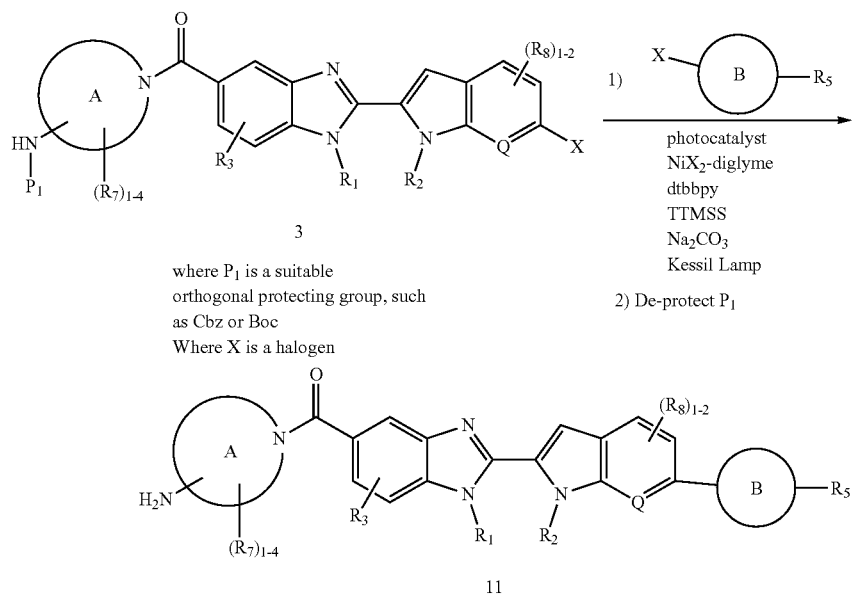

where P$_1$ is a suitable orthogonal protecting group, such as Cbz or Boc
Where X is a halogen 1) photocatalyst
NiX$_2$-diglyme
dtbbpy
TTMSS
Na$_2$CO$_3$
Kessil Lamp 2) De-protect P$_1$

11 where "B" is a saturated ring with or without embedded heteroatoms and substituent R$_5$ Description of Analytical LCMS Methods:

Method 1: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.5 min hold at 100% B; Flow: 1 mL/min; Detection: MS and UV (220 nm).

Method 2: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.5 min hold at 100% B; Flow: 1 mL/min; Detection: MS and UV (220 nm).

Method 3: Waters Acquity UPLC BEH C18, 2.1×50 mm, 1.7 μm particles; Mobile Phase A: water with 0.05% TFA; Mobile Phase B: ACN with 0.05% TFA; Gradient: 2-98% B over 1 minute, then a 0.5 minute hold at 98% B; Flow: 0.8 mL/min; Detection: UV at 254 nm.

The structures drawn in the current application generically as A below (FIG. 1) are meant as a representation of the fully chiral structure B, with the chiral azabicycloheptane moiety named as ((1R,4R,7R)-7-amino-2-azabicyclo[2.2.1]heptan-2-yl).

FIG. 1

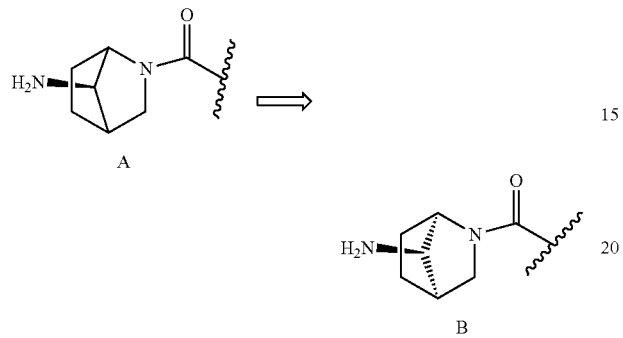

Intermediate 1

2-(6-chloro-1-(cyclopropylmethyl)-1H-pyrrolo[2,3-b]pyridin-2-yl)-7-methoxy-1-methyl-1H-benzo[d]imidazole-5-carboxylic acid Intermediate 1

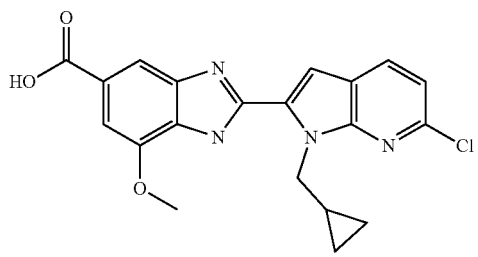

The methyl 2-(6-chloro-1-(cyclopropylmethyl)-1H-pyrrolo[2,3-b]pyridin-2-yl)-7-methoxy-1-methyl-1H-benzo[d]imidazole-5-carboxylate (4 g, 9.41 mmol) [for this starting material see: WO 2017/0100594)] was dissolved in THF (45 mL), MeOH (15 mL) and 2M LiOH aq (9.41 mL). This was stirred at 70° C. for 90 min. To add to this, the reaction was repeated as follows: The methyl 2-(6-chloro-1-(cyclopropylmethyl)-1H-pyrrolo[2,3-b]pyridin-2-yl)-7-methoxy-1-methyl-1H-benzo[d]imidazole-5-carboxylate (2.9 g, 6.83 mmol) was dissolved in THF (24 mL), MeOH (8 mL) and 2M LiOH aq (6.83 ml). The saponification was found to be over as per LCMS. This crude was combined with the earlier reaction crude. The mixture was slowly treated with 2N HCl until the pH reached ~6. At this stage a tan colored solid precipitated out as 2-(6-chloro-1-(cyclopropylmethyl)-1H-pyrrolo[2,3-b]pyridin-2-yl)-7-methoxy-1-methyl-1H-benzo[d]imidazole-5-carboxylic acid (6.9 g): $^1$H NMR (400 MHz, DMSO-$d_6$) δ 12.83 (br s, 1H), 8.20 (d, J=8.3 Hz, 1H), 7.96 (s, 1H), 7.41 (s, 1H), 7.28 (d, J=8.2 Hz, 1H), 7.17 (s, 1H), 4.44 (br d, J=6.9 Hz, 2H), 4.15 (s, 3H), 4.02 (s, 3H), 1.18-1.04 (m, 1H), 0.36-0.27 (m, 2H), 0.13 (q, J=4.7 Hz, 2H), LCMS (M+H)+=411.3, retention time=1.01 min (Method 3).

Intermediate 2 tert-butyl ((1R,4R,7R)-2-(2-(6-chloro-1-(cyclopropylmethyl)-1H-pyrrolo[2,3-b]pyridin-2-yl)-7-methoxy-1-methyl-1H-benzo[d]imidazole-5-carbonyl)-2-azabicyclo[2.2.1]heptan-7-yl)carbamate Intermediate 2

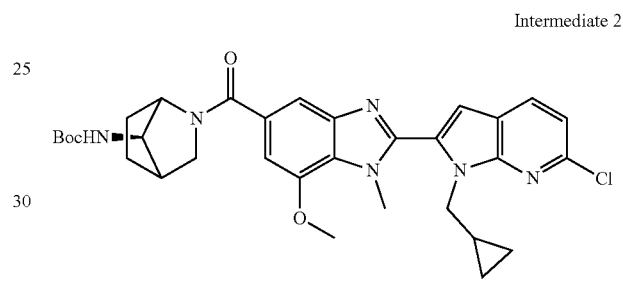

To a mixture of 5-(6-chloro-1-(cyclopropylmethyl)-1H-pyrrolo[2,3-b]pyridin-2-yl)-7-methoxy-1-methyl-1H-benzo[d]imidazole-5-carboxylic acid (5.8 g, 14.12 mmol), tert-butyl ((7R)-2-azabicyclo[2.2.1]heptan-7-yl)carbamate (3.30 g, 15.53 mmol), and Hunig's Base (7.40 ml, 42.4 mmol) was added DMF (35 mL). The mixture became a solid, and therefore, additional DMF (100 ml) was added (became a slurry). Next, this was treated with HATU (6.44 g, 16.94 mmol) in portions to ensure that the HATU was dissolved before adding the next portion. The reaction eventually went into a yellow colored solution. After 2 h of stirring at rt, the reaction was found to be complete. The reaction mixture was diluted with EtOAc and washed with 10% LiCl aq (2×) followed by brine. The combined aq layer was extracted with EtOAc. The combined organic layer was dried (MgSO4), filtered, and concentrated to a dark yellow brown oil. This brown oil was purified by flash chromatography (EtOAc/Hexane), and the product fractions were combined and concentrated to give tert-butyl ((1R,4R,7R)-2-(2-(6-chloro-1-(cyclopropylmethyl)-1H-pyrrolo[2,3-b]pyridin-2-yl)-7-methoxy-1-methyl-1H-benzo[d]imidazole-5-carbonyl)-2-azabicyclo[2.2.1]heptan-7-yl)carbamate (11 g): $^1$H NMR (400 MHz, DMSO-$d_6$) δ 8.19 (d, J=8.2 Hz, 1H), 7.51-7.36 (m, 1H), 7.27 (d, J=8.2 Hz, 1H), 7.13 (s, 1H), 7.01-6.95 (m, 1H), 4.44 (br d, J=7.1 Hz, 2H), 4.12 (s, 3H), 4.00 (s, 3H), 3.74-3.45 (m, 2H), 3.32 (s, 1H), 3.11-3.03 (m, 1H), 2.48-2.37 (m, 1H), 2.00-1.89 (m, 1H), 1.80 (br s, 2H), 1.52-1.44 (m, 1H), 1.44-1.28 (m, 9H), 1.15-1.05 (m, J=4.6 Hz, 1H), 0.30 (br d, J=7.7 Hz, 2H), 0.13 (br d, J=4.8 Hz, 2H), LCMS (M+H)+=605.3, retention time=1.05 min (Method 3).

Intermediate 3 tert-butyl ((1R,4R,7R)-2-(2-(6-chloro-1-(cyclopropylmethyl)-1H-pyrrolo[2,3-b]pyridin-2-yl)-7-methoxy-1-methyl-1H-benzo[d]imidazole-5-carbonyl)-2-azabicyclo[2.2.1]heptan-7-yl)carbamate Intermediate 3

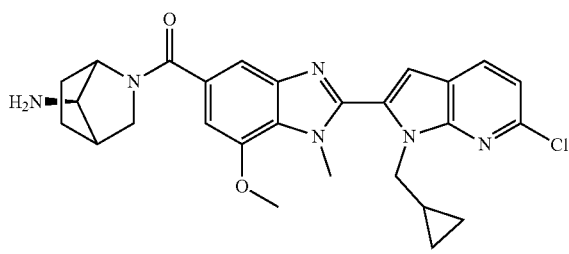

A portion of the above tert-butyl ((1R,4R,7R)-2-(2-(6-chloro-1-(cyclopropylmethyl)-1H-pyrrolo[2,3-b]pyridin-2-yl)-7-methoxy-1-methyl-1H-benzo[d]imidazole-5-carbonyl)-2-azabicyclo[2.2.1]heptan-7-yl)carbamate (9 g) was dissolved in DCM (100 mL) and treated with TFA (25 mL). After 2 h, additional TFA (15 mL) was added. After 1 h, the reaction was concentrated and then it was dissolved in EtOAc. It was made basic with a very slow addition of solid NaHCO$_3$. After the effervescence subsided, it was allowed to stir for 30 min more. The organic layer was separated and washed with brine. Combined aq layer was extracted with EtOAc. Combined organic layer was dried (MgSO4), filtered and concentrated to yield ((1R,4R,7R)-7-amino-2-azabicyclo[2.2.1]heptan-2-yl)(2-(6-chloro-1-(cyclopropylmethyl)-1H-pyrrolo[2,3-b]pyridin-2-yl)-7-methoxy-1-methyl-1H-benzo[d]imidazol-5-yl)methanone (7 g) as a yellow foamy solid: $^1$H NMR (400 MHz, DMSO-d$_6$) δ 8.20 (d, J=8.2 Hz, 1H), 7.55-7.39 (m, 1H), 7.28 (d, J=8.2 Hz, 1H), 7.15 (s, 1H), 7.02-6.95 (m, 1H), 4.44 (br d, J=6.9 Hz, 2H), 4.13 (s, 3H), 4.07-4.04 (m, 1H), 4.00 (s, 3H), 3.79-3.40 (m, 2H), 3.19-3.10 (m, 1H), 2.48-2.43 (m, 1H), 1.97-1.81 (m, 3H), 1.62-1.53 (m, 1H), 1.14-1.02 (m, 1H), 0.35-0.28 (m, 2H), 0.12 (br s, 2H); LCMS (M+H)+=505.3, retention time=0.86 min (Method 3).

Example 1

6-(2-(5-((1R,4R,7R)-7-amino-2-azabicyclo[2.2.1] heptane-2-carbonyl)-1-methyl-1H-benzo[d]imidazol-2-yl)-1-(cyclopropylmethyl)-1H-pyrrolo[2,3-b]pyridin-6-yl)-3,4-dihydroquinolin-2(1H)-one Example 1

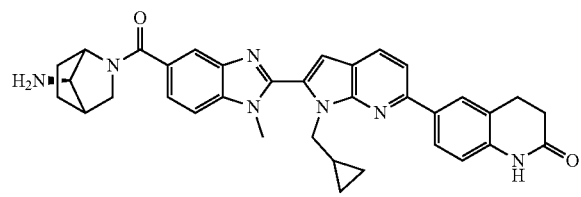

A 2 dr pressure vial was charged with ((1R,4R,7R)-7-amino-2-azabicyclo[2.2.1]heptan-2-yl)(2-(6-chloro-1-(cyclopropylmethyl)-1H-pyrrolo[2,3-b]pyridin-2-yl)-1-methyl-1H-benzo[d]imidazol-5-yl)methanone (25 mg, 0.053 mmol), 6-(4,4,5,5-tetramethyl-1,3,2-dioxaborolan-2-yl)-3,4-dihydroquinolin-2(1H)-one (17.25 mg, 0.063 mmol), 3M potassium phosphate tribasic aq (0.053 mL, 0.158 mmol) and 1,1'-Bis(diphenylphosphino)ferrocene-palladium(II)dichloride dichloromethane complex (4.30 mg, 5.26 μmol) in THF (1 mL). The vial was capped and the reaction mixture was made anaerobic by a pump/backfill with nitrogen cycle (5×). The reaction was set to stir at 70° C. for 7 h. The mixture was concentrated and dried in vacuo. It was dissolved in DMF and purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 15% B, 15-55% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation. The purified material was then diluted with DMF, treated with Si-Pyridine and shaken for a minimum of 2 h. The resulting mixture was filtered and dried via centrifugal evaporation to give 6-(2-(5-((1R,4R,7R)-7-amino-2-azabicyclo[2.2.1]heptane-2-carbonyl)-1-methyl-1H-benzo[d]imidazol-2-yl)-1-(cyclopropylmethyl)-1H-pyrrolo [2,3-b]pyridin-6-yl)-3,4-dihydroquinolin-2(1H)-one (12 mg): $^1$H NMR (500 MHz, DMSO-d$_6$) δ 10.08 (s, 1H), 8.15 (d, J=8.2 Hz, 1H), 8.02-7.97 (m, 2H), 7.89-7.78 (m, 1H), 7.76-7.69 (m, 2H), 7.45 (br d, J=8.6 Hz, 1H), 7.10 (s, 1H), 7.01 (d, J=8.2 Hz, 1H), 4.64 (br d, J=7.0 Hz, 2H), 3.99 (s, 3H), 3.74 (br s, 1H), 3.63-3.48 (m, 1H), 3.35-3.27 (m, 1H), 3.17-3.04 (m, 1H), 3.01 (br t, J=7.5 Hz, 2H), 2.56-2.52 (m, 3H), 2.23 (br s, 1H), 2.06-1.91 (m, 2H), 1.72 (br t, J=9.3 Hz, 1H), 1.49-1.39 (m, 1H), 1.23 (br d, J=8.4 Hz, 1H), 0.32 (br d, J=7.8 Hz, 2H), 0.23 (br s, 2H); LC/MS (M+H)=585.9; Retention Time=1.43 min (Method 1).

Example 2

((1R,4R,7R)-7-amino-2-azabicyclo[2.2.1]heptan-2-yl)(2-(1-(cyclopropylmethyl)-6-((6-fluoropyridin-3-yl)oxy)-1H-indol-2-yl)-7-methoxy-1-methyl-1H-benzo[d]imidazol-5-yl)methanone Example 2

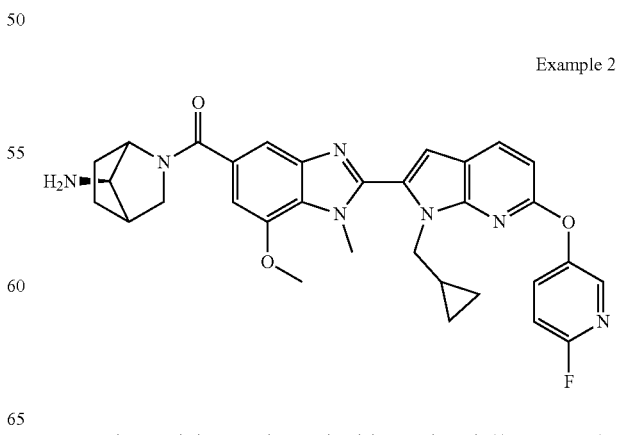

A 1 dram vial was charged with tert-butyl ((1R,4R,7R)-2-(2-(6-bromo-1-(cyclopropylmethyl)-1H-indol-2-yl)-7- methoxy-1-methyl-1H-benzo[d]imidazole-5-carbonyl)-2-azabicyclo[2.2.1]heptan-7-yl)carbamate (0.037 g, 0.040 mmol), 2-fluoro-5-hydroxypyridine (5.42 mg, 0.048 mmol), cesium carbonate (0.020 g, 0.060 mmol) and Rockphos Pd G3 (3.35 mg, 3.99 µmol) in dioxane (1 mL). The vial was capped and the reaction mixture was made anaerobic by a pump/backfill with nitrogen cycle (5×). The reaction was set to stir at 90° C. overnight. After cooling, the mixture was diluted with EtOAc, dried (MgSO4), filtered, and concentrated. The resulting residue was dissolved in dichloromethane (1 mL) and treated with TFA (0.5 ml, 6.49 mmol). Mixture was stirred at rt for 90 min before it was concentrated. The residue was dissolved in DMF, filtered and purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 26-66% B over 20 minutes, then a 4-minute hold at 100% B; Flow: 20 mL/min. Fractions containing the desired product were combined and dried via centrifugal evaporation. The purified material was then diluted with DMF, treated with Si-Pyridine and shaken for a minimum of 2 h. The resulting mixture was filtered and concentrated via centrifugal evaporation to give ((1R,4R,7R)-7-amino-2-azabicyclo[2.2.1]heptan-2-yl)(2-(1-(cyclopropylmethyl)-6-((6-fluoropyridin-3-yl)oxy)-1H-indol-2-yl)-7-methoxy-1-methyl-1H-benzo[d]imidazol-5-yl)methanone (4.1 mg): $^1$H NMR (500 MHz, DMSO-d$_6$) δ 8.03 (br s, 1H), 7.72 (br d, J=8.5 Hz, 1H), 7.68 (br t, J=6.0 Hz, 1H), 7.44 (br s, 1H), 7.34 (s, 1H), 7.21 (br dd, J=8.7, 2.9 Hz, 1H), 7.06 (s, 1H), 6.95-6.90 (m, 2H), 4.37 (br d, J=6.4 Hz, 2H), 4.10 (s, 3H), 3.98 (s, 3H), 3.75 (br s, 1H), 3.66-3.48 (m, 1H), 3.17 (s, 1H), 3.08-2.99 (m, 1H), 2.21 (br s, 1H), 2.04-1.91 (m, 2H), 1.74 (br t, J=9.5 Hz, 1H), 1.48-1.40 (m, 1H), 1.23 (s, 2H), 1.04-0.94 (m, 1H), 0.26 (br d, J=7.9 Hz, 2H), −0.02 (br s, 2H); LC/MS (M+H)=581.3; Retention Time=1.75 min (Method 1).

Example 3

((1R,4R,7R)-7-amino-2-azabicyclo[2.2.1]heptan-2-yl)(2-(1-(cyclopropylmethyl)-6-(pyridin-4-ylthio)-1H-pyrrolo[2,3-b]pyridin-2-yl)-7-methoxy-1-methyl-1H-benzo[d]imidazol-5-yl)methanone Example 3

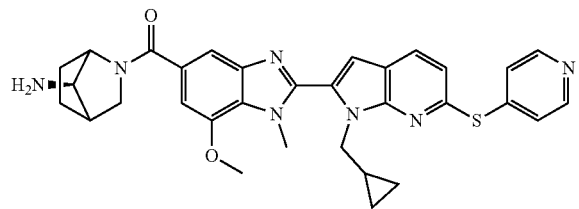

A mixture of tert-butyl ((1R,4R,7R)-2-(2-(6-chloro-1-(cyclopropylmethyl)-1H-pyrrolo[2,3-b]pyridin-2-yl)-7-methoxy-1-methyl-1H-benzo[d]imidazole-5-carbonyl)-2-azabicyclo[2.2.1]heptan-7-yl)carbamate (47 mg, 0.078 mmol), Pd2(dba)3 (14.22 mg, 0.016 mmol), (2R)-1-[(1R)-1-[bis (1,1-dimethylethyl)phosphino]ethyl]-2-(dicyclohexylphosphino)ferrocene (8.61 mg, 0.016 mmol) in DME (1.5 mL) was treated with potassium tert-butoxide (10.46 mg, 0.093 mmol). The vial was sealed and the reaction mixture was made anaerobic by a pump/backfill with nitrogen cycle (5×). The reaction was set to stir at rt for 10 min. The vial cap was opened under a nitrogen flush and treated with 4-mercaptopyridine (10.36 mg, 0.093 mmol). The vial was capped and made anaerobic by pump/backfill w/N2 (3×). The reaction mixture was stirred at 110° C. overnight. As per LCMS, desired product was observed along with some starting material. In order to gain more product, the reaction was repeated and the details follow: A mixture of tert-butyl ((1R,4R,7R)-2-(2-(6-chloro-1-(cyclopropylmethyl)-1H-pyrrolo[2,3-b]pyridin-2-yl)-7-methoxy-1-methyl-1H-benzo[d]imidazole-5-carbonyl)-2-azabicyclo[2.2.1]heptan-7-yl)carbamate (110 mg, 0.182 mmol) (2R)-1-[(1R)-1-[bis (1,1-dimethylethyl)phosphino]ethyl]-2-(dicyclohexylphosphino)ferrocene (20.16 mg, 0.036 mmol), Pd2(dba)3 (33.3 mg, 0.036 mmol) in dioxane (2 mL) under a nitrogen flush was treated with potassium tert-butoxide (24.48 mg, 0.218 mmol). The vial was sealed and the reaction mixture was made anaerobic by a pump/backfill with nitrogen cycle (5×). The reaction was set to stir at rt for 10 min. The vial cap was opened under a nitrogen flush and treated with 4-mercaptopyridine (24.25 mg, 0.218 mmol). The vial was capped and made anaerobic by pump/backfill w/N2 (3×). The reaction mixture was stirred at 110° for 20 h. After cooling, the reaction was quenched with satd. NH4Cl aq. It was diluted with EtOAc and then washed with water followed by brine. The combined aq layer was extracted with EtOAc. The combined organic layer was dried (MgSO4). Crude products from the two experiments were combined and purified by flash chromatography (12 g ISCO cartridge was used with EtOAc-Hexanes). The product fractions were combined and concentrated (crude weight=0.1 g). The resulting residue was dissolved in DCM (1 mL) and treated with TFA (0.5 ml, 6.49 mmol). After 1 h, the solution was concentrated and the residue was dissolved the residue in DMF, filtered and purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 24% B, 24-64% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation. The purified material was then diluted with DMF, treated with Si-Pyridine and shaken for a minimum of 2 h. The resulting mixture was filtered and dried via centrifugal evaporation to give ((1R,4R,7R)-7-amino-2-azabicyclo[2.2.1]heptan-2-yl)(2-(1-(cyclopropylmethyl)-6-(pyridin-4-ylthio)-1H-pyrrolo[2,3-b]pyridin-2-yl)-7-methoxy-1-methyl-1H-benzo[d]imidazol-5-yl)methanone (10.1 mg): $^1$H NMR (500 MHz, DMSO-d$_6$) δ 8.49 (br s, 2H), 8.21 (br d, J=7.9 Hz, 1H), 7.41-7.35 (m, 4H), 7.15 (s, 1H), 6.98-6.93 (m, 1H), 4.37 (br d, J=6.1 Hz, 2H), 4.14 (s, 3H), 4.00 (br s, 3H), 3.71 (br s, 2H), 3.57-3.47 (m, 1H), 3.10 (br d, J=11.0 Hz, 1H), 2.91 (s, 1H), 2.75 (s, 1H), 1.92 (br s, 4H), 1.48 (br t, J=8.4 Hz, 1H), 1.08-1.00 (m, 1H), 0.27 (br d, J=7.6 Hz, 2H), 0.00 (br s, 2H); LC/MS (M+H)=580.4; Retention Time=1.58 min (Method 1).

Example 4

(((1R,4R,7R)-7-amino-2-azabicyclo[2.2.1]heptan-2-yl)(2-(1-(cyclopropylmethyl)-6-(pyridin-4-ylsulfonyl)-1H-indol-2-yl)-7-methoxy-1-methyl-1H-benzo[d]imidazol-5-yl)methanone

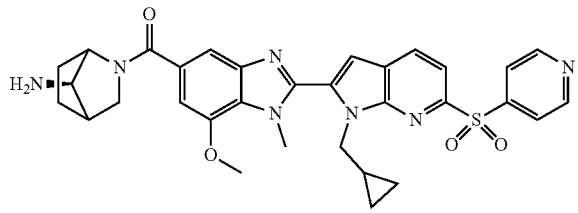

Example 4

A mixture of tert-butyl ((1R,4R,7R)-2-(2-(6-bromo-1-(cyclopropylmethyl)-1H-indol-2-yl)-7-methoxy-1-methyl-1H-benzo[d]imidazole-5-carbonyl)-2-azabicyclo[2.2.1]heptan-7-yl)carbamate (120 mg, 0.185 mmol), (2R)-1-[(1R)-1-[bis (1,1-dimethylethyl)phosphino]ethyl]-2-(dicyclohexylphosphino)ferrocene (20.52 mg, 0.037 mmol), Pd2(dba)3 (33.9 mg, 0.037 mmol) in dioxane (2 mL) under a nitrogen flush was treated with potassium tert-butoxide (24.91 mg, 0.222 mmol). The vial was sealed and the reaction mixture was made anaerobic by a pump/backfill with nitrogen cycle (5×). The reaction was stirred at rt for 10 min. The vial cap was opened under a nitrogen flush and treated with 4-mercaptopyridine (30.8 mg, 0.278 mmol). The vial was capped and made anaerobic by pump/backfill w/N2 (3×). The reaction mixture was stirred at 110° C. overnight. The reaction was quenched with satd. NH4Cl aq. It was diluted with EtOAc and then washed with water followed by brine. The combined aq layer was extracted with EtOAc. The combined organic layer was dried (MgSO4), filtered, and concentrated. The resulting residue was purified by flash chromatographed (EtOAc/Hexane) to yield tert-butyl ((1R,4R,7R)-2-(2-(1-(cyclopropylmethyl)-6-(pyridin-4-ylthio)-1H-indol-2-yl)-7-methoxy-1-methyl-1H-benzo[d]imidazole-5-carbonyl)-2-azabicyclo[2.2.1]heptan-7-yl)carbamate (38 mg, 0.056 mmol, 30.3% yield) as a brownish oil which was dissolved in acetone (1.5 mL) and was treated with water (1.500 ml) followed by oxone (103 mg, 0.168 mmol). This was stirred overnight. The reaction was diluted with EtOAc and then washed with 1.5M K2HPO4 aq followed by brine. The combined aq layer was extracted with EtOAc. The combined organic layer was dried (MgSO4), filtered and concentrated. The resulting residue was dissolved in CH2Cl2 (1 mL) and treated with TFA (0.5 ml, 6.49 mmol). After stirring for 1 h, the deprotection was found complete. Concentrated and dried in vacuo briefly. The residue was dissolved in DMF and purified via preparative LC/MS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 12% B, 12-52% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation. The purified material was then diluted with DMF, treated with Si-Pyridine and shaken for a minimum of 2 h. The resulting mixture was filtered and dried via centrifugal evaporation to give ((1R,4R,7R)-7-amino-2-azabicyclo[2.2.1]heptan-2-yl)(2-(1-(cyclopropylmethyl)-6-(pyridin-4-ylsulfonyl)-1H-indol-2-yl)-7-methoxy-1-methyl-1H-benzo[d]imidazol-5-yl)methanone (12.6 mg, 0.020 mmol, 10.8% yield): $^1$H NMR (500 MHz, DMSO-$d_6$) δ 8.80 (br d, J=5.5 Hz, 2H), 8.38 (br s, 1H), 7.90 (br d, J=5.2 Hz, 2H), 7.87 (br d, J=8.5 Hz, 1H), 7.62 (br d, J=8.5 Hz, 1H), 7.35 (s, 1H), 7.49-7.34 (m, 1H), 7.15 (s, 1H), 6.96-6.88 (m, 1H), 4.48 (br d, J=7.0 Hz, 2H), 4.02 (s, 3H), 3.93 (br s, 3H), 3.74-3.50 (m, 1H), 3.44-3.39 (m, 1H), 3.15-3.07 (m, 1H), 2.61 (br s, 1H), 1.96-1.77 (m, 3H), 1.65-1.52 (m, 1H), 1.01-0.94 (m, J=5.8 Hz, 1H), 0.26 (br d, J=7.6 Hz, 2H), 0.00 (br s, 2H); LC/MS (M+H)=611.37; Retention Time=1.45 min (Method 1).

Example 5

((1R,4R,7R)-7-amino-2-azabicyclo[2.2.1]heptan-2-yl)(2-(1-(cyclopropylmethyl)-6-((4-hydroxyphenyl)amino)-1H-pyrrolo[2,3-b]pyridin-2-yl)-7-methoxy-1-methyl-1H-benzo[d]imidazol-5-yl)methanone

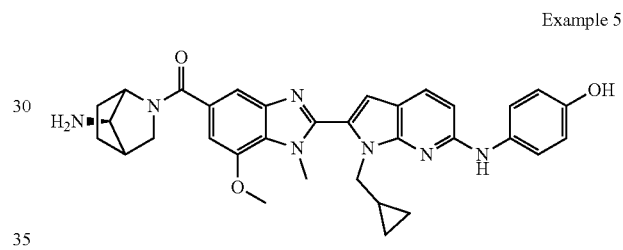

Example 5

A vial was charged with tert-butyl ((1R,4R,7R)-2-(2-(6-chloro-1-(cyclopropylmethyl)-1H-pyrrolo[2,3-b]pyridin-2-yl)-7-methoxy-1-methyl-1H-benzo[d]imidazole-5-carbonyl)-2-azabicyclo[2.2.1]heptan-7-yl)carbamate (25 mg, 0.041 mmol), 4-aminophenol (6.76 mg, 0.062 mmol), cesium carbonate (40.4 mg, 0.124 mmol) and $2^{nd}$ generation X-Phos precatalyst (3.25 mg, 4.13 μmol) in dioxane (1 mL) and tBuOH (0.25 mL). The vial was capped and the reaction mixture was made anaerobic by a pump/backfill with nitrogen cycle (5×). The reaction was stirred at 70° C. overnight. After cooling, the mixture was diluted with EtOAc and dried (MgSO4), filtered and concentrated. The resulting residue was dissolved in CH$_2$Cl2 (1 mL) and treated with TFA (0.5 ml, 6.49 mmol). This mixture was stirred at rt for 2 hrs before it was concentrated. The resulting residue was dissolved in DMF and was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 17% B, 17-57% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation. The purified material was then diluted with DMF, treated with Si-Pyridine and shaken for a minimum of 2 h. The resulting mixture was filtered and dried via centrifugal evaporation to give ((1R,4R,7R)-7-amino-2-azabicyclo[2.2.1]heptan-2-yl)(2-(1-(cyclopropylmethyl)-6-((4-hydroxyphenyl)amino)-1H-pyrrolo[2,3-b]pyridin-2-yl)-7- methoxy-1-methyl-1H-benzo[d]imidazol-5-yl)methanone (13.8 mg, 0.024 mmol, 57.8% yield): $^1$H NMR (500 MHz, DMSO-$d_6$) δ 8.83 (s, 1H), 7.75 (d, J=8.5 Hz, 1H), 7.56 (br d, J=8.9 Hz, 2H), 7.40-7.27 (m, 1H), 6.89-6.79 (m, 2H), 6.68 (br d, J=8.9 Hz, 2H), 6.59 (d, J=8.5 Hz, 1H), 4.39 (br d, J=6.7 Hz, 2H), 4.08 (s, 3H), 3.93 (s, 3H), 3.73 (br s, 1H), 3.65-3.42 (m, 1H), 3.16-2.95 (m, 2H), 2.22-2.07 (m, 1H), 2.00-1.87 (m, 2H), 1.77-1.60 (m, 1H), 1.44-1.28 (m, 1H), 1.11 (br s, 1H), 0.25 (br d, J=7.9 Hz, 2H), 0.13 (br d, J=4.0 Hz, 2H); LC/MS (M+H)=578.26; Retention Time=1.41 min (Method 1).

Intermediate 4

2-(5-(((1R,4R,7R)-7-((tert-butoxycarbonyl)amino)-2-azabicyclo[2.2.1]heptane-2-carbonyl)-7-methoxy-1-methyl-1H-benzo[d]imidazol-2-yl)-1-(cyclopropylmethyl)-1H-indole-6-carboxylic acid Intermediate 4

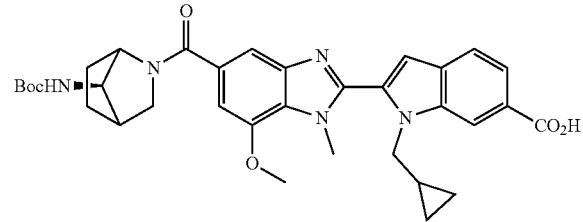

To a solution of tert-butyl ((1R,4R,7R)-2-(2-(6-bromo-1-(cyclopropylmethyl)-1H-indol-2-yl)-7-methoxy-1-methyl-1H-benzo[d]imidazole-5-carbonyl)-2-azabicyclo[2.2.1]heptan-7-yl)carbamate (0.36 g, 0.555 mmol), DPPF (0.062 g, 0.111 mmol) and TEA (0.232 mL, 1.665 mmol) in DMF (2 mL) and MeOH (0.500 mL) was bubbled CO (g) for 5 min following which the reaction solution was treated with palladium (II) acetate (0.037 g, 0.056 mmol). CO (g) was bubbled for another min. The vial was sealed and a balloon containing carbon monoxide was connected to the vial via a needle. This was then stirred at 90° C.

After stirring overnight, the reaction was found to be incomplete. Additional amounts of DPPF (0.062 g, 0.111 mmol), MeOH (0.500 mL) and palladium (II) acetate (0.037 g, 0.056 mmol) were added to the reaction and the solution was saturated with CO (g) by bubbling for 5 min. The vial was sealed and a CO (g) balloon was attached. The mixture was stirred at 90° C. for another 18 h. After cooling, the mixture was diluted with EtOAc and filtered through Celite. The mixture was then washed with 10% LiCl (aq) (2×) followed by brine. The combined aq. layer was extracted with EtOAc. The combined organic layer was dried (MgSO4), filtered and concentrated. The resulting residue was purified via flash chromatographed (EtOAc/Hexane) to give the methyl ester as a brown oil, which was then dissolved in THF (2 mL) and MeOH (0.5 mL). This solution was treated with 2M LiOH aq (0.555 mL, 1.110 mmol). The reaction was stirred at 70° C. for 2 h. The temperature was then raised to 80° C. After 1 h, the reaction was still not complete and 2M LiOH aq (0.278 mL, 0.555 mmol) was added and stirring was continued at 80° C. After 7 h the saponification was complete. After cooling, the mixture was diluted with EtOAc and 2M HCl was added (pH=5). The organic layer was separated and then washed with brine. It was dried (MgSO4), filtered, and concentrated to give the intermediate 2-(5-((1R,4R,7R)-7-((tert-butoxycarbonyl)amino)-2-azabicyclo[2.2.1]heptane-2-carbonyl)-7-methoxy-1-methyl-1H-benzo[d]imidazol-2-yl)-1-(cyclopropylmethyl)-1H-indole-6-carboxylic acid: LC/MS (M+H)=614.3; Retention Time=0.87 min (Method 3).

Example 6

2-(5-((1R,4R,7R)-7-amino-2-azabicyclo[2.2.1]heptane-2-carbonyl)-7-methoxy-1-methyl-1H-benzo[d]imidazol-2-yl)-1-(cyclopropylmethyl)-N-(pyridin-4-yl)-1H-indole-6-carboxamide

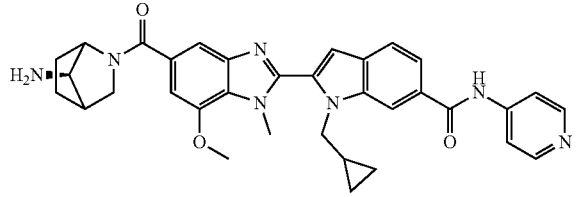

Example 6

A mixture of 2-(5-((1R,4R,7R)-7-((tert-butoxycarbonyl)amino)-2-azabicyclo[2.2.1]heptane-2-carbonyl)-7-methoxy-1-methyl-1H-benzo[d]imidazol-2-yl)-1-(cyclopropylmethyl)-1H-indole-6-carboxylic acid (30 mg, 0.049 mmol—from the above procedure), 4-aminopyridine (4.38 μl, 0.059 mmol) and Hunig's Base (0.026 ml, 0.147 mmol) in DMF (1 mL) at rt was treated with HATU (22.30 mg, 0.059 mmol). The reaction was stirred overnight at rt. The reaction mixture was then diluted with EtOAc and washed with 10% LiCl (aq) followed by brine. The combined aq layer was extracted with EtOAc. The combined organic layer was dried (MgSO4), filtered, and concentrated. The resulting residue was dissolved in CH2Cl2 (1 mL) and treated with TFA (0.5 ml, 6.49 mmol). After stirring 1 h, the reaction was evaporated. This residue was dissolved in DMF and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 14-54% B over 20 minutes, then a 4-minute hold at 100% B; Flow: 20 mL/min. Fractions containing the desired product were combined and dried via centrifugal evaporation. The purified material was then diluted with DMF, treated with Si-Pyridine and shaken for a minimum of 2 h. The resulting mixture was filtered and dried via centrifugal evaporation to give 2-(5-((1R,4R,7R)-7-amino-2-azabicyclo[2.2.1]heptane-2-carbonyl)-7-methoxy-1-methyl-1H-benzo[d]imidazol-2-yl)-1-(cyclopropylmethyl)-N-(pyridin-4-yl)-1H-indole-6-carboxamide (5.9 mg, 10.01 μmol, 20.47% yield): $^1$H NMR (500 MHz, DMSO-$d_6$) δ 8.45 (br t, J=5.4 Hz, 1H), 8.16-8.13 (m, 1H), 7.71-7.67 (m, 1H), 7.65-7.60 (m, 1H), 7.44-7.31 (m, 1H), 7.02 (s, 1H), 6.95-6.88 (m, 1H), 4.41 (br d, J=6.7 Hz, 2H), 4.13 (br d, J=8.3 Hz, 1H), 4.06 (s, 3H), 3.95 (s, 3H), 3.78-3.66 (m, 3H), 3.61 (q, J=7.7 Hz, 1H), 3.49 (br dd, J=8.3, 5.4 Hz, 1H), 3.34-3.22 (m, 1H), 3.04 (br d, J=11.5 Hz, 1H), 2.52 (br s, 1H), 2.24-2.12 (m, 1H), 2.02-1.88 (m, 3H), 1.78-1.68 (m, 1H), 1.62 (dq, J=12.9, 6.5 Hz, 1H), 1.42 (br s, 1H), 1.20 (br s, 1H), 1.06 (br s, 1H), 0.28 (br d, J=7.8 Hz, 2H), 0.00 (br s, 2H); LC/MS (M+H)=590.36; Retention Time=1.25 min (Method 3).

Example 7

6-(2-(5-(((1R,4R,7R)-7-amino-2-azabicyclo[2.2.1]heptane-2-carbonyl)-7-methoxy-1-methyl-1H-benzo[d]imidazol-2-yl)-1-(cyclopropylmethyl)-1H-pyrrolo[2,3-b]pyridin-6-yl)-3,4-dihydroquinolin-2(1H)-one

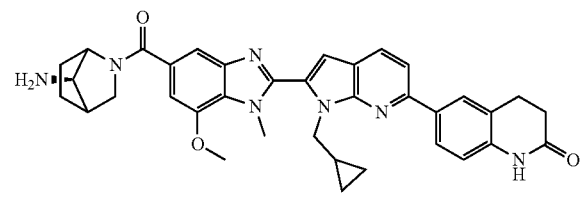

Example 7

A 2 dr vial was charged with ((1R,4R,7R)-7-amino-2-azabicyclo[2.2.1]heptan-2-yl)(2-(6-chloro-1-(cyclopropylmethyl)-1H-pyrrolo[2,3-b]pyridin-2-yl)-7-methoxy-1-methyl-1H-benzo[d]imidazol-5-yl)methanone (125 mg, 0.248 mmol), 6-(4,4,5,5-tetramethyl-1,3,2-dioxaborolan-2-yl)-3,4-dihydroquinolin-2(1H)-one (81 mg, 0.297 mmol), potassium phosphate tribasic, 3M in water (0.248 mL, 0.743 mmol) and 1,1'-Bis(diphenylphosphino)ferrocene-palladium(II)dichloride dichloromethane complex (20.21 mg, 0.025 mmol) in THF (2 mL). The vial was capped and the reaction mixture was made anaerobic by a pump/backfill with nitrogen cycle (5×). The reaction was stirred at 70° C. for overnight. After cooling, the mixture was concentrated and dried in vacuo. It was dissolved in DMF and purified via prep HPLC. Prep HPLC conditions: Start % B=20, Final % B=70, Gradient Time=15 min, Flow Rate=30 ml/min, Wavelength=254, Solvent Pair=MeCN-H20-TFA; Solvent A=0.1% TFA in water; Solvent B=0.1% TFA in MeCN; Column 2=1: Luna 5 u C18 30×100 mm AXIA Product eluted at 7.92 min. The desired fractions were combined and it was diluted with EtOAc and then washed with 1.5M K2HPO4 (aq) followed by brine. The combined aq layer was extracted with EtOAc. The combined organic layer was dried (MgSO4), filtered and concentrated. The residue was dissolved in DCM-MeOH and treated with 25 mgs of Py-resin. This was shaken for over 2 h before it was filtered and concentrated. The residue was dissolved into a mixture of water-acetonitrile, frozen and lyophilized to give 6-(2-(5-((1R,4R,7R)-7-amino-2-azabicyclo[2.2.1]heptane-2-carbonyl)-7-methoxy-1-methyl-1H-benzo[d]imidazol-2-yl)-1-(cyclopropylmethyl)-1H-pyrrolo[2,3-b]pyridin-6-yl)-3,4-dihydroquinolin-2(1H)-one (55 mg, 0.086 mmol, 34.6% yield) as a white fluffy solid: $^1$H NMR (500 MHz, DMSO-$d_6$) δ 10.08 (s, 1H), 8.15 (d, J=8.2 Hz, 1H), 8.02-7.97 (m, 2H), 7.89-7.78 (m, 1H), 7.76-7.69 (m, 2H), 7.45 (br d, J=8.6 Hz, 1H), 7.10 (s, 1H), 7.01 (d, J=8.2 Hz, 1H), 4.64 (br d, J=7.0 Hz, 2H), 3.99 (s, 3H), 3.74 (br s, 1H), 3.63-3.48 (m, 1H), 3.35-3.27 (m, 1H), 3.17-3.04 (m, 1H), 3.01 (br t, 0.1=7.5 Hz, 2H), 2.56-2.52 (m, 3H), 2.23 (br s, 1H), 2.06-1.91 (m, 2H), 1.72 (br t, J=9.3 Hz, 1H), 1.49-1.39 (m, 1H), 1.23 (br d, J=8.4 Hz, 1H), 0.32 (br d, J=7.8 Hz, 2H), 0.23 (br s, 2H) LCMS=(M+H)+=616.3; retention time=0.7 min (Method 3).

Example 8

((1R,4R,7R)-7-amino-2-azabicyclo[2.2.1]heptan-2-yl)(2-(1-(cyclopropylmethyl)-6-(oxetan-3-yl)-1H-pyrrolo[2,3-b]pyridin-2-yl)-7-methoxy-1-methyl-1H-benzo[d]imidazol-5-yl)methanone

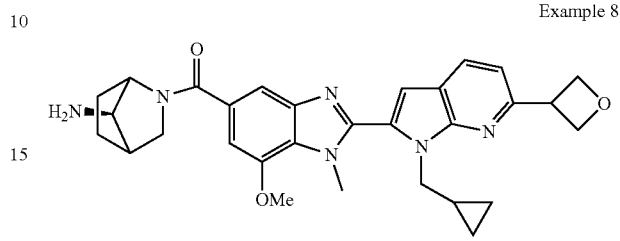

Example 8

The tert-butyl ((1R,4R,7R)-2-(2-(6-chloro-1-(cyclopropylmethyl)-1H-pyrrolo[2,3-b]pyridin-2-yl)-7-methoxy-1-methyl-1H-benzo[d]imidazole-5-carbonyl)-2-azabicyclo[2.2.1]heptan-7-yl)carbamate (30 mg, 0.050 mmol) was dissolved in dioxane (0.5 mL) prior to the addition of 3-bromooxetane (6.79 mg, 0.050 mmol), (Ir[DF(CF3)PPY]2(DTBPY))PF6 (1.112 mg, 0.992 µmol), sodium carbonate (0.011 mL, 0.198 mmol), 4,4'-di-tert-butyl-2,2'-bipyridine (0.798 mg, 2.97 µmol), tris(trimethylsilyl)silane (0.023 mL, 0.074 mmol), nickel (II) chloride ethylene glycol dimethyl ether complex (0.545 mg, 2.479 µmol) and a nitrogen purge followed. This was stirred overnight in front of two Kessil lamps with fan cooling of the reaction vial. After cooling EtOAc was added and this was filtered and concentrated. The resulting residue was dissolved in DCM (1 mL) prior to the addition of T-FA (2 mL). After 30 min, the mixture was concentrated. The resulting residue was purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 10% B, 10-50% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation. The purified material was then diluted with DMF, treated with Si-Pyridine and shaken for a minimum of 2 h. The resulting mixture was filtered and dried via centrifugal evaporation to give ((1R,4R,7R)-7-amino-2-azabicyclo[2.2.1]heptan-2-yl)(2-(1-(cyclopropylmethyl)-6-(oxetan-3-yl)-1H-pyrrolo[2,3-b]pyridin-2-yl)-7-methoxy-1-methyl-1H-benzo[d]imidazol-5-yl)methanone (5.8 mg, 0.01 mmol, 22.2%): $^1$H NMR (500 MHz, DMSO-$d_6$, rotamers) S 8.07-8.00 (m, 1H), 7.44 (m, 0.33H), 7.36-7.31 (m, 0.71H), 7.14-7.08 (m, 1H), 7.03-6.99 (m, 1H), 6.95-6.85 (m, 1H), 4.94-4.89 (m, 2H), 4.88-4.83 (m, 2H), 4.52-4.42 (m, 3H), 4.14 (m, 0.25H), 4.07 (s, 3H), 3.94 (s, 3H), 3.79-3.72 (m, 0.53H), 3.52-3.38 (m, 1H), 3.18-3.11 (m, 0.49H), 3.07-2.95 (m, 1H), 2.22 (m, 0.76H), 2.14 (m, 0.41H), 1.99-1.78 (m, 2H), 1.77-1.62 (m, 1H), 1.48-1.30 (m, 11H), 1.13-1.01 (m, 1H), 0.32-0.20 (m, 2H), 0.17-0.06 (m, 2H); LCMS (M+H)+=527.4; Retention Time: 1.37 min (Method 1).

The Examples in the tables below were prepared in the same manner as that outlined for Examples 1-8 above.

TABLE 1

| Cmpd # | Structure | Name | Obs. MS Ion | HPLC Method IDs | RT (min) |
|---|---|---|---|---|---|
| 9. | 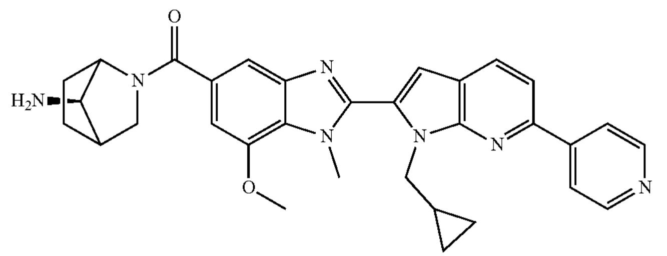 [SMILES: COc1cc(C(=O)N2CC3CCC2[C@@H]3N)cc2nc(-c3cc4ccc(-c5ccncc5)nc4n3CC3CC3)n(C)c12] | (1R,4R,7R)-2-{2-[1-(cyclopropylmethyl)-6-(pyridin-4-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 548 | 1 | 1.6 |
| 10. | 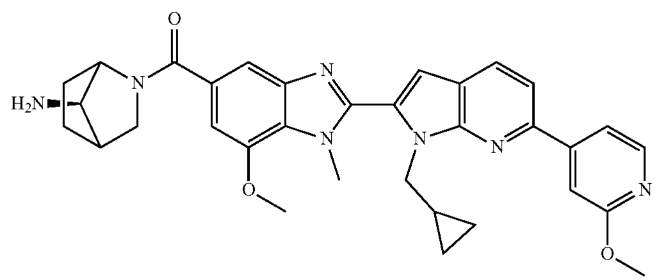 [SMILES: COc1cc(-c2ccc3cc(-c4nc5cc(C(=O)N6CC7CCC6[C@@H]7N)cc(OC)c5n4C)n(CC4CC4)c3n2)ccn1] | (1R,4R,7R)-2-{2-[1-(cyclopropylmethyl)-6-(2-methoxypyridin-4-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 578.3 | 1 | 1.76 |
| 11. | 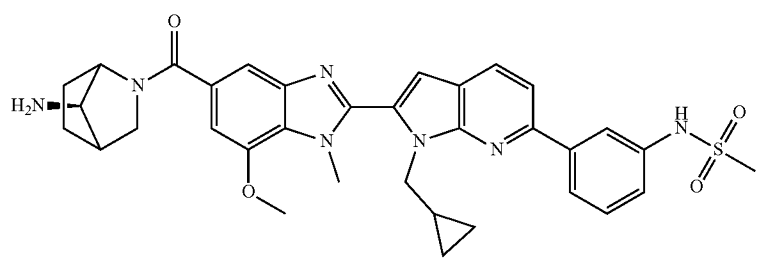 [SMILES: COc1cc(C(=O)N2CC3CCC2[C@@H]3N)cc2nc(-c3cc4ccc(-c5cccc(NS(C)(=O)=O)c5)nc4n3CC3CC3)n(C)c12] | N-[3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]methanesulfonamide | 640.2 | 2 | 1.41 |

TABLE 1-continued

| Cmpd # | Structure | Name | Obs. MS Ion | HPLC Method IDs | RT (min) |
|---|---|---|---|---|---|
| 12. | 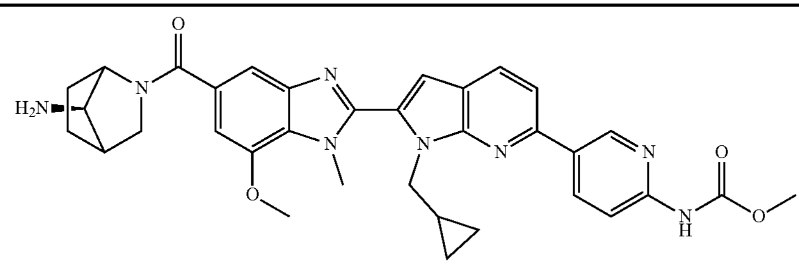 | methyl N-[5-(2-{5-[(1R,4R,7R)-7-amino-2-azabicyclo[2.2.1]heptane-2-carbonyl]-7-methoxy-1H-1,3 benzodiazol-2-yl}-1-(cyclopropylmethyl)-1H-pyrrolo[2,3-b]pyridin-6-yl)pyridin-2-yl]carbamate | 621.2 | 1 | 1.57 |
| 13. | 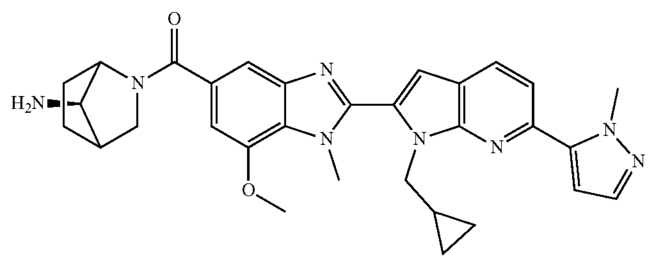 [SMILES: COc1cc(C(=O)N2CC3CCC2[C@@H]3N)cc2nc(-c3cc4ccc(-c5ccnn5C)nc4n3CC3CC3)n(C)c12] | (1R,4R,7R)-2-{2-[1-(cyclopropylmethyl)-6-(1-methyl-1H-pyrazol-5-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 551 | 2 | 1.47 |
| 14. | 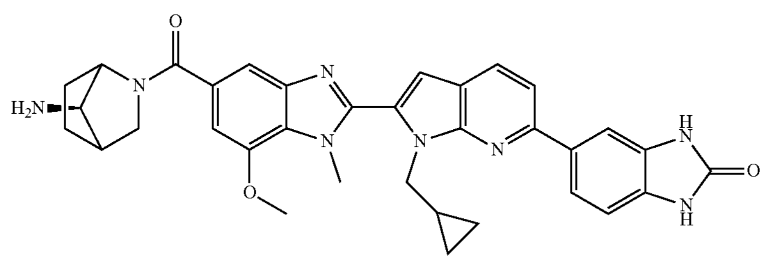 [SMILES: COc1cc(C(=O)N2CC3CCC2[C@@H]3N)cc2nc(-c3cc4ccc(-c5ccc6[nH]c(=O)[nH]c6c5)nc4n3CC3CC3)n(C)c12] | 5-(2-{5-[(1R,4R,7R)-7-amino-2-azabicyclo[2.2.1]heptane-2-carbonyl]-7-methoxy-1H-1,3-benzodiazol-2-yl}-1-(cyclopropylmethyl)-1H-pyrrolo[2,3-b]pyridin-6-yl)-2,3-dihydro-1H-1,3-benzodiazol-2-one | 603.1 | 1 | 1.31 |
| 15. | 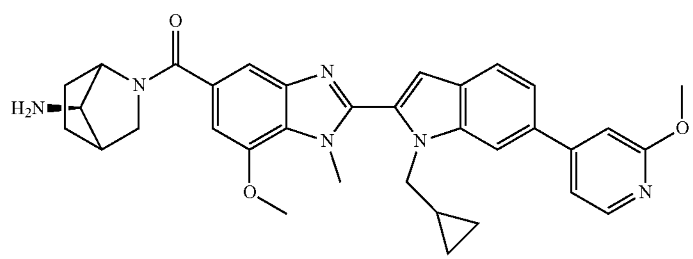 [SMILES: COc1cc(-c2ccc3cc(-c4nc5cc(C(=O)N6CC7CCC6[C@@H]7N)cc(OC)c5n4C)n(CC4CC4)c3c2)ccn1] | (1R,4R,7R)-2-{2-[1-(cyclopropylmethyl)-6-(2-methoxypyridin-4-yl)-1H-indol-2-yl]-7-methoxy-1-methyl-1H-1,3-benzodiazole-5-carbonyl}-2-azabicyclo[2.2.1]heptan-7-amine | 577.2 | 2 | 1.4 |

TABLE 1-continued

| Cmpd # | Structure | Name | Obs. MS Ion | HPLC Method IDs | RT (min) |
|---|---|---|---|---|---|
| 16. | 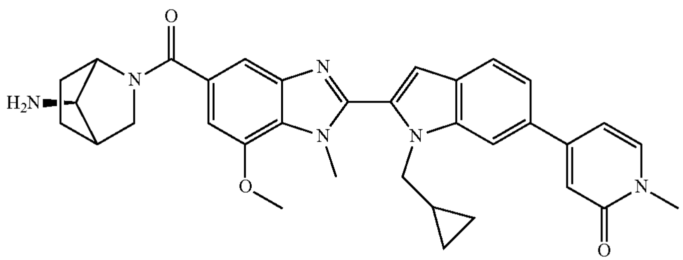 [SMILES: COc1cc(C(=O)N2CC3CCC2[C@@H]3N)cc2nc(-c3cc4ccc(-c5ccn(C)c(=O)c5)cc4n3CC3CC3)n(C)c12] | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-1-methyl-1,2-dihydropyridin-2-one | 577.1 | 1 | 1.34 |
| 17. | 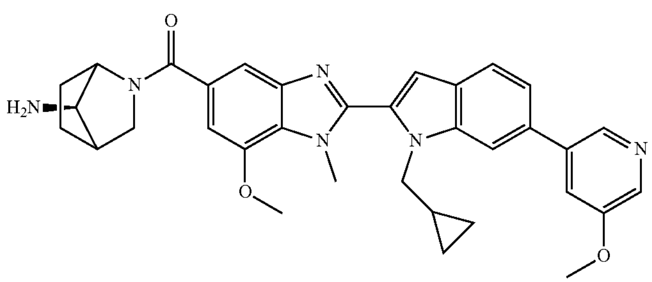 [SMILES: COc1cncc(-c2ccc3cc(-c4nc5cc(C(=O)N6CC7CCC6[C@@H]7N)cc(OC)c5n4C)n(CC4CC4)c3c2)c1] | (1R,4R,7R)-2-{2-[1-(cyclopropylmethyl)-6-(5-methoxypyridin-3-yl)-1H-indol-2-yl]-7-methoxy-1-methyl-1H-1,3-benzodiazole-5-carbonyl}-2-azabicyclo[2.2.1]heptan-7-amine | 577.3 | 1 | 1.57 |
| 18. | 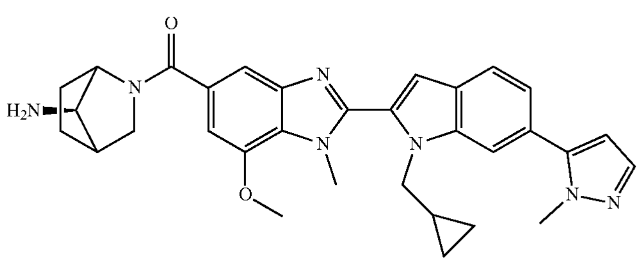 [SMILES: COc1cc(C(=O)N2CC3CCC2[C@@H]3N)cc2nc(-c3cc4ccc(-c5ccnn5C)cc4n3CC3CC3)n(C)c12] | (1R,4R,7R)-2-{2-[1-(cyclopropylmethyl)-6-(1-methyl-1H-pyrazol-5-yl)-1H-indol-2-yl]-7-methoxy-1-methyl-1H-1,3-benzodiazole-5-carbonyl}-2-azabicyclo[2.2.1]heptan-7-amine | 550.4 | 1 | 1.42 |

TABLE 1-continued

| Cmpd # | Structure | Name | Obs. MS Ion | HPLC Method IDs | RT (min) |
|---|---|---|---|---|---|
| 19. | 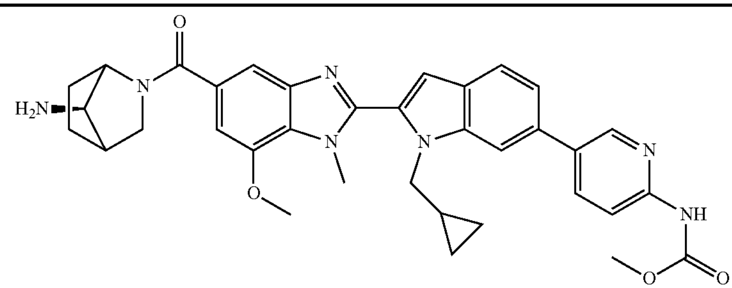 | methyl N-[5-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)pyridin-2-yl]carbamate | 620.2 | 2 | 1.26 |
| 20. | 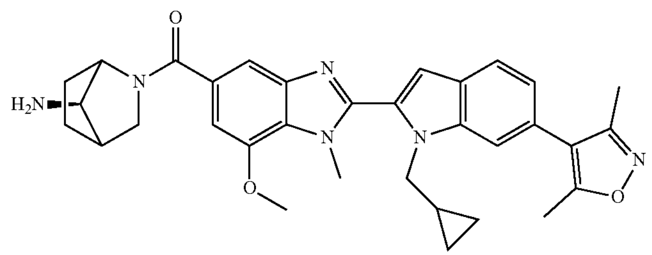 [SMILES: COc1cc(C(=O)N2CC3CCC2[C@@H]3N)cc2nc(-c3cc4ccc(-c5c(C)noc5C)cc4n3CC3CC3)n(C)c12] | (1R,4R,7R)-2-{2-[1-(cyclopropylmethyl)-6-(3,5-dimethyl-1,2-oxazol-4-yl)-1H-indol-2-yl]-7-methoxy-1-methyl-1H-1,3-benzodiazole-5-carbonyl}-2-azabicyclo[2.2.1]heptan-7-amine | 565.4 | 2 | 1.46 |
| 21. | 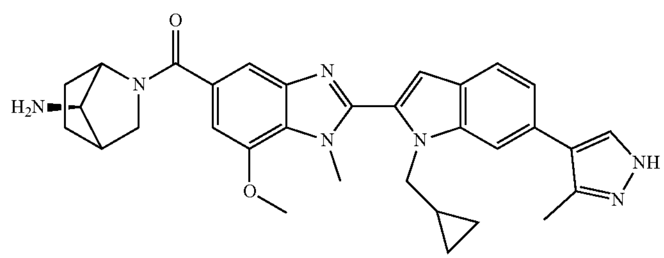 [SMILES: COc1cc(C(=O)N2CC3CCC2[C@@H]3N)cc2nc(-c3cc4ccc(-c5c[nH]nc5C)cc4n3CC3CC3)n(C)c12] | (1R,4R,7R)-2-{2-[1-(cyclopropylmethyl)-6-(3-methyl-1H-pyrazol-4-yl)-1H-indol-2-yl]-7-methoxy-1-methyl-1H-1,3-benzodiazole-5-carbonyl}-2-azabicyclo[2.2.1]heptan-7-amine | 550.4 | 1 | 1.32 |

TABLE 1-continued

| Cmpd # | Structure | Name | Obs. MS Ion | HPLC Method IDs | RT (min) |
|---|---|---|---|---|---|
| 22. | 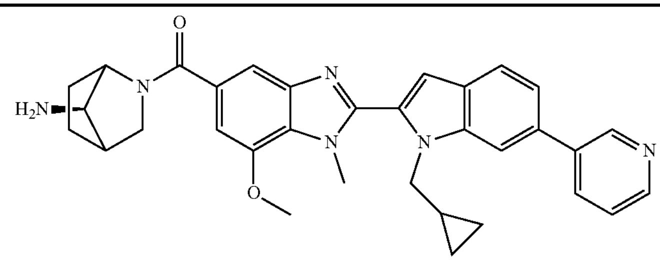 | (1R,4R,7R)-2-{2-[1-(cyclopropylmethyl)-6-(pyridin-3-yl)-1H-indol-2-yl]-7-methoxy-1-methyl-1H-1,3-benzodiazole-5-carbonyl}-2-azabicyclo[2.2.1]heptan-7-amine | 547.4 | 1 | 1.49 |
| 23. | 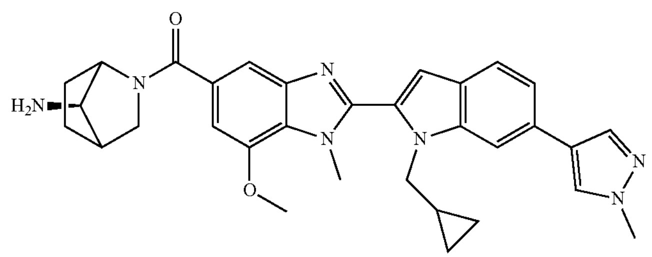 [SMILES: COc1cc(C(=O)N2CC3CCC2[C@@H]3N)cc2nc(-c3cc4ccc(-c5cnn(C)c5)cc4n3CC3CC3)n(C)c12] | (1R,4R,7R)-2-{2-[1-(cyclopropylmethyl)-6-(1-methyl-1H-pyrazol-4-yl)-1H-indol-2-yl]-7-methoxy-1-methyl-1H-1,3-benzodiazole-5-carbonyl}-2-azabicyclo[2.2.1]heptan-7-amine | 550.2 | 1 | 1.77 |
| 24. | 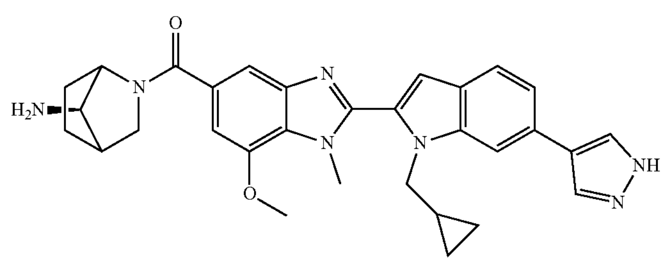 [SMILES: COc1cc(C(=O)N2CC3CCC2[C@@H]3N)cc2nc(-c3cc4ccc(-c5cn[nH]c5)cc4n3CC3CC3)n(C)c12] | (1R,4R,7R)-2-{2-[1-(cyclopropylmethyl)-6-(1H-pyrazol-4-yl)-1H-indol-2-yl]-7-methoxy-1-methyl-1H-1,3-benzodiazole-5-carbonyl}-2-azabicyclo[2.2.1]heptan-7-amine | 536.3 | 1 | 1.22 |

TABLE 1-continued

| Cmpd # | Structure | Name | Obs. MS Ion | HPLC Method IDs | RT (min) |
|---|---|---|---|---|---|
| 25. | 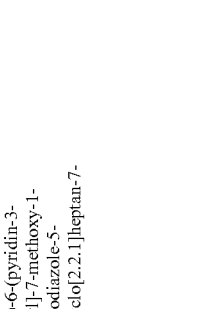 | (1R,4R,7R)-2-{2-[1-(cyclopropylmethyl)-6-(pyridin-3-yloxy)-1H-indol-2-yl]-7-methoxy-1-methyl-1H-1,3-benzodiazole-5-carbonyl}-2-azabicyclo[2.2.1]heptan-7-amine | 563 | 1 | 1.53 |
| 26. | 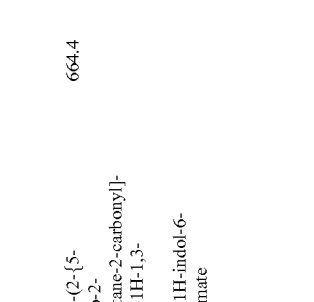 | 2-methoxyethyl N-[5-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)pyridin-2-yl]carbamate | 664.4 | 1 | 1.59 |
| 27. | 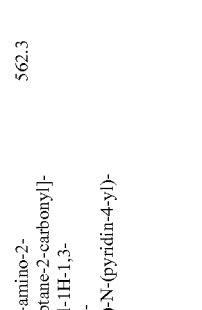 | 2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-N-(pyridin-4-yl)-1H-indol-6-amine | 562.3 | 1 | 1.15 |

TABLE 1-continued

| Cmpd # | Structure | Name | Obs. MS Ion | HPLC Method IDs | RT (min) |
|---|---|---|---|---|---|
| 28 | 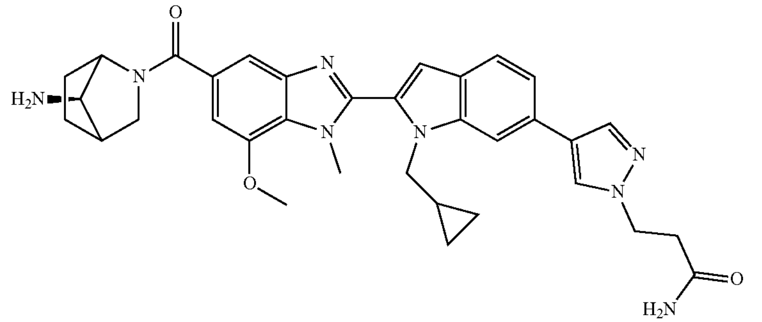 [SMILES: COc1cc(C(=O)N2CC3CCC2[C@@H]3N)cc2nc(-c3cc4ccc(-c5cnn(CCC(N)=O)c5)cc4n3CC3CC3)n(C)c12] | 3-[4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-1H-pyrazol-1-yl]propanamide | 607.1 | 1 | 1.18 |
| 29. | 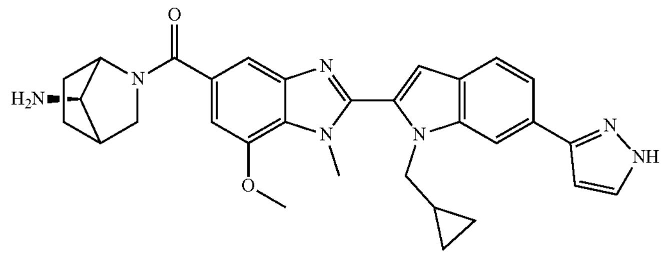 [SMILES: COc1cc(C(=O)N2CC3CCC2[C@@H]3N)cc2nc(-c3cc4ccc(-c5cc[nH]n5)cc4n3CC3CC3)n(C)c12] | (1R,4R,7R)-2-{2-[1-(cyclopropylmethyl)-6-(1H-pyrazol-3-yl)-1H-indol-2-yl]-7-methoxy-1-methyl-1H-1,3-benzodiazole-5-carbonyl}-2-azabicyclo[2.2.1]heptan-7-amine | 536.3 | 1 | 1.39 |
| 30. | 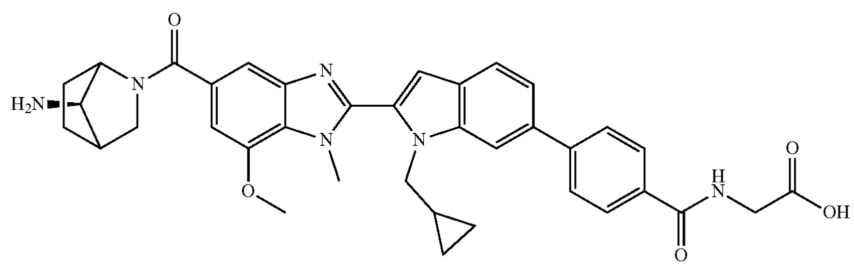 [SMILES: COc1cc(C(=O)N2CC3CCC2[C@@H]3N)cc2nc(-c3cc4ccc(-c5ccc(C(=O)NCC(=O)O)cc5)cc4n3CC3CC3)n(C)c12] | 2-[[4-(2-{5-[(1R,4R,7R)-7-amino-2-azabicyclo[2.2.1]heptane-2-carbonyl]-7-methoxy-1-methyl-1H,1,3-benzodiazol-2-yl}-1-(cyclopropylmethyl)-1H-indol-6-yl)phenyl]foramido]acetic acid | 647.1 | 1 | 1.15 |

TABLE 1-continued

| Cmpd # | Structure | Name | Obs. MS Ion | HPLC Method IDs | RT (min) |
|---|---|---|---|---|---|
| 31. | 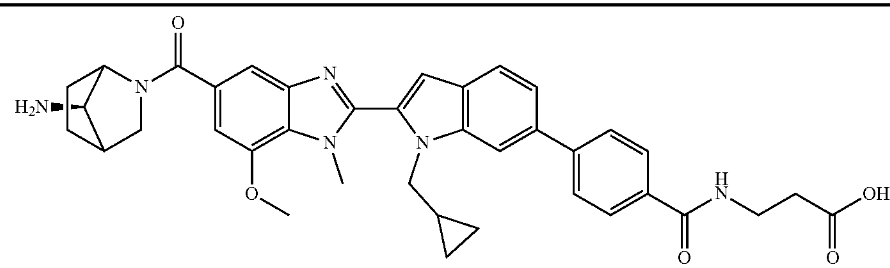 | 3-[[4-(2-{5-[(1R,4R,7R)-7-amino-2-azabicyclo[2.2.1]heptane-2-carbonyl]-7-methoxy-1-methyl-1H-1,3-benzodiazol-2-yl]-1-(cyclopropylmethyl)-1H-indol-6-yl)phenyl]foramido}propanpoic acid | 661.2 | 1 | 1.19 |
| 32. | 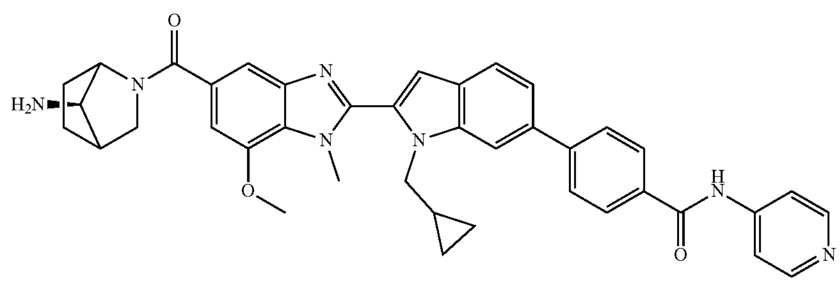 [SMILES: COc1cc(C(=O)N2CC3CCC2[C@@H]3N)cc2nc(-c3cc4ccc(-c5ccc(C(=O)Nc6ccncc6)cc5)cc4n3CC3CC3)n(C)c12] | 4-(2-{5-[(1R,4R,7R)-7-amino-2-azabicyclo[2.2.1]heptane-2-carbonyl]-7-methoxy-1-methyl-1H-1,3-benzodiazol-2-yl]-1-(cyclopropylmethyl)-1H-indol-6-yl)-N-(pyridin-4-yl)benzamide | 666 | 2 | 1.2 |
| 33. | 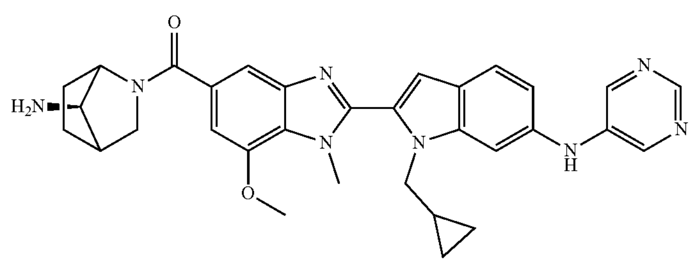 [SMILES: COc1cc(C(=O)N2CC3CCC2[C@@H]3N)cc2nc(-c3cc4ccc(Nc5cncnc5)cc4n3CC3CC3)n(C)c12] | 2-{5-[(1R,4R,7R)-7-amino-2-azabicycio[2.2.1]heptane-2-carbonyl]-7-methoxy-1-methyl-1H-1,3-benzodiazol-2-yl]-1-(cyclopropylmethyl)-1H-indol-6-yl}-N-(pyrimidin-5-yl)-1H-indol-6-amine | 563.3 | 2 | 1.07 |

TABLE 1-continued

| Cmpd # | Structure | Name | Obs. MS Ion | HPLC Method IDs | RT (min) |
|---|---|---|---|---|---|
| 34. | 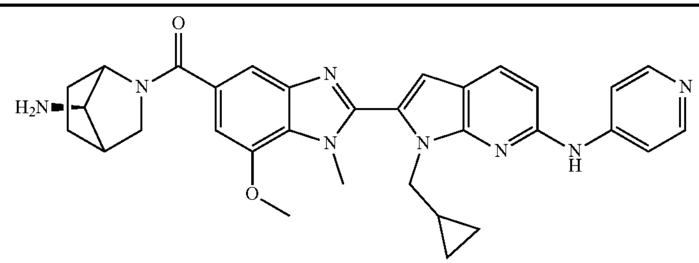 | (1R,4R,7R)-2-{2-[1-(cyclopropylmethyl)-6-[(pyridin-4-yl)amino]-1H-pyrrolo[2,3-b]pyridin-2-yl]-7-methoxy-1-methyl-1H-1,3-benzodiazole-5-carbonyl}-2-azabicyclo[2.2.1]heptan-7-amine | | 1 | |
| 35. | 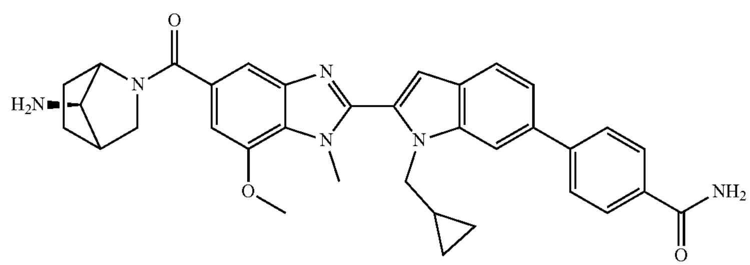 [SMILES: COc1cc(C(=O)N2CC3CCC2[C@@H]3N)cc2nc(-c3cc4ccc(-c5ccc(C(N)=O)cc5)cc4n3CC3CC3)n(C)c12] | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)benzamide | 589.4 | 1 | 1.42 |
| 36. | 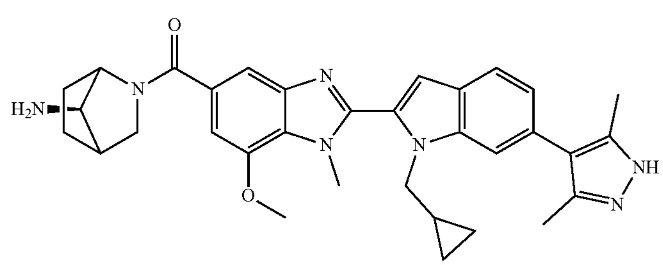 [SMILES: COc1cc(C(=O)N2CC3CCC2[C@@H]3N)cc2nc(-c3cc4ccc(-c5c(C)n[nH]c5C)cc4n3CC3CC3)n(C)c12] | (1R,4R,7R)-2-{2-[1-(cyclopropylmethyl)-6-(3,5-dimethyl-1H-pyrazol-4-yl)-1H-indol-2-yl]-7-methoxy-1-methyl-1H-1,3-benzodiazole-5-carbonyl}-2-azabicyclo[2.2.1]heptan-7-amine | 564.4 | 1 | 1.36 |

TABLE 1-continued

| Cmpd # | Structure | Name | Obs. MS Ion | HPLC Method IDs | RT (min) |
|---|---|---|---|---|---|
| 37. | 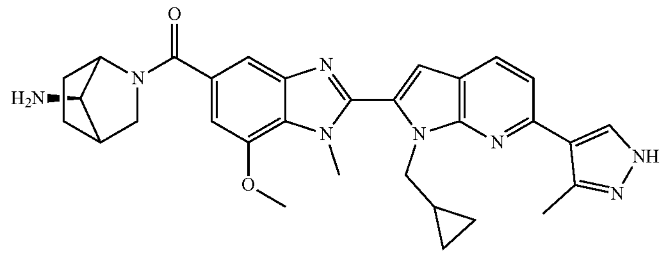 [SMILES: COc1cc(C(=O)N2CC3CCC2[C@@H]3N)cc2nc(-c3cc4ccc(-c5c[nH]nc5C)nc4n3CC3CC3)n(C)c12] | (1R,4R,7R)-2-{2-[1-(cyclopropylmethyl)-6-(3-methyl-1H-pyrazol-4-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 551.3 | 1 | 1.32 |
| 38. | 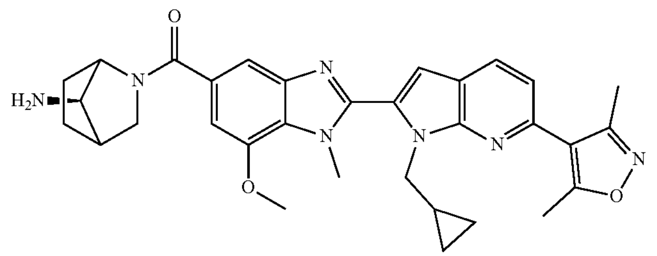 [SMILES: COc1cc(C(=O)N2CC3CCC2[C@@H]3N)cc2nc(-c3cc4ccc(-c5c(C)noc5C)nc4n3CC3CC3)n(C)c12] | (1R,4R,7R)-2-{2-[1-(cyclopropylmethyl)-6-(3,5-dimethyl-1,2-oxazol-4-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 566.3 | 1 | 1.62 |
| 39. | 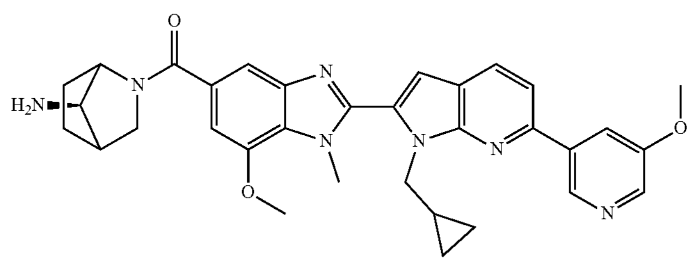 [SMILES: COc1cncc(-c2ccc3cc(-c4nc5cc(C(=O)N6CC7CCC6[C@@H]7N)cc(OC)c5n4C)n(CC4CC4)c3n2)c1] | (1R,4R,7R)-2-{2-[1-(cyclopropylmethyl)-6-(5-methoxypyridin-3-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 577.9 | 1 | 1.55 |

TABLE 1-continued

| Cmpd # | Structure | Name | Obs. MS Ion | HPLC Method IDs | RT (min) |
|---|---|---|---|---|---|
| 40. | 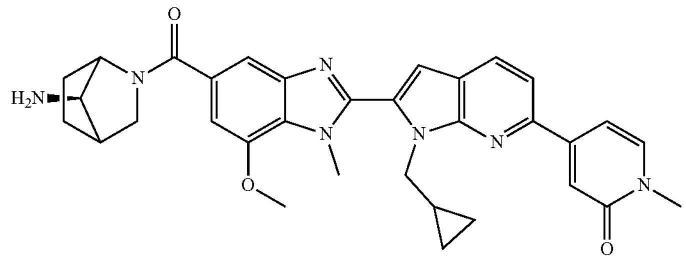 [SMILES: COc1cc(C(=O)N2CC3CCC2[C@@H]3N)cc2nc(-c3cc4ccc(-c5ccn(C)c(=O)c5)nc4n3CC3CC3)n(C)c12] | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1-methyl-1,2-dihydropyridin-2-one | 578.1 | 2 | 1.16 |
| 41. | 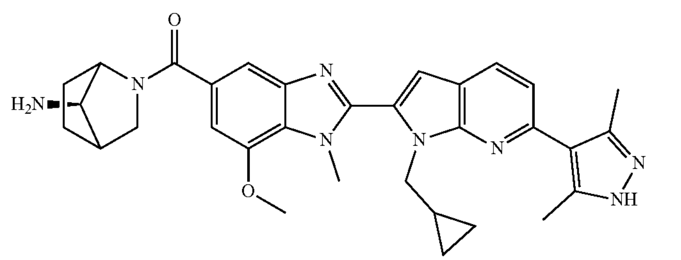 [SMILES: COc1cc(C(=O)N2CC3CCC2[C@@H]3N)cc2nc(-c3cc4ccc(-c5c(C)n[nH]c5C)nc4n3CC3CC3)n(C)c12] | (1R,4R,7R)-2-{2-[1-(cyclopropylmethyl)-6-(3,5-dimethyl-1H-pyrazol-4-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 565.2 | 1 | 1.38 |
| 42. | 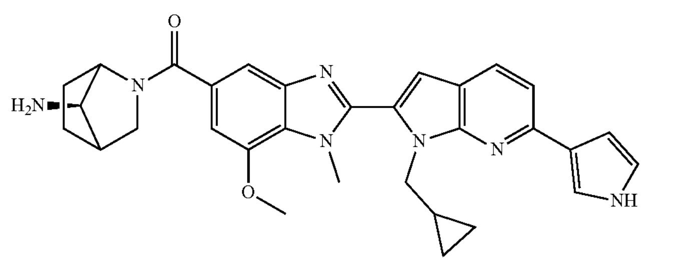 [SMILES: COc1cc(C(=O)N2CC3CCC2[C@@H]3N)cc2nc(-c3cc4ccc(-c5cc[nH]c5)nc4n3CC3CC3)n(C)c12] | (1R,4R,7R)-2-{2-[1-(cyclopropylmethyl)-6-(1H-pyrrol-3-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 536.1 | 2 | 1.25 |

TABLE 1-continued

| Cmpd # | Structure | Name | Obs. MS Ion | HPLC Method IDs | RT (min) |
|---|---|---|---|---|---|
| 43. | 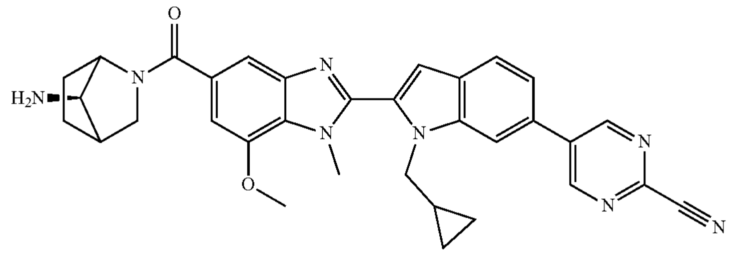 [SMILES: COc1cc(C(=O)N2CC3CCC2[C@@H]3N)cc2nc(-c3cc4ccc(-c5cnc(C#N)nc5)cc4n3CC3CC3)n(C)c12] | 5-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)pyrimidine-2-carbonitrile | 573.4 | 1 | 1.64 |
| 44. | 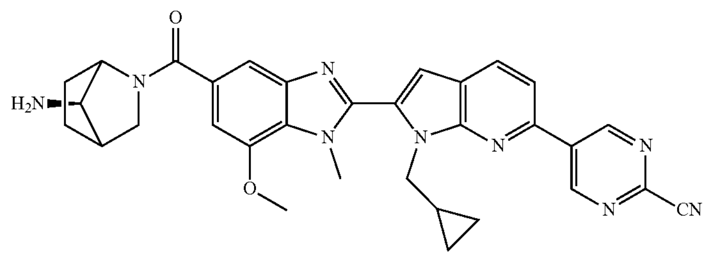 [SMILES: COc1cc(C(=O)N2CC3CCC2[C@@H]3N)cc2nc(-c3cc4ccc(-c5cnc(C#N)nc5)nc4n3CC3CC3)n(C)c12] | 5-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)pyrimidine-2-carbonitrile | 574.1 | 1 | 1.61 |
| 45. | 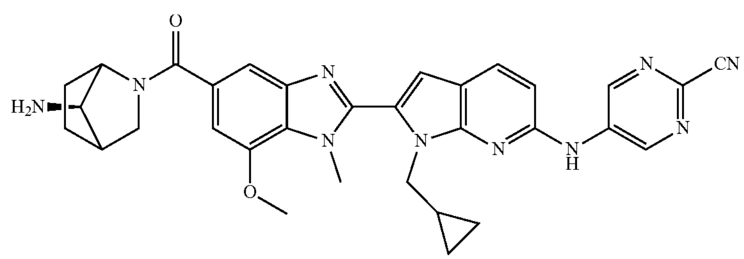 [SMILES: COc1cc(C(=O)N2CC3CCC2[C@@H]3N)cc2nc(-c3cc4ccc(Nc5cnc(C#N)nc5)nc4n3CC3CC3)n(C)c12] | 5-[(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)amino]pyrimidine-2-carbonitrile | 588.4 | 2 | 1.36 |

TABLE 2

| Cmpd # | Structure | Name | Obs. MS Ion | HPLC Method IDs | RT (min) |
|---|---|---|---|---|---|
| 46. | 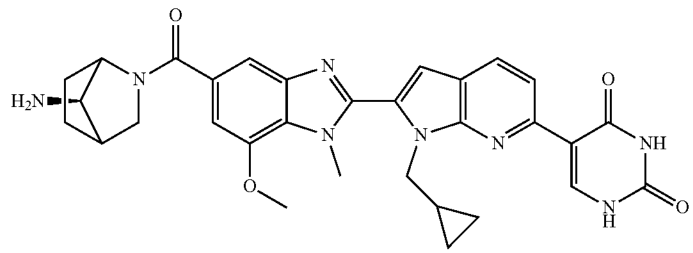 [SMILES: COc1cc(C(=O)N2CC3CCC2[C@@H]3N)cc2nc(-c3cc4ccc(-c5c[nH]c(=O)[nH]c5=O)nc4n3CC3CC3)n(C)c12] | 5-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1,2,3,4-tetrahydropyrimidine-2,4-dione | 581.4 | 1 | 1.12 |
| 47. | 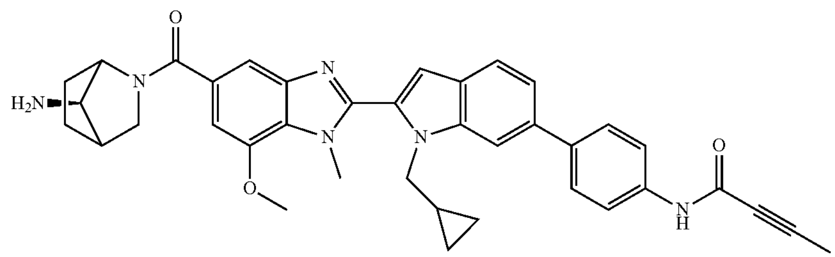 [SMILES: CC#CC(=O)Nc1ccc(-c2ccc3cc(-c4nc5cc(C(=O)N6CC7CCC6[C@@H]7N)cc(OC)c5n4C)n(CC4CC4)c3c2)cc1] | N-[4-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)phenyl]but-2-ynamide | 627.2 | 1 | 1.66 |
| 48. | 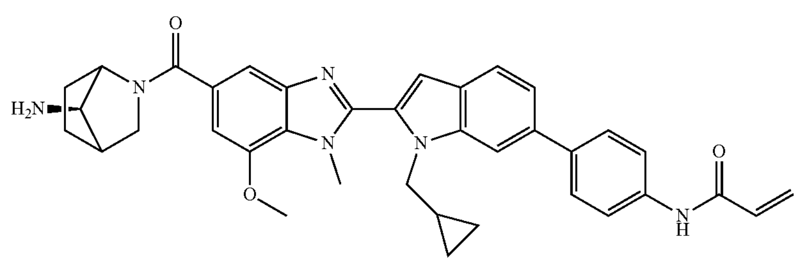 [SMILES: C=CC(=O)Nc1ccc(-c2ccc3cc(-c4nc5cc(C(=O)N6CC7CCC6[C@@H]7N)cc(OC)c5n4C)n(CC4CC4)c3c2)cc1] | N-[4-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)phenyl]prop-2-enamide | 615.2 | 2 | 1.44 |

TABLE 2-continued

| Cmpd # | Structure | Name | Obs. MS Ion | HPLC Method IDs | RT (min) |
|---|---|---|---|---|---|
| 49. | 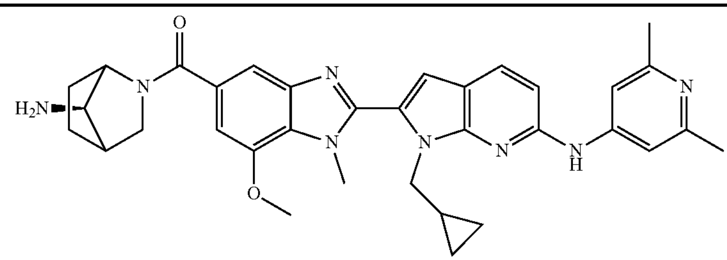 | (1R,4R,7R)-2-{2-[1-(cyclopropylmethyl)-6-[(2,6-dimethylpyridin-4-yl)amino]-1H-pyrrolo[2,3-b]pyridin-2-yl]-7-methoxy-1-methyl-1H-1,3-benzodiazole-5-carbonyl}-2-azabicyclo[2.2.1]heptan-7-amine | 591.4 | 1 | 1.2 |
| 50. | 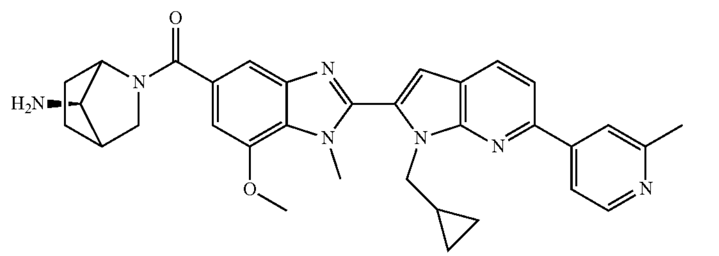 [SMILES: COc1cc(C(=O)N2CC3CCC2[C@@H]3N)cc2nc(-c3cc4ccc(-c5ccnc(C)c5)nc4n3CC3CC3)n(C)c12] | (1R,4R,7R)-2-{2-[1-(cyclopropylmethyl)-6-(2-methylpyridin-4-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 562.2 | 1 | 1.53 |
| 51. | 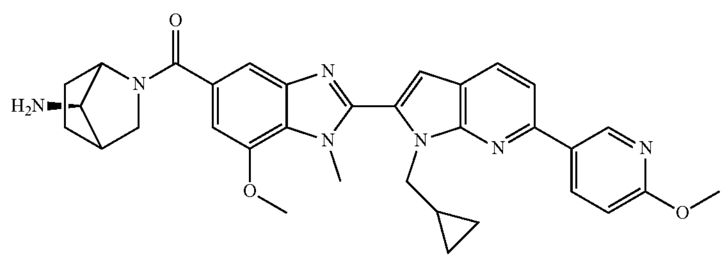 [SMILES: COc1ccc(-c2ccc3cc(-c4nc5cc(C(=O)N6CC7CCC6[C@@H]7N)cc(OC)c5n4C)n(CC4CC4)c3n2)cn1] | (1R,4R,7R)-2-{2-[1-(cyclopropylmethyl)-6-(6-methoxypyridin-3-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 578 | 1 | 1.96 |
| 52. | 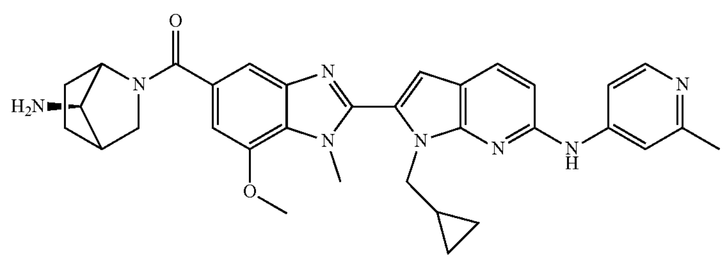 [SMILES: COc1cc(C(=O)N2CC3CCC2[C@@H]3N)cc2nc(-c3cc4ccc(Nc5ccnc(C)c5)nc4n3CC3CC3)n(C)c12] | (1R,4R,7R)-2-{2-[1-(cyclopropylmethyl)-6-[(2-methylpyridin-4-yl)amino]-1H-pyrrolo[2,3-b]pyridin-2-yl]-7-methoxy-1-methyl-1H-1,3-benzodiazole-5-carbonyl}-2-azabicyclo[2.2.1]heptan-7-amine | 577 | 1 | 1.4 |

TABLE 2-continued

| Cmpd # | Structure | Name | Obs. MS Ion | HPLC Method IDs | RT (min) |
|---|---|---|---|---|---|
| 53. | 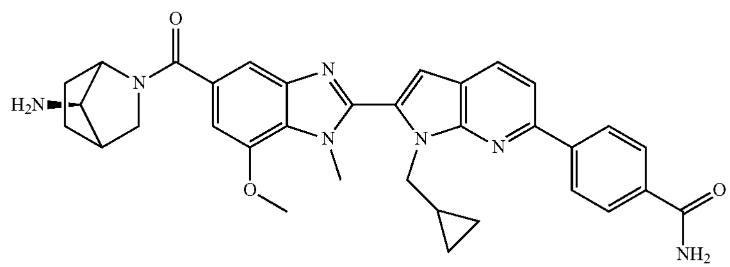 | 4-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)benzamide | 590.3 | 2 | 1.2 |
| 54. | 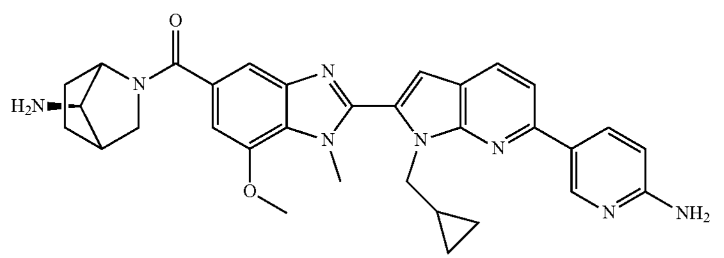 [SMILES: COc1cc(C(=O)N2CC3CCC2[C@@H]3N)cc2nc(-c3cc4ccc(-c5ccc(N)nc5)nc4n3CC3CC3)n(C)c12] | (1R,4R,7R)-2-{2-[6-(6-aminopyridin-3-yl)-1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 563.4 | 2 | 1.01 |
| 55. | 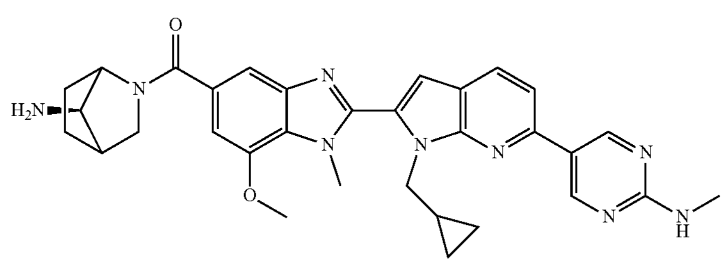 [SMILES: CNc1ncc(-c2ccc3cc(-c4nc5cc(C(=O)N6CC7CCC6[C@@H]7N)cc(OC)c5n4C)n(CC4CC4)c3n2)cn1] | (1R,4R,7R)-2-{2-[1-(cyclopropylmethyl)-6-[2-(methylamino)pyrimidin-5-yl]-1H-pyrrolo[2,3-b]pyridin-2-yl]-7-methoxy-1-methyl-1H-1,3-benzodiazole-5-carbonyl}-2-azabicyclo[2.2.1]heptan-7-amine | 578.3 | 1 | 1.48 |

TABLE 2-continued

| Cmpd # | Structure | Name | Obs. MS Ion | HPLC Method IDs | RT (min) |
|---|---|---|---|---|---|
| 56. | 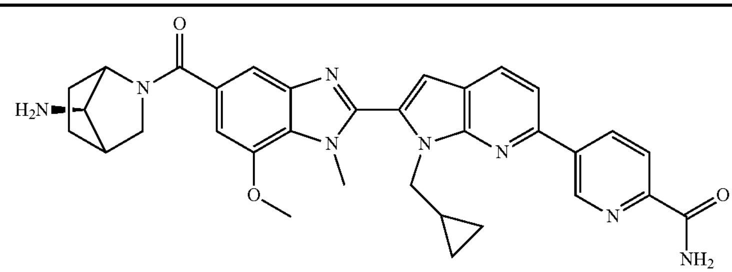 | 5-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)pyridine-2-carboxamide | 591.1 | 1 | 1.41 |
| 57. | 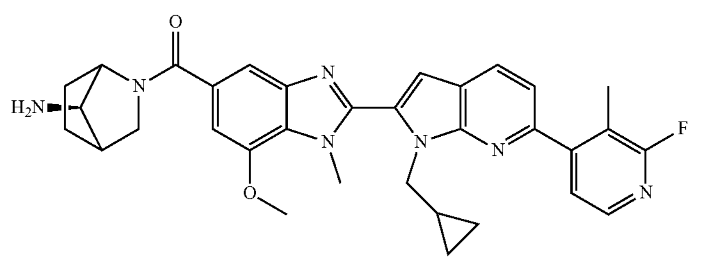 [SMILES: COc1cc(C(=O)N2CC3CCC2[C@@H]3N)cc2nc(-c3cc4ccc(-c5ccnc(F)c5C)nc4n3CC3CC3)n(C)c12] | (1R,4R,7R)-2-{2-[1-(cyclopropylmethy)-6-(2-fluoro-3-methylpyridin-4-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 580.4 | 2 | 1.56 |
| 58. | 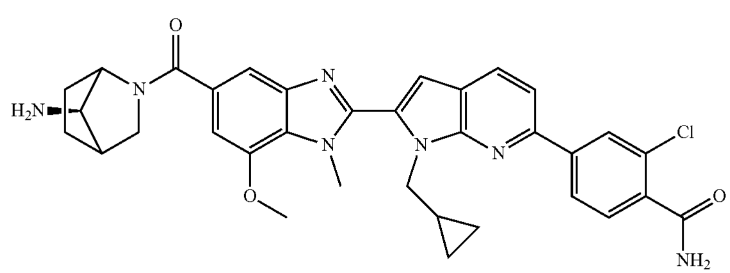 [SMILES: COc1cc(C(=O)N2CC3CCC2[C@@H]3N)cc2nc(-c3cc4ccc(-c5ccc(C(N)=O)c(Cl)c5)nc4n3CC3CC3)n(C)c12] | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-chlorobenzamide | 624.3 | 1 | 1.42 |

TABLE 2-continued

| Cmpd # | Structure | Name | Obs. MS Ion | HPLC Method IDs | RT (min) |
|---|---|---|---|---|---|
| 59. | 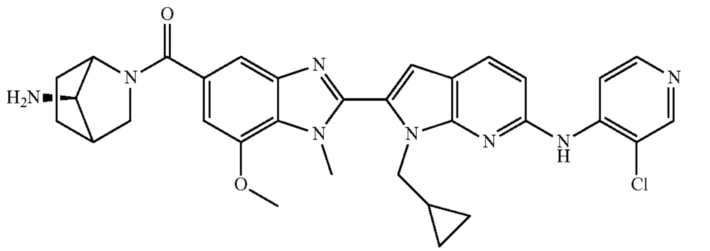 [SMILES: COc1cc(C(=O)N2CC3CCC2[C@@H]3N)cc2nc(-c3cc4ccc(Nc5ccncc5Cl)nc4n3CC3CC3)n(C)c12] | (1R,4R,7R)-2-(2-{6-[(3-chloropyridin-4-yl)amino]-1-(cyclopropylmethyl)-1H-pyrrolo[2,3-b]pyridin-2-yl}-7-methoxy-1-methyl-1H-1,3-benzodiazole-5-carbonyl)-2-azabicyclo[2.2.1]heptan-7-amine | 597.3 | 1 | 1.67 |
| 60. | 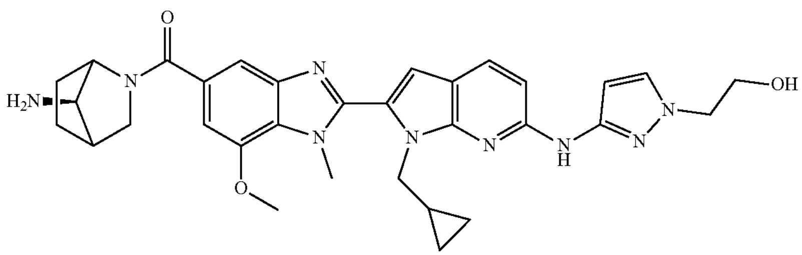 [SMILES: COc1cc(C(=O)N2CC3CCC2[C@@H]3N)cc2nc(-c3cc4ccc(Nc5ccn(CCO)n5)nc4n3CC3CC3)n(C)c12] | 2-{3-[(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)amino]-1H-pyrazol-1-yl}ethan-1-ol | 596.2 | 1 | 1.22 |
| 61. | 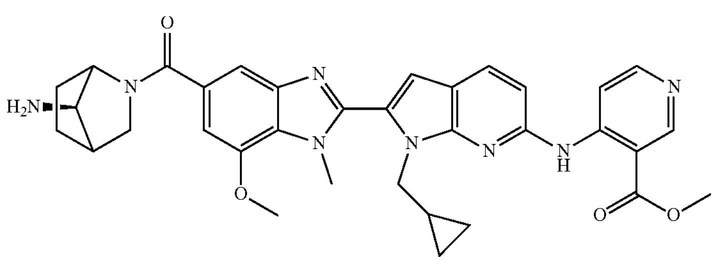 [SMILES: COC(=O)c1cnccc1Nc1ccc2cc(-c3nc4cc(C(=O)N5CC6CCC5[C@@H]6N)cc(OC)c4n3C)n(CC3CC3)c2n1] | methyl 4-[(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)amino]pyridine-3-carboxylate | 621.4 | 2 | 1.15 |

TABLE 2-continued

| Cmpd # | Structure | Name | Obs. MS Ion | HPLC Method IDs | RT (min) |
|---|---|---|---|---|---|
| 62. | 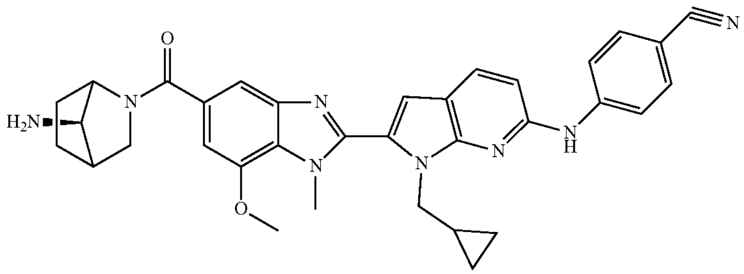 [SMILES: COc1cc(C(=O)N2CC3CCC2[C@@H]3N)cc2nc(-c3cc4ccc(Nc5ccc(C#N)cc5)nc4n3CC3CC3)n(C)c12] | 4-[(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)amino]benzonitrile | 587.4 | 1 | 1.75 |
| 63. | 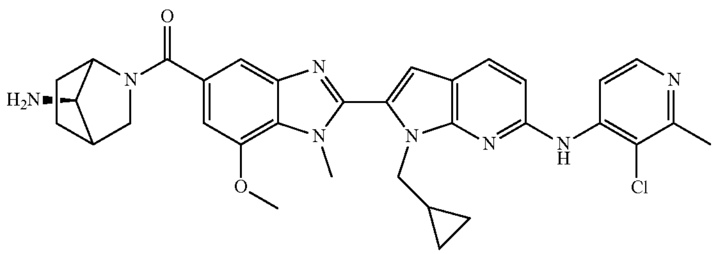 [SMILES: COc1cc(C(=O)N2CC3CCC2[C@@H]3N)cc2nc(-c3cc4ccc(Nc5ccnc(C)c5Cl)nc4n3CC3CC3)n(C)c12] | (1R,4R,7R)-2-(2-{6-((3-chloro-2-methylpyridin-4-yl)amino]-1-(cyclopropylmethyl)-1H-pyrrolo[2,3-b]pyridin-2-yl}-7-methoxy-1-methyl-1H-1,3-benzodiazole-5-carbonyl)-2-azabicyclo[2.2.1]heptan-7-amine | 611.1 | 1 | 1.76 |
| 64. | 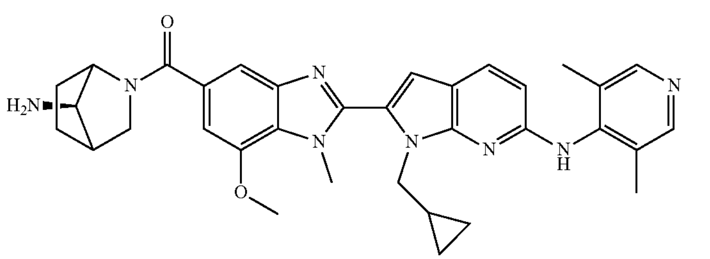 [SMILES: COc1cc(C(=O)N2CC3CCC2[C@@H]3N)cc2nc(-c3cc4ccc(Nc5c(C)cncc5C)nc4n3CC3CC3)n(C)c12] | (1R,4R,7R)-2-[2-[1-(cyclopropylmethyl)-6-[(3,5-dimethylpyridin-4-yl)amino]-1H-pyrrolo[2,3-b]pyridin-2-yl]-7-methoxy-1-methyl-1H-1,3-benzodiazole-5-carbonyl]-2-azabicyclo[2.2.1]heptan-7-amine | 591.1 | 2 | 0.99 |

TABLE 2-continued

| Cmpd # | Structure | Name | Obs. MS Ion | HPLC Method IDs | RT (min) |
|---|---|---|---|---|---|
| 65. | 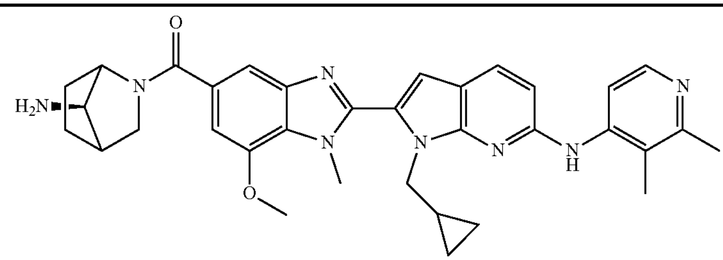 | (1R,4R,7R)-2-{2-[1-(cyclopropylmethyl)-6-[(2,3-dimethylpyridin-4-yl)amino]-1H-pyrrolo[2,3-b]pyridin-2-yl]-7-methoxy-1-methyl-1H-1,3-benzodiazole-5-carbonyl}-2-azabicyclo[2.2.1]heptan-7-amine | 591.5 | 2 | 1.1 |
| 66. | 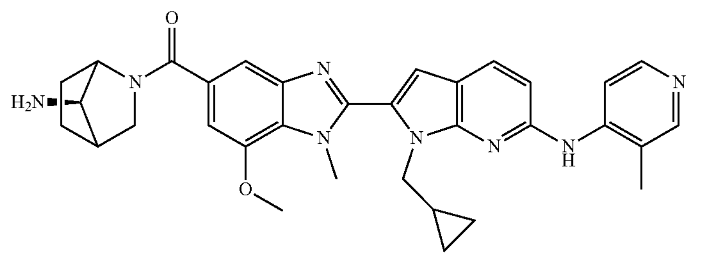 [SMILES: COc1cc(C(=O)N2CC3CCC2[C@@H]3N)cc2nc(-c3cc4ccc(Nc5ccncc5C)nc4n3CC3CC3)n(C)c12] | (1R,4R,7R)-2-{2-[1-(cyclopropylmethyl)-6-[(3-methylpyridin-4-yl)amino]-1H-pyrrolo[2,3-b]pyridin-2-yl]-7-methoxy-1-methyl-1H-1,3-benzodiazole-5-carbonyl}-2-azabicyclo[2.2.1]heptan-7-amine | 577.2 | 1 | 1.25 |
| 67. | 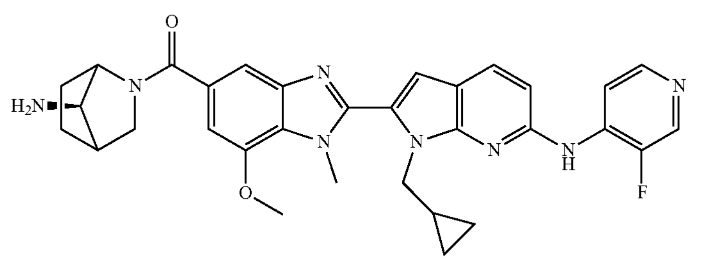 [SMILES: COc1cc(C(=O)N2CC3CCC2[C@@H]3N)cc2nc(-c3cc4ccc(Nc5ccncc5F)nc4n3CC3CC3)n(C)c12] | (1R,4R,7R)-2-{2-[1-(cyclopropylmethyl)-6-[(3-fluoropyridin-4-yl)amino]-1H-pyrrolo[2,3-b]pyridin-2-yl]-7-methoxy-1-methyl-1H-1,3-benzodiazole-5-carbonyl}-2-azabicyclo[2.2.1]heptan-7-amine | 581.3 | 2 | 0.97 |
| 68. | 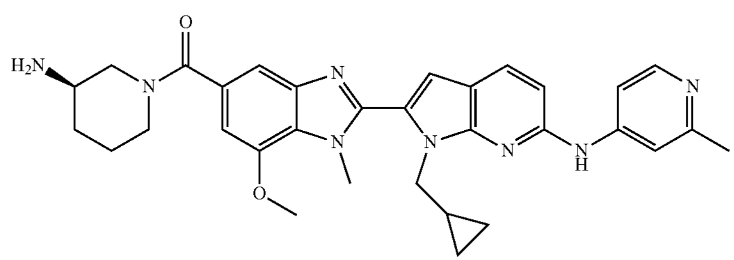 [SMILES: COc1cc(C(=O)N2CCC[C@@H](N)C2)cc2nc(-c3cc4ccc(Nc5ccnc(C)c5)nc4n3CC3CC3)n(C)c12] | N-(2-{5-[(3R)-3-aminopiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-methylpyridin-4-amine | 565.2 | 2 | 1.1 |

TABLE 2-continued

| Cmpd # | Structure | Name | Obs. MS Ion | HPLC Method IDs | RT (min) |
|---|---|---|---|---|---|
| 69. | 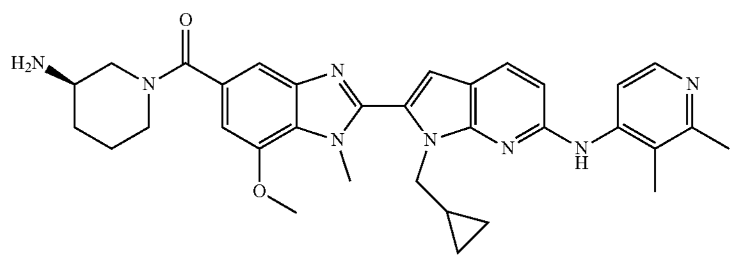 | N-(2-{5-[(3R)-3-aminopiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2,3-dimethylpyridin-4-amine | 579.2 | 2 | 1.14 |
| 70. | 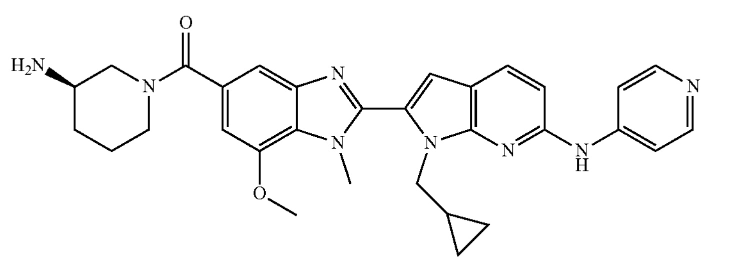 [SMILES: COc1cc(C(=O)N2CCC[C@@H](N)C2)cc2nc(-c3cc4ccc(Nc5ccncc5)nc4n3CC3CC3)n(C)c12] | N-(2-{5-[(3R)-3-aminopiperidine-1-carbonyl]-7-methoxy-1-methyl-1H-1,3-benzodiazol-2-yl}-1-(cyclopropylmethyl)-1H-pyrrolo[2,3-b]pyridin-6-yl)pyridin-4-amine | 551.1 | 1 | 1.13 |
| 71. | 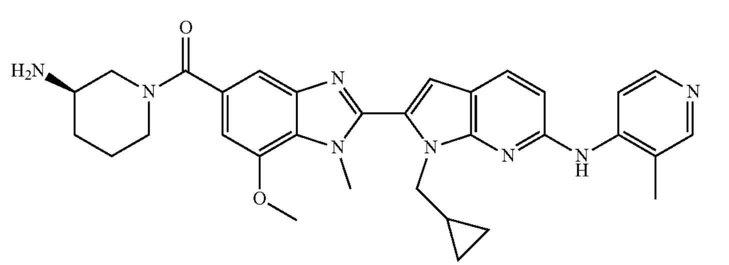 [SMILES: COc1cc(C(=O)N2CCC[C@@H](N)C2)cc2nc(-c3cc4ccc(Nc5ccncc5C)nc4n3CC3CC3)n(C)c12] | N-(2-{5-[(3R)-3-aminopiperidine-1-carbonyl]-7-methoxy-1-methyl-1H-1,3-benzodiazol-2-yl}-1-(cyclopropylmethyl)-1H-pyrrolo[2,3-b]pyridin-6-yl)-3-methylpyridin-4-amine | 565.4 | 2 | 0.96 |

TABLE 2-continued

| Cmpd # | Structure | Name | Obs. MS Ion | HPLC Method IDs | RT (min) |
|---|---|---|---|---|---|
| 72. | 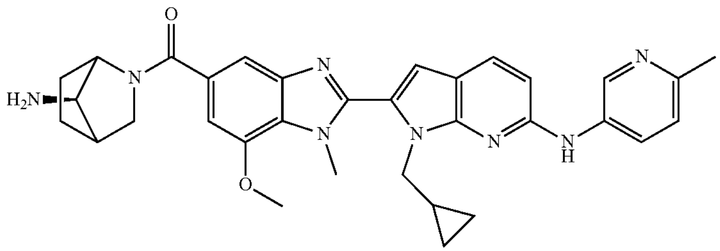 [SMILES: COc1cc(C(=O)N2CC3CCC2[C@@H]3N)cc2nc(-c3cc4ccc(Nc5ccc(C)nc5)nc4n3CC3CC3)n(C)c12] | (1R,4R,7R)-2-{2-[1-(cyclopropylmethyl)-6-[(6-methylpyridin-3-yl)amino]-1H-pyrrolo[2,3-b]pyridin-2-yl]-7-methoxy-1-methyl-1H-1,3-benzodiazole-5-carbonyl}-2-azabicyclo[2.2.1]heptan-7-amine | 577.4 | 1 | 1.54 |
| 73. | 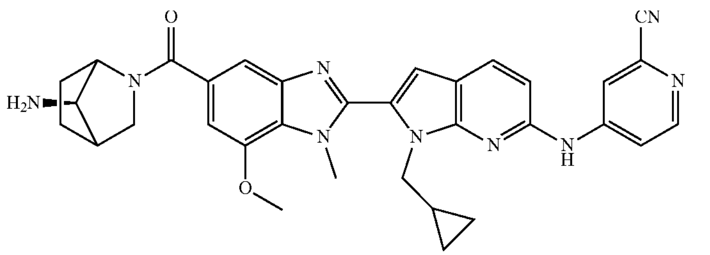 [SMILES: COc1cc(C(=O)N2CC3CCC2[C@@H]3N)cc2nc(-c3cc4ccc(Nc5ccnc(C#N)c5)nc4n3CC3CC3)n(C)c12] | 4-[(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)amino]pyridine-2-carbonitrile | 588.2 | 1 | 1.54 |
| 74. | 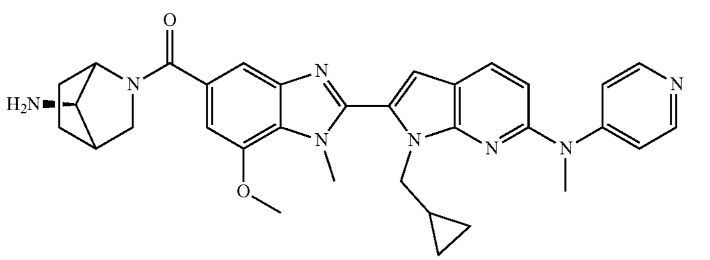 [SMILES: COc1cc(C(=O)N2CC3CCC2[C@@H]3N)cc2nc(-c3cc4ccc(N(C)c5ccncc5)nc4n3CC3CC3)n(C)c12] | (1R,4R,7R)-2-{2-[1-(cyclopropylmethyl)-6-[methyl(pyridin-4-yl)amino]-1H-pyrrolo[2,3-b]pyridin-2-yl]-7-methoxy-1-methyl-1H-1,3-benzodiazole-5-carbonyl}-2-azabicyclo[2.2.1]heptan-7-amine | 577.4 | 2 | 1 |
| 75. | 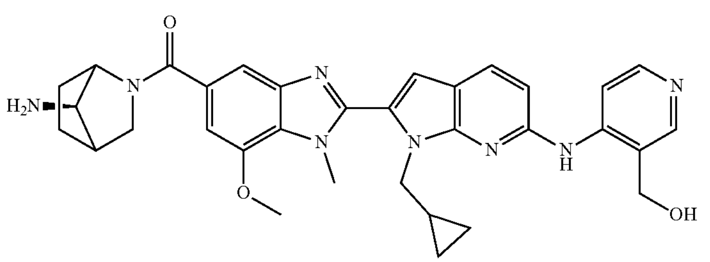 [SMILES: COc1cc(C(=O)N2CC3CCC2[C@@H]3N)cc2nc(-c3cc4ccc(Nc5ccncc5CO)nc4n3CC3CC3)n(C)c12] | {4-[(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)amino]pyridin-3-yl}methanol | 593.2 | 2 | 1.21 |

TABLE 2-continued

| Cmpd # | Structure | Name | Obs. MS Ion | HPLC Method IDs | RT (min) |
|---|---|---|---|---|---|
| 76. | 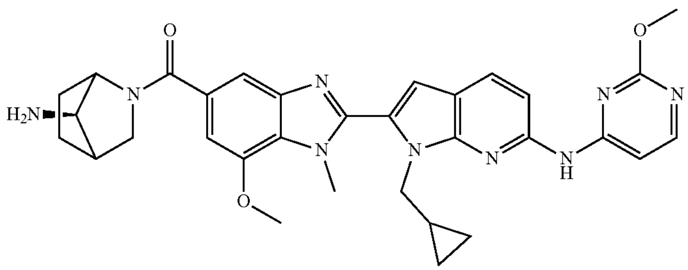 [SMILES: COc1nccc(Nc2ccc3cc(-c4nc5cc(C(=O)N6CC7CCC6[C@@H]7N)cc(OC)c5n4C)n(CC4CC4)c3n2)n1] | (1R,4R,7R)-2-{2-[1-(cyclopropylmethyl)-6-[(2-methoxypyrimidin-4-yl)amino]-1H-pyrrolo[2,3-b]pyridin-2-yl]-7-methoxy-1-methyl-1H-1,3-benzodiazole-5-carbonyl}-2-azabicyclo[2.2.1]heptan-7-amine | 594.2 | 1 | 1.6 |
| 77. | 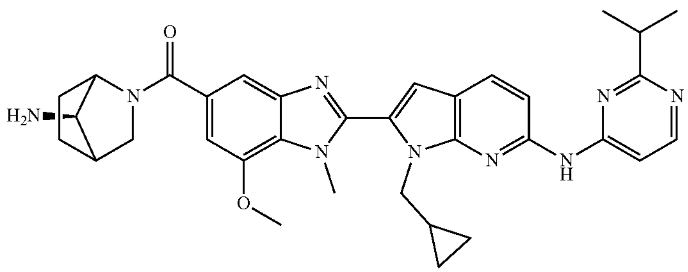 [SMILES: COc1cc(C(=O)N2CC3CCC2[C@@H]3N)cc2nc(-c3cc4ccc(Nc5ccnc(C(C)C)n5)nc4n3CC3CC3)n(C)c12] | (1R,4R,7R)-2-{2-[1-(cyclopropylmethyl)-6-{[2-(propan-2-yl)pyrimidin-4-yl]amino}-1H-pyrrolo[2,3-b]pyridin-2-yl]-7-methoxy-1-methyl-1H-1,3-benzodiazole-5-carbonyl}-2-azabicyclo[2.2.1]heptan-7-amine | 606.2 | 1 | 1.84 |
| 78. | 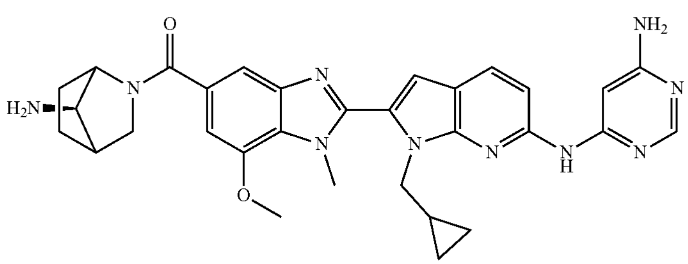 | N4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)pyrimidine-4,6-diamine | 579.5 | 1 | 1.2 |

TABLE 2-continued

| Cmpd # | Structure | Name | Obs. MS Ion | HPLC Method IDs | RT (min) |
|---|---|---|---|---|---|
| 79. | 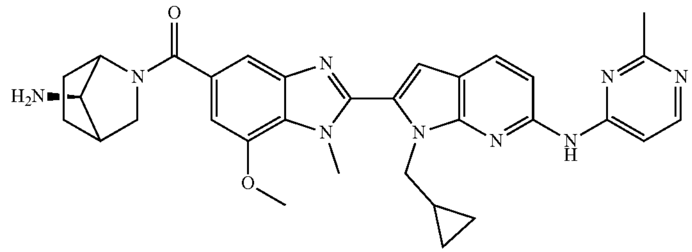 [SMILES: COc1cc(C(=O)N2CC3CCC2[C@@H]3N)cc2nc(-c3cc4ccc(Nc5ccnc(C)n5)nc4n3CC3CC3)n(C)c12] | (1R,4R,7R)-2-{2-[1-(cyclopropylmethyl)-6-[(2-methylpyrimidin-4-yl)amino]-1H-pyrrolo[2,3-b]pyridin-2-yl]-7-methoxy-1-methyl-1H-1,3-benzodiazole-5-carbonyl}-2-azabicyclo[2.2.1]heptan-7-amine | 578.2 | 1 | 1.54 |
| 80. | 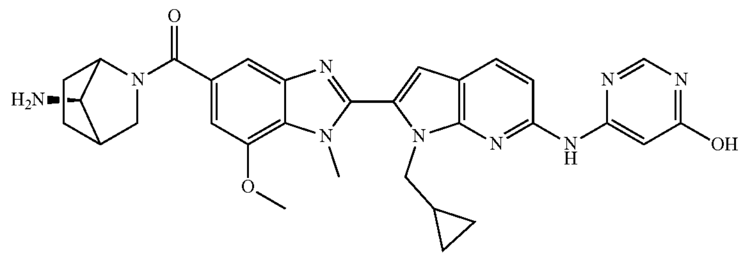 [SMILES: COc1cc(C(=O)N2CC3CCC2[C@@H]3N)cc2nc(-c3cc4ccc(Nc5cc(O)ncn5)nc4n3CC3CC3)n(C)c12] | 6-[(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)amino]pyrimidin-4-ol | 580.1 | 1 | 1.29 |
| 81. | 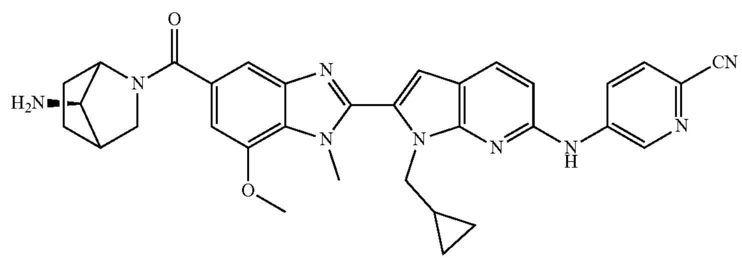 [SMILES: COc1cc(C(=O)N2CC3CCC2[C@@H]3N)cc2nc(-c3cc4ccc(Nc5ccc(C#N)nc5)nc4n3CC3CC3)n(C)c12] | 5-[(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)amino]pyridine-2-carbonitrile | 588.2 | 2 | 1.46 |

TABLE 2-continued

| Cmpd # | Structure | Name | Obs. MS Ion | HPLC Method IDs | RT (min) |
|---|---|---|---|---|---|
| 82. | 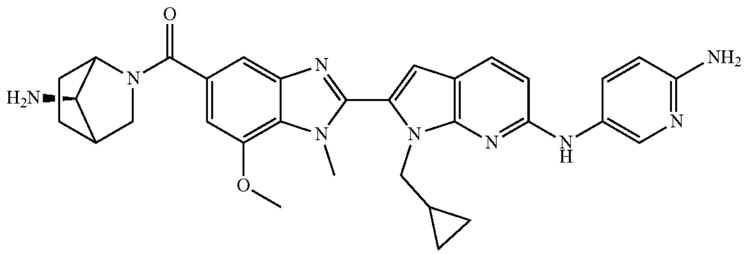 [SMILES: COc1cc(C(=O)N2CC3CCC2[C@@H]3N)cc2nc(-c3cc4ccc(Nc5ccc(N)nc5)nc4n3CC3CC3)n(C)c12] | N5-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)pyridine-2,5-diamine | 578.4 | 1 | 1.22 |
| 83. | 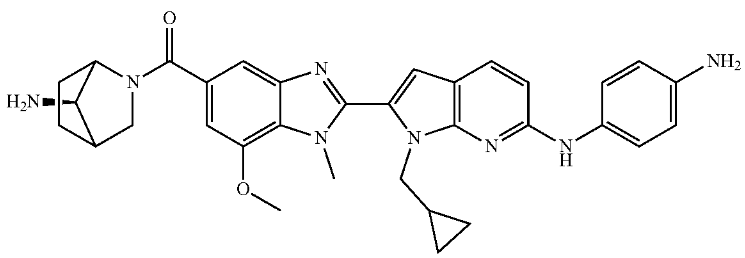 | N1-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)benzene-1,4-diamine | 577.4 | 2 | 0.93 |
| 84. | 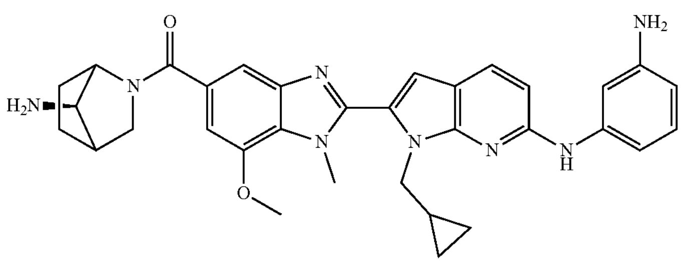 [SMILES: COc1cc(C(=O)N2CC3CCC2[C@@H]3N)cc2nc(-c3cc4ccc(Nc5cccc(N)c5)nc4n3CC3CC3)n(C)c12] | N1-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)benzene-1,3-diamine | 577.3 | 1 | 1.44 |

TABLE 2-continued

| Cmpd # | Structure | Name | Obs. MS Ion | HPLC Method IDs | RT (min) |
|---|---|---|---|---|---|
| 85. | 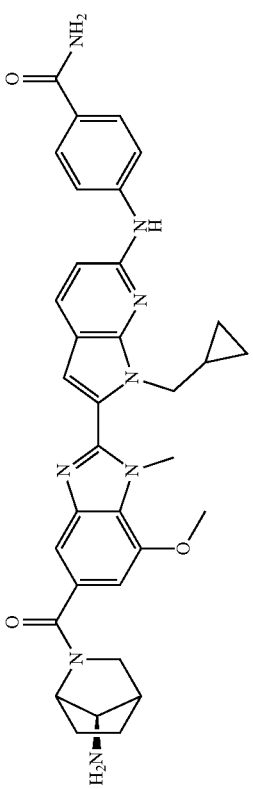 | 4-[2-(5-{[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)amino]benzamide | 605.4 | 1 | 1.34 |
| 86. | 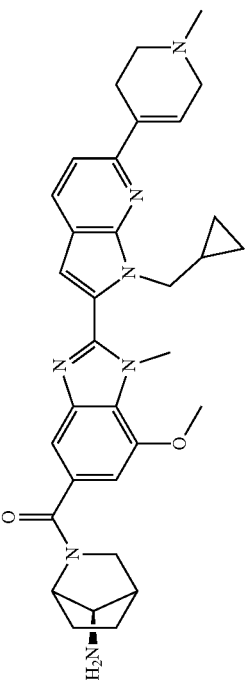 | (1R,4R,7R)-2-{2-[1-(cyclopropylmethyl)-6-(1-methyl-1,2,3,6-tetrahydropyridin-4-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 566.6 | 1 | 1.17 |
| 87. | 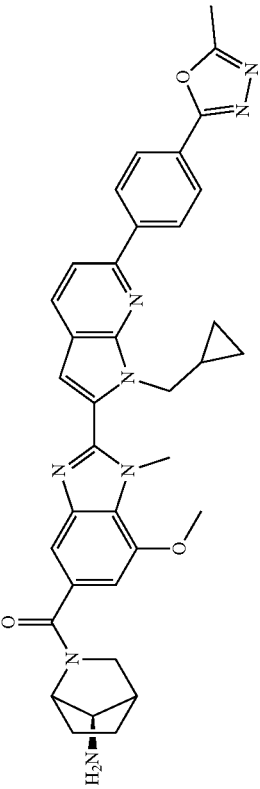 | (1R,4R,7R)-2-{2-[1-(cyclopropytmethyl)-6-[4-(5-methyl-1,3,4-oxadiazol-2-yl)phenyl]-1H-pyrrolo[2,3-b]pyridin-2-yl]-7-methoxy-1-methyl-1H-1,3-benzodiazole-5-carbonyl}-2-azabicyclo[2.2.1]heptan-7-amine | 629.2 | 2 | 1.55 |

TABLE 2-continued

| Cmpd # | Structure | Name | Obs. MS Ion | HPLC Method IDs | RT (min) |
|---|---|---|---|---|---|
| 88. | 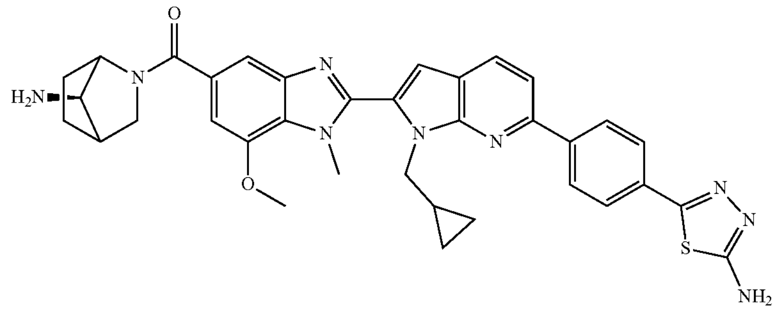 [SMILES: COc1cc(C(=O)N2CC3CCC2[C@@H]3N)cc2nc(-c3cc4ccc(-c5ccc(-c6nnc(N)s6)cc5)nc4n3CC3CC3)n(C)c12] | (1R,4R,7R)-2-(2-{6-[4-(5-amino-1,3,4-thiadiazol-2-yl)phenyl]-1-(cyclopropylmethyl)-1H-pyrrolo[2,3-b]pyridin-2-yl}-7-methoxy-1-methyl-1H-1,3-benzodiazole-5-carbonyl)-2-azabicyclo[2.2.1]heptan-7-amine | 646.2 | 1 | 1.72 |
| 89. | 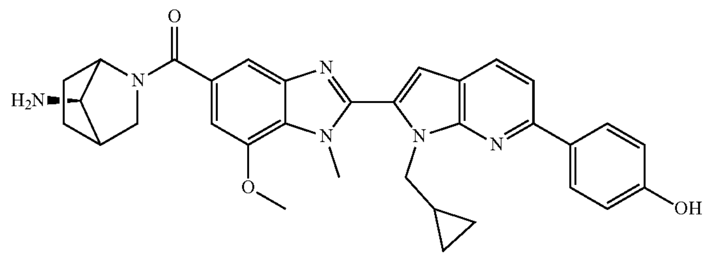 | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenol | 563.4 | 1 | 1.56 |
| 90. | 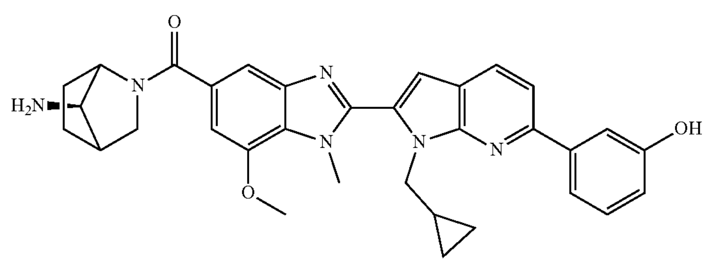 [SMILES: COc1cc(C(=O)N2CC3CCC2[C@@H]3N)cc2nc(-c3cc4ccc(-c5cccc(O)c5)nc4n3CC3CC3)n(C)c12] | 3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenol | 563.2 | 2 | 1.46 |

TABLE 2-continued

| Cmpd # | Structure | Name | Obs. MS Ion | HPLC Method IDs | RT (min) |
|---|---|---|---|---|---|
| 91. | 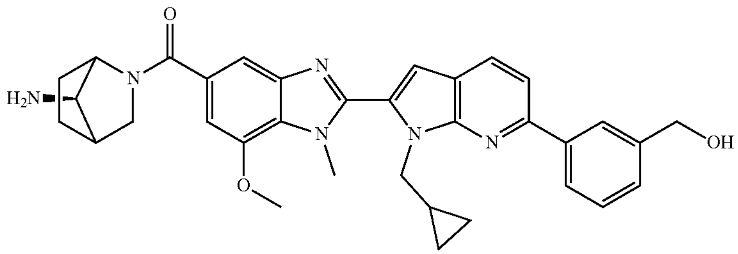 [SMILES: COc1cc(C(=O)N2CC3CCC2[C@@H]3N)cc2nc(-c3cc4ccc(-c5cccc(CO)c5)nc4n3CC3CC3)n(C)c12] | [3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]methanol | 576.9 | 2 | 1.42 |
| 92. | 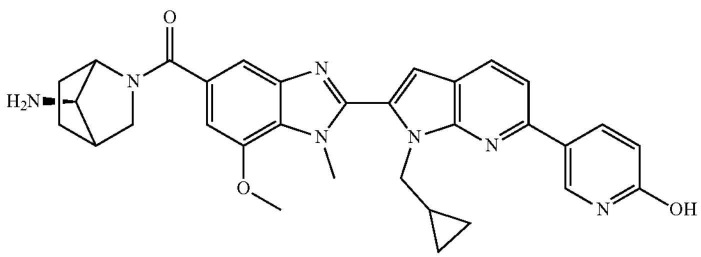 [SMILES: COc1cc(C(=O)N2CC3CCC2[C@@H]3N)cc2nc(-c3cc4ccc(-c5ccc(O)nc5)nc4n3CC3CC3)n(C)c12] | 5-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)pyridine-2-carbonitrile | 573.2 | 2 | 1.52 |
| 93. | 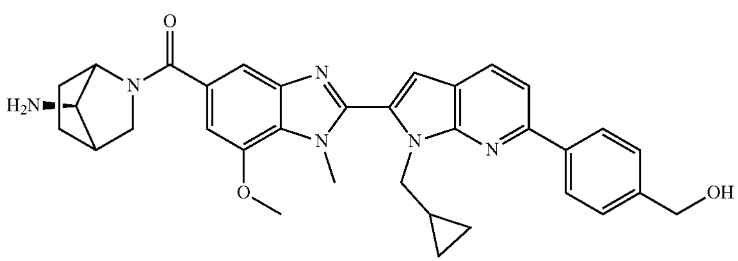 [SMILES: COc1cc(C(=O)N2CC3CCC2[C@@H]3N)cc2nc(-c3cc4ccc(-c5ccc(CO)cc5)nc4n3CC3CC3)n(C)c12] | [4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]methanol | 577.5 | 2 | 1.35 |

TABLE 2-continued

| Cmpd # | Structure | Name | Obs. MS Ion | HPLC Method IDs | RT (min) |
|---|---|---|---|---|---|
| 94. | 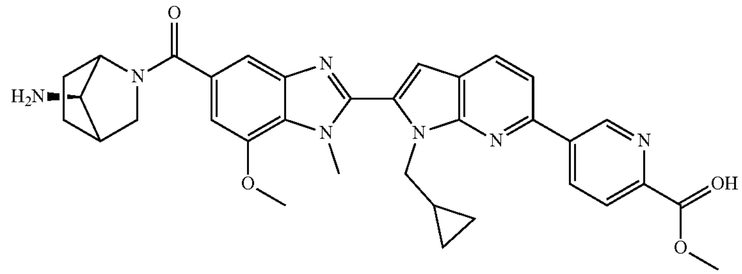 [SMILES: COC(=O)c1ccc(-c2ccc3cc(-c4nc5cc(C(=O)N6CC7CCC6[C@@H]7N)cc(OC)c5n4C)n(CC4CC4)c3n2)cn1] | methyl 5-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)pyridine-2-carboxylate | 606.2 | 1 | 1.65 |
| 95. | 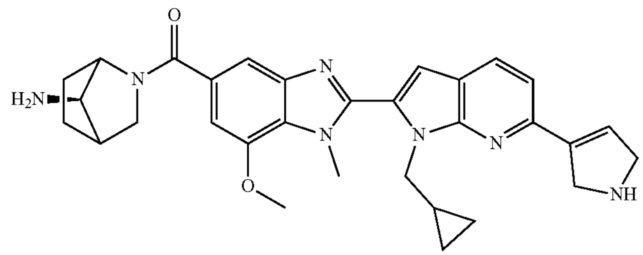 [SMILES: COc1cc(C(=O)N2CC3CCC2[C@@H]3N)cc2nc(-c3cc4ccc(C5=CCNC5)nc4n3CC3CC3)n(C)c12] | (1R,4R,7R)-2-{2-[1-(cyclopropylmethyl)-6-(2,5-dihydro-1H-pyrrol-3-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 538.4 | 1 | 1.03 |
| 96. | 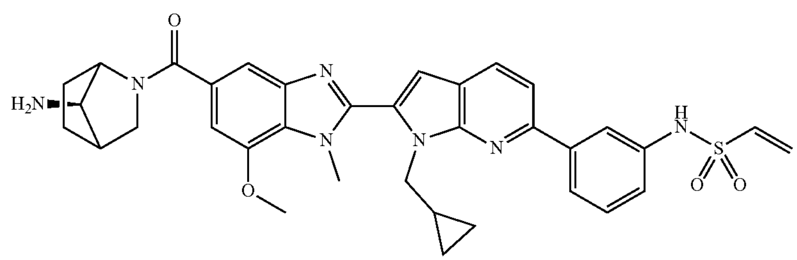 [SMILES: C=CS(=O)(=O)Nc1cccc(-c2ccc3cc(-c4nc5cc(C(=O)N6CC7CCC6[C@@H]7N)cc(OC)c5n4C)n(CC4CC4)c3n2)c1] | N-[3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]ethene-1-sulfonamide | 652.5 | 2 | 1.57 |

TABLE 2-continued

| Cmpd # | Structure | Name | Obs. MS Ion | HPLC Method IDs | RT (min) |
|---|---|---|---|---|---|
| 97. | 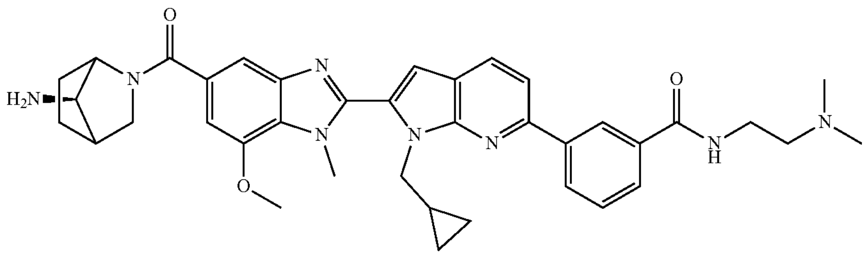 [SMILES: COc1cc(C(=O)N2CC3CCC2[C@@H]3N)cc2nc(-c3cc4ccc(-c5cccc(C(=O)NCCN(C)C)c5)nc4n3CC3CC3)n(C)c12] | 3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-N-[2-(dimethylamino)ethyl]benzamide | 661.5 | 1 | 1.28 |
| 98. | 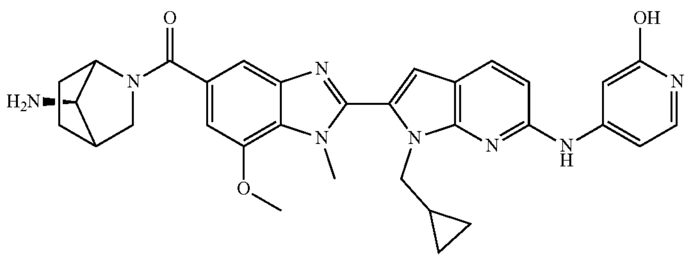 [SMILES: COc1cc(C(=O)N2CC3CCC2[C@@H]3N)cc2nc(-c3cc4ccc(Nc5ccnc(O)c5)nc4n3CC3CC3)n(C)c12] | 4-[(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)amino]pyridin-2-ol | 579.4 | 1 | 1.15 |
| 99. | 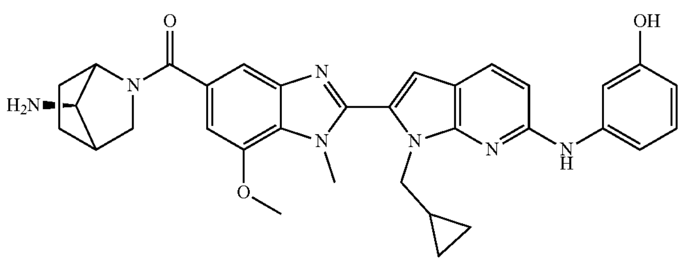 | 3-[(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)amino]phenol | 578.4 | 2 | 1.26 |

TABLE 2-continued
| Cmpd # | Structure | Name | Obs. MS Ion | HPLC Method IDs | RT (min) |
|---|---|---|---|---|---|
| 100. | 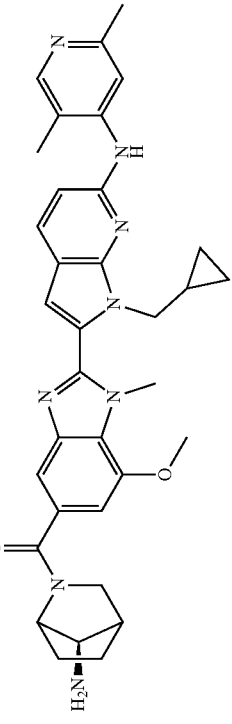 | (1R,4R,7R)-2-{2-[1-(cyclopropylmethyl)-6-[(2,5-dimethylpyridin-4-yl)amino]-1H-pyrrolo[2,3-b]pyridin-2-yl]-7-methoxy-1-methyl-1H-1,3-benzodiazole-5-carbonyl}-2-azabicyclo[2.2.1]heptan-7-amine | 591.5 | 1 | 1.26 |
| 101. | 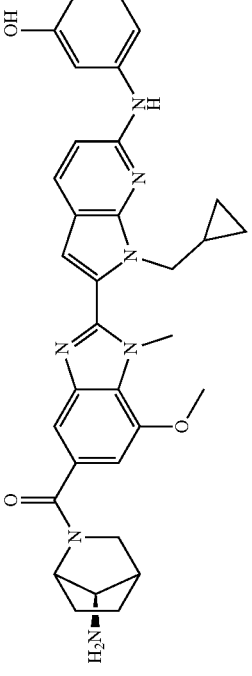 | 3-[(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)amino]phenol | 577.4 | 1 | 1.53 |

TABLE 2-continued
| Cmpd # | Structure | Name | Obs. MS Ion | HPLC Method IDs | RT (min) |
|---|---|---|---|---|---|
| 102. | 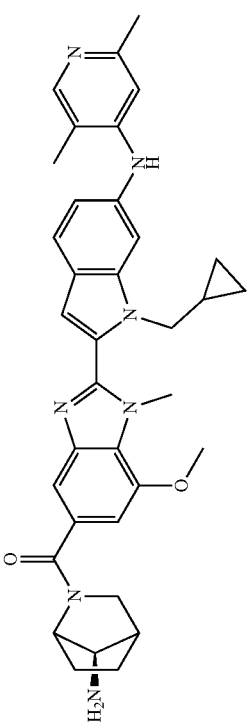 | 2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-N-(2,5-dimethylpyridin-4-yl)-1H-indol-6-amine | 590.5 | 1 | 1.17 |
| 103. | 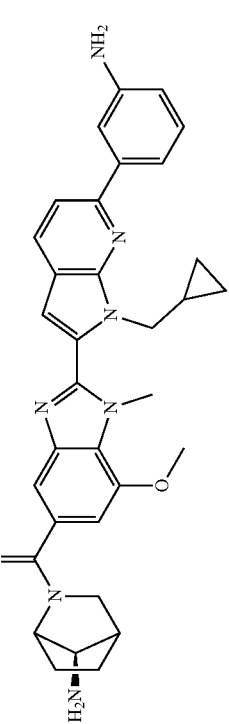 | (1R,4R,7R)-2-{2-[6-(3-aminophenyl)-1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 562.4 | 2 | 1.07 |

TABLE 3

| Cmpd # | Structure | Name | Obs. MS Ion | HPLC Method IDs | RT (min) |
|---|---|---|---|---|---|
| 104. | 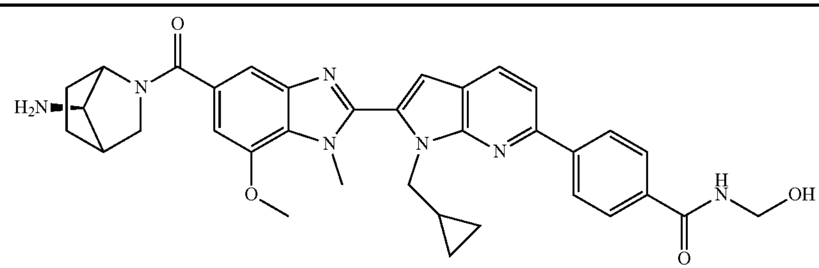 | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-N-(2-hydroxyethyl)benzamide | 634.1 | 1 | 1.46 |
| 105. | 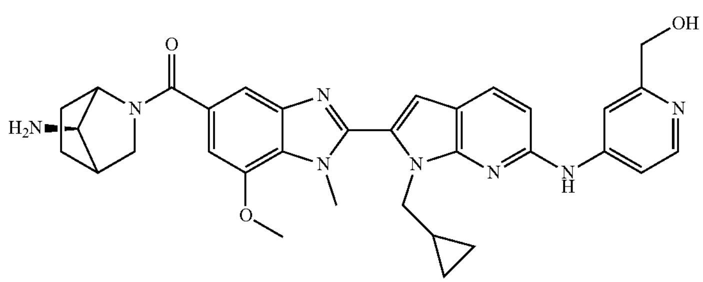 [SMILES: COc1cc(C(=O)N2CC3CCC2[C@@H]3N)cc2nc(-c3cc4ccc(Nc5ccnc(CO)c5)nc4n3CC3CC3)n(C)c12] | {4-[(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)amino]pyridin-2-yl}methanol | 593.2 | 2 | 1.13 |
| 106. | 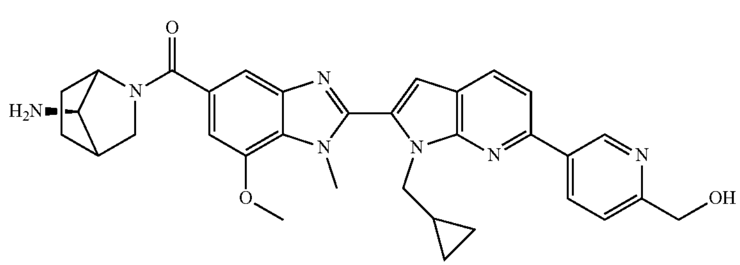 [SMILES: COc1cc(C(=O)N2CC3CCC2[C@@H]3N)cc2nc(-c3cc4ccc(-c5ccc(CO)nc5)nc4n3CC3CC3)n(C)c12] | [5-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)pyridin-2-yl]methanol | 578.5 | 1 | 1.35 |

TABLE 3-continued

| Cmpd # | Structure | Name | Obs. MS Ion | HPLC Method IDs | RT (min) |
|---|---|---|---|---|---|
| 107. | 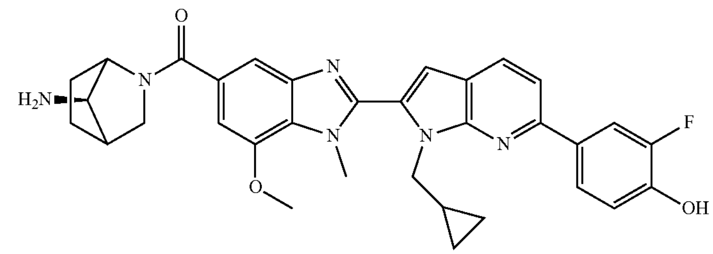 [SMILES: COc1cc(C(=O)N2CC3CCC2[C@@H]3N)cc2nc(-c3cc4ccc(-c5ccc(O)c(F)c5)nc4n3CC3CC3)n(C)c12] | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-fluorophenol | 581.4 | 2 | 1.4 |
| 108. | 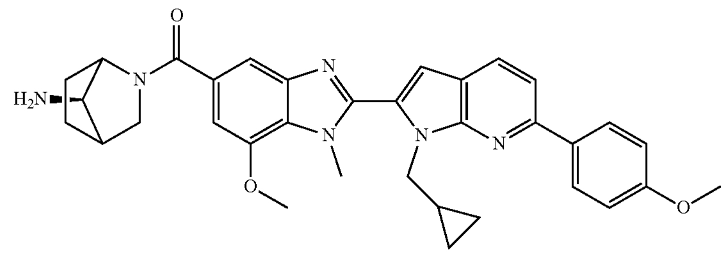 [SMILES: COc1ccc(-c2ccc3cc(-c4nc5cc(C(=O)N6CC7CCC6[C@@H]7N)cc(OC)c5n4C)n(CC4CC4)c3n2)cc1] | (1R,4R,7R)-2-{2-[1-(cyclopropylmethyl)-6-(4-methoxyphenyl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 577.2 | 1 | 1.96 |
| 109. | 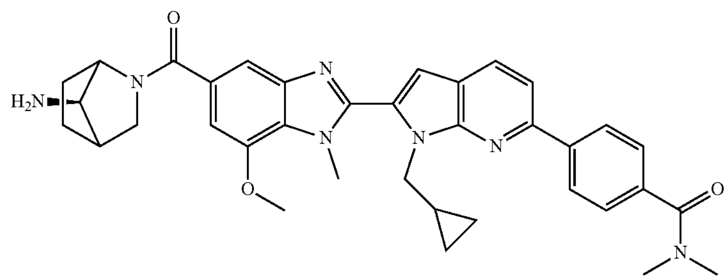 [SMILES: COc1cc(C(=O)N2CC3CCC2[C@@H]3N)cc2nc(-c3cc4ccc(-c5ccc(C(=O)N(C)C)cc5)nc4n3CC3CC3)n(C)c12] | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-N,N-dimethylbenzamide | 618.5 | 2 | 1.38 |
| 110. | 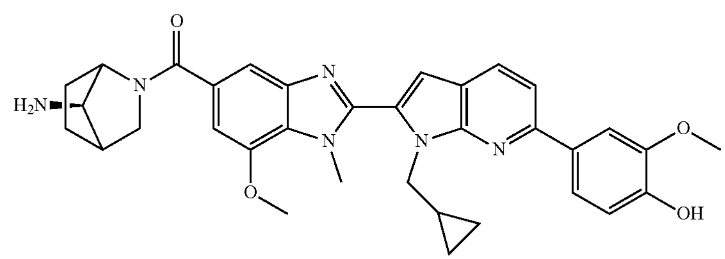 [SMILES: COc1cc(-c2ccc3cc(-c4nc5cc(C(=O)N6CC7CCC6[C@@H]7N)cc(OC)c5n4C)n(CC4CC4)c3n2)ccc1O] | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-methoxyphenol | 593.4 | 2 | 1.39 |

TABLE 3-continued

| Cmpd # | Structure | Name | Obs. MS Ion | HPLC Method IDs | RT (min) |
|---|---|---|---|---|---|
| 111. | 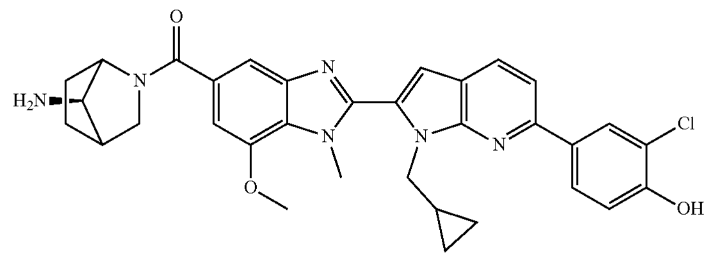 | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-chlorophenol | 597.4 | 2 | 1.49 |
| 112. | 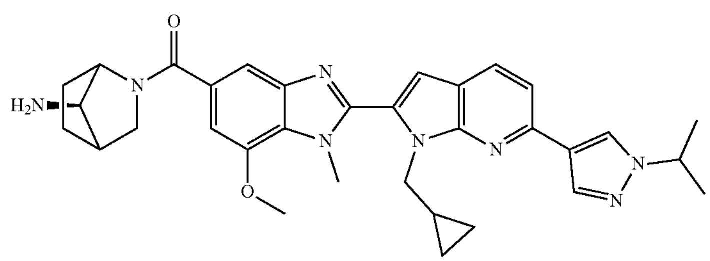 [SMILES: COc1cc(C(=O)N2CC3CCC2[C@@H]3N)cc2nc(-c3cc4ccc(-c5cnn(C(C)C)c5)nc4n3CC3CC3)n(C)c12] | (1R,4R,7R)-2-{2-[1-(cyclopropylmethyl)-6-[1-(propan-2-yl)-1H-pyrazol-4-yl]-1H-pyrrolo[2,3-b]pyridin-2-yl]-7-methoxy-1-methyl-1H-1,3-benzodiazole-5-carbonyl}-2-azabicyclo[2.2.1]heptan-7-amine | 579.4 | 1 | 1.65 |
| 113. | 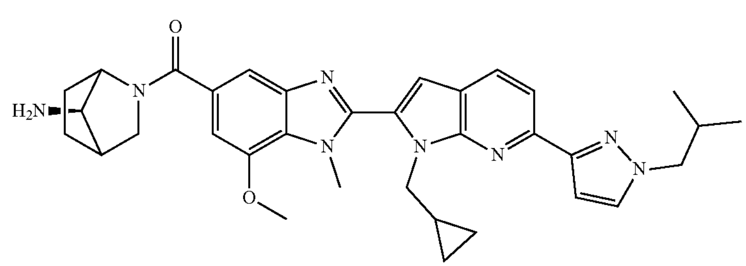 [SMILES: COc1cc(C(=O)N2CC3CCC2[C@@H]3N)cc2nc(-c3cc4ccc(-c5ccn(CC(C)C)n5)nc4n3CC3CC3)n(C)c12] | (1R,4R,7R)-2-{2-[1-(cyclopropylmethyl)-6-[1-(2-methylpropyl)-1H-pyrazol-3-yl]-1H-pyrrolo[2,3-b]pyridin-2-yl]-7-methoxy-1-methyl-1H-1,3-benzodiazole-5-carbonyl}-2-azabicyclo[2.2.1]heptan-7-amine | 593.5 | 1 | 1.83 |

TABLE 3-continued

| Cmpd # | Structure | Name | Obs. MS Ion | HPLC Method IDs | RT (min) |
|---|---|---|---|---|---|
| 114. | 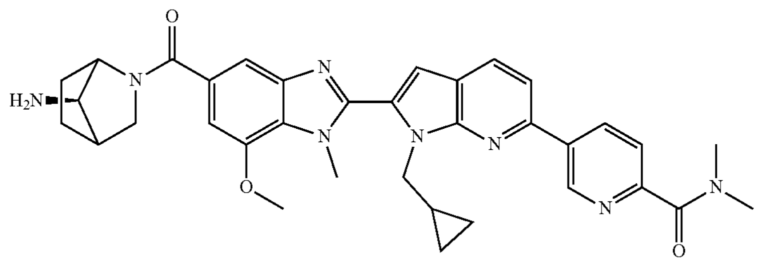 [SMILES: COc1cc(C(=O)N2CC3CCC2[C@@H]3N)cc2nc(-c3cc4ccc(-c5ccc(C(=O)N(C)C)nc5)nc4n3CC3CC3)n(C)c12] | 5-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-N,N-dimethylpyridine-2-carboxamide | 619.2 | 1 | 1.39 |
| 115. | 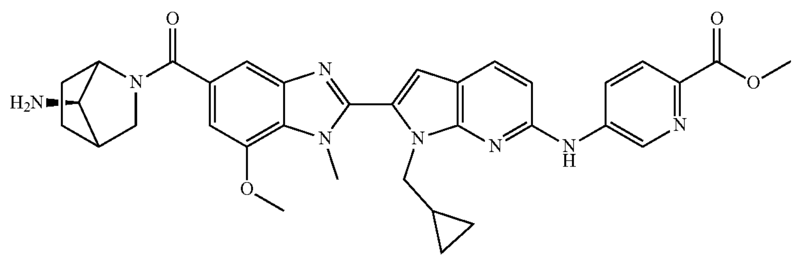 [SMILES: COC(=O)c1ccc(Nc2ccc3cc(-c4nc5cc(C(=O)N6CC7CCC6[C@@H]7N)cc(OC)c5n4C)n(CC4CC4)c3n2)cn1] | methyl 5-[(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)amino]pyridine-2-carboxylate | 621.2 | 2 | 1.26 |
| 116. | 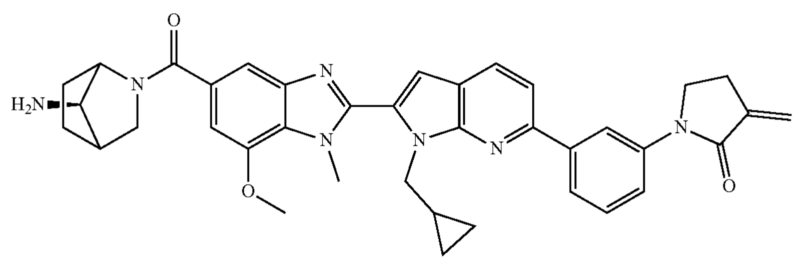 [SMILES: C=C1CCN(c2cccc(-c3ccc4cc(-c5nc6cc(C(=O)N7CC8CCC7[C@@H]8N)cc(OC)c6n5C)n(CC5CC5)c4n3)c2)C1=O] | 1-[3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]-3-methylidenepyrrolidin-2-one | 642.2 | 2 | 1.54 |
| 117. | 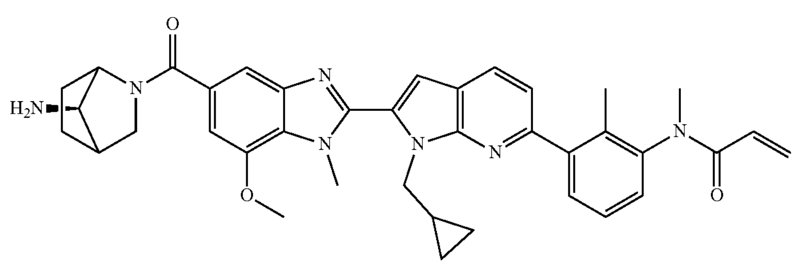 [SMILES: C=CC(=O)N(C)c1cccc(-c2ccc3cc(-c4nc5cc(C(=O)N6CC7CCC6[C@@H]7N)cc(OC)c5n4C)n(CC4CC4)c3n2)c1C] | N-[3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-methylphenyl]-N-methylprop-2-enamide | 644.2 | 1 | 1.93 |

TABLE 3-continued

| Cmpd # | Structure | Name | Obs. MS Ion | HPLC Method IDs | RT (min) |
|---|---|---|---|---|---|
| 118. | 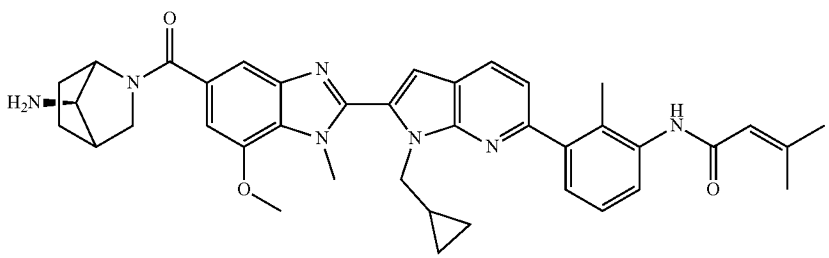 [SMILES: COc1cc(C(=O)N2CC3CCC2[C@@H]3N)cc2nc(-c3cc4ccc(-c5cccc(NC(=O)C=C(C)C)c5C)nc4n3CC3CC3)n(C)c12] | N-[3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-methylphenyl]-3-methylbut-2-enamide | 658.2 | 2 | 1.53 |
| 119. | 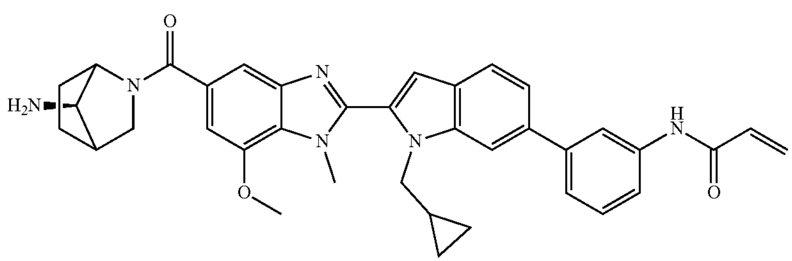 [SMILES: C=CC(=O)Nc1cccc(-c2ccc3cc(-c4nc5cc(C(=O)N6CC7CCC6[C@@H]7N)cc(OC)c5n4C)n(CC4CC4)c3c2)c1] | N-[3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)phenyl]prop-2-enamide | 615.2 | 1 | 1.9 |
| 120. | 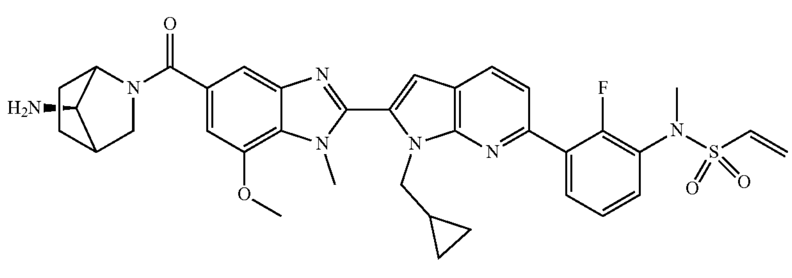 [SMILES: C=CS(=O)(=O)N(C)c1cccc(-c2ccc3cc(-c4nc5cc(C(=O)N6CC7CCC6[C@@H]7N)cc(OC)c5n4C)n(CC4CC4)c3n2)c1F] | N-[3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-fluorophenyl]-N-methylethene-1-sulfonamide | 683.9 | 1 | 2.01 |

TABLE 3-continued

| Cmpd # | Structure | Name | Obs. MS Ion | HPLC Method IDs | RT (min) |
|---|---|---|---|---|---|
| 121. | 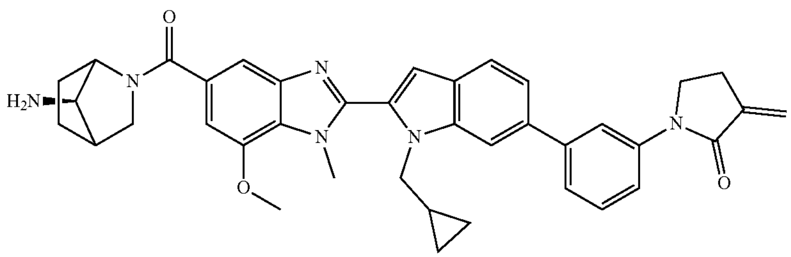 [SMILES: C=C1CCN(c2cccc(-c3ccc4cc(-c5nc6cc(C(=O)N7CC8CCC7[C@@H]8N)cc(OC)c6n5C)n(CC5CC5)c4c3)c2)C1=O] | 1-[3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)phenyl]-3-methylidenepyrrolidin-2-one | 641.2 | 1 | 1.97 |
| 122. | 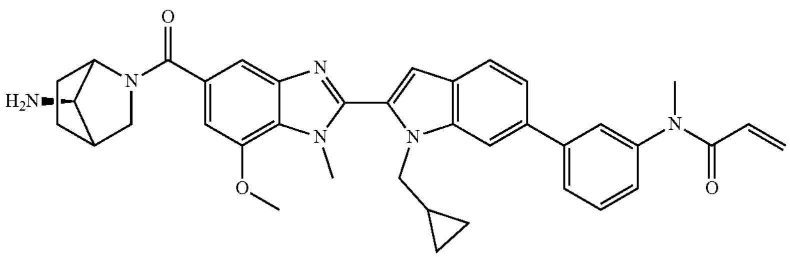 [SMILES: C=CC(=O)N(C)c1cccc(-c2ccc3cc(-c4nc5cc(C(=O)N6CC7CCC6[C@@H]7N)cc(OC)c5n4C)n(CC4CC4)c3c2)c1] | N-[3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)phenyl]-N-methylprop-2-enamide | 629.2 | 1 | 1.9 |
| 123. | 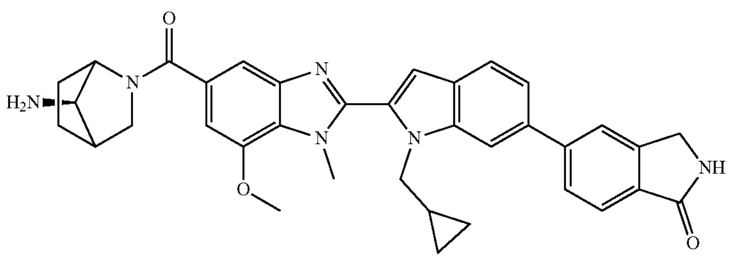 [SMILES: COc1cc(C(=O)N2CC3CCC2[C@@H]3N)cc2nc(-c3cc4ccc(-c5ccc6c(c5)CNC6=O)cc4n3CC3CC3)n(C)c12] | 5-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-2,3-dihydro-1H-isoindol-1-one | 601.1 | 1 | 1.53 |
| 124. | 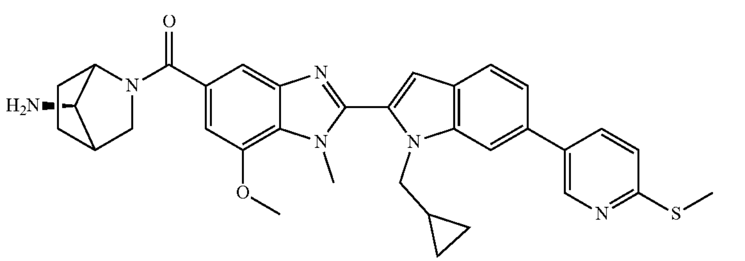 [SMILES: COc1cc(C(=O)N2CC3CCC2[C@@H]3N)cc2nc(-c3cc4ccc(-c5ccc(SC)nc5)cc4n3CC3CC3)n(C)c12] | (1R,4R,7R)-2-{2-[1-(cyclopropylmethyl)-6-[6-(methylsulfanyl)pyridin-3-yl]-1H-indol-2-yl]-7-methoxy-1-methyl-1H-1,3-benzodiazole-5-carbonyl}-2-azabicyclo[2.2.1]heptan-7-amine | 593.3 | 2 | 1.62 |

TABLE 3-continued

| Cmpd # | Structure | Name | Obs. MS Ion | HPLC Method IDs | RT (min) |
|---|---|---|---|---|---|
| 125. | 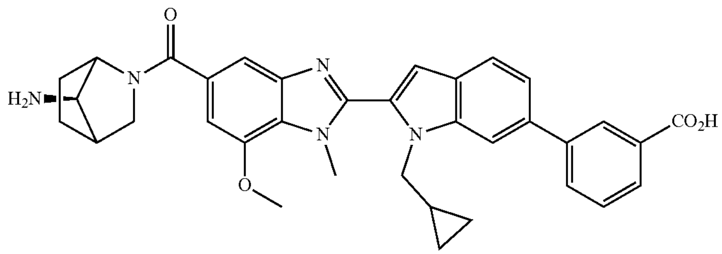 [SMILES: COc1cc(C(=O)N2CC3CCC2[C@@H]3N)cc2nc(-c3cc4ccc(-c5cccc(C(=O)O)c5)cc4n3CC3CC3)n(C)c12] | 3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)benzoic acid | 590.2 | 2 | 1.5 |
| 126. | 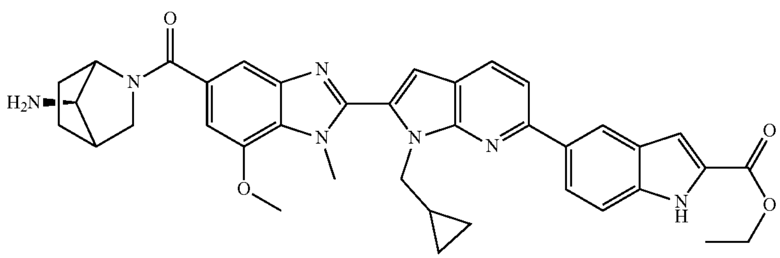 [SMILES: CCOC(=O)c1cc2cc(-c3ccc4cc(-c5nc6cc(C(=O)N7CC8CCC7[C@@H]8N)cc(OC)c6n5C)n(CC5CC5)c4n3)ccc2[nH]1] | ethyl 5-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1H-indole-2-carboxylate | 329.7 | 2 | 1.81 |
| 127. | 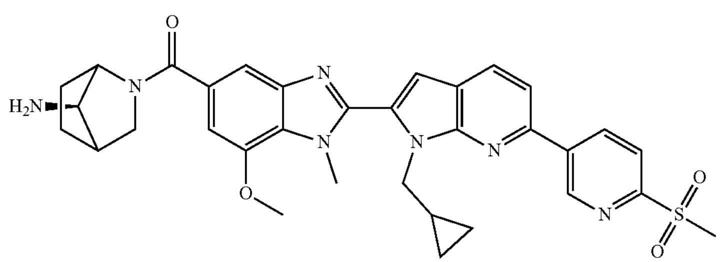 [SMILES: COc1cc(C(=O)N2CC3CCC2[C@@H]3N)cc2nc(-c3cc4ccc(-c5ccc(S(C)(=O)=O)nc5)nc4n3CC3CC3)n(C)c12] | (1R,4R,7R)-2-{2-[1-(cyclopropylmethyl)-6-(6-methanesulfonylpyridin-3-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 626.4 | 1 | 1.61 |

TABLE 3-continued

| Cmpd # | Structure | Name | Obs. MS Ion | HPLC Method IDs | RT (min) |
|---|---|---|---|---|---|
| 128. | 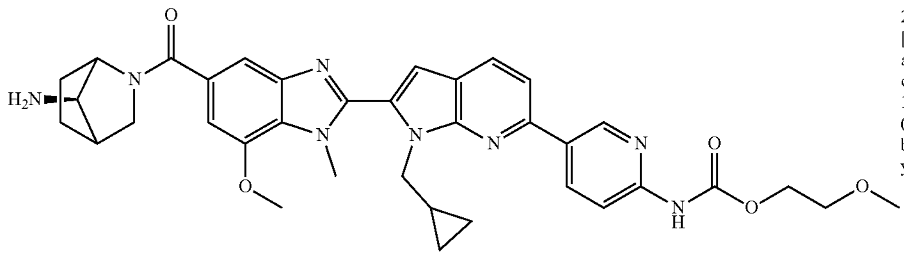 [SMILES: COCCOC(=O)Nc1ccc(-c2ccc3cc(-c4nc5cc(C(=O)N6CC7CCC6[C@@H]7N)cc(OC)c5n4C)n(CC4CC4)c3n2)cn1] | 2-methoxyethyl N-[5-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)pyridin-2-yl]carbamate | 333.2 | 1 | 1.75 |
| 129. | 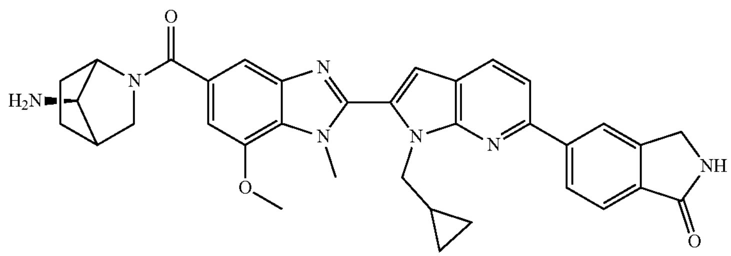 [SMILES: COc1cc(C(=O)N2CC3CCC2[C@@H]3N)cc2nc(-c3cc4ccc(-c5ccc6c(c5)CNC6=O)nc4n3CC3CC3)n(C)c12] | 5-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2,3-dihydro-1H-isoindol-1-one | 602.2 | 2 | 1.41 |
| 130. | 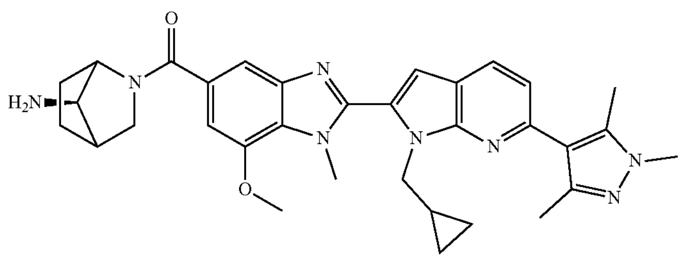 | (1R,4R,7R)-2-{2-[1-(cyclopropylmethyl)-6-(1,3,5-trimethyl-1H-pyrazol-4-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 579.4 | 1 | 1.75 |
| 131. | 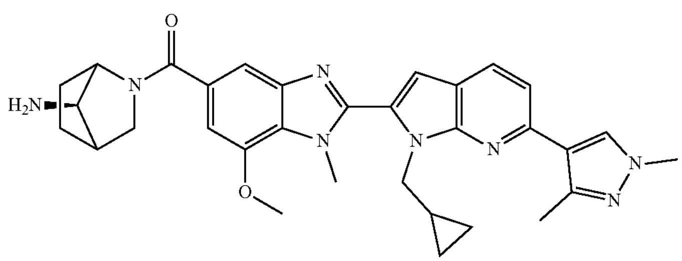 [SMILES: COc1cc(C(=O)N2CC3CCC2[C@@H]3N)cc2nc(-c3cc4ccc(-c5cn(C)nc5C)nc4n3CC3CC3)n(C)c12] | (1R,4R,7R)-2-{2-[1-(cyclopropylmethyl)-6-(1,3-dimethyl-1H-pyrazol-4-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 565.4 | 1 | 1.52 |

TABLE 3-continued

| Cmpd # | Structure | Name | Obs. MS Ion | HPLC Method IDs | RT (min) |
|---|---|---|---|---|---|
| 132. | 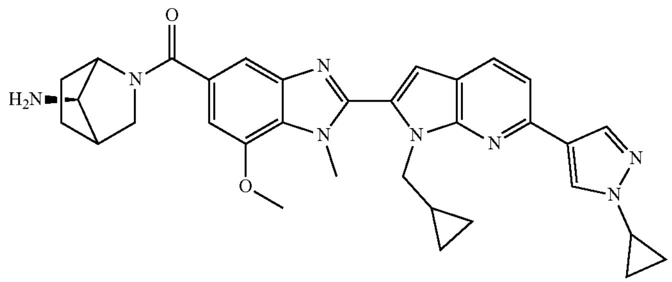 [SMILES: COc1cc(C(=O)N2CC3CCC2[C@@H]3N)cc2nc(-c3cc4ccc(-c5cnn(C6CC6)c5)nc4n3CC3CC3)n(C)c12] | (1R,4R,7R)-2-{2-[6-(1-cyclopropyl-1H-pyrazol-4-yl)-1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 577.4 | 2 | 1.51 |
| 133. | 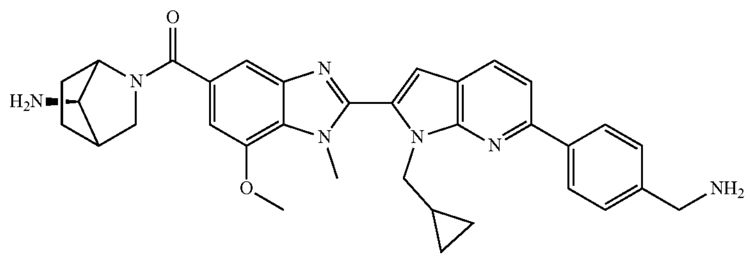 [SMILES: COc1cc(C(=O)N2CC3CCC2[C@@H]3N)cc2nc(-c3cc4ccc(-c5ccc(CN)cc5)nc4n3CC3CC3)n(C)c12] | (1R,4R,7R)-2-(2-{6-[4-(aminomethyl)phenyl]-1-(cyclopropylmethyl)-1H-pyrrolo[2,3-b]pyridin-2-yl}-7-methoxy-1-methyl-1H-1,3-benzodiazole-5-carbonyl)-2-azabicyclo[2.2.1]heptan-7-amine | 576.5 | 1 | 1.27 |
| 134. | 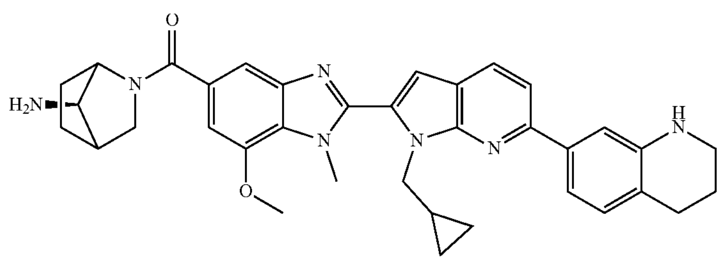 [SMILES: COc1cc(C(=O)N2CC3CCC2[C@@H]3N)cc2nc(-c3cc4ccc(-c5ccc6c(c5)NCCC6)nc4n3CC3CC3)n(C)c12] | (1R,4R,7R)-2-{2-[1-(cyclopropylmethyl)-6-(1,2,3,4-tetrahydroquinolin-7-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 602.2 | 1 | 2.13 |

TABLE 3-continued

| Cmpd # | Structure | Name | Obs. MS Ion | HPLC Method IDs | RT (min) |
|---|---|---|---|---|---|
| 135. | 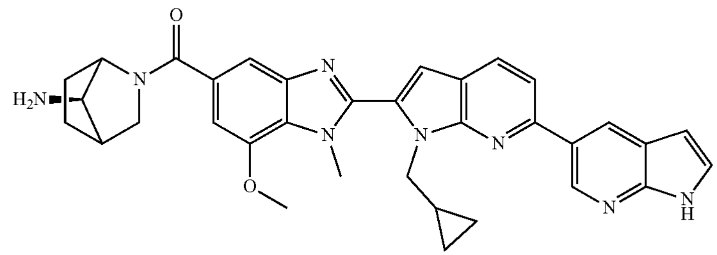 [SMILES: COc1cc(C(=O)N2CC3CCC2[C@@H]3N)cc2nc(-c3cc4ccc(-c5cnc6[nH]ccc6c5)nc4n3CC3CC3)n(C)c12] | (1R,4R,7R)-2-{2-[1-(cyclopropylmethyl)-6-{1H-pyrrolo[2,3-b]pyridin-5-yl}-1H-pyrrolo[2,3-b]pyridin-2-yl]-7-methoxy-1-methyl-1H-1,3-benzodiazole-5-carbonyl}-2-azabicyclo[2.2.1]heptan-7-amine | 587.2, 587.2 | 1 | |
| 136. | 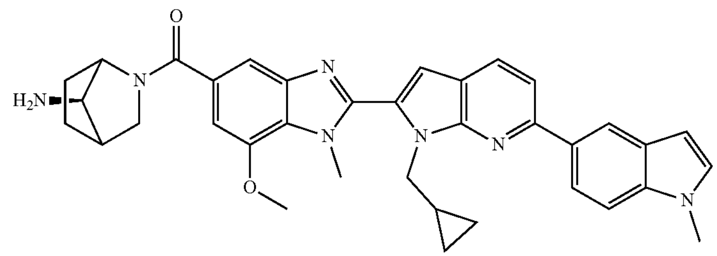 [SMILES: COc1cc(C(=O)N2CC3CCC2[C@@H]3N)cc2nc(-c3cc4ccc(-c5ccc6c(ccn6C)c5)nc4n3CC3CC3)n(C)c12] | (1R,4R,7R)-2-{2-[1-(cyclopropylmethyl)-6-(1-methyl-1H-indol-5-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 600.4 | 2 | 1.7 |
| 137. | 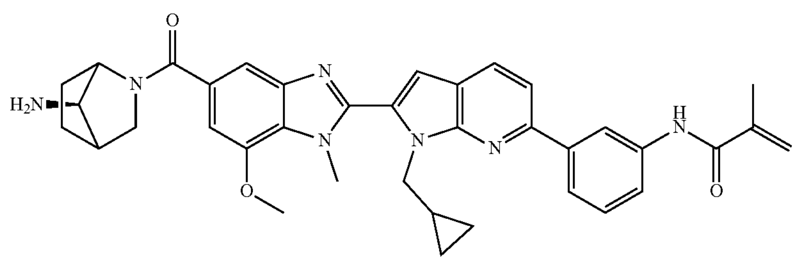 [SMILES: C=C(C)C(=O)Nc1cccc(-c2ccc3cc(-c4nc5cc(C(=O)N6CC7CCC6[C@@H]7N)cc(OC)c5n4C)n(CC4CC4)c3n2)c1] | N-[3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]-2-methylprop-2-enamide | 630.5 | 1 | 1.8 |
| 138. | 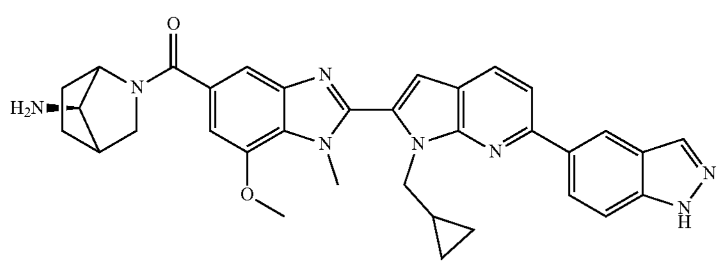 [SMILES: COc1cc(C(=O)N2CC3CCC2[C@@H]3N)cc2nc(-c3cc4ccc(-c5ccc6[nH]ncc6c5)nc4n3CC3CC3)n(C)c12] | (1R,4R,7R)-2-{2-[1-(cyclopropylmethyl)-6-((1H-indazol-5-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 587.4 | 1 | 1.58 |

TABLE 3-continued

| Cmpd # | Structure | Name | Obs. MS Ion | HPLC Method IDs | RT (min) |
|---|---|---|---|---|---|
| 139. | 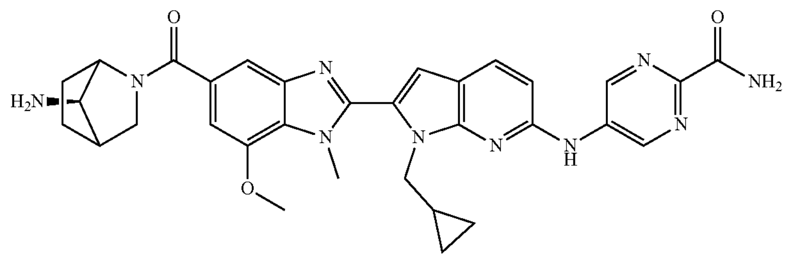 [SMILES: COc1cc(C(=O)N2CC3CCC2[C@@H]3N)cc2nc(-c3cc4ccc(Nc5cnc(C(N)=O)nc5)nc4n3CC3CC3)n(C)c12] | 5-[(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)amino]pyrimidine-2-carboxamide | 607.1 | 1 | 1.34 |
| 140. | 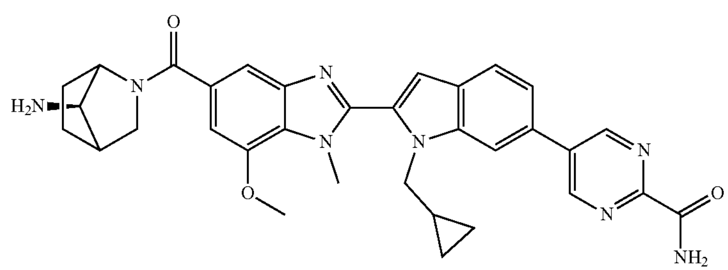 [SMILES: COc1cc(C(=O)N2CC3CCC2[C@@H]3N)cc2nc(-c3cc4ccc(-c5cnc(C(N)=O)nc5)cc4n3CC3CC3)n(C)c12] | 5-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)pyrimidine-2-carboxamide | 591.1 | 1 | 1.38 |
| 141. | 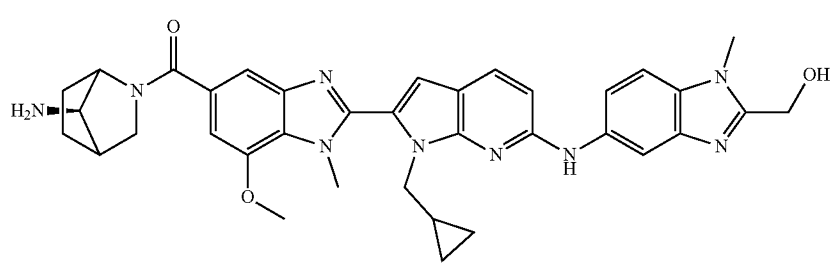 [SMILES: COc1cc(C(=O)N2CC3CCC2[C@@H]3N)cc2nc(-c3cc4ccc(Nc5ccc6c(c5)nc(CO)n6C)nc4n3CC3CC3)n(C)c12] | {5-[(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)amino]-1-methyl-1H-1,3-benzodiazol-2-yl}methanol | 646.5 | 2 | 1.08 |

TABLE 3-continued

| Cmpd # | Structure | Name | Obs. MS Ion | HPLC Method IDs | RT (min) |
|---|---|---|---|---|---|
| 142. | 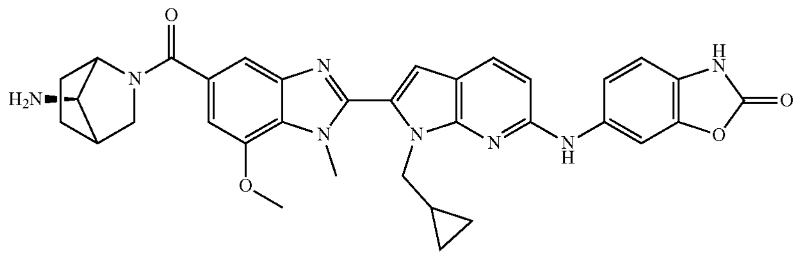 [SMILES: COc1cc(C(=O)N2CC3CCC2[C@@H]3N)cc2nc(-c3cc4ccc(Nc5ccc6[nH]c(=O)oc6c5)nc4n3CC3CC3)n(C)c12] | 6-[(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)amino]-2,3-dihydro-1,3-benzoxazol-2-one | 619.4 | 2 | 1.24 |
| 143. | 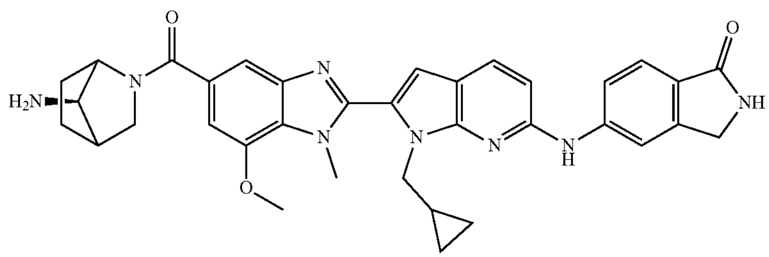 [SMILES: COc1cc(C(=O)N2CC3CCC2[C@@H]3N)cc2nc(-c3cc4ccc(Nc5ccc6c(c5)CNC6=O)nc4n3CC3CC3)n(C)c12] | 5-[(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)amino]-2,3-dihydro-1H-isoindol-1-one | 617.5 | 1 | 1.51 |
| 144. | 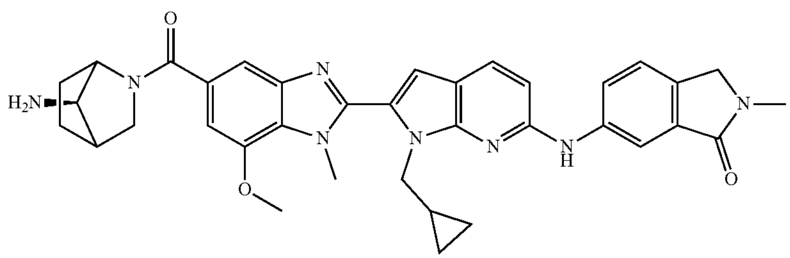 [SMILES: COc1cc(C(=O)N2CC3CCC2[C@@H]3N)cc2nc(-c3cc4ccc(Nc5ccc6c(c5)C(=O)N(C)C6)nc4n3CC3CC3)n(C)c12] | 5-[(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)amino]-2-methyl-2,3-dihydro-1H-isoindol-1-one | 631.5 | 1 | 1.52 |
| 145. | 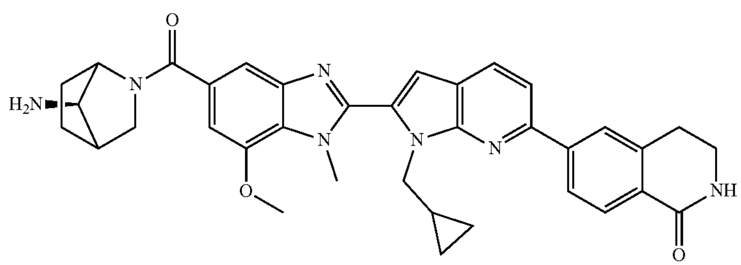 [SMILES: COc1cc(C(=O)N2CC3CCC2[C@@H]3N)cc2nc(-c3cc4ccc(-c5ccc6c(c5)CCNC6=O)nc4n3CC3CC3)n(C)c12] | 6-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1,2,3,4-tetrahydroisoquinolin-1-one | 616.5 | 2 | 1.33 |

TABLE 3-continued

| Cmpd # | Structure | Name | Obs. MS Ion | HPLC Method IDs | RT (min) |
|---|---|---|---|---|---|
| 146. | 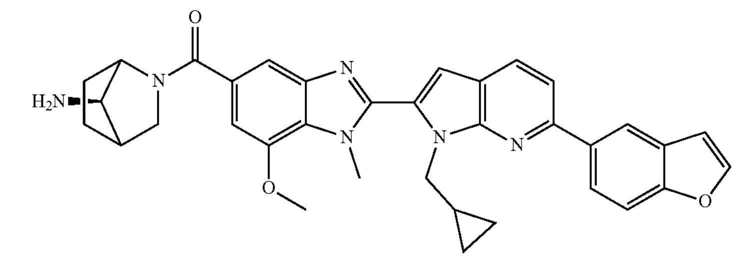 [SMILES: COc1cc(C(=O)N2CC3CCC2[C@@H]3N)cc2nc(-c3cc4ccc(-c5ccc6occc6c5)nc4n3CC3CC3)n(C)c12] | (1R,4R,7R)-2-{2-[6-(1-benzofuran-5-yl)-1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 587.4 | 1 | 2.1 |
| 147. | 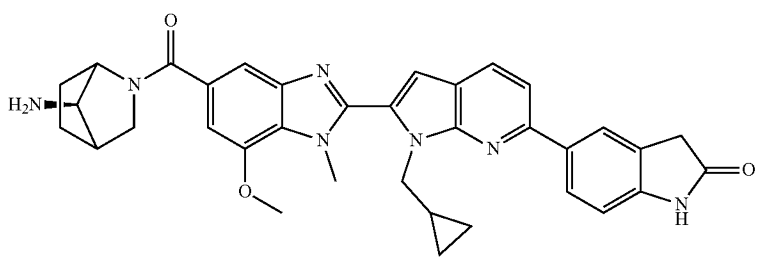 [SMILES: COc1cc(C(=O)N2CC3CCC2[C@@H]3N)cc2nc(-c3cc4ccc(-c5ccc6c(c5)CC(=O)N6)nc4n3CC3CC3)n(C)c12] | 5-(2-{5-[(1R,4R,7R)-7-amino-2-azabicyclo[2.2.1]heptane-2-carbonyl]-7-methoxy-1-methyl-1H-1,3-benodiazol-2-yl}-1-(cyclopropylmethyl)-1H-pyrrolo[2,3-b]pyridin-6-yl)-2,3-dihydro-1H-indol-2-one | 602.4 | 2 | 1.29 |
| 148. | 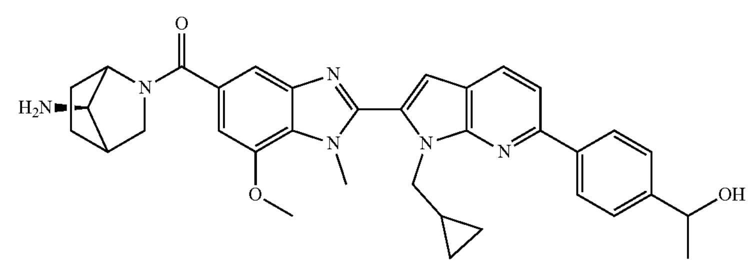 [SMILES: COc1cc(C(=O)N2CC3CCC2[C@@H]3N)cc2nc(-c3cc4ccc(-c5ccc(C(C)O)cc5)nc4n3CC3CC3)n(C)c12] | 1-[4-(2-{5-[(1R,4R,7R)-7-amino-2-azabicyclo[2.2.1]heptane-2-carbonyl]-7-methoxy-1-methyl-1H-1,3-benodiazol-2-yl}-1-(cyclopropylmethyl)-1H-pyrrolo[2,3-b]pyridin-6-yl)phenyl]ethan-1-ol | 591.5 | 2 | 1.46 |
| 149. | 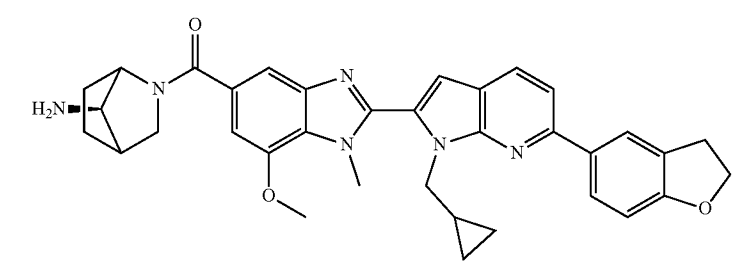 [SMILES: COc1cc(C(=O)N2CC3CCC2[C@@H]3N)cc2nc(-c3cc4ccc(-c5ccc6c(c5)CCO6)nc4n3CC3CC3)n(C)c12] | (1R,4R,7R)-2-{2-[1-(cyclopropylmethyl)-6-(2,3-dihydro-1-benzofuran-5-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 589.4 | 1 | 2.02 |

TABLE 3-continued

| Cmpd # | Structure | Name | Obs. MS Ion | HPLC Method IDs | RT (min) |
|---|---|---|---|---|---|
| 150. | 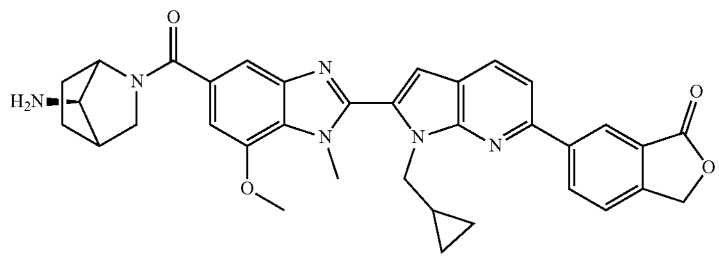 [SMILES: COc1cc(C(=O)N2CC3CCC2[C@@H]3N)cc2nc(-c3cc4ccc(-c5ccc6c(c5)C(=O)OC6)nc4n3CC3CC3)n(C)c12] | 6-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1,3-dihydro-2-benzofuran-1-one | 603.4 | 1 | 1.61 |
| 151. | 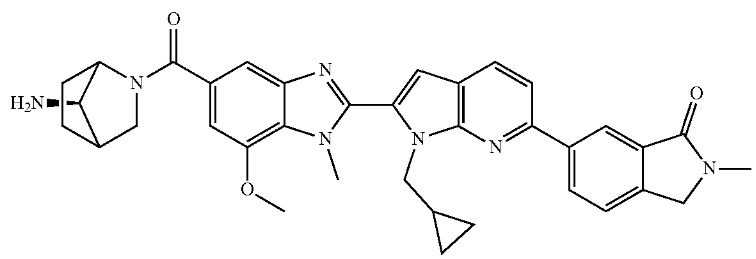 [SMILES: COc1cc(C(=O)N2CC3CCC2[C@@H]3N)cc2nc(-c3cc4ccc(-c5ccc6c(c5)C(=O)N(C)C6)nc4n3CC3CC3)n(C)c12] | 6-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-methyl-2,3-dihydro-1H-isoindol-1-one | 616.5 | 1 | 1.57 |
| 152. | 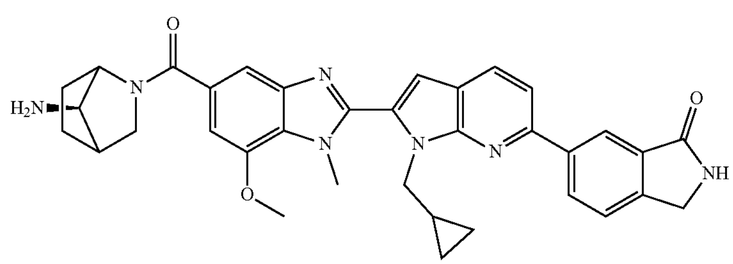 [SMILES: COc1cc(C(=O)N2CC3CCC2[C@@H]3N)cc2nc(-c3cc4ccc(-c5ccc6c(c5)C(=O)NC6)nc4n3CC3CC3)n(C)c12] | 6-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2,3-dihydro-1H-isoindol-1-one | 602.4 | 1 | 1.48 |

TABLE 4

| Cmpd # | Structure | Name | Obs. MS Ion | HPLC Method IDs | RT (min) |
|---|---|---|---|---|---|
| 153. | 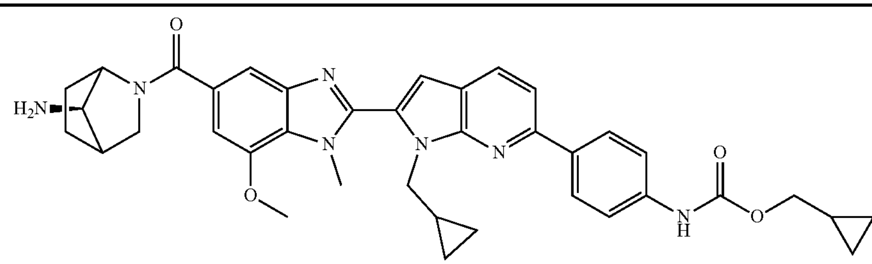 | cyclopropylmethyl N-[4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]carbamate | 660.5 | 1 | 2.03 |
| 154. | 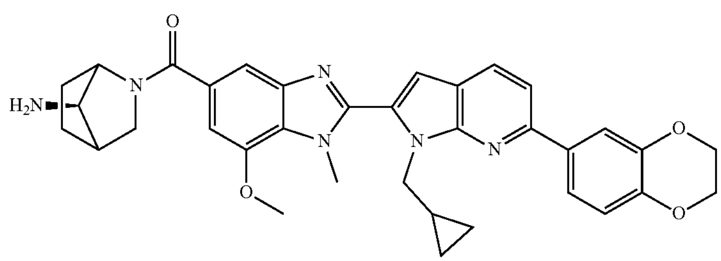 [SMILES: COc1cc(C(=O)N2CC3CCC2[C@@H]3N)cc2nc(-c3cc4ccc(-c5ccc6c(c5)OCCO6)nc4n3CC3CC3)n(C)c12] | (1R,4R,7R)-2-{2-[1-(cyclopropylmethyl)-6-(2,3-dihydro-1,4-benzodioxin-6-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 605.4 | 2 | 1.68 |
| 155. | 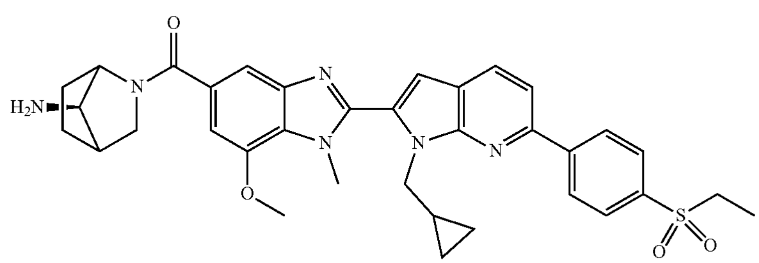 [SMILES: CCS(=O)(=O)c1ccc(-c2ccc3cc(-c4nc5cc(C(=O)N6CC7CCC6[C@@H]7N)cc(OC)c5n4C)n(CC4CC4)c3n2)cc1] | (1R,4R,7R)-2-{2-[1-(cyclopropylmethyl)-6-[4-(ethanesulfonyl)phenyl]-1H-pyrrolo[2,3-b]pyridin-2-yl]-7-methoxy-1-methyl-1H-1,3-benzodiazole-5-carbonyl}-2-azabicyclo[2.2.1]heptan-7-amine | 639.4 | 2 | 1.52 |

TABLE 4-continued

| Cmpd # | Structure | Name | Obs. MS Ion | HPLC Method IDs | RT (min) |
|---|---|---|---|---|---|
| 156. | 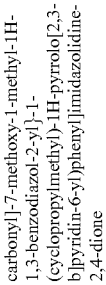 | 5-[4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]imidazolidine-2,4-dione | 645.4 | 2 | 1.19 |
| 157. | 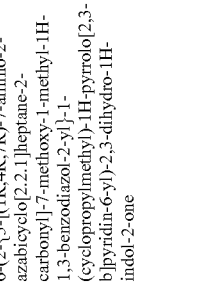 | 6-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2,3-dihydro-1H-indol-2-one | 602.4 | 1 | 1.51 |
| 158. | 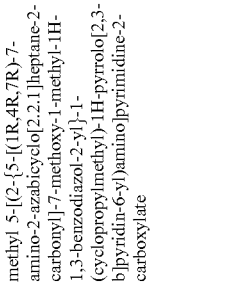 | methyl 5-[(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)amino]pyrimidine-2-carboxylate | 622.5 | 1 | 1.36 |

TABLE 4-continued

| Cmpd # | Structure | Name | Obs. MS Ion | HPLC Method IDs | RT (min) |
|---|---|---|---|---|---|
| 159. | 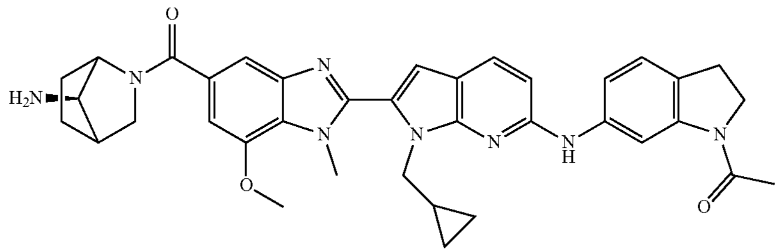 [SMILES: COc1cc(C(=O)N2CC3CCC2[C@@H]3N)cc2nc(-c3cc4ccc(Nc5ccc6c(c5)N(C(C)=O)CC6)nc4n3CC3CC3)n(C)c12] | 1-{6-[(2-{5-[(1R,4R,7R)-7-amino-2-azabicyclo[2.2.1]heptane-2-carbonyl]-7-methoxy-1H-1,3-benzodiazol-2-yl}-1-(cyclopropylmethyl)-1H-pyrrolo[2,3-b]pyridin-6-yl)amino]-2,3-dihydro-1H-indol-1-yl}ethan-1-one | 645.5 | 2 | 1.32 |
| 160. | 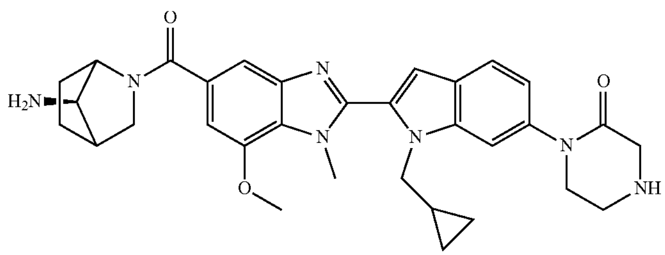 [SMILES: COc1cc(C(=O)N2CC3CCC2[C@@H]3N)cc2nc(-c3cc4ccc(N5CCNCC5=O)cc4n3CC3CC3)n(C)c12] | 1-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)piperazin-2-one | 568.5 | 1 | 1.11 |
| 161. | 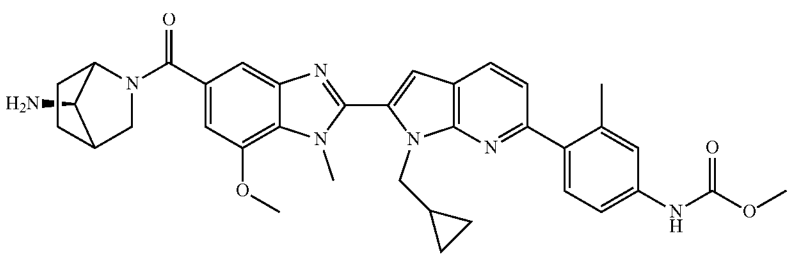 [SMILES: COC(=O)Nc1ccc(-c2ccc3cc(-c4nc5cc(C(=O)N6CC7CCC6[C@@H]7N)cc(OC)c5n4C)n(CC4CC4)c3n2)c(C)c1] | methyl N-[4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-3-methylphenyl]carbamate | 634.3 | 2 | 1.5 |
| 162. | 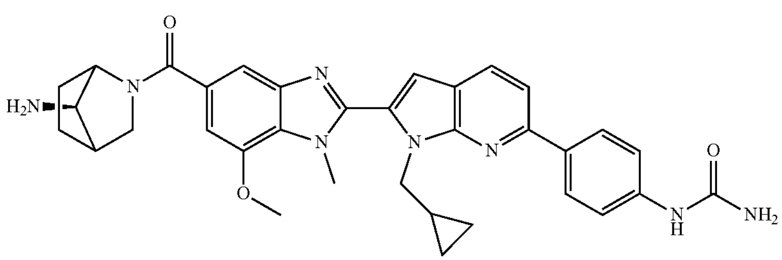 [SMILES: COc1cc(C(=O)N2CC3CCC2[C@@H]3N)cc2nc(-c3cc4ccc(-c5ccc(NC(N)=O)cc5)nc4n3CC3CC3)n(C)c12] | [4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]urea | 605.2 | 1 | 1.37 |

TABLE 4-continued

| Cmpd # | Structure | Name | Obs. MS Ion | HPLC Method IDs | RT (min) |
|---|---|---|---|---|---|
| 163. | 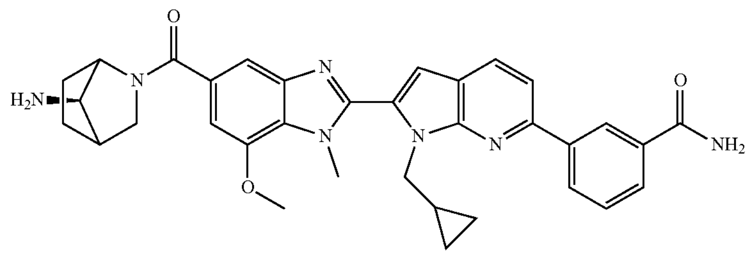 [SMILES: COc1cc(C(=O)N2CC3CCC2[C@@H]3N)cc2nc(-c3cc4ccc(-c5cccc(C(N)=O)c5)nc4n3CC3CC3)n(C)c12] | 3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)benzamide | 590 | 1 | 1.57 |
| 164. | 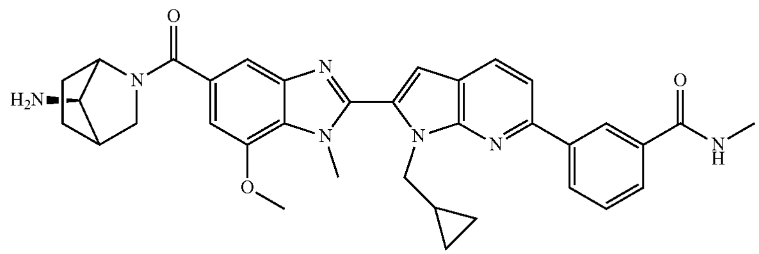 [SMILES: CNC(=O)c1cccc(-c2ccc3cc(-c4nc5cc(C(=O)N6CC7CCC6[C@@H]7N)cc(OC)c5n4C)n(CC4CC4)c3n2)c1] | 3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-N-methylbenzamide | 604.4 | 1 | 1.5 |
| 165. | 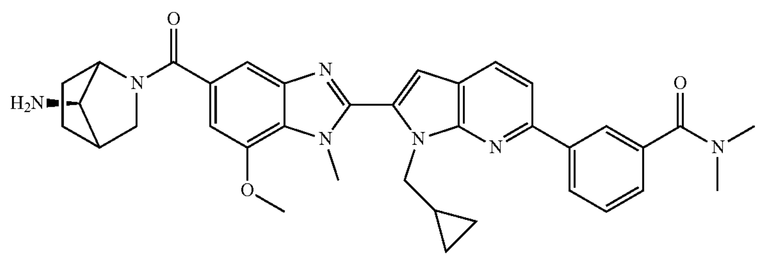 [SMILES: COc1cc(C(=O)N2CC3CCC2[C@@H]3N)cc2nc(-c3cc4ccc(-c5cccc(C(=O)N(C)C)c5)nc4n3CC3CC3)n(C)c12] | 3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-N,N-dimethylbenzamide | 618.3 | 2 | 1.39 |
| 166. | 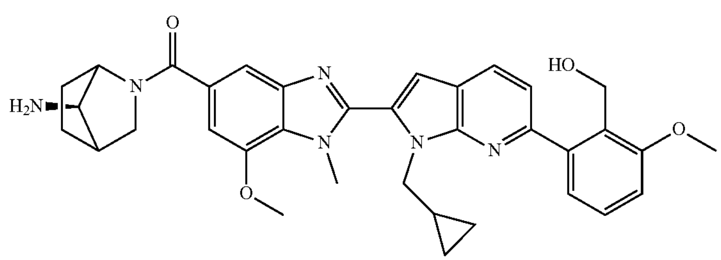 [SMILES: COc1cccc(-c2ccc3cc(-c4nc5cc(C(=O)N6CC7CCC6[C@@H]7N)cc(OC)c5n4C)n(CC4CC4)c3n2)c1CO] | [2-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-6-methoxyphenyl]methanol | 607 | 1 | 1.65 |

TABLE 4-continued

| Cmpd # | Structure | Name | Obs. MS Ion | HPLC Method IDs | RT (min) |
|---|---|---|---|---|---|
| 167. | 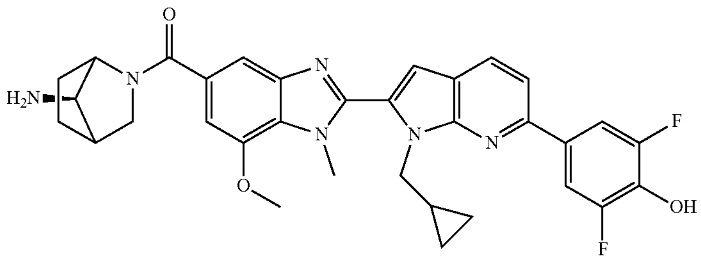 | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2,6-difluorophenol | 598.9 | 1 | 1.78 |
| 168. | 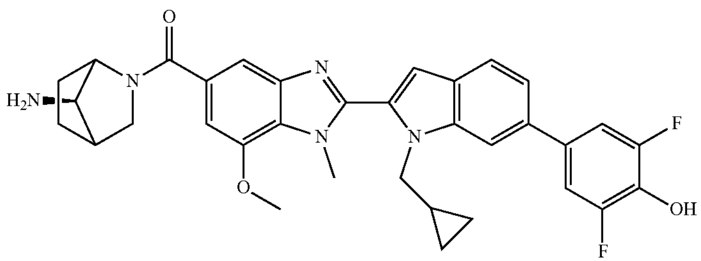 [SMILES: COc1cc(C(=O)N2CC3CCC2[C@@H]3N)cc2nc(-c3cc4ccc(-c5cc(F)c(O)c(F)c5)cc4n3CC3CC3)n(C)c12] | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-2,6-difluorophenol | 598.4 | 2 | 1.49 |
| 169. | 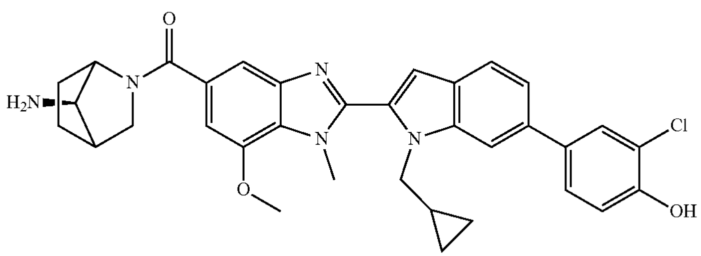 [SMILES: COc1cc(C(=O)N2CC3CCC2[C@@H]3N)cc2nc(-c3cc4ccc(-c5ccc(O)c(Cl)c5)cc4n3CC3CC3)n(C)c12] | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-2-chlorophenol | 596.4 | 2 | 1.52 |
| 170. | 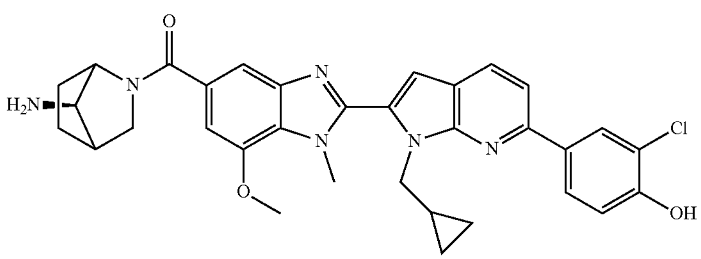 | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-chlorophenol | 603.4 | 2 | 1.55 |

TABLE 4-continued

| Cmpd # | Structure | Name | Obs. MS Ion | HPLC Method IDs | RT (min) |
|---|---|---|---|---|---|
| 171. | 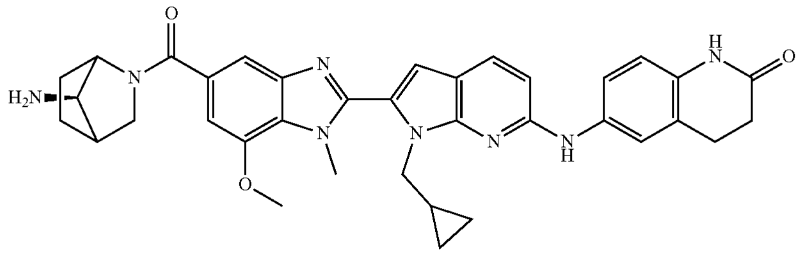 [SMILES: COc1cc(C(=O)N2CC3CCC2[C@@H]3N)cc2nc(-c3cc4ccc(Nc5ccc6c(c5)CCC(=O)N6)nc4n3CC3CC3)n(C)c12] | 6-[2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)amino]-1,2,3,4-tetrahydroquinolin-2-one | 631.2 | 2 | 1.32 |
| 172. | 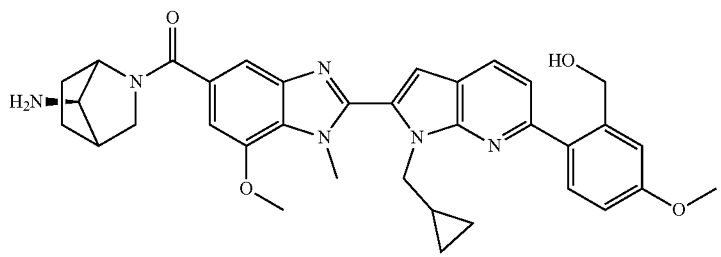 [SMILES: COc1ccc(-c2ccc3cc(-c4nc5cc(C(=O)N6CC7CCC6[C@@H]7N)cc(OC)c5n4C)n(CC4CC4)c3n2)c(CO)c1] | [2-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-5-methoxyphenyl]methanol | 607.5 | 2 | 1.52 |
| 173. | 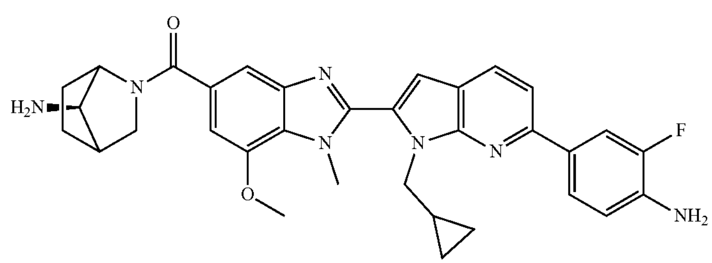 | (1R,4R,7R)-2-{2-[6-(4-amino-3-fluorophenyl)-1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 580.2 | 2 | 1.41 |

TABLE 4-continued

| Cmpd # | Structure | Name | Obs. MS Ion | HPLC Method IDs | RT (min) |
|---|---|---|---|---|---|
| 174. | 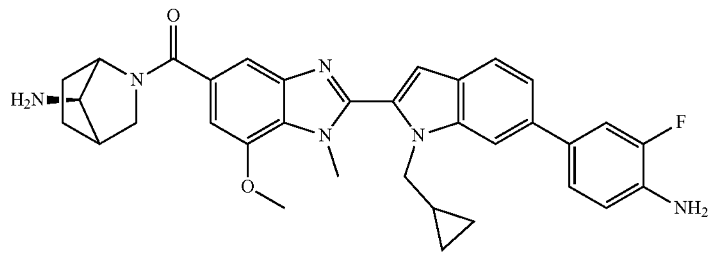 [SMILES: COc1cc(C(=O)N2CC3CCC2[C@@H]3N)cc2nc(-c3cc4ccc(-c5ccc(N)c(F)c5)cc4n3CC3CC3)n(C)c12] | (1R,4R,7R)-2-{2-[6-(4-amino-3-fluorophenyl)-1-(cyclopropylmethyl)-1H-indol-2-yl]-7-methoxy-1-methyl-1H-1,3-benzodiazole-5-carbonyl}-2-azabicyclo[2.2.1]heptan-7-amine | 579.5 | 1 | 1.74 |
| 175. | 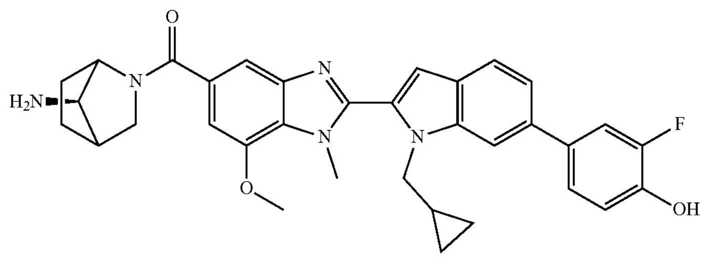 [SMILES: COc1cc(C(=O)N2CC3CCC2[C@@H]3N)cc2nc(-c3cc4ccc(-c5ccc(O)c(F)c5)cc4n3CC3CC3)n(C)c12] | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-2-fluorophenol | 580.4 | 1 | 1.66 |
| 176. | 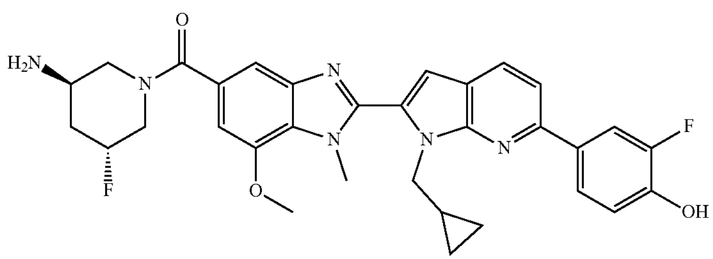 [SMILES: COc1cc(C(=O)N2C[C@H](N)C[C@@H](F)C2)cc2nc(-c3cc4ccc(-c5ccc(O)c(F)c5)nc4n3CC3CC3)n(C)c12] | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-fluorophenol | 587.4 | 2 | 1.47 |
| 177. | 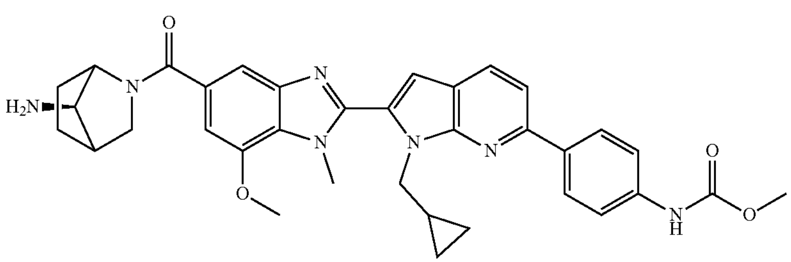 [SMILES: COC(=O)Nc1ccc(-c2ccc3cc(-c4nc5cc(C(=O)N6CC7CCC6[C@@H]7N)cc(OC)c5n4C)n(CC4CC4)c3n2)cc1] | methyl N-[4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]carbamate | 620.5 | 1 | 1.73 |

TABLE 4-continued

| Cmpd # | Structure | Name | Obs. MS Ion | HPLC Method IDs | RT (min) |
|---|---|---|---|---|---|
| 178. | 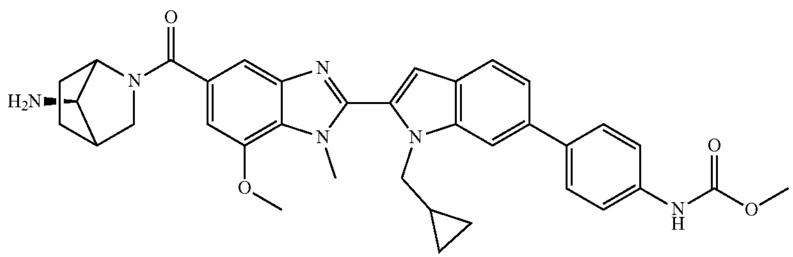 [SMILES: COC(=O)Nc1ccc(-c2ccc3cc(-c4nc5cc(C(=O)N6CC7CCC6[C@@H]7N)cc(OC)c5n4C)n(CC4CC4)c3c2)cc1] | methyl N-[4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)phenyl]carbamate | 619.2 | 2 | 1.66 |
| 179. | 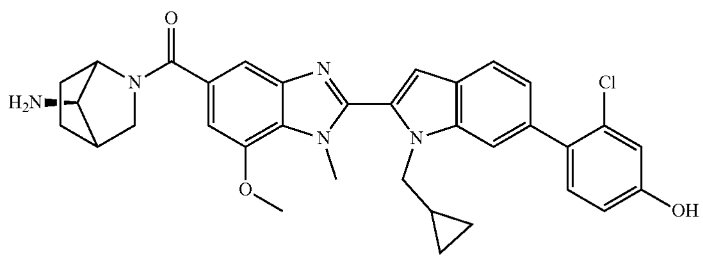 | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-3-chlorophenol | 596 | 1 | 1.86 |
| 180. | 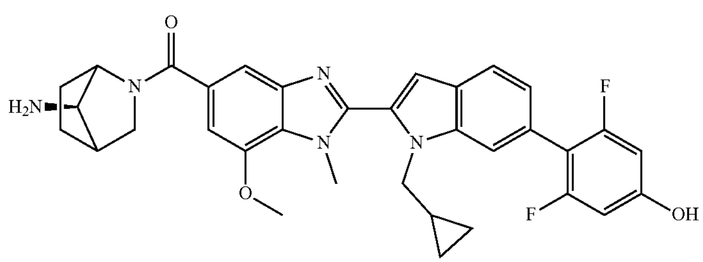 [SMILES: COc1cc(C(=O)N2CC3CCC2[C@@H]3N)cc2nc(-c3cc4ccc(-c5c(F)cc(O)cc5F)cc4n3CC3CC3)n(C)c12] | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-3,5-difluorophenol | 598.4 | 1 | 1.65 |

TABLE 4-continued

| Cmpd # | Structure | Name | Obs. MS Ion | HPLC Method IDs | RT (min) |
|---|---|---|---|---|---|
| 181. | 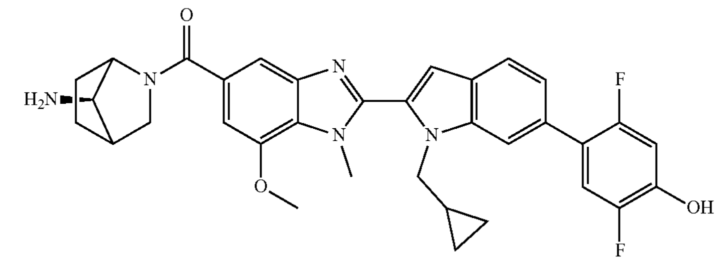 | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-2,5-difluorophenol | 597.9 | 1 | 1.85 |
| 182. | 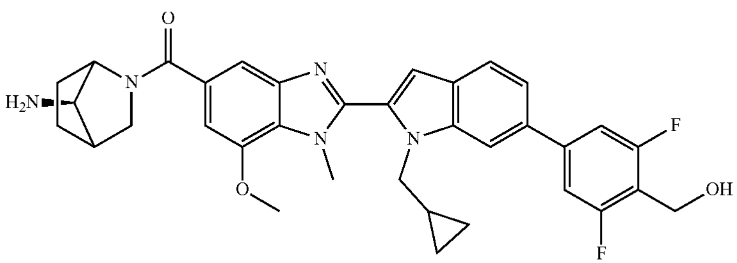 [SMILES: COc1cc(C(=O)N2CC3CCC2[C@@H]3N)cc2nc(-c3cc4ccc(-c5cc(F)c(CO)c(F)c5)cc4n3CC3CC3)n(C)c12] | [4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-2,6-difluorophenyl]methanol | 611.9 | 2 | 1.5 |
| 183. | 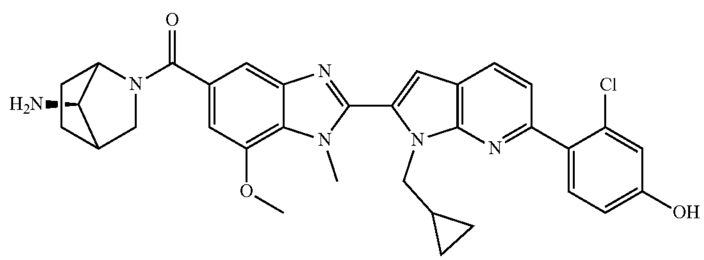 [SMILES: COc1cc(C(=O)N2CC3CCC2[C@@H]3N)cc2nc(-c3cc4ccc(-c5ccc(O)cc5Cl)nc4n3CC3CC3)n(C)c12] | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-3-chlorophenol | 597.3 | 2 | 1.46 |
| 184. | 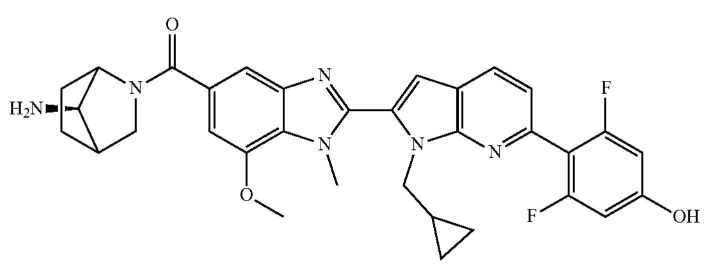 [SMILES: COc1cc(C(=O)N2CC3CCC2[C@@H]3N)cc2nc(-c3cc4ccc(-c5c(F)cc(O)cc5F)nc4n3CC3CC3)n(C)c12] | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-3,5-difluorophenol | 599 | 1 | 1.76 |

TABLE 4-continued

| Cmpd # | Structure | Name | Obs. MS Ion | HPLC Method IDs | RT (min) |
|---|---|---|---|---|---|
| 185. | 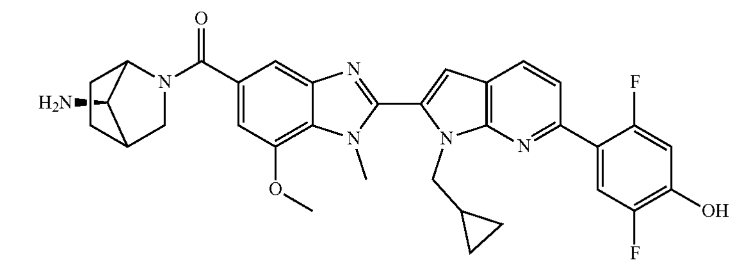 [SMILES: COc1cc(C(=O)N2CC3CCC2[C@@H]3N)cc2nc(-c3cc4ccc(-c5cc(F)c(O)cc5F)nc4n3CC3CC3)n(C)c12] | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2,5-difluorophenol | 599.2 | 2 | 1.48 |
| 186. | 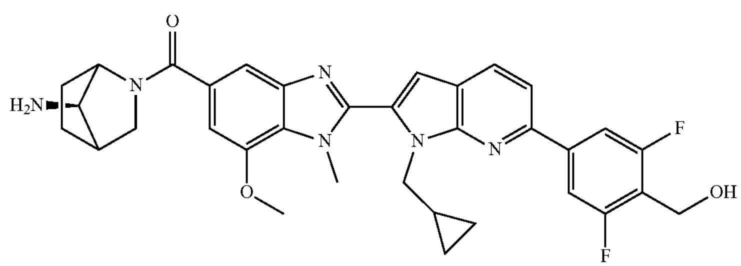 | [4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2,6-difluorophenyl]methanol | 613.2 | 1 | 1.82 |
| 187. | 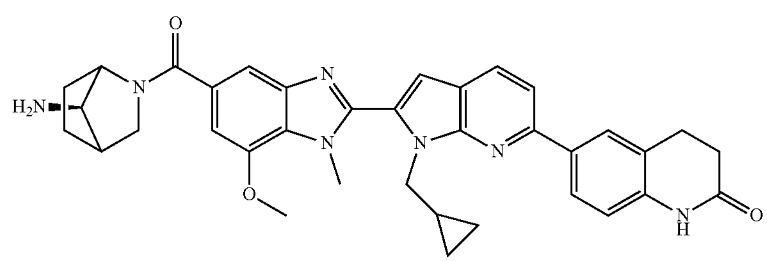 [SMILES: COc1cc(C(=O)N2CC3CCC2[C@@H]3N)cc2nc(-c3cc4ccc(-c5ccc6c(c5)CCC(=O)N6)nc4n3CC3CC3)n(C)c12] | 6-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1,2,3,4-tetrahydroquinolin-2-one | 615.5 | 2 | 1.34 |

TABLE 4-continued

| Cmpd # | Structure | Name | Obs. MS Ion | HPLC Method IDs | RT (min) |
|---|---|---|---|---|---|
| 188. | 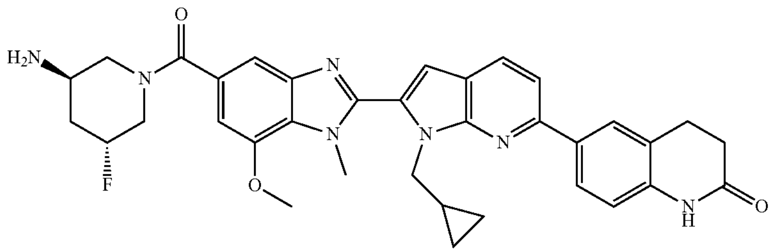 [SMILES: COc1cc(C(=O)N2C[C@H](N)C[C@@H](F)C2)cc2nc(-c3cc4ccc(-c5ccc6c(c5)CCC(=O)N6)nc4n3CC3CC3)n(C)c12] | 6-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-1,2,3,4-tetrahydroquinolin-2-one | 622 | 1 | 1.66 |
| 189. | 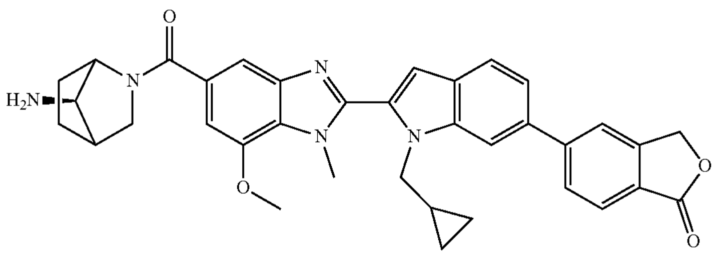 [SMILES: COc1cc(C(=O)N2CC3CCC2[C@@H]3N)cc2nc(-c3cc4ccc(-c5ccc6c(c5)COC6=O)cc4n3CC3CC3)n(C)c12] | 5-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-1,3-dihydro-2-benzofuran-1-one | 602.5 | 2 | 1.48 |
| 190. | 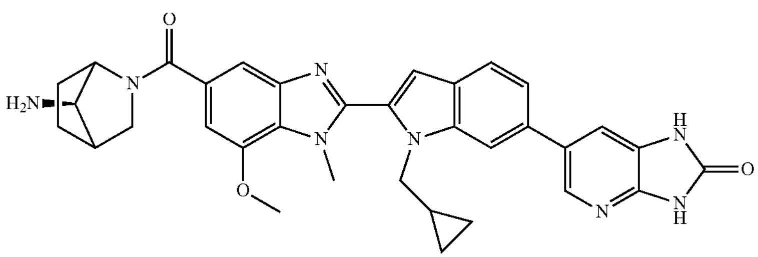 [SMILES: COc1cc(C(=O)N2CC3CCC2[C@@H]3N)cc2nc(-c3cc4ccc(-c5cnc6[nH]c(=O)[nH]c6c5)cc4n3CC3CC3)n(C)c12] | 6-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-1H,2H,3H-imidazo[4,5-b]pyridin-2-one | 603 | 2 | 1.23 |
| 191. | 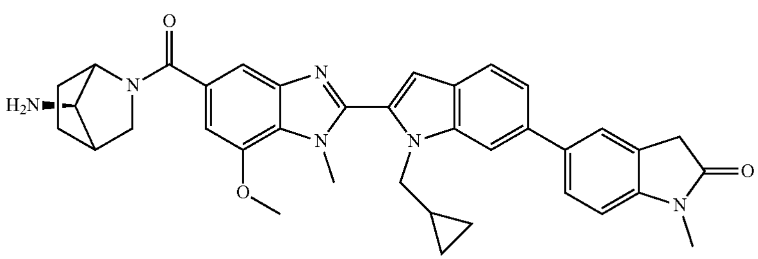 [SMILES: COc1cc(C(=O)N2CC3CCC2[C@@H]3N)cc2nc(-c3cc4ccc(-c5ccc6c(c5)CC(=O)N6C)cc4n3CC3CC3)n(C)c12] | 2'-{5-[(1R,4R,7R)-7-amino-2-azabicyclo[2.2.1]heptane-2-carbonyl]-7-methoxy-1-methyl-1H-1,3-benzodiazol-2-yl}-1'H-[5,6-biindole]-2-one | 615.4 | 1 | 1.77 |

TABLE 4-continued

| Cmpd # | Structure | Name | Obs. MS Ion | HPLC Method IDs | RT (min) |
|---|---|---|---|---|---|
| 192. | 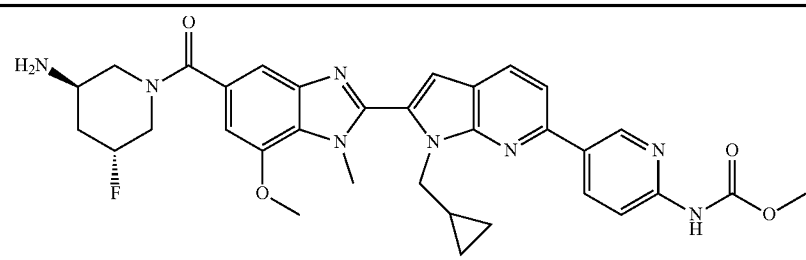 | methyl N-[5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)pyridin-2-yl]carbamate | 626.9 | 2 | 1.48 |
| 193. | 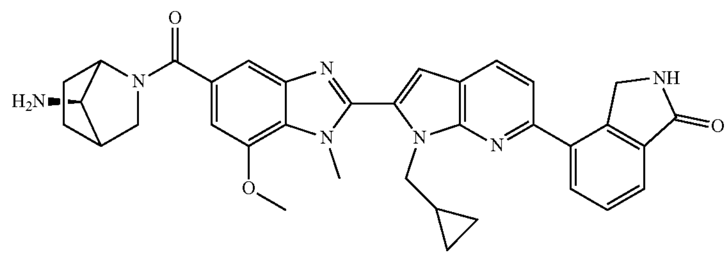 [SMILES: COc1cc(C(=O)N2CC3CCC2[C@@H]3N)cc2nc(-c3cc4ccc(-c5cccc6c5CNC6=O)nc4n3CC3CC3)n(C)c12] | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2,3-dihydro-1H-isoindol-1-one | 602.5 | 2 | 1.33 |
| 194. | 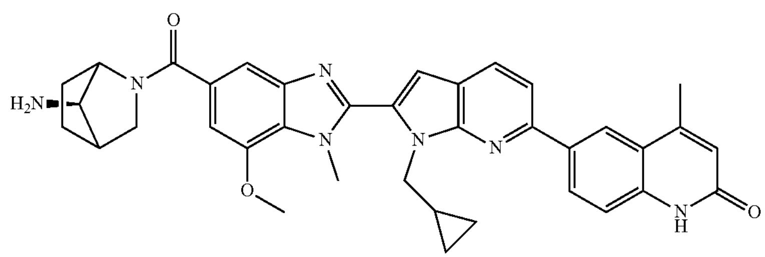 [SMILES: COc1cc(C(=O)N2CC3CCC2[C@@H]3N)cc2nc(-c3cc4ccc(-c5ccc6[nH]c(=O)cc(C)c6c5)nc4n3CC3CC3)n(C)c12] | 6-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-4-methyl-1,2-dihydroquinolin-2-one | 628.5 | 1 | 1.51 |
| 195. | 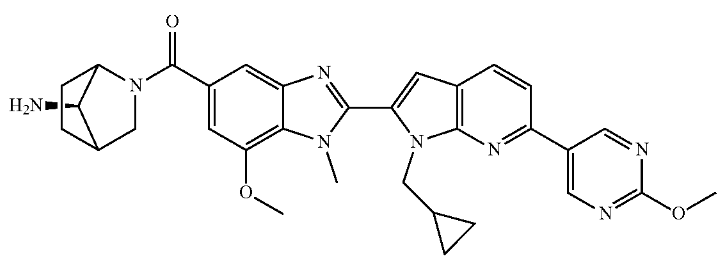 [SMILES: COc1ncc(-c2ccc3cc(-c4nc5cc(C(=O)N6CC7CCC6[C@@H]7N)cc(OC)c5n4C)n(CC4CC4)c3n2)cn1] | (1R,4R,7R)-2-{2-[1-(cyclopropylmethyl)-6-(2-methoxypyrimidin-5-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 579.3 | 1 | 1.55 |

TABLE 4-continued

| Cmpd # | Structure | Name | Obs. MS Ion | HPLC Method IDs | RT (min) |
|---|---|---|---|---|---|
| 196. | 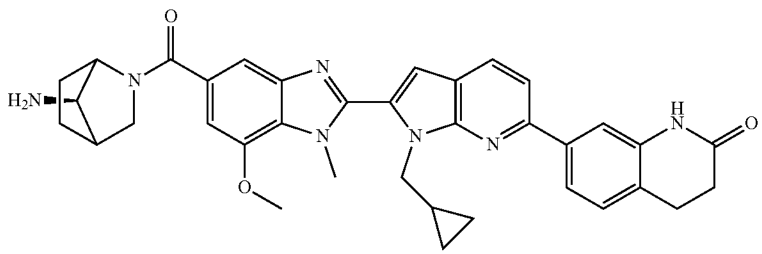 [SMILES: COc1cc(C(=O)N2CC3CCC2[C@@H]3N)cc2nc(-c3cc4ccc(-c5ccc6c(c5)NC(=O)CC6)nc4n3CC3CC3)n(C)c12] | 7-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1,2,3,4-tetrahydroquinolin-2-one | 616.4 | 1 | 1.55 |
| 197. | 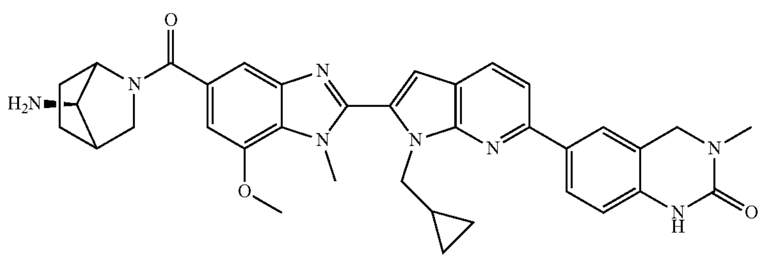 [SMILES: COc1cc(C(=O)N2CC3CCC2[C@@H]3N)cc2nc(-c3cc4ccc(-c5ccc6c(c5)CN(C)C(=O)N6)nc4n3CC3CC3)n(C)c12] | 6-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-3-methyl-1,2,3,4-tetrahydroquinazolin-2-one | 631.3 | 2 | 1.33 |
| 198. | 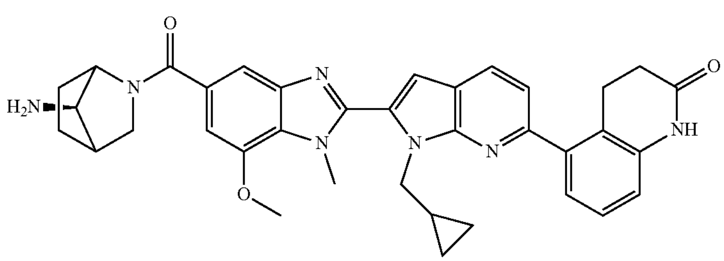 [SMILES: COc1cc(C(=O)N2CC3CCC2[C@@H]3N)cc2nc(-c3cc4ccc(-c5cccc6c5CCC(=O)N6)nc4n3CC3CC3)n(C)c12] | 5-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1,2,3,4-tetrahydroquinolin-2-one | 616.5 | 1 | 1.5 |

TABLE 4-continued

| Cmpd # | Structure | Name | Obs. MS Ion | HPLC Method IDs | RT (min) |
|---|---|---|---|---|---|
| 199. | 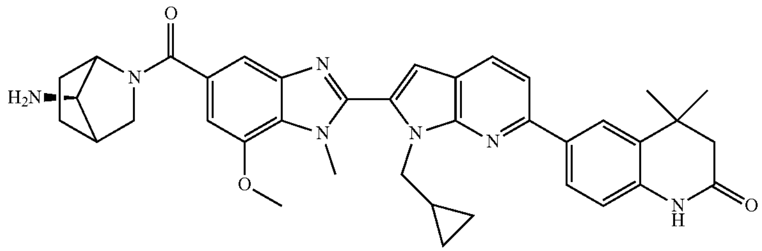 [SMILES: COc1cc(C(=O)N2CC3CCC2[C@@H]3N)cc2nc(-c3cc4ccc(-c5ccc6c(c5)C(C)(C)CC(=O)N6)nc4n3CC3CC3)n(C)c12] | 6-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-4,4-dimethyl-1,2,3,4-tetrahydroquinazolin-2-one | 644.4 | 1 | 1.73 |
| 200. | 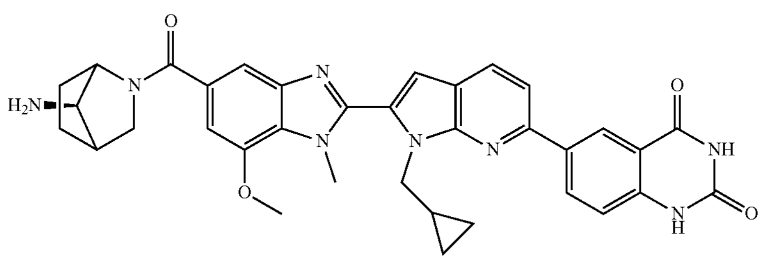 [SMILES: COc1cc(C(=O)N2CC3CCC2[C@@H]3N)cc2nc(-c3cc4ccc(-c5ccc6[nH]c(=O)[nH]c(=O)c6c5)nc4n3CC3CC3)n(C)c12] | 6-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1,2,3,4-tetrahydroquinazoline-2,4-dione | 631.4 | 2 | 1.19 |

TABLE 5

| Cmpd # | Structure | Name | Obs. MS Ion | HPLC Method IDs | RT (min) |
|---|---|---|---|---|---|
| 201. | 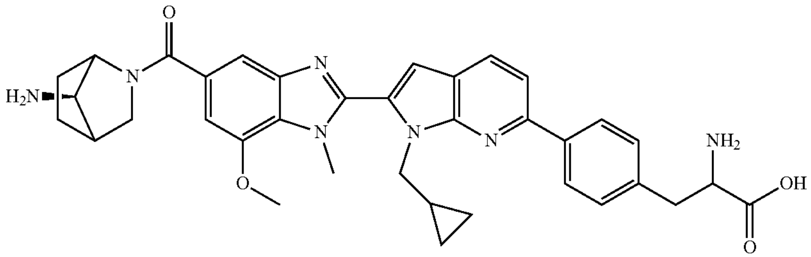 [SMILES: COc1cc(C(=O)N2CC3CCC2[C@@H]3N)cc2nc(-c3cc4ccc(-c5ccc(CC(N)C(=O)O)cc5)nc4n3CC3CC3)n(C)c12] | 2-amino-3-[4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]propanoic acid | 634.5 | 2 | 1.12 |
| 202. | 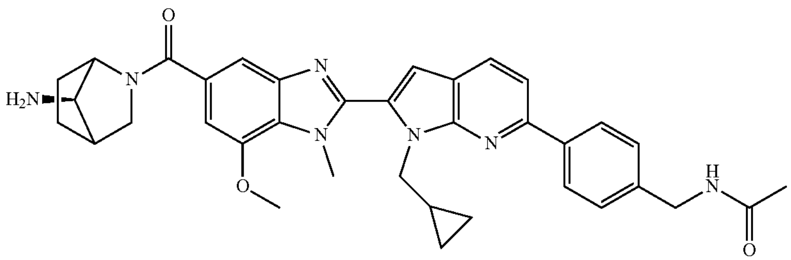 [SMILES: COc1cc(C(=O)N2CC3CCC2[C@@H]3N)cc2nc(-c3cc4ccc(-c5ccc(CNC(C)=O)cc5)nc4n3CC3CC3)n(C)c12] | N-{[4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]methyl}acetamide | 618.5 | 1 | 1.29 |
| 203. | 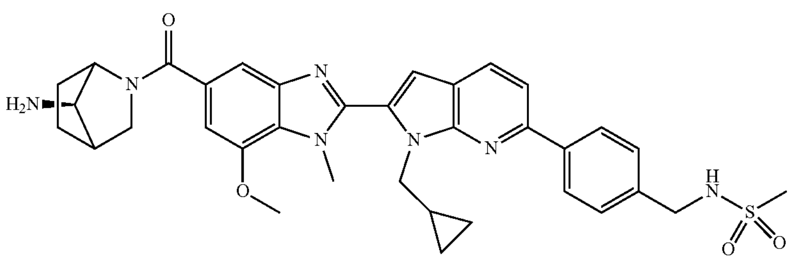 [SMILES: COc1cc(C(=O)N2CC3CCC2[C@@H]3N)cc2nc(-c3cc4ccc(-c5ccc(CNS(C)(=O)=O)cc5)nc4n3CC3CC3)n(C)c12] | N-{[4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]methyl}methanesulfonamide | 654.2 | 2 | 1.52 |

TABLE 5-continued

| Cmpd # | Structure | Name | Obs. MS Ion | HPLC Method IDs | RT (min) |
|---|---|---|---|---|---|
| 204. | 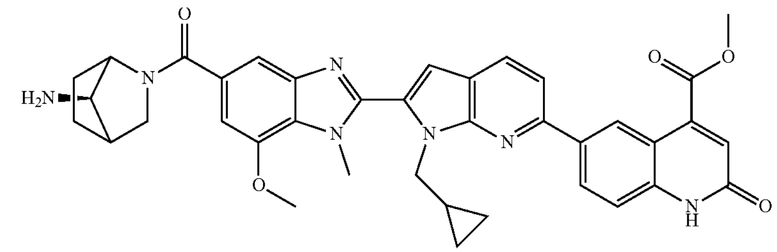 [SMILES: COC(=O)c1cc(=O)[nH]c2ccc(-c3ccc4cc(-c5nc6cc(C(=O)N7CC8CCC7[C@@H]8N)cc(OC)c6n5C)n(CC5CC5)c4n3)cc12] | methyl 6-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-oxo-1,2-dihydroquinoline-4-carboxylate | 672.1 | 2 | 1.7 |
| 205. | 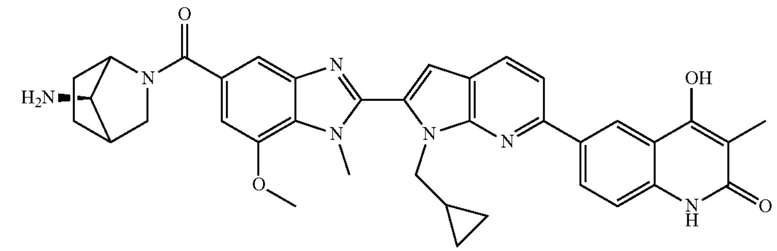 [SMILES: COc1cc(C(=O)N2CC3CCC2[C@@H]3N)cc2nc(-c3cc4ccc(-c5ccc6[nH]c(=O)c(C)c(O)c6c5)nc4n3CC3CC3)n(C)c12] | 6-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-4-hydroxy-3-methyl-1,2-dihydroquinolin-2-one | 644.4 | 1 | 1.21 |
| 206. | 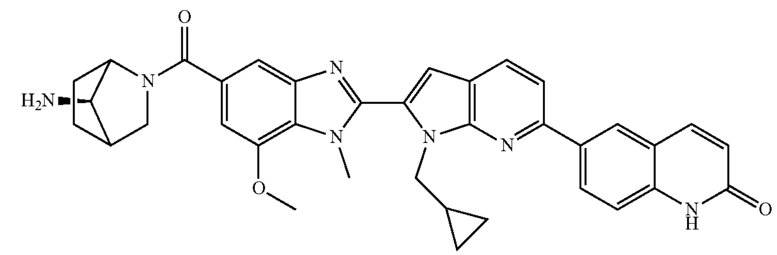 [SMILES: COc1cc(C(=O)N2CC3CCC2[C@@H]3N)cc2nc(-c3cc4ccc(-c5ccc6[nH]c(=O)ccc6c5)nc4n3CC3CC3)n(C)c12] | 6-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1,2-dihydroquinolin-2-one | 614.3 | 2 | 1.45 |
| 207. | 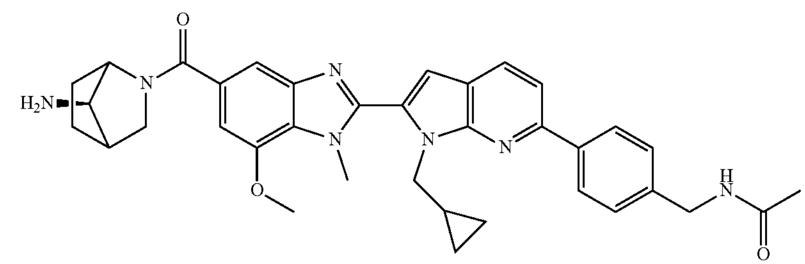 [SMILES: COc1cc(C(=O)N2CC3CCC2[C@@H]3N)cc2nc(-c3cc4ccc(-c5ccc(CNC(C)=O)cc5)nc4n3CC3CC3)n(C)c12] | N-{[4-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)phenyl]methyl}acetamide | 617.1 | 1 | 1.48 |

TABLE 5-continued

| Cmpd # | Structure | Name | Obs. MS Ion | HPLC Method IDs | RT (min) |
|---|---|---|---|---|---|
| 208. | 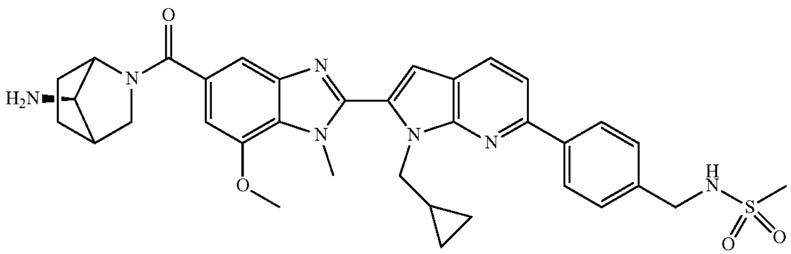 [SMILES: COc1cc(C(=O)N2CC3CCC2[C@@H]3N)cc2nc(-c3cc4ccc(-c5ccc(CNS(C)(=O)=O)cc5)nc4n3CC3CC3)n(C)c12] | N-[{4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)phenyl]methyl}methanesulfonamide | 653.2 | 2 | 1.83 |
| 209. | 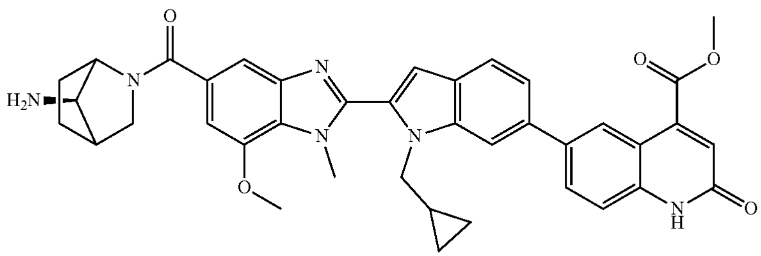 [SMILES: COC(=O)c1cc(=O)[nH]c2ccc(-c3ccc4cc(-c5nc6cc(C(=O)N7CC8CCC7[C@@H]8N)cc(OC)c6n5C)n(CC5CC5)c4c3)cc12] | methyl 6-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-2-oxo-1,2-dihydroquinoline-4-carboxylate | 671.3 | 2 | 1.72 |
| 210. | 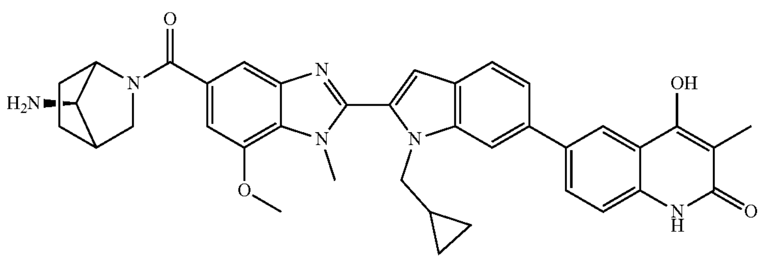 [SMILES: COc1cc(C(=O)N2CC3CCC2[C@@H]3N)cc2nc(-c3cc4ccc(-c5ccc6[nH]c(=O)c(C)c(O)c6c5)cc4n3CC3CC3)n(C)c12] | 6-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-4-hydroxy-3-methyl-1,2-dihydroquinolin-2-one | 643.2 | 1 | 1.21 |
| 211. | 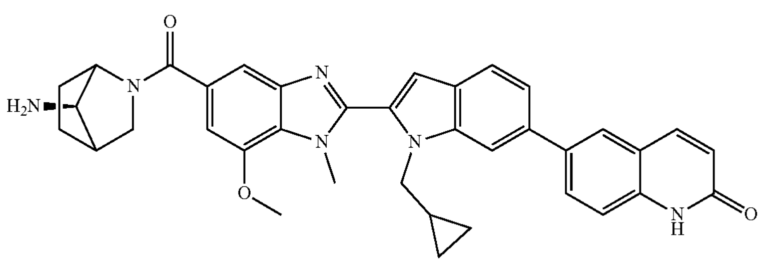 [SMILES: COc1cc(C(=O)N2CC3CCC2[C@@H]3N)cc2nc(-c3cc4ccc(-c5ccc6[nH]c(=O)ccc6c5)cc4n3CC3CC3)n(C)c12] | 6-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-1,2-dihydroquinolin-2-one | 613.1 | 1 | 1.45 |

TABLE 5-continued

| Cmpd # | Structure | Name | Obs. MS Ion | HPLC Method IDs | RT (min) |
|---|---|---|---|---|---|
| 212. | 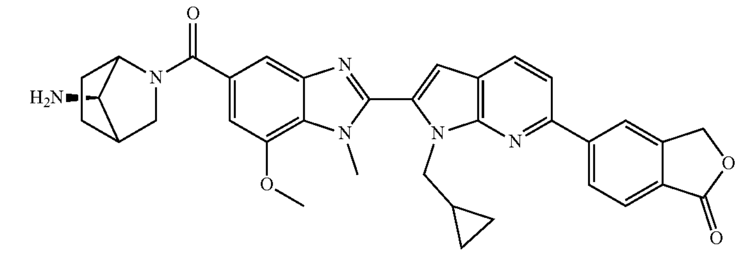 [SMILES: COc1cc(C(=O)N2CC3CCC2[C@@H]3N)cc2nc(-c3cc4ccc(-c5ccc6c(c5)COC6=O)nc4n3CC3CC3)n(C)c12] | 5-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1,3-dihydro-2-benzofuran-1-one | 603.4 | 2 | 1.78 |
| 213. | 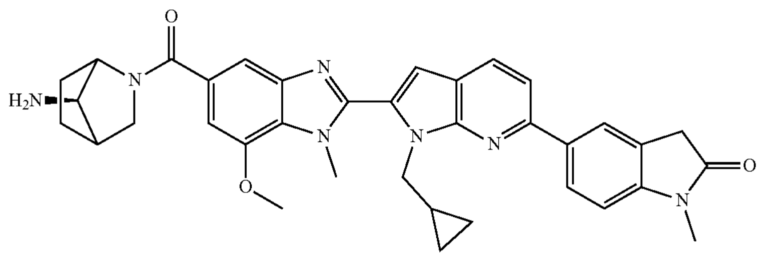 [SMILES: COc1cc(C(=O)N2CC3CCC2[C@@H]3N)cc2nc(-c3cc4ccc(-c5ccc6c(c5)CC(=O)N6C)nc4n3CC3CC3)n(C)c12] | 5-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1-methyl-2,3-dihydro-1H-indol-2-one | 616.5 | 1 | 1.42 |
| 214. | 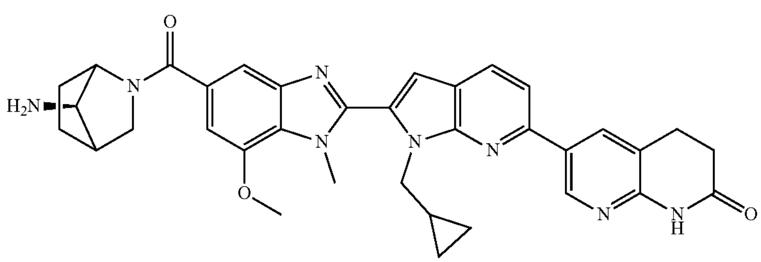 [SMILES: COc1cc(C(=O)N2CC3CCC2[C@@H]3N)cc2nc(-c3cc4ccc(-c5cnc6c(c5)CCC(=O)N6)nc4n3CC3CC3)n(C)c12] | 6-(2-{5-[(1R,4R,7R)-7-amino-2-azabicyclo[2.2.1]heptane-2-carbonyl]-7-methoxyl-methyl-1H-1,3-benzodiazol-2-yl}-1-(cyclopropylmethyl)-1H-pyrrolo[2,3-b]pyridin-6-yl)-1,2,3,4-tetrahydro-1,8-naphthyridin-2-one | 617.2 | 2 | 1.64 |

TABLE 5-continued

| Cmpd # | Structure | Name | Obs. MS Ion | HPLC Method IDs | RT (min) |
|---|---|---|---|---|---|
| 215. | 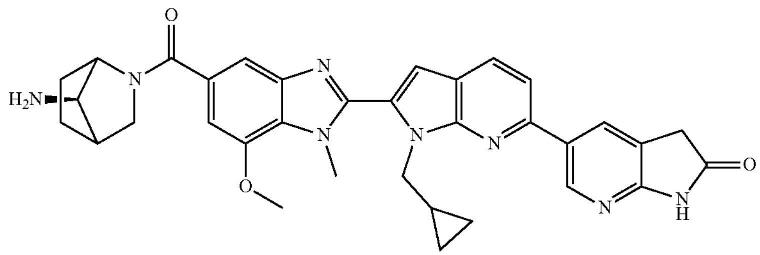 | 5-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1H,2H,3H-pyrrolo[2,3-b]pyridin-2-one | 603.4 | 2 | 1.32 |
| 216. | 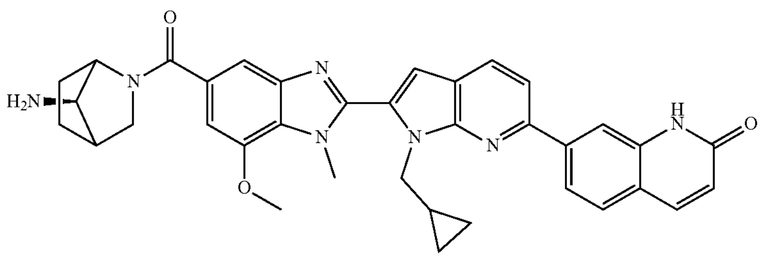 [SMILES: COc1cc(C(=O)N2CC3CCC2[C@@H]3N)cc2nc(-c3cc4ccc(-c5ccc6ccc(=O)[nH]c6c5)nc4n3CC3CC3)n(C)c12] | 7-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1,2-dihydroquinolin-2-one | 614.1 | 1 | 1.53 |
| 217. | 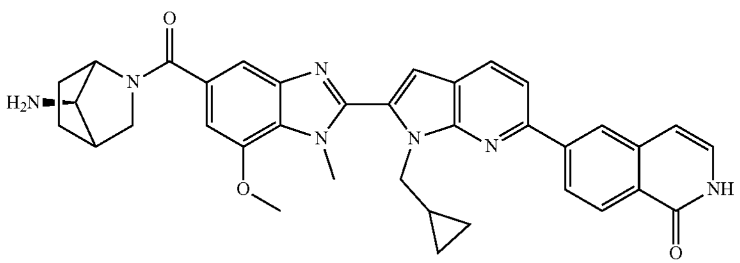 | 6-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1,2-dihydroisoquinolin-1-one | 614.1 | 2 | 1.6 |
| 218. | 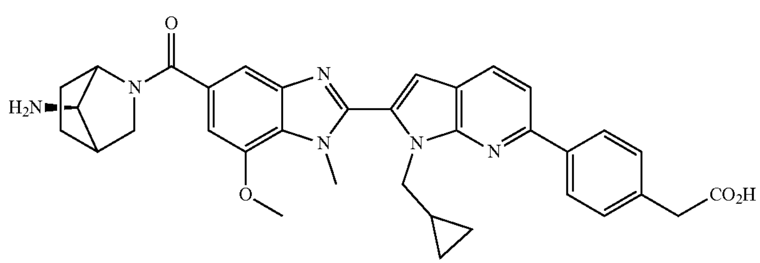 [SMILES: COc1cc(C(=O)N2CC3CCC2[C@@H]3N)cc2nc(-c3cc4ccc(-c5ccc(CC(=O)O)cc5)nc4n3CC3CC3)n(C)c12] | 2-[4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]acetic acid | 605.3 | 1 | 1.57 |

TABLE 5-continued

| Cmpd # | Structure | Name | Obs. MS Ion | HPLC Method IDs | RT (min) |
|---|---|---|---|---|---|
| 219. | 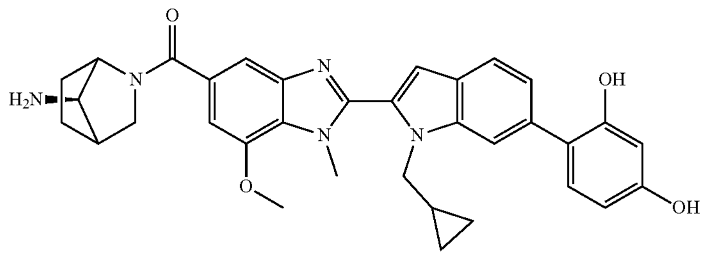 [SMILES: COc1cc(C(=O)N2CC3CCC2[C@@H]3N)cc2nc(-c3cc4ccc(-c5ccc(O)cc5O)cc4n3CC3CC3)n(C)c12] | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)benzene-1,3-diol | 578 | 1 | 1.28 |
| 220. | 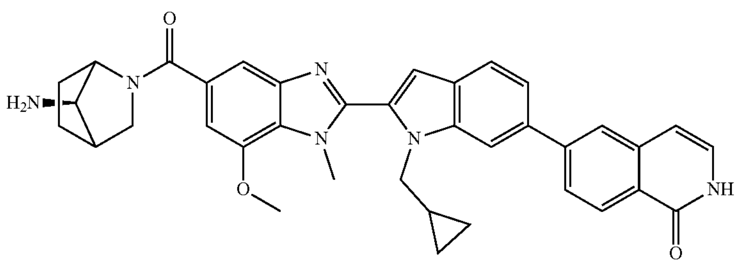 [SMILES: COc1cc(C(=O)N2CC3CCC2[C@@H]3N)cc2nc(-c3cc4ccc(-c5ccc6c(=O)[nH]ccc6c5)cc4n3CC3CC3)n(C)c12] | 6-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-1,2-dihydroisoquinolin-1-one | 613.4 | 2 | 1.5 |
| 221. | 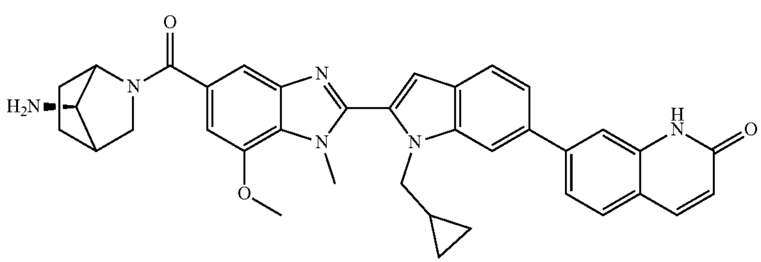 [SMILES: COc1cc(C(=O)N2CC3CCC2[C@@H]3N)cc2nc(-c3cc4ccc(-c5ccc6ccc(=O)[nH]c6c5)cc4n3CC3CC3)n(C)c12] | 7-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-1,2-dihydroquinolin-2-one | 613.4 | 1 | 1.35 |

TABLE 5-continued

| Cmpd # | Structure | Name | Obs. MS Ion | HPLC Method IDs | RT (min) |
|---|---|---|---|---|---|
| 222. | 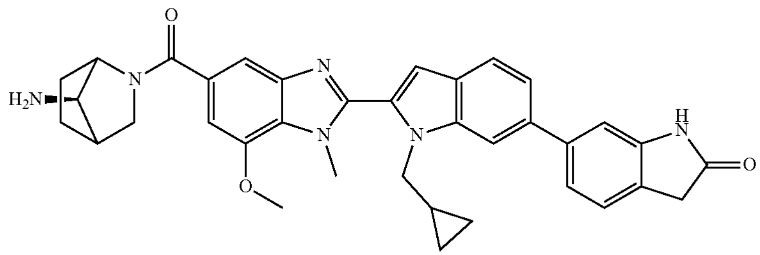 [SMILES: COc1cc(C(=O)N2CC3CCC2[C@@H]3N)cc2nc(-c3cc4ccc(-c5ccc6c(c5)NC(=O)C6)cc4n3CC3CC3)n(C)c12] | 2'-{5-[(1R,4R,7R)-7-amino-2-azabicyclo[2.2.1]heptane-2-carbonyl]-7-methoxy-1-methyl-1H-1,3-benzodiazol-2-yl}-1'-(cyclopropylmethyl)-2,3-dihydro-1H,1'H-[6,6'-biindole]-2-one | 601.5 | 1 | 1.33 |
| 223. | 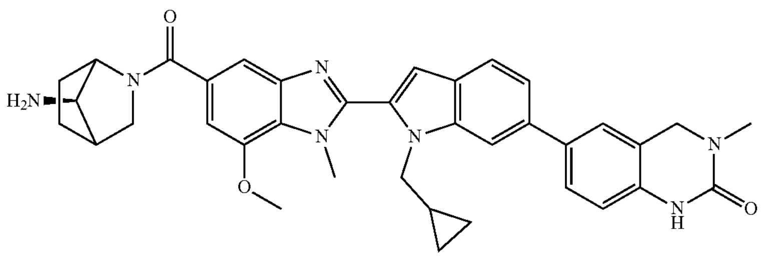 [SMILES: COc1cc(C(=O)N2CC3CCC2[C@@H]3N)cc2nc(-c3cc4ccc(-c5ccc6c(c5)CN(C)C(=O)N6)cc4n3CC3CC3)n(C)c12] | 6-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-3-methyl-1,2,3,4-tetrahydroquinazolin-2-one | 630.5 | 2 | 1.52 |
| 224. | 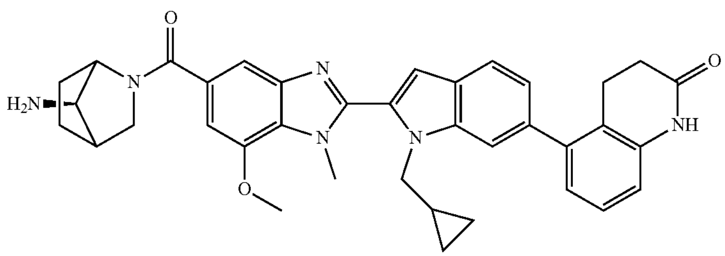 [SMILES: COc1cc(C(=O)N2CC3CCC2[C@@H]3N)cc2nc(-c3cc4ccc(-c5cccc6c5CCC(=O)N6)cc4n3CC3CC3)n(C)c12] | 5-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-1,2,3,4-tetrahydroquinolin-2-one | 615.5 | 1 | 1.36 |
| 225. | 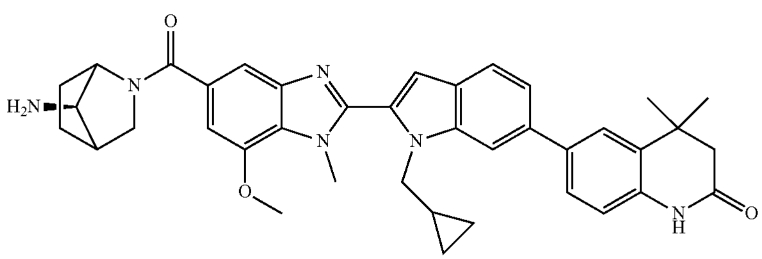 [SMILES: COc1cc(C(=O)N2CC3CCC2[C@@H]3N)cc2nc(-c3cc4ccc(-c5ccc6c(c5)C(C)(C)CC(=O)N6)cc4n3CC3CC3)n(C)c12] | 6-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-4,4-dimethyl-1,2,3,4-tetrahydroquinolin-2-one | 643.2 | 1 | 1.61 |

TABLE 5-continued

| Cmpd # | Structure | Name | Obs. MS Ion | HPLC Method IDs | RT (min) |
|---|---|---|---|---|---|
| 226. | 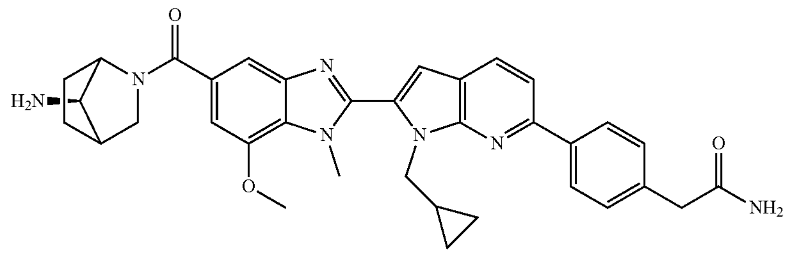 [SMILES: COc1cc(C(=O)N2CC3CCC2[C@@H]3N)cc2nc(-c3cc4ccc(-c5ccc(CC(N)=O)cc5)nc4n3CC3CC3)n(C)c12] | 2-[4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]acetamide | 604.2 | 2 | 1.51 |
| 227. | 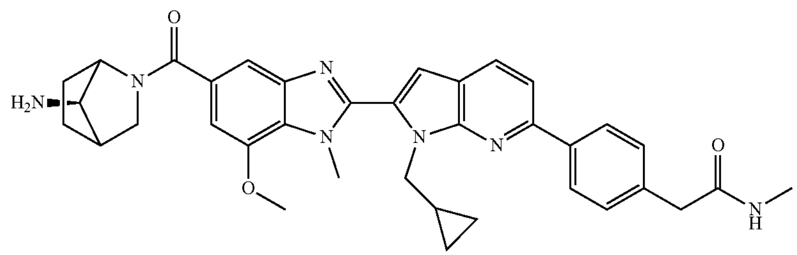 [SMILES: CNC(=O)Cc1ccc(-c2ccc3cc(-c4nc5cc(C(=O)N6CC7CCC6[C@@H]7N)cc(OC)c5n4C)n(CC4CC4)c3n2)cc1] | 2-[4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]-N-methylacetamide | 618.2 | 1 | 1.38 |
| 228. | 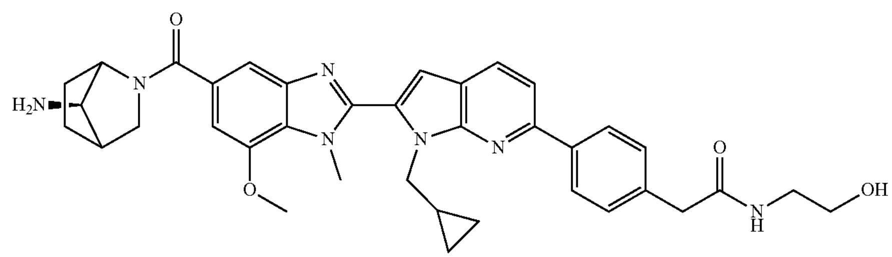 [SMILES: COc1cc(C(=O)N2CC3CCC2[C@@H]3N)cc2nc(-c3cc4ccc(-c5ccc(CC(=O)NCCO)cc5)nc4n3CC3CC3)n(C)c12] | 2-[4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]-N-(2-hydroxyethyl)acetamide | 648.2 | 1 | 1.31 |
| 229. | 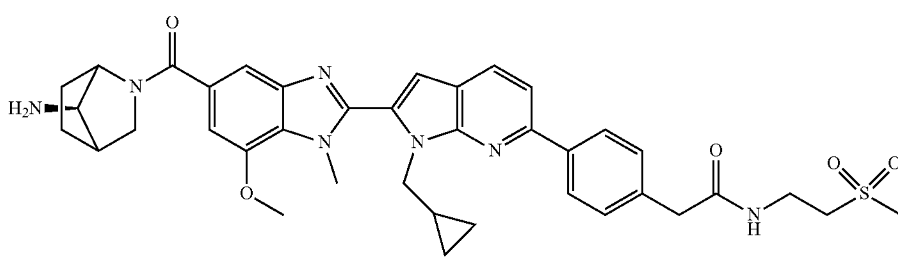 [SMILES: COc1cc(C(=O)N2CC3CCC2[C@@H]3N)cc2nc(-c3cc4ccc(-c5ccc(CC(=O)NCCS(C)(=O)=O)cc5)nc4n3CC3CC3)n(C)c12] | 2-[4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]-N-(2-methanesulfonylethyl)acetamide | 710.3 | 1 | 1.38 |

TABLE 5-continued

| Cmpd # | Structure | Name | Obs. MS Ion | HPLC Method IDs | RT (min) |
|---|---|---|---|---|---|
| 230. | 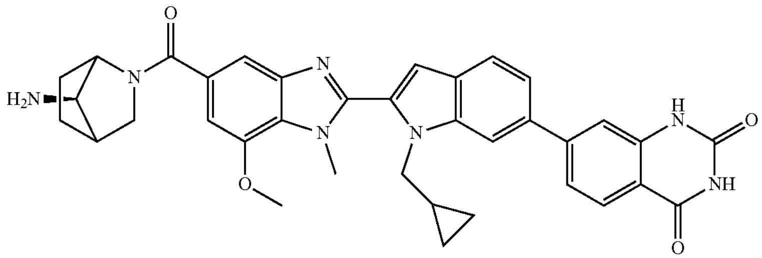 [SMILES: COc1cc(C(=O)N2CC3CCC2[C@@H]3N)cc2nc(-c3cc4ccc(-c5ccc6c(=O)[nH]c(=O)[nH]c6c5)cc4n3CC3CC3)n(C)c12] | 7-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-1,2,3,4-tetrahydroquinazoline-2,4-dione | 629.9 | 2 | 1.54 |
| 231. | 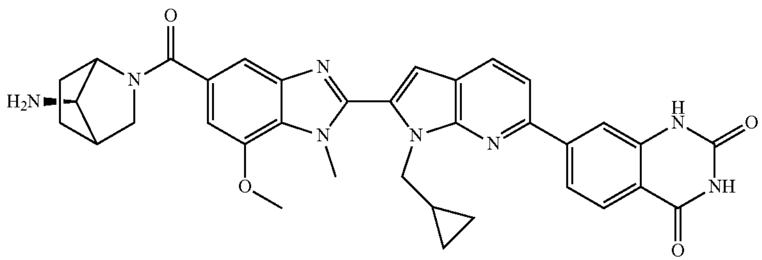 | 7-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1,2,3,4-tetrahydroquinazoline-2,4-dione | 631.2 | 2 | 1.5 |
| 232. | 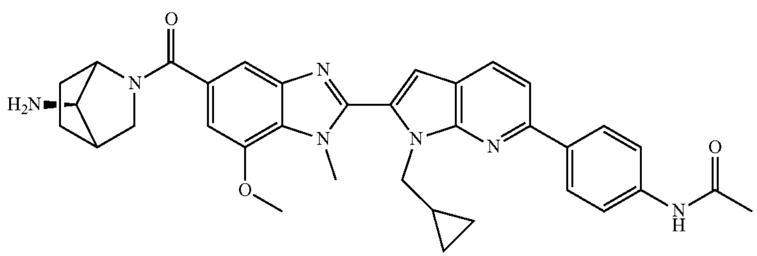 [SMILES: COc1cc(C(=O)N2CC3CCC2[C@@H]3N)cc2nc(-c3cc4ccc(-c5ccc(NC(C)=O)cc5)nc4n3CC3CC3)n(C)c12] | N-[4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]acetamide | 604.1 | 1 | 1.42 |
| 233. | 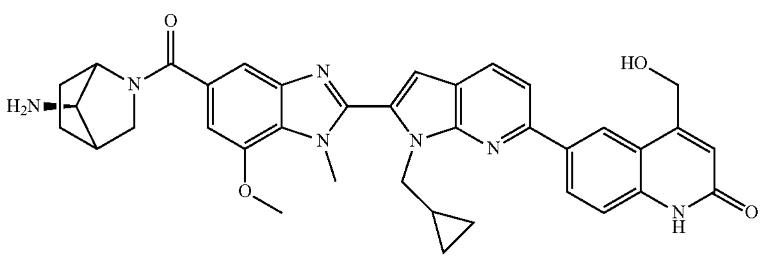 | 6-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-4-(hydroxymethyl)-1,2-dihydroquinolin-2-one | 644.4 | 1 | 1.29 |

TABLE 5-continued

| Cmpd # | Structure | Name | Obs. MS Ion | HPLC Method IDs | RT (min) |
|---|---|---|---|---|---|
| 234. | 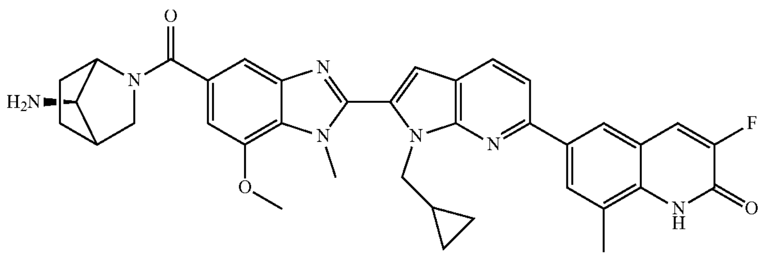 [SMILES: COc1cc(C(=O)N2CC3CCC2[C@@H]3N)cc2nc(-c3cc4ccc(-c5cc(C)c6[nH]c(=O)c(F)cc6c5)nc4n3CC3CC3)n(C)c12] | 6-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-3-fluoro-8-methyl-1,2-dihydroquinolin-2-one | 646.2 | 1 | 1.42 |
| 235. | 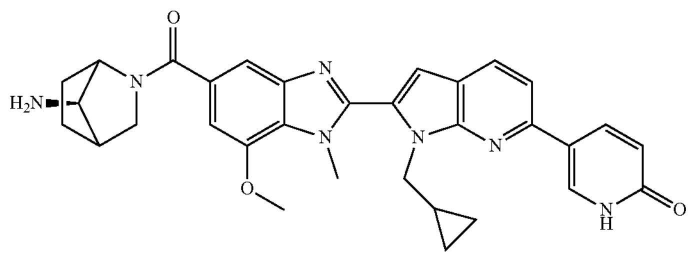 [SMILES: COc1cc(C(=O)N2CC3CCC2[C@@H]3N)cc2nc(-c3cc4ccc(-c5ccc(=O)[nH]c5)nc4n3CC3CC3)n(C)c12] | 5-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1,2-dihydropyridin-2-one | 564.6 | 2 | 1.24 |
| 236. | 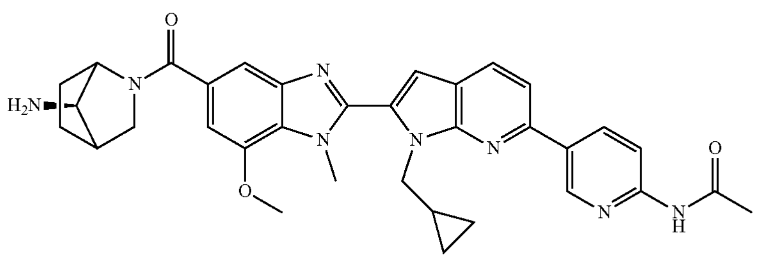 [SMILES: COc1cc(C(=O)N2CC3CCC2[C@@H]3N)cc2nc(-c3cc4ccc(-c5ccc(NC(C)=O)nc5)nc4n3CC3CC3)n(C)c12] | N-[5-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)pyridin-2-yl]acetamide | 605.1 | 1 | 1.28 |
| 237. | 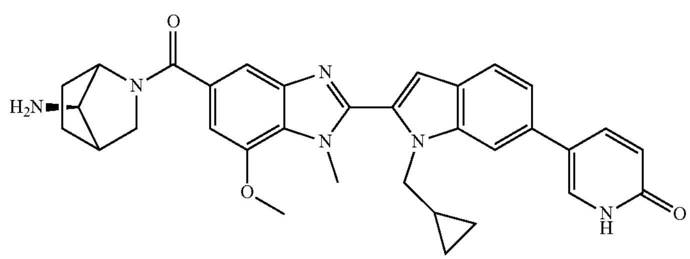 [SMILES: COc1cc(C(=O)N2CC3CCC2[C@@H]3N)cc2nc(-c3cc4ccc(-c5ccc(=O)[nH]c5)cc4n3CC3CC3)n(C)c12] | 2-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-1,2-dihydropyridin-2-one | 563.1 | 2 | 1.41 |

TABLE 5-continued

| Cmpd # | Structure | Name | Obs. MS Ion | HPLC Method IDs | RT (min) |
|---|---|---|---|---|---|
| 238. | 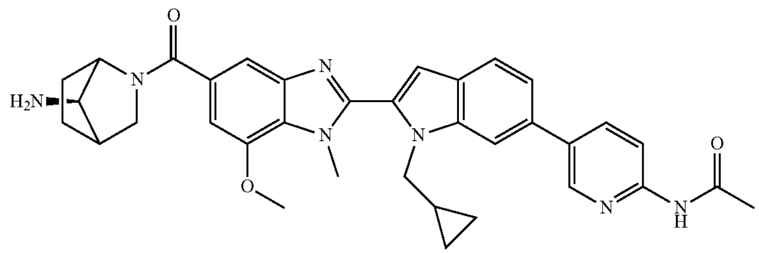 | N-[5-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)pyridin-2-yl]acetamide | 604.2 | 1 | 1.13 |
| 239. | 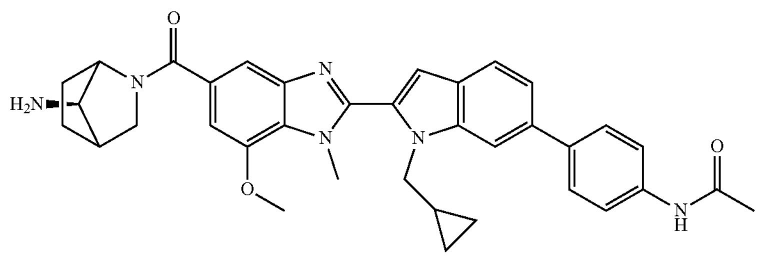 | N-[4-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)phenyl]acetamide | 603.1 | 1 | 1.43 |
| 240. | 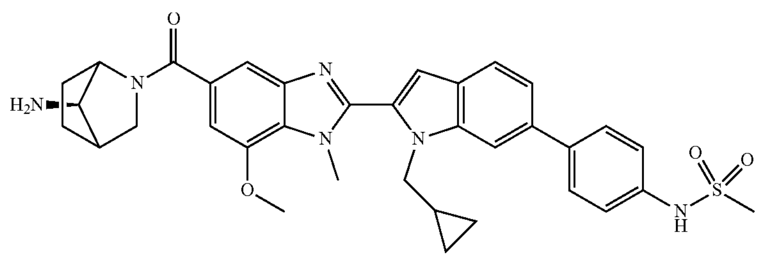 [SMILES: COc1cc(C(=O)N2CC3CCC2[C@@H]3N)cc2nc(-c3cc4ccc(-c5ccc(NS(C)(=O)=O)cc5)cc4n3CC3CC3)n(C)c12] | N-[4-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)phenyl]methanesulfonamide | 639.3 | 1 | 1.37 |
| 241. | 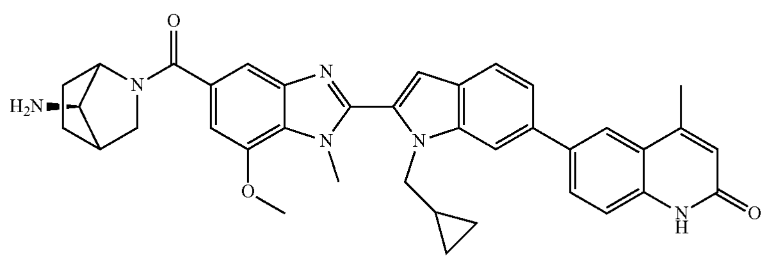 | 6-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-4-methyl-1,2-dihydroquinolin-2-one | 627.2 | 1 | 1.31 |

TABLE 5-continued

| Cmpd # | Structure | Name | Obs. MS Ion | HPLC Method IDs | RT (min) |
|---|---|---|---|---|---|
| 242. | 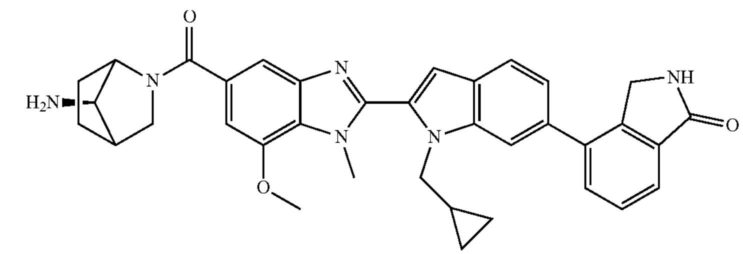 | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-2,3-dihydro-1H-isoindol-1-one | 601.6 | 2 | 1.49 |
| 243. | 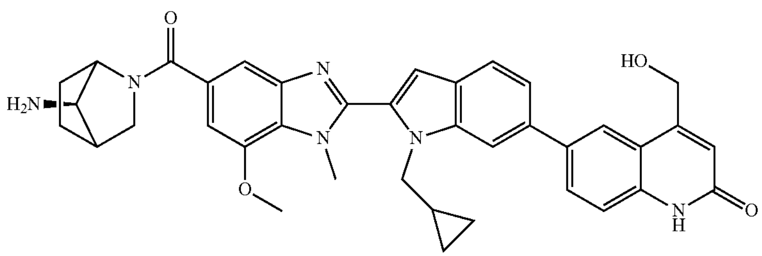 [SMILES: COc1cc(C(=O)N2CC3CCC2[C@@H]3N)cc2nc(-c3cc4ccc(-c5ccc6[nH]c(=O)cc(CO)c6c5)cc4n3CC3CC3)n(C)c12] | 6-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-4-(hydroxymethyl)-1,2-dihydroquinolin-2-one | 643.2 | 2 | 1.44 |
| 244. | 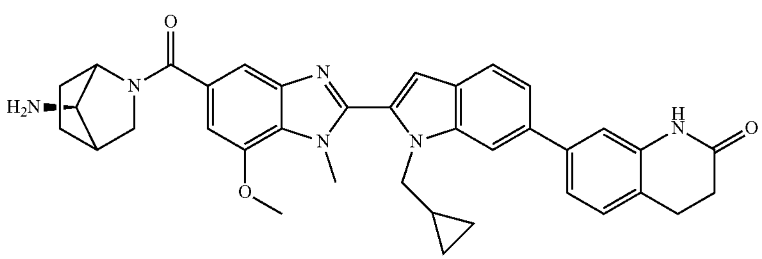 [SMILES: COc1cc(C(=O)N2CC3CCC2[C@@H]3N)cc2nc(-c3cc4ccc(-c5ccc6c(c5)NC(=O)CC6)cc4n3CC3CC3)n(C)c12] | 7-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-1,2,3,4-tetrahydroquinolin-2-one | 615.1 | 1 | 1.51 |
| 245. | 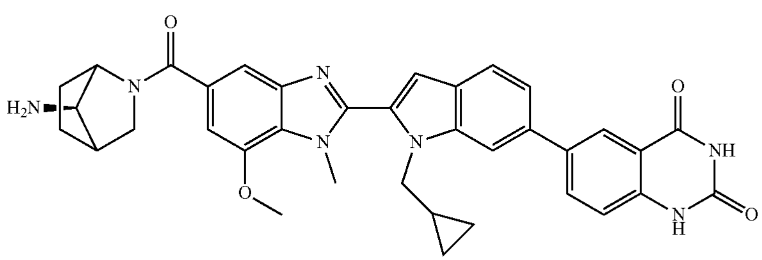 [SMILES: COc1cc(C(=O)N2CC3CCC2[C@@H]3N)cc2nc(-c3cc4ccc(-c5ccc6[nH]c(=O)[nH]c(=O)c6c5)cc4n3CC3CC3)n(C)c12] | 6-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-1,2,3,4-tetrahydroquinazoline-2,4-dione | 630.2 | 2 | 2.12 |

TABLE 5-continued

| Cmpd # | Structure | Name | Obs. MS Ion | HPLC Method IDs | RT (min) |
|---|---|---|---|---|---|
| 246. | 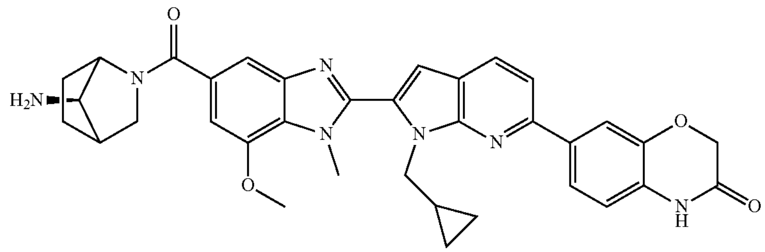 | 7-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-3,4-dihydro-2H-1,4-benzoxazin-3-one | 617.9 | 2 | 1.71 |
| 247. | 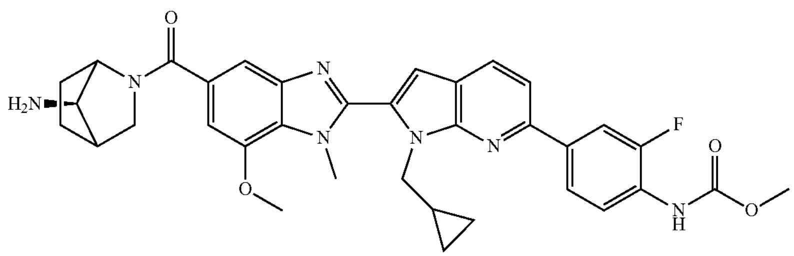 [SMILES: COC(=O)Nc1ccc(-c2ccc3cc(-c4nc5cc(C(=O)N6CC7CCC6[C@@H]7N)cc(OC)c5n4C)n(CC4CC4)c3n2)cc1F] | methyl N-[4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-fluorophenyl]carbamate | 638.5 | 1 | 1.62 |
| 248. | 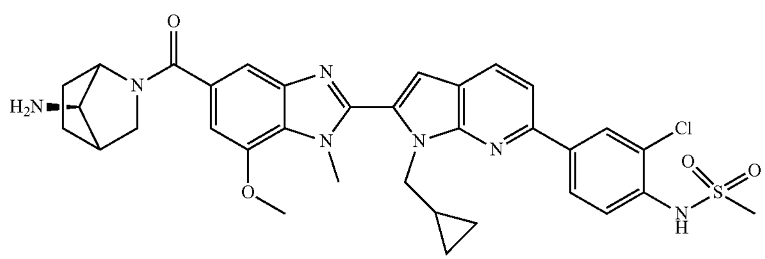 [SMILES: COc1cc(C(=O)N2CC3CCC2[C@@H]3N)cc2nc(-c3cc4ccc(-c5ccc(NS(C)(=O)=O)c(Cl)c5)nc4n3CC3CC3)n(C)c12] | N-[4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-chlorophenyl]methanesulfonamide | 674.1 | 2 | 1.86 |

TABLE 6

| Comp. # | Structure | Name | Obs. MS Ion | HPLC Method IDs | RT (min) |
|---|---|---|---|---|---|
| 249. | 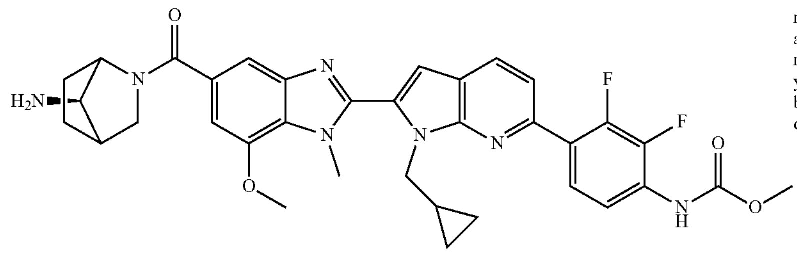 | methyl N-[4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2,3-difluorophenyl]carbamate | 656.1 | 1 | 1.84 |
| 250. | 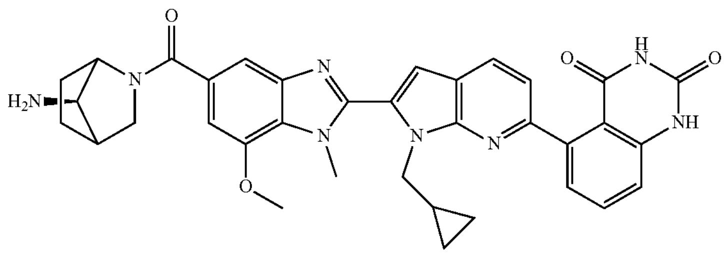 [SMILES: COc1cc(C(=O)N2CC3CCC2[C@@H]3N)cc2nc(-c3cc4ccc(-c5cccc6[nH]c(=O)[nH]c(=O)c56)nc4n3CC3CC3)n(C)c12] | 5-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1,2,3,4-tetrahydroquinazoline-2,4-dione | 631.5 | 2 | 1.22 |
| 251. | 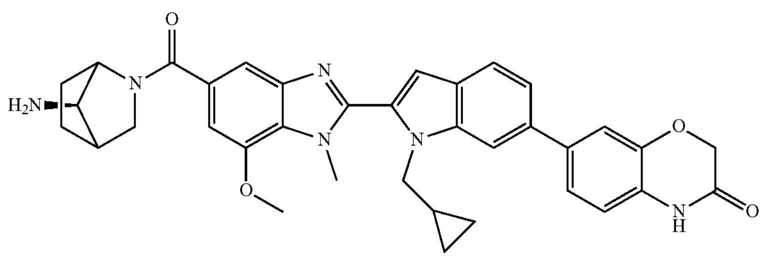 [SMILES: COc1cc(C(=O)N2CC3CCC2[C@@H]3N)cc2nc(-c3cc4ccc(-c5ccc6c(c5)OCC(=O)N6)cc4n3CC3CC3)n(C)c12] | 7-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-3,4-dihydro-2H-1,4-benzoxazin-3-one | 617.2 | 1 | 1.73 |
| 252. | 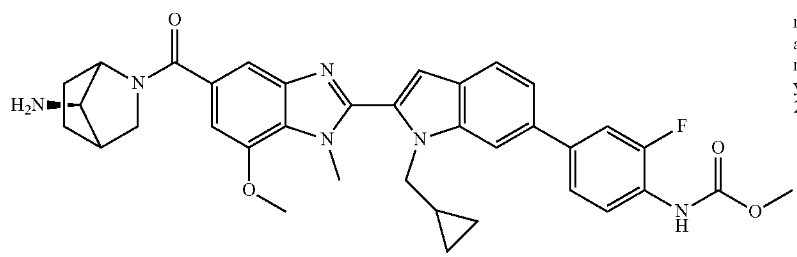 | methyl N-[4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-2-fluorophenyl]carbamate | 637.5 | 2 | 1.61 |

TABLE 6-continued

| Comp. # | Structure | Name | Obs. MS Ion | HPLC Method IDs | RT (min) |
|---|---|---|---|---|---|
| 253. | 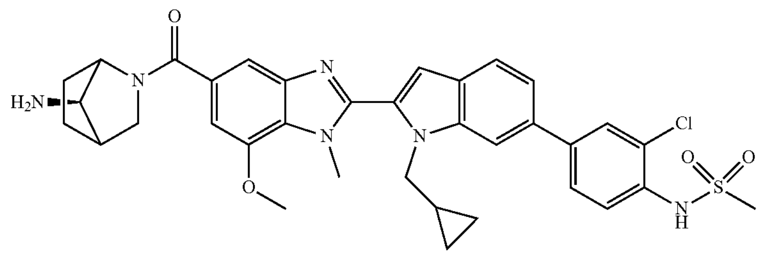 [SMILES: COc1cc(C(=O)N2CC3CCC2[C@@H]3N)cc2nc(-c3cc4ccc(-c5ccc(NS(C)(=O)=O)c(Cl)c5)cc4n3CC3CC3)n(C)c12] | N-[4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-2-chlorophenyl]methanesulfonamide | 673.2 | 1 | 1.88 |
| 254. | 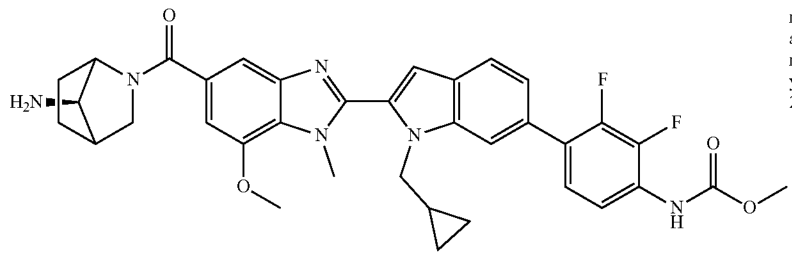 | methyl N-[4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-2,3-difluorophenyl]carbamate | 655.2 | 1 | 1.91 |
| 255. | 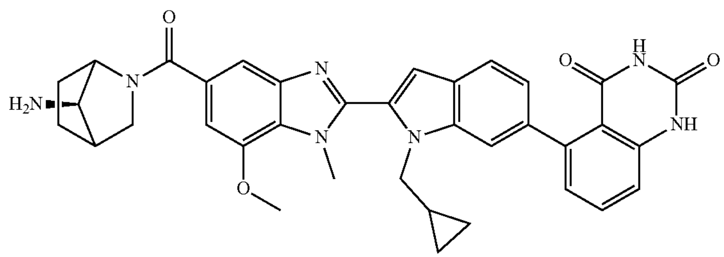 [SMILES: COc1cc(C(=O)N2CC3CCC2[C@@H]3N)cc2nc(-c3cc4ccc(-c5cccc6[nH]c(=O)[nH]c(=O)c56)cc4n3CC3CC3)n(C)c12] | 5-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-1,2,3,4-tetrahydroquinazoline-2,4-dione | 630.5 | 2 | 1.26 |
| 256. | 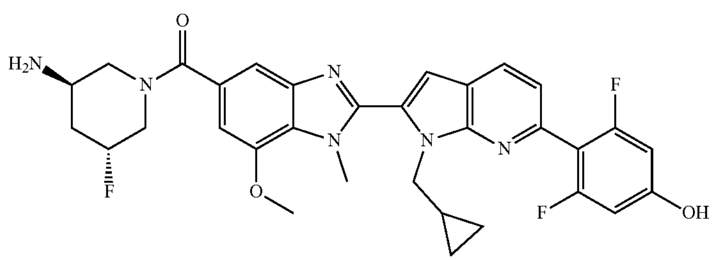 [SMILES: COc1cc(C(=O)N2C[C@H](N)C[C@@H](F)C2)cc2nc(-c3cc4ccc(-c5c(F)cc(O)cc5F)nc4n3CC3CC3)n(C)c12] | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-3,5-difluorophenol | 605.1 | 2 | 1.58 |

TABLE 6-continued

| Comp. # | Structure | Name | Obs. MS Ion | HPLC Method IDs | RT (min) |
|---|---|---|---|---|---|
| 257. | 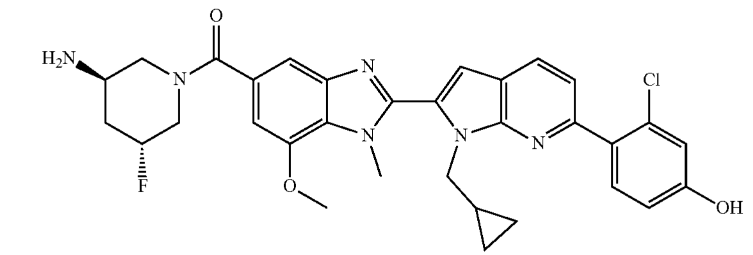 [SMILES: COc1cc(C(=O)N2C[C@H](N)C[C@@H](F)C2)cc2nc(-c3cc4ccc(-c5ccc(O)cc5Cl)nc4n3CC3CC3)n(C)c12] | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-3-chlorophenol | 603.3 | 2 | 1.58 |
| 258. | 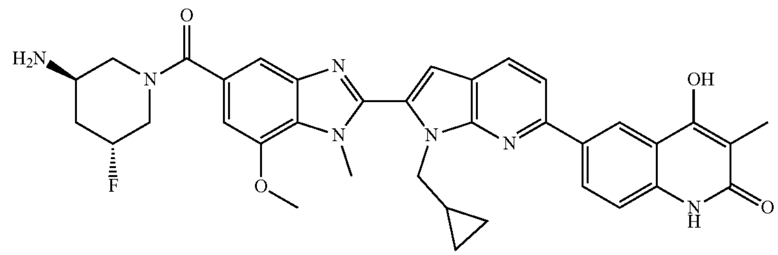 [SMILES: COc1cc(C(=O)N2C[C@H](N)C[C@@H](F)C2)cc2nc(-c3cc4ccc(-c5ccc6[nH]c(=O)c(C)c(O)c6c5)nc4n3CC3CC3)n(C)c12] | 6-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-4-hydroxy-3-methyl-1,2-dihydroquinolin-2-one | 650.1 | 2 | 1.41 |
| 259. | 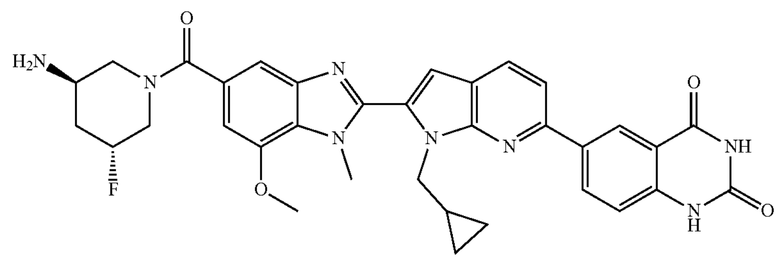 [SMILES: COc1cc(C(=O)N2C[C@H](N)C[C@@H](F)C2)cc2nc(-c3cc4ccc(-c5ccc6[nH]c(=O)[nH]c(=O)c6c5)nc4n3CC3CC3)n(C)c12] | 6-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-1,2,3,4-tetrahydroquinazoline-2,4-dione | 637.1 | 2 | 1.35 |
| 260. | 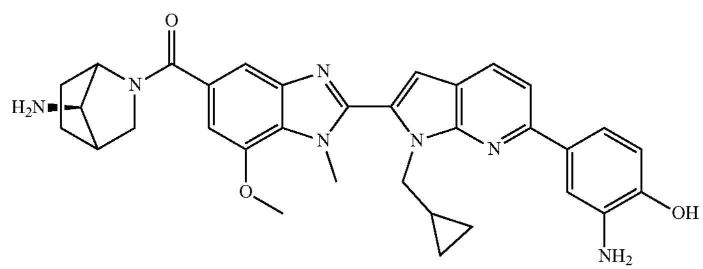 [SMILES: COc1cc(C(=O)N2CC3CCC2[C@@H]3N)cc2nc(-c3cc4ccc(-c5ccc(O)c(N)c5)nc4n3CC3CC3)n(C)c12] | 2-amino-4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenol | 578.4 | 1 | 1.34 |

TABLE 6-continued

| Comp. # | Structure | Name | Obs. MS Ion | HPLC Method IDs | RT (min) |
|---|---|---|---|---|---|
| 261. | 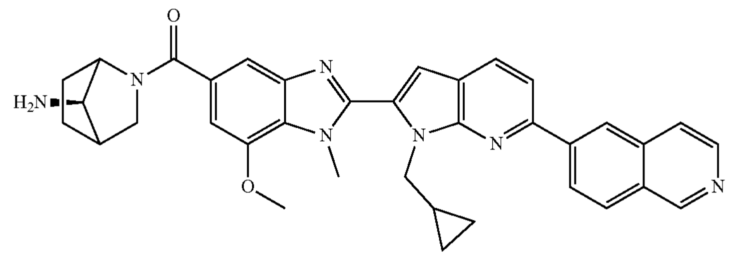 [SMILES: COc1cc(C(=O)N2CC3CCC2[C@@H]3N)cc2nc(-c3cc4ccc(-c5ccc6cnccc6c5)nc4n3CC3CC3)n(C)c12] | (1R,4R,7R)-2-{2-[1-(cyclopropylmethyl)-6-(isoquinolin-6-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 598.2 | 2 | 1.26 |
| 262. | 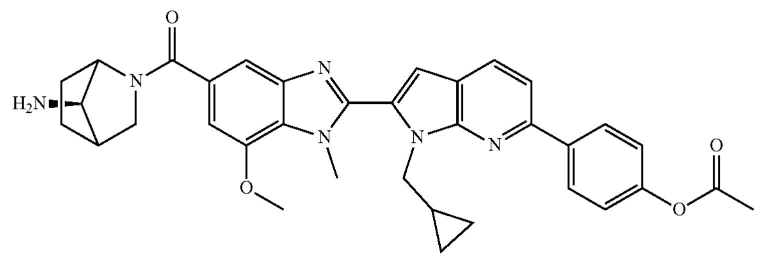 [SMILES: COc1cc(C(=O)N2CC3CCC2[C@@H]3N)cc2nc(-c3cc4ccc(-c5ccc(OC(C)=O)cc5)nc4n3CC3CC3)n(C)c12] | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl acetate | 605.2 | 1 | 1.94 |
| 263. | 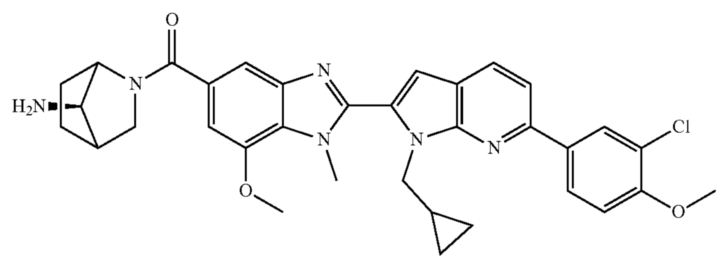 [SMILES: COc1ccc(-c2ccc3cc(-c4nc5cc(C(=O)N6CC7CCC6[C@@H]7N)cc(OC)c5n4C)n(CC4CC4)c3n2)cc1Cl] | (1R,4R,7R)-2-{2-[6-(3-chloro-4-methoxyphenyl)-1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 611.4 | 1 | 2.05 |
| 264. | 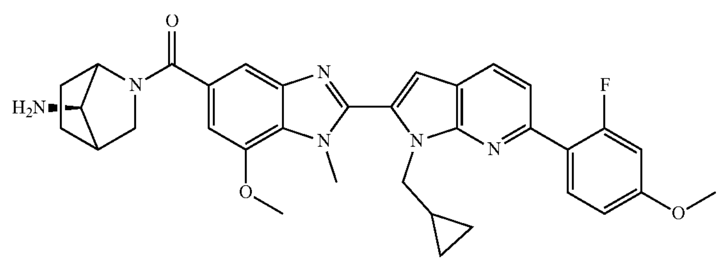 [SMILES: COc1ccc(-c2ccc3cc(-c4nc5cc(C(=O)N6CC7CCC6[C@@H]7N)cc(OC)c5n4C)n(CC4CC4)c3n2)c(F)c1] | (1R,4R,7R)-2-{2-[1-(cyclopropylmethyl)-6-(2-fluoro-4-methoxyphenyl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 595.3 | 1 | 2.01 |

TABLE 6-continued

| Comp. # | Structure | Name | Obs. MS Ion | HPLC Method IDs | RT (min) |
|---|---|---|---|---|---|
| 265. | 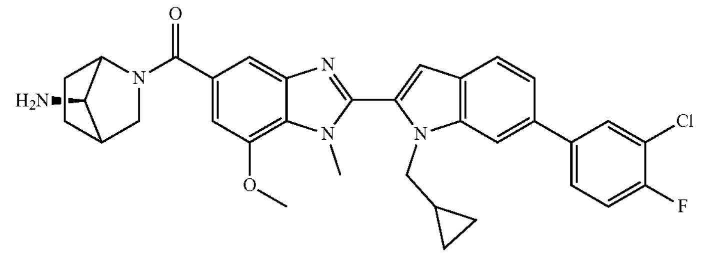 [SMILES: COc1cc(C(=O)N2CC3CCC2[C@@H]3N)cc2nc(-c3cc4ccc(-c5ccc(F)c(Cl)c5)cc4n3CC3CC3)n(C)c12] | (1R,4R,7R)-2-{2-[6-(3-chloro-4-fluorophenyl)-1-(cyclopropylmethyl)-1H-indol-2-yl]-7-methoxy-1-methyl-1H-1,3-benzodiazole-5-carbonyl}-2-azabicyclo[2.2.1]heptan-7-amine | 598.1 | 1 | 1.97 |
| 266. | 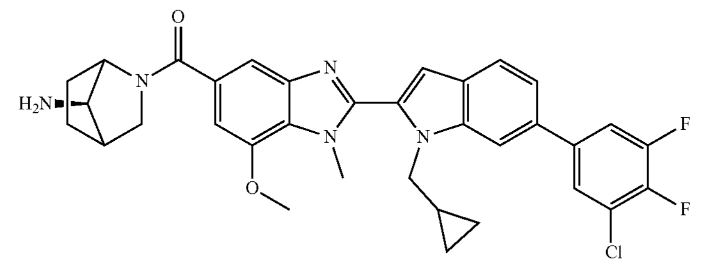 [SMILES: COc1cc(C(=O)N2CC3CCC2[C@@H]3N)cc2nc(-c3cc4ccc(-c5cc(F)c(F)c(Cl)c5)cc4n3CC3CC3)n(C)c12] | (1R,4R,7R)-2-{2-[6-(3-chloro-4,5-difluorophenyl)-1-(cyclopropylmethyl)-1H-indol-2-yl]-7-methoxy-1-methyl-1H-1,3-benzodiazole-5-carbonyl}-2-azabicyclo[2.2.1]heptan-7-amine | 616.4 | 1 | 2.38 |
| 267. | 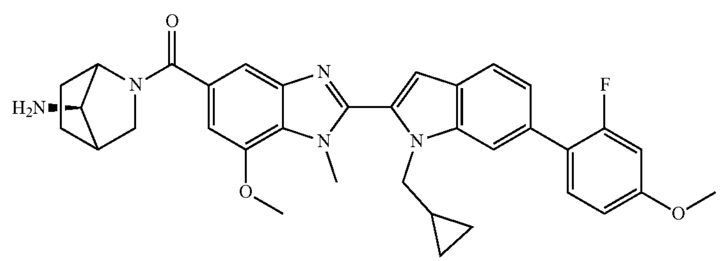 [SMILES: COc1ccc(-c2ccc3cc(-c4nc5cc(C(=O)N6CC7CCC6[C@@H]7N)cc(OC)c5n4C)n(CC4CC4)c3c2)c(F)c1] | (1R,4R,7R)-2-{2-[1-(cyclopropylmethyl)-6-(2-fluoro-4-methoxyphenyl)-1H-indol-2-yl]-7-methoxy-1-methyl-1H-1,3-benzodiazole-5-carbonyl}-2-azabicyclo[2.2.1]heptan-7-amine | 594.1 | 1 | 2.02 |
| 268. | 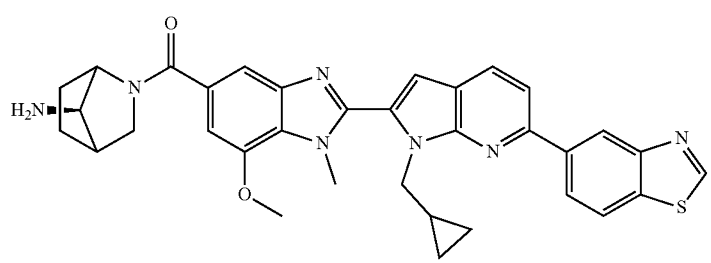 [SMILES: COc1cc(C(=O)N2CC3CCC2[C@@H]3N)cc2nc(-c3cc4ccc(-c5ccc6scnc6c5)nc4n3CC3CC3)n(C)c12] | (1R,4R,7R)-2-{2-[6-(1,3-benzothiazol-5-yl)-1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 604.5 | 1 | 1.87 |

TABLE 6-continued

| Comp. # | Structure | Name | Obs. MS Ion | HPLC Method IDs | RT (min) |
|---|---|---|---|---|---|
| 269. | 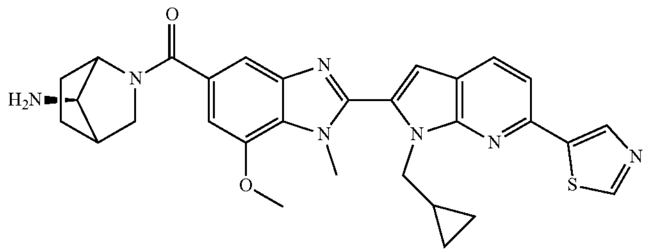 [SMILES: COc1cc(C(=O)N2CC3CCC2[C@@H]3N)cc2nc(-c3cc4ccc(-c5cncs5)nc4n3CC3CC3)n(C)c12] | (1R,4R,7R)-2-{2-[1-(cyclopropylmethyl)-6-(1,3-thiazol-5-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 554.4 | 1 | 1.59 |
| 270. | 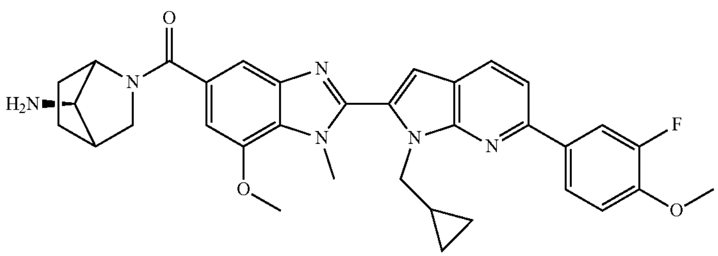 [SMILES: COc1ccc(-c2ccc3cc(-c4nc5cc(C(=O)N6CC7CCC6[C@@H]7N)cc(OC)c5n4C)n(CC4CC4)c3n2)cc1F] | (1R,4R,7R)-2-{2-[1-(cyclopropylmethyl)-6-(3-fluoro-4-methoxyphenyl)-1H-pyrrolo[2,3-b]pyridin-2-yl]-7-methoxy-1H-1,3-benzodiazole-5-carbonyl}-2-azabicyclo[2.2.1]heptan-7-amine | 595.5 | 2 | 1.74 |
| 271. | 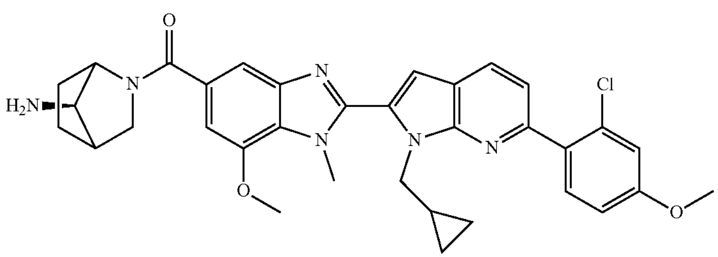 [SMILES: COc1ccc(-c2ccc3cc(-c4nc5cc(C(=O)N6CC7CCC6[C@@H]7N)cc(OC)c5n4C)n(CC4CC4)c3n2)c(Cl)c1] | (1R,4R,7R)-2-{2-[6-(2-chloro-4-methoxyphenyl)-1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 611.1 | 2 | 1.88 |
| 272. | 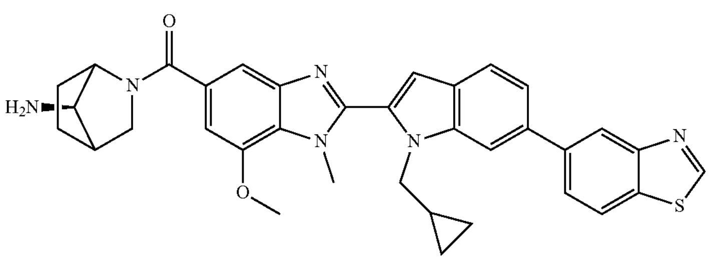 [SMILES: COc1cc(C(=O)N2CC3CCC2[C@@H]3N)cc2nc(-c3cc4ccc(-c5ccc6scnc6c5)cc4n3CC3CC3)n(C)c12] | (1R,4R,7R)-2-{2-[6-(1,3-benzothiazol-5-yl)-1-(cyclopropylmethyl)-1H-indol-2-yl]-7-methoxy-1-methyl-1H-1,3-benzodiazole-5-carbonyl}-2-azabicyclo[2.2.1]heptan-7-amine | 603.2 | 1 | 2.03 |

TABLE 6-continued

| Comp. # | Structure | Name | Obs. MS Ion | HPLC Method IDs | RT (min) |
|---|---|---|---|---|---|
| 273. | 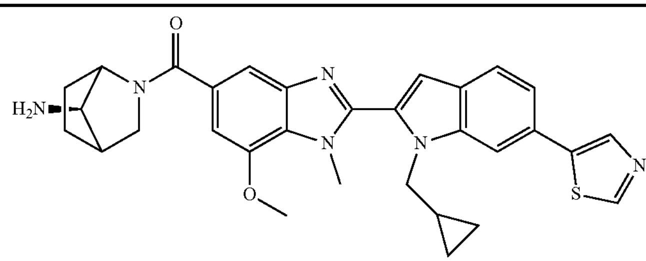 | (1R,4R,7R)-2-{2-[1-(cyclopropylmethyl)-6-(1,3-thiazol-5-yl)-1H-indol-2-yl]-7-methoxy-1-methyl-1H-1,3-benzodiazole-5-carbonyl}-2-azabicyclo[2.2.1]heptan-7-amine | 553.5 | 1 | 1.61 |
| 274. | 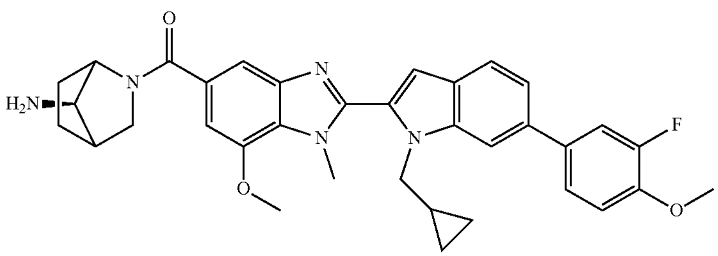 | (1R,4R,7R)-2-{2-[1-(cyclopropylmethyl)-6-(3-fluoro-4-methoxyphenyl)-1H-indol-2-yl]-7-methoxy-1-methyl-1H-1,3-benzodiazole-5-carbonyl}-2-azabicyclo[2.2.1]heptan-7-amine | 594.2 | 2 | 1.64 |
| 275. | 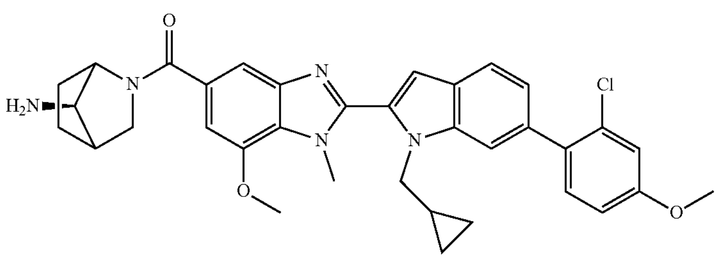 [SMILES: COc1ccc(-c2ccc3cc(-c4nc5cc(C(=O)N6CC7CCC6[C@@H]7N)cc(OC)c5n4C)n(CC4CC4)c3c2)c(Cl)c1] | (1R,4R,7R)-2-{2-[6-(2-chloro-4-methoxyphenyl)-1-(cyclopropylmethyl)-1H-indol-2-yl]-7-methoxy-1-methyl-1H-1,3-benzodiazole-5-carbonyl}-2-azabicyclo[2.2.1]heptan-7-amine | 610.4 | 1 | 2.15 |
| 276. | 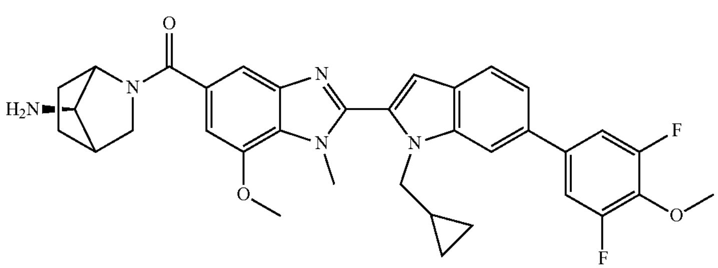 [SMILES: COc1c(F)cc(-c2ccc3cc(-c4nc5cc(C(=O)N6CC7CCC6[C@@H]7N)cc(OC)c5n4C)n(CC4CC4)c3c2)cc1F] | (1R,4R,7R)-2-{2-[1-(cyclopropylmethyl)-6-(3,5-difluoro-4-methoxyphenyl)-1H-indol-2-yl]-7-methoxy-1-methyl-1H-1,3-benzodiazole-5-carbonyl}-2-azabicyclo[2.2.1]heptan-7-amine | 612.5 | 1 | 2.14 |

TABLE 6-continued

| Comp. # | Structure | Name | Obs. MS Ion | HPLC Method IDs | RT (min) |
|---|---|---|---|---|---|
| 277. | 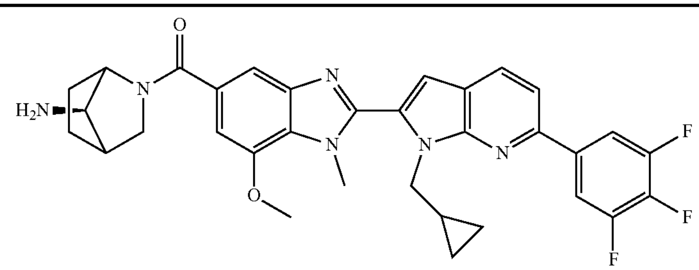 | (1R,4R,7R)-2-{2-[1-(cyclopropylmethyl)-6-(3,4,5-trifluorophenyl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 601.4 | 1 | 2.23 |
| 278. | 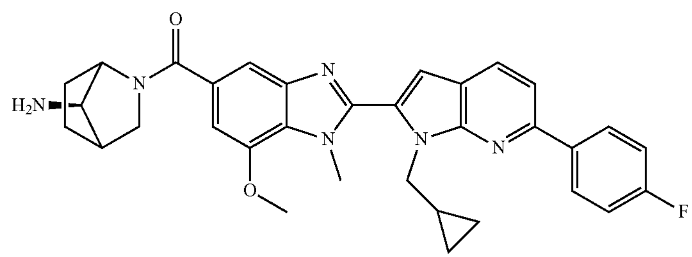 [SMILES: COc1cc(C(=O)N2CC3CCC2[C@@H]3N)cc2nc(-c3cc4ccc(-c5ccc(F)cc5)nc4n3CC3CC3)n(C)c12] | (1R,4R,7R)-2-{2-[1-(cyclopropylmethyl)-6-(4-fluorophenyl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 565.1 | 1 | 2.12 |
| 279. | 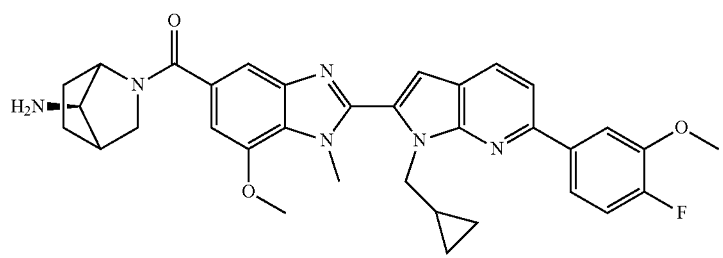 | (1R,4R,7R)-2-{2-[1-(cyclopropylmethyl)-6-(4-fluoro-3-methoxyphenyl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 595.4 | 1 | 2.15 |
| 280. | 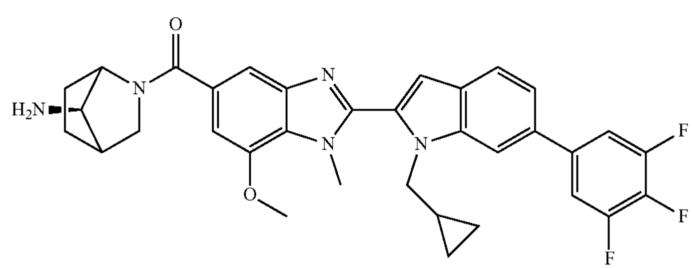 [SMILES: COc1cc(C(=O)N2CC3CCC2[C@@H]3N)cc2nc(-c3cc4ccc(-c5cc(F)c(F)c(F)c5)cc4n3CC3CC3)n(C)c12] | (1R,4R,7R)-2-{2-[1-(cyclopropylmethyl)-6-(3,4,5-trifluorophenyl)-1H-indol-2-yl]-7-methoxy-1-methyl-1H-1,3-benzodiazole-5-carbonyl}-2-azabicyclo[2.2.1]heptan-7-amine | 600.4 | 2 | 1.84 |

TABLE 6-continued

| Comp. # | Structure | Name | Obs. MS Ion | HPLC Method IDs | RT (min) |
|---|---|---|---|---|---|
| 281. | 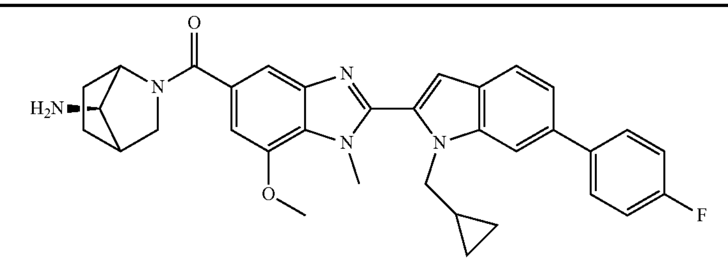 | (1R,4R,7R)-2-{2-[1-(cyclopropylmethyl)-6-(4-fluorophenyl)-1H-indol-2-yl]-7-methoxy-1-methyl-1H-1,3-benzodiazole-5-carbonyl}-2-azabicyclo[2.2.1]heptan-7-amine | 564.1 | 2 | 1.83 |
| 282. | 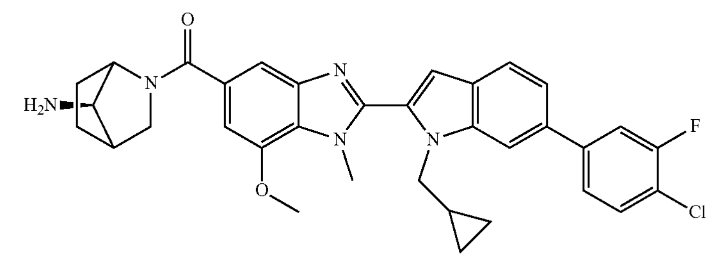 [SMILES: COc1cc(C(=O)N2CC3CCC2[C@@H]3N)cc2nc(-c3cc4ccc(-c5ccc(Cl)c(F)c5)cc4n3CC3CC3)n(C)c12] | (1R,4R,7R)-2-{2-[6-(4-chloro-3-fluorophenyl)-1-(cyclopropylmethyl)-1H-indol-2-yl]-7-methoxy-1-methyl-1H-1,3-benzodiazole-5-carbonyl}-2-azabicyclo[2.2.1]heptan-7-amine | 598.4 | 1 | 2.29 |
| 283. | 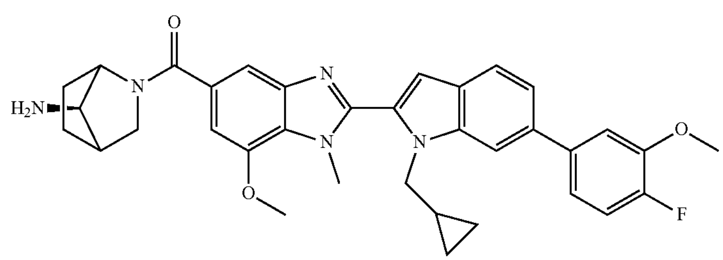 [SMILES: COc1cc(-c2ccc3cc(-c4nc5cc(C(=O)N6CC7CCC6[C@@H]7N)cc(OC)c5n4C)n(CC4CC4)c3c2)ccc1F] | (1R,4R,7R)-2-{2-[1-(cyclopropylmethyl)-6-(4-fluoro-3-methoxyphenyl)-1H-indol-2-yl]-7-methoxy-1-methyl-1H-1,3-benzodiazole-5-carbonyl}-2-azabicyclo[2.2.1]heptan-7-amine | 594.3 | 2 | 1.58 |
| 284. | 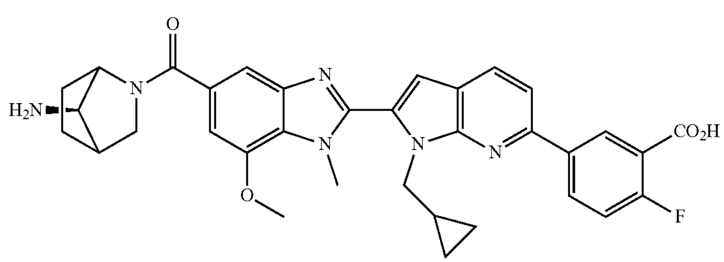 | 5-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-fluorobenzoic acid | 609 | 1 | 1.14 |

TABLE 6-continued

| Comp. # | Structure | Name | Obs. MS Ion | HPLC Method IDs | RT (min) |
|---|---|---|---|---|---|
| 285. | 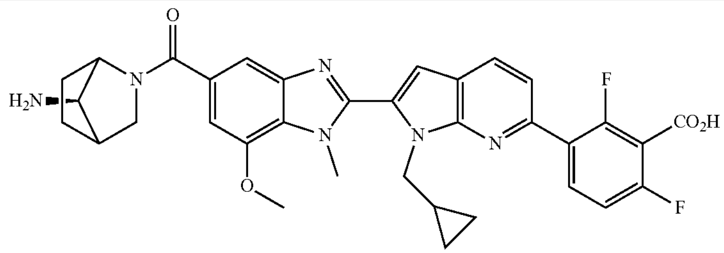 [SMILES: COc1cc(C(=O)N2CC3CCC2[C@@H]3N)cc2nc(-c3cc4ccc(-c5ccc(F)c(C(=O)O)c5F)nc4n3CC3CC3)n(C)c12] | 3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2,6-difluorobenzoic acid | 627.1 | 1 | 1.22 |
| 286. | 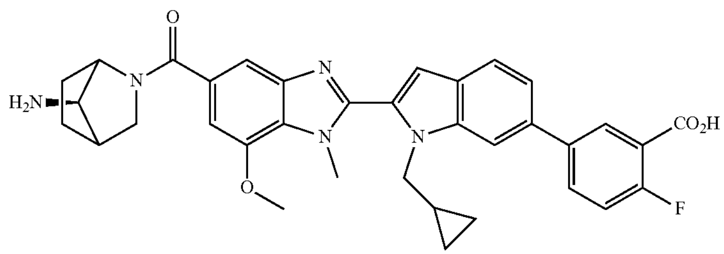 [SMILES: COc1cc(C(=O)N2CC3CCC2[C@@H]3N)cc2nc(-c3cc4ccc(-c5ccc(F)c(C(=O)O)c5)cc4n3CC3CC3)n(C)c12] | 5-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-2-fluorobenzoic acid | 608.2 | 1 | 1.41 |
| 287. | 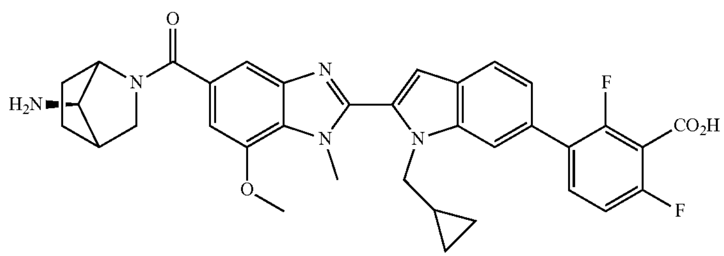 [SMILES: COc1cc(C(=O)N2CC3CCC2[C@@H]3N)cc2nc(-c3cc4ccc(-c5ccc(F)c(C(=O)O)c5F)cc4n3CC3CC3)n(C)c12] | 3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-2,6-difluorobenzoic acid | 626 | 2 | 1.48 |
| 288. | 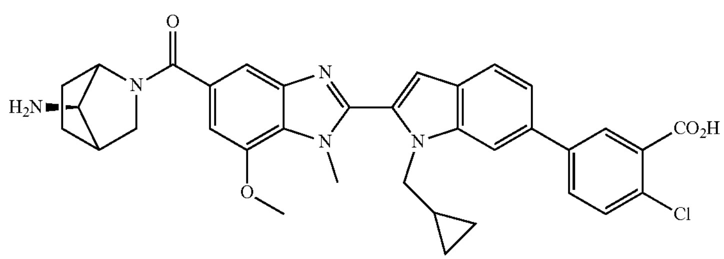 | 5-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-2-chlorobenzoic acid | 624.3 | 2 | 1.57 |

TABLE 6-continued

| Comp. # | Structure | Name | Obs. MS Ion | HPLC Method IDs | RT (min) |
|---|---|---|---|---|---|
| 289. | 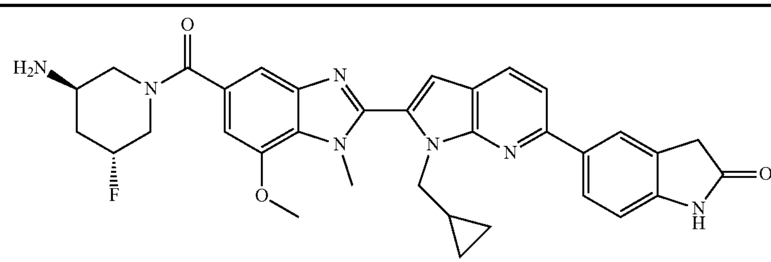 | 5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2,3-dihydro-1H-indol-2-one | 608.5 | 1 | 1.34 |
| 290. | 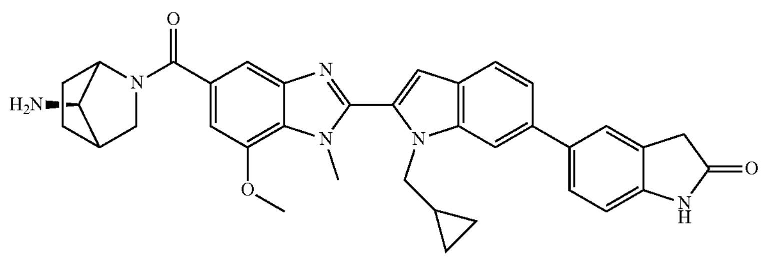 [SMILES: COc1cc(C(=O)N2CC3CCC2[C@@H]3N)cc2nc(-c3cc4ccc(-c5ccc6c(c5)CC(=O)N6)cc4n3CC3CC3)n(C)c12] | 2'-{5-[(1R,4R,7R)-7-amino-2-azabicyclo[2.2.1]heptane-2-carbonyl]-7-methoxy-1-methyl-1H-1,3-benzodinzol-2-yl}-1'-(cyclopropylmethyl)-2,3-dihydro-1H,1'H-[5,6'-biindole]-2-one | 601.5 | 2 | 1.25 |
| 291. | 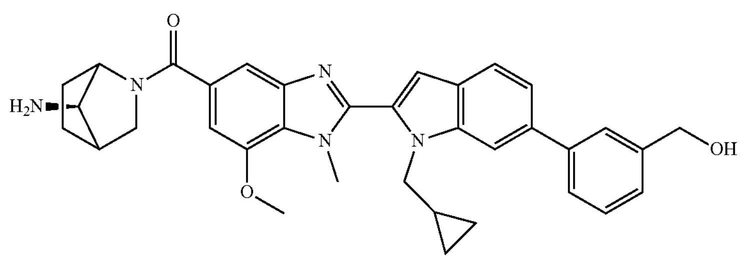 [SMILES: COc1cc(C(=O)N2CC3CCC2[C@@H]3N)cc2nc(-c3cc4ccc(-c5cccc(CO)c5)cc4n3CC3CC3)n(C)c12] | [3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)phenyl]methanol | 576 | 1 | 1.81 |
| 292. | 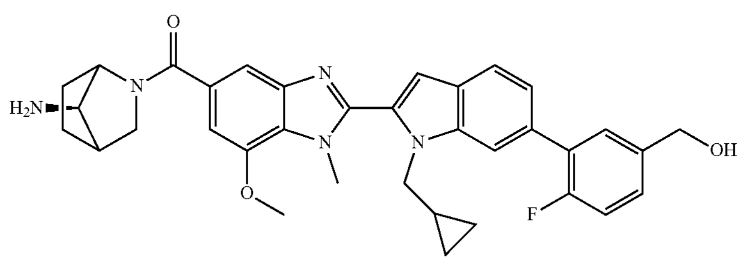 | [3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-4-fluorophenyl]methanol | 594.5 | 1 | 1.59 |

TABLE 6-continued

| Comp. # | Structure | Name | Obs. MS Ion | HPLC Method IDs | RT (min) |
|---|---|---|---|---|---|
| 293. | 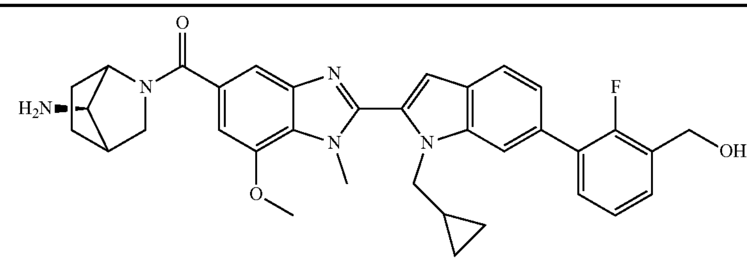 | [3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-2-fluorophenyl]methanol | 594.6 | 2 | 1.49 |
| 294. | 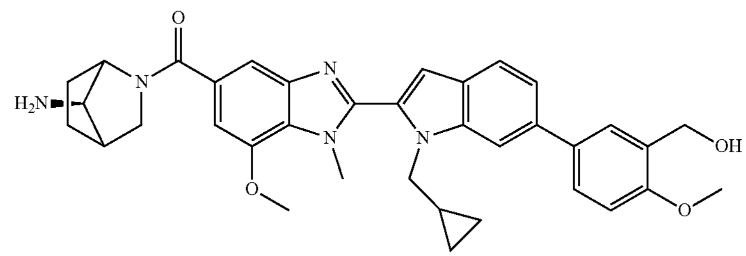 [SMILES: COc1ccc(-c2ccc3cc(-c4nc5cc(C(=O)N6CC7CCC6[C@@H]7N)cc(OC)c5n4C)n(CC4CC4)c3c2)cc1CO] | [5-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-2-methoxyphenyl]methanol | 606.6 | 2 | 1.52 |
| 295. | 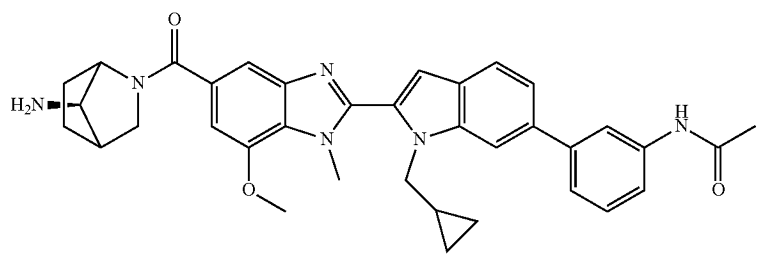 [SMILES: COc1cc(C(=O)N2CC3CCC2[C@@H]3N)cc2nc(-c3cc4ccc(-c5cccc(NC(C)=O)c5)cc4n3CC3CC3)n(C)c12] | N-[3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)phenyl]acetamide | 603.3 | 1 | 1.78 |
| 296. | 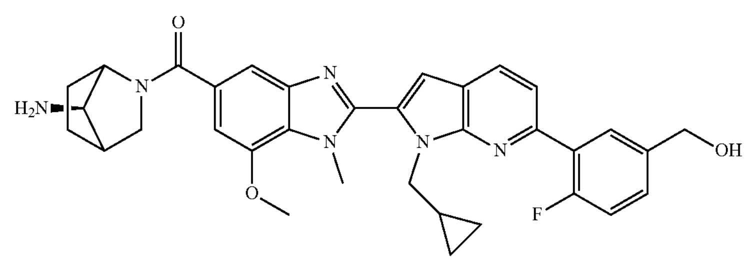 [SMILES: COc1cc(C(=O)N2CC3CCC2[C@@H]3N)cc2nc(-c3cc4ccc(-c5cc(CO)ccc5F)nc4n3CC3CC3)n(C)c12] | [3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-4-fluorophenyl]methanol | 595.4 | 1 | 1.57 |

TABLE 6-continued

| Comp. # | Structure | Name | Obs. MS Ion | HPLC Method IDs | RT (min) |
|---|---|---|---|---|---|
| 297. | 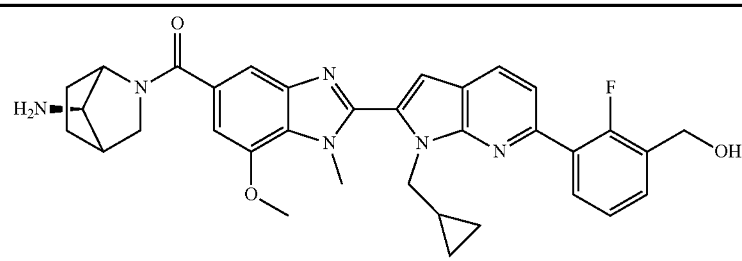 | [3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-fluorophenyl]methanol | 595.3 | 2 | 1.35 |
| 298. | 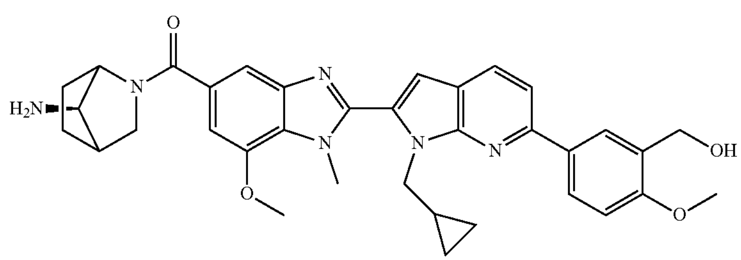 | [5-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-methoxyphenyl]methanol | 607.1 | 2 | 1.39 |

TABLE 7

| Cmpd# | Structure | Name | Obs. MS Ion | HPLC Method IDs | RT (min) |
|---|---|---|---|---|---|
| 299. | 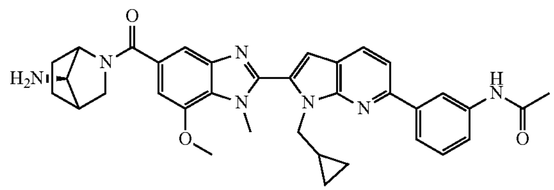 [SMILES: COc1cc(C(=O)N2CC3CCC2[C@@H]3N)cc2nc(-c3cc4ccc(-c5cccc(NC(C)=O)c5)nc4n3CC3CC3)n(C)c12] | N-[3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]acetamide | 604.1 | 1 | 1.34 |
| 300. | 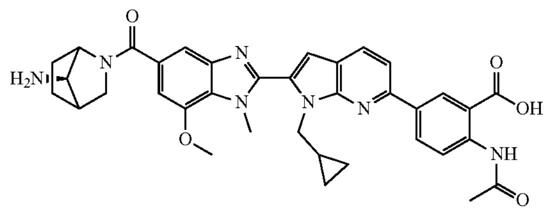 [SMILES: COc1cc(C(=O)N2CC3CCC2[C@@H]3N)cc2nc(-c3cc4ccc(-c5ccc(NC(C)=O)c(C(=O)O)c5)nc4n3CC3CC3)n(C)c12] | 5-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-acetamidobenzoic acid | 648.2 | 1 | 1.34 |
| 301. | 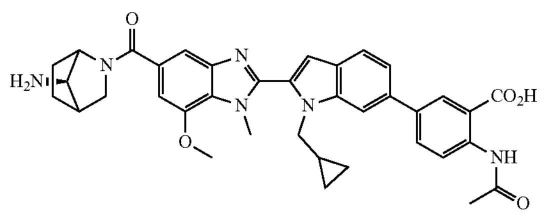 [SMILES: COc1cc(C(=O)N2CC3CCC2[C@@H]3N)cc2nc(-c3cc4ccc(-c5ccc(NC(C)=O)c(C(=O)O)c5)cc4n3CC3CC3)n(C)c12] | 5-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-2-acetamidobenzoic acid | 647.5 | 2 | 1.24 |
| 302. | 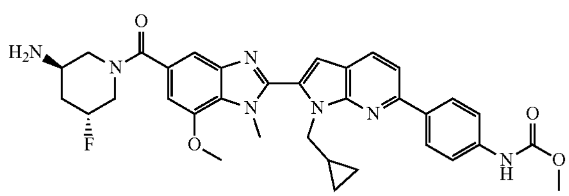 [SMILES: COC(=O)Nc1ccc(-c2ccc3cc(-c4nc5cc(C(=O)N6C[C@H](N)C[C@@H](F)C6)cc(OC)c5n4C)n(CC4CC4)c3n2)cc1] | methyl N-[4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)phenyl]carbamate | 626.2 | 2 | 1.64 |
| 303. | 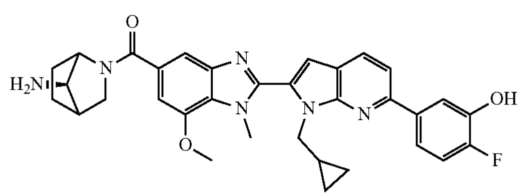 [SMILES: COc1cc(C(=O)N2CC3CCC2[C@@H]3N)cc2nc(-c3cc4ccc(-c5ccc(F)c(O)c5)nc4n3CC3CC3)n(C)c12] | 5-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-fluorophenol | 581.1 | 2 | 1.76 |

TABLE 7-continued

| Cmpd# | Structure | Name | Obs. MS Ion | HPLC Method IDs | RT (min) |
|---|---|---|---|---|---|
| 304. | 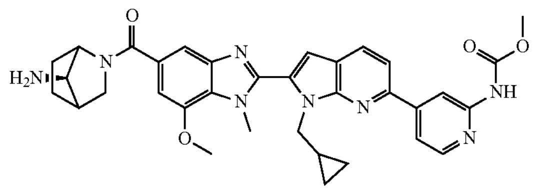 [SMILES: COC(=O)Nc1cc(-c2ccc3cc(-c4nc5cc(C(=O)N6CC7CCC6[C@@H]7N)cc(OC)c5n4C)n(CC4CC4)c3n2)ccn1] | methyl N-[4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)pyridin-2-yl]carbamate | 621.4 | 2 | 1.62 |
| 305. | 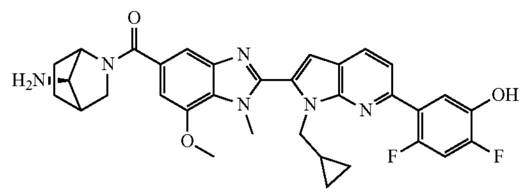 [SMILES: COc1cc(C(=O)N2CC3CCC2[C@@H]3N)cc2nc(-c3cc4ccc(-c5cc(O)c(F)cc5F)nc4n3CC3CC3)n(C)c12] | 5-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2,4-difluorophenol | 599.3 | 1 | 1.62 |
| 306. | 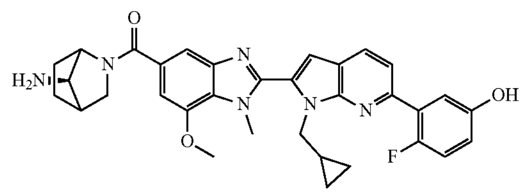 | 3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-4-fluorophenol | 581.1 | 1 | 1.56 |
| 307. | 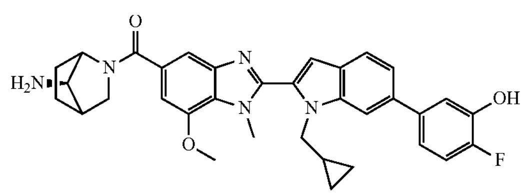 [SMILES: COc1cc(C(=O)N2CC3CCC2[C@@H]3N)cc2nc(-c3cc4ccc(-c5ccc(F)c(O)c5)cc4n3CC3CC3)n(C)c12] | 5-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-2-fluorophenol | 580.4 | 2 | 1.73 |
| 308. | 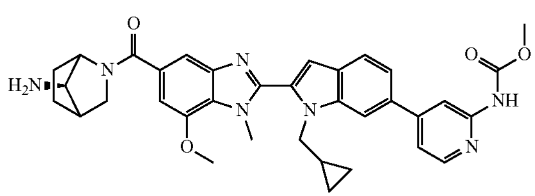 [SMILES: COC(=O)Nc1cc(-c2ccc3cc(-c4nc5cc(C(=O)N6CC7CCC6[C@@H]7N)cc(OC)c5n4C)n(CC4CC4)c3c2)ccn1] | methyl N-[4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)pyridin-2-yl]carbamate | 620.5 | 1 | 1.15 |

TABLE 7-continued

| Cmpd# | Structure | Name | Obs. MS Ion | HPLC Method IDs | RT (min) |
|---|---|---|---|---|---|
| 309. | 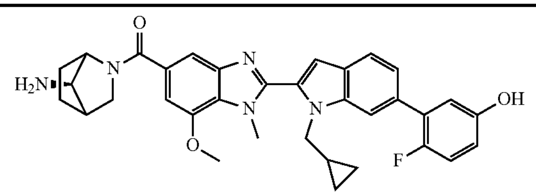 | 3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-4-fluorophenol | 580.5 | 1 | 1.47 |
| 310. | 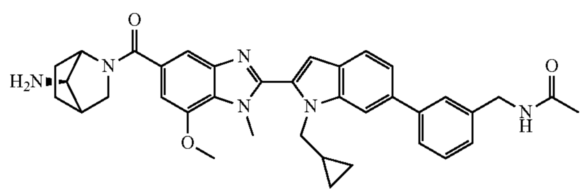 [SMILES: COc1cc(C(=O)N2CC3CCC2[C@@H]3N)cc2nc(-c3cc4ccc(-c5cccc(CNC(C)=O)c5)cc4n3CC3CC3)n(C)c12] | N-{[3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)phenyl]methyl}acetamide | 617.5 | 2 | 1.58 |
| 311. | 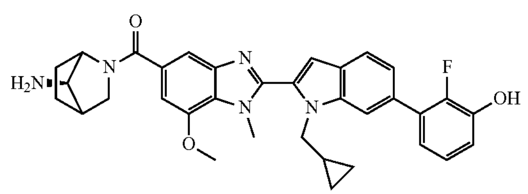 [SMILES: COc1cc(C(=O)N2CC3CCC2[C@@H]3N)cc2nc(-c3cc4ccc(-c5cccc(O)c5F)cc4n3CC3CC3)n(C)c12] | 3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-2-fluorophenol | 580.4 | 2 | 1.7 |
| 312. | 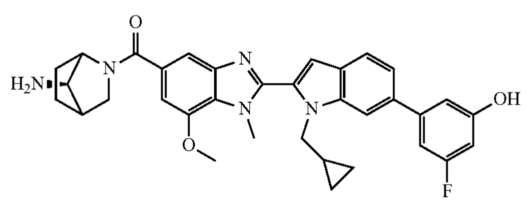 [SMILES: COc1cc(C(=O)N2CC3CCC2[C@@H]3N)cc2nc(-c3cc4ccc(-c5cc(O)cc(F)c5)cc4n3CC3CC3)n(C)c12] | 3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-5-fluorophenol | 580.2 | 2 | 1.86 |
| 313. | 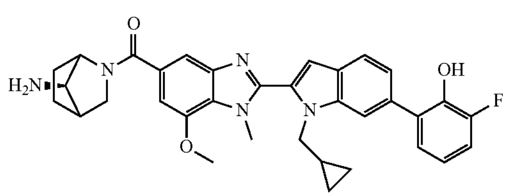 [SMILES: COc1cc(C(=O)N2CC3CCC2[C@@H]3N)cc2nc(-c3cc4ccc(-c5cccc(F)c5O)cc4n3CC3CC3)n(C)c12] | 2-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-6-fluorophenol | 580.2 | 2 | 1.88 |

TABLE 7-continued

| Cmpd# | Structure | Name | Obs. MS Ion | HPLC Method IDs | RT (min) |
|---|---|---|---|---|---|
| 314. | 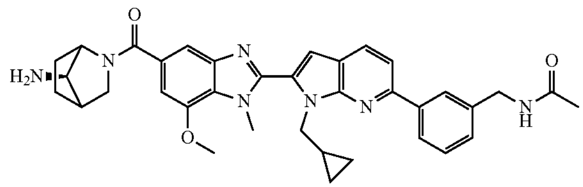 [SMILES: COc1cc(C(=O)N2CC3CCC2[C@@H]3N)cc2nc(-c3cc4ccc(-c5cccc(CNC(C)=O)c5)nc4n3CC3CC3)n(C)c12] | N-{[3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]methyl}acetamide | 617.9 | 2 | 1.74 |
| 315. | 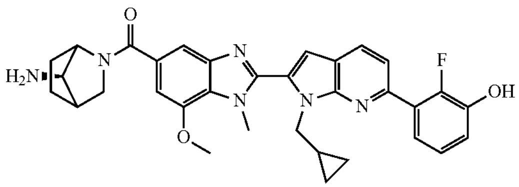 | 3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-fluorophenol | 581.3 | 2 | 1.72 |
| 316. | 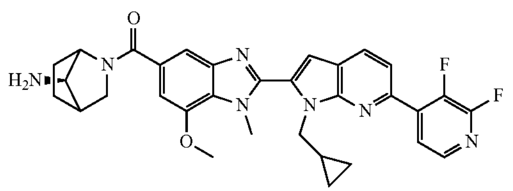 [SMILES: COc1cc(C(=O)N2CC3CCC2[C@@H]3N)cc2nc(-c3cc4ccc(-c5ccnc(F)c5F)nc4n3CC3CC3)n(C)c12] | (1R,4R,7R)-2-{2-[1-(cyclopropylmethyl)-6-(2,3-difluoropyridin-4-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 584.4 | 1 | 1.63 |
| 317. | 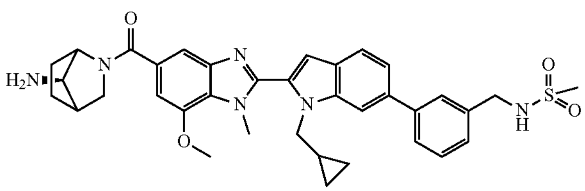 [SMILES: COc1cc(C(=O)N2CC3CCC2[C@@H]3N)cc2nc(-c3cc4ccc(-c5cccc(CNS(C)(=O)=O)c5)cc4n3CC3CC3)n(C)c12] | N-{[3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]methyl}methanesulfonamide | 654.1 | 2 | 1.79 |
| 318. | 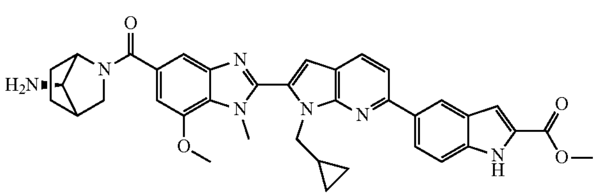 [SMILES: COC(=O)c1cc2cc(-c3ccc4cc(-c5nc6cc(C(=O)N7CC8CCC7[C@@H]8N)cc(OC)c6n5C)n(CC5CC5)c4n3)ccc2[nH]1] | methyl 5-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1H-indole-2-carboxylate | 644 | 1 | 1.73 |

TABLE 7-continued

| Cmpd# | Structure | Name | Obs. MS Ion | HPLC Method IDs | RT (min) |
|---|---|---|---|---|---|
| 319. | 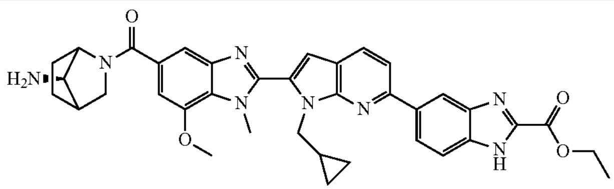 [SMILES: CCOC(=O)c1nc2cc(-c3ccc4cc(-c5nc6cc(C(=O)N7CC8CCC7[C@@H]8N)cc(OC)c6n5C)n(CC5CC5)c4n3)ccc2[nH]1] | ethyl 5-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1H-1,3-benzodiazole-2-carboxylate | 659.4 | 1 | 1.42 |
| 320. | 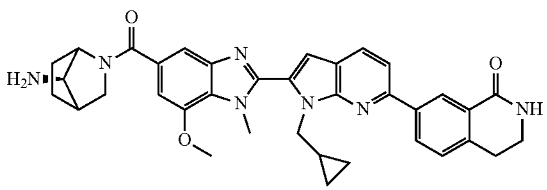 [SMILES: COc1cc(C(=O)N2CC3CCC2[C@@H]3N)cc2nc(-c3cc4ccc(-c5ccc6c(c5)C(=O)NCC6)nc4n3CC3CC3)n(C)c12] | 7-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1,2,3,4-tetrahydroisoquinolin-1-one | 616.2 | 1 | 1.45 |
| 321. | 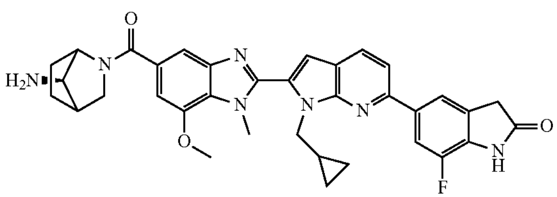 [SMILES: COc1cc(C(=O)N2CC3CCC2[C@@H]3N)cc2nc(-c3cc4ccc(-c5cc(F)c6c(c5)CC(=O)N6)nc4n3CC3CC3)n(C)c12] | 5-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-7-fluoro-2,3-dihydro-1H-indol-2-one | 620 | 2 | 1.69 |
| 322. | 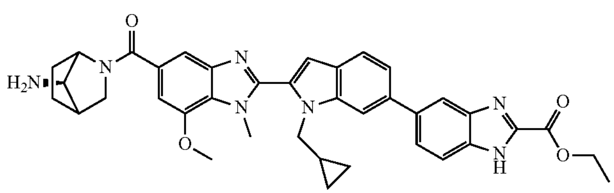 [SMILES: CCOC(=O)c1nc2cc(-c3ccc4cc(-c5nc6cc(C(=O)N7CC8CCC7[C@@H]8N)cc(OC)c6n5C)n(CC5CC5)c4c3)ccc2[nH]1] | ethyl 5-(2-{[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-1H-1,3-benzodiazole-2-carboxylate | 658 | 2 | 1.77 |
| 323. | 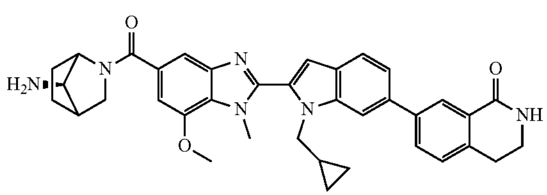 [SMILES: COc1cc(C(=O)N2CC3CCC2[C@@H]3N)cc2nc(-c3cc4ccc(-c5ccc6c(c5)C(=O)NCC6)cc4n3CC3CC3)n(C)c12] | 7-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-1,2,3,4-tetrahydroisoquinolin-1-one | 615 | 1 | 1.48 |

TABLE 7-continued

| Cmpd# | Structure | Name | Obs. MS Ion | HPLC Method IDs | RT (min) |
|---|---|---|---|---|---|
| 324. | 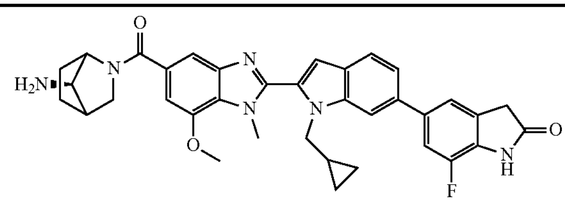 | 2'-{5-[(1R,4R,7R)-7-amino-2-azabicyclo[2.2.1]heptane-2-carbonyl]-7-methoxy-1-methyl-1H-1,3-benzodiazol-2-yl}-1'-(cyclopropylmethyl)-7-fluoro-2,3-dihydro-1H,1'H-[5,6-biindole]-2-one | 618.9 | 1 | 1.44 |
| 325. | 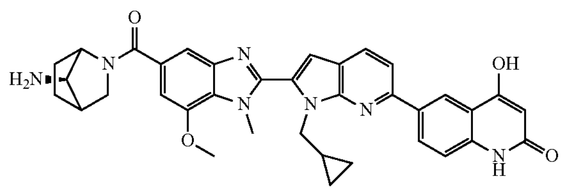 [SMILES: COc1cc(C(=O)N2CC3CCC2[C@@H]3N)cc2nc(-c3cc4ccc(-c5ccc6[nH]c(=O)cc(O)c6c5)nc4n3CC3CC3)n(C)c12] | 6-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-4-hydroxy-1,2-dihydroquinolin-2-one | 630 | 2 | 1.48 |
| 326. | 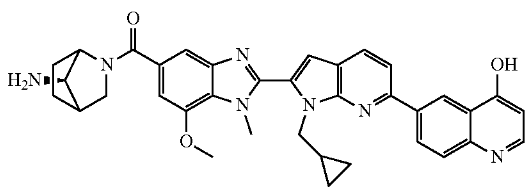 [SMILES: COc1cc(C(=O)N2CC3CCC2[C@@H]3N)cc2nc(-c3cc4ccc(-c5ccc6nccc(O)c6c5)nc4n3CC3CC3)n(C)c12] | 6-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)quinolin-4-ol | 613.92, 613.96 | 2 | |
| 327. | 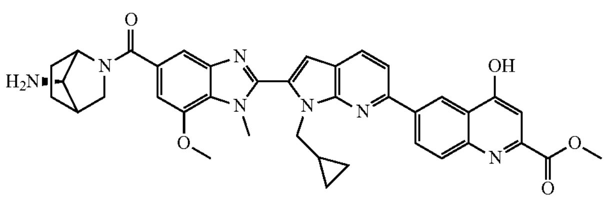 | methyl 6-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-4-hydroxyquinoline-2-carboxylate | 672.2 | 2 | 1.58 |
| 328. | 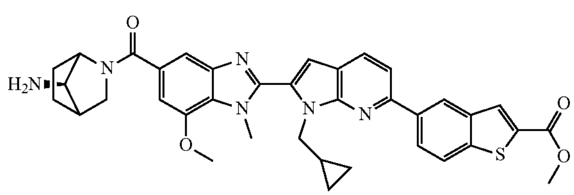 [SMILES: COC(=O)c1cc2cc(-c3ccc4cc(-c5nc6cc(C(=O)N7CC8CCC7[C@@H]8N)cc(OC)c6n5C)n(CC5CC5)c4n3)ccc2s1] | methyl 5-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1-benzothiophene-2-carboxylate | 661 | 1 | 2.02 |

TABLE 7-continued

| Cmpd# | Structure | Name | Obs. MS Ion | HPLC Method IDs | RT (min) |
|---|---|---|---|---|---|
| 329. | 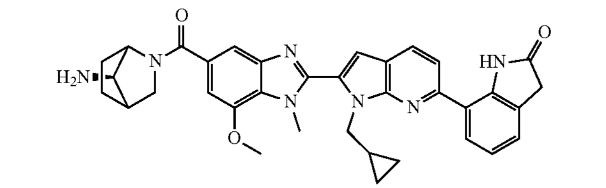 [SMILES: COc1cc(C(=O)N2CC3CCC2[C@@H]3N)cc2nc(-c3cc4ccc(-c5cccc6c5NC(=O)C6)nc4n3CC3CC3)n(C)c12] | 7-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2,3-dihydro-1H-indol-2-one | 602.2 | 1 | 1.61 |
| 330. | 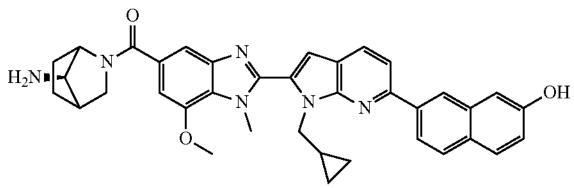 [SMILES: COc1cc(C(=O)N2CC3CCC2[C@@H]3N)cc2nc(-c3cc4ccc(-c5ccc6ccc(O)cc6c5)nc4n3CC3CC3)n(C)c12] | 7-(2-{[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)naphthalen-2-ol | 613.3 | 2 | 1.87 |
| 331. | 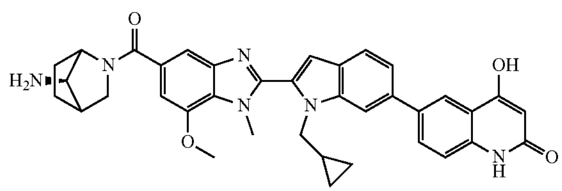 [SMILES: COc1cc(C(=O)N2CC3CCC2[C@@H]3N)cc2nc(-c3cc4ccc(-c5ccc6[nH]c(=O)cc(O)c6c5)cc4n3CC3CC3)n(C)c12] | 6-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-4-hydroxy-1,2-dihydroquinolin-2-one | 629.2 | 1 | 1.22 |
| 332. | 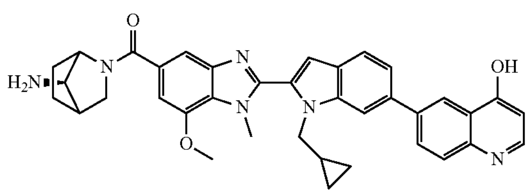 [SMILES: COc1cc(C(=O)N2CC3CCC2[C@@H]3N)cc2nc(-c3cc4ccc(-c5ccc6nccc(O)c6c5)cc4n3CC3CC3)n(C)c12] | 6-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)quinolin-4-ol | 613.2 | 2 | 1.56 |
| 333. | 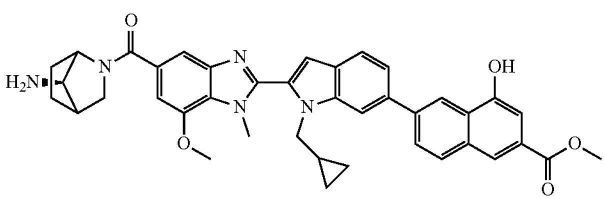 [SMILES: COC(=O)c1cc(O)c2cc(-c3ccc4cc(-c5nc6cc(C(=O)N7CC8CCC7[C@@H]8N)cc(OC)c6n5C)n(CC5CC5)c4c3)ccc2c1] | methyl 6-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-4-hydroxynaphthalene-2-carboxylate | 671.1 | 2 | 1.49 |

TABLE 7-continued

| Cmpd# | Structure | Name | Obs. MS Ion | HPLC Method IDs | RT (min) |
|---|---|---|---|---|---|
| 334. | 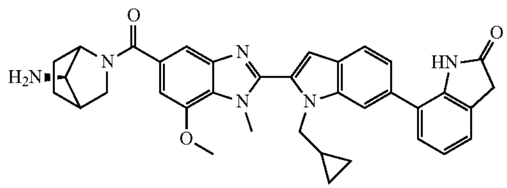 [SMILES: COc1cc(C(=O)N2CC3CCC2[C@@H]3N)cc2nc(-c3cc4ccc(-c5cccc6c5NC(=O)C6)cc4n3CC3CC3)n(C)c12] | 2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-2',3'-dihydro-1H,1'H-[6,7'-biindole]-2'-one | 601 | 1 | 1.48 |
| 335. | 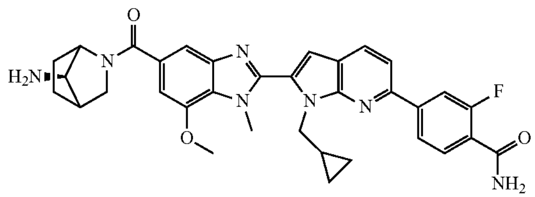 [SMILES: COc1cc(C(=O)N2CC3CCC2[C@@H]3N)cc2nc(-c3cc4ccc(-c5ccc(C(N)=O)c(F)c5)nc4n3CC3CC3)n(C)c12] | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-fluorobenzamide | 608.3 | 2 | 1.5 |
| 336. | 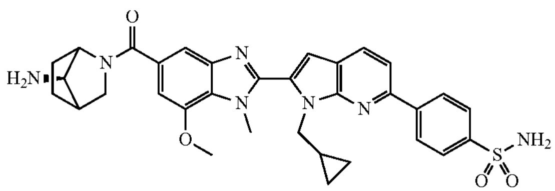 [SMILES: COc1cc(C(=O)N2CC3CCC2[C@@H]3N)cc2nc(-c3cc4ccc(-c5ccc(S(N)(=O)=O)cc5)nc4n3CC3CC3)n(C)c12] | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)benzene-1-sulfonamide | 626.2 | 1 | 1.37 |
| 337. | 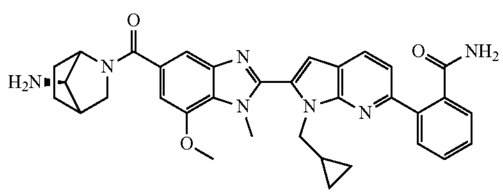 [SMILES: COc1cc(C(=O)N2CC3CCC2[C@@H]3N)cc2nc(-c3cc4ccc(-c5ccccc5C(N)=O)nc4n3CC3CC3)n(C)c12] | 2-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)benzamide | 590.3 | 2 | 1.4 |
| 338. | 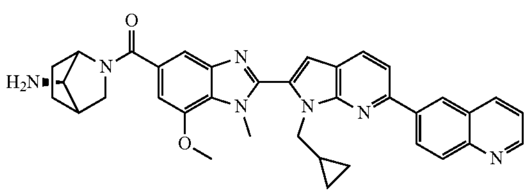 [SMILES: COc1cc(C(=O)N2CC3CCC2[C@@H]3N)cc2nc(-c3cc4ccc(-c5ccc6ncccc6c5)nc4n3CC3CC3)n(C)c12] | (1R,4R,7R)-2-{2-[1-(cyclopropylmethyl)-6-(quinolin-6-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 598.1 | 2 | 1.68 |

TABLE 7-continued

| Cmpd# | Structure | Name | Obs. MS Ion | HPLC Method IDs | RT (min) |
|---|---|---|---|---|---|
| 339. | 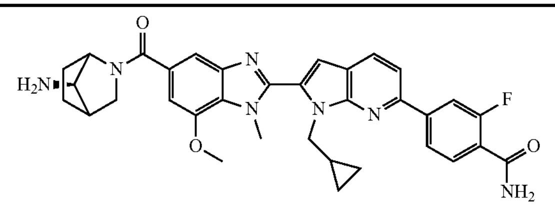 | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-2-fluorobenzamide | 607.2 | 2 | 1.49 |
| 340. | 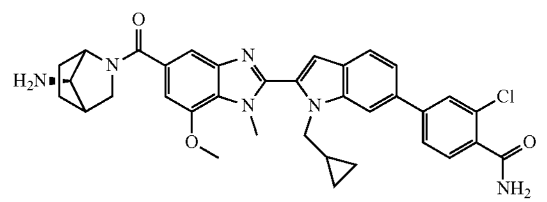 [SMILES: COc1cc(C(=O)N2CC3CCC2[C@@H]3N)cc2nc(-c3cc4ccc(-c5ccc(C(N)=O)c(F)c5)nc4n3CC3CC3)n(C)c12] | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-2-chlorobenzamide | 623.3 | 2 | 1.48 |
| 341. | 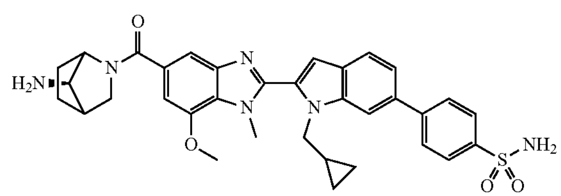 [SMILES: COc1cc(C(=O)N2CC3CCC2[C@@H]3N)cc2nc(-c3cc4ccc(-c5ccc(S(N)(=O)=O)cc5)cc4n3CC3CC3)n(C)c12] | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)benzene-1-sulfonamide | 625.2 | 2 | 1.42 |
| 342. | 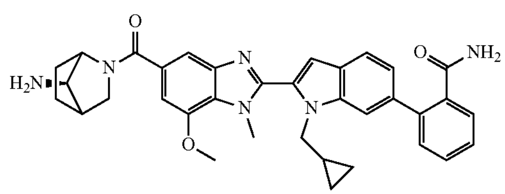 [SMILES: COc1cc(C(=O)N2CC3CCC2[C@@H]3N)cc2nc(-c3cc4ccc(-c5ccccc5C(N)=O)cc4n3CC3CC3)n(C)c12] | 2-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)benzamide | 589.2 | 1 | 1.25 |
| 343. | 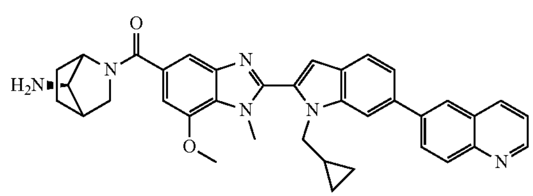 [SMILES: COc1cc(C(=O)N2CC3CCC2[C@@H]3N)cc2nc(-c3cc4ccc(-c5ccc6ncccc6c5)cc4n3CC3CC3)n(C)c12] | (1R,4R,7R)-2-{2-[1-(cyclopropylmethyl)-6-(quinolin-6-yl)-1H-indol-2-yl]-7-methoxy-1-methyl-1H-1,3-benzodiazole-5-carbonyl}-2-azabicyclo[2.2.1]heptan-7-amine | 597.3 | 1 | 1.13 |

TABLE 7-continued

| Cmpd# | Structure | Name | Obs. MS Ion | HPLC Method IDs | RT (min) |
|---|---|---|---|---|---|
| 344. | 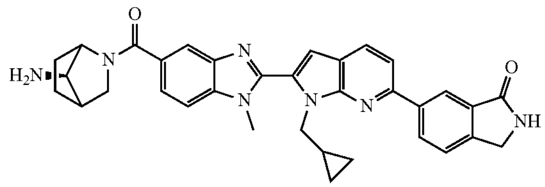 [SMILES: Cn1c(-c2cc3ccc(-c4ccc5c(c4)C(=O)NC5)nc3n2CC2CC2)nc2cc(C(=O)N3CC4CCC3[C@@H]4N)ccc21] | 6-(2-{5-[(1R,4R,7R)-7-amino-2-azabicyclo[2.2.1]heptane-2-carbonyl]-1-methyl-1H-1,3-benzodiazol-2-yl}-1-(cyclopropylmethyl)-1H-pyrrolo[2,3-b]pyridin-6-yl)-2,3-dihydro-1H-isoindol-1-one | 572.1 | 2 | 1.28 |
| 345. | 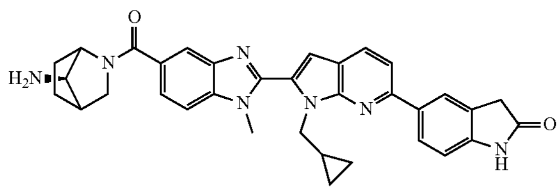 [SMILES: Cn1c(-c2cc3ccc(-c4ccc5c(c4)CC(=O)N5)nc3n2CC2CC2)nc2cc(C(=O)N3CC4CCC3[C@@H]4N)ccc21] | 5-(2-{5-[(1R,4R,7R)-7-amino-2-azabicyclo[2.2.1]heptane-2-carbonyl]-1-methyl-1H-1,3-benzodiazol-2-yl}-1-(cyclopropylmethyl)-1H-pyrrolo[2,3-b]pyridin-6-yl)-2,3-dihydro-1H-indol-2-one | 571.9 | 2 | 1.39 |
| 346. | 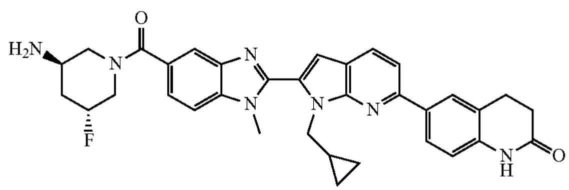 [SMILES: Cn1c(-c2cc3ccc(-c4ccc5c(c4)CCC(=O)N5)nc3n2CC2CC2)nc2cc(C(=O)N3C[C@H](N)C[C@@H](F)C3)ccc21] | 6-(2-{[(3R,5R)-3-amino-5-fluoropiperidine-1-carbonyl]-1-methyl-1H-1,3-benzodiazol-2-yl}-1-(cyclopropylmethyl)-1H-pyrrolo[2,3-b]pyridin-6-yl)-1,2,3,4-tetrahydroquinolin-2-one | 592.1 | 1 | 1.32 |
| 347. | 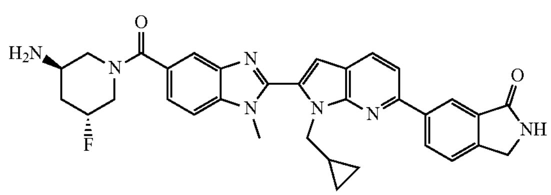 [SMILES: Cn1c(-c2cc3ccc(-c4ccc5c(c4)C(=O)NC5)nc3n2CC2CC2)nc2cc(C(=O)N3C[C@H](N)C[C@@H](F)C3)ccc21] | 6-(2-{5-[(3R,5R)-3-amino-5-fluoropiperidine-1-carbonyl]-1-methyl-1H-1,3-benzodiazol-2-yl}-1-(cyclopropylmethyl)-1H-pyrrolo[2,3-b]pyridin-6-yl)-2,3-dihydro-1H-isoindol-1-one | 578.1 | 2 | 1.42 |

TABLE 8

| Cmpd # | Structure | Name | Obs. MS Ion | HPLC Method IDs | RT (min) |
|---|---|---|---|---|---|
| 348. | 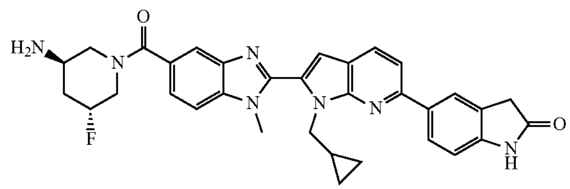 [SMILES: Cn1c(-c2cc3ccc(-c4ccc5c(c4)CC(=O)N5)nc3n2CC2CC2)nc2cc(C(=O)N3C[C@H](N)C[C@@H](F)C3)ccc21] | 5-(2-{5-[(3R,5R)-3-amino-5-fluoropiperidine-1-carbonyl]-1-methyl-1H-1,3-benzodiazol-2-yl}-1-(cyclopropylmethyl)-1H-pyrrolo[2,3-b]pyridin-6-yl)-2,3-dihydro-1H-indol-2-one | 578.1 | 1 | 1.43 |
| 349. | 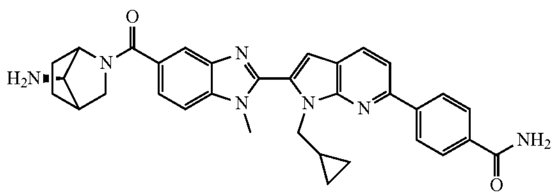 [SMILES: Cn1c(-c2cc3ccc(-c4ccc(C(N)=O)cc4)nc3n2CC2CC2)nc2cc(C(=O)N3CC4CCC3[C@@H]4N)ccc21] | 4-(2-{5-[(1R,4R,7R)-7-amino-2-azabicyclo[2.2.1]heptane-2-carbonyl]-1-methyl-1H-1,3-benzodiazol-2-yl}-1-(cyclopropylmethyl)-1H-pyrrolo[2,3-b]pyridin-6-yl)benzamide | 560.2 | 2 | 1.2 |
| 350. | 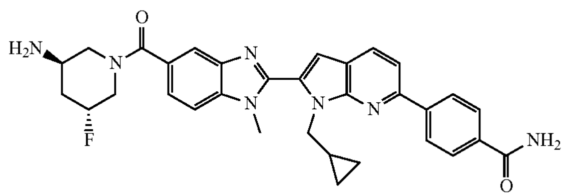 [SMILES: Cn1c(-c2cc3ccc(-c4ccc(C(N)=O)cc4)nc3n2CC2CC2)nc2cc(C(=O)N3C[C@H](N)C[C@@H](F)C3)ccc21] | 4-(2-{5-[(3R,5R)-3-amino-5-fluoropiperidine-1-carbonyl]-1-methyl-1H-1,3-benzodiazol-2-yl}-1-(cyclopropylmethyl)-1H-pyrrolo[2,3-b]pyridin-6-yl)benzamide | 566.2 | 1 | 1.28 |
| 351. | 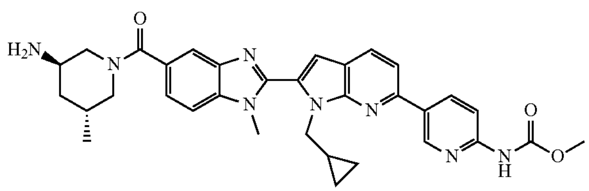 [SMILES: COC(=O)Nc1ccc(-c2ccc3cc(-c4nc5cc(C(=O)N6C[C@H](C)C[C@@H](N)C6)ccc5n4C)n(CC4CC4)c3n2)cn1] | methyl N-[5-(2-{5-[(3R,5R)-3-amino-5-fluoropiperidine-1-carbonyl]-1-methyl-1H-1,3-benzodiazol-2-yl}-1-(cyclopropylmethyl)-1H-pyrrolo[2,3-b]pyridin-6-yl)pyridin-2-yl]carbamate | 597.3 | 1 | 1.43 |
| 352. | 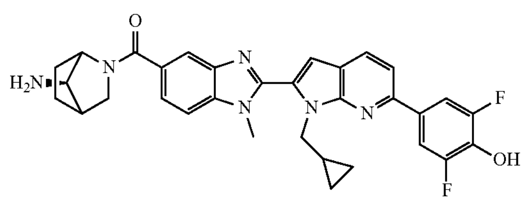 [SMILES: Cn1c(-c2cc3ccc(-c4cc(F)c(O)c(F)c4)nc3n2CC2CC2)nc2cc(C(=O)N3CC4CCC3[C@@H]4N)ccc21] | 4-(2-{5-[(1R,4R,7R)-7-amino-2-azabicyclo[2.2.1]heptane-2-carbonyl]-1-methyl-1H-1,3-benzodiazol-2-yl}-1-(cyclopropylmethyl)-1H-pyrrolo[2,3-b]pyridin-6-yl)-2,6-difluorophenol | 569.2 | 2 | 1.46 |

TABLE 8-continued

| Cmpd # | Structure | Name | Obs. MS Ion | HPLC Method IDs | RT (min) |
|---|---|---|---|---|---|
| 353. | 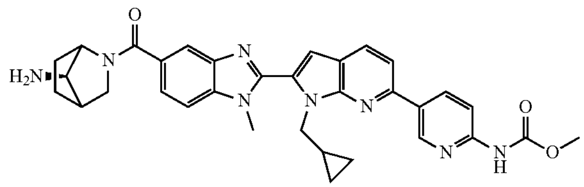 [SMILES: COC(=O)Nc1ccc(-c2ccc3cc(-c4nc5cc(C(=O)N6CC7CCC6[C@@H]7N)ccc5n4C)n(CC4CC4)c3n2)cn1] | methyl N-[5-(2-{5-[((1R,4R,7R)-7-amino-2-azabicyclo[2.2.1]heptane-2-carbonyl]-1-methyl-1H-1,3-benzodiazol-2-yl}-1-(cyclopropylmethyl)-1H-pyrrolo[2,3-b]pyridin-6-yl)pyridin-2-yl]carbamate | 591.3 | 1 | 1.47 |
| 354. | 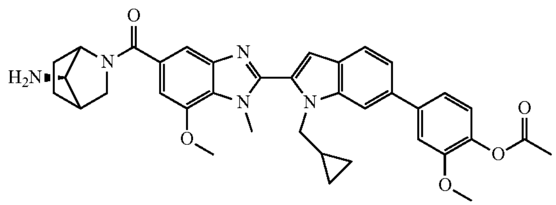 | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-2-methoxyphenyl acetate | 634.3 | 2 | 1.69 |
| 355. | 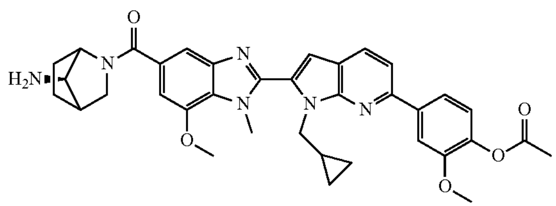 [SMILES: COc1cc(-c2ccc3cc(-c4nc5cc(C(=O)N6CC7CCC6[C@@H]7N)cc(OC)c5n4C)n(CC4CC4)c3c2)ccc1OC(C)=O] | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-methoxyphenyl acetate | 635 | 1 | 2.04 |
| 356 | 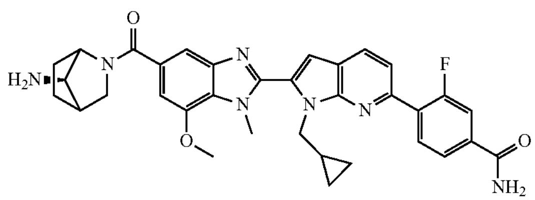 | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-3-fluorobenzamide | 608.2 | 1 | 1.4 |
| 357. | 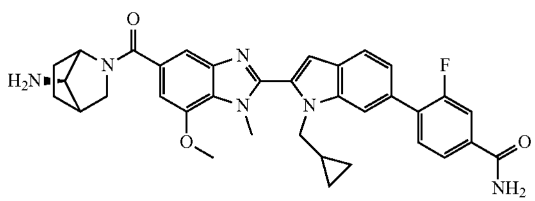 | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-3-fluorobenzamide | 607.4 | 1 | 1.42 |

TABLE 8-continued

| Cmpd # | Structure | Name | Obs. MS Ion | HPLC Method IDs | RT (min) |
|---|---|---|---|---|---|
| 358. | 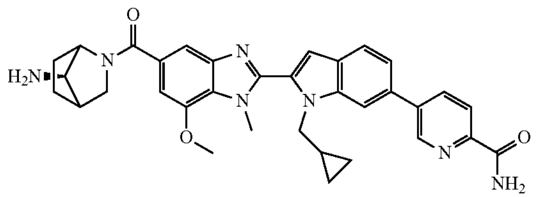 [SMILES: COc1cc(C(=O)N2CC3CCC2[C@@H]3N)cc2nc(-c3cc4ccc(-c5ccc(C(N)=O)cc5F)nc4n3CC3CC3)n(C)c12] | 5-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)pyridine-2-carboxamide | 589.9 | 2 | 1.36 |
| 359 | 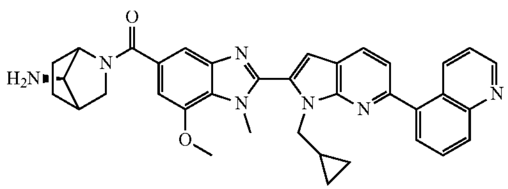 [SMILES: COc1cc(C(=O)N2CC3CCC2[C@@H]3N)cc2nc(-c3cc4ccc(-c5cccc6ncccc56)nc4n3CC3CC3)n(C)c12] | (1R,4R,7R)-2-{2-[1-(cyclopropylmethyl)-6-(quinolin-5-yl)-1H-pyrrolo[2,3-b]pyridin-2-yl]-7-methoxy-1-methyl-1H-1,3-benzodiazol-5-carbonyl}-2-azabicyclo[2.2.1]heptan-7-amine | 598.2 | 1 | 1.7 |
| 360. | 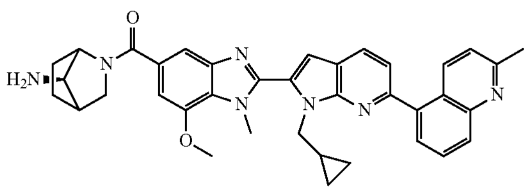 [SMILES: COc1cc(C(=O)N2CC3CCC2[C@@H]3N)cc2nc(-c3cc4ccc(-c5cccc6nc(C)ccc56)nc4n3CC3CC3)n(C)c12] | (1R,4R,7R)-2-{2-[1-(cyclopropylmethyl)-6-(2-methylquinolin-5-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 612 | 2 | 1.31 |
| 361. | 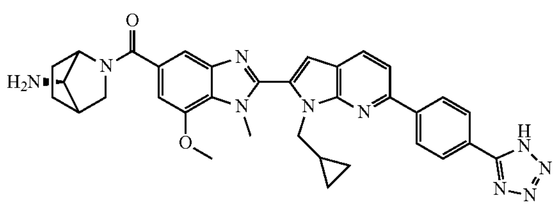 [SMILES: COc1cc(C(=O)N2CC3CCC2[C@@H]3N)cc2nc(-c3cc4ccc(-c5ccc(-c6nnn[nH]6)cc5)nc4n3CC3CC3)n(C)c12] | (1R,4R,7R)-2-{2-[1-(cyclopropylmethyl)-6-[4-(1H-1,2,3,4-tetrazol-5-yl)phenyl]-1H-pyrrolo[2,3-b]pyridin-2-yl]-7-methoxy-1-methyl-1H-1,3-benzodiazole-5-carbonyl}-2-azabicyclo[2.2.1]heptan-7-amine | 615 | 1 | 1.36 |
| 362. | 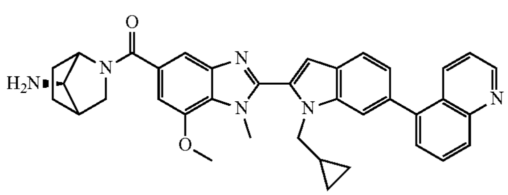 [SMILES: COc1cc(C(=O)N2CC3CCC2[C@@H]3N)cc2nc(-c3cc4ccc(-c5cccc6ncccc56)cc4n3CC3CC3)n(C)c12] | (1R,4R,7R)-2-{2-[1-(cyclopropylmethyl)-6-(quinolin-5-yl)-1H-indol-2-yl]-7-methoxy-1-methyl-1H-1,3-benzodiazole-5-carbonyl}-2-azabicyclo[2.2.1]heptan-7-amine | 597.2 | 2 | 1.32 |

TABLE 8-continued

| Cmpd # | Structure | Name | Obs. MS Ion | HPLC Method IDs | RT (min) |
|---|---|---|---|---|---|
| 363. | 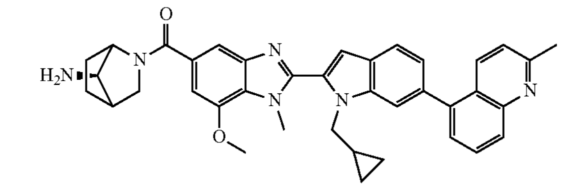 [SMILES: COc1cc(C(=O)N2CC3CCC2[C@@H]3N)cc2nc(-c3cc4ccc(-c5cccc6nc(C)ccc56)cc4n3CC3CC3)n(C)c12] | (1R,4R,7R)-2-{2-[1-(cyclopropylmethyl)-6-(2-methylquinolin-5-yl)-1H-indol-2-yl]-7-methoxy-1-methyl-1H-1,3-benzodiazole-5-carbonyl}-2-azabicyclo[2.2.1]heptan-7-amine | 611.3 | 2 | 1.23 |
| 364. | 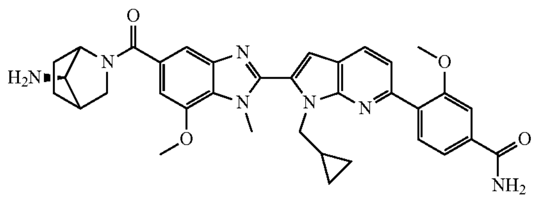 | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-3-methoxybenzamide | 310.6 | 2 | 1.34 |
| 365. | 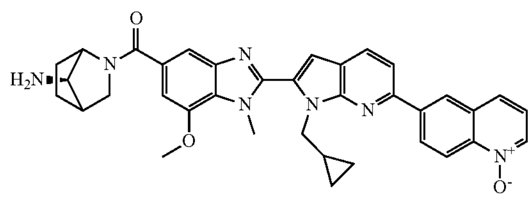 [SMILES: COc1cc(C(=O)N2CC3CCC2[C@@H]3N)cc2nc(-c3cc4ccc(-c5ccc6c(ccc[n+]6[O-])c5)nc4n3CC3CC3)n(C)c12] | 6-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)quinolin-1-ium-1-olate | 614.1 | 1 | 1.56 |
| 366. | 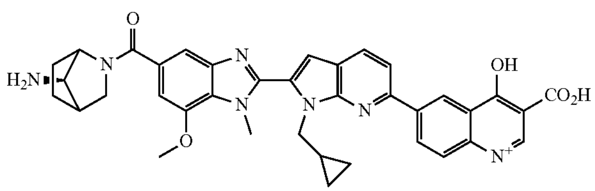 [SMILES: COc1cc(C(=O)N2CC3CCC2[C@@H]3N)cc2nc(-c3cc4ccc(-c5ccc6[nH+]cc(C(=O)O)c(O)c6c5)nc4n3CC3CC3)n(C)c12] | 6-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-4-hydroxyquinoline-3-carboxylic acid | 658.3, 658.17, 658.31 | 1 | |
| 367. | 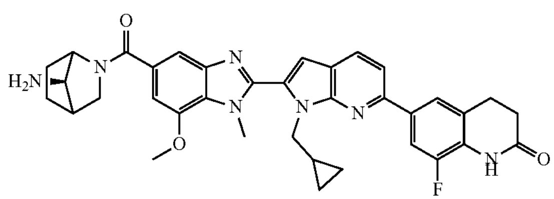 | 6-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-8-fluoro-1,2,3,4-tetrahydroquinolin-2-one | 634.2 | 1 | 1.68 |

TABLE 8-continued

| Cmpd # | Structure | Name | Obs. MS Ion | HPLC Method IDs | RT (min) |
|---|---|---|---|---|---|
| 368. | 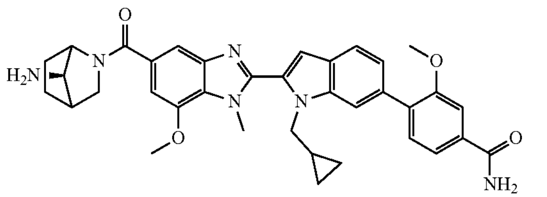 [SMILES: COc1cc(C(N)=O)ccc1-c1ccc2cc(-c3nc4cc(C(=O)N5CC6CCC5[C@@H]6N)cc(OC)c4n3C)n(CC3CC3)c2c1] | 4-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-3-methoxybenzamide | 619.4 | 1 | 1.54 |
| 369. | 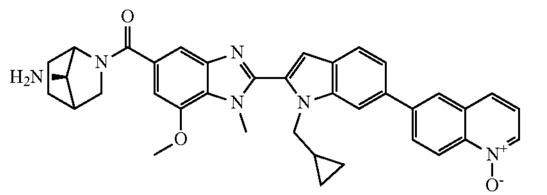 [SMILES: COc1cc(C(=O)N2CC3CCC2[C@@H]3N)cc2nc(-c3cc4ccc(-c5ccc6c(ccc[n+]6[O-])c5)cc4n3CC3CC3)n(C)c12] | 6-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)quinolin-1-ium-1-olate | 613.2 | 1 | 1.57 |
| 370. | 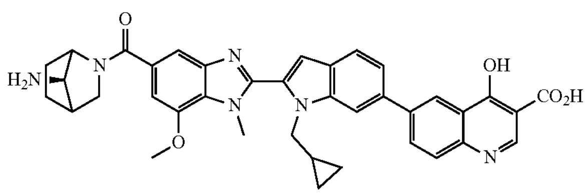 [SMILES: COc1cc(C(=O)N2CC3CCC2[C@@H]3N)cc2nc(-c3cc4ccc(-c5ccc6ncc(C(=O)O)c(O)c6c5)cc4n3CC3CC3)n(C)c12] | 6-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-4-hydroxyquinoline-3-carboxylic acid | 657.3 | 2 | 1.41 |
| 371. | 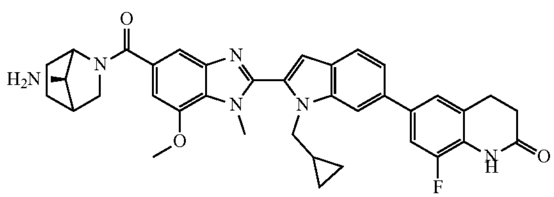 | 6-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-8-fluoro-1,2,3,4-tetrahydroquinolin-2-one | 633.4 | 2 | 1.39 |
| 372. | 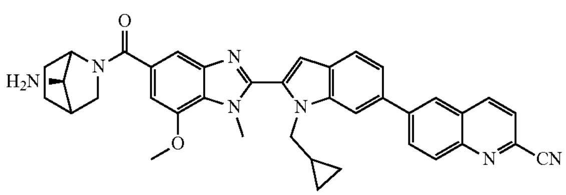 [SMILES: COc1cc(C(=O)N2CC3CCC2[C@@H]3N)cc2nc(-c3cc4ccc(-c5ccc6nc(C#N)ccc6c5)cc4n3CC3CC3)n(C)c12] | 6-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)quinoline-2-carbonitrile | 622.3 | 2 | 1.79 |

TABLE 8-continued

| Cmpd # | Structure | Name | Obs. MS Ion | HPLC Method IDs | RT (min) |
|---|---|---|---|---|---|
| 373. | 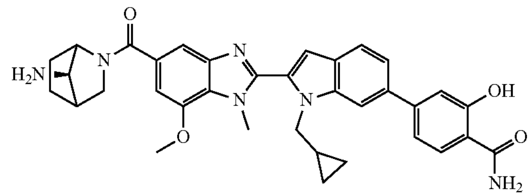 | 4-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-2-hydroxybenzamide | 605.3 | 2 | 1.43 |
| 374. | 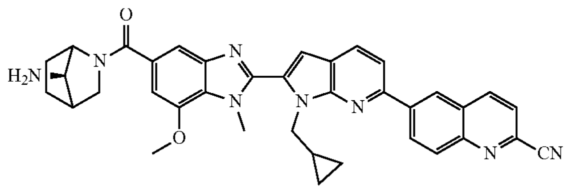 [SMILES: COc1cc(C(=O)N2CC3CCC2[C@@H]3N)cc2nc(-c3cc4ccc(-c5ccc6nc(C#N)ccc6c5)nc4n3CC3CC3)n(C)c12] | 6-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)quinoline-2-carbonitrile | 623.4 | 1 | 1.99 |
| 375. | 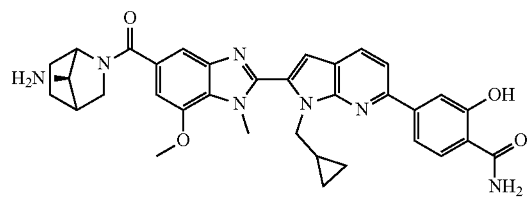 [SMILES: COc1cc(C(=O)N2CC3CCC2[C@@H]3N)cc2nc(-c3cc4ccc(-c5ccc(C(N)=O)c(O)c5)nc4n3CC3CC3)n(C)c12] | 4-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-hydroxybenzamide | 606.3 | 2 | 1.34 |
| 376. | 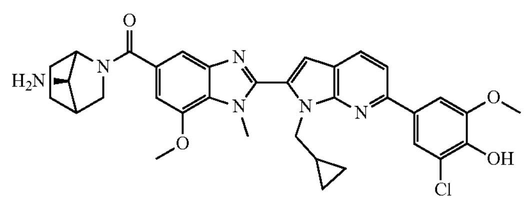 [SMILES: COc1cc(-c2ccc3cc(-c4nc5cc(C(=O)N6CC7CCC6[C@@H]7N)cc(OC)c5n4C)n(CC4CC4)c3n2)cc(Cl)c1O] | 4-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-chloro-6-methoxyphenol | 627.3 | 1 | 1.83 |
| 377. | 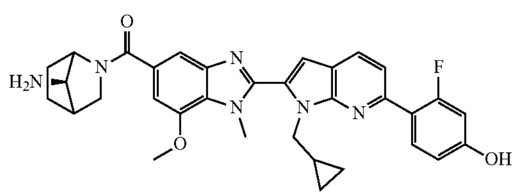 [SMILES: COc1cc(C(=O)N2CC3CCC2[C@@H]3N)cc2nc(-c3cc4ccc(-c5ccc(O)cc5F)nc4n3CC3CC3)n(C)c12] | 4-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-3-fluorophenol | 581.4 | 1 | 1.55 |

TABLE 8-continued

| Cmpd # | Structure | Name | Obs. MS Ion | HPLC Method IDs | RT (min) |
|---|---|---|---|---|---|
| 378. | 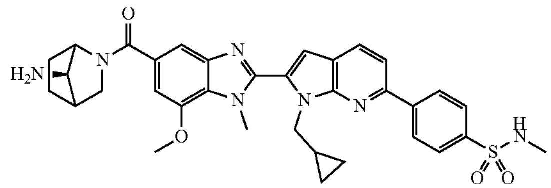 | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-N-methylbenzene-1-sulfonamide | 640.4 | 1 | 1.71 |
| 379. | 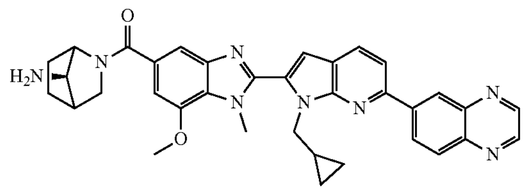 [SMILES: COc1cc(C(=O)N2CC3CCC2[C@@H]3N)cc2nc(-c3cc4ccc(-c5ccc6nccnc6c5)nc4n3CC3CC3)n(C)c12] | (1R,4R,7R)-2-{2-[1-(cyclopropylmethyl)-6-(quinoxalin-6-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 598.9 | 2 | 1.55 |
| 380. | 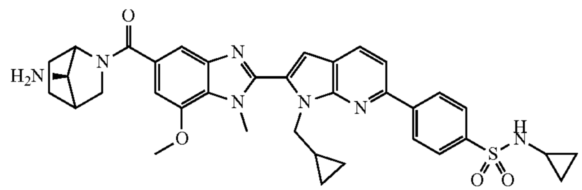 | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-N-cyclopropylbenzene-1-sulfonamide | 666.2 | 1 | 1.89 |
| 381. | 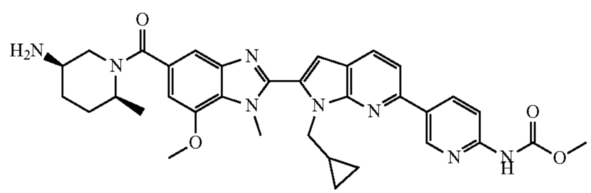 | methyl N-[5-(2-{5-[(2S,5R)-5-amino-2-methylpiperidine-1-carbonyl]-7-methoxy-1-methyl-1H-1,3-benzodiazol-2-yl}-1-(cyclopropylmethyl)-1H-pyrrolo[2,3-b]pyridin-6-yl)pyridin-2-yl]carbamate | 623 | 1 | 1.59 |
| 382. | 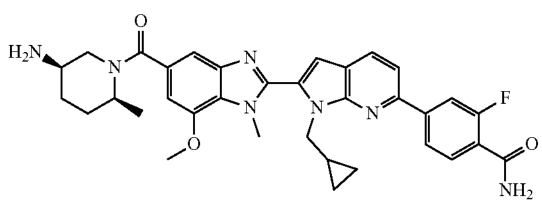 | 4-(2-{5-[(2S,5R)-5-amino-2-methylpiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-fluorobenzamide | 610.3 | 2 | 1.36 |

TABLE 8-continued

| Cmpd # | Structure | Name | Obs. MS Ion | HPLC Method IDs | RT (min) |
|---|---|---|---|---|---|
| 383. | 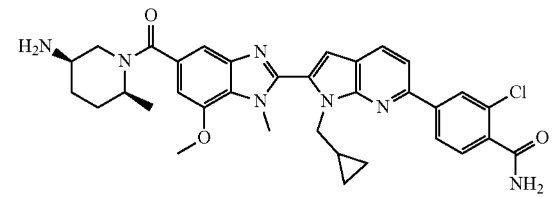 [SMILES: COc1cc(C(=O)N2C[C@H](N)CC[C@@H]2C)cc2nc(-c3cc4ccc(-c5ccc(C(N)=O)c(F)c5)nc4n3CC3CC3)n(C)c12] | 4-(2-{5-[(2S,5R)-5-amino-2-methylpiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-chlorobenzamide | 626.2 | 2 | 1.36 |
| 384. | 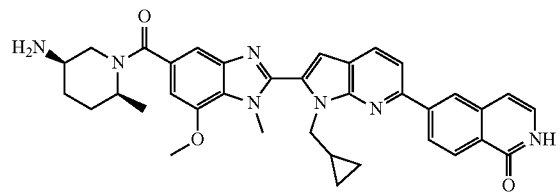 | 6-(2-{5-[(2S,5R)-5-amino-2-methylpiperidine-1-carbonyl]-7-methoxy-1-methyl-1H-1,3-benzodiazol-2-yl}-1-(cyclopropylmethyl)-1H-pyrrolo[2,3-b]pyridin-6-yl)-1,2-dihydroisoquinolin-1-one | 616.2 | 1 | 1.51 |
| 385. | 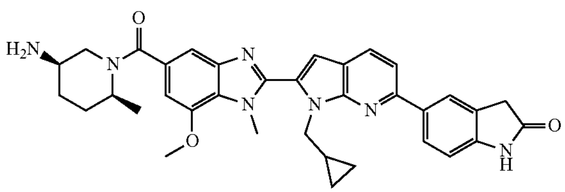 [SMILES: COc1cc(C(=O)N2C[C@H](N)CC[C@@H]2C)cc2nc(-c3cc4ccc(-c5ccc6c(c5)CC(=O)N6)nc4n3CC3CC3)n(C)c12] | 5-(2-{5-[(2S,5R)-5-amino-2-methylpiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2,3-dihydro-1H-indol-2-one | 604.4 | 1 | 1.49 |
| 386. | 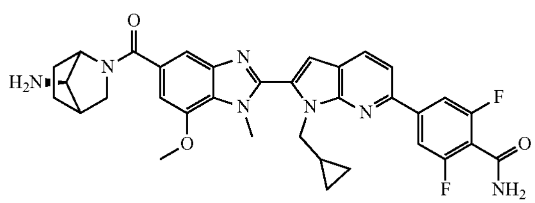 [SMILES: COc1cc(C(=O)N2CC3CCC2[C@@H]3N)cc2nc(-c3cc4ccc(-c5cc(F)c(C(N)=O)c(F)c5)nc4n3CC3CC3)n(C)c12] | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2,6-difluorobenzamide | 626.4 | 1 | 1.49 |
| 387. | 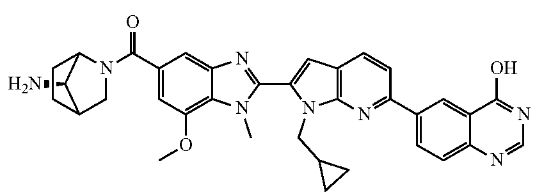 [SMILES: COc1cc(C(=O)N2CC3CCC2[C@@H]3N)cc2nc(-c3cc4ccc(-c5ccc6ncnc(O)c6c5)nc4n3CC3CC3)n(C)c12] | 6-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)quinazolin-4-ol | 615.3 | 2 | 1.3 |

TABLE 8-continued

| Cmpd # | Structure | Name | Obs. MS Ion | HPLC Method IDs | RT (min) |
|---|---|---|---|---|---|
| 388. | 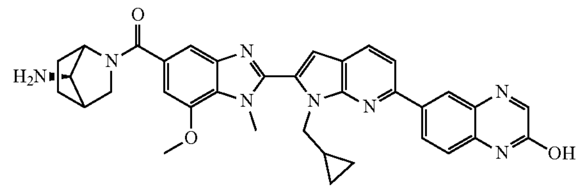 [SMILES: COc1cc(C(=O)N2CC3CCC2[C@@H]3N)cc2nc(-c3cc4ccc(-c5ccc6nc(O)cnc6c5)nc4n3CC3CC3)n(C)c12] | 6-(2-{5-[((1R,4R,7R)-7-amino-2-azabicyclo[2.2.1]heptane-2-carbonyl]-7-methoxy-1-methyl-1H-1,3-benzodiazol-2-yl]-1-(cyclopropylmethyl)-1H-pyrrolo[2,3-b]pyridin-6-yl)quinoxalin-2-ol | 615.3 | 2 | 1.24 |
| 389. | 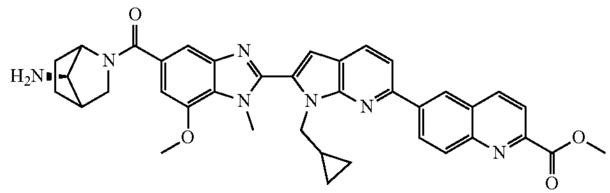 [SMILES: COC(=O)c1ccc2cc(-c3ccc4cc(-c5nc6cc(C(=O)N7CC8CCC7[C@@H]8N)cc(OC)c6n5C)n(CC5CC5)c4n3)ccc2n1] | methyl 6-{5-[((1R,4R,7R)-7-amino-2-azabicyclo[2.2.1]heptane-2-carbonyl]-7-methoxy-1-methyl-1H-1,3-benzodiazol-2-yl]-1-(cyclopropylmethyl)-1H-pyrrolo[2,3-b]pyridin-6-yl)quinoline-2-carboxylate | 656.37, 656.37 | 1 | 1 |
| 390. | 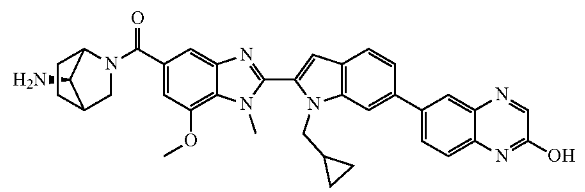 [SMILES: COc1cc(C(=O)N2CC3CCC2[C@@H]3N)cc2nc(-c3cc4ccc(-c5ccc6nc(O)cnc6c5)cc4n3CC3CC3)n(C)c12] | 6-(2-{5-[((1R,4R,7R)-7-amino-2-azabicyclo[2.2.1]heptane-2-carbonyl]-7-methoxy-1-methyl-1H-1,3-benzodiazol-2-yl]-1-(cyclopropylmethyl)-1H-indol-6-yl)quinoxalin-2-ol | 614.2 | 1 | 1.49 |
| 391. | 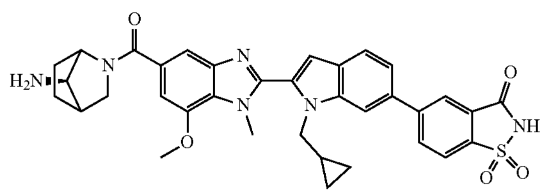 [SMILES: COc1cc(C(=O)N2CC3CCC2[C@@H]3N)cc2nc(-c3cc4ccc(-c5ccc6c(c5)C(=O)NS6(=O)=O)cc4n3CC3CC3)n(C)c12] | 5-(2-{5-[((1R,4R,7R)-7-amino-2-azabicyclo[2.2.1]heptane-2-carbonyl]-7-methoxy-1-methyl-1H-1H-benzo[d]imidazol-2-yl]-1-(cyclopropylmethyl)-1H-indol-6-yl)benzo[d]isothiazol-3(2H)-one 1,1-dioxide | 651.3 | 2 | 1.26 |
| 392. | 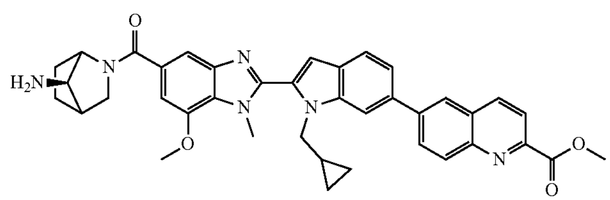 | methyl 6-(2-{5-[((1R,4R,7R)-7-amino-2-azabicyclo[2.2.1]heptane-2-carbonyl]-7-methoxy-1-methyl-1H-1,3-benzodiazol-2-yl]-1-(cyclopropylmethyl)-1H-indol-6-yl)quinoline-2-carboxylate | 655.4 | 2 | 1.57 |

TABLE 8-continued

| Cmpd # | Structure | Name | Obs. MS Ion | HPLC Method IDs | RT (min) |
|---|---|---|---|---|---|
| 393. | 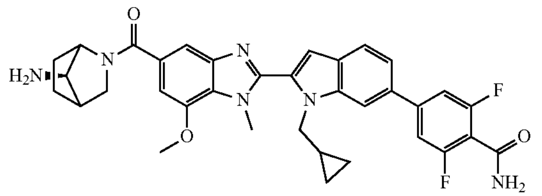 | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-2,6-difluorobenzamide | 625.3 | 1 | 1.55 |
| 394. | 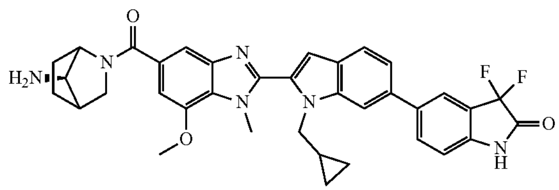 [SMILES: COc1cc(C(=O)N2CC3CCC2[C@@H]3N)cc2nc(-c3cc4ccc(-c5ccc6c(c5)C(F)(F)C(=O)N6)cc4n3CC3CC3)n(C)c12] | 2'-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-3,3-difluoro-2,3-dihydro-1H,1'H-[5,6-biindole]-2-one | 637.3 | 2 | 1.56 |
| 395. | 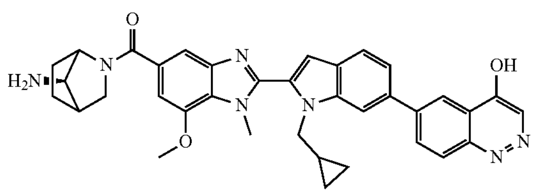 [SMILES: COc1cc(C(=O)N2CC3CCC2[C@@H]3N)cc2nc(-c3cc4ccc(-c5ccc6nncc(O)c6c5)cc4n3CC3CC3)n(C)c12] | 6-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)cinnolin-4-ol | 613.9 | 2 | 1.35 |
| 396. | 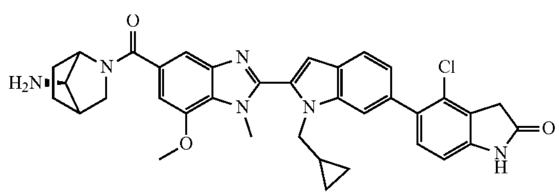 [SMILES: COc1cc(C(=O)N2CC3CCC2[C@@H]3N)cc2nc(-c3cc4ccc(-c5ccc6c(c5Cl)CC(=O)N6)cc4n3CC3CC3)n(C)c12] | 2'-{5-[(1R,4R,7R)-7-amino-2-azabicyclo[2.2.1]heptane-2-carbonyl]-7-methoxy-1-methyl-1H-1,3-benzodiazol-2-yl}-4-chloro-1'-(cyclopropylmethyl)-2,3-dihydro-1H,1'H-[5,6-biindole]-2-one | 635.2 | 2 | 1.37 |

TABLE 9

| Cmpd # | Structure | Name | Obs. MS Ion | HPLC Method IDs | RT (min) |
|---|---|---|---|---|---|
| 397. | 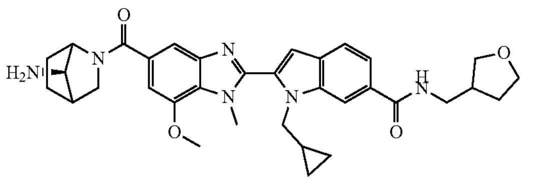 | 2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-N-[(oxolan-3-yl)methyl]-1H-indole-6-carboxamide | 597.2 | 1 | 1.28 |
| 398. | 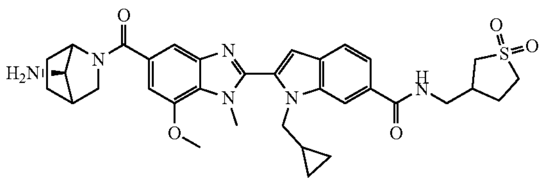 | 2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-N-[(1,1-dioxidotetrahydrothiophen-3-yl)methyl]-1H-indole-6-carboxamide | 645.1 | 1 | 1.21 |
| 399. | 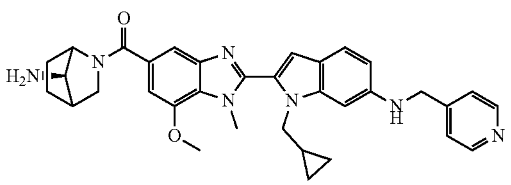 | 2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-N-[(pyridin-4-yl)methyl]-1H-indol-6-amine | 576.3 | 1 | 1.3 |
| 400. | 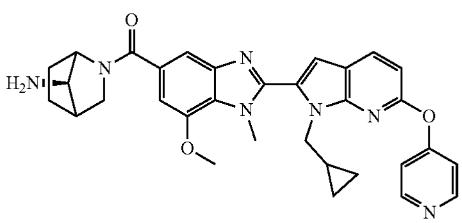 [SMILES: COc1cc(C(=O)N2CC3CCC2[C@@H]3N)cc2nc(-c3cc4ccc(Oc5ccncc5)nc4n3CC3CC3)n(C)c12] | (1R,4R,7R)-2-{2-[1-(cyclopropylmethyl)-6-(pyridin-4-yloxy)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 564.3 | 2 | 1 |
| 401. | 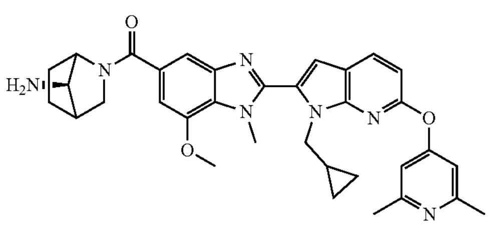 [SMILES: COc1cc(C(=O)N2CC3CCC2[C@@H]3N)cc2nc(-c3cc4ccc(Oc5cc(C)nc(C)c5)nc4n3CC3CC3)n(C)c12] | (1R,4R,7R)-2-{2-[1-(cyclopropylmethyl)-6-[(2,6-dimethylpyridin-4-yl)oxy]-1H-pyrrolo[2,3-b]pyridin-2-yl]-7-methoxy-1-methyl-1H-1,3-benzodiazole-5-carbonyl}-2-azabicyclo[2.2.1]heptan-7-amine | 592.3 | 1 | 1.75 |
| 402 | 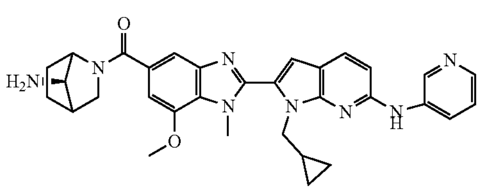 | (1R,4R,7R)-2-(2-{1-(cyclopropylmethyl)-6-[(pyridin-3-yl)amino]-1H-pyrrolo[2,3-b]pyridin-2-yl}-7-methoxy-1-methyl-1H-1,3-benzodiazole-5-carbonyl)-2-azabicyclo[22.1]heptan-7-amine | 563.2 | 1 | 1.48 |
| 403. | 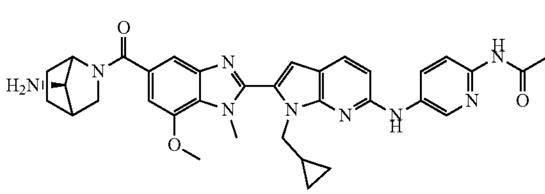 | N-{5-[(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)amino]pyridin-2-yl}acetamide | 620.2 | 1 | 1.43 |

TABLE 9-continued

| Cmpd # | Structure | Name | Obs. MS Ion | HPLC Method IDs | RT (min) |
|---|---|---|---|---|---|
| 404. | 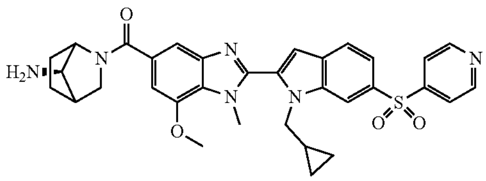 [SMILES: COc1cc(C(=O)N2CC3CCC2[C@@H]3N)cc2nc(-c3cc4ccc(S(=O)(=O)c5ccncc5)cc4n3CC3CC3)n(C)c12] | (1R,4R,7R)-2-{2-[1-(cyclopropylmethyl)-6-(pyridine-4-sulfonyl)-1H-indol-2-yl]-7-methoxy-1-methyl-1H-1,3-benzodiazole-5-carbonyl}-2-azabicyclo[2.2.1]heptan-7-amine | 611.4 | 1 | 1.45 |
| 405. | 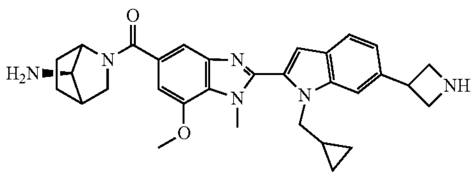 [SMILES: COc1cc(C(=O)N2CC3CCC2[C@@H]3N)cc2nc(-c3cc4ccc(C5CNC5)cc4n3CC3CC3)n(C)c12] | (1R,4R,7R)-2-{2-[6-(azetidin-3-yl)-1-(cyclopropylmethyl)-1H-indol-2-yl]-7-methoxy-1-methyl-1H-1,3-benzodiazole-5-carbonyl}-2-azabicyclo[2.2.1]heptan-7-amine | 525.2 | 1 | 1.04 |
| 406. | 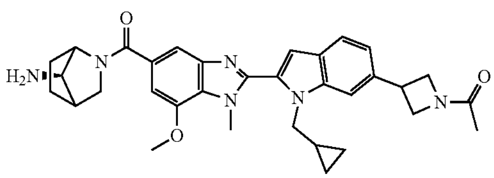 [SMILES: COc1cc(C(=O)N2CC3CCC2[C@@H]3N)cc2nc(-c3cc4ccc(C5CN(C(C)=O)C5)cc4n3CC3CC3)n(C)c12] | 1-[3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)azetidin-1-yl]ethan-1-one | 567.4 | 1 | 1.33 |

TABLE 10

| Cmpd # | Structure | Name | Obs. MS Ion | HPLC Method IDs | RT (min) |
|---|---|---|---|---|---|
| 407. | 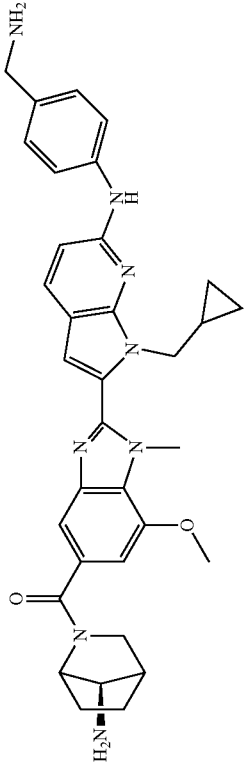 | (1R,4R,7R)-2-[2-(6-{[4-(aminomethyl)phenyl]amino}-1-(cyclopropylmethyl)-1H-pyrrolo[2,3-b]pyridin-2-yl)-7-methoxy-1-methyl-1H-1,3-benzodiazole-5-carbonyl]-2-azabicyclo[2.2.1]heptan-7-amine | 591.4 | 1 | 1.18 |
| 408. | 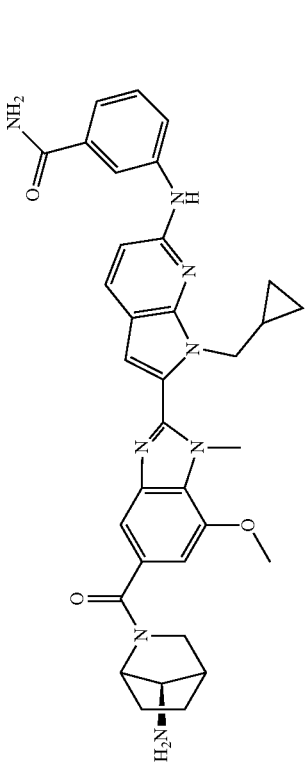 | 3-[(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)amino]benzamide | 605.4 | 1 | 1.34 |
| 409. | 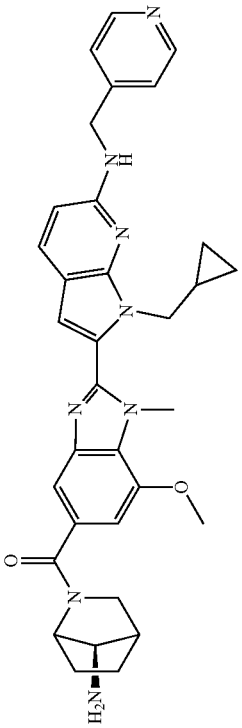 | (1R,4R,7R)-2-{2-[1-(cyclopropylmethyl)-6-{[(pyridin-4-yl)methyl]amino}-1H-pyrrolo[2,3-b]pyridin-2-yl]-7-methoxy-1-methyl-1H-1,3-benzodiazole-5-carbonyl}-2-azabicyclo[2.2.1]heptan-7-amine | 577.4 | 1 | 1.42 |

TABLE 10-continued

| Cmpd # | Structure | Name | Obs. MS Ion | HPLC Method IDs | RT (min) |
|---|---|---|---|---|---|
| 410. | 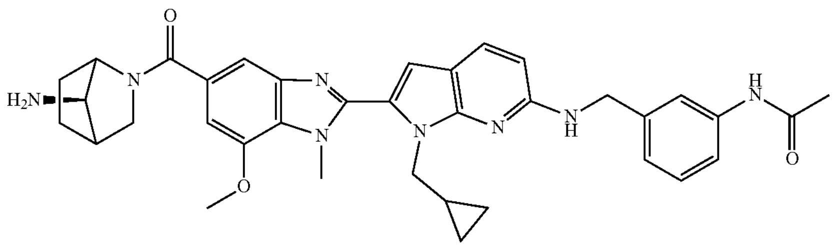 [SMILES: COc1cc(C(=O)N2CC3CCC2[C@@H]3N)cc2nc(-c3cc4ccc(NCc5cccc(NC(C)=O)c5)nc4n3CC3CC3)n(C)c12] | N-(3-{[(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)amino]methyl}phenyl)acetamide | 633.5 | 2 | 1.17 |
| 411. | 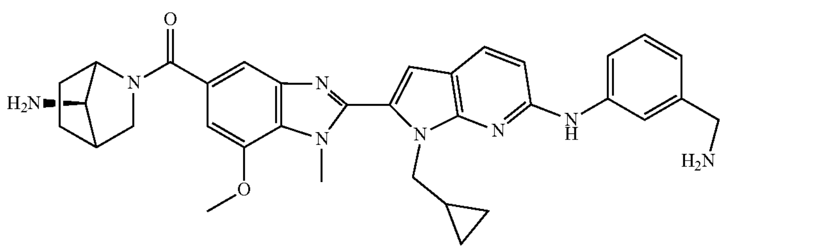 [SMILES: COc1cc(C(=O)N2CC3CCC2[C@@H]3N)cc2nc(-c3cc4ccc(Nc5cccc(CN)c5)nc4n3CC3CC3)n(C)c12] | (1R,4R,7R)-2-[2-(6-{[3-(aminomethyl)phenyl]amino}-1-(cyclopropylmethyl)-1H-pyrrolo[2,3-b]pyridin-2-yl)-7-methoxy-1-methyl-1H-1,3-benzodiazole-5-carbonyl]-2-azabicyclo[2.2.1]heptan-7-amine | 591.2 | 2 | 1.11 |
| 412. | 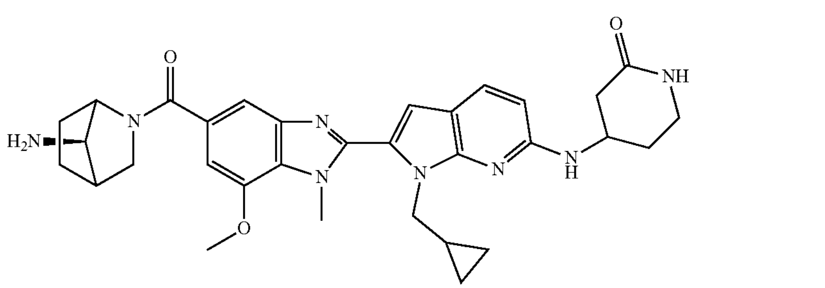 [SMILES: COc1cc(C(=O)N2CC3CCC2[C@@H]3N)cc2nc(-c3cc4ccc(NC5CCNC(=O)C5)nc4n3CC3CC3)n(C)c12] | 4-[(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)amino]piperidin-2-one | 583.4 | 1 | 1.01 |

TABLE 10-continued

| Cmpd # | Structure | Name | Obs. MS Ion | HPLC Method IDs | RT (min) |
|---|---|---|---|---|---|
| 413. | 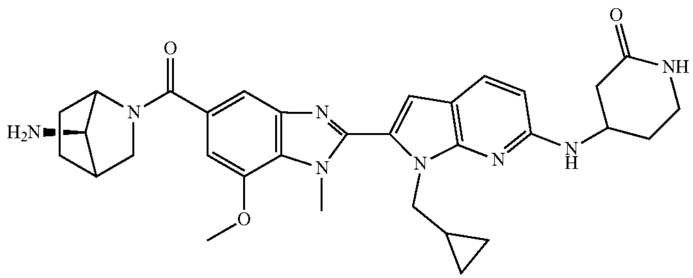 [SMILES: COc1cc(C(=O)N2CC3CCC2[C@@H]3N)cc2nc(-c3cc4ccc(NC5CCNC(=O)C5)nc4n3CC3CC3)n(C)c12] | 4-[(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)amino]piperidin-2-one | 583 | 1 | 1.3 |
| 414. | 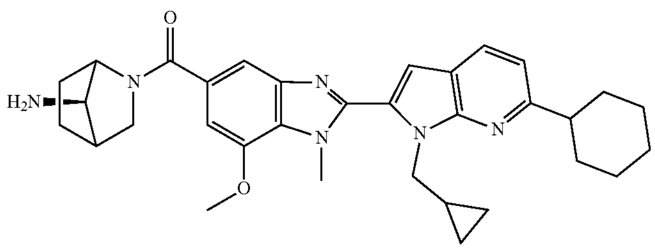 [SMILES: COc1cc(C(=O)N2CC3CCC2[C@@H]3N)cc2nc(-c3cc4ccc(C5CCCCC5)nc4n3CC3CC3)n(C)c12] | (1R,4R,7R)-2-{2-[6-cyclohexyl-1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 553.4 | 1 | 2.33 |
| 415. | 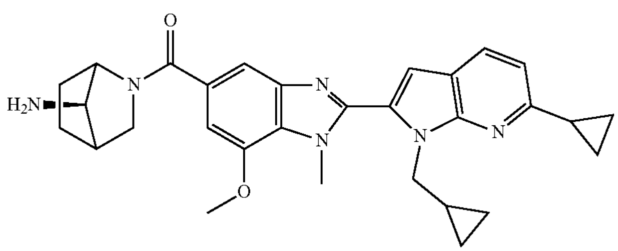 [SMILES: COc1cc(C(=O)N2CC3CCC2[C@@H]3N)cc2nc(-c3cc4ccc(C5CC5)nc4n3CC3CC3)n(C)c12] | (1R,4R,7R)-2-{2-[6-cyclopropyl-1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 511.2 | 2 | 1.4 |
| 416. | 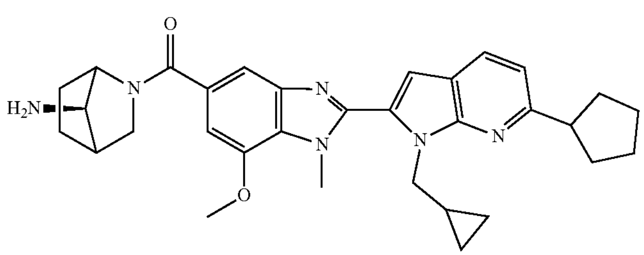 [SMILES: COc1cc(C(=O)N2CC3CCC2[C@@H]3N)cc2nc(-c3cc4ccc(C5CCCC5)nc4n3CC3CC3)n(C)c12] | (1R,4R,7R)-2-{2-[6-cyclopentyl-1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 539.4 | 1 | 2.25 |

TABLE 10-continued

| Cmpd # | Name | Obs. MS Ion | HPLC Method IDs | RT (min) |
|---|---|---|---|---|
| 417. | (1R,4R,7R)-2-{2-[1-(cyclopropylmethyl)-6-(2-ethoxypyrimidin-5-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 593.4 | 1 | 1.74 |
| 418. | (1R,4R,7R)-2-{2-[1-(cyclopropylmethyl)-6-[(oxolan-3-yl)methyl]-1H-pyrrolo[2,3-b]pyridin-2-yl]-7-methoxy-1-methyl-1H-1,3-benzodiazole-5-carbonyl}-2-azabicyclo[2.2.1]heptan-7-amine | 555.5 | 1 | 1.6 |
| 419. | (1R,4R,7R)-2-{2-[1-(cyclopropylmethyl)-6-(oxetan-3-yl)-1H-indol-2-yl]-7-methoxy-1-methyl-1H-1,3-benzodiazole-5-carbonyl}-2-azabicyclo[2.2.1]heptan-7-amine | 526.1 | 2 | 1.36 |
| 420. | (1R,4R,7R)-2-{2-[1-(cyclopropylmethyl)-6-(piperidin-4-yl)-1H-indol-2-yl]-7-methoxy-1-methyl-1H-1,3-benzodiazole-5-carbonyl}-2-azabicyclo[2.2.1]heptan-7-amine | 553.5 | 2 | 0.95 |

TABLE 10-continued

| Cmpd # | Structure | Name | Obs. MS Ion | HPLC Method IDs | RT (min) |
|---|---|---|---|---|---|
| 421. | 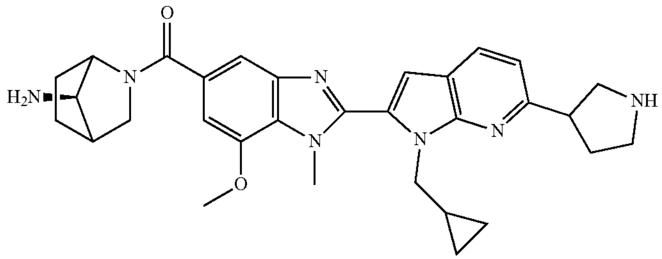 [SMILES: COc1cc(C(=O)N2CC3CCC2[C@@H]3N)cc2nc(-c3cc4ccc(C5CCNC5)nc4n3CC3CC3)n(C)c12] | (1R,4R,7R)-2-{2-[1-(cyclopropylmethyl)-6-(pyrrolidin-3-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 539.9 | 2 | 1.08 |
| 422. | 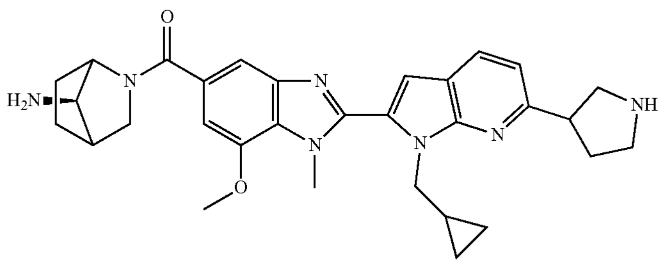 [SMILES: COc1cc(C(=O)N2CC3CCC2[C@@H]3N)cc2nc(-c3cc4ccc(C5CCNC5)nc4n3CC3CC3)n(C)c12] | (1R,4R,7R)-2-{2-[1-(cyclopropylmethyl)-6-(pyrrolidin-3-yl)-1H-indol-2-yl]-7-methoxy-1-methyl-1H-1,3-benzodiazole-5-carbonyl}-2-azabicyclo[2.2.1]heptan-7-amine | 539.2 | 1 | 1.31 |
| 423. | 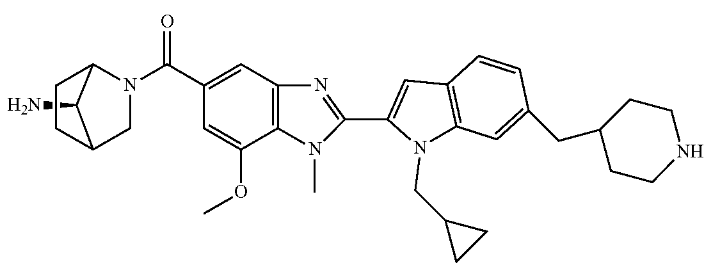 [SMILES: COc1cc(C(=O)N2CC3CCC2[C@@H]3N)cc2nc(-c3cc4ccc(CC5CCNCC5)cc4n3CC3CC3)n(C)c12] | (1R,4R,7R)-2-{2-[1-(cyclopropylmethyl)-6-[(piperidin-4-yl)methyl]-1H-indol-2-yl]-7-methoxy-1-methyl-1H-1,3-benzodiazole-5-carbonyl}-2-azabicyclo[2.2.1]heptan-7-amine | 567.6 | 2 | 1.05 |

TABLE 10-continued

| Cmpd # | Name | Obs. MS Ion | HPLC Method IDs | RT (min) |
|---|---|---|---|---|
| 424. | 1-[4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)piperidin-1-yl]ethan-1-one | 595.5 | 1 | 1.53 |
| 425. | 3-[2-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)ethyl]-1,3-oxazolidin-2-one | 583.4 | 1 | 1.45 |
| 426. | (1R,4R,7R)-2-{2-[1-(cyclopropylmethyl)-6-(piperidin-4-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 554.3 | 1 | 1.26 |

TABLE 10-continued

| Cmpd # | Structure | Name | Obs. MS Ion | HPLC Method IDs | RT (min) |
|---|---|---|---|---|---|
| 427. | 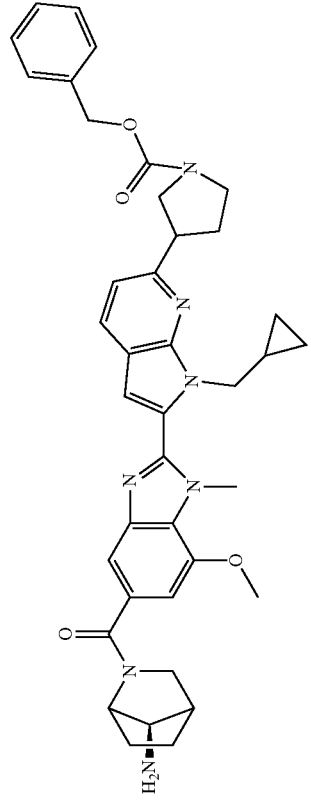 | benzyl 3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)pyrrolidine-1-carboxylate | 674.15, 674.08 | 2 | 1.67, 1.72 |
| 428. | 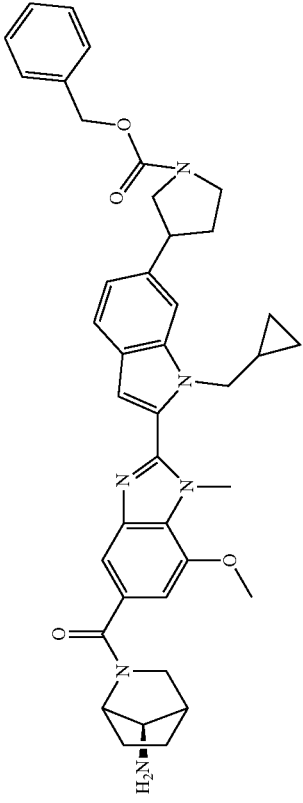 | benzyl 3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)pyrrolidine-1-carboxylate | 673.24, 673.26 | 1 | 1.86 |
| 429. | 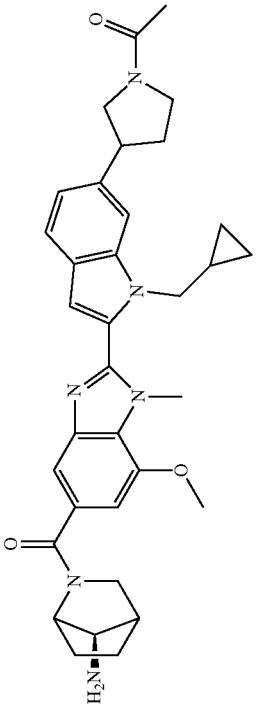 | 1-[3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)pyrrolidin-1-yl]ethan-1-one | 581.6 | 2 | 1.2 |

TABLE 10-continued

| Cmpd # | Name | Obs. MS Ion | HPLC Method IDs | RT (min) |
|---|---|---|---|---|
| 430. | (1R,4R,7R)-2-{2-[1-(cyclopropylmethyl)-6-(1-methyl-1H-1,2,3-benzotriazol-6-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 602.4 | 2 | 1.37 |
| 431. | (1R,4R,7R)-2-{2-[1-(cyclopropylmethyl)-6-(1-methyl-1H-1,2,3-benzotriazol-6-yl)-1H-indol-2-yl]-7-methoxy-1-methyl-1H-1,3-benzodiazole-5-carbonyl}-2-azabicyclo[2.2.1]heptan-7-amine | 601.2 | 2 | 1.6 |
| 432. | 5-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-2,3-dihydro-1,3-benzoxazol-2-one | 603.1 | 1 | 1.61 |

TABLE 10-continued

| Cmpd # | Structure | Name | Obs. MS Ion | HPLC Method IDs | RT (min) |
|---|---|---|---|---|---|
| 433. | 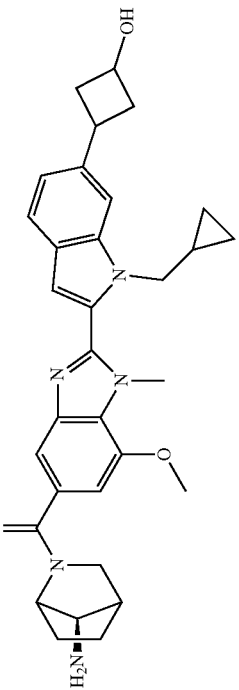 | 3-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)cyclobutan-1-ol | 540.1 | 2 | 1.19 |
| 434. | 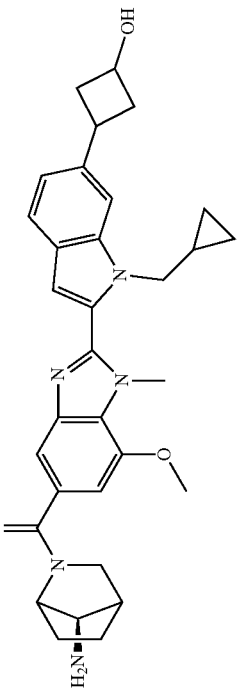 | 3-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)cyclobutan-1-ol | 540.4 | 2 | 1.29 |
| 435. | 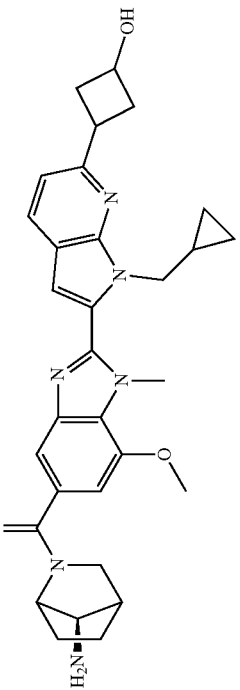 | (1r,3r)-3-(2-{5-[((1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)cyclobutan-1-ol | 541.0 | 3 | 0.66 |

TABLE 10-continued

| Cmpd # | Structure | Name | Obs. MS Ion | HPLC Method IDs | RT (min) |
|---|---|---|---|---|---|
| 436. | 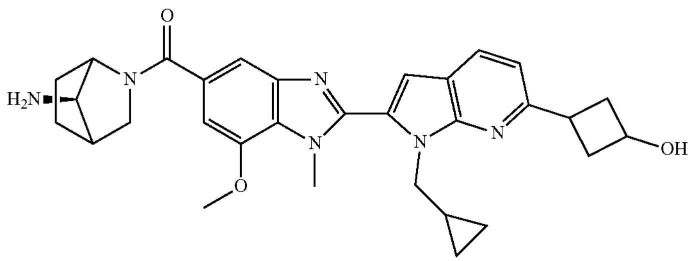 [SMILES: COc1cc(C(=O)N2CC3CCC2[C@@H]3N)cc2nc(-c3cc4ccc(C5CC(O)C5)nc4n3CC3CC3)n(C)c12] | (1s,3s)-3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)cyclobutan-1-ol | 541.0 | 3 | 0.65 |
| 437. | 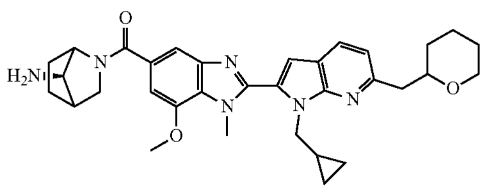 [SMILES: COc1cc(C(=O)N2CC3CCC2[C@@H]3N)cc2nc(-c3cc4ccc(CC5CCCCO5)nc4n3CC3CC3)n(C)c12] | (1R,4R,7R)-2-{2-[1-(cyclopropylmethyl)-6-{[(2R)-oxan-2-yl]methyl}-1H-pyrrolo[2,3-b]pyridin-2-yl]-7-methoxy-1-methyl-1H-1,3-benzodiazole-5-carbonyl}-2-azabicyclo[2.2.1]heptan-7-amine | 569.3 | 1 | 1.68 |
| 438. | 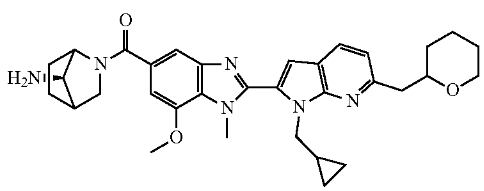 [SMILES: COc1cc(C(=O)N2CC3CCC2[C@@H]3N)cc2nc(-c3cc4ccc(CC5CCCCO5)nc4n3CC3CC3)n(C)c12] | (1R,4R,7R)-2-{2-[1-(cyclopropylmethyl)-6-{[(2R)-oxan-2-yl]methyl}-1H-pyrrolo[2,3-b]pyridin-2-yl]-7-methoxy-1-methyl-1H-1,3-benzodiazole-5-carbonyl}-2-azabicyclo[2.2.1]heptan-7-amine | 569.2 | 1 | 1.77 |
| 439. | 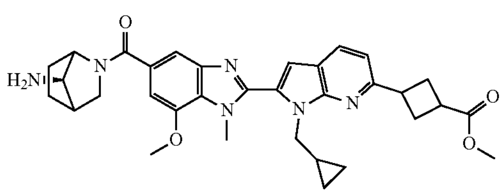 [SMILES: COC(=O)C1CC(c2ccc3cc(-c4nc5cc(C(=O)N6CC7CCC6[C@@H]7N)cc(OC)c5n4C)n(CC4CC4)c3n2)C1] | methyl 3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)cyclobutane-1-carboxylate | 583.4 | 2 | 1.49 |
| 440. | 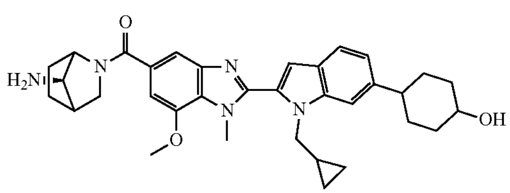 [SMILES: COc1cc(C(=O)N2CC3CCC2[C@@H]3N)cc2nc(-c3cc4ccc(C5CCC(O)CC5)cc4n3CC3CC3)n(C)c12] | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)cyclohexan-1-ol | 569.3 | 2 | 1.26 |

TABLE 10-continued

| Cmpd # | Structure | Name | Obs. MS Ion | HPLC Method IDs | RT (min) |
|---|---|---|---|---|---|
| 441. | 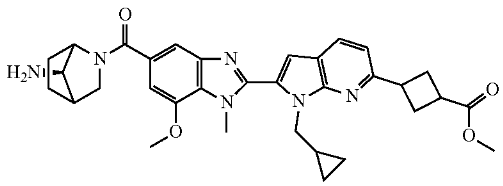 [SMILES: COC(=O)C1CC(c2ccc3cc(-c4nc5cc(C(=O)N6CC7CCC6[C@@H]7N)cc(OC)c5n4C)n(CC4CC4)c3n2)C1] | methyl (1s,3s)-3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)cyclobutane-1-carboxylate | 583.4 | 2 | 1.51 |
| 442. | 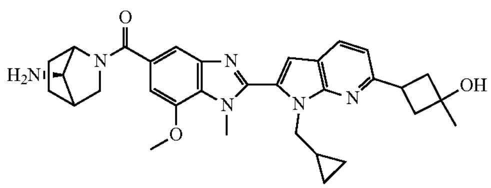 [SMILES: COc1cc(C(=O)N2CC3CCC2[C@@H]3N)cc2nc(-c3cc4ccc(C5CC(C)(O)C5)nc4n3CC3CC3)n(C)c12] | 3-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1-methylcyclobutan-1-ol | 555.2 | 2 | 1.23 |
| 443. | 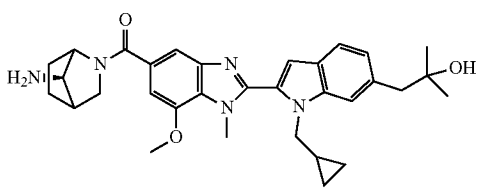 [SMILES: COc1cc(C(=O)N2CC3CCC2[C@@H]3N)cc2nc(-c3cc4ccc(CC(C)(C)O)cc4n3CC3CC3)n(C)c12] | 1-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-2-methylpropan-2-ol | 542.4 | 1 | 1.48 |
| 444. | 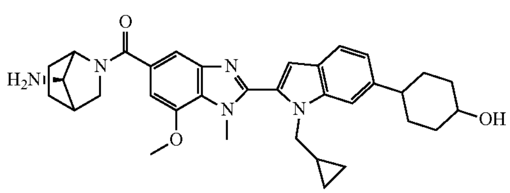 [SMILES: COc1cc(C(=O)N2CC3CCC2[C@@H]3N)cc2nc(-c3cc4ccc(C5CCC(O)CC5)cc4n3CC3CC3)n(C)c12] | 4-(2-{5-[(1R,4R,7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)cyclohexan-1-ol | 568.2 | 2 | 1.4 |

Other examples with experimental details are shown below for Examples 445-448.

Example 445

((3R,5R)-3-amino-5-fluoropiperidin-1-yl)(2-(1-(cyclopropylmethyl)-6-(1,1-difluoroethyl)-1H-pyrrolo[2,3-b]pyridin-2-yl)-7-methoxy-1-methyl-1H-benzo[d]imidazol-5-yl)methanone

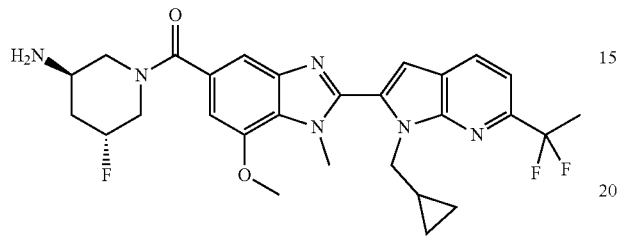

Example 445

Step A: methyl 2-(6-acetyl-1-(cyclopropylmethyl)-1H-pyrrolo[2,3-b]pyridin-2-yl)-7-methoxy-1-methyl-1H-benzo[d]imidazole-5-carboxylate

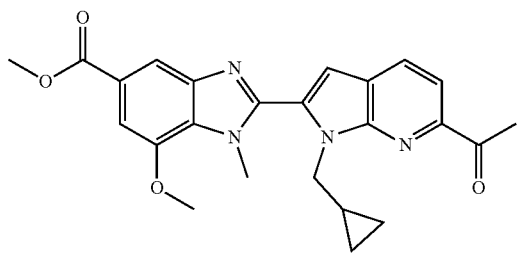 [SMILES: COC(=O)c1cc(OC)c2c(c1)nc(-c1cc3ccc(C(C)=O)nc3n1CC1CC1)n2C]

Example 445A

A mixture of methyl 2-(6-chloro-1-(cyclopropylmethyl)-1H-pyrrolo[2,3-b]pyridin-2-yl)-7-methoxy-1-methyl-1H-benzo[d]imidazole-5-carboxylate (890 mg, 2.095 mmol) [for this starting material see: WO 2017/0100594)], 1-ethoxyvinyltri-n-butyltin (0.856 mL, 2.51 mmol), xantphos (364 mg, 0.628 mmol) and Pd$_2$(dba)$_3$ (192 mg, 0.209 mmol) in degassed dioxane (10 mL) under nitrogen was stirred at 100° C. for 18 hours. The mixture cooled to rt. A solution of 1.0 M aqueous HCl (2.095 mL, 2.095 mmol) was added and the mixture was stirred at RT for 1 hours. The mixture was diluted with EtOAc (15 mL) and was washed with a solution of aqueous saturated sodium bicarbonate (2×15 mL). The organic layer was dried over sodium sulfate and concentrated. The resulting residue was subjected to ISCO flash chromatography (silica gel/hexane-EtOAc 100:0 to 0:100 gradient) to yield methyl 2-(6-acetyl-1-(cyclopropylmethyl)-1H-pyrrolo[2,3-b]pyridin-2-yl)-7-methoxy-1-methyl-1H-benzo[d]imidazole-5-carboxylate 445A (850 mg, 1.769 mmol, 84% yield) as light brown solid: LCMS (M+H)=433.4, retention time=1.06 min (Method 3).

Step B: methyl (E)-2-(1-(cyclopropylmethyl)-6-(1-(hydroxyimino)ethyl)-1H-pyrrolo[2,3-b]pyridin-2-yl)-7-methoxy-1-methyl-1H-benzo[d]imidazole-5-carboxylate

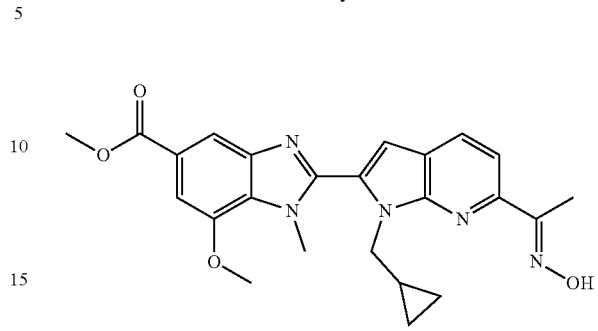

Example 445B

A mixture of methyl 2-(6-acetyl-1-(cyclopropylmethyl)-1H-pyrrolo[2,3-b]pyridin-2-yl)-7-methoxy-1-methyl-1H-benzo[d]imidazole-5-carboxylate 445A (400 mg, 0.925 mmol), hydroxylamine hydrochloride (70.7 mg, 1.017 mmol) in MeOH (12 mL) was stirred at 60° C. for 3 hours (J. Med. Chem. 2012, 55, 3364). The mixture was concentrated. The mixture was diluted with EtOAc (15 mL) and was washed with a solution of aqueous saturated sodium bicarbonate (2×15 mL). The organic layer was dried over sodium sulfate and concentrated to give crude methyl (E)-2-(1-(cyclopropylmethyl)-6-(1-(hydroxyimino)ethyl)-1H-pyrrolo[2,3-b]pyridin-2-yl)-7-methoxy-1-methyl-1H-benzo[d]imidazole-5-carboxylate 445B as off-white solid: LCMS (M+H)=448.5, retention time=0.95 min (Method 3), which was taken to next step.

Step C: methyl 2-(1-(cyclopropylmethyl)-6-(1,1-difluoroethyl)-1H-pyrrolo[2,3-b]pyridin-2-yl)-7-methoxy-1-methyl-1H-benzo[d]imidazole-5-carboxylate

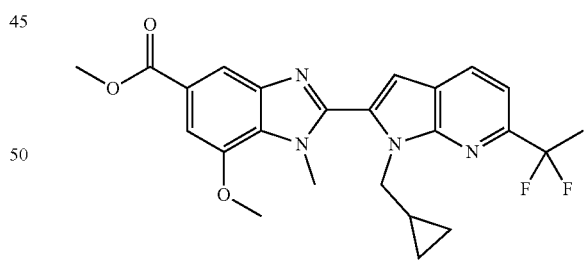

Example 445C

To a solution of methyl (E)-2-(1-(cyclopropylmethyl)-6-(1-(hydroxyimino)ethyl)-1H-pyrrolo[2,3-b]pyridin-2-yl)-7-methoxy-1-methyl-1H-benzo[d]imidazole-5-carboxylate 445B from above in DCM (5.0 mL) in a capped syringe tube at −78° C. under nitrogen was added 70% HF-pyridine (1310 mg, 9.25 mmol), the mixture was stirred at −78° C. for 15 min. A solution of tert-butyl nitrite (286 mg, 2.77 mmol) in DCM (5.0 mL) was added dropwise to the mixture, the reaction was stirred at −78° C. for 30 min. and rt for 1 hour.

The mixture was then added to sulfuric acid (1.0 mL) and ice water (200 g) and the mixture was stirred at rt for 30 min. The organic layer was collected and was washed with a solution of aqueous saturated sodium bicarbonate (35 mL). The organic layer was dried over sodium sulfate and concentrated. The resulting residue was subjected to ISCO flash chromatography (silica gel/hexane-EtOAc 100:0 to 50:50 gradient) to give methyl 2-(1-(cyclopropylmethyl)-6-(1,1-difluoroethyl)-1H-pyrrolo[2,3-b]pyridin-2-yl)-7-methoxy-1-methyl-1H-benzo[d]imidazole-5-carboxylate (92 mg, 0.192 mmol, 20.79% yield) 445C as white solid: ¹H NMR (499 MHz, chloroform-d) δ 8.23 (d, J=1.2 Hz, 1H), 8.09 (d, J=8.1 Hz, 1H), 7.56 (d, J=8.1 Hz, 1H), 7.52-7.47 (m, 1H), 6.84 (s, 1H), 4.55 (d, J=7.2 Hz, 2H), 4.18 (s, 3H), 4.09-4.06 (m, 3H), 3.99 (s, 3H), 2.16 (t, J=18.5 Hz, 3H), 1.22-1.12 (m, 1H), 0.39-0.31 (m, 2H), 0.23-0.17 (m, 2H); LCMS (M+H)=455.4, retention time=1.09 min (Method 3).

Step D: 2-(1-(cyclopropylmethyl)-6-(1,1-difluoroethyl)-1H-pyrrolo[2,3-b]pyridin-2-yl)-7-methoxy-1-methyl-1H-benzo[d]imidazole-5-carboxylic acid

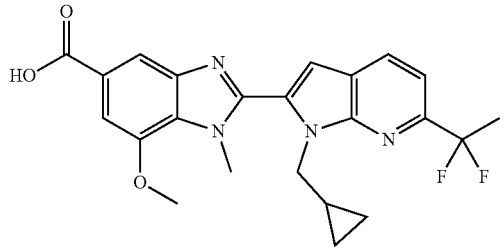 [SMILES: COc1cc(C(=O)O)cc2nc(-c3cc4ccc(C(C)(F)F)nc4n3CC3CC3)n(C)c12]

Example 445D

A mixture of methyl 2-(1-(cyclopropylmethyl)-6-(1,1-difluoroethyl)-1H-pyrrolo[2,3-b]pyridin-2-yl)-7-methoxy-1-methyl-1H-benzo[d]imidazole-5-carboxylate 445C (102 mg, 0.224 mmol) and 2.0 M aqueous lithium hydroxide (561 µl, 1.122 mmol) in THF (5.0 mL) was stirred at 50° C. for 18 hours. A solution of 1.0 M aqueous HCl (1.20 mL) was added and the mixture was concentrated. The mixture was extracted with EtOAc (2×15 mL) and the ethyl acetate layer was dried over sodium sulfate and concentrated to give crude 2-(1-(cyclopropylmethyl)-6-(1,1-difluoroethyl)-1H-pyrrolo[2,3-b]pyridin-2-yl)-7-methoxy-1-methyl-1H-benzo[d]imidazole-5-carboxylic acid 445D (101 mg, 0.218 mmol, 97% yield) as white solid: LCMS (M+H)=441.4, retention time=0.96 min (Method 3).

Example 445: ((3R,5R)-3-amino-5-fluoropiperidin-1-yl)(2-(1-(cyclopropylmethyl)-6-(1,1-difluoroethyl)-1H-pyrrolo[2,3-b]pyridin-2-yl)-7-methoxy-1-methyl-1H-benzo[d]imidazol-5-yl)methanone Example 445

A mixture of 2-(1-(cyclopropylmethyl)-6-(1,1-difluoroethyl)-1H-pyrrolo[2,3-b]pyridin-2-yl)-7-methoxy-1-methyl-1H-benzo[d]imidazole-5-carboxylic acid 445D (20 mg, 0.045 mmol), tert-butyl ((3R,5R)-5-fluoropiperidin-3-yl)carbamate (9.91 mg, 0.045 mmol), BOP (22.09 mg, 0.050 mmol) and TEA (31.6 µl, 0.227 mmol) in DMF (1.0 mL) was stirred at rt for 2 hours. The mixture was diluted with EtOAc (5 mL) and was washed with a solution of aqueous saturated sodium bicarbonate (2×5 mL). The organic layer was dried over sodium sulfate and concentrated to give crude tert-butyl ((3R,5R)-1-(2-(1-(cyclopropylmethyl)-6-(1,1-difluoroethyl)-1H-pyrrolo[2,3-b]pyridin-2-yl)-7-methoxy-1-methyl-1H-benzo[d]imidazole-5-carbonyl)-5-fluoropiperidin-3-yl)carbamate: LCMS (M+H)=641.6, retention time=1.00 min (Method 3), which was taken to next step. A mixture of tert-butyl ((3R,5R)-1-(2-(1-(cyclopropylmethyl)-6-(1,1-difluoroethyl)-1H-pyrrolo[2,3-b]pyridin-2-yl)-7-methoxy-1-methyl-1H-benzo[d]imidazole-5-carbonyl)-5-fluoropiperidin-3-yl)carbamate in DCM (1.0 mL) and TFA (1.0 mL) was stirred at rt for 30 min. The mixture was concentrated. The resulting residue was purified by prep-HPLC (Phenomenex, Luna 5 micron 30×250 mm, flow rate=30 ml/min., gradient=20% A to 100% B in 30 min., A=H2O/ACN/TFA(90:10:0.1), B=H2O/ACN/TFA (10:90:0.1)). The pure product fraction was loaded onto Strata-X-C 33 um cation mixed-mode polymer cartridge (0.30 g), the cartridge was washed with methanol (20 ml) and the product was eluted with 0.5 N NH₃ in methanol (5.0 mL). The NH₃ eluent was concentrated and the pure product was lyophilized with ACN/H2O (1:1, 10 mL) to yield ((3R,5R)-3-amino-5-fluoropiperidin-1-yl)(2-(1-(cyclopropylmethyl)-6-(1,1-difluoroethyl)-1H-pyrrolo[2,3-b]pyridin-2-yl)-7-methoxy-1-methyl-1H-benzo[d]imidazol-5-yl) methanone 445 (16.90 mg, 0.031 mmol, 67.5% yield) as white powder: ¹H NMR (499 MHz, METHANOL-d₄) δ 8.22 (d, J=8.1 Hz, 1H), 7.55 (d, J=8.2 Hz, 1H), 7.44 (s, 1H), 7.05 (s, 1H), 7.02-6.95 (m, 1H), 4.82-4.64 (m, 1H), 4.48 (d, J=7.2 Hz, 2H), 4.06 (s, 7H), 3.43-3.35 (m, 2H), 3.26-3.06 (m, 1H), 3.01-2.53 (m, 1H), 2.45-2.28 (m, 11H), 2.12 (t, J=18.5 Hz, 3H), 1.72-1.50 (m, 11H), 1.05-0.97 (m, 1H), 0.38-0.30 (m, 2H), 0.14-0.04 (m, 2H); LCMS (M+H)=541.5, retention time=0.83 min (Method 3).

Example 446

((3R,5R)-3-amino-5-fluoropiperidin-1-yl)(2-(6-(1-cyclobutyl-1-hydroxyethyl)-1-(cyclopropylmethyl)-1H-pyrrolo[2,3-b]pyridin-2-yl)-7-methoxy-1-methyl-1H-benzo[d]imidazol-5-yl)methanone

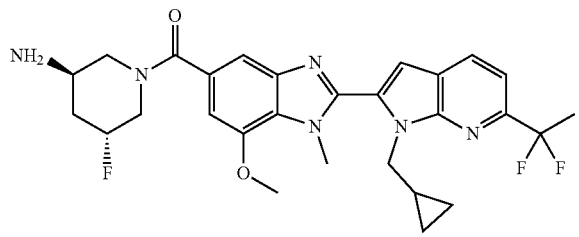 [SMILES: COc1cc(C(=O)N2C[C@H](N)C[C@@H](F)C2)cc2nc(-c3cc4ccc(C(C)(F)F)nc4n3CC3CC3)n(C)c12]

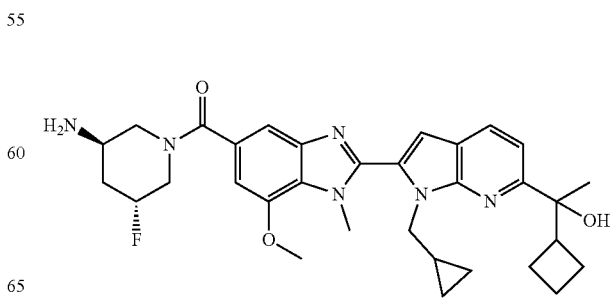

Example 446

Step A: tert-butyl ((3R,5R)-1-(2-(6-acetyl-1-(cyclopropylmethyl)-1H-pyrrolo[2,3-b]pyridin-2-yl)-7-methoxy-1-methyl-1H-benzo[d]imidazole-5-carbonyl)-5-fluoropiperidin-3-yl)carbamate

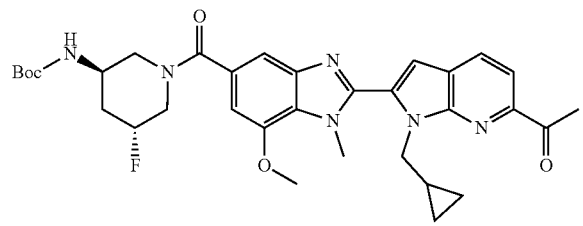 [SMILES: COc1cc(C(=O)N2C[C@H](F)C[C@@H](NC(=O)OC(C)(C)C)C2)cc2nc(-c3cc4ccc(C(C)=O)nc4n3CC3CC3)n(C)c12]

Example 446A tert-butyl ((3R,5R)-1-(2-(6-acetyl-1-(cyclopropylmethyl)-1H-pyrrolo[2,3-b]pyridin-2-yl)-7-methoxy-1-methyl-1H-benzo[d]imidazole-5-carbonyl)-5-fluoropiperidin-3-yl)carbamate was prepared using the procedure of example 445, step A, but starting with tert-butyl ((3R,5R)-1-(2-(6-chloro-1-(cyclopropylmethyl)-1H-pyrrolo[2,3-b]pyridin-2-yl)-7-methoxy-1-methyl-1H-benzo[d]imidazole-5-carbonyl)-5-fluoropiperidin-3-yl)carbamate to give tert-butyl ((3R,5R)-1-(2-(6-acetyl-1-(cyclopropylmethyl)-1H-pyrrolo[2,3-b]pyridin-2-yl)-7-methoxy-1-methyl-1H-benzo[d]imidazole-5-carbonyl)-5-fluoropiperidin-3-yl)carbamate 446A: LCMS (M+H)=619.4, retention time=0.89 min (Method 3).

Example 446: ((3R,5R)-3-amino-5-fluoropiperidin-1-yl)(2-(6-(1-cyclobutyl-1-hydroxyethyl)-1-(cyclopropylmethyl)-1H-pyrrolo[2,3-b]pyridin-2-yl)-7-methoxy-1-methyl-1H-benzo[d]imidazol-5-yl)methanone

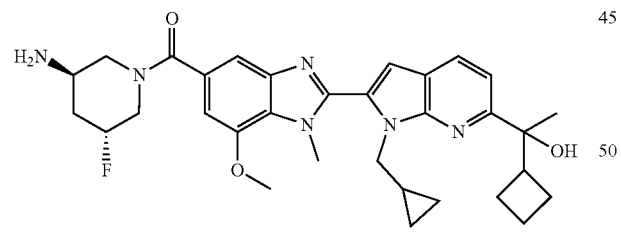

Example 446

To a solution of tert-butyl ((3R,5R)-1-(2-(6-acetyl-1-(cyclopropylmethyl)-1H-pyrrolo[2,3-b]pyridin-2-yl)-7-methoxy-1-methyl-1H-benzo[d]imidazole-5-carbonyl)-5-fluoropiperidin-3-yl)carbamate 446A (20 mg, 0.032 mmol) in THF (1.0 mL) was added a solution of 0.5 M cyclobutylmagnesium bromide in 2-methyltetrahydrofuran (194 µl, 0.097 mmol), the mixture was stirred at rt for 60 min. The mixture was added to a solution of 10% aqueous ammonium chloride solution (10 mL). The mixture was extracted with EtOAc (15 mL). The organic layer was dried over sodium sulfate and concentrated to give crude tert-butyl ((3R,5R)-1-(2-(6-(1-cyclobutyl-1-hydroxyethyl)-1-(cyclopropylmethyl)-1H-pyrrolo[2,3-b]pyridin-2-yl)-7-methoxy-1-methyl-1H-benzo[d]imidazole-5-carbonyl)-5-fluoropiperidin-3-yl)carbamate: LCMS (M+H)=675.4, retention time=0.94 min (Method 3), which was taken to next step.

A mixture of tert-butyl ((3R,5R)-1-(2-(6-(1-cyclobutyl-1-hydroxyethyl)-1-(cyclopropylmethyl)-1H-pyrrolo[2,3-b]pyridin-2-yl)-7-methoxy-1-methyl-1H-benzo[d]imidazole-5-carbonyl)-5-fluoropiperidin-3-yl)carbamate in DCM (1.0 mL) and TFA (0.40 mL) was stirred at rt for 30 min. The mixture was concentrated. The resulting residue was purified by prep-HPLC (Phenomenex, Luna 5 micron 30×250 mm, flow rate=30 ml/min., gradient=20% A to 100% B in 30 min., A=H2O/ACN/TFA(90:10:0.1), B=H2O/ACN/TFA (10:90:0.1)). The pure product fraction was loaded onto Strata-X-C 33 um cation mixed-mode polymer cartridge (0.30 g), the cartridge was washed with methanol (20 ml) and the product was then eluted with 0.5 N NH3 in methanol (5.0 mL). The NH3 eluent was concentrated and the product was lyophilized with ACN/H2O (1:1, 5 mL) to give ((3R,5R)-3-amino-5-fluoropiperidin-1-yl)(2-(6-(1-cyclobutyl-1-hydroxyethyl)-1-(cyclopropylmethyl)-1H-pyrrolo[2,3-b]pyridin-2-yl)-7-methoxy-1-methyl-1H-benzo[d]imidazol-5-yl)methanone 446 (8.19 mg, 0.014 mmol, 41.9% yield) as white powder: $^1$H NMR (499 MHz, methanol-$d_4$) δ 8.08 (d, J=8.2 Hz, 1H), 7.41 (d, J=8.3 Hz, 2H), 6.99-6.95 (m, 2H), 4.83-4.63 (m, 1H), 4.48 (br s, 2H), 4.26-3.96 (m, 7H), 3.47-3.35 (m, 1H), 3.24-3.15 (m, 1H), 3.03-2.92 (m, 1H), 2.79-2.53 (m, 1H), 2.46-2.14 (m, 2H), 2.05-1.93 (m, 2H), 1.88-1.75 (m, 1H), 1.74-1.46 (m, 7H), 1.03-0.91 (m, 1H), 0.33 (br d, J=8.1 Hz, 2H), 0.07 (br d, J=4.1 Hz, 2H); LCMS (M+H)=575.4, retention time=0.91 min (Method 3).

Example 447

((3R,5R)-3-amino-5-fluoropiperidin-1-yl)(2-(1-(cyclopropylmethyl)-6-(1,3-difluoro-2-hydroxypropan-2-yl)-1H-pyrrolo[2,3-b]pyridin-2-yl)-7-methoxy-1-methyl-1H-benzo[d]imidazol-5-yl)methanone

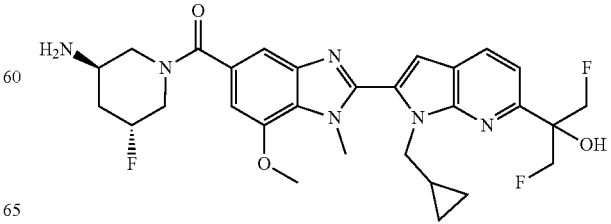

Example 447

Step A: tert-butyl ((3R,5R)-1-(2-(1-(cyclopropylmethyl)-6-(1,3-difluoro-2-hydroxypropan-2-yl)-1H-pyrrolo[2,3-b]pyridin-2-yl)-7-methoxy-1-methyl-1H-benzo[d]imidazole-5-carbonyl)-5-fluoropiperidin-3-yl)carbamate

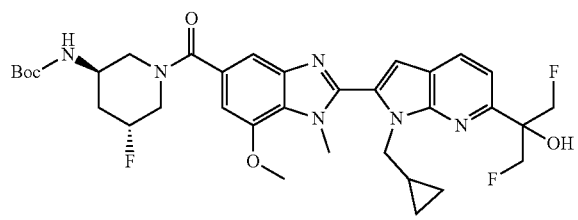 [SMILES: COc1cc(C(=O)N2C[C@H](F)C[C@@H](NC(=O)OC(C)(C)C)C2)cc2nc(-c3cc4ccc(C(O)(CF)CF)nc4n3CC3CC3)n(C)c12]

Example 447A

To a solution of tert-butyl ((3R,5R)-1-(2-(6-bromo-1-(cyclopropylmethyl)-1H-pyrrolo[2,3-b]pyridin-2-yl)-7-methoxy-1-methyl-1H-benzo[d]imidazole-5-carbonyl)-5-fluoropiperidin-3-yl)carbamate (85 mg, 0.130 mmol) [made in a similar fashion to Intermediate 2 but starting with ethyl 6-bromo-1H-pyrrolo[2,3-b]pyridine-2-carboxylate] in anhydrous ethyl ether (10 mL) and anhydrous THF (3.0 mL) under nitrogen at −78° C. was added a solution of 1.60 M n-butyllithium in hexane (203 μl, 0.324 mmol), the mixture was stirred at −78° C. for 30 min. 1,3-difluoropropan-2-one (14.63 mg, 0.156 mmol) was then added to the mixture at −78° C., the mixture was stirred at −78° C. for 10 min and rt for 1 hours. The mixture was diluted with EtOAc (15 mL) and was washed with a solution of aqueous saturated sodium bicarbonate (2×15 mL). The organic layer was dried over sodium sulfate and concentrated. The resulting residue was subjected to ISCO flash chromatography (silica gel/hexane-5% MeOH/EtOAc 100:0 to 0:100 gradient) to give tert-butyl ((3R,5R)-1-(2-(1-(cyclopropylmethyl)-6-(1,3-difluoro-2-hydroxypropan-2-yl)-1H-pyrrolo[2,3-b]pyridin-2-yl)-7-methoxy-1-methyl-1H-benzo[d]imidazole-5-carbonyl)-5-fluoropiperidin-3-yl)carbamate 447A (35 mg, 0.052 mmol, 40.2% yield): LCMS (M+H)=671.5, retention time=0.86 min (Method 3).

Example 447: ((3R,5R)-3-amino-5-fluoropiperidin-1-yl)(2-(1-(cyclopropylmethyl)-6-(1,3-difluoro-2-hydroxypropan-2-yl)-1H-pyrrolo[2,3-b]pyridin-2-yl)-7-methoxy-1-methyl-1H-benzo[d]imidazol-5-yl)methanone

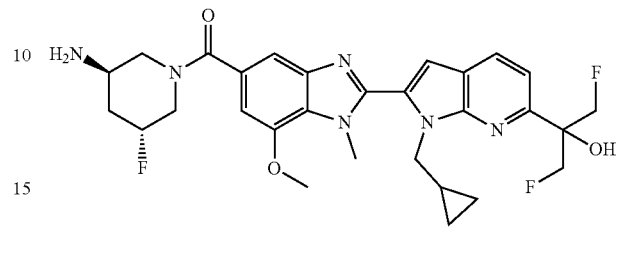

Example 447

A mixture of tert-butyl ((3R,5R)-1-(2-(1-(cyclopropylmethyl)-6-(1,3-difluoro-2-hydroxypropan-2-yl)-1H-pyrrolo[2,3-b]pyridin-2-yl)-7-methoxy-1-methyl-1H-benzo[d]imidazole-5-carbonyl)-5-fluoropiperidin-3-yl)carbamate 447A (35 mg, 0.052 mmol, 40.2% yield) in DCM (1.0 mL) and TFA (1.0 mL) was stirred at rt for 30 min. The solution was concentrated and the resulting residue was purified by prep-HPLC (Phenomenex, Luna 5 micron 30×250 mm, flow rate=30 ml/min., gradient=20% A to 100% B in 30 min., A=H2O/ACN/TFA(90:10:0.1), B=H2O/ACN/TFA(10:90:0.1)). The pure product fraction was loaded onto Strata-X-C 33 um cation mixed-mode polymer cartridge (0.30 g), the cartridge was washed with methanol (20 ml) and then the product was eluted with 0.5 N $NH_3$ in methanol (5.0 mL). The product $NH_3$ eluent was concentrated and the product was lyophilized with ACN/H2O (1:1, 5 mL) to give ((3R,5R)-3-amino-5-fluoropiperidin-1-yl)(2-(1-(cyclopropylmethyl)-6-(1,3-difluoro-2-hydroxypropan-2-yl)-1H-pyrrolo[2,3-b]pyridin-2-yl)-7-methoxy-1-methyl-1H-benzo[d]imidazol-5-yl)methanone 447 (16.30 mg, 0.029 mmol, 22.03% yield): $^1$H NMR (500 MHz, DMSO-$d_6$) δ 7.97 (d, J=8.2 Hz, 1H), 7.36 (d, J=8.2 Hz, 1H), 7.13 (s, 1H), 6.87 (s, 1H), 6.66 (s, 1H), 4.92-4.48 (m, 6H), 4.44-4.17 (m, 3H), 4.01-3.62 (m, 6H), 2.79-2.43 (m, 2H), 2.04-1.88 (m, 1H), 1.47-1.16 (m, 1H), 1.08-0.87 (m, 2H), 0.19-0.10 (m, 4H); LCMS (M+H)=571.3, retention time=1.39 min (Method 2).

Example 448

2-(4-(2-(5-(((1R,4R,7R)-7-amino-2-azabicyclo[2.2.1]heptane-2-carbonyl)-7-methoxy-1-methyl-1H-benzo[d]imidazol-2-yl)-1-(cyclopropylmethyl)-1H-pyrrolo[2,3-b]pyridin-6-yl)phenoxy)acetamide

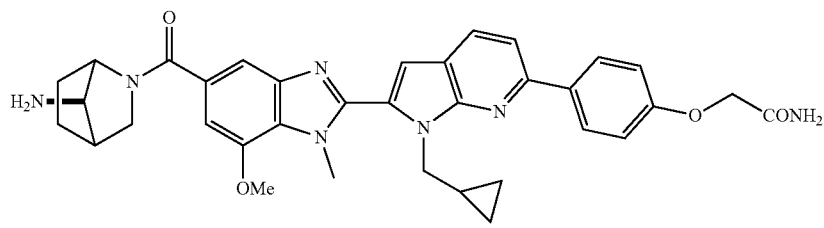 [SMILES: COc1cc(C(=O)N2CC3CCC2[C@@H]3N)cc2nc(-c3cc4ccc(-c5ccc(OCC(N)=O)cc5)nc4n3CC3CC3)n(C)c12]

Example 448

A mixture of of (((1R,4R,7R)-7-amino-2-azabicyclo[2.2.1]heptan-2-yl)(2-(6-chloro-1-(cyclopropylmethyl)-1H-pyrrolo[2,3-b]pyridin-2-yl)-7-methoxy-1-methyl-1H-benzo[d]imidazol-5-yl)methanone (1.5 g, 2.495 mmol), 4,4,4',4',5,5,5',5'-octamethyl-2,2'-bi(1,3,2-dioxaborolane) (0.760 g, 2.99 mmol), and potassium acetate (0.612 g, 6.24 mmol) in dioxane (12 ml) in a 2 dr vial was sonicated and treated with 1,1'-bis(diphenylphosphino)ferrocene-palladium(II)dichloride dichloromethane complex (0.102 g, 0.125 mmol) and the vial was capped. This reaction mixture was made anaerobic by a pump/backfill with nitrogen cycle (5×). It was set to stir at 90° C. for 5 h and the starting material was found to be consumed. The reaction mixture was evaporated and dried in vacuo. The resulting brown solid was used or the next step. A portion of this material (45 mg, 0.047 mmol), 2-(4-bromophenoxy)acetamide (13.08 mg, 0.057 mmol), sodium carbonate, 2N in water (0.071 mL, 0.142 mmol) and 1,1'-bis(diphenylphosphino)ferrocene-palladium(II)dichloride dichloromethane complex (3.87 mg, 4.74 µmol) in DMF (1 mL). The vial was capped and the reaction mixture was made anaerobic by a pump/backfill with nitrogen cycle (5×). The reaction was stirred at 70° C. for overnight. After cooling to rt, the solution was diluted with DMF, filtered and purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 11% B, 11-51% B over 20 minutes, then a 4-minute hold at 100% B; Flow Rate: 20 mL/min; Column Temperature: 25 C. Fraction collection was triggered by product MS signals. Fractions containing the desired product were combined and dried via centrifugal evaporation. The purified product was then diluted with DMF, treated with Si-Pyridine resin and shaken for a minimum of 2 h. The resulting mixture was filtered and dried via centrifugal evaporation to give 2-(4-(2-(5-(((1R,4R,7R)-7-amino-2-azabicyclo[2.2.1]heptane-2-carbonyl)-7-methoxy-1-methyl-1H-benzo[d]imidazol-2-yl)-1-(cyclopropylmethyl)-1H-pyrrolo[2,3-b]pyridin-6-yl)phenoxy)acetamide 448 (20.6 mg): $^1$H NMR (500 MHz, DMSO-$d_6$) δ 8.17-8.13 (m, 3H), 7.95-7.92 (m, 1H), 7.78-7.74 (m, 1H), 7.62-7.53 (m, 2H), 7.44-7.40 (m, 1H), 7.11-7.08 (m, 2H), 7.08-7.06 (m, 1H), 7.02-6.94 (m, 1H), 4.57-4.52 (m, 2H), 4.52-4.50 (m, 2H), 4.18-4.12 (m, 3H), 4.03-3.95 (m, 3H), 3.83-3.71 (m, 1H), 3.66-3.54 (m, 1H), 3.53-3.44 (m, 1H), 3.22-3.15 (m, 1H), 2.69-2.57 (m, 1H), 2.02-1.85 (m, 3H), 1.74-1.59 (m, 1H), 1.28-1.11 (m, 2H), 0.35-0.29 (m, 2H), 0.20 (br s, 2H); LCMS (M+H)=620.0, retention time=1.58 min (Method 1).

From the methods above, the following compounds were synthesized.

| # | Structure | Name | Obs. MS Ion | HPLC Method ID | RT |
|---|---|---|---|---|---|
| 449. | 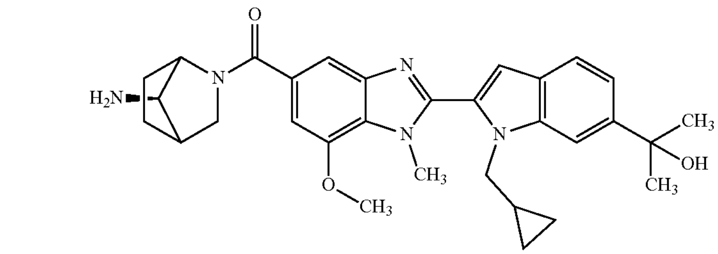 [SMILES: COc1cc(C(=O)N2CC3CCC2[C@@H]3N)cc2nc(-c3cc4ccc(C(C)(C)O)cc4n3CC3CC3)n(C)c12] | 2-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)propan-2-ol | 528.1 | 2 | 1.31 |
| 450. | 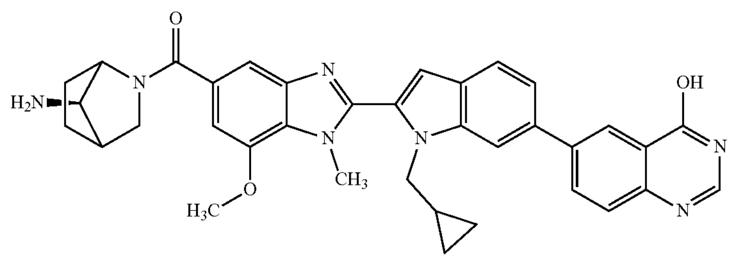 [SMILES: COc1cc(C(=O)N2CC3CCC2[C@@H]3N)cc2nc(-c3cc4ccc(-c5ccc6ncnc(O)c6c5)cc4n3CC3CC3)n(C)c12] | 6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)quinazolin-4-ol | 614.2 | 2 | 1.2 |
| 451. | 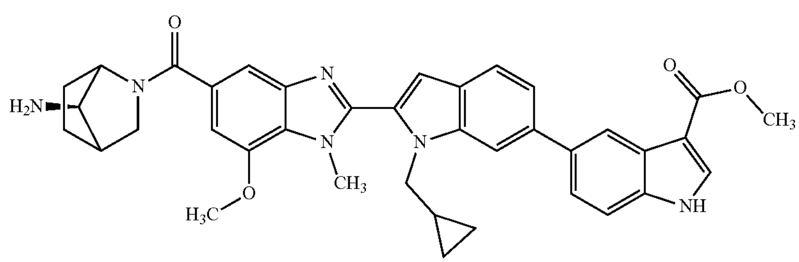 [SMILES: COC(=O)c1c[nH]c2ccc(-c3ccc4cc(-c5nc6cc(C(=O)N7CC8CCC7[C@@H]8N)cc(OC)c6n5C)n(CC5CC5)c4c3)cc12] | methyl 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-1H-pyrrolo[2,3-b]pyridine-3-carboxylate | 644.2 | 1 | 1.62 |

| # | Structure | Name | Obs. MS Ion | HPLC Method ID | RT |
|---|---|---|---|---|---|
| 452. | 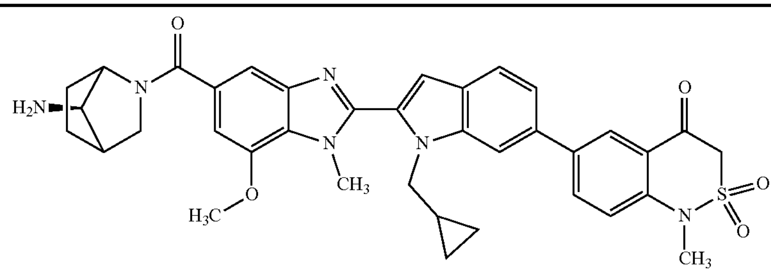 | 6-(2-{5-[(7R)-7-amino-2-azabicyclo[2.2.1]heptane-2-carbonyl]-7-methoxy-1-methyl-1H-benzo[d]imidazol-2-yl}-1-(cyclopropylmethyl)-1H-indol-6-yl)-1-methyl-1H-benzo[c][1,2]thiazin-4(3H)-one 2,2-dioxide | 679 | 1 | 1.76 |
| 453. | 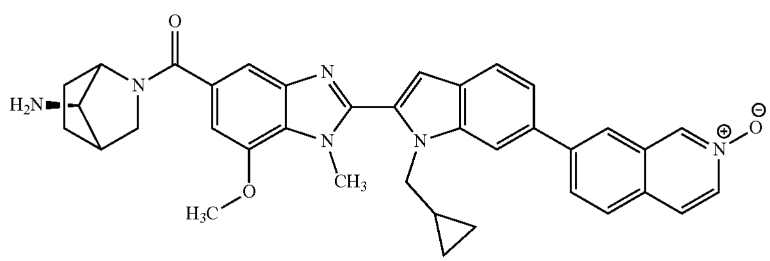 [SMILES: COc1cc(C(=O)N2CC3CCC2[C@@H]3N)cc2nc(-c3cc4ccc(-c5ccc6cc[n+]([O-])cc6c5)cc4n3CC3CC3)n(C)c12] | 7-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)isoquinolin-2-ium-2-olate | 613.1 | 1 | 1.43 |
| 454. | 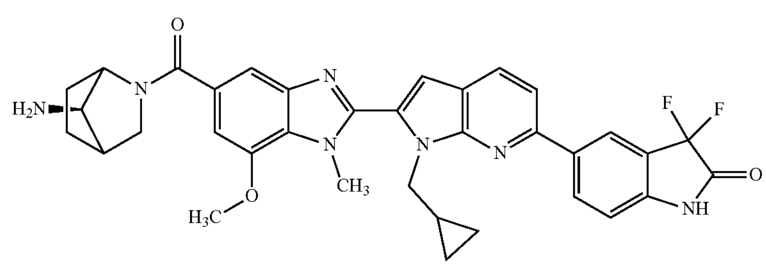 [SMILES: COc1cc(C(=O)N2CC3CCC2[C@@H]3N)cc2nc(-c3cc4ccc(-c5ccc6c(c5)C(F)(F)C(=O)N6)nc4n3CC3CC3)n(C)c12] | 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-3,3-difluoro-2,3-dihydro-1H-indol-2-one | 638.3 | 2 | 1.51 |

| # | Structure | Name | Obs. MS Ion | HPLC Method ID | RT |
|---|---|---|---|---|---|
| 455. | 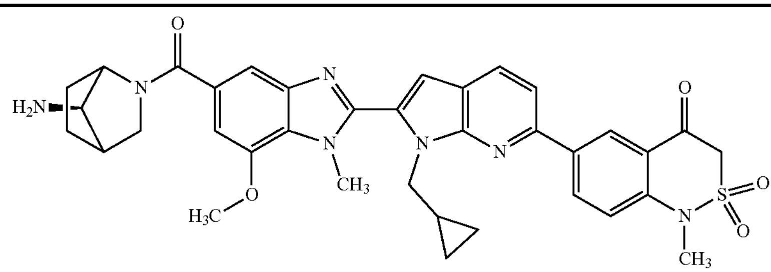 | 6-(2-(5-((7R)-7-amino-2-azabicyclo[2.2.1]heptane-2-carbonyl)-7-methoxy-1-methyl-1H-benzo[d]imidazol-2-yl)-1-(cyclopropylmethyl)-1H-pyrrolo[2,3-b]pyridin-6-yl)-1-methyl-1H-benzo[c][1,2]thiazin-4(3H)-one 2,2-dioxide | 680.4 | 1 | 1.79 |
| 456. | 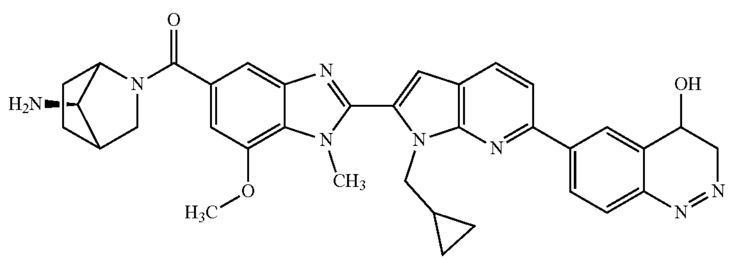 [SMILES: COc1cc(C(=O)N2CC3CCC2[C@@H]3N)cc2nc(-c3cc4ccc(-c5ccc6c(c5)C(O)CN=N6)nc4n3CC3CC3)n(C)c12] | 6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)cinnolin-4-ol | 615.1 | 1 | 1.41 |
| 457. | 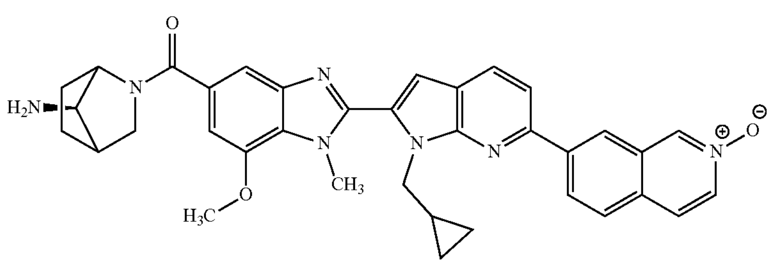 [SMILES: COc1cc(C(=O)N2CC3CCC2[C@@H]3N)cc2nc(-c3cc4ccc(-c5ccc6cc[n+](O)cc6c5)nc4n3CC3CC3)n(C)c12] | 7-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)isoquinolin-2-ium-2-olate | 614.4 | 2 | 1.21 |

| # | Structure | Name | Obs. MS Ion | HPLC Method ID | RT |
|---|---|---|---|---|---|
| 458. | 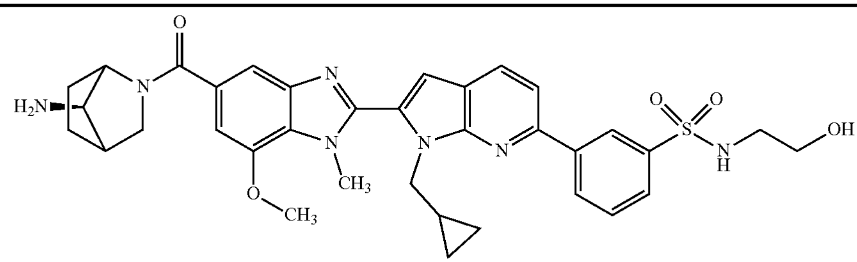 | 5-[3-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]-2-hydroxyethane-1-sulfonamido | 670.1 | 2 | 1.39 |
| 459. | 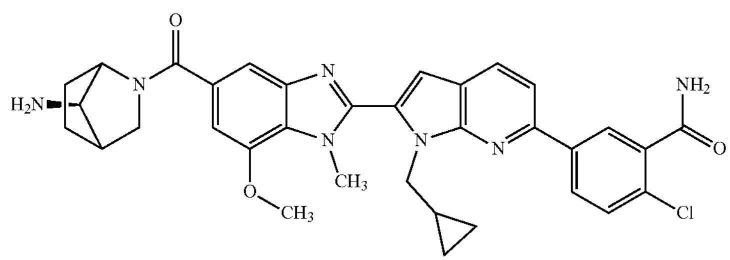 [SMILES: COc1cc(C(=O)N2CC3CCC2[C@@H]3N)cc2nc(-c3cc4ccc(-c5ccc(F)c(C(N)=O)c5)nc4n3CC3CC3)n(C)c12] | 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-chlorobenzamide | 624.3 | 2 | 1.33 |
| 460. | 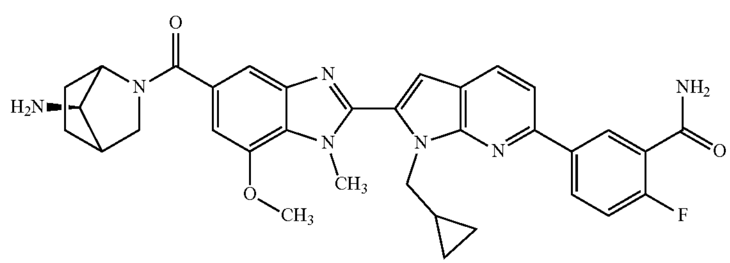 | 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-fluorobenzamide | 608.2 | 2 | 1.29 |

| # | Structure | Name | Obs. MS Ion | HPLC Method ID | RT |
|---|---|---|---|---|---|
| 461. | 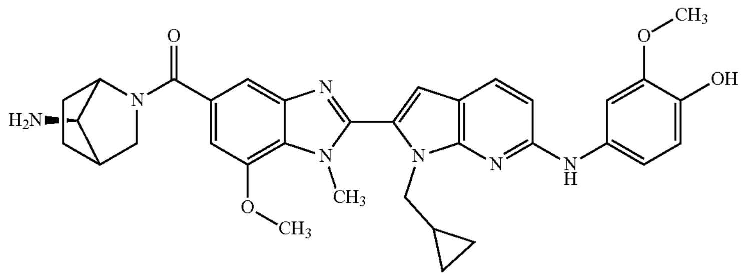 [SMILES: COc1cc(Nc2ccc3cc(-c4nc5cc(C(=O)N6CC7CCC6[C@@H]7N)cc(OC)c5n4C)n(CC4CC4)c3n2)ccc1O] | 4-[(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)amino]-2-methoxyphenol | 608.1 | 2 | 1.21 |
| 462. | 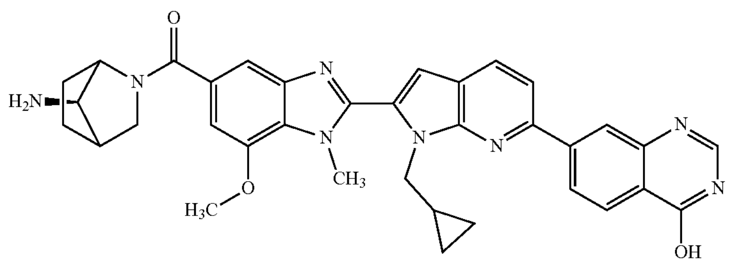 [SMILES: COc1cc(C(=O)N2CC3CCC2[C@@H]3N)cc2nc(-c3cc4ccc(-c5ccc6c(O)ncnc6c5)nc4n3CC3CC3)n(C)c12] | 7-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)quinazolin-4-ol | 615 | 2 | 1.29 |
| 463. | 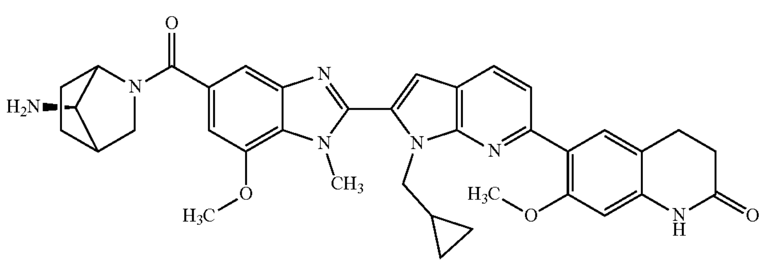 [SMILES: COc1cc2c(cc1-c1ccc3cc(-c4nc5cc(C(=O)N6CC7CCC6[C@@H]7N)cc(OC)c5n4C)n(CC4CC4)c3n1)CCC(=O)N2] | 6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-7-methoxy-1,2,3,4-tetrahydroquinolin-2-one | 646.4 | 1 | 1.53 |

-continued

| # | Structure | Name | Obs. MS Ion | HPLC Method ID | RT |
|---|---|---|---|---|---|
| 464. | 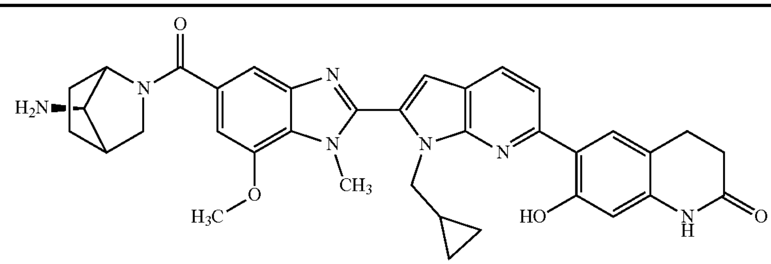 | 6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-7-hydroxy-1,2,3,4-tetrahydroquinolin-2-one | 632.4 | 2 | 1.37 |
| 465. | 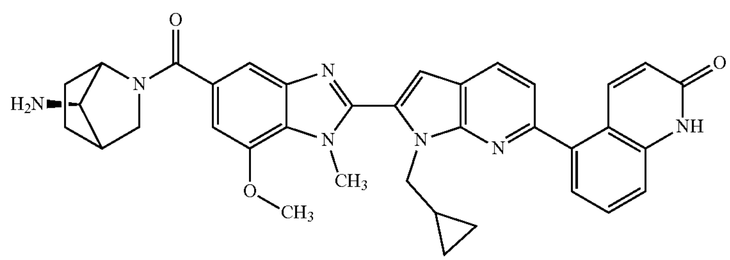 [SMILES: COc1cc(C(=O)N2CC3CCC2[C@@H]3N)cc2nc(-c3cc4ccc(-c5cccc6[nH]c(=O)ccc56)nc4n3CC3CC3)n(C)c12] | 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1,2-dihydroquinolin-2-one | 614 | 1 | 1.56 |
| 466. | 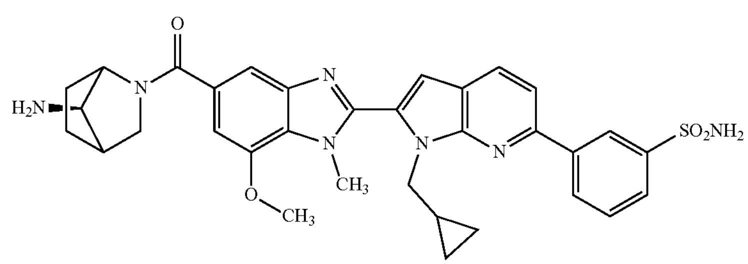 [SMILES: COc1cc(C(=O)N2CC3CCC2[C@@H]3N)cc2nc(-c3cc4ccc(-c5cccc(S(N)(=O)=O)c5)nc4n3CC3CC3)n(C)c12] | 3-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)benzene-1-sulfonamide | 626.4 | 1 | 1.49 |

| # | Structure | Name | Obs. MS Ion | HPLC Method ID | RT |
|---|---|---|---|---|---|
| 467. | 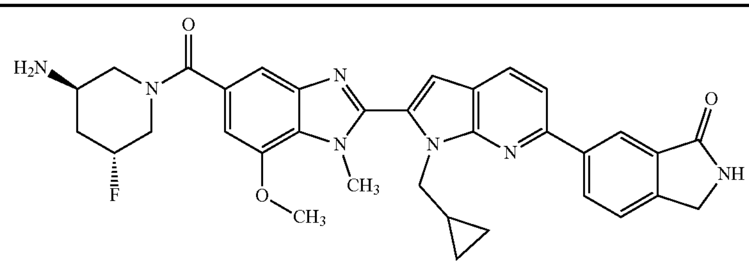 | 6-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)-2,3-dihydro-1H-isoindol-1-one | 606.9 | 1 | 1.62 |
| 468. | 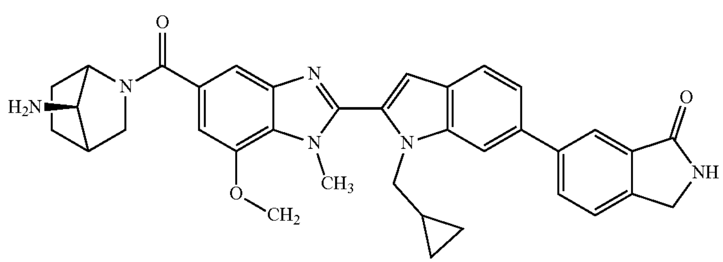 [SMILES: COc1cc(C(=O)N2CC3CCC2[C@@H]3N)cc2nc(-c3cc4ccc(-c5ccc6c(c5)C(=O)NC6)cc4n3CC3CC3)n(C)c12] | 6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-2,3-dihydro-1H-isoindol-1-one | 601.5 | 2 | 1.3 |
| 469. | 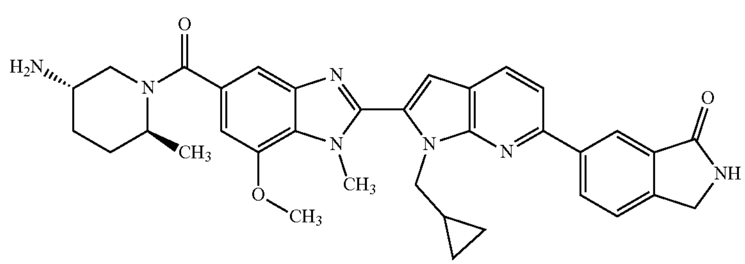 [SMILES: COc1cc(C(=O)N2C[C@@H](N)CC[C@@H]2C)cc2nc(-c3cc4ccc(-c5ccc6c(c5)C(=O)NC6)nc4n3CC3CC3)n(C)c12] | 6-(2-{5-[(2S,5R)-5-amino-2-methylpiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2,3-dihydro-1H-isoindol-1-one | 604.4 | 1 | 1.44 |

| # | Structure | Name | Obs. MS Ion | HPLC Method ID | RT |
|---|---|---|---|---|---|
| 470. | 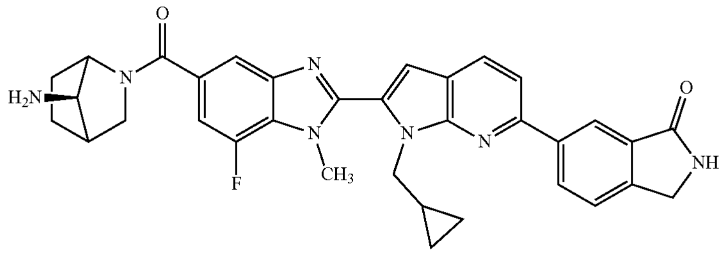 [SMILES: Cn1c(-c2cc3ccc(-c4ccc5c(c4)C(=O)NC5)nc3n2CC2CC2)nc2cc(C(=O)N3CC4CCC3[C@@H]4N)cc(F)c21] | 6-(2-{5-[(7R)-7-amino-2-azabicyclo[2.2.1]heptane-2-carbonyl]-7-fluoro-1-methyl-1H-1,3-benzodiazol-2-yl}-1-(cyclopropylmethyl)-1H-pyrrolo[2,3-b]pyridin-6-yl)-2,3-dihydro-1H-isoindol-1-one | 590.4 | 2 | 1.33 |
| 471. | 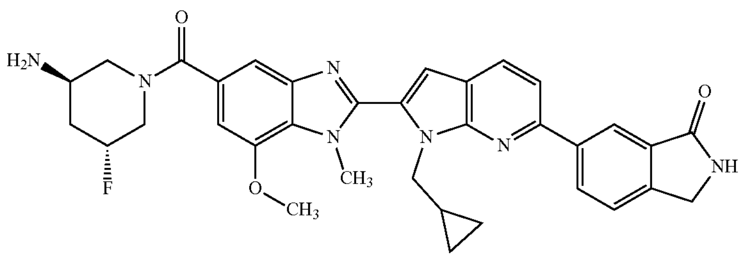 [SMILES: COc1cc(C(=O)N2C[C@H](N)C[C@@H](F)C2)cc2nc(-c3cc4ccc(-c5ccc6c(c5)C(=O)NC6)nc4n3CC3CC3)n(C)c12] | 6-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2,3-dihydro-1H-isoindol-1-one | 608.2 | 2 | 1.43 |
| 472. | 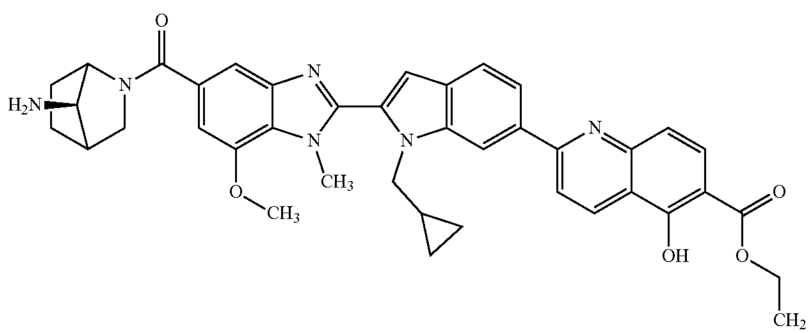 [SMILES: CCOC(=O)c1ccc2nc(-c3ccc4cc(-c5nc6cc(C(=O)N7CC8CCC7[C@@H]8N)cc(OC)c6n5C)n(CC5CC5)c4c3)ccc2c1O] | ethyl 7-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-4-hydroxyquinoline-3-carboxylate | 685.2 | 2 | 1.45 |

| # | Structure | Name | Obs. MS Ion | HPLC Method ID | RT |
|---|---|---|---|---|---|
| 473. | 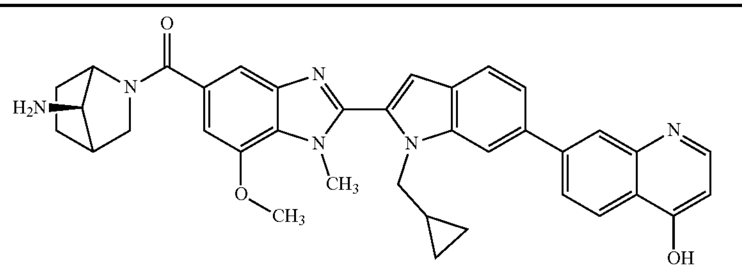 | 7-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)quinolin-4-ol | 613.3 | 1 | 1.4 |
| 474. | 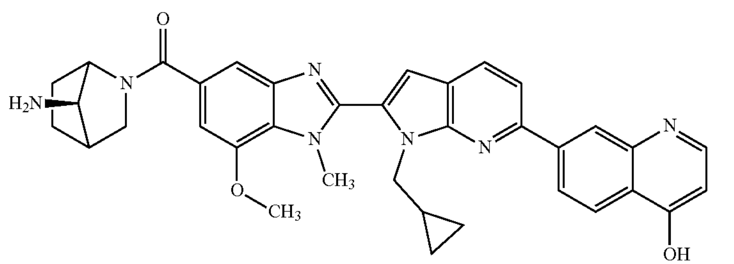 [SMILES: COc1cc(C(=O)N2CC3CCC2[C@@H]3N)cc2nc(-c3cc4ccc(-c5ccc6c(O)ccnc6c5)nc4n3CC3CC3)n(C)c12] | 7-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)quinolin-4-ol | 614.1 | 1 | 1.35 |
| 475. | 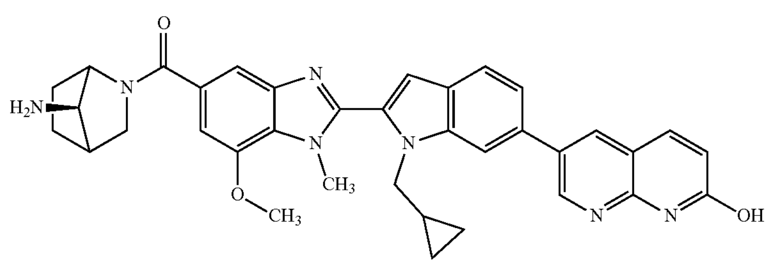 [SMILES: COc1cc(C(=O)N2CC3CCC2[C@@H]3N)cc2nc(-c3cc4ccc(-c5cnc6nc(O)ccc6c5)cc4n3CC3CC3)n(C)c12] | 6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-1,8-naphthyridin-2-ol | 614.3 | 2 | 1.3 |

-continued

| # | Structure | Name | Obs. MS Ion | HPLC Method ID | RT |
|---|---|---|---|---|---|
| 476. | 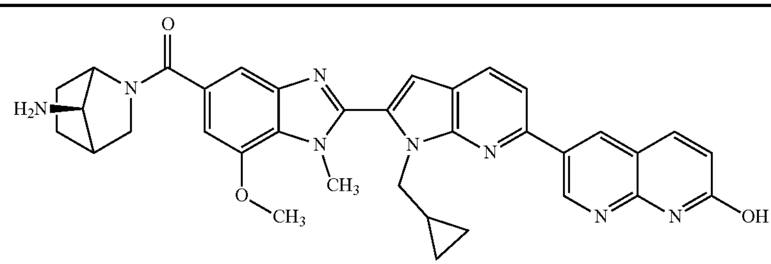 | 6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1,8-naphthyridin-2-ol | 615.4 | 2 | 1.19 |
| 477. | 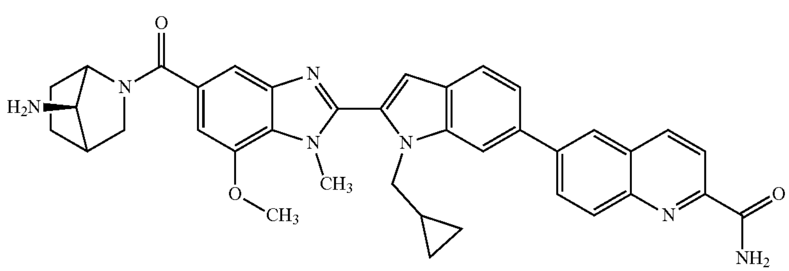 [SMILES: COc1cc(C(=O)N2CC3CCC2[C@@H]3N)cc2nc(-c3cc4ccc(-c5ccc6nc(C(N)=O)ccc6c5)cc4n3CC3CC3)n(C)c12] | 6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)quinoline-2-carboxamide | 641.5 | 2 | 1.43 |
| 478. | 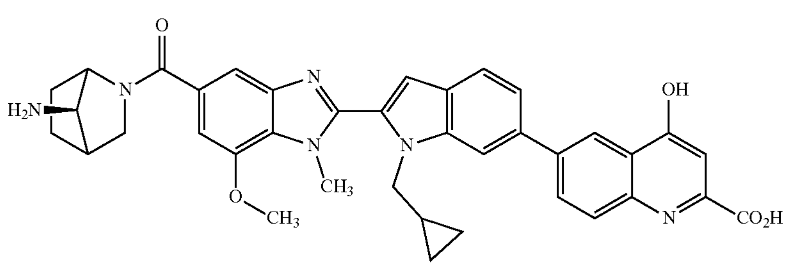 [SMILES: COc1cc(C(=O)N2CC3CCC2[C@@H]3N)cc2nc(-c3cc4ccc(-c5ccc6nc(C(=O)O)cc(O)c6c5)cc4n3CC3CC3)n(C)c12] | 6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-4-hydroxyquinoline-2-carboxylic acid | 657.2 | 1 | 1.14 |

| # | Structure | Name | Obs. MS Ion | HPLC Method ID | RT |
|---|---|---|---|---|---|
| 479. | 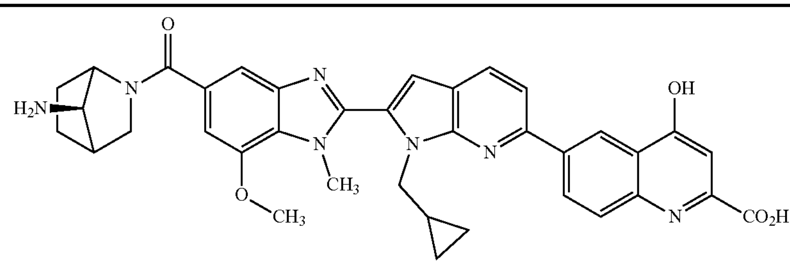 | 6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-4-hydroxyquinoline-2-carboxylic acid | 658.4 | 2 | 1.14 |
| 480. | 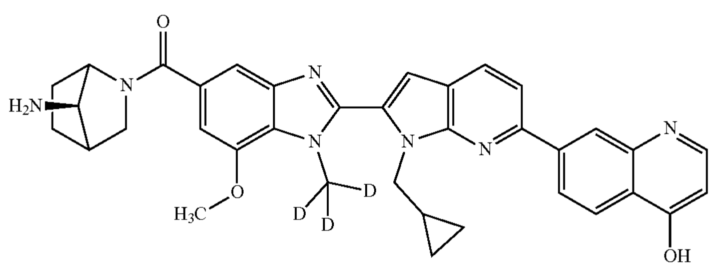 [SMILES: [2H]C([2H])([2H])n1c(-c2cc3ccc(-c4ccc5c(O)ccnc5c4)nc3n2CC2CC2)nc2cc(C(=O)N3CC4CCC3[C@@H]4N)cc(OC)c21] | ((7R)-7-amino-2-azabicyclo[2.2.1]heptan-2-yl)(2-(l-(cyclopropylmethyl)-6-(4-hydroxyquinolin-7-yl)-1H-pyrrolo[2,3-b]pyridin-2-yl)-7-methoxy-1-(methyl-d3)-1H-benzo[d]imidazol-5-yl)methanone | 617.4 | 2 | 1.15 |
| 481. | 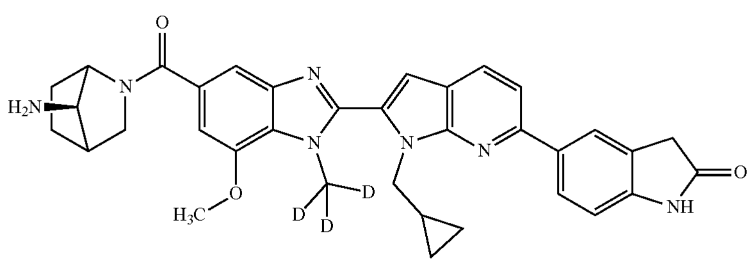 [SMILES: [2H]C([2H])([2H])n1c(-c2cc3ccc(-c4ccc5c(c4)CC(=O)N5)nc3n2CC2CC2)nc2cc(C(=O)N3CC4CCC3[C@@H]4N)cc(OC)c21] | 5-(2-(5-((7R)-7-amino-2-azabicyclo[2.2.1]heptane-2-carbonyl)-7-methoxy-1-(methyl-d3)-1H-benzo[d]imidazol-2-yl)-1-(cyclopropylmethyl)-1H-pyrrolo[2,3-b]pyridin-6-yl)indolin-2-one | 605.2 | 2 | 1.24 |

| # | Structure | Name | Obs. MS Ion | HPLC Method ID | RT |
|---|---|---|---|---|---|
| 482. | 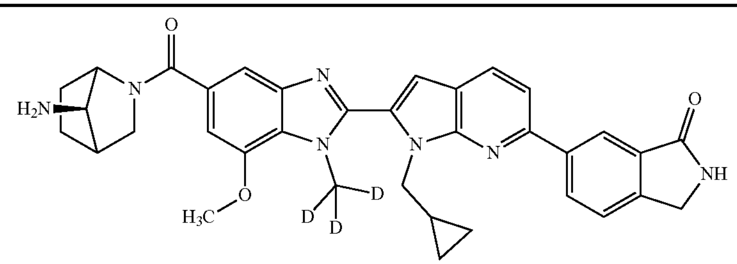 | 6-(2-(5-((7R)-7-amino-2-azabicyclo[2.2.1]heptane-2-carbonyl)-7-methoxy-1-(methyl-d3)-1H-benzo[d]imidazol-2-yl)-1-(cyclopropylmethyl)-1H-pyrrolo[2,3-b]pyridin-6-yl)isoindolin-1-one | 605.4 | 2 | 1.24 |
| 483. | 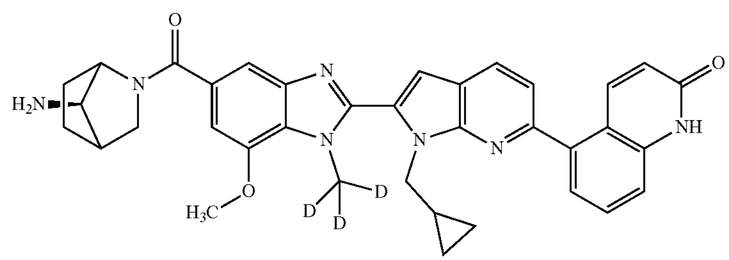 [SMILES: [2H]C([2H])([2H])n1c(-c2cc3ccc(-c4cccc5[nH]c(=O)ccc45)nc3n2CC2CC2)nc2cc(C(=O)N3CC4CCC3[C@@H]4N)cc(OC)c21] | 5-(2-(5-((7R)-7-amino-2-azabicyclo[2.2.1]heptane-2-carbonyl)-7-methoxy-1-(methyl-d3)-1H-benzo[d]imidazol-2-yl)-1-(cyclopropylmethyl)-1H-pyrrolo[2,3-b]pyridin-6-yl)quinolin-2(1H)-one | 617.4 | 1 | 1.55 |
| 484. | 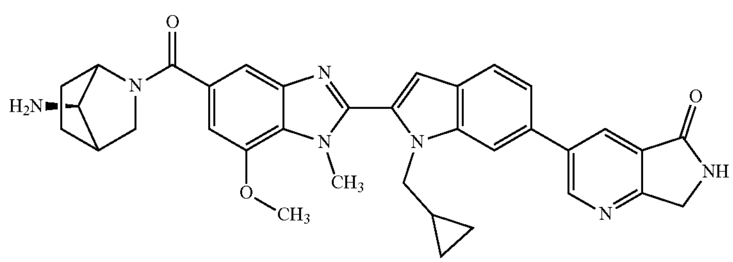 [SMILES: COc1cc(C(=O)N2CC3CCC2[C@@H]3N)cc2nc(-c3cc4ccc(-c5cnc6c(c5)C(=O)NC6)cc4n3CC3CC3)n(C)c12] | 3-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-5H,6H,7H-pyrrolo[3,4-b]pyridin-5-one | 602.3 | 2 | 1.11 |

-continued

| # | Structure | Name | Obs. MS Ion | HPLC Method ID | RT |
|---|---|---|---|---|---|
| 485. | 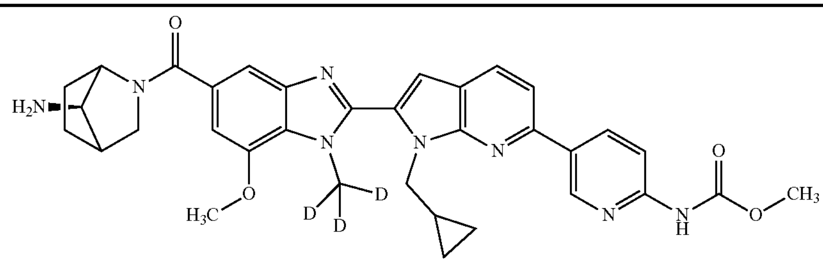 | methyl (5-(2-(5-((7R)-7-amino-2-azabicyclo[2.2.1]heptane-2-carbonyl)-7-methoxy-1-(methyl-d3)-1H-benzo[d]imidazol-2-yl)-1-(cyclopropylmethyl)-1H-pyrrolo[2,3-b]pyridin-6-yl)pyridin-2-yl)carbamate | 624.1 | 1 | 1.72 |
| 486. | 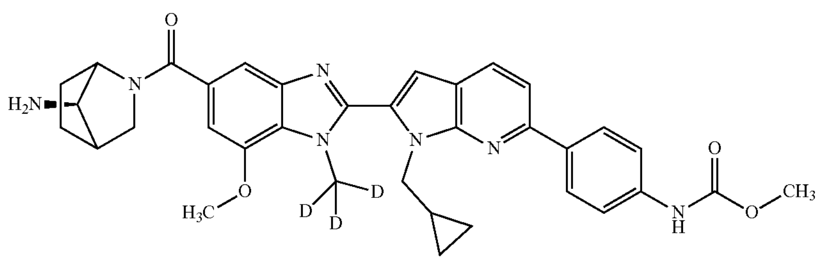 [SMILES: [2H]C([2H])([2H])n1c(-c2cc3ccc(-c4ccc(NC(=O)OC)cc4)nc3n2CC2CC2)nc2cc(C(=O)N3CC4CCC3[C@@H]4N)cc(OC)c21] | methyl (4-(2-(5-((7R)-7-amino-2-azabicyclo[2.2.1]heptane-2-carbonyl)-7-methoxy-1-(methyl-d3)-1H-benzo[d]imidazol-2-yl)-1-(cyclopropylmethyl)-1H-pyrrolo[2,3-b]pyridin-6-yl)phenyl)carbamate | 623.4 | 1 | 1.81 |
| 487. | 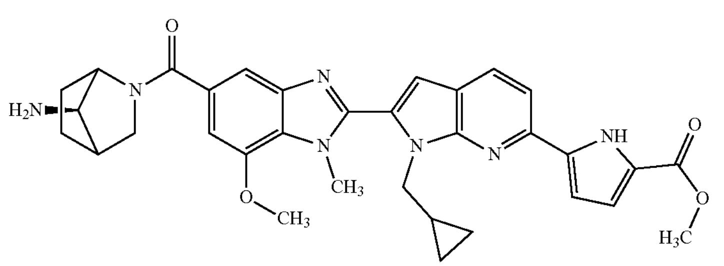 [SMILES: COC(=O)c1ccc(-c2ccc3cc(-c4nc5cc(C(=O)N6CC7CCC6[C@@H]7N)cc(OC)c5n4C)n(CC4CC4)c3n2)[nH]1] | methyl 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1H-pyrrole-2-carboxylate | 594.2 | 2 | 1.67 |

| # | Structure | Name | Obs. MS Ion | HPLC Method ID | RT |
|---|---|---|---|---|---|
| 488. | 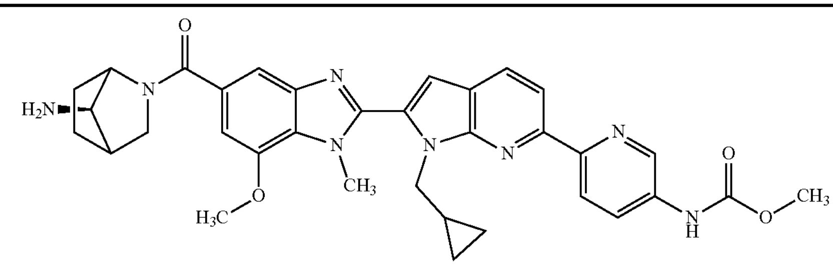 | methyl N-[6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl]pyridin-3-yl]carbamate | 621.4 | 1 | 1.55 |
| 489. | 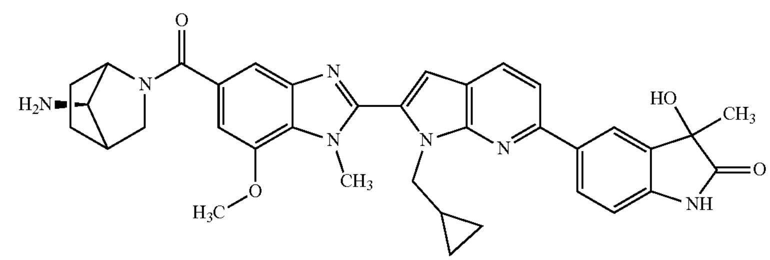 [SMILES: COc1cc(C(=O)N2CC3CCC2[C@@H]3N)cc2nc(-c3cc4ccc(-c5ccc6c(c5)C(C)(O)C(=O)N6)nc4n3CC3CC3)n(C)c12] | 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-3-hydroxy-3-methyl-2,3-dihydro-1H-indol-2-one | 632.4 | 2 | 1.2 |
| 490. | 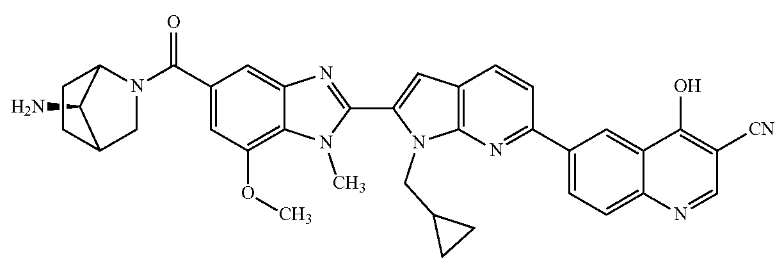 | 6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-4-hydroxyquinoline-3-carbonitrile | 639.2 | 1 | 1.48 |
| 491. | 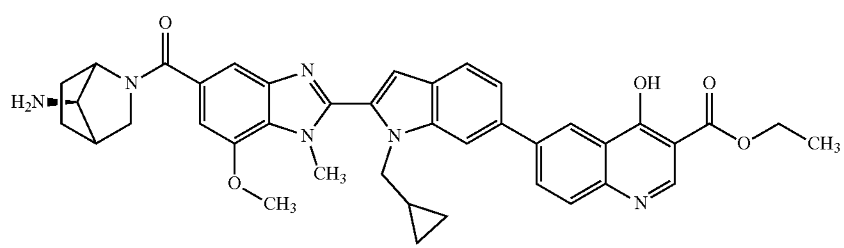 [SMILES: CCOC(=O)c1cnc2ccc(-c3ccc4cc(-c5nc6cc(C(=O)N7CC8CCC7[C@@H]8N)cc(OC)c6n5C)n(CC5CC5)c4c3)cc2c1O] | ethyl 6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-4-hydroxyquinoline-3-carboxylate | 685.4 | 2 | 1.3 |

-continued

| # | Structure | Name | Obs. MS Ion | HPLC Method ID | RT |
|---|---|---|---|---|---|
| 492. | 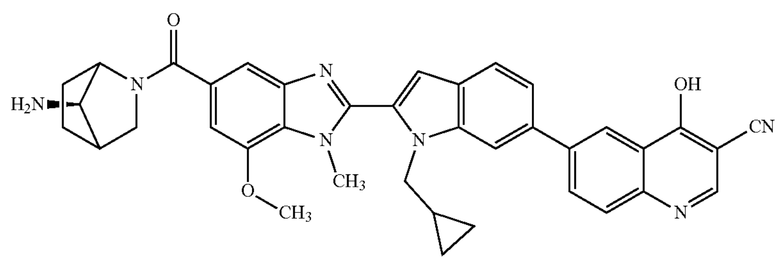 [SMILES: COc1cc(C(=O)N2CC3CCC2[C@@H]3N)cc2nc(-c3cc4ccc(-c5ccc6ncc(C#N)c(O)c6c5)cc4n3CC3CC3)n(C)c12] | 6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-4-hydroxyquinoline-3-carbonitrile | 638.2 | 1 | 1.54 |
| 493. | 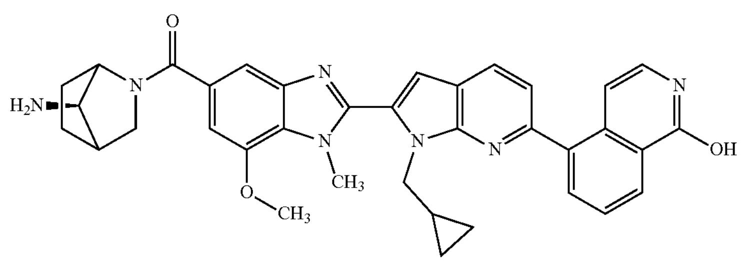 | 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)isoquinolin-1-ol | 614.2 | 1 | 1.57 |
| 494. | 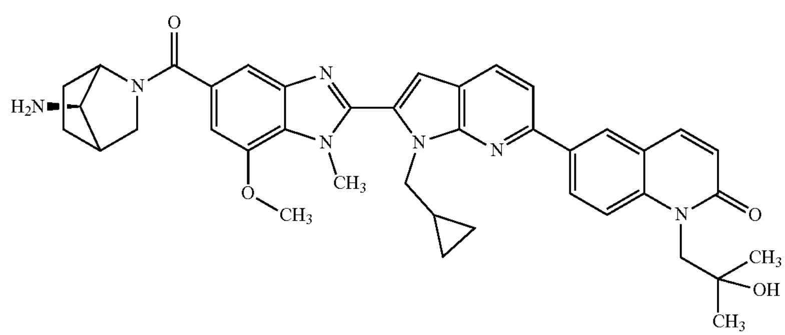 [SMILES: COc1cc(C(=O)N2CC3CCC2[C@@H]3N)cc2nc(-c3cc4ccc(-c5ccc6c(ccc(=O)n6CC(C)(C)O)c5)nc4n3CC3CC3)n(C)c12] | 6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1-(2-hydroxy-2-methylpropyl)-1,2-dihydroquinolin-2-one | 686.3 | 2 | 1.43 |

| # | Structure | Name | Obs. MS Ion | HPLC Method ID | RT |
|---|---|---|---|---|---|
| 495. | 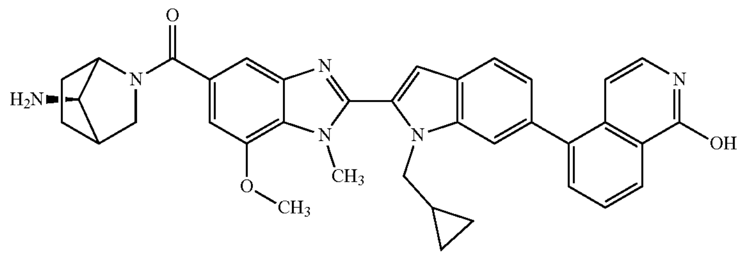 [SMILES: COc1cc(C(=O)N2CC3CCC2[C@@H]3N)cc2nc(-c3cc4ccc(-c5cccc6c(O)nccc56)cc4n3CC3CC3)n(C)c12] | 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)isoquinolin-1-ol | 613.3 | 1 | 1.65 |
| 496. | 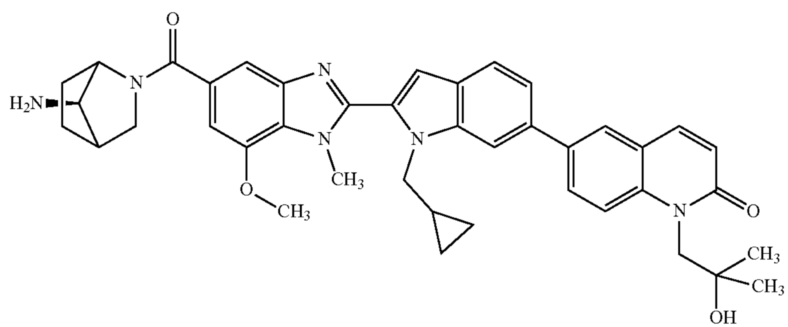 [SMILES: COc1cc(C(=O)N2CC3CCC2[C@@H]3N)cc2nc(-c3cc4ccc(-c5ccc6c(ccc(=O)n6CC(C)(C)O)c5)cc4n3CC3CC3)n(C)c12] | 6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-1-(2-hydroxy-2-methylpropyl)-1,2-dihydroquinolin-2-one | 685.2 | 1 | 1.75 |
| 497. | 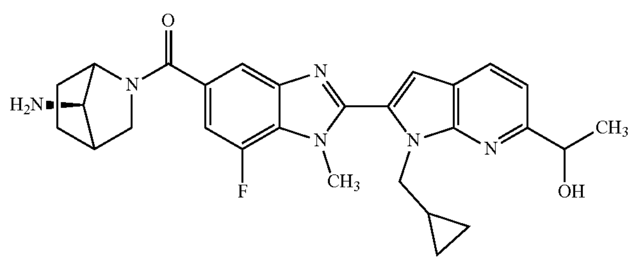 [SMILES: CC(O)c1ccc2cc(-c3nc4cc(C(=O)N5CC6CCC5[C@@H]6N)cc(F)c4n3C)n(CC3CC3)c2n1] | 1-(2-{5-[(7R)-7-amino-2-azabicyclo[2.2.1]heptane-2-carbonyl]-7-fluoro-1-methyl-1H-1,3-benzodiazol-2-yl}-1-(cyclopropylmethyl)-1H-pyrrolo[2,3-b]pyridin-6-yl)ethan-1-ol (mixture of diastereomers) | 503.3 | 1 | 1.44 |

| # | Structure | Name | Obs. MS Ion | HPLC Method ID | RT |
|---|---|---|---|---|---|
| 498. | 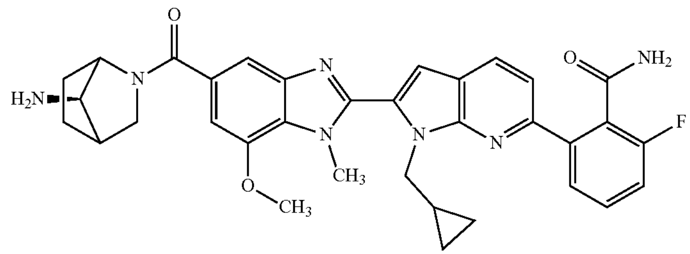 [SMILES: COc1cc(C(=O)N2CC3CCC2[C@@H]3N)cc2nc(-c3cc4ccc(-c5cccc(F)c5C(N)=O)nc4n3CC3CC3)n(C)c12] | 2-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-5-fluorobenzamide | 608.4 | 1 | 1.33 |
| 499. | 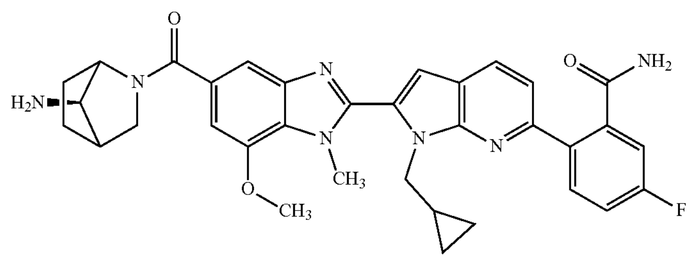 | 2-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-5-fluorobenzamide | 608.4 | 1 | 1.43 |
| 500. | 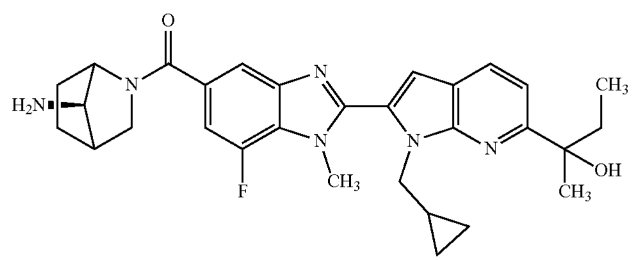 [SMILES: CCC(C)(O)c1ccc2cc(-c3nc4cc(C(=O)N5CC6CCC5[C@@H]6N)cc(F)c4n3C)n(CC3CC3)c2n1] | 2-(2-{5-[(7R)-7-amino-2-azabicyclo[2.2.1]heptane-2-carbonyl]-7-fluoro-1-methyl-1H-1,3-benzodiazol-2-yl}-1-(cyclopropylmethyl)-1H-pyrrolo[2,3-b]pyridin-6-yl)butan-2-ol (mixture of diastereomers) | 531.4 | 1 | 1.55 |

| # | Structure | Name | Obs. MS Ion | HPLC Method ID | RT |
|---|---|---|---|---|---|
| 501. | 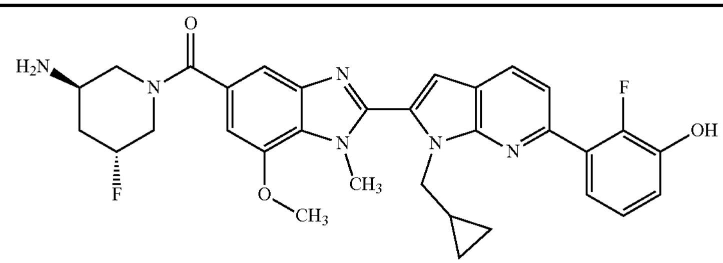 | 3-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-fluorophenol | 587.4 | 1 | 1.64 |
| 502. | 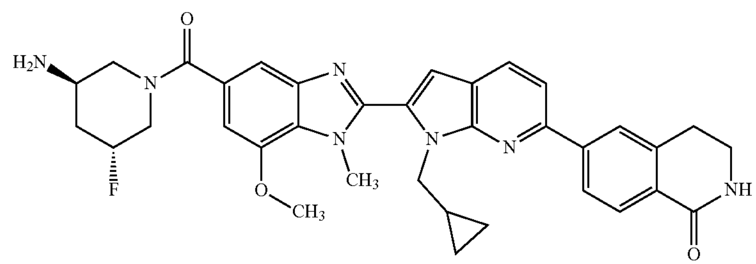 [SMILES: COc1cc(C(=O)N2C[C@H](N)C[C@@H](F)C2)cc2nc(-c3cc4ccc(-c5ccc6c(c5)CCNC6=O)nc4n3CC3CC3)n(C)c12] | 6-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-1,2,3,4-tetrahydroisoquinolin-1-one | 622.3 | 1 | 1.66 |
| 503. | 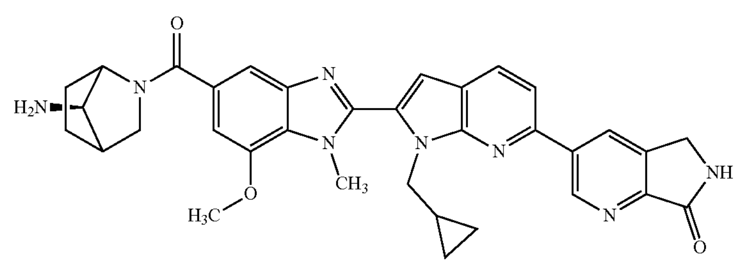 [SMILES: COc1cc(C(=O)N2CC3CCC2[C@@H]3N)cc2nc(-c3cc4ccc(-c5cnc6c(c5)CNC6=O)nc4n3CC3CC3)n(C)c12] | 3-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-5H,6H,7H-pyrrolo[3,4-b]pyridin-7-one | 603.4 | 2 | 1.1 |

| # | Structure | Name | Obs. MS Ion | HPLC Method ID | RT |
|---|---|---|---|---|---|
| 504. | 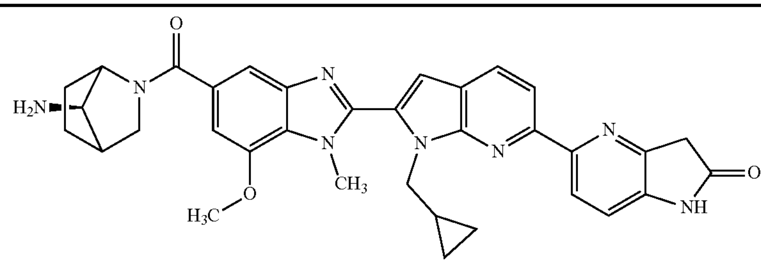 | 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1H,2H,3H-pyrrolo[3,2-b]pyridin-2-one | 603.1 | 1 | 1.45 |
| 505. | 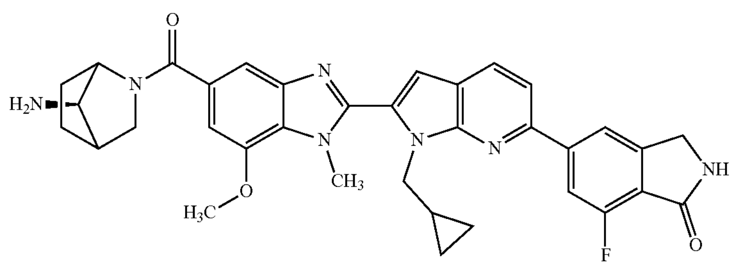 [SMILES: COc1cc(C(=O)N2CC3CCC2[C@@H]3N)cc2nc(-c3cc4ccc(-c5cc(F)c6c(c5)CNC6=O)nc4n3CC3CC3)n(C)c12] | 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-7-fluoro-2,3-dihydro-1H-isoindol-1-one | 620.2 | 1 | 1.57 |
| 506. | 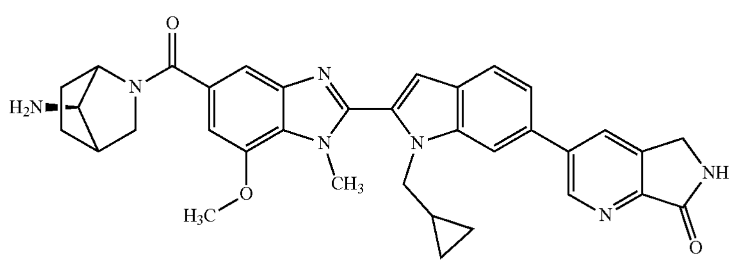 [SMILES: COc1cc(C(=O)N2CC3CCC2[C@@H]3N)cc2nc(-c3cc4ccc(-c5cnc6c(c5)CNC6=O)cc4n3CC3CC3)n(C)c12] | 3-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-5H,6H,7H-pyrrolo[3,4-b]pyridin-7-one | 602.2 | 1 | 1.41 |

| # | Structure | Name | Obs. MS Ion | HPLC Method ID | RT |
|---|---|---|---|---|---|
| 507. | 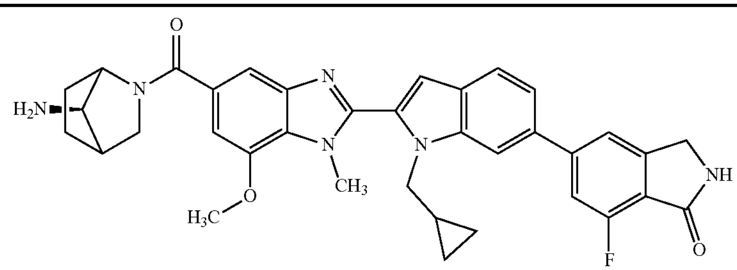 | 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-7-fluoro-2,3-dihydro-1H-isoindol-1-one | 619.4 | 2 | 1.28 |
| 508. | 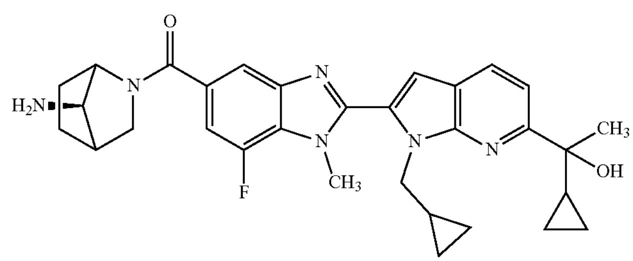 [SMILES: Cn1c(-c2cc3ccc(C(C)(O)C4CC4)nc3n2CC2CC2)nc2cc(C(=O)N3CC4CCC3[C@@H]4N)cc(F)c21] | 1-(2-{5-[(7R)-7-amino-2-azabicyclo[2.2.1]heptane-2-carbonyl]-7-fluoro-1-methyl-1H-1,3-benzodiazol-2-yl}-1-(cyclopropylmethyl)-1H-pyrrolo[2,3-b]pyridin-6-yl)-1-cyclopropylethan-1-ol (mixture of diastereomers) | 543.4 | 2 | 1.55 |
| 509. | 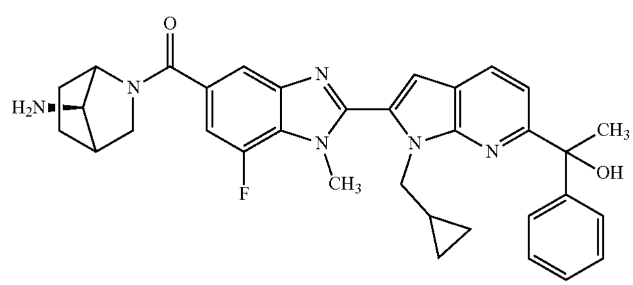 [SMILES: Cn1c(-c2cc3ccc(C(C)(O)c4ccccc4)nc3n2CC2CC2)nc2cc(C(=O)N3CC4CCC3[C@@H]4N)cc(F)c21] | 1-(2-{5-[(7R)-7-amino-2-azabicyclo[2.2.1]heptane-2-carbonyl]-7-fluoro-1-methyl-1H-1,3-benzodiazol-2-yl}-1-(cyclopropylmethyl)-1H-pyrrolo[2,3-b]pyridin-6-yl)-1-phenylethan-1-ol (mixture of diastereomers) | 579.4 | 2 | 1.62 |

| # | Structure | Name | Obs. MS Ion | HPLC Method ID | RT |
|---|---|---|---|---|---|
| 510. | 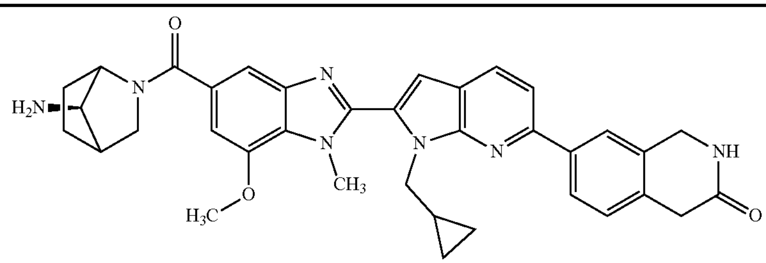 | 7-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1,2,3,4-tetrahydroisoquinolin-3-one | 616.2 | 1 | 1.56 |
| 511. | 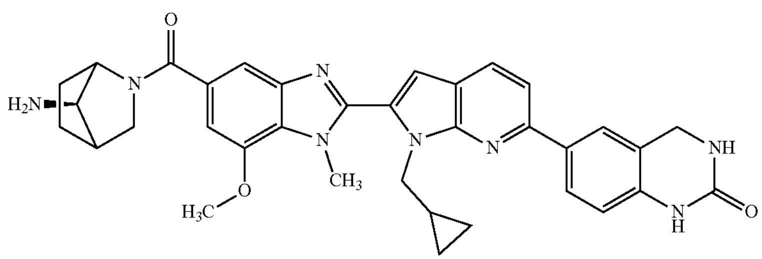 [SMILES: COc1cc(C(=O)N2CC3CCC2[C@@H]3N)cc2nc(-c3cc4ccc(-c5ccc6c(c5)CNC(=O)N6)nc4n3CC3CC3)n(C)c12] | 6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1,2,3,4-tetrahydroquinazolin-2-one | 616.9 | 1 | 1.5 |
| 512. | 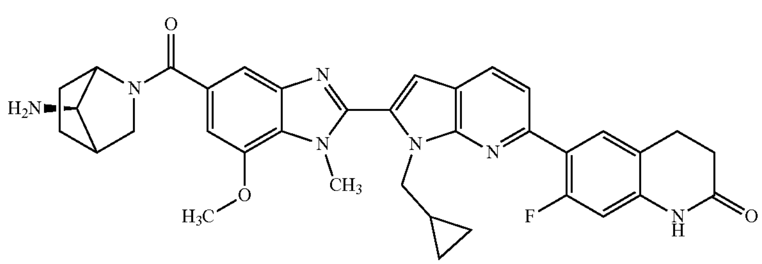 [SMILES: COc1cc(C(=O)N2CC3CCC2[C@@H]3N)cc2nc(-c3cc4ccc(-c5cc6c(cc5F)NC(=O)CC6)nc4n3CC3CC3)n(C)c12] | 6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-7-fluoro-1,2,3,4-tetrahydroquinolin-2-one | 634.2 | 2 | 1.47 |

| # | Structure | Name | Obs. MS Ion | HPLC Method ID | RT |
|---|---|---|---|---|---|
| 513. | 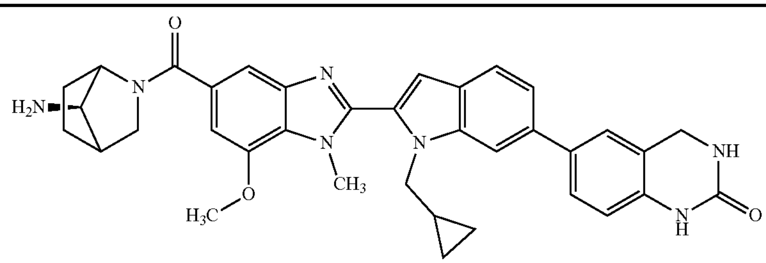 | 6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-1,2,3,4-tetrahydroquinazolin-2-one | 616.2 | 1 | 1.67 |
| 514. | 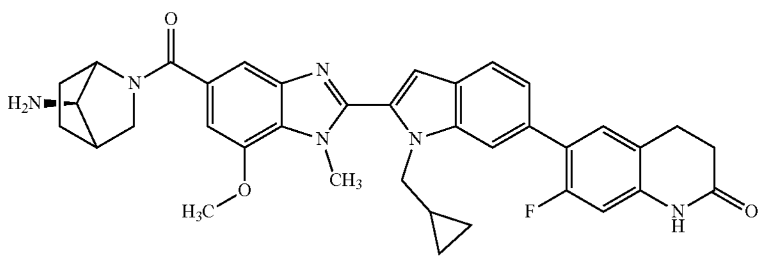 [SMILES: COc1cc(C(=O)N2CC3CCC2[C@@H]3N)cc2nc(-c3cc4ccc(-c5cc6c(cc5F)NC(=O)CC6)cc4n3CC3CC3)n(C)c12] | 6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-7-fluoro-1,2,3,4-tetrahydroquinolin-2-one | 633.2 | 2 | 1.44 |
| 515. | 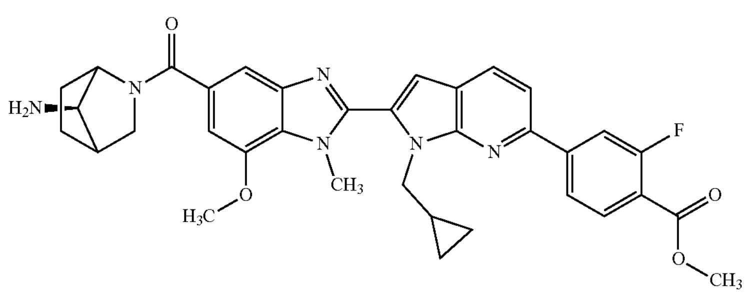 [SMILES: COC(=O)c1ccc(-c2ccc3cc(-c4nc5cc(C(=O)N6CC7CCC6[C@@H]7N)cc(OC)c5n4C)n(CC4CC4)c3n2)cc1F] | methyl 4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-fluorobenzoate | 623.4 | 2 | 1.78 |

| # | Structure | Name | Obs. MS Ion | HPLC Method ID | RT |
|---|---|---|---|---|---|
| 516. | 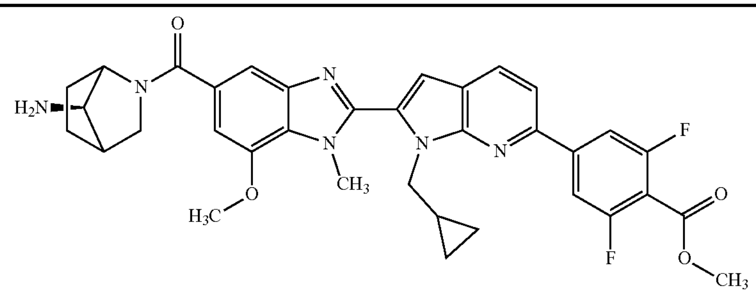 | methyl 4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2,6-difluorobenzoate | 640.9 | 1 | 2.12 |
| 517. | 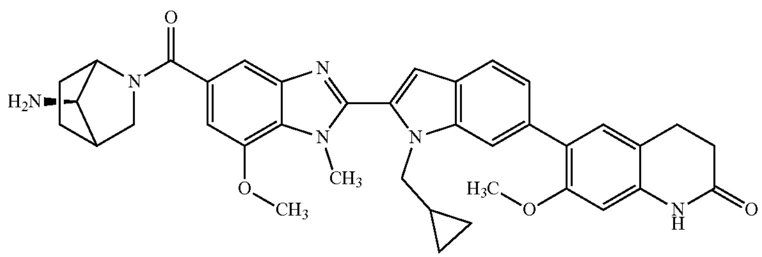 [SMILES: COc1cc2c(cc1-c1ccc3cc(-c4nc5cc(C(=O)N6CC7CCC6[C@@H]7N)cc(OC)c5n4C)n(CC4CC4)c3c1)CCC(=O)N2] | 6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-7-methoxy-1,2,3,4-tetrahydroquinolin-2-one | 645 | 2 | 1.42 |
| 518. | 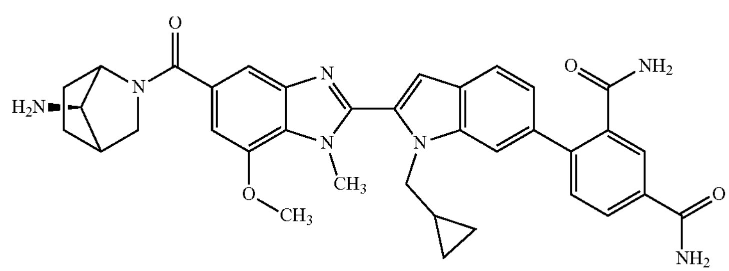 [SMILES: COc1cc(C(=O)N2CC3CCC2[C@@H]3N)cc2nc(-c3cc4ccc(-c5ccc(C(N)=O)cc5C(N)=O)cc4n3CC3CC3)n(C)c12] | 2-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-6-fluorobenzamide | 607.3 | 1 | 1.41 |

| # | Structure | Name | Obs. MS Ion | HPLC Method ID | RT |
|---|---|---|---|---|---|
| 519. | 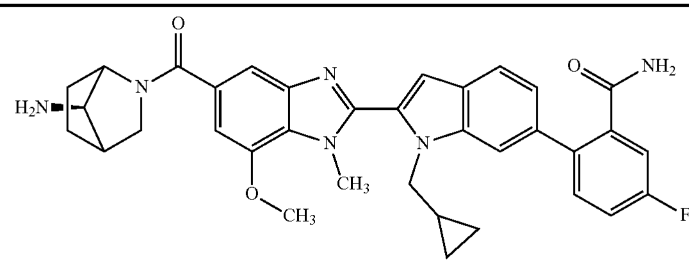 | 2-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-5-fluorobenzamide | 607 | 1 | 1.61 |
| 520. | 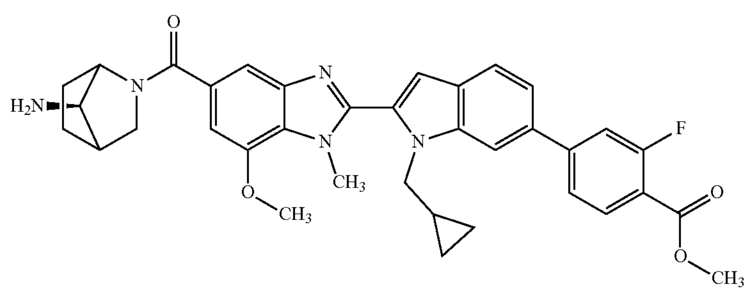 [SMILES: COC(=O)c1ccc(-c2ccc3cc(-c4nc5cc(C(=O)N6CC7CCC6[C@@H]7N)cc(OC)c5n4C)n(CC4CC4)c3c2)cc1F] | methyl 4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-2-fluorobenzoate | 622.2 | 2 | 1.79 |
| 521. | 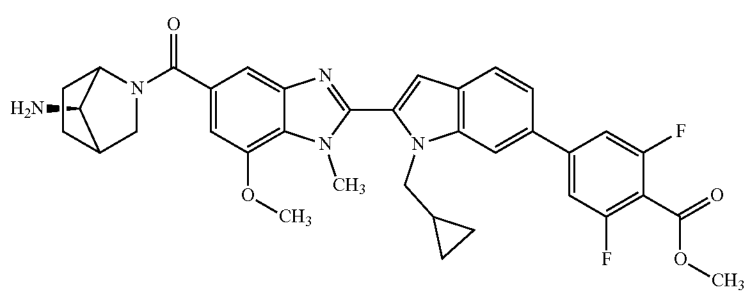 [SMILES: COC(=O)c1c(F)cc(-c2ccc3cc(-c4nc5cc(C(=O)N6CC7CCC6[C@@H]7N)cc(OC)c5n4C)n(CC4CC4)c3c2)cc1F] | methyl 4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-2,6-difluorobenzoate | 640.4 | 2 | 1.75 |

| # | Structure | Name | Obs. MS Ion | HPLC Method ID | RT |
|---|---|---|---|---|---|
| 522. | 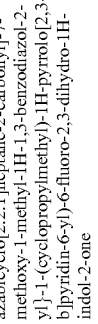 | 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-6-fluoro-2,3-dihydro-1H-indol-2-one | 620.1 | 1 | 1.74 |
| 523. | 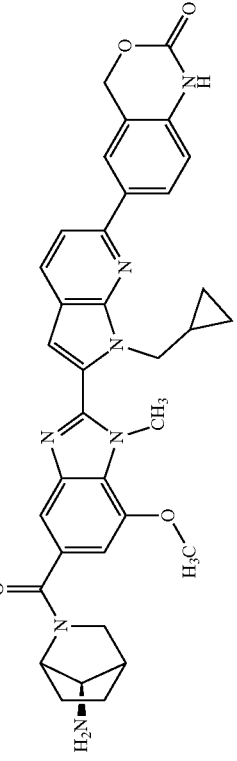 | 6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2,4-dihydro-1H-3,1-benzoxazin-2-one | 618.4 | 2 | 1.31 |
| 524. | 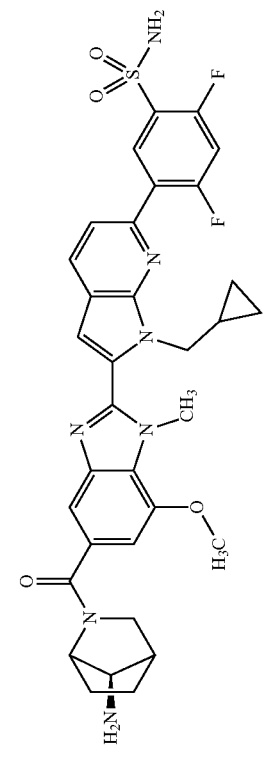 | 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2,4-difluorobenzene-1-sulfonamide | 662.2 | 1 | 1.68 |

| # | Structure | Name | Obs. MS Ion | HPLC Method ID | RT |
|---|---|---|---|---|---|
| 525. | 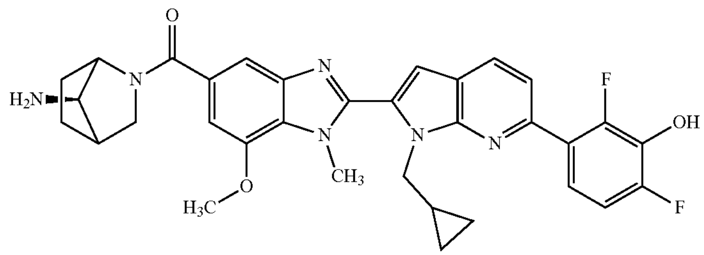 | 3-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2,6-difluorophenol | 599.2 | 2 | 1.54 |
| 526. | 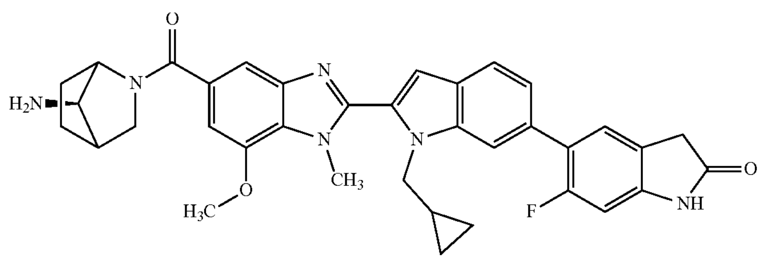 [SMILES: COc1cc(C(=O)N2CC3CCC2[C@@H]3N)cc2nc(-c3cc4ccc(-c5cc6c(cc5F)NC(=O)C6)cc4n3CC3CC3)n(C)c12] | 2'-{5-[(7R)-7-amino-2-azabicyclo[2.2.1]heptane-2-carbonyl]-7-methoxy-1-methyl-1H-1,3-benzodiazol-2-yl}-1'-(cyclopropylmethyl)-6-fluoro-2,3-dihydro-1H,1'H-[5,6-biindole]-2-one | 619.2 | 2 | 1.38 |
| 527. | 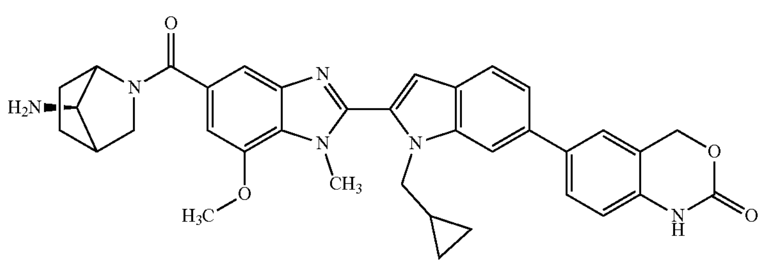 [SMILES: COc1cc(C(=O)N2CC3CCC2[C@@H]3N)cc2nc(-c3cc4ccc(-c5ccc6c(c5)COC(=O)N6)cc4n3CC3CC3)n(C)c12] | 6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-2,4-dihydro-1H-3,1-benzoxazin-2-one | 617.3 | 1 | 1.75 |

-continued

| # | Structure | Name | Obs. MS Ion | HPLC Method ID | RT |
|---|---|---|---|---|---|
| 528. | 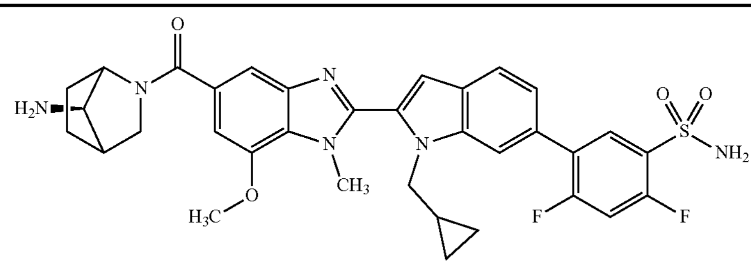 | 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-2,4-difluorobenzene-1-sulfonamide | 661.1 | 1 | 1.79 |
| 529. | 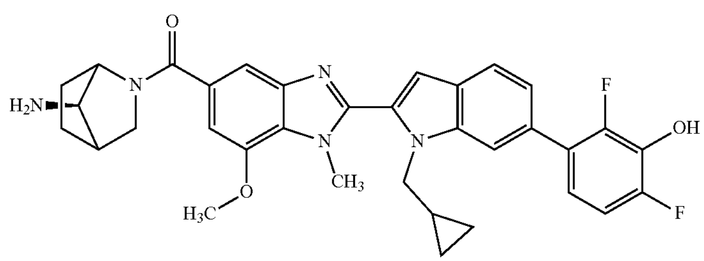 [SMILES: COc1cc(C(=O)N2CC3CCC2[C@@H]3N)cc2nc(-c3cc4ccc(-c5ccc(F)c(O)c5F)cc4n3CC3CC3)n(C)c12] | 3-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-2,6-difluorophenol | 598.2 | 1 | 1.82 |
| 530. | 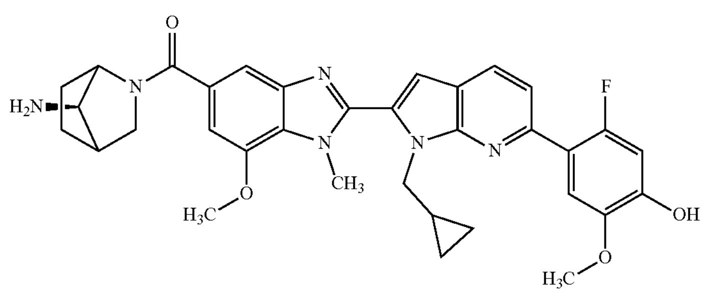 [SMILES: COc1cc(-c2ccc3cc(-c4nc5cc(C(=O)N6CC7CCC6[C@@H]7N)cc(OC)c5n4C)n(CC4CC4)c3n2)c(F)cc1O] | 4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-5-fluoro-2-methoxyphenol | 611.2 | 2 | 1.45 |

| # | Structure | Name | Obs. MS Ion | HPLC Method ID | RT |
|---|---|---|---|---|---|
| 531. | 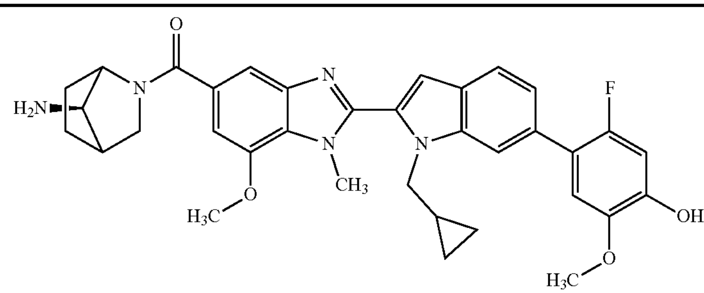 | 4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-5-fluoro-2-methoxyphenol | 610.2 | 2 | 1.42 |
| 532. | 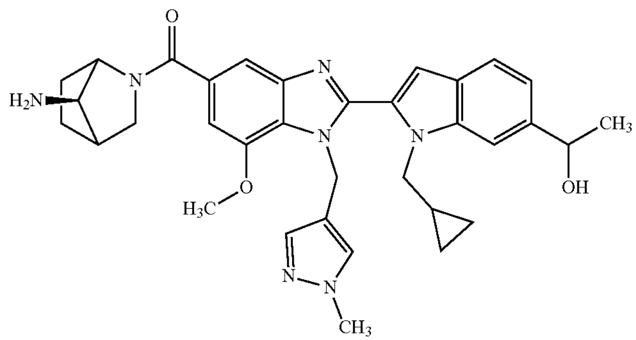 [SMILES: COc1cc(C(=O)N2CC3CCC2[C@@H]3N)cc2nc(-c3cc4ccc(C(C)O)cc4n3CC3CC3)n(Cc3cnn(C)c3)c12] | 1-(2-{5-[(7R)-7-amino-2-azabicyclo[2.2.1]heptane-2-carbonyl]-7-methoxy-1-[(1-methyl-1H-pyrazol-4-yl)methyl]-1H-1,3-benzodiazol-2-yl}-1-(cyclopropylmethyl)-1H-indol-6-yl)ethan-1-ol (mixture of diastereomers) | 594.2 | 1 | 1.38 |
| 533. | 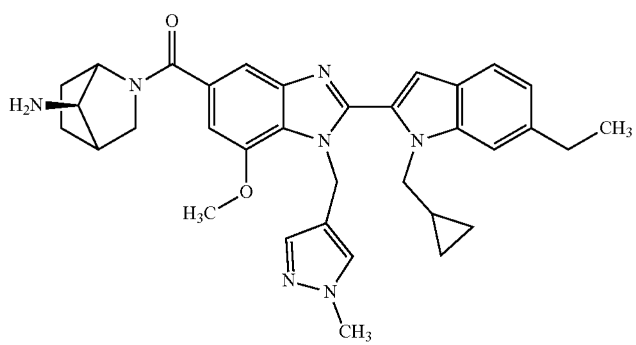 [SMILES: CCc1ccc2cc(-c3nc4cc(C(=O)N5CC6CCC5[C@@H]6N)cc(OC)c4n3Cc3cnn(C)c3)n(CC3CC3)c2c1] | (7R)-2-{2-[1-(cyclopropylmethyl)-6-ethyl-1H-indol-2-yl]-7-methoxy-1-((1-methyl-1H-pyrazol-4-yl)methyl]-1H-1,3-benodiazole-5-carbonyl}-2-azabicyclo[2.2.1]heptan-7-amine | 578.1 | 2 | 1.63 |

| # | Structure | Name | Obs. MS Ion | HPLC Method ID | RT |
|---|---|---|---|---|---|
| 534. | 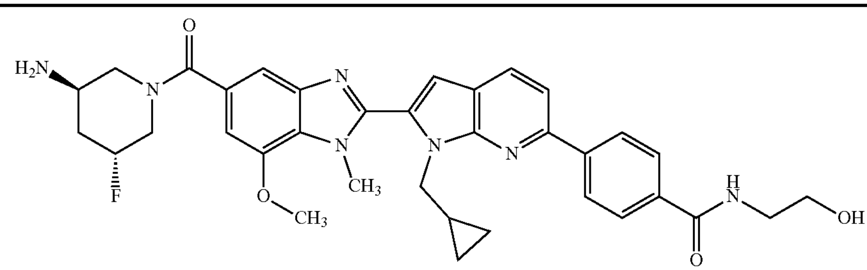 | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-N-(2-hydroxyethyl)benzamide | 640.4 | 2 | 1.25 |
| 535. | 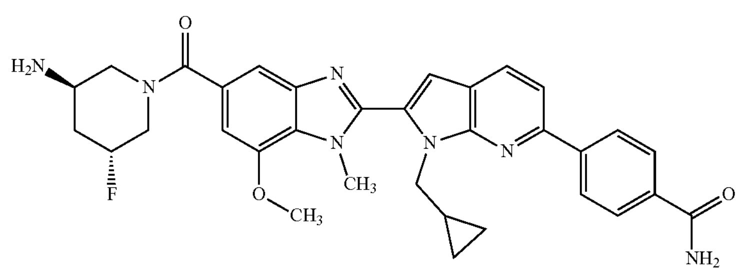 [SMILES: COc1cc(C(=O)N2C[C@H](N)C[C@@H](F)C2)cc2nc(-c3cc4ccc(-c5ccc(C(N)=O)cc5)nc4n3CC3CC3)n(C)c12] | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)benzamide | 596.4 | 1 | 1.58 |
| 536. | 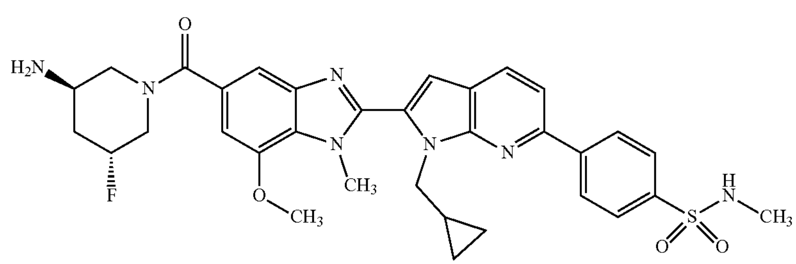 [SMILES: CNS(=O)(=O)c1ccc(-c2ccc3cc(-c4nc5cc(C(=O)N6C[C@H](N)C[C@@H](F)C6)cc(OC)c5n4C)n(CC4CC4)c3n2)cc1] | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-N-methylbenzene-1-sulfonamide | 646.4 | 2 | 1.48 |

| # | Structure | Name | Obs. MS Ion | HPLC Method ID | RT |
|---|---|---|---|---|---|
| 537. | 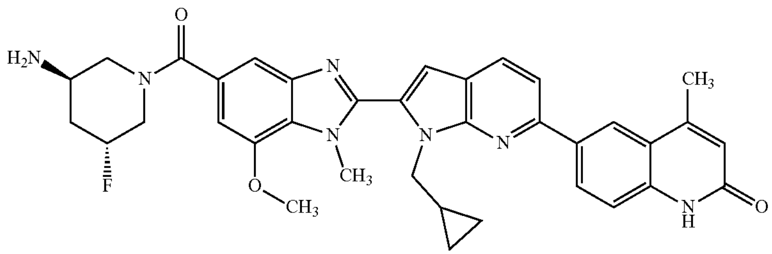 [SMILES: COc1cc(C(=O)N2C[C@H](N)C[C@@H](F)C2)cc2nc(-c3cc4ccc(-c5ccc6[nH]c(=O)cc(C)c6c5)nc4n3CC3CC3)n(C)c12] | 6-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-4-methyl-1,2-dihydroquinolin-2-one | 634.4 | 2 | 1.37 |
| 538. | 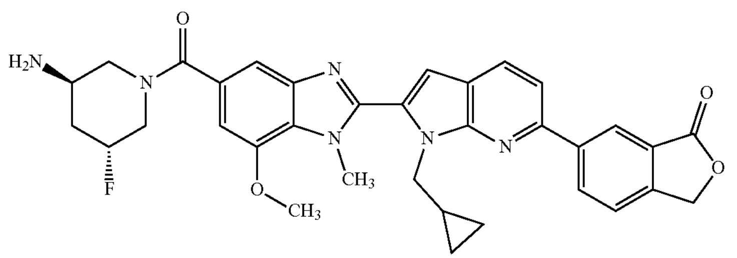 [SMILES: COc1cc(C(=O)N2C[C@H](N)C[C@@H](F)C2)cc2nc(-c3cc4ccc(-c5ccc6c(c5)C(=O)OC6)nc4n3CC3CC3)n(C)c12] | 6-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-1,3-dihydro-2-benzofuran-1-one | 609.3 | 1 | 1.83 |
| 539. | 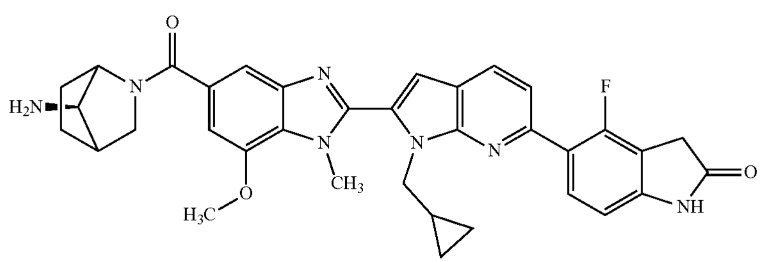 [SMILES: COc1cc(C(=O)N2CC3CCC2[C@@H]3N)cc2nc(-c3cc4ccc(-c5ccc6c(c5F)CC(=O)N6)nc4n3CC3CC3)n(C)c12] | 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-4-fluoro-2,3-dihydro-1H-indol-2-one | 620.1 | 1 | 1.61 |

| # | Structure | Name | Obs. MS Ion | HPLC Method ID | RT |
|---|---|---|---|---|---|
| 540. | 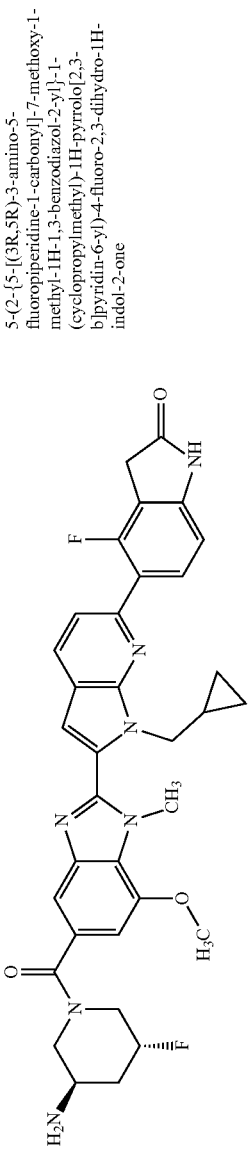 | 5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-4-fluoro-2,3-dihydro-1H-indol-2-one | 626.4 | 2 | 1.39 |
| 541. | 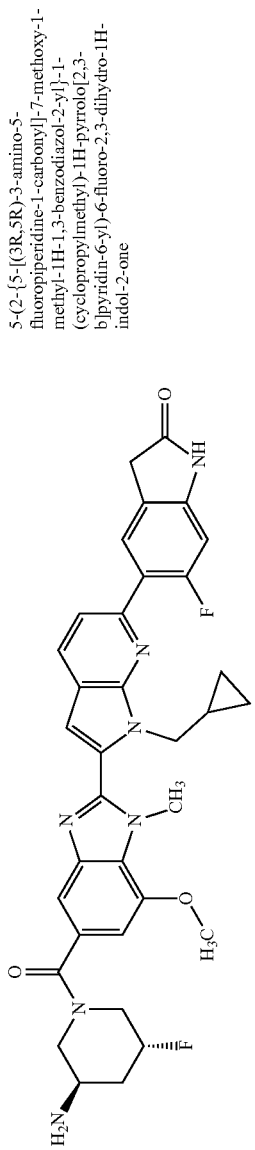 | 5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-6-fluoro-2,3-dihydro-1H-indol-2-one | 626.4 | 2 | 1.39 |
| 542. | 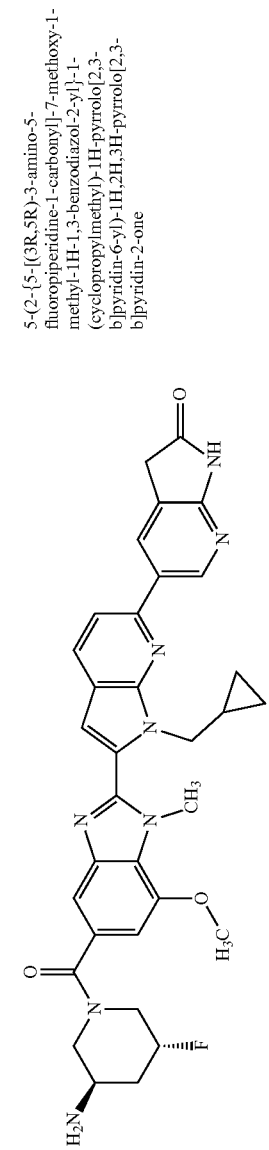 | 5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-1H,2H,3H-pyrrolo[2,3-b]pyridin-2-one | 609.4 | 2 | 1.29 |

| # | Structure | Name | Obs. MS Ion | HPLC Method ID | RT |
|---|---|---|---|---|---|
| 543. | 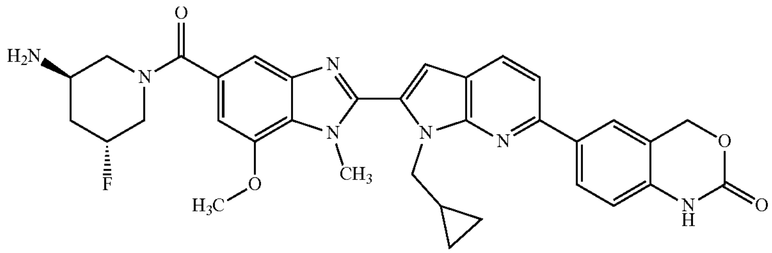 [SMILES: COc1cc(C(=O)N2C[C@H](N)C[C@@H](F)C2)cc2nc(-c3cc4ccc(-c5ccc6c(c5)COC(=O)N6)nc4n3CC3CC3)n(C)c12] | 6-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2,4-dihydro-1H-3,1-benzoxazin-2-one | 624.4 | 1 | 1.66 |
| 544. | 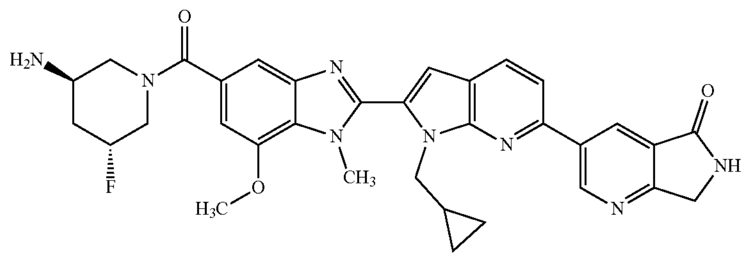 [SMILES: COc1cc(C(=O)N2C[C@H](N)C[C@@H](F)C2)cc2nc(-c3cc4ccc(-c5cnc6c(c5)C(=O)NC6)nc4n3CC3CC3)n(C)c12] | 3-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-5H,6H,7H-pyrrolo[3,4-b]pyridin-5-one | 609.4 | 1 | 1.45 |
| 545. | 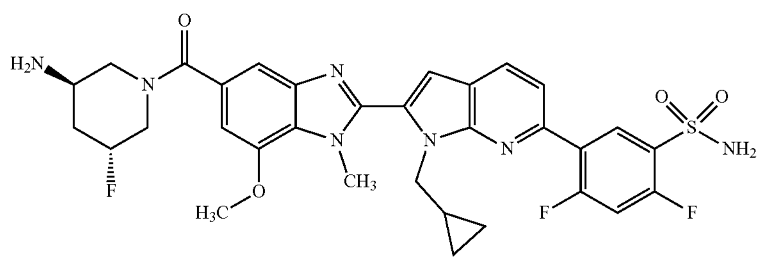 [SMILES: COc1cc(C(=O)N2C[C@H](N)C[C@@H](F)C2)cc2nc(-c3cc4ccc(-c5cc(S(N)(=O)=O)c(F)cc5F)nc4n3CC3CC3)n(C)c12] | 5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2,4-difluorobenzene-1-sulfonamide | 668.2 | 1 | 1.75 |

| # | Structure | Name | Obs. MS Ion | HPLC Method ID | RT |
|---|---|---|---|---|---|
| 546. | 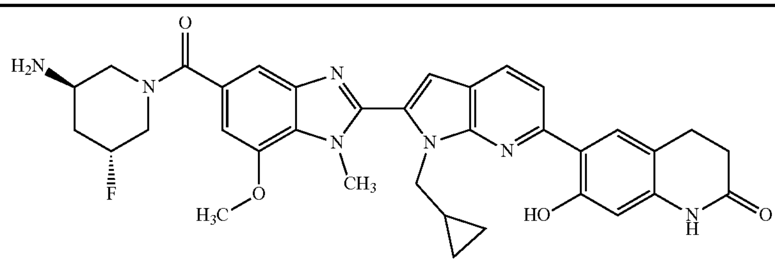 | 6-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-7-hydroxy-1,2,3,4-tetrahydroquinolin-2-one | 638.5 | 2 | 1.4 |
| 547. | 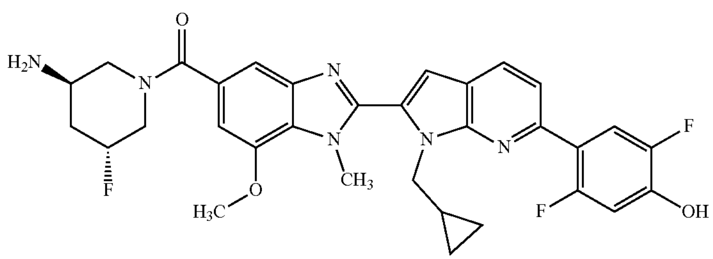 [SMILES: COc1cc(C(=O)N2C[C@H](N)C[C@@H](F)C2)cc2nc(-c3cc4ccc(-c5cc(F)c(O)cc5F)nc4n3CC3CC3)n(C)c12] | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2,5-difluorophenol | 605.3 | 1 | 1.88 |
| 548. | 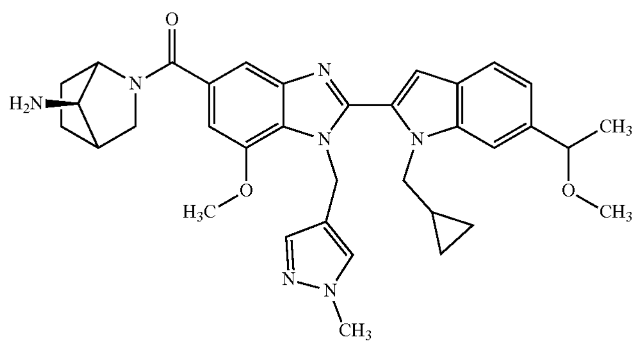 [SMILES: COc1cc(C(=O)N2CC3CCC2[C@@H]3N)cc2nc(-c3cc4ccc(C(C)OC)cc4n3CC3CC3)n(Cc3cnn(C)c3)c12] | (7R)-2-{2-[1-(cyclopropylmethyl)-6-(1-methoxyethyl)-1H-indol-2-yl]-7-methoxy-1-[(1-methyl-1H-pyrazol-4-yl)methyl]-1H-1,3-benzodiazole-5-carbonyl}-2-azabicyclo[2.2.1]heptan-7-amine (mixture of diastereomers) | 608.4 | 2 | 1.4 |

| # | Structure | Name | Obs. MS Ion | HPLC Method ID | RT |
|---|---|---|---|---|---|
| 549. | 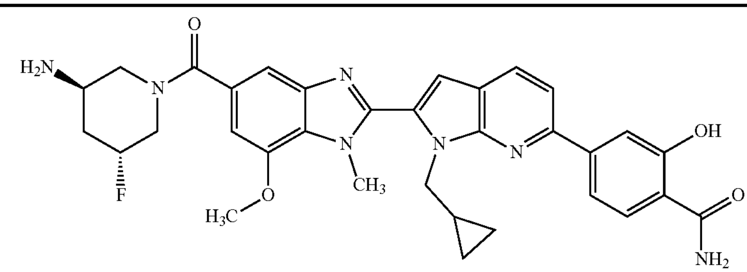 | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-hydroxybenzamide | 612.2 | 1 | 1.67 |
| 550. | 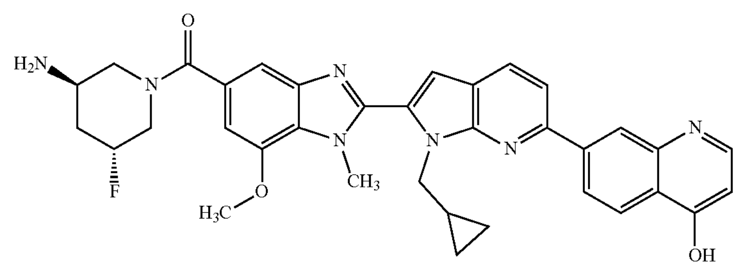 [SMILES: COc1cc(C(=O)N2C[C@H](N)C[C@@H](F)C2)cc2nc(-c3cc4ccc(-c5ccc6c(O)ccnc6c5)nc4n3CC3CC3)n(C)c12] | 7-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)quinolin-4-ol | 620 | 2 | 1.18 |
| 551. | 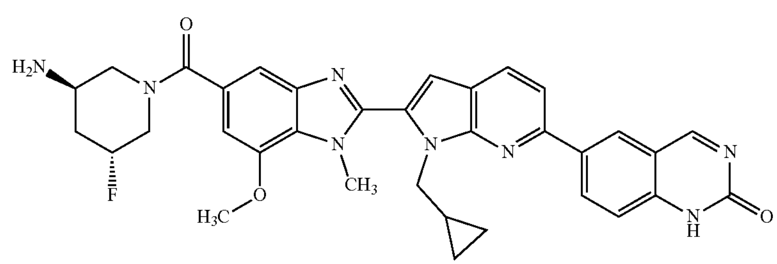 [SMILES: COc1cc(C(=O)N2C[C@H](N)C[C@@H](F)C2)cc2nc(-c3cc4ccc(-c5ccc6[nH]c(=O)ncc6c5)nc4n3CC3CC3)n(C)c12] | 6-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-1,2-dihydroquinazolin-2-one | 621.4 | 2 | 1.4 |

| # | Structure | Name | Obs. MS Ion | HPLC Method ID | RT |
|---|---|---|---|---|---|
| 552. | 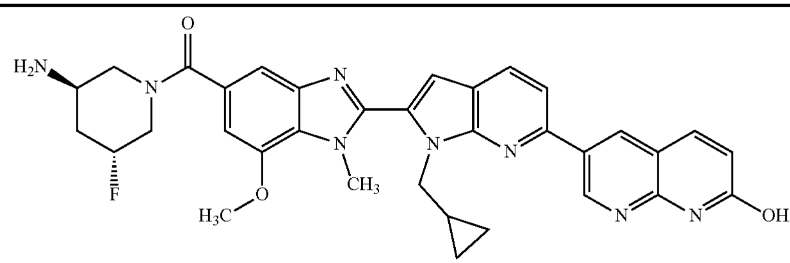 | 6-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-1,8-naphthyridin-2-ol | 621.2 | 2 | 1.22 |
| 553. | 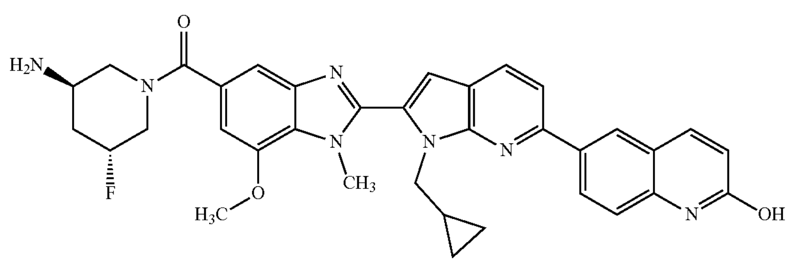 [SMILES: COc1cc(C(=O)N2C[C@H](N)C[C@@H](F)C2)cc2nc(-c3cc4ccc(-c5cnc6nc(O)ccc6c5)nc4n3CC3CC3)n(C)c12] | 6-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)quinolin-2-ol | 620.1 | 1 | 1.65 |
| 554. | 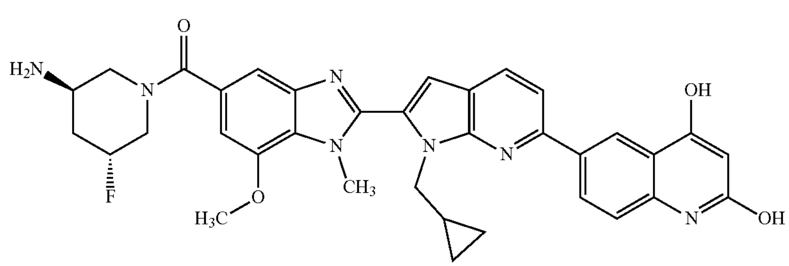 [SMILES: COc1cc(C(=O)N2C[C@H](N)C[C@@H](F)C2)cc2nc(-c3cc4ccc(-c5ccc6nc(O)cc(O)c6c5)nc4n3CC3CC3)n(C)c12] | 6-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)quinoline-2,4-diol | 636.4 | 1 | 1.45 |

| # | Structure | Name | Obs. MS Ion | HPLC Method ID | RT |
|---|---|---|---|---|---|
| 555. | 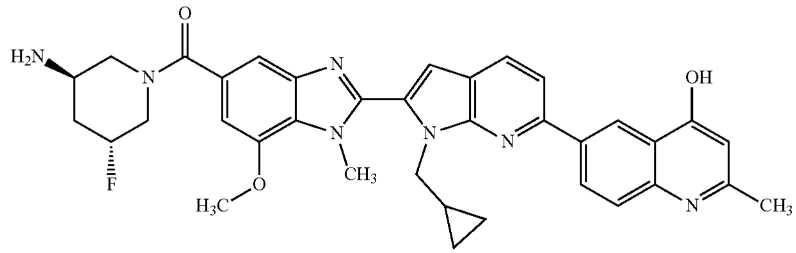 [SMILES: COc1cc(C(=O)N2C[C@H](N)C[C@@H](F)C2)cc2nc(-c3cc4ccc(-c5ccc6nc(C)cc(O)c6c5)nc4n3CC3CC3)n(C)c12] | 6-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-methylquinolin-4-ol | 634.2 | 1 | 1.55 |
| 556. | 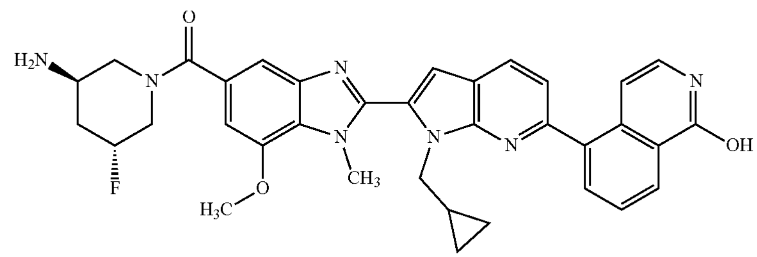 [SMILES: COc1cc(C(=O)N2C[C@H](N)C[C@@H](F)C2)cc2nc(-c3cc4ccc(-c5cccc6c(O)nccc56)nc4n3CC3CC3)n(C)c12] | 5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)isoquinolin-1-ol | 620.3 | 1 | 1.62 |
| 557. | 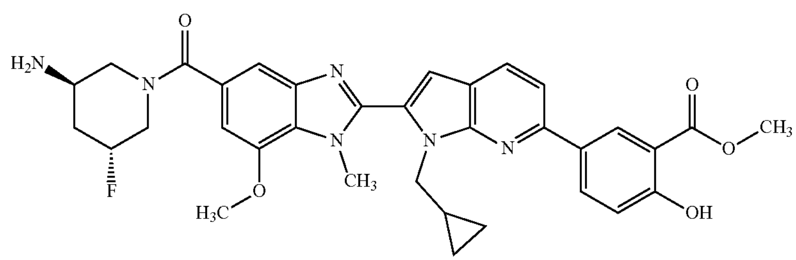 [SMILES: COC(=O)c1cc(-c2ccc3cc(-c4nc5cc(C(=O)N6C[C@H](N)C[C@@H](F)C6)cc(OC)c5n4C)n(CC4CC4)c3n2)ccc1O] | methyl 5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-hydroxybenzoate | 627 | 1 | 2.17 |

| # | Structure | Name | Obs. MS Ion | HPLC Method ID | RT |
|---|---|---|---|---|---|
| 558. | 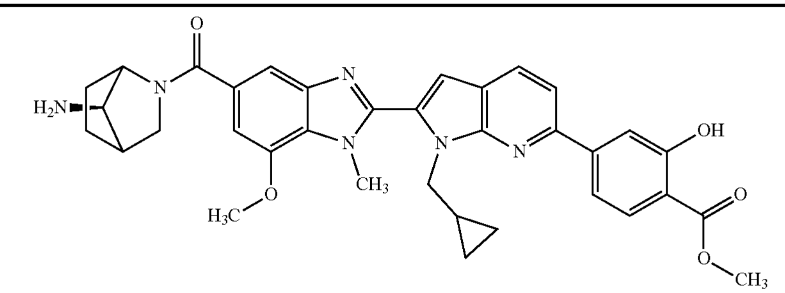 | methyl 4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-hydroxybenzoate | 621.2 | 1 | 2.19 |
| 559. | 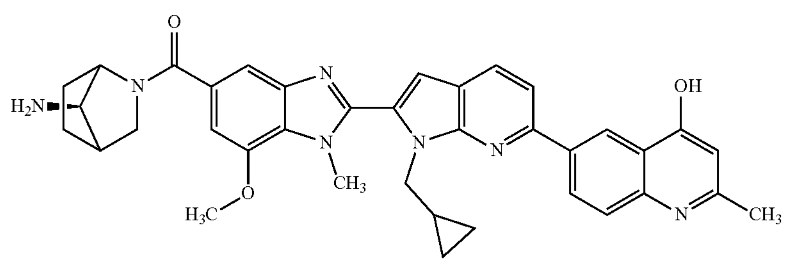 [SMILES: COc1cc(C(=O)N2CC3CCC2[C@@H]3N)cc2nc(-c3cc4ccc(-c5ccc6nc(C)cc(O)c6c5)nc4n3CC3CC3)n(C)c12] | 6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-methylquinolin-4-ol | 628.2 | 1 | 1.53 |
| 560. | 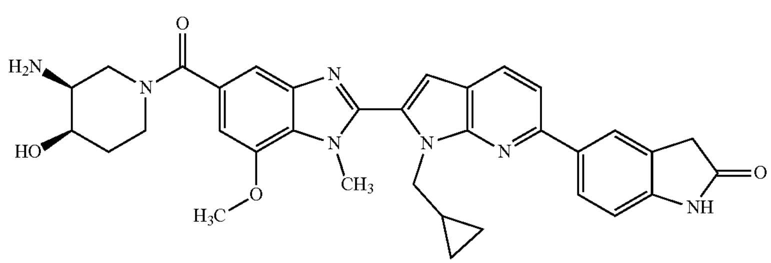 [SMILES: COc1cc(C(=O)N2CC[C@@H](O)[C@@H](N)C2)cc2nc(-c3cc4ccc(-c5ccc6c(c5)CC(=O)N6)nc4n3CC3CC3)n(C)c12] | 5-(2-{5-[(3S,4R)-3-amino-4-hydroxypiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2,3-dihydro-1H-indol-2-one | 606.2 | 2 | 1.35 |

| # | Structure | Name | Obs. MS Ion | HPLC Method ID | RT |
|---|---|---|---|---|---|
| 561. | 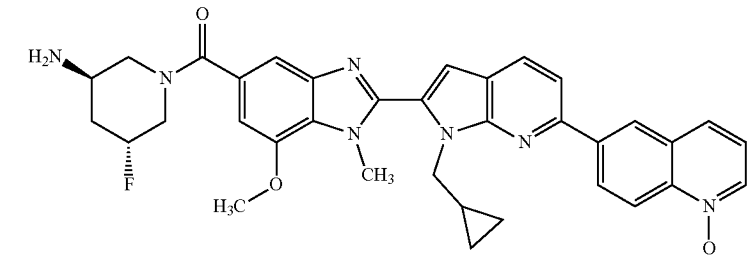 | 6-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)quinolin-1-ium-1-olate | 620.4 | 1 | 1.39 |
| 562. | 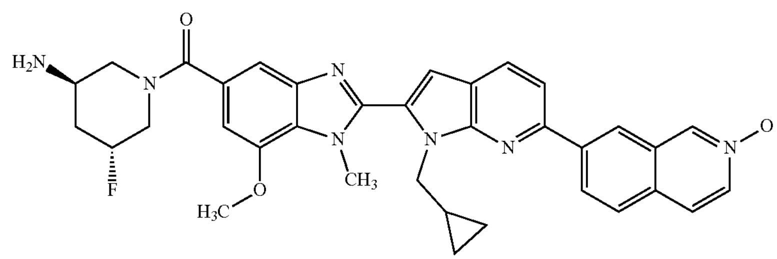 | 7-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)isoquinolin-2-ium-2-olate | 620.1 | 1 | 1.57 |
| 563. | 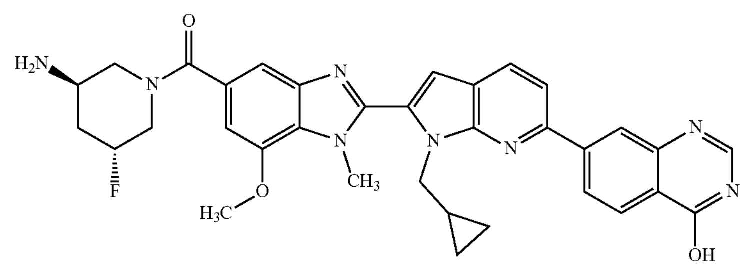 [SMILES: COc1cc(C(=O)N2C[C@H](N)C[C@@H](F)C2)cc2nc(-c3cc4ccc(-c5ccc6c(O)ncnc6c5)nc4n3CC3CC3)n(C)c12] | 7-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)quinazolin-4-ol | 621.2 | 2 | 1.22 |

| # | Structure | Name | Obs. MS Ion | HPLC Method ID | RT |
|---|---|---|---|---|---|
| 564. | 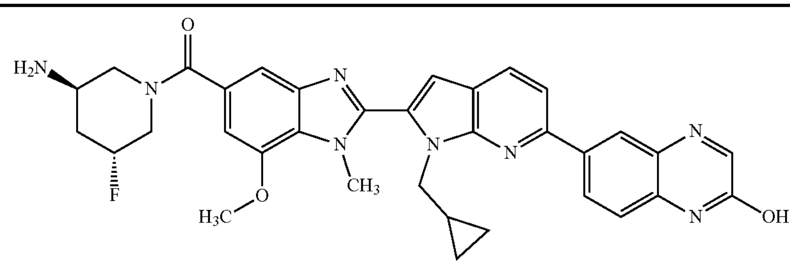 | 6-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)quinoxalin-2-ol | 621.4 | 2 | 1.26 |
| 565. | 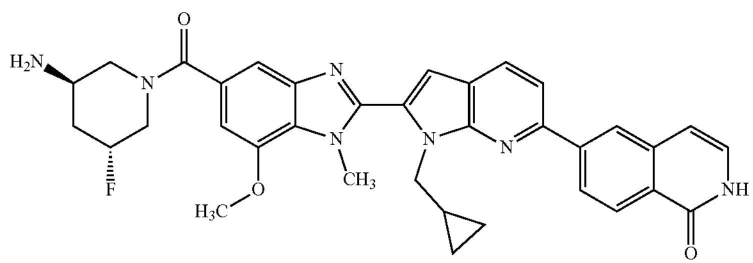 [SMILES: COc1cc(C(=O)N2C[C@H](N)C[C@@H](F)C2)cc2nc(-c3cc4ccc(-c5ccc6c(=O)[nH]ccc6c5)nc4n3CC3CC3)n(C)c12] | 6-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-1,2-dihydroisoquinolin-1-one | 620.2 | 2 | 1.47 |
| 566. | 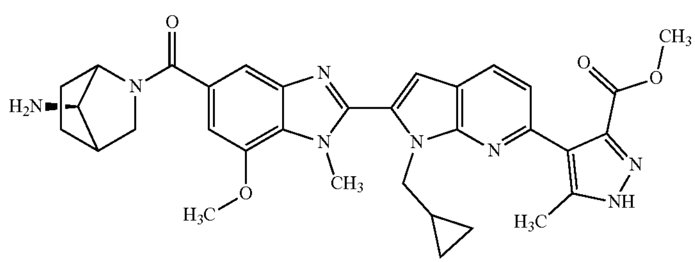 [SMILES: COC(=O)c1n[nH]c(C)c1-c1ccc2cc(-c3nc4cc(C(=O)N5CC6CCC5[C@@H]6N)cc(OC)c4n3C)n(CC3CC3)c2n1] | methyl 4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-5-methyl-1H-pyrazole-3-carboxylate | 609.1 | 2 | 1.14 |

| # | Structure | Name | Obs. MS Ion | HPLC Method ID | RT |
|---|---|---|---|---|---|
| 567. | 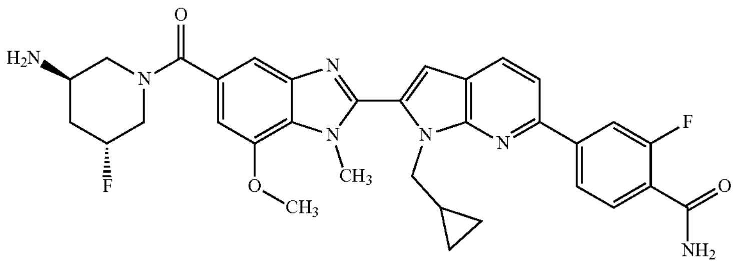 | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-fluorobenzamide | 614.4 | 1 | 1.44 |
| 568. | 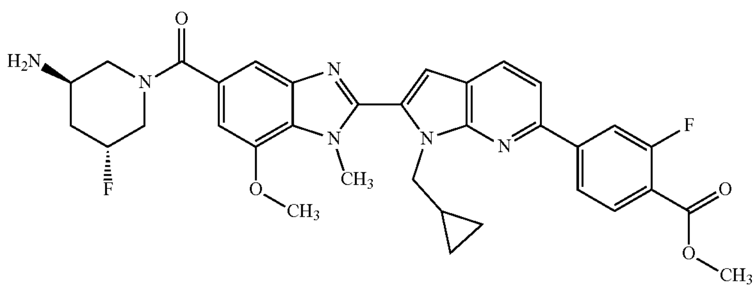 [SMILES: COC(=O)c1ccc(-c2ccc3cc(-c4nc5cc(C(=O)N6C[C@H](N)C[C@@H](F)C6)cc(OC)c5n4C)n(CC4CC4)c3n2)cc1F] | methyl 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-fluorobenzoate | 629.1 | 2 | 1.83 |
| 569. | 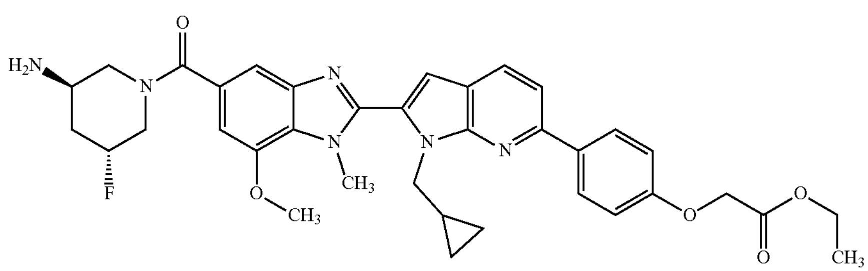 [SMILES: CCOC(=O)COc1ccc(-c2ccc3cc(-c4nc5cc(C(=O)N6C[C@H](N)C[C@@H](F)C6)cc(OC)c5n4C)n(CC4CC4)c3n2)cc1] | ethyl 2-[4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)phenoxy]acetate | 655.2 | 2 | 1.68 |

| # | Structure | Name | Obs. MS Ion | HPLC Method ID | RT |
|---|---|---|---|---|---|
| 570. | 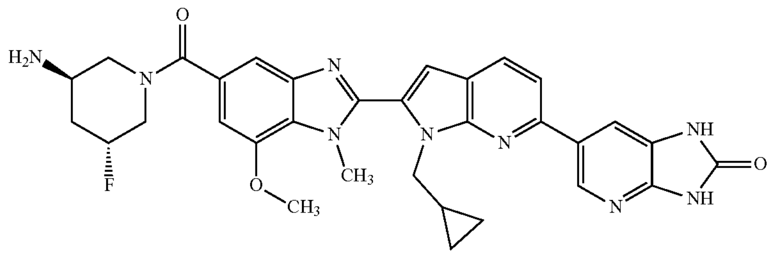 [SMILES: COc1cc(C(=O)N2C[C@H](N)C[C@@H](F)C2)cc2nc(-c3cc4ccc(-c5cnc6[nH]c(=O)[nH]c6c5)nc4n3CC3CC3)n(C)c12] | 6-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-1H,2H,3H-imidazo[4,5-b]pyridin-2-one | 610.3 | 1 | 1.21 |
| 571. | 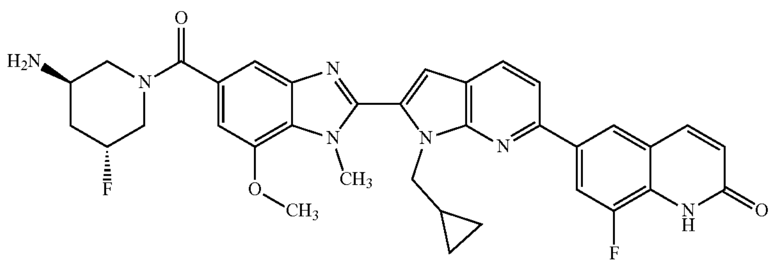 [SMILES: COc1cc(C(=O)N2C[C@H](N)C[C@@H](F)C2)cc2nc(-c3cc4ccc(-c5cc(F)c6[nH]c(=O)ccc6c5)nc4n3CC3CC3)n(C)c12] | 6-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-8-fluoro-1,2-dihydroquinolin-2-one | 638.1 | 1 | 1.58 |
| 572. | 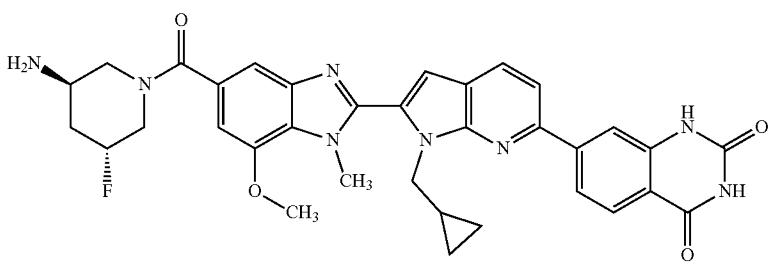 [SMILES: COc1cc(C(=O)N2C[C@H](N)C[C@@H](F)C2)cc2nc(-c3cc4ccc(-c5ccc6c(=O)[nH]c(=O)[nH]c6c5)nc4n3CC3CC3)n(C)c12] | 7-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-1,2,3,4-tetrahydroquinazoline-2,4-dione | 637.1 | 1 | 1.49 |

| # | Structure | Name | Obs. MS Ion | HPLC Method ID | RT |
|---|---|---|---|---|---|
| 573. | 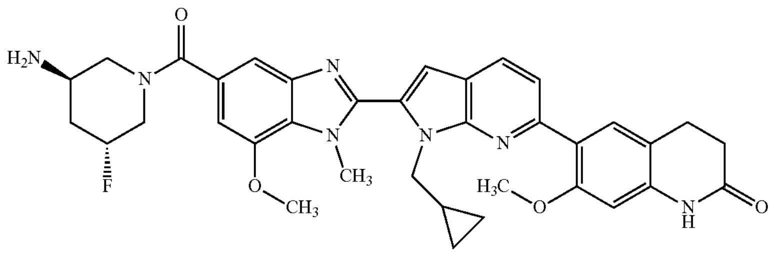 [SMILES: COc1cc2c(cc1-c1ccc3cc(-c4nc5cc(C(=O)N6C[C@H](N)C[C@@H](F)C6)cc(OC)c5n4C)n(CC4CC4)c3n1)CCC(=O)N2] | 6-(2-{5-[((3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-7-methoxy-1,2,3,4-tetrahydroquinolin-2-one | 652.2 | 1 | 1.54 |
| 574. | 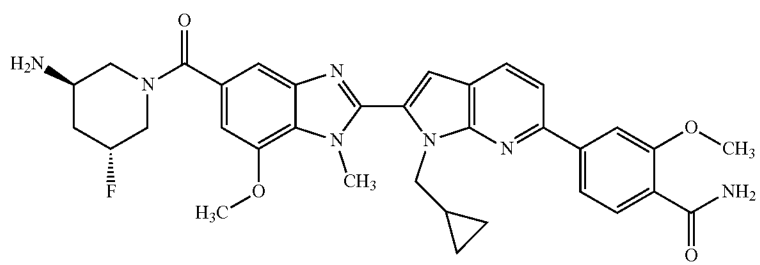 [SMILES: COc1cc(-c2ccc3cc(-c4nc5cc(C(=O)N6C[C@H](N)C[C@@H](F)C6)cc(OC)c5n4C)n(CC4CC4)c3n2)ccc1C(N)=O] | 4-(2-{5-[((3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-methoxybenzamide | 626.5 | 1 | 1.37 |
| 575. | 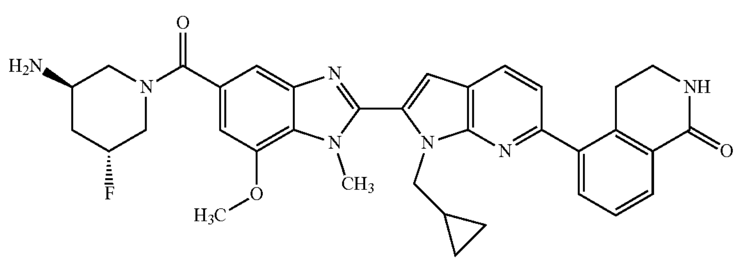 [SMILES: COc1cc(C(=O)N2C[C@H](N)C[C@@H](F)C2)cc2nc(-c3cc4ccc(-c5cccc6c5CCNC6=O)nc4n3CC3CC3)n(C)c12] | 5-(2-{5-[((3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-1,2,3,4-tetrahydroisoquinolin-1-one | 622.2 | 1 | 1.56 |

| # | Structure | Name | Obs. MS Ion | HPLC Method ID | RT |
|---|---|---|---|---|---|
| 576. | 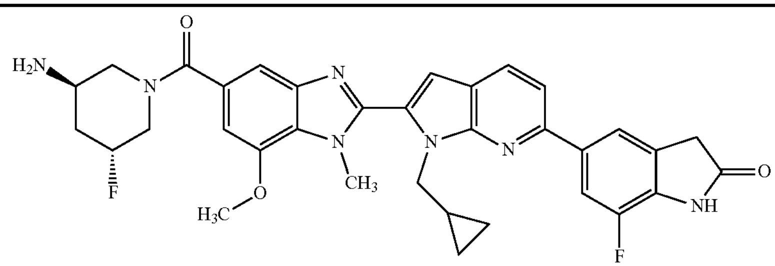 | 5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-7-fluoro-2,3-dihydro-1H-indol-2-one | 626.4 | 2 | 1.38 |
| 577. | 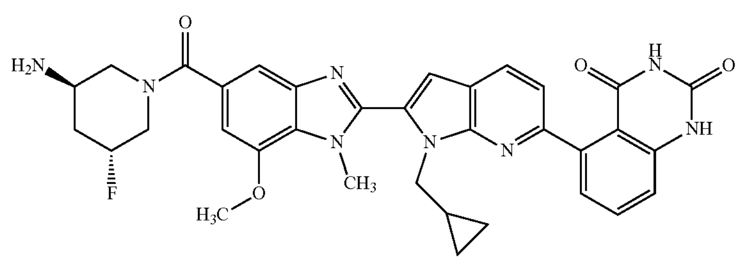 [SMILES: COc1cc(C(=O)N2C[C@H](N)C[C@@H](F)C2)cc2nc(-c3cc4ccc(-c5cccc6[nH]c(=O)[nH]c(=O)c56)nc4n3CC3CC3)n(C)c12] | 5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-1,2,3,4-tetrahydroquinazoline-2,4-dione | 637.5 | 1 | 1.29 |
| 578. | 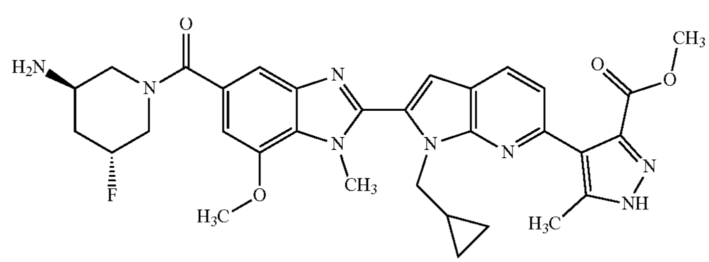 [SMILES: COC(=O)c1n[nH]c(C)c1-c1ccc2cc(-c3nc4cc(C(=O)N5C[C@H](N)C[C@@H](F)C5)cc(OC)c4n3C)n(CC3CC3)c2n1] | methyl 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-5-methyl-1H-pyrazole-3-carboxylate | 615.1 | 2 | 1.3 |

| # | Structure | Name | Obs. MS Ion | HPLC Method ID | RT |
|---|---|---|---|---|---|
| 579. | 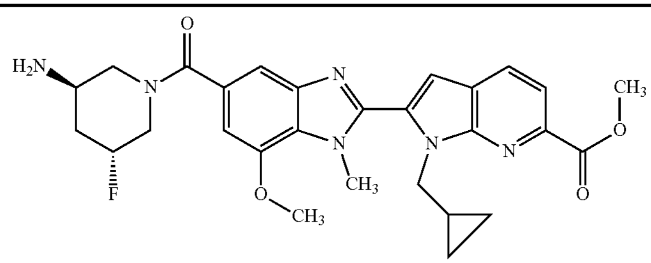 | methyl 2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridine-6-carboxylate | 535.4 | 2 | 1.4 |
| 580. | 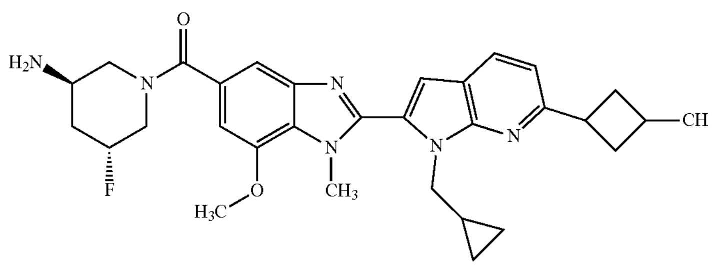 [SMILES: COc1cc(C(=O)N2C[C@H](N)C[C@@H](F)C2)cc2nc(-c3cc4ccc(C5CC(C)C5)nc4n3CC3CC3)n(C)c12] | 3-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)cyclobutan-1-ol (mixture of diastereomers) | 547.4 | 2 | 1.2 |
| 581. | 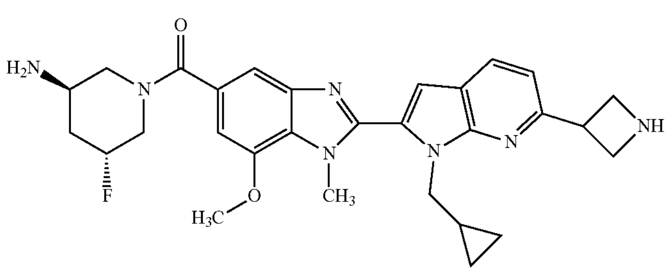 [SMILES: COc1cc(C(=O)N2C[C@H](N)C[C@@H](F)C2)cc2nc(-c3cc4ccc(C5CNC5)nc4n3CC3CC3)n(C)c12] | (3R,5R)-1-(2-[6-(azetidin-3-yl)-1-(cyclopropylmethyl)-1H-pyrrolo[2,3-b]pyridin-2-yl]-7-methoxy-1-methyl-1H-1,3-benzodiazole-5-carbonyl)-5-fluoropiperidin-3-amine | 532.5 | 1 | 1.02 |

| # | Structure | Name | Obs. MS Ion | HPLC Method ID | RT |
|---|---|---|---|---|---|
| 582. | 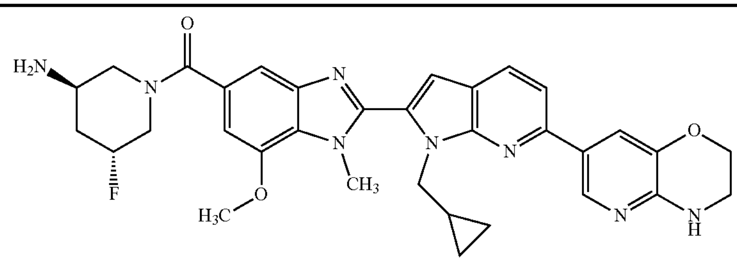 | (3R,5R)-1-{2-[1-(cyclopropylmethyl)-6-{2H,3H,4H-pyrido[3,2-b][1,4]oxazin-7-yl}-1H-pyrrolo[2,3-b]pyridin-2-yl]-7-methoxy-1-methyl-1H-1,3-benzodiazole-5-carbonyl}-5-fluoropiperidin-3-amine | 611.4 | 1 | 1.5 |
| 583. | 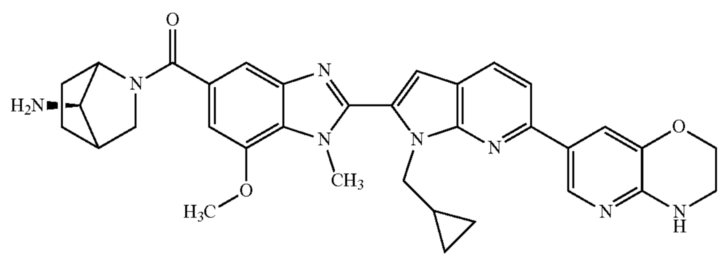 [SMILES: COc1cc(C(=O)N2CC3CCC2[C@@H]3N)cc2nc(-c3cc4ccc(-c5cnc6c(c5)OCCN6)nc4n3CC3CC3)n(C)c12] | (7R)-2-{2-[1-(cyclopropylmethyl)-6-{2H,3H,4H-pyrido[3,2-b][1,4]oxazin-7-yl}-1H-pyrrolo[2,3-b]pyridin-2-yl]-7-methoxy-1-methyl-1H-1,3-benzodiazole-5-carbonyl}-2-azabicyclo[2.2.1]heptan-7-amine | 605.5 | 1 | 1.52 |
| 584. | 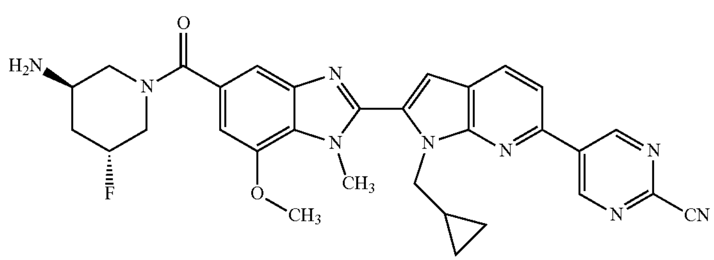 [SMILES: COc1cc(C(=O)N2C[C@H](N)C[C@@H](F)C2)cc2nc(-c3cc4ccc(-c5cnc(C#N)nc5)nc4n3CC3CC3)n(C)c12] | 5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)pyrimidine-2-carbonitrile | 580.4 | 2 | 1.56 |
| 585. | 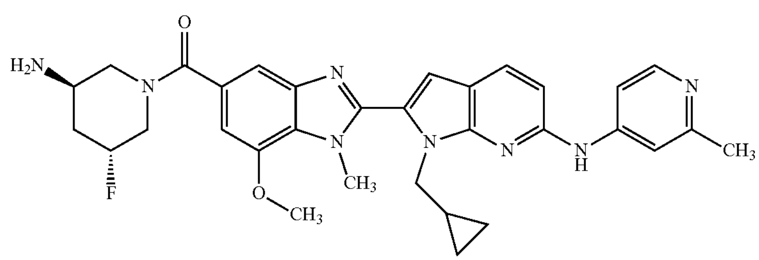 [SMILES: COc1cc(C(=O)N2C[C@H](N)C[C@@H](F)C2)cc2nc(-c3cc4ccc(Nc5ccnc(C)c5)nc4n3CC3CC3)n(C)c12] | N-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-methylpyridin-4-amine | 583.4 | 1 | 1.21 |

| # | Structure | Name | Obs. MS Ion | HPLC Method ID | RT |
|---|---|---|---|---|---|
| 586. | 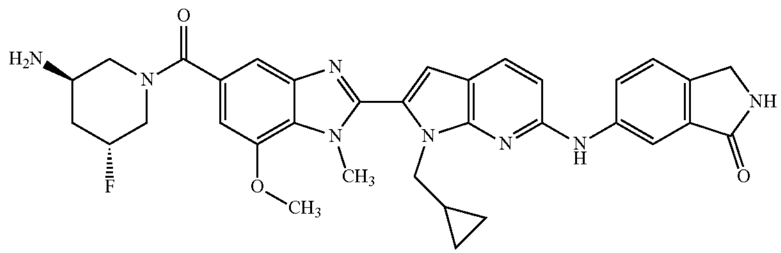 [SMILES: COc1cc(C(=O)N2C[C@H](N)C[C@@H](F)C2)cc2nc(-c3cc4ccc(Nc5ccc6c(c5)C(=O)NC6)nc4n3CC3CC3)n(C)c12] | 6-[(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)amino]-2,3-dihydro-1H-isoindol-1-one | 623.4 | 1 | 1.35 |
| 587. | 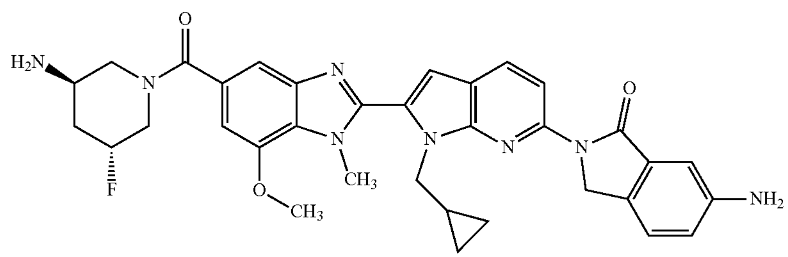 [SMILES: COc1cc(C(=O)N2C[C@H](N)C[C@@H](F)C2)cc2nc(-c3cc4ccc(N5Cc6ccc(N)cc6C5=O)nc4n3CC3CC3)n(C)c12] | 6-amino-2-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2,3-dihydro-1H-isoindol-1-one | 623.5 | 1 | 1.5 |
| 588. | 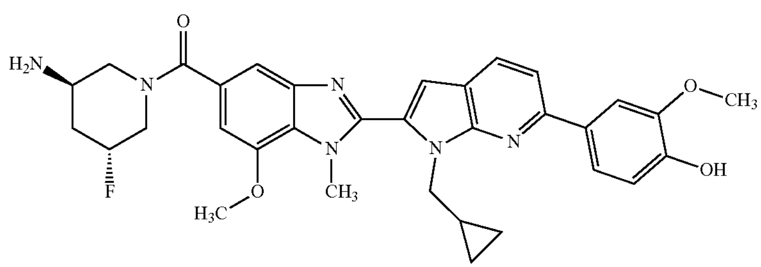 [SMILES: COc1cc(-c2ccc3cc(-c4nc5cc(C(=O)N6C[C@H](N)C[C@@H](F)C6)cc(OC)c5n4C)n(CC4CC4)c3n2)ccc1O] | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-methoxyphenol | 599.3 | 1 | 1.65 |

| # | Structure | Name | Obs. MS Ion | HPLC Method ID | RT |
|---|---|---|---|---|---|
| 589. | 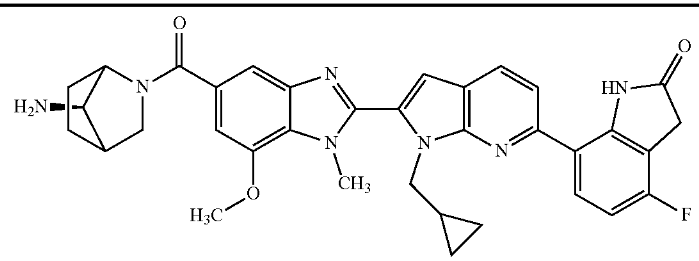 | 7-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-4-fluoro-2,3-dihydro-1H-indol-2-one | 620.4 | 2 | 1.62 |
| 590. | 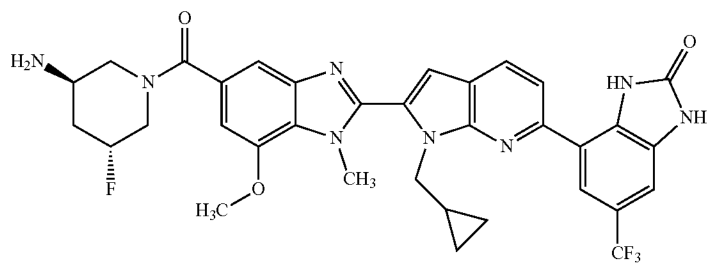 [SMILES: COc1cc(C(=O)N2C[C@H](N)C[C@@H](F)C2)cc2nc(-c3cc4ccc(-c5cc(C(F)(F)F)cc6[nH]c(=O)[nH]c56)nc4n3CC3CC3)n(C)c12] | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-6-(trifluoromethyl)-1H-pyrrolo[2,3-b]pyridin-6-yl)-2,3-dihydro-1H-1,3-benzodiazol-2-one | 677.1 | 1 | 2.03 |
| 591. | 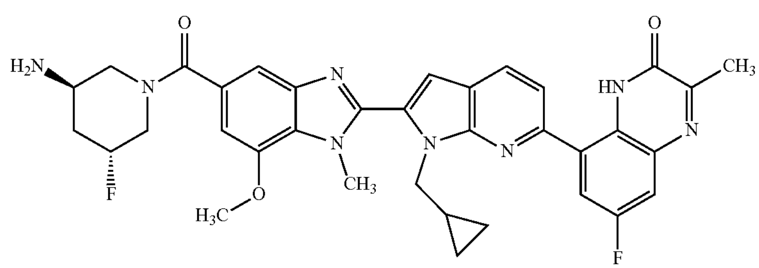 [SMILES: COc1cc(C(=O)N2C[C@H](N)C[C@@H](F)C2)cc2nc(-c3cc4ccc(-c5cc(F)cc6nc(C)c(=O)[nH]c56)nc4n3CC3CC3)n(C)c12] | 8-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-6-fluoro-3-methyl-1,2-dihydroquinoxalin-2-one | 653.2 | 1 | 1.87 |

| # | Structure | Name | Obs. MS Ion | HPLC Method ID | RT |
|---|---|---|---|---|---|
| 592. | 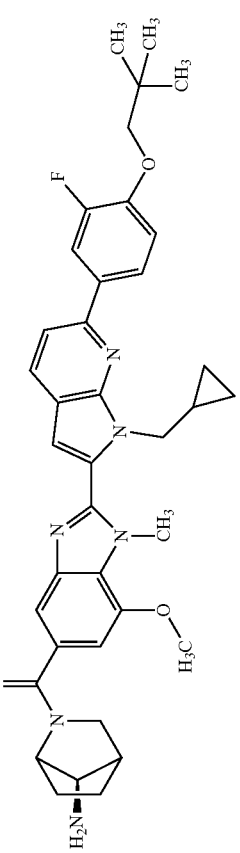 | 1-[4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-fluorophenoxy]-2-methylpropan-2-ol | 653.5 | 2 | 1.61 |
| 593. | 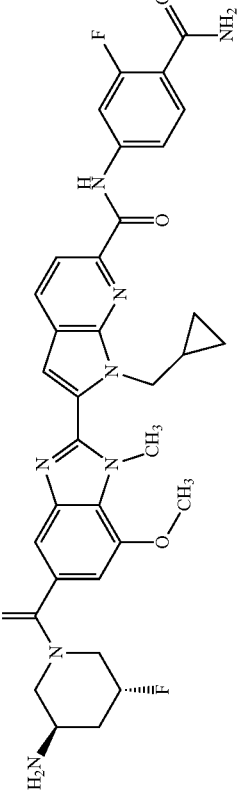 | 2-{5-[(3R,5R)-3-amino-5-fluoropiperidine-1-carbonyl]-7-methoxy-1-methyl-1H-1,3-benzodiazol-2-yl}-N-(4-carbamoyl-3-fluorophenyl)-1-(cyclopropylmethyl)-1H-pyrrolo[2,3-b]pyridine-6-carboxamide | 657.4 | 1 | 1.52 |
| 594. | 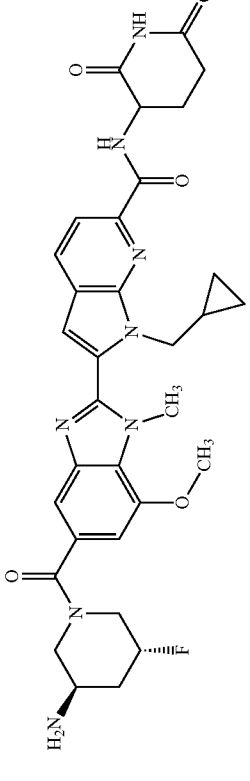 | 2-{5-[(3R,5R)-3-amino-5-fluoropiperidine-1-carbonyl]-7-methoxy-1-methyl-1H-1,3-benzodiazol-2-yl}-1-(cyclopropylmethyl)-N-(2,6-dioxopiperidin-3-yl)-1H-pyrrolo[2,3-b]pyridine-6-carboxamide | 631.4 | 1 | 1.27 |

| # | Structure | Name | Obs. MS Ion | HPLC Method ID | RT |
|---|---|---|---|---|---|
| 595. | 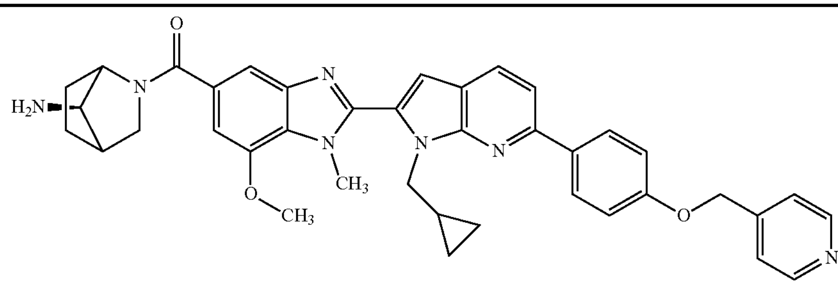 | (7R)-2-{2-[1-(cyclopropylmethyl)-6-{4-[(pyridin-4-yl)methoxy]phenyl}-1H-pyrrolo[2,3-b]pyridin-2-yl]-7-methoxy-1-methyl-1H-1,3-benzodiazole-5-carbonyl}-2-azabicyclo[2.2.1]heptan-7-amine | 654.4 | 1 | 1.94 |
| 596. | 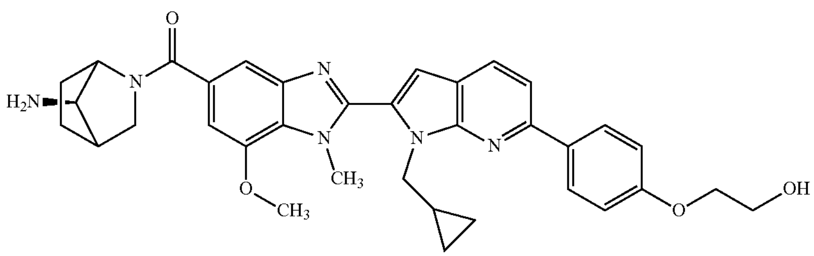 [SMILES: COc1cc(C(=O)N2CC3CCC2[C@@H]3N)cc2nc(-c3cc4ccc(-c5ccc(OCCO)cc5)nc4n3CC3CC3)n(C)c12] | 2-[4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenoxy]ethan-1-ol | 607.5 | 1 | 1.64 |
| 597. | 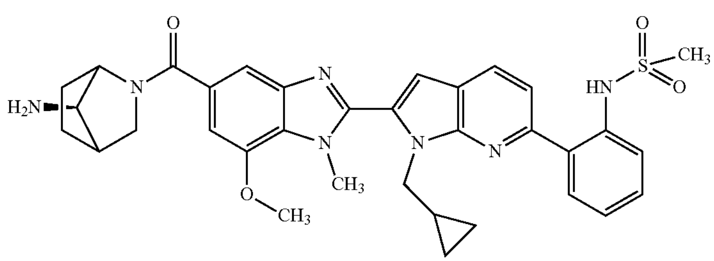 [SMILES: COc1cc(C(=O)N2CC3CCC2[C@@H]3N)cc2nc(-c3cc4ccc(-c5ccccc5NS(C)(=O)=O)nc4n3CC3CC3)n(C)c12] | N-[2-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]methanesulfonamide | 640 | 1 | 1.91 |

-continued

| # | Structure | Name | Obs. MS Ion | HPLC Method ID | RT |
|---|---|---|---|---|---|
| 598. | 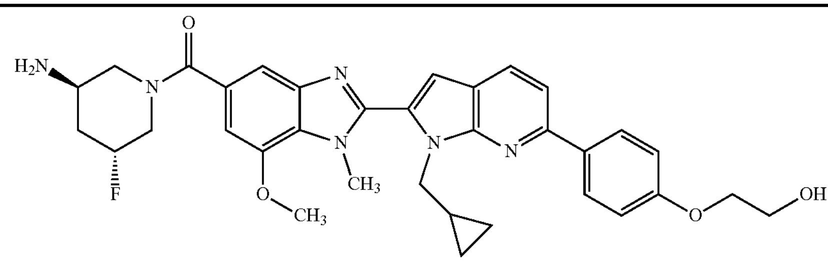 | 2-[4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)phenoxy]ethan-1-ol | 613.4 | 2 | 1.47 |
| 599. | 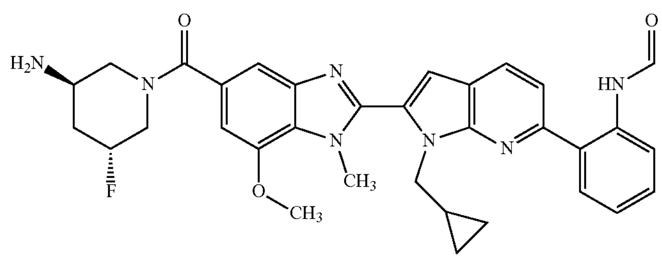 [SMILES: COc1cc(C(=O)N2C[C@H](N)C[C@@H](F)C2)cc2nc(-c3cc4ccc(-c5ccccc5NC=O)nc4n3CC3CC3)n(C)c12] | N-[2-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)phenyl]formamide | 596.2 | 2 | 1.62 |
| 600. | 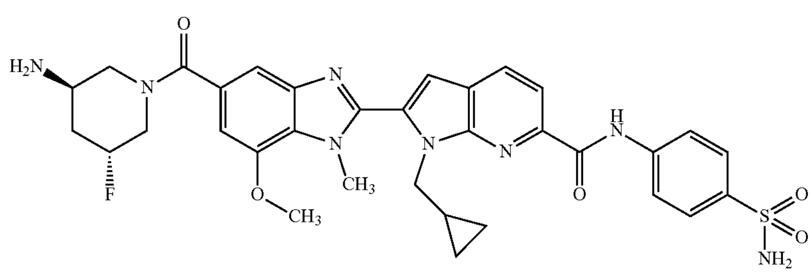 [SMILES: COc1cc(C(=O)N2C[C@H](N)C[C@@H](F)C2)cc2nc(-c3cc4ccc(C(=O)Nc5ccc(S(N)(=O)=O)cc5)nc4n3CC3CC3)n(C)c12] | 2-{5-[(3R,5R)-3-amino-5-fluoropiperidine-1-carbonyl]-7-methoxy-1-methyl-1H-1,3-benzodiazol-2-yl}-1-(cyclopropylmethyl)-N-(4-sulfamoylphenyl)-1H-pyrrolo[2,3-b]pyridine-6-carboxamide | 675 | 1 | 1.57 |

| # | Name | Obs. MS Ion | HPLC Method ID | RT |
|---|---|---|---|---|
| 601. | 2-{5-[(3R,5R)-3-amino-5-fluoropiperidine-1-carbonyl]-7-methoxy-1-methyl-1H-1,3-benzodiazol-2-yl}-1-(cyclopropylmethyl)-N-(4-hydroxy-3-methoxyphenyl)-1H-pyrrolo[2,3-b]pyridine-6-carboxamide | 642.5 | 1 | 1.52 |
| 602. | 2-{5-[(3R,5R)-3-amino-5-fluoropiperidine-1-carbonyl]-7-methoxy-1-methyl-1H-1,3-benzodiazol-2-yl}-N-[3-(hydroxymethyl)pyridin-4-yl]-1-(cyclopropylmethyl)-1H-pyrrolo[2,3-b]pyridine-6-carboxamide | 627.4 | 1 | 1.46 |
| 603. | 2-{5-[(3R,5R)-3-amino-5-fluoropiperidine-1-carbonyl]-7-methoxy-1-methyl-1H-1,3-benzodiazol-2-yl}-1-(cyclopropylmethyl)-N-(3-sulfamoylphenyl)-1H-pyrrolo[2,3-b]pyridine-6-carboxamide | 675.2 | 1 | 1.5 |

| # | Structure | Name | Obs. MS Ion | HPLC Method ID | RT |
|---|---|---|---|---|---|
| 604. | 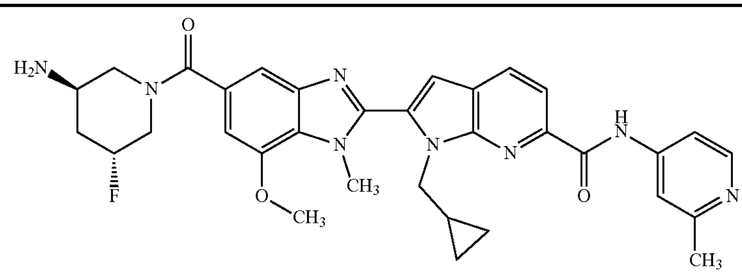 | 2-{5-[(3R,5R)-3-amino-5-fluoropiperidine-1-carbonyl]-7-methoxy-1-methyl-1H-1,3-benzodiazol-2-yl}-1-(cyclopropylmethyl)-N-(2-methylpyridin-4-yl)-1H-pyrrolo[2,3-b]pyridine-6-carboxamide | 611.4 | 1 | 1.58 |
| 605. | 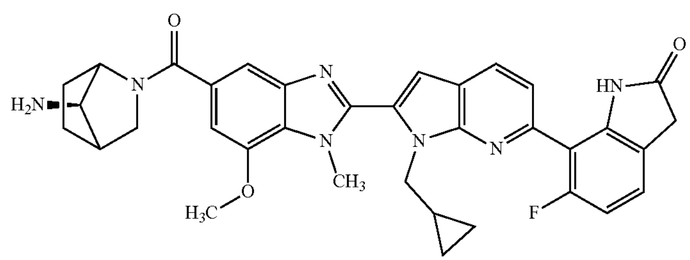 [SMILES: COc1cc(C(=O)N2CC3CCC2[C@@H]3N)cc2nc(-c3cc4ccc(-c5c(F)ccc6c5NC(=O)C6)nc4n3CC3CC3)n(C)c12] | 7-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-6-fluoro-2,3-dihydro-1H-indol-2-one | 620.5 | 1 | 1.83 |
| 606. | 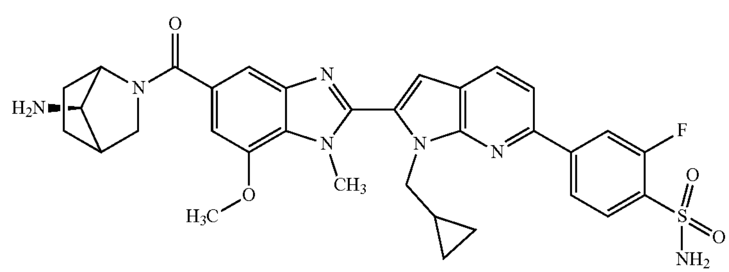 [SMILES: COc1cc(C(=O)N2CC3CCC2[C@@H]3N)cc2nc(-c3cc4ccc(-c5ccc(S(N)(=O)=O)c(F)c5)nc4n3CC3CC3)n(C)c12] | 4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-fluorobenzene-1-sulfonamide | 644.4 | 1 | 1.58 |

| # | Structure | Name | Obs. MS Ion | HPLC Method ID | RT |
|---|---|---|---|---|---|
| 607. | 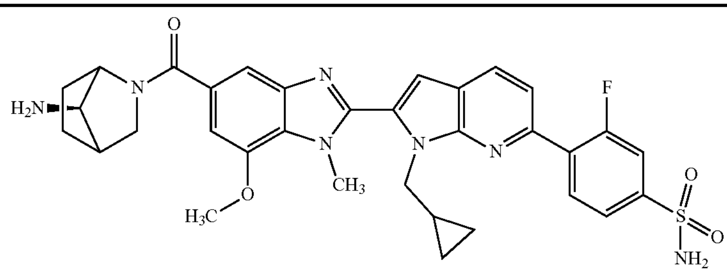 | 4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-3-fluorobenzene-1-sulfonamide | 644.4 | 2 | 1.41 |
| 608. | 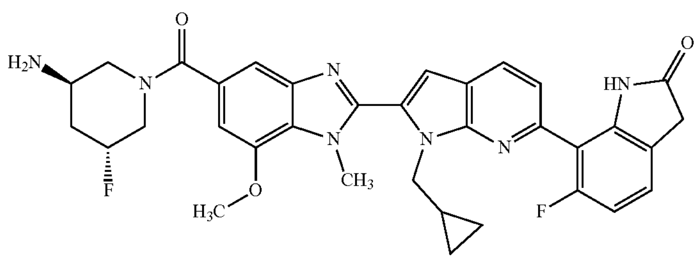 [SMILES: COc1cc(C(=O)N2C[C@H](N)C[C@@H](F)C2)cc2nc(-c3cc4ccc(-c5c(F)ccc6c5NC(=O)C6)nc4n3CC3CC3)n(C)c12] | 7-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-6-fluoro-2,3-dihydro-1H-indol-2-one | 626.2 | 2 | 1.57 |
| 609. | 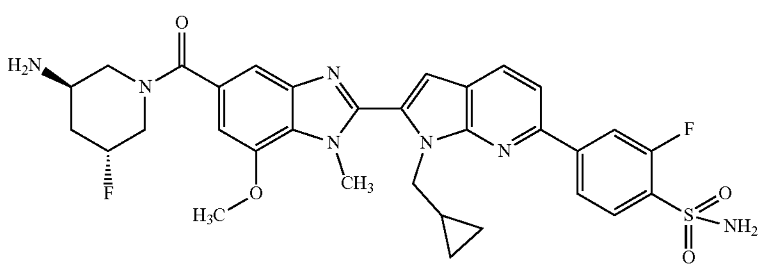 [SMILES: COc1cc(C(=O)N2C[C@H](N)C[C@@H](F)C2)cc2nc(-c3cc4ccc(-c5ccc(S(N)(=O)=O)c(F)c5)nc4n3CC3CC3)n(C)c12] | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-fluorobenzene-1-sulfonamide | 650.4 | 1 | 1.56 |

| # | Structure | Name | Obs. MS Ion | HPLC Method ID | RT |
|---|---|---|---|---|---|
| 610. | 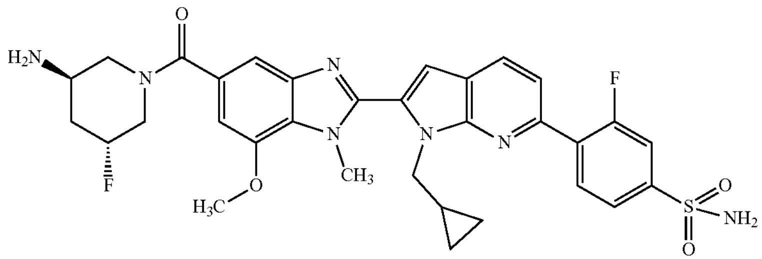 [SMILES: COc1cc(C(=O)N2C[C@H](N)C[C@@H](F)C2)cc2nc(-c3cc4ccc(-c5ccc(S(N)(=O)=O)cc5F)nc4n3CC3CC3)n(C)c12] | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-3-fluorobenzene-1-sulfonamide | 650.4 | 2 | 1.41 |
| 611. | 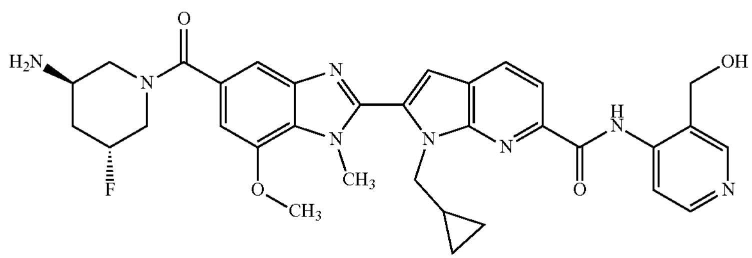 [SMILES: COc1cc(C(=O)N2C[C@H](N)C[C@@H](F)C2)cc2nc(-c3cc4ccc(C(=O)Nc5ccncc5CO)nc4n3CC3CC3)n(C)c12] | 2-{5-[(3R,5R)-3-amino-5-fluoropiperidine-1-carbonyl]-7-methoxy-1-methyl-1H-1,3-benzodiazol-2-yl}-1-(cyclopropylmethyl)-N-[3-(hydroxymethyl)pyridin-4-yl]-1H-pyrrolo[2,3-b]pyridine-6-carboxamide | 627.2 | 2 | 0.98 |
| 612. | 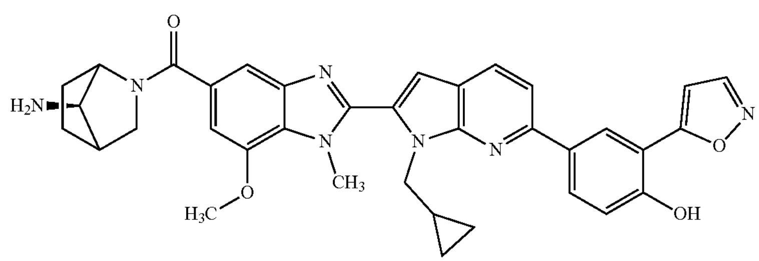 [SMILES: COc1cc(C(=O)N2CC3CCC2[C@@H]3N)cc2nc(-c3cc4ccc(-c5ccc(O)c(-c6ccno6)c5)nc4n3CC3CC3)n(C)c12] | 4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-(1,2-oxazol-5-yl)phenol | 630.4 | 1 | 1.43 |

-continued

| # | Structure | Name | Obs. MS Ion | HPLC Method ID | RT |
|---|---|---|---|---|---|
| 613. | 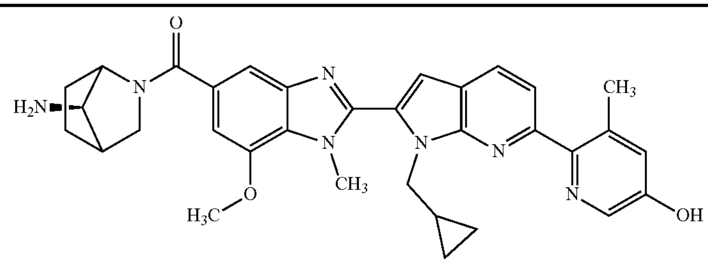 | 6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-5-methylpyridin-3-ol | 578.1 | 1 | 1.57 |
| 614. | 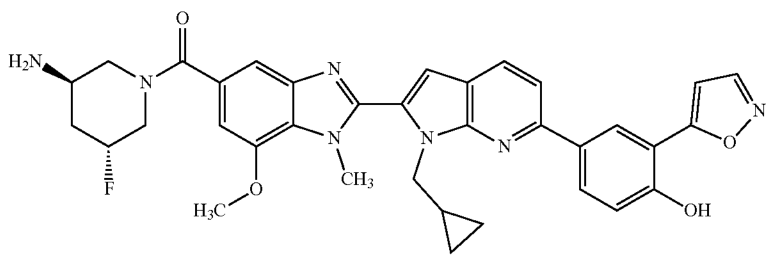 [SMILES: COc1cc(C(=O)N2C[C@H](N)C[C@@H](F)C2)cc2nc(-c3cc4ccc(-c5ccc(O)c(-c6ccno6)c5)nc4n3CC3CC3)n(C)c12] | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-(1,2-oxazol-5-yl)phenol | 636.2 | 1 | 1.44 |
| 615. | 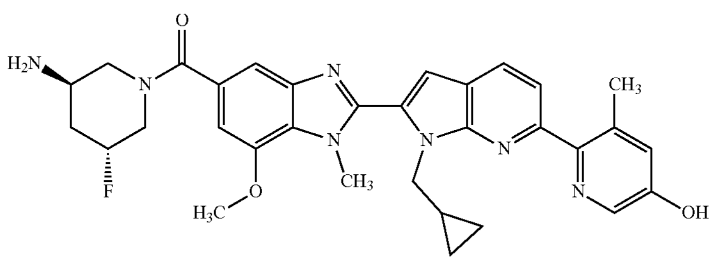 [SMILES: COc1cc(C(=O)N2C[C@H](N)C[C@@H](F)C2)cc2nc(-c3cc4ccc(-c5ncc(O)cc5C)nc4n3CC3CC3)n(C)c12] | 6-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-5-methylpyridin-3-ol | 584 | 2 | 1.19 |
| 616. | 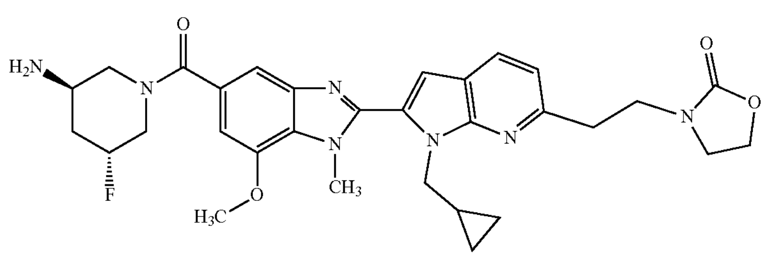 [SMILES: COc1cc(C(=O)N2C[C@H](N)C[C@@H](F)C2)cc2nc(-c3cc4ccc(CCN5CCOC5=O)nc4n3CC3CC3)n(C)c12] | 3-[2-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)ethyl]-1,3-oxazolidin-2-one | 590 | 2 | 1.26 |

| # | Structure | Name | Obs. MS Ion | HPLC Method ID | RT |
|---|---|---|---|---|---|
| 617. | 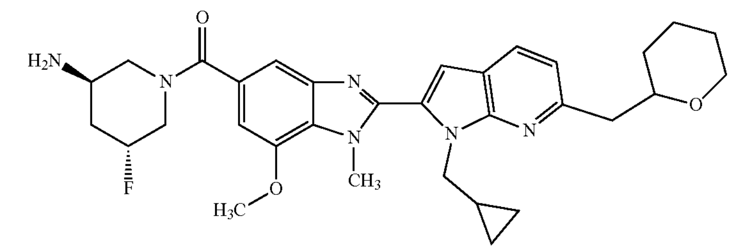 [SMILES: COc1cc(C(=O)N2C[C@H](N)C[C@@H](F)C2)cc2nc(-c3cc4ccc(CC5CCCCO5)nc4n3CC3CC3)n(C)c12] | (3R,5R)-1-{2-[1-(cyclopropylmethyl)-6-[(oxan-2-yl)methyl]-1H-pyrrolo[2,3-b]pyridin-2-yl]-7-methoxy-1-methyl-1H-1,3-benzodiazole-5-carbonyl}-5-fluoropiperidin-3-amine | 575.02 | 2 | |
| 618. | 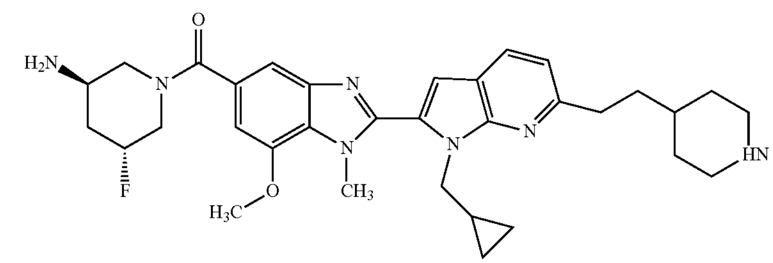 [SMILES: COc1cc(C(=O)N2C[C@H](N)C[C@@H](F)C2)cc2nc(-c3cc4ccc(CCC5CCNCC5)nc4n3CC3CC3)n(C)c12] | (3R,5R)-1-{2-[1-(cyclopropylmethyl)-6-[2-(piperidin-4-yl)ethyl]-1H-pyrrolo[2,3-b]pyridin-2-yl]-7-methoxy-1-methyl-1H-1,3-benzodiazole-5-carbonyl}-5-fluoropiperidin-3-amine | 588.5 | 1 | 1.34 |
| 619. | 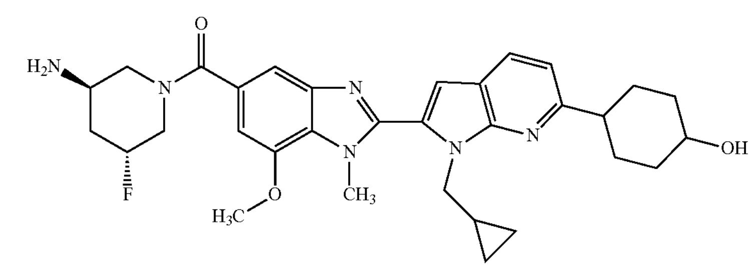 [SMILES: COc1cc(C(=O)N2C[C@H](N)C[C@@H](F)C2)cc2nc(-c3cc4ccc(C5CCC(O)CC5)nc4n3CC3CC3)n(C)c12] | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)cyclohexan-1-ol (mixture of diastereomers) | 575.46 | 1 | |

| # | Structure | Name | Obs. MS Ion | HPLC Method ID | RT |
|---|---|---|---|---|---|
| 620. | 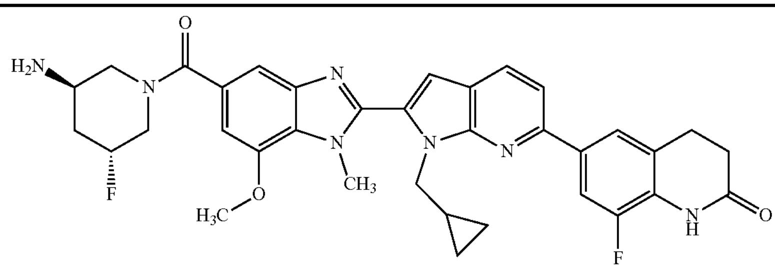 | 6-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-8-fluoro-1,2,3,4-tetrahydroquinolin-2-one | 640.2 | 1 | 1.77 |
| 621. | 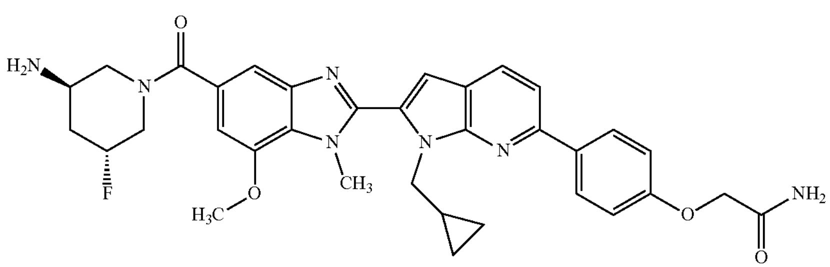 [SMILES: COc1cc(C(=O)N2C[C@H](N)C[C@@H](F)C2)cc2nc(-c3cc4ccc(-c5ccc(OCC(N)=O)cc5)nc4n3CC3CC3)n(C)c12] | 2-[4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)phenoxy]acetamide | 626.2 | 1 | 1.53 |
| 622. | 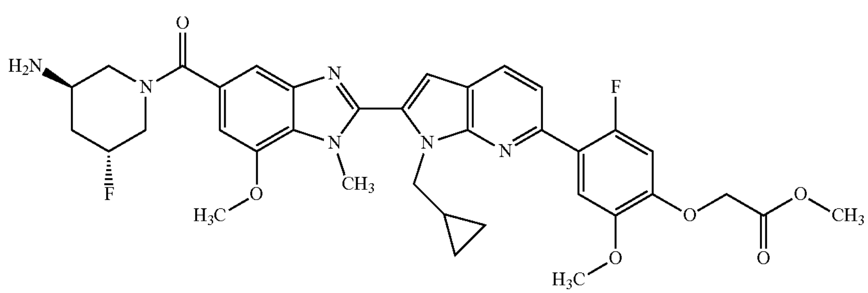 [SMILES: COC(=O)COc1cc(F)c(-c2ccc3cc(-c4nc5cc(C(=O)N6C[C@H](N)C[C@@H](F)C6)cc(OC)c5n4C)n(CC4CC4)c3n2)cc1OC] | methyl 2-[4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-5-fluoro-2-methoxyphenoxy]acetate | 689.2 | 1 | 1.97 |

| # | Structure | Name | Obs. MS Ion | HPLC Method ID | RT |
|---|---|---|---|---|---|
| 623. | 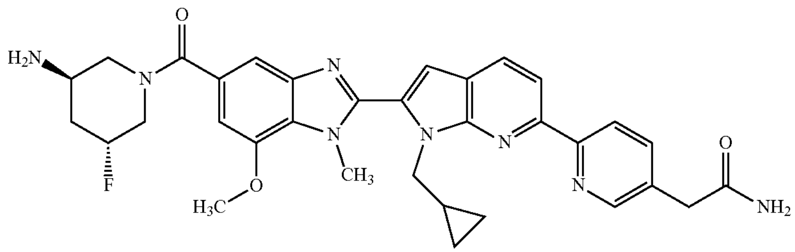 [SMILES: COc1cc(C(=O)N2C[C@H](N)C[C@@H](F)C2)cc2nc(-c3cc4ccc(-c5ccc(CC(N)=O)cn5)nc4n3CC3CC3)n(C)c12] | 2-[6-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)pyridin-3-yl]acetamide | 611.3 | 1 | 1.37 |
| 624. | 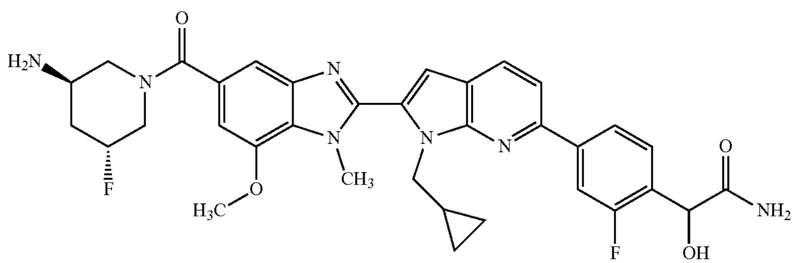 [SMILES: COc1cc(C(=O)N2C[C@H](N)C[C@@H](F)C2)cc2nc(-c3cc4ccc(-c5ccc(C(O)C(N)=O)c(F)c5)nc4n3CC3CC3)n(C)c12] | 2-[4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-fluorophenyl]-2-hydroxyacetamide (mixture of diastereomers) | 644.2 | 2 | 1.12 |
| 625. | 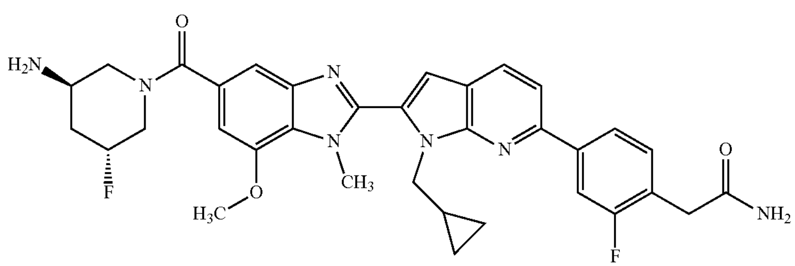 [SMILES: COc1cc(C(=O)N2C[C@H](N)C[C@@H](F)C2)cc2nc(-c3cc4ccc(-c5ccc(CC(N)=O)c(F)c5)nc4n3CC3CC3)n(C)c12] | 2-[4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-fluorophenyl]acetamide | 628.2 | 2 | 1.37 |

| # | Structure | Name | Obs. MS Ion | HPLC Method ID | RT |
|---|---|---|---|---|---|
| 626. | 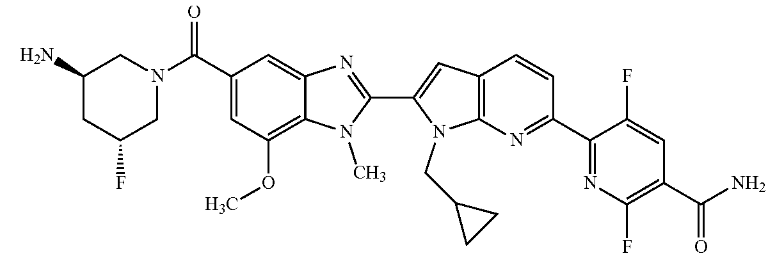 [SMILES: COc1cc(C(=O)N2C[C@H](N)C[C@@H](F)C2)cc2nc(-c3cc4ccc(-c5nc(F)c(C(N)=O)cc5F)nc4n3CC3CC3)n(C)c12] | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2,5-difluorobenzamide | 632.1 | 1 | 1.7 |
| 627. | 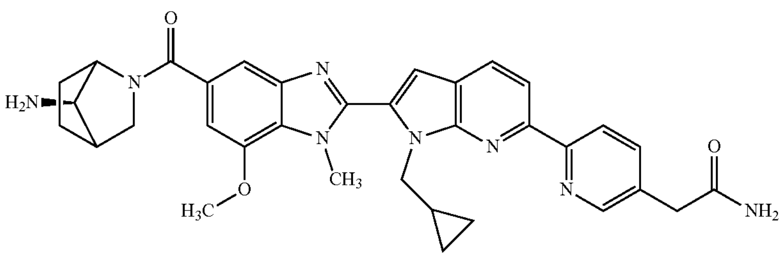 [SMILES: COc1cc(C(=O)N2CC3CCC2[C@@H]3N)cc2nc(-c3cc4ccc(-c5ccc(CC(N)=O)cn5)nc4n3CC3CC3)n(C)c12] | 2-[6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-3-yl]acetamide | 605.2 | 1 | 1.38 |
| 628. | 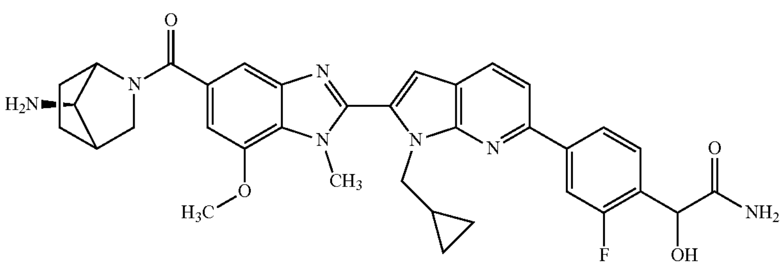 [SMILES: COc1cc(C(=O)N2CC3CCC2[C@@H]3N)cc2nc(-c3cc4ccc(-c5ccc(C(O)C(N)=O)c(F)c5)nc4n3CC3CC3)n(C)c12] | 2-[4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-fluorophenyl]-2-hydroxyacetamide (mixture of diastereomers) | 638.3 | 2 | 1.1 |

| # | Structure | Name | Obs. MS Ion | HPLC Method ID | RT |
|---|---|---|---|---|---|
| 629. | 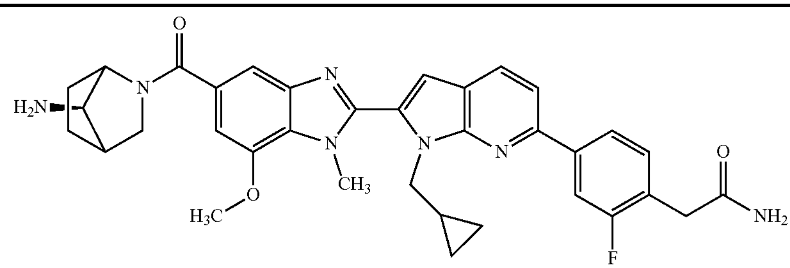 | 2-[4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-fluorophenyl]acetamide | 622.2 | 1 | 1.6 |
| 630. | 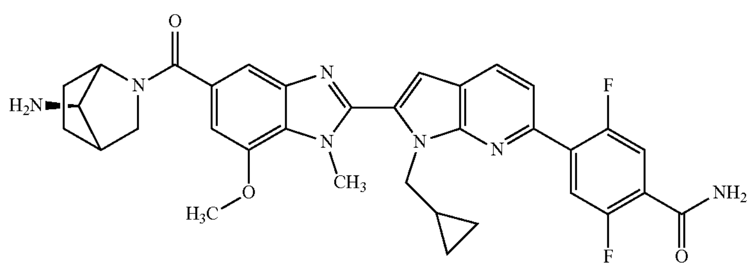 [SMILES: COc1cc(C(=O)N2CC3CCC2[C@@H]3N)cc2nc(-c3cc4ccc(-c5cc(F)c(C(N)=O)cc5F)nc4n3CC3CC3)n(C)c12] | 4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2,5-difluorobenzamide | 626.4 | 2 | 1.3 |
| 631. | 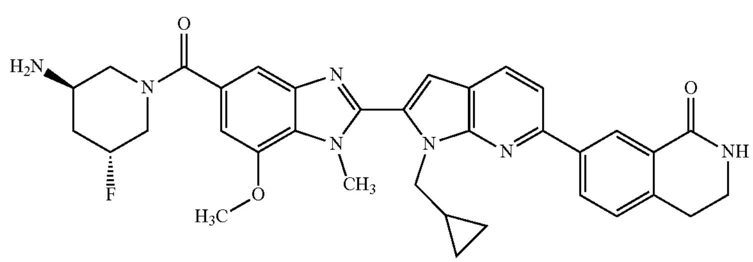 [SMILES: COc1cc(C(=O)N2C[C@H](N)C[C@@H](F)C2)cc2nc(-c3cc4ccc(-c5ccc6c(c5)C(=O)NCC6)nc4n3CC3CC3)n(C)c12] | 7-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-1,2,3,4-tetrahydroisoquinolin-1-one | 621.9 | 1 | 1.68 |

| # | Structure | Name | Obs. MS Ion | HPLC Method ID | RT |
|---|---|---|---|---|---|
| 632. | 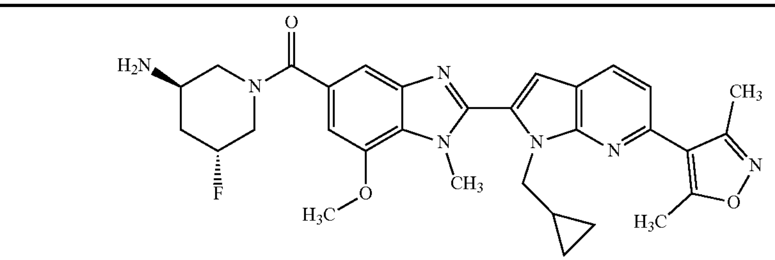 | (3R,5R)-1-{2-[1-(cyclopropylmethyl)-6-(3,5-dimethyl-1,2-oxazol-4-yl)-1H-pyrrolo[2,3-b]pyridin-2-yl]-7-methoxy-1-methyl-1H-1,3-benzodiazole-5-carbonyl}-5-fluoropiperidin-3-amine | 572.2 | 1 | 1.72 |
| 633. | 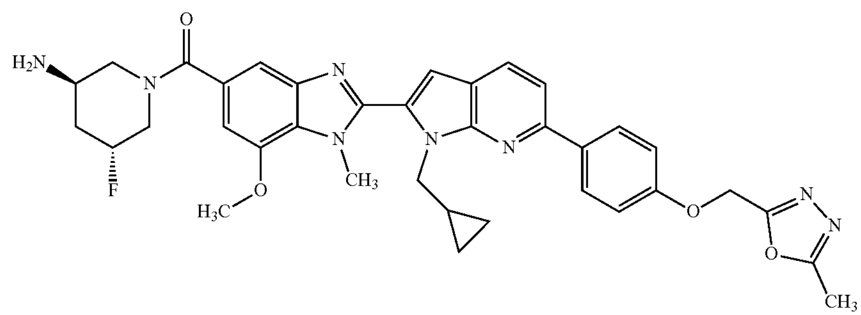 [SMILES: COc1cc(C(=O)N2C[C@H](N)C[C@@H](F)C2)cc2nc(-c3cc4ccc(-c5ccc(OCc6nnc(C)o6)cc5)nc4n3CC3CC3)n(C)c12] | (3R,5R)-1-{2-[1-(cyclopropylmethyl)-6-{4-[(5-methyl-1,3,4-oxadiazol-2-yl)methoxy]phenyl}-1H-pyrrolo[2,3-b]pyridin-2-yl]-7-methoxy-1-methyl-1H-1,3-benzodiazole-5-carbonyl}-5-fluoropiperidin-3-amine | 665.1 | 1 | 1.68 |
| 634. | 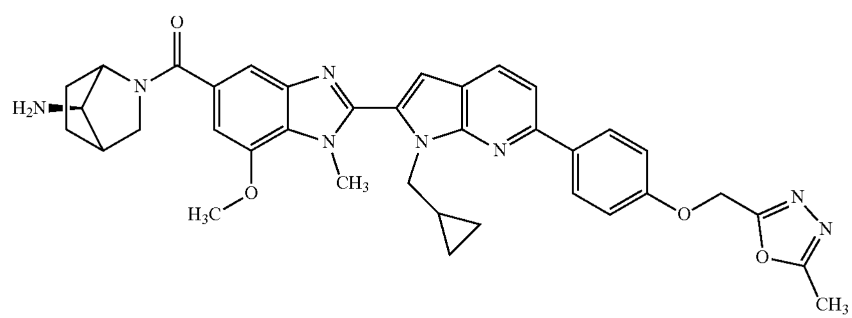 [SMILES: COc1cc(C(=O)N2CC3CCC2[C@@H]3N)cc2nc(-c3cc4ccc(-c5ccc(OCc6nnc(C)o6)cc5)nc4n3CC3CC3)n(C)c12] | (7R)-2-{2-[1-(cyclopropylmethyl)-6-{4-[(5-methyl-1,3,4-oxadiazol-2-yl)methoxy]phenyl}-1H-pyrrolo[2,3-b]pyridin-2-yl]-7-methoxy-1-methyl-1H-1,3-benzodiazole-5-carbonyl}-2-azabicyclo[2.2.1]heptan-7-amine | 659.2 | 2 | 1.48 |

| # | Structure | Name | Obs. MS Ion | HPLC Method ID | RT |
|---|---|---|---|---|---|
| 635. | 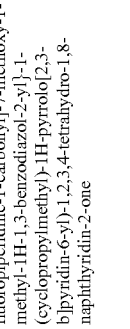 | 6-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-1,2,3,4-tetrahydro-1,8-naphthyridin-2-one | 623.3 | 3 | 0.68 |
| 636. | 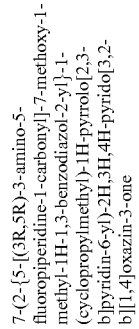 | 7-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2H,3H,4H-pyrido[3,2-b][1,4]oxazin-3-one | 625.2 | 2 | 1.4 |
| 637. | 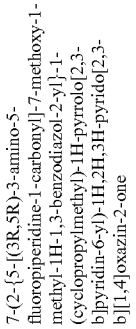 | 7-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-1H,2H,3H-pyrido[2,3-b][1,4]oxazin-2-one | 625.1 | 2 | 1.35 |
| 638. | 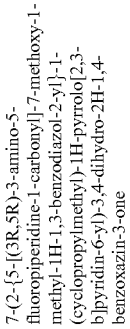 | 7-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-3,4-dihydro-2H-1,4-benzoxazin-3-one | 624.2 | 1 | 1.58 |

| # | Structure | Name | Obs. MS Ion | HPLC Method ID | RT |
|---|---|---|---|---|---|
| 639. | 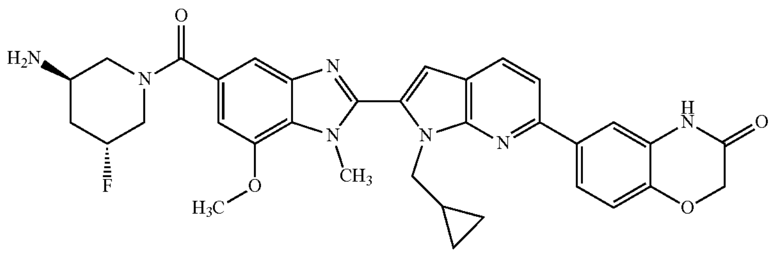 [SMILES: COc1cc(C(=O)N2C[C@H](N)C[C@@H](F)C2)cc2nc(-c3cc4ccc(-c5ccc6c(c5)NC(=O)CO6)nc4n3CC3CC3)n(C)c12] | 6-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-3,4-dihydro-2H-1,4-benzoxazin-3-one | 624.1 | 2 | 1.45 |
| 640. | 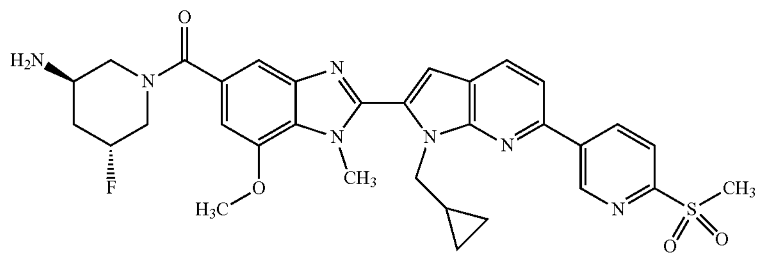 [SMILES: COc1cc(C(=O)N2C[C@H](N)C[C@@H](F)C2)cc2nc(-c3cc4ccc(-c5ccc(S(C)(=O)=O)nc5)nc4n3CC3CC3)n(C)c12] | (3R,5R)-1-{2-[1-(cyclopropylmethyl)-6-(6-methanesulfonylpyridin-3-yl)-1H-pyrrolo[2,3-b]pyridin-2-yl]-7-methoxy-1-methyl-1H-1,3-benzodiazole-5-carbonyl}-5-fluoropiperidin-3-amine | 632.2 | 2 | 1.35 |
| 641. | 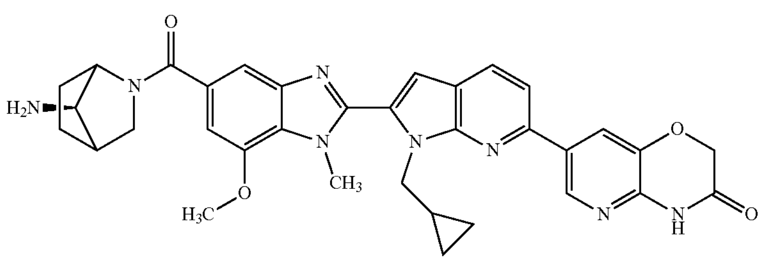 [SMILES: COc1cc(C(=O)N2CC3CCC2[C@@H]3N)cc2nc(-c3cc4ccc(-c5cnc6c(c5)OCC(=O)N6)nc4n3CC3CC3)n(C)c12] | 7-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2H,3H,4H-pyrido[3,2-b][1,4]oxazin-3-one | 619.2 | 1 | 1.58 |

| # | Structure | Name | Obs. MS Ion | HPLC Method ID | RT |
|---|---|---|---|---|---|
| 642. | 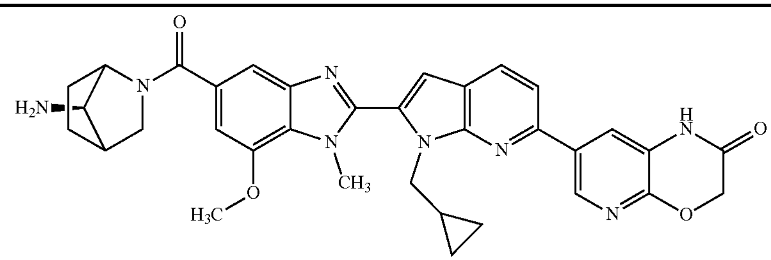 | 7-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1H,2H,3H-pyrido[2,3-b][1,4]oxazin-2-one | 619.3 | 1 | 1.37 |
| 643. | 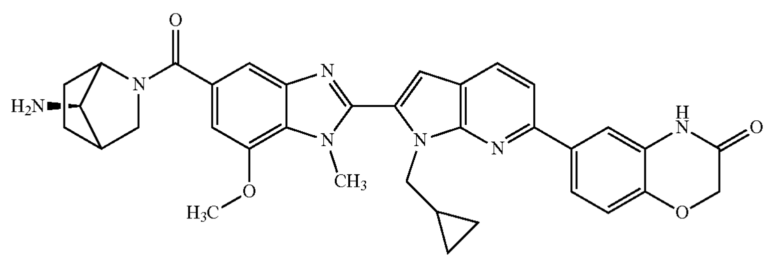 [SMILES: COc1cc(C(=O)N2CC3CCC2[C@@H]3N)cc2nc(-c3cc4ccc(-c5ccc6c(c5)NC(=O)CO6)nc4n3CC3CC3)n(C)c12] | 6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-3,4-dihydro-2H-1,4-benzoxazin-3-one | 618.2 | 1 | 1.64 |
| 644. | 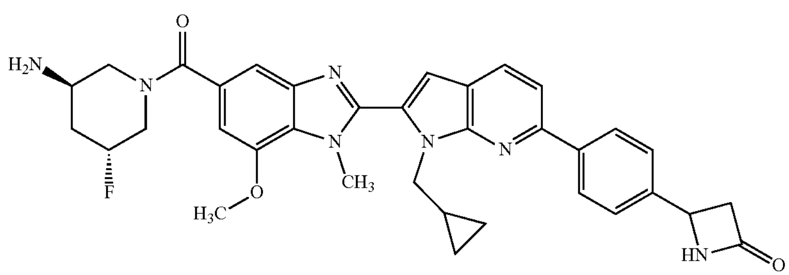 [SMILES: COc1cc(C(=O)N2C[C@H](N)C[C@@H](F)C2)cc2nc(-c3cc4ccc(-c5ccc(C6CC(=O)N6)cc5)nc4n3CC3CC3)n(C)c12] | 4-[4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)phenyl]azetidin-2-one | 622.2 | 1 | 1.76 |

| # | Structure | Name | Obs. MS Ion | HPLC Method ID | RT |
|---|---|---|---|---|---|
| 645. | 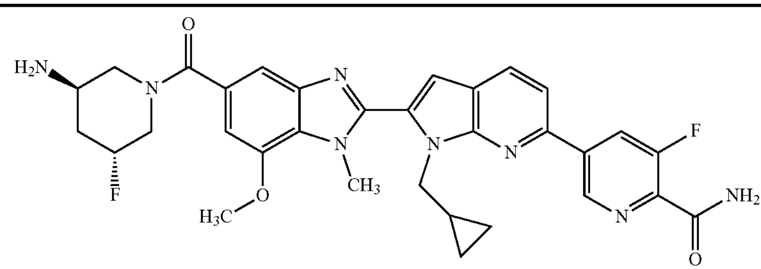 | 5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-3-fluoropyridine-2-carboxamide | 615.1 | 1 | 1.46 |
| 646. | 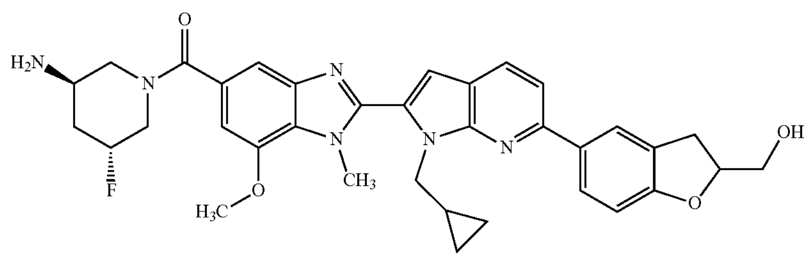 [SMILES: COc1cc(C(=O)N2C[C@H](N)C[C@@H](F)C2)cc2nc(-c3cc4ccc(-c5ccc6c(c5)CC(CO)O6)nc4n3CC3CC3)n(C)c12] | [5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2,3-dihydro-1-benzofuran-2-yl]methanol | 625.2 | 2 | 1.53 |
| 647. | 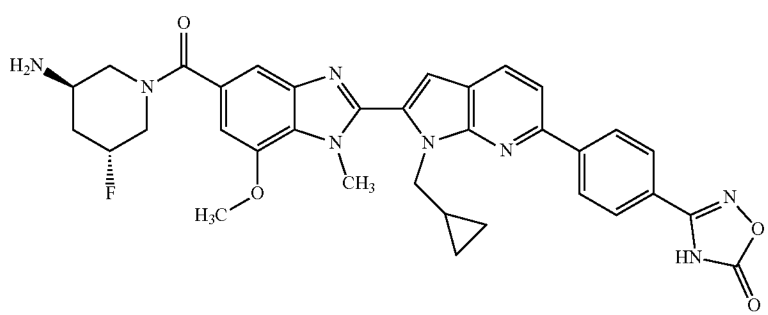 [SMILES: COc1cc(C(=O)N2C[C@H](N)C[C@@H](F)C2)cc2nc(-c3cc4ccc(-c5ccc(-c6noc(=O)[nH]6)cc5)nc4n3CC3CC3)n(C)c12] | 3-[4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)phenyl]-4,5-dihydro-1,2,4-oxadiazol-5-one | 637.1 | 2 | 1.59 |

| # | Structure | Name | Obs. MS Ion | HPLC Method ID | RT |
|---|---|---|---|---|---|
| 648. | 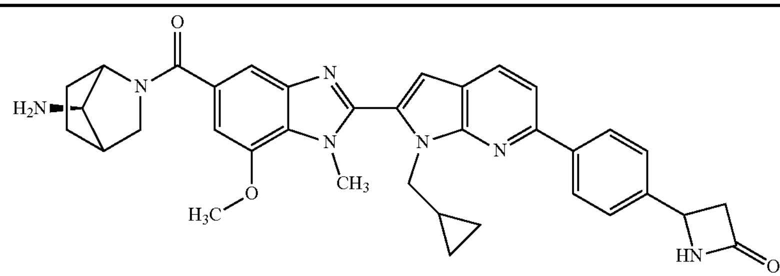 | 4-[4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]azetidin-2-one | 616 | 2 | 1.45 |
| 649. | 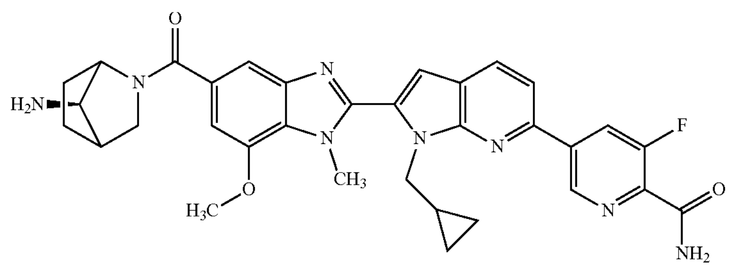 | 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-3-fluoropyridine-2-carboxamide | 609.2 | 2 | 1.34 |
| 650. | 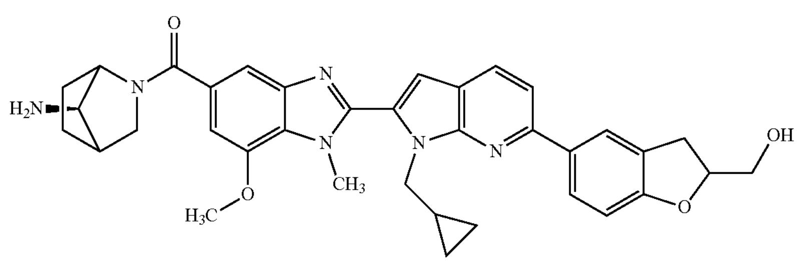 [SMILES: COc1cc(C(=O)N2CC3CCC2[C@@H]3N)cc2nc(-c3cc4ccc(-c5ccc6c(c5)CC(CO)O6)nc4n3CC3CC3)n(C)c12] | [5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2,3-dihydro-1-benzofuran-2-yl]methanol | 619.2 | 2 | 1.5 |

| # | Structure | Name | Obs. MS Ion | HPLC Method ID | RT |
|---|---|---|---|---|---|
| 651. | 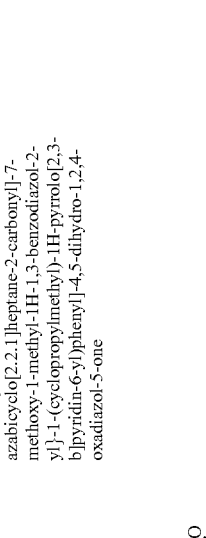 | 3-[4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]-4,5-dihydro-1,2,4-oxadiazol-5-one | 631.4 | 2 | 3.43 |
| 652. | 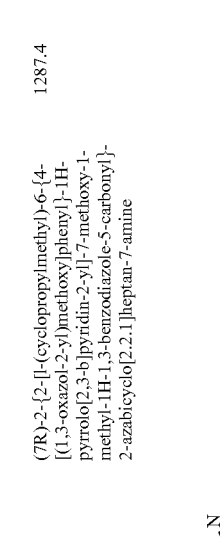 | (7R)-2-{2-[1-(cyclopropylmethyl)-6-{4-[(1,3-oxazol-2-yl)methoxy]phenyl}-1H-pyrrolo[2,3-b]pyridin-2-yl]-7-methoxy-1-methyl-1H-1,3-benzodiazole-5-carbonyl}-2-azabicyclo[2.2.1]heptan-7-amine | 1287.4 | 1 | 1.93 |
| 653. | 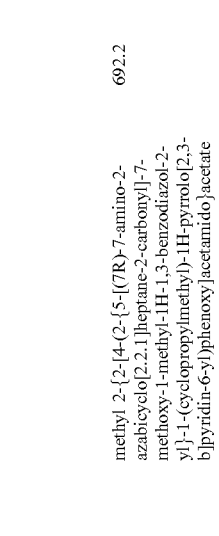 | methyl 2-{2-[4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenoxy]acetamido}acetate | 692.2 | 2 | 1.52 |

| # | Structure | Name | Obs. MS Ion | HPLC Method ID | RT |
|---|---|---|---|---|---|
| 654. | 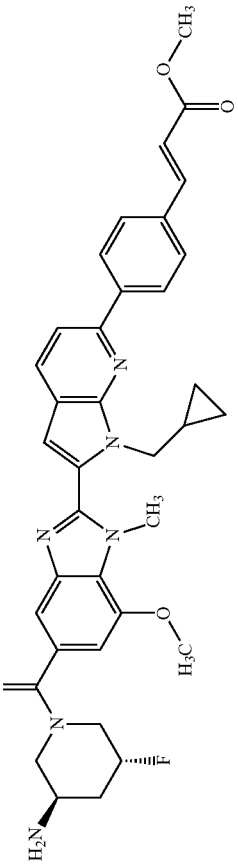 | methyl (2E)-3-[4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)phenyl]prop-2-enoate | 637.2 | 1 | 2 |
| 655. | 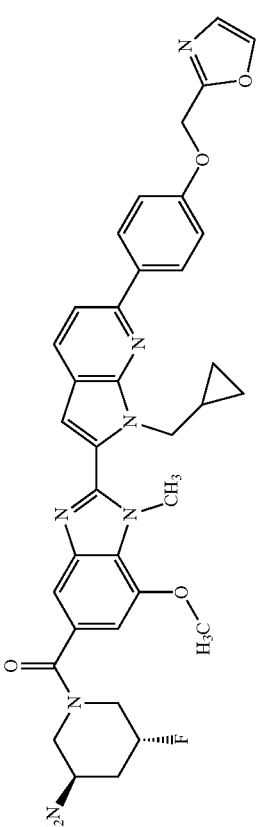 | (3R,5R)-1-{2-[1-(cyclopropylmethyl)-6-{4-[(1,3-oxazol-2-yl)methoxy]phenyl}-1H-pyrrolo[2,3-b]pyridin-2-yl]-7-methoxy-1-methyl-1H-1,3-benzodiazole-5-carbonyl}-5-fluoropiperidin-3-amine | 650.1 | 1 | 1.9 |
| 656. | 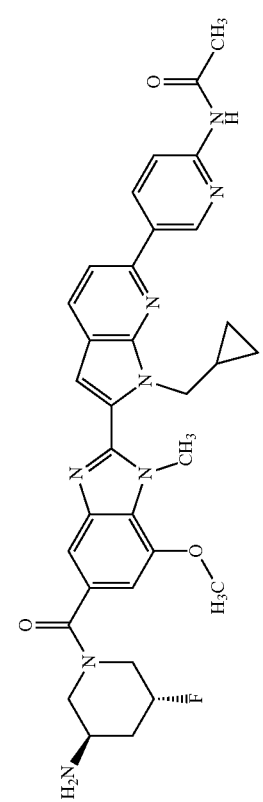 | N-[5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)pyridin-2-yl]acetamide | 306 | 2 | 1.32 |

| # | Structure | Name | Obs. MS Ion | HPLC Method ID | RT |
|---|---|---|---|---|---|
| 657. | 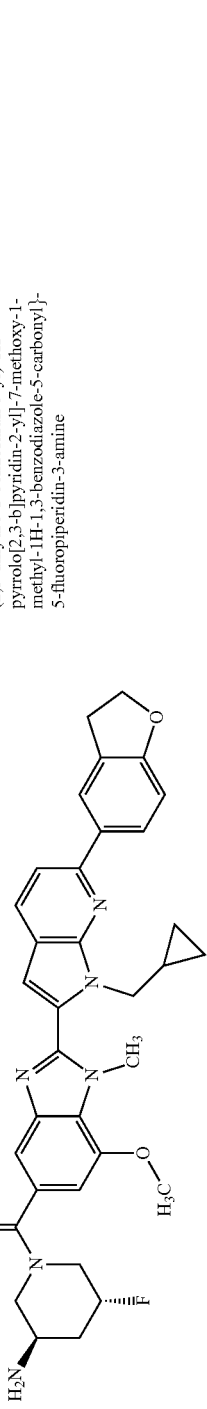 | (3R,5R)-1-{2-[1-(cyclopropylmethyl)-6-(2,3-dihydro-1-benzofuran-5-yl)-1H-pyrrolo[2,3-b]pyridin-2-yl]-7-methoxy-1-methyl-1H-1,3-benzodiazole-5-carbonyl}-5-fluoropiperidin-3-amine | 595.2 | 1 | 2.05 |
| 658. | 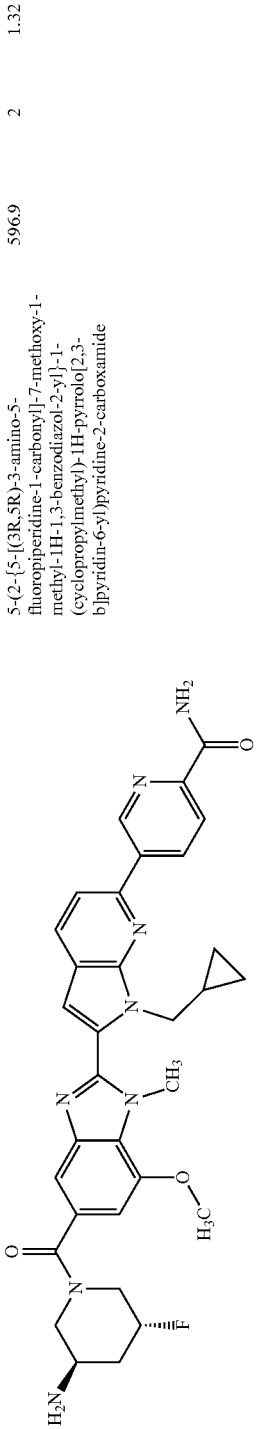 | 5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)pyridine-2-carboxamide | 596.9 | 2 | 1.32 |
| 659. | 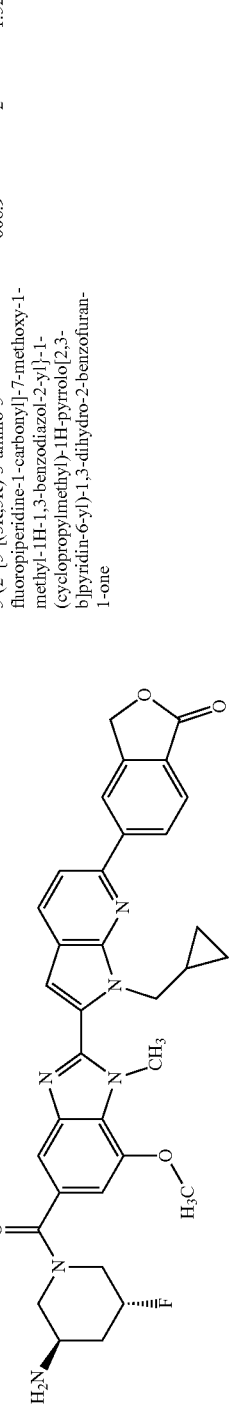 | 5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-1,3-dihydro-2-benzofuran-1-one | 608.9 | 2 | 1.52 |
| 660. | 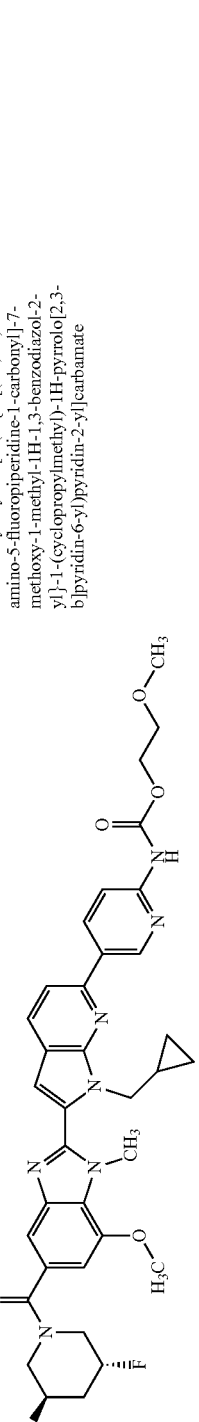 | 2-methoxyethyl N-[5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)pyridin-2-yl]carbamate | 336.3 | 1 | 1.71 |

| # | Structure | Name | Obs. MS Ion | HPLC Method ID | RT |
|---|---|---|---|---|---|
| 661. | 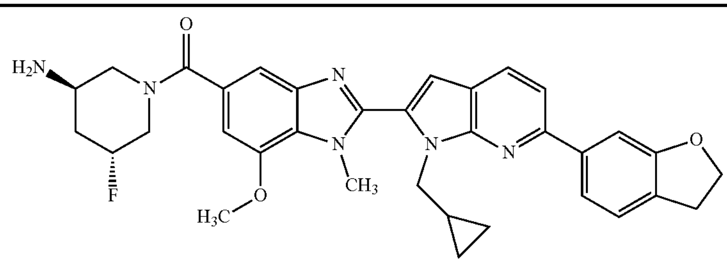 | (3R,5R)-1-{2-[1-(cyclopropylmethyl)-6-(2,3-dihydro-1-benzofuran-6-yl)-1H-pyrrolo[2,3-b]pyridin-2-yl]-7-methoxy-1-methyl-1H-1,3-benzodiazole-5-carbonyl}-5-fluoropiperidin-3-amine | 595.2 | 1 | 1.97 |
| 662. | 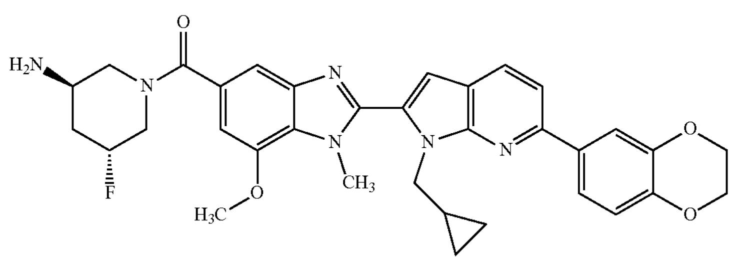 [SMILES: COc1cc(C(=O)N2C[C@H](N)C[C@@H](F)C2)cc2nc(-c3cc4ccc(-c5ccc6c(c5)OCCO6)nc4n3CC3CC3)n(C)c12] | (3R,5R)-1-{2-[1-(cyclopropylmethyl)-6-(2,3-dihydro-1,4-benzodioxin-6-yl)-1H-pyrrolo[2,3-b]pyridin-2-yl]-7-methoxy-1-methyl-1H-1,3-benzodiazole-5-carbonyl}-5-fluoropiperidin-3-amine | 611.2 | 2 | 1.68 |
| 663. | 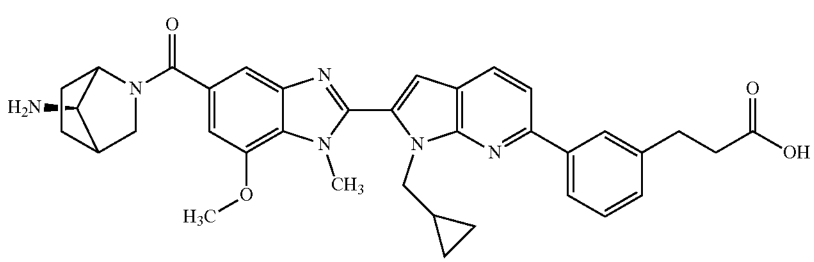 [SMILES: COc1cc(C(=O)N2CC3CCC2[C@@H]3N)cc2nc(-c3cc4ccc(-c5cccc(CCC(=O)O)c5)nc4n3CC3CC3)n(C)c12] | 3-[3-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]propanoic acid | 619.2 | 1 | 1.44 |

| # | Structure | Name | Obs. MS Ion | HPLC Method ID | RT |
|---|---|---|---|---|---|
| 664. | 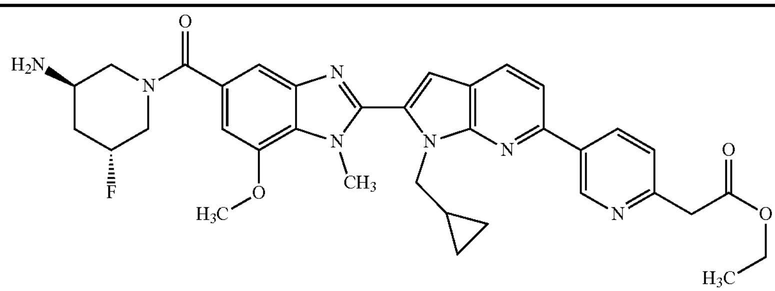 | ethyl 2-[5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)pyridin-2-yl]acetate | 640.2 | 2 | 1.42 |
| 665. | 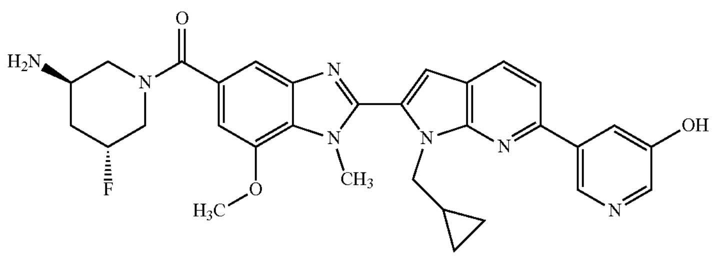 [SMILES: COc1cc(C(=O)N2C[C@H](N)C[C@@H](F)C2)cc2nc(-c3cc4ccc(-c5cncc(O)c5)nc4n3CC3CC3)n(C)c12] | 5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)pyridin-3-ol | 570.1 | 1 | 1.42 |
| 666. | 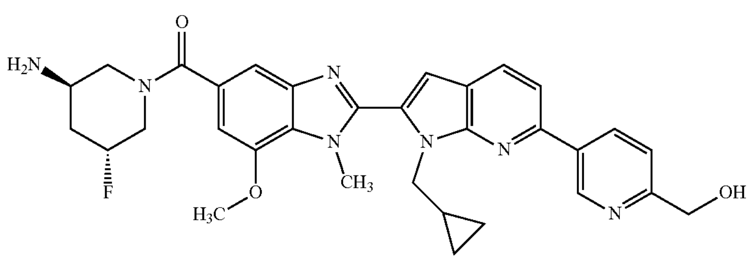 [SMILES: COc1cc(C(=O)N2C[C@H](N)C[C@@H](F)C2)cc2nc(-c3cc4ccc(-c5ccc(CO)nc5)nc4n3CC3CC3)n(C)c12] | [5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)pyridin-2-yl]methanol | 584.2 | 1 | 1.41 |

| # | Structure | Name | Obs. MS Ion | HPLC Method ID | RT |
|---|---|---|---|---|---|
| 667. | 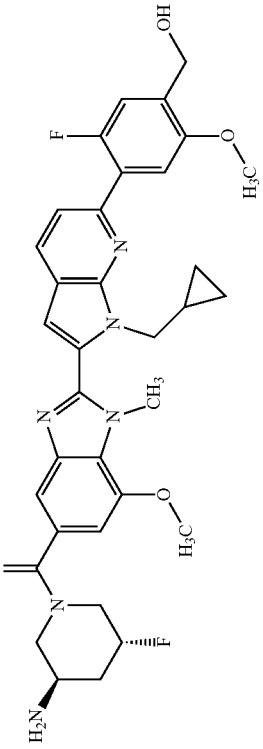 | [4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-5-fluoro-2-methoxyphenyl]methanol | 631.2 | 2 | 1.6 |
| 668. | 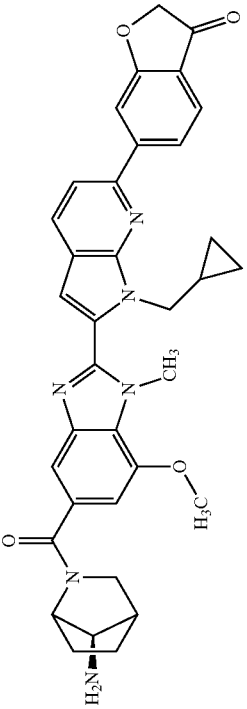 | 6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2,3-dihydro-1-benzofuran-3-one | 603.2 | 1 | 1.85 |
| 669. | 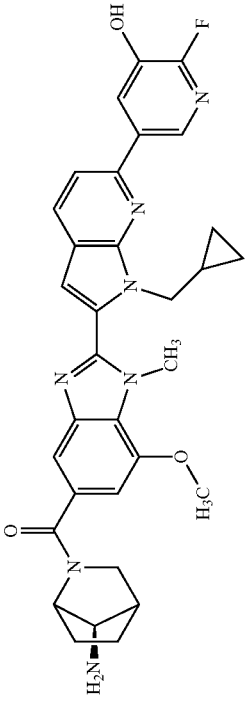 | 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-fluoropyridin-3-ol | 582.2 | 2 | 1.43 |

| # | Structure | Name | Obs. MS Ion | HPLC Method ID | RT |
|---|---|---|---|---|---|
| 670. | 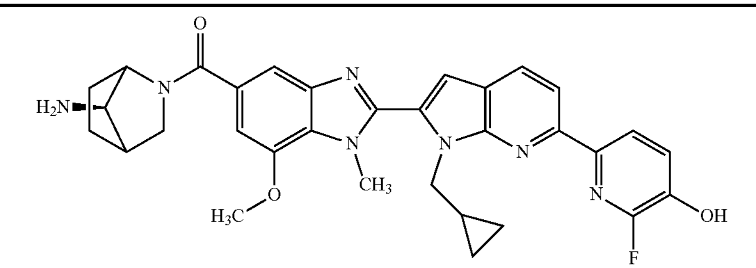 | 6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-fluoropyridin-3-ol | 582.2 | 2 | 1.49 |
| 671. | 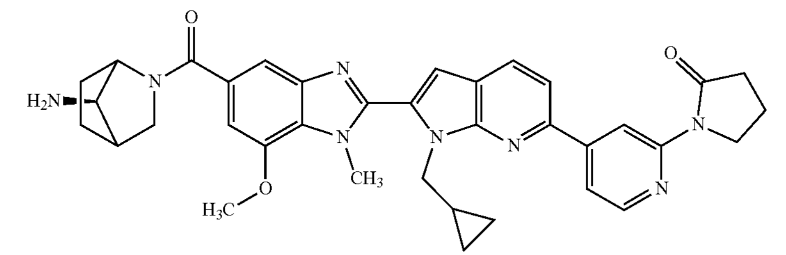 [SMILES: COc1cc(C(=O)N2CC3CCC2[C@@H]3N)cc2nc(-c3cc4ccc(-c5ccnc(N6CCCC6=O)c5)nc4n3CC3CC3)n(C)c12] | 1-[4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)pyridin-2-yl]pyrrolidin-2-one | 316 | 2 | 1.48 |
| 672. | 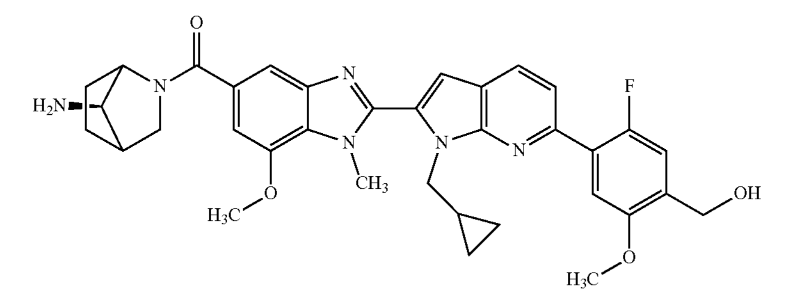 [SMILES: COc1cc(-c2ccc3cc(-c4nc5cc(C(=O)N6CC7CCC6[C@@H]7N)cc(OC)c5n4C)n(CC4CC4)c3n2)c(F)cc1CO] | [4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-5-fluoro-2-methoxyphenyl]methanol | 625.2 | 2 | 1.56 |

| # | Structure | Name | Obs. MS Ion | HPLC Method ID | RT |
|---|---|---|---|---|---|
| 673. | 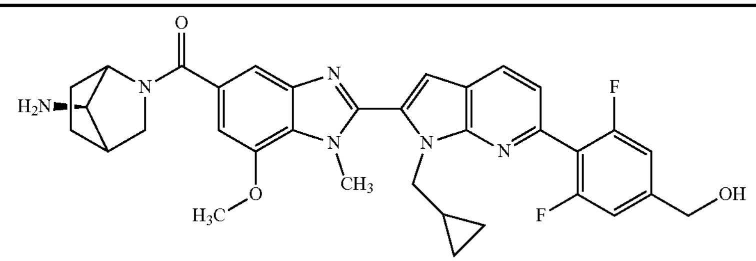 | [4-(2-{5-[(7R)-7-amino-2-azabicyclo[2.2.1]heptane-2-carbonyl]-7-methoxy-1H-1,3-benzodiazol-2-yl}-1-(cyclopropylmethyl)-1H-pyrrolo[2,3-b]pyridin-6-yl)-3,5-difluorophenyl]methanol | 613.2 | 1 | 1.6 |
| 674. | 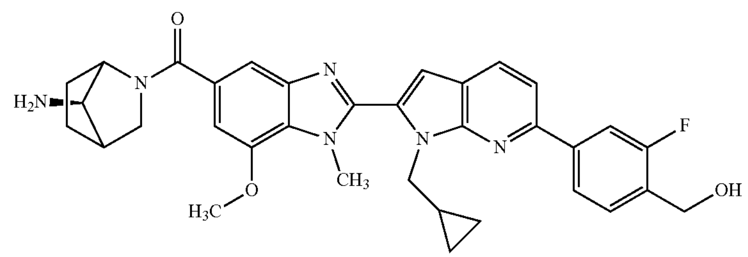 [SMILES: COc1cc(C(=O)N2CC3CCC2[C@@H]3N)cc2nc(-c3cc4ccc(-c5ccc(CO)c(F)c5)nc4n3CC3CC3)n(C)c12] | [4-(2-{5-[(7R)-7-amino-2-azabicyclo[2.2.1]heptane-2-carbonyl]-7-methoxy-1H-1,3-benzodiazol-2-yl}-1-(cyclopropylmethyl)-1H-pyrrolo[2,3-b]pyridin-6-yl)-2-fluorophenyl]methanol | 595.2 | 2 | 1.52 |
| 675. | 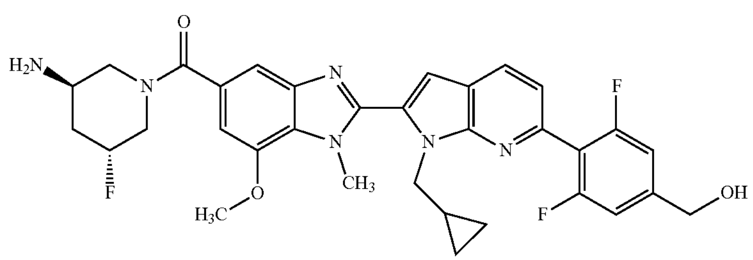 [SMILES: COc1cc(C(=O)N2C[C@H](N)C[C@@H](F)C2)cc2nc(-c3cc4ccc(-c5c(F)cc(CO)cc5F)nc4n3CC3CC3)n(C)c12] | [4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-3,5-difluorophenyl]methanol | 619.2 | 1 | 1.65 |
| 676. | 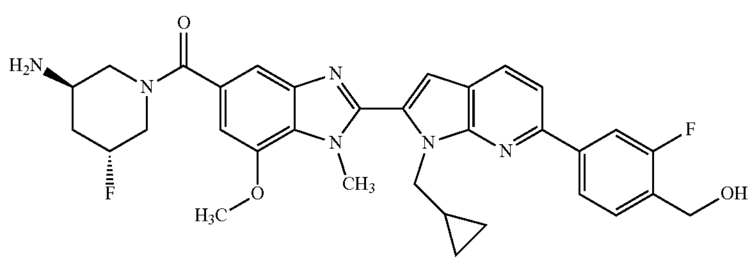 [SMILES: COc1cc(C(=O)N2C[C@H](N)C[C@@H](F)C2)cc2nc(-c3cc4ccc(-c5ccc(CO)c(F)c5)nc4n3CC3CC3)n(C)c12] | [4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-fluorophenyl]methanol | 601.2 | 1 | 1.69 |

| # | Structure | Name | Obs. MS Ion | HPLC Method ID | RT |
|---|---|---|---|---|---|
| 677. | 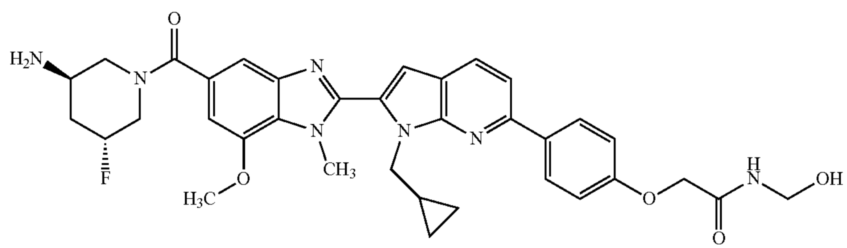 [SMILES: COc1cc(C(=O)N2C[C@H](N)C[C@@H](F)C2)cc2nc(-c3cc4ccc(-c5ccc(OCC(=O)NCO)cc5)nc4n3CC3CC3)n(C)c12] | 2-[4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)phenoxy]-N-(cyanomethyl)acetamide | 665.2 | 2 | 1.51 |
| 678. | 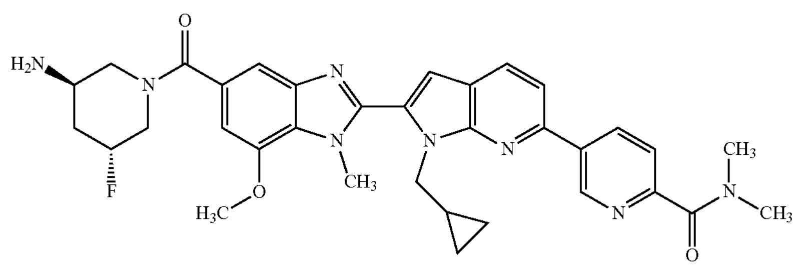 [SMILES: COc1cc(C(=O)N2C[C@H](N)C[C@@H](F)C2)cc2nc(-c3cc4ccc(-c5ccc(C(=O)N(C)C)nc5)nc4n3CC3CC3)n(C)c12] | 5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-N,N-dimethylpyridine-2-carboxamide | 625.2 | 2 | 1.27 |
| 679. | 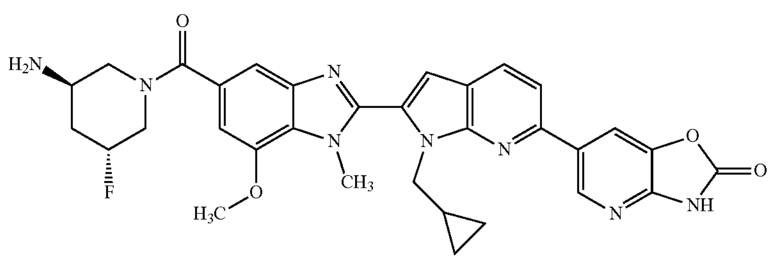 [SMILES: COc1cc(C(=O)N2C[C@H](N)C[C@@H](F)C2)cc2nc(-c3cc4ccc(-c5cnc6[nH]c(=O)oc6c5)nc4n3CC3CC3)n(C)c12] | 6-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2H,3H-[1,3]oxazolo[4,5-b]pyridin-2-one | 611.2 | 1 | 1.43 |

| # | Structure | Name | Obs. MS Ion | HPLC Method ID | RT |
|---|---|---|---|---|---|
| 680. | 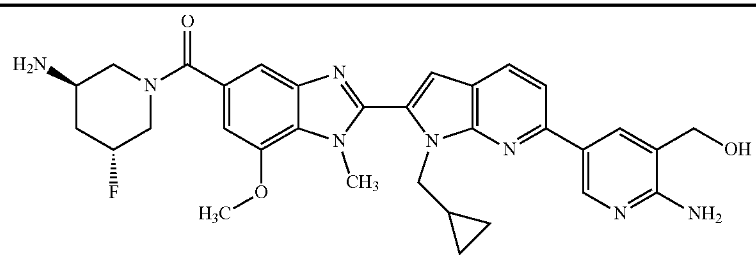 | [2-amino-5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)pyridin-3-yl]methanol | 599.2 | 1 | 1.24 |
| 681. | 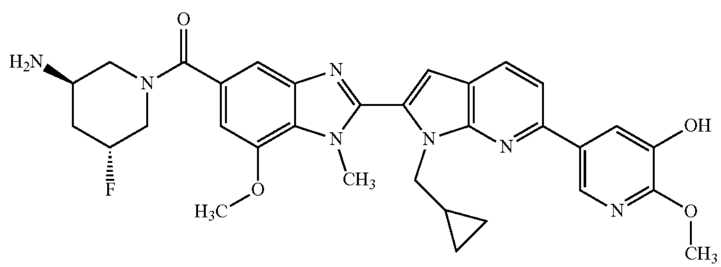 [SMILES: COc1ncc(-c2ccc3cc(-c4nc5cc(C(=O)N6C[C@H](N)C[C@@H](F)C6)cc(OC)c5n4C)n(CC4CC4)c3n2)cc1O] | 5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-methoxypyridin-3-ol | 600.1 | 2 | 1.35 |
| 682. | 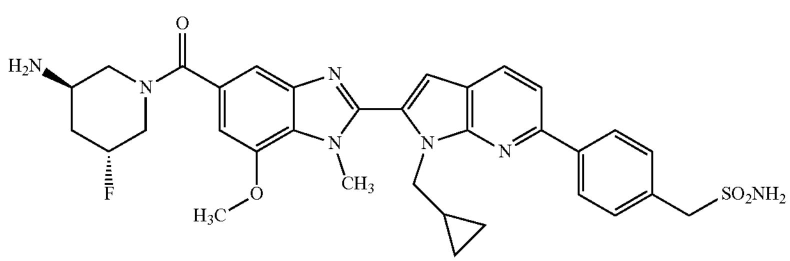 [SMILES: COc1cc(C(=O)N2C[C@H](N)C[C@@H](F)C2)cc2nc(-c3cc4ccc(-c5ccc(CS(N)(=O)=O)cc5)nc4n3CC3CC3)n(C)c12] | [4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)phenyl]methanesulfonamide | 646.1 | 2 | 1.42 |

| # | Structure | Name | Obs. MS Ion | HPLC Method ID | RT |
|---|---|---|---|---|---|
| 683. | 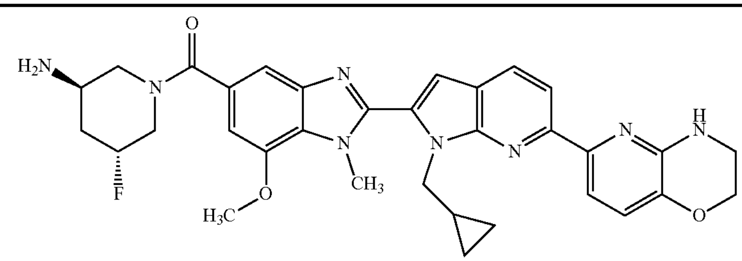 | (3R,5R)-1-{2-[1-(cyclopropylmethyl)-6-{2H,3H,4H-pyrido[3,2-b][1,4]oxazin-6-yl}-1H-pyrrolo[2,3-b]pyridin-2-yl]-7-methoxy-1-methyl-1H-1,3-benzodiazole-5-carbonyl}-5-fluoropiperidin-3-amine | 611.2 | 2 | 1.34 |
| 684. | 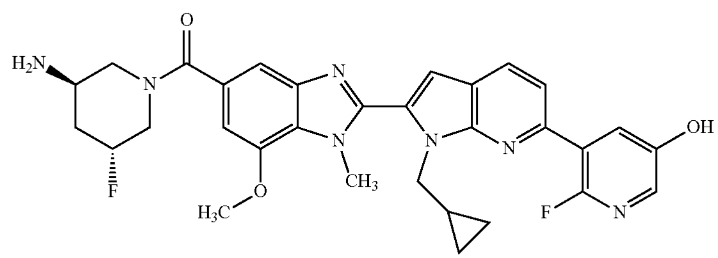 [SMILES: COc1cc(C(=O)N2C[C@H](N)C[C@@H](F)C2)cc2nc(-c3cc4ccc(-c5cc(O)cnc5F)nc4n3CC3CC3)n(C)c12] | 5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-6-fluoropyridin-3-ol | 588.1 | 1 | 1.6 |
| 685. | 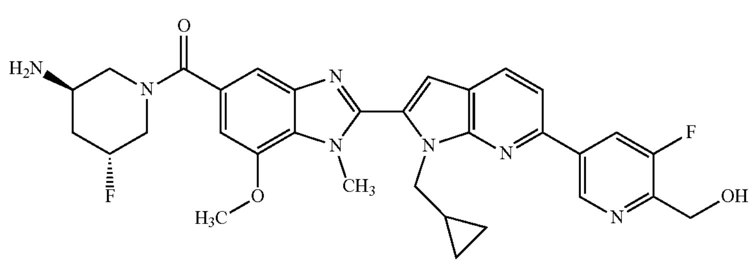 [SMILES: COc1cc(C(=O)N2C[C@H](N)C[C@@H](F)C2)cc2nc(-c3cc4ccc(-c5cnc(CO)c(F)c5)nc4n3CC3CC3)n(C)c12] | [5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-3-fluoropyridin-2-yl]methanol | 602.1 | 2 | 1.24 |

| # | Structure | Name | Obs. MS Ion | HPLC Method ID | RT |
|---|---|---|---|---|---|
| 686. | 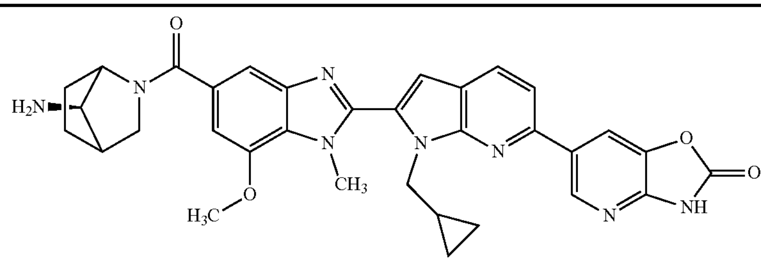 | 6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2H,3H-[1,3]oxazolo[4,5-b]pyridin-2-one | 605.2 | 1 | 1.45 |
| 687. | 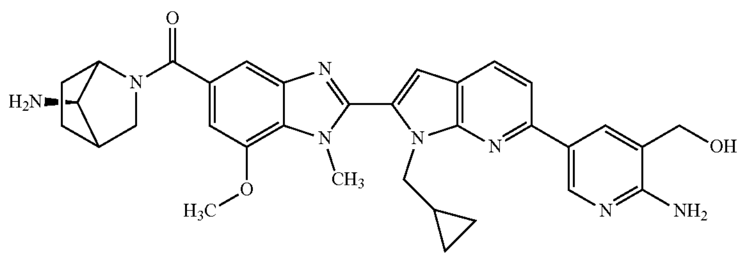 [SMILES: COc1cc(C(=O)N2CC3CCC2[C@@H]3N)cc2nc(-c3cc4ccc(-c5cnc(N)c(CO)c5)nc4n3CC3CC3)n(C)c12] | [2-amino-5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)pyridin-3-yl]methanol | 593.3 | 1 | 1.27 |
| 688. | 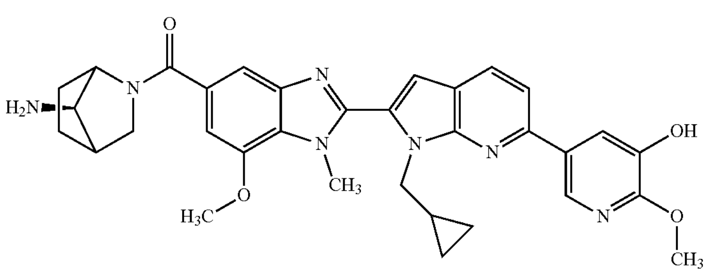 | 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-methoxypyridin-3-ol | 594.2 | 1 | 1.55 |

| # | Structure | Name | Obs. MS Ion | HPLC Method ID | RT |
|---|---|---|---|---|---|
| 689. | 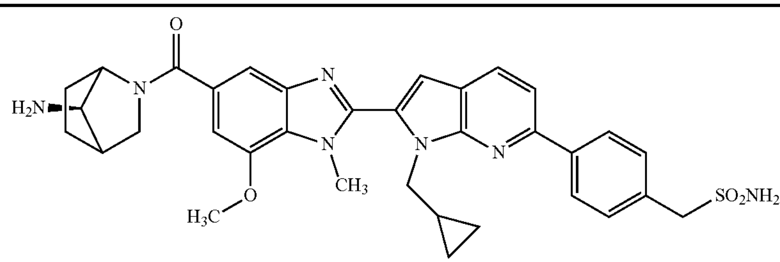 | [4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]methanesulfonamide | 640.1 | 2 | 1.26 |
| 690. | 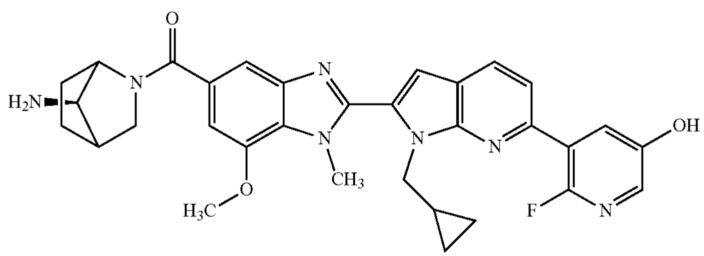 [SMILES: COc1cc(C(=O)N2CC3CCC2[C@@H]3N)cc2nc(-c3cc4ccc(-c5cc(O)cnc5F)nc4n3CC3CC3)n(C)c12] | 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-6-fluoropyridin-3-ol | 582 | 1 | 1.51 |
| 691. | 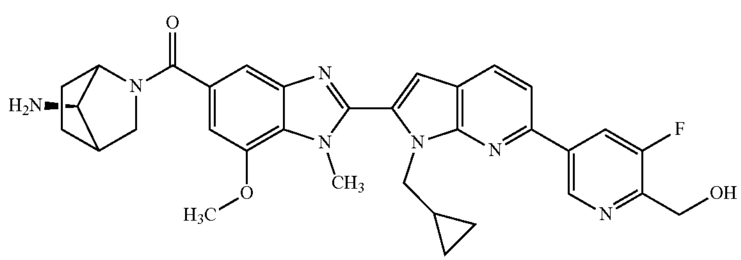 | [5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-3-fluoropyridin-2-yl]methanol | 596.2 | 1 | 1.59 |

| # | Structure | Name | Obs. MS Ion | HPLC Method ID | RT |
|---|---|---|---|---|---|
| 692. | 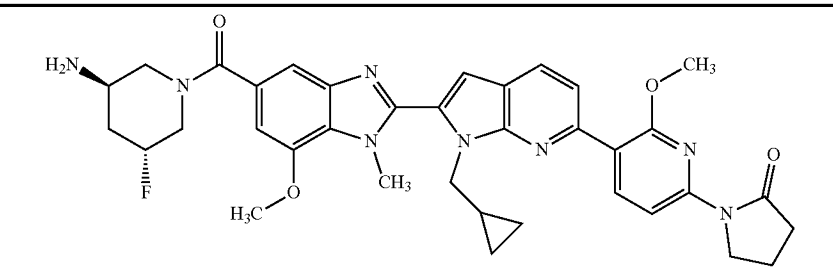 | 1-[5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-6-methoxypyridin-2-yl]pyrrolidin-2-one | 667.1 | 1 | 1.93 |
| 693. | 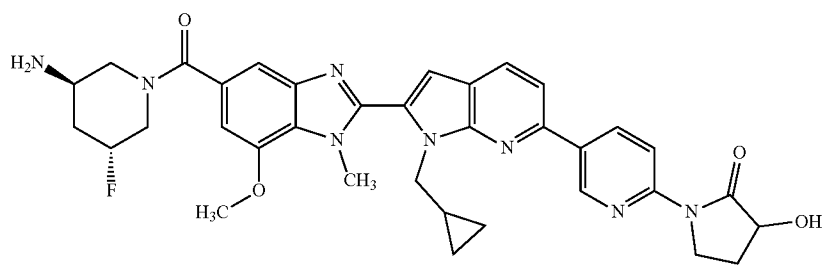 [SMILES: COc1cc(C(=O)N2C[C@H](N)C[C@@H](F)C2)cc2nc(-c3cc4ccc(-c5ccc(N6CCC(O)C6=O)nc5)nc4n3CC3CC3)n(C)c12] | 1-[5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)pyridin-2-yl]-3-hydroxypyrrolidin-2-one (mixture of diastereomers) | 653.3 | 1 | 1.42 |
| 694. | 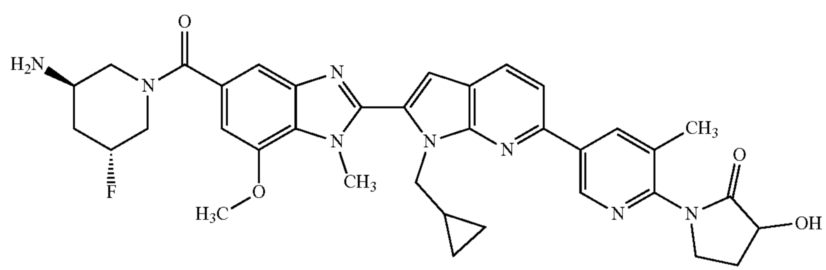 [SMILES: COc1cc(C(=O)N2C[C@H](N)C[C@@H](F)C2)cc2nc(-c3cc4ccc(-c5cnc(N6CCC(O)C6=O)c(C)c5)nc4n3CC3CC3)n(C)c12] | 1-[5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-3-methylpyridin-2-yl]-3-hydroxypyrrolidin-2-one (mixture of diastereomers) | 667.1 | 1 | 1.35 |

| # | Structure | Name | Obs. MS Ion | HPLC Method ID | RT |
|---|---|---|---|---|---|
| 695. | 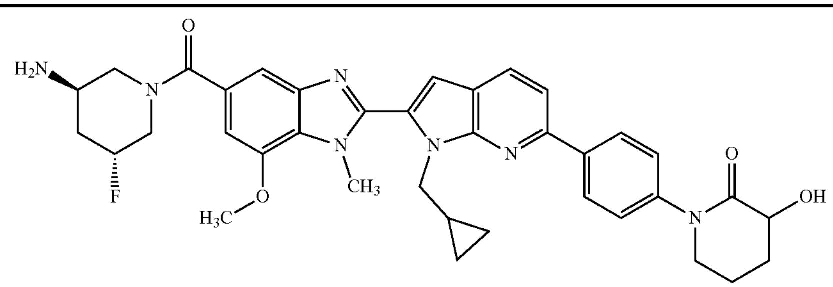 | 1-[4-(2-{5-[(3R,5R)-3-amino-5-fluoropiperidine-1-carbonyl]-7-methoxy-1-methyl-1H-1,3-benzodiazol-2-yl]-1-(cyclopropylmethyl)-1H-pyrrolo[2,3-b]pyridin-6-yl}phenyl]-3-hydroxypiperidin-2-one (mixture of diastereomers) | 666 | 2 | 1.51 |
| 696. | 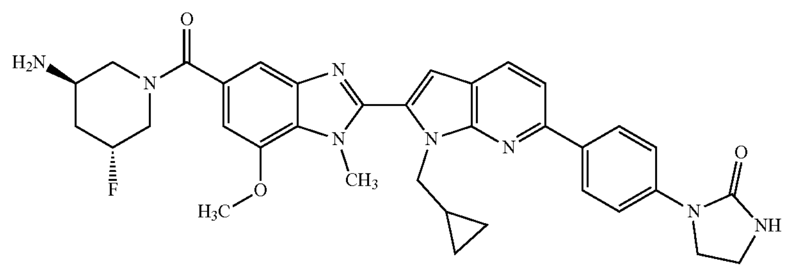 [SMILES: COc1cc(C(=O)N2C[C@H](N)C[C@@H](F)C2)cc2nc(-c3cc4ccc(-c5ccc(N6CCNC6=O)cc5)nc4n3CC3CC3)n(C)c12] | 1-[4-(2-{5-[(3R,5R)-3-amino-5-fluoropiperidine-1-carbonyl]-7-methoxy-1-methyl-1H-1,3-benzodiazol-2-yl]-1-(cyclopropylmethyl)-1H-pyrrolo[2,3-b]pyridin-6-yl}phenyl]imidazolidin-2-one | 637.3 | 2 | 1.36 |
| 697. | 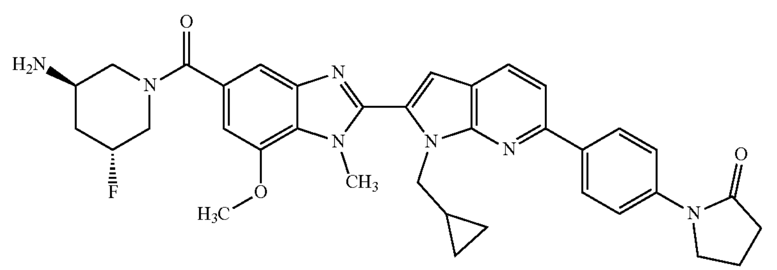 [SMILES: COc1cc(C(=O)N2C[C@H](N)C[C@@H](F)C2)cc2nc(-c3cc4ccc(-c5ccc(N6CCCC6=O)cc5)nc4n3CC3CC3)n(C)c12] | 1-[4-(2-{5-[(3R,5R)-3-amino-5-fluoropiperidine-1-carbonyl]-7-methoxy-1-methyl-1H-1,3-benzodiazol-2-yl]-1-(cyclopropylmethyl)-1H-pyrrolo[2,3-b]pyridin-6-yl}phenyl]pyrrolidin-2-one | 636 | 2 | 1.64 |

| # | Structure | Name | Obs. MS Ion | HPLC Method ID | RT |
|---|---|---|---|---|---|
| 698. | 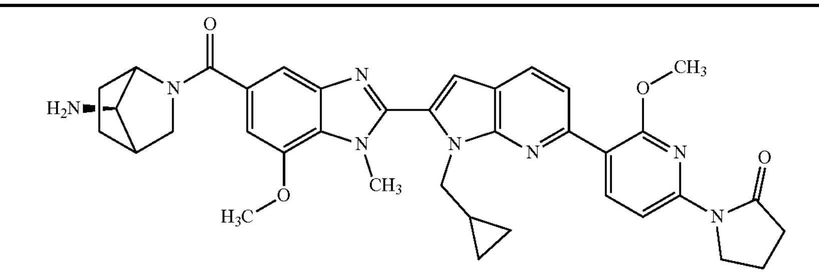 | 1-[5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-6-methoxypyridin-2-yl]pyrrolidin-2-one | 661.1 | 2 | 1.68 |
| 699. | 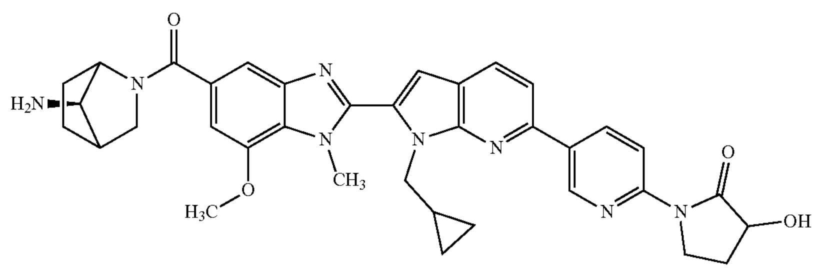 [SMILES: COc1cc(C(=O)N2CC3CCC2[C@@H]3N)cc2nc(-c3cc4ccc(-c5ccc(N6CCC(O)C6=O)nc5)nc4n3CC3CC3)n(C)c12] | 1-[5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)pyridin-2-yl]-3-hydroxypyrrolidin-2-one (mixture of diastereomers) | 647.1 | 1 | 1.45 |
| 700. | 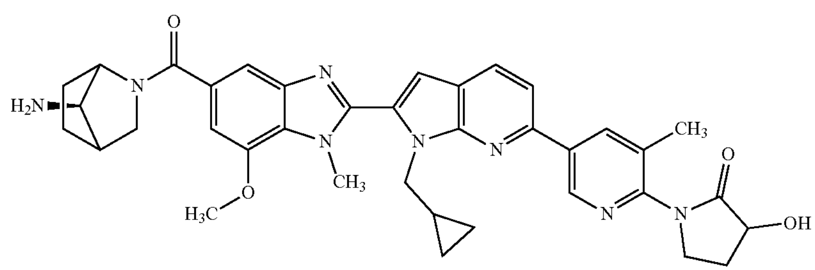 [SMILES: COc1cc(C(=O)N2CC3CCC2[C@@H]3N)cc2nc(-c3cc4ccc(-c5cnc(N6CCC(O)C6=O)c(C)c5)nc4n3CC3CC3)n(C)c12] | 1-[5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-3-methylpyridin-2-yl]-3-hydroxypyrrolidin-2-one (mixture of diastereomers) | 661.2 | 2 | 1.2 |

| # | Structure | Name | Obs. MS Ion | HPLC Method ID | RT |
|---|---|---|---|---|---|
| 701. | 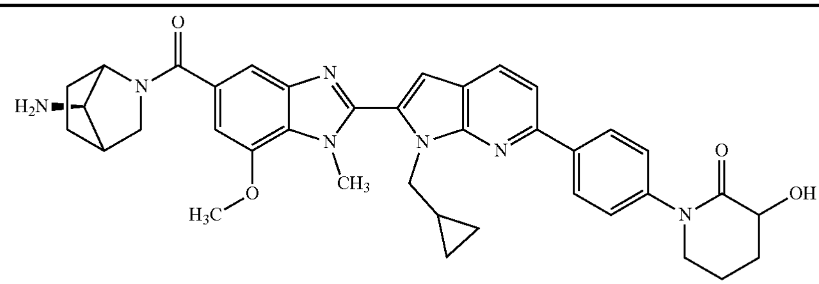 | 1-[4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]-3-hydroxypiperidin-2-one (mixture of diastereomers) | 660.4 | 1 | 1.48 |
| 702. | 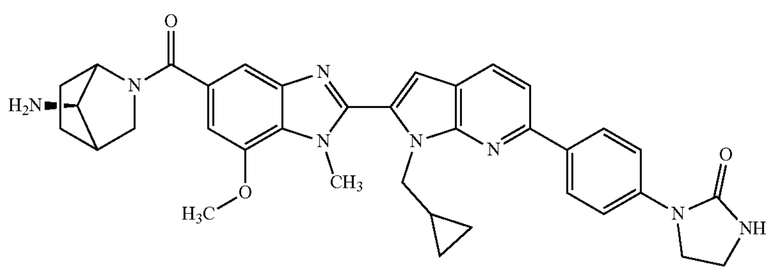 [SMILES: COc1cc(C(=O)N2CC3CCC2[C@@H]3N)cc2nc(-c3cc4ccc(-c5ccc(N6CCNC6=O)cc5)nc4n3CC3CC3)n(C)c12] | 1-[4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]imidazolidin-2-one | 631.2 | 2 | 1.33 |
| 703. | 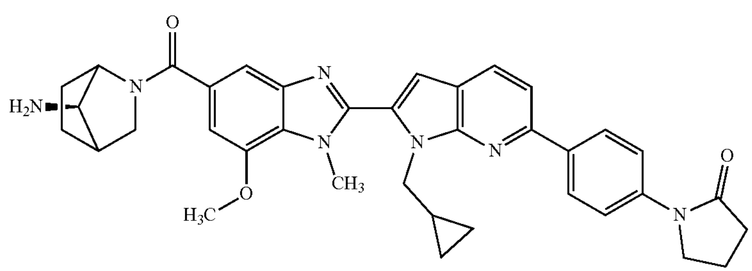 [SMILES: COc1cc(C(=O)N2CC3CCC2[C@@H]3N)cc2nc(-c3cc4ccc(-c5ccc(N6CCCC6=O)cc5)nc4n3CC3CC3)n(C)c12] | 1-[4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]pyrrolidin-2-one | 630.2 | 2 | 1.6 |

| # | Structure | Name | Obs. MS Ion | HPLC Method ID | RT |
|---|---|---|---|---|---|
| 704. | 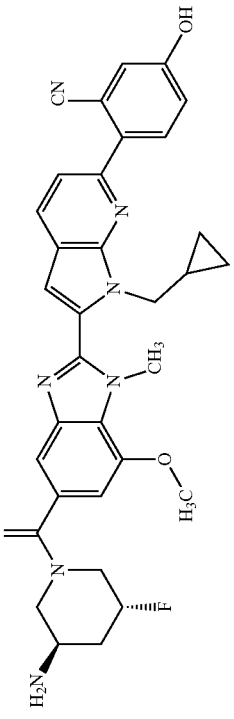 | 2-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-5-hydroxybenzonitrile | 594.2 | 2 | 1.5 |
| 705. | 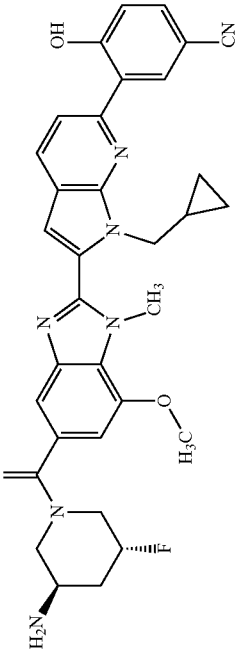 | 3-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-4-hydroxybenzonitrile | 594.3 | 1 | 1.79 |
| 706. | 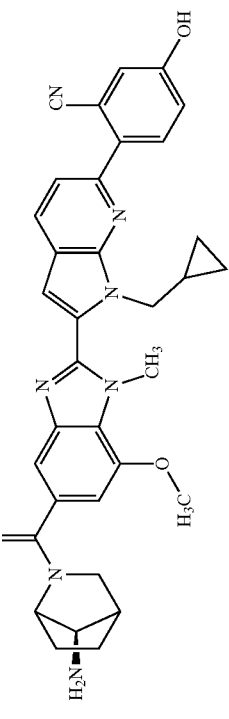 | 2-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-5-hydroxybenzonitrile | 588.3 | 1 | 1.55 |

| # | Structure | Name | Obs. MS Ion | HPLC Method ID | RT |
|---|---|---|---|---|---|
| 707. | 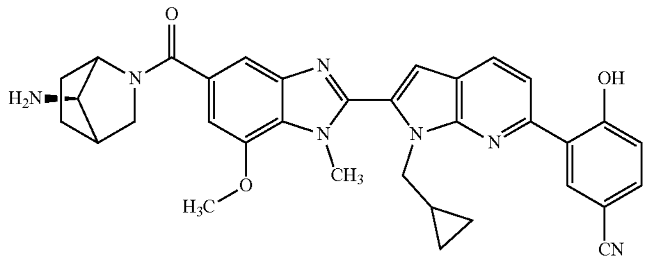 [SMILES: COc1cc(C(=O)N2CC3CCC2[C@@H]3N)cc2nc(-c3cc4ccc(-c5cc(C#N)ccc5O)nc4n3CC3CC3)n(C)c12] | 3-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-4-hydroxybenzonitrile | 588.1 | 2 | 1.7 |
| 708. | 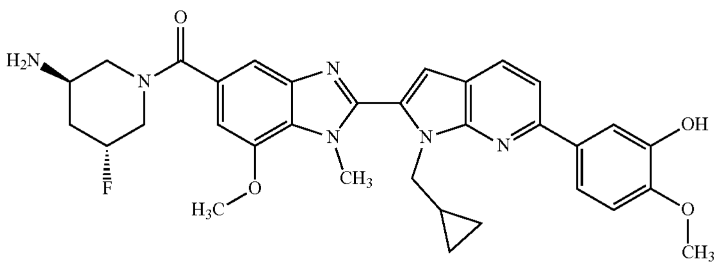 | 5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-methoxyphenol | 599.3 | 1 | 1.62 |
| 709. | 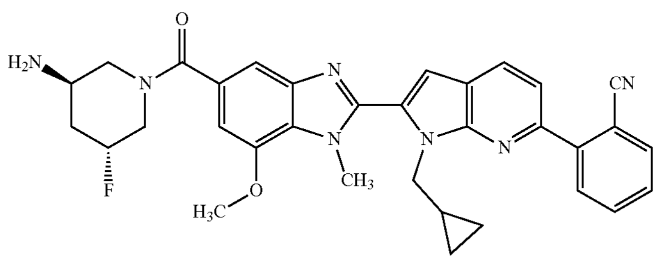 [SMILES: COc1cc(C(=O)N2C[C@H](N)C[C@@H](F)C2)cc2nc(-c3cc4ccc(-c5ccccc5C#N)nc4n3CC3CC3)n(C)c12] | 2-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)benzonitrile | 578.1 | 2 | 1.72 |

| # | Structure | Name | Obs. MS Ion | HPLC Method ID | RT |
|---|---|---|---|---|---|
| 710. | 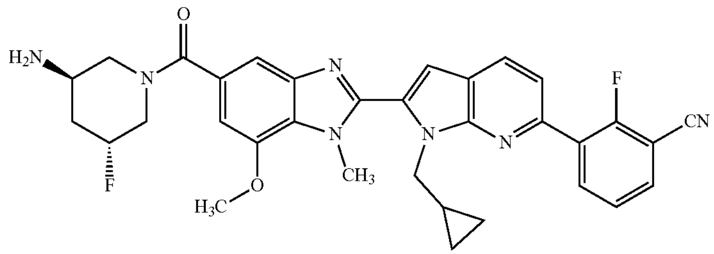 [SMILES: COc1cc(C(=O)N2C[C@H](N)C[C@@H](F)C2)cc2nc(-c3cc4ccc(-c5cccc(C#N)c5F)nc4n3CC3CC3)n(C)c12] | 3-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-fluorobenzonitrile | 596 | 1 | 1.86 |
| 711. | 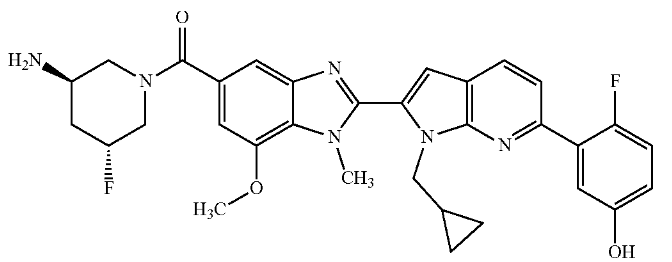 [SMILES: COc1cc(C(=O)N2C[C@H](N)C[C@@H](F)C2)cc2nc(-c3cc4ccc(-c5cc(O)ccc5F)nc4n3CC3CC3)n(C)c12] | 3-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-4-fluorophenol | 587.1 | 2 | 1.5 |
| 712. | 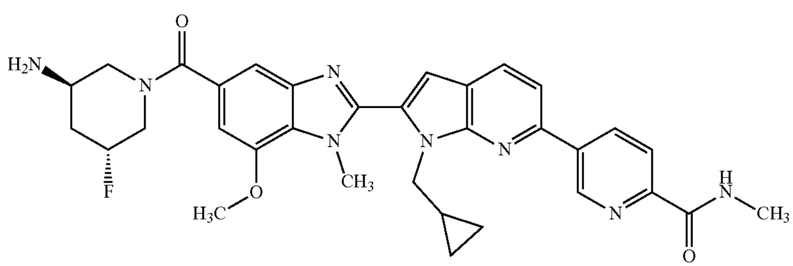 [SMILES: CNC(=O)c1ccc(-c2ccc3cc(-c4nc5cc(C(=O)N6C[C@H](N)C[C@@H](F)C6)cc(OC)c5n4C)n(CC4CC4)c3n2)cn1] | 5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-N-methylpyridine-2-carboxamide | 611.1 | 1 | 1.49 |

| # | Structure | Name | Obs. MS Ion | HPLC Method ID | RT |
|---|---|---|---|---|---|
| 713. | 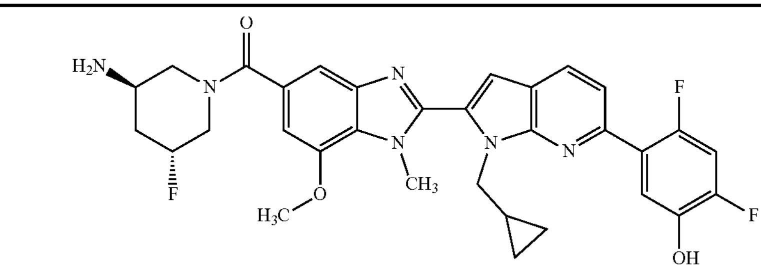 | 5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2,4-difluorophenol | 605.2 | 1 | 1.74 |
| 714. | 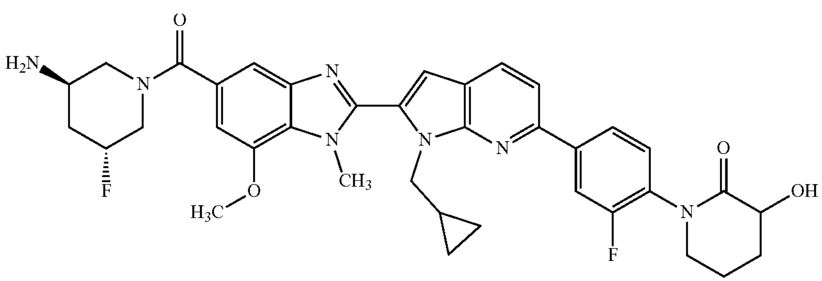 [SMILES: COc1cc(C(=O)N2C[C@H](N)C[C@@H](F)C2)cc2nc(-c3cc4ccc(-c5ccc(N6CCCC(O)C6=O)c(F)c5)nc4n3CC3CC3)n(C)c12] | 1-[4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-fluorophenyl]-3-hydroxypiperidin-2-one (mixture of diastereomers) | 684.3 | 2 | 1.41 |
| 715. | 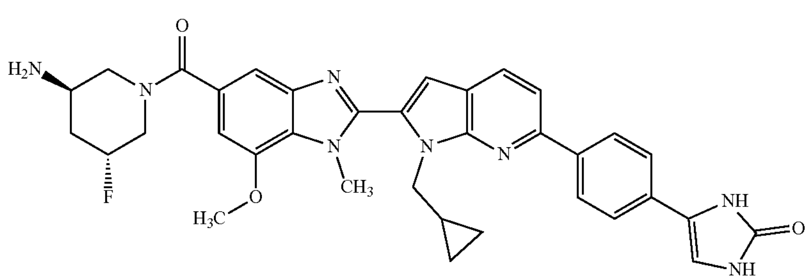 [SMILES: COc1cc(C(=O)N2C[C@H](N)C[C@@H](F)C2)cc2nc(-c3cc4ccc(-c5ccc(-c6c[nH]c(=O)[nH]6)cc5)nc4n3CC3CC3)n(C)c12] | 4-[4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)phenyl]-2,3-dihydro-1H-imidazol-2-one | 635.4 | 2 | 1.22 |

| # | Structure | Name | Obs. MS Ion | HPLC Method ID | RT |
|---|---|---|---|---|---|
| 716. | 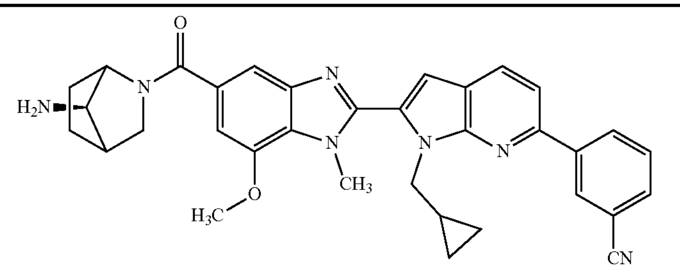 | 3-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)benzonitrile | 572.2 | 1 | 2.04 |
| 717. | 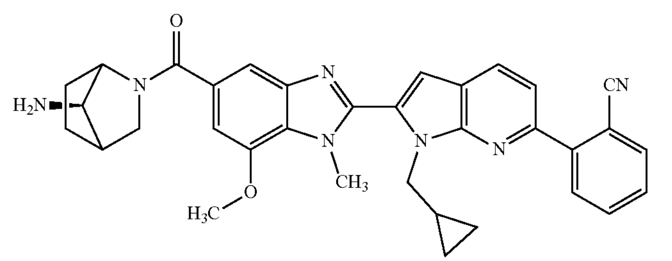 [SMILES: COc1cc(C(=O)N2CC3CCC2[C@@H]3N)cc2nc(-c3cc4ccc(-c5ccccc5C#N)nc4n3CC3CC3)n(C)c12] | 2-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)benzonitrile | 572.4 | 1 | 1.9 |
| 718. | 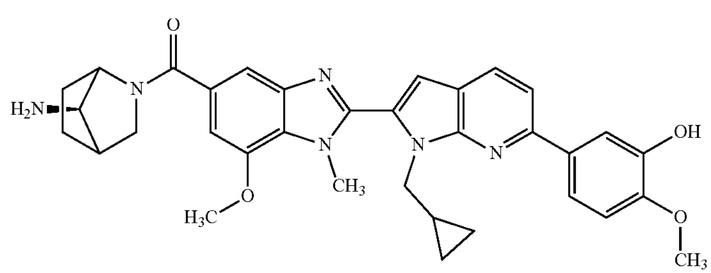 [SMILES: COc1ccc(-c2ccc3cc(-c4nc5cc(C(=O)N6CC7CCC6[C@@H]7N)cc(OC)c5n4C)n(CC4CC4)c3n2)cc1O] | 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-methoxyphenol | 593.2 | 1 | 1.76 |

| # | Structure | Name | Obs. MS Ion | HPLC Method ID | RT |
|---|---|---|---|---|---|
| 719. | 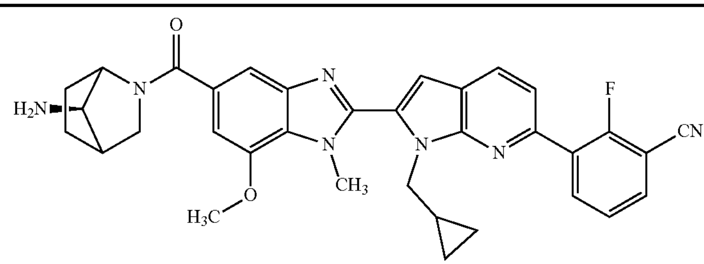 | 3-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-fluorobenzonitrile | 590.2 | 1 | 1.9 |
| 720. | 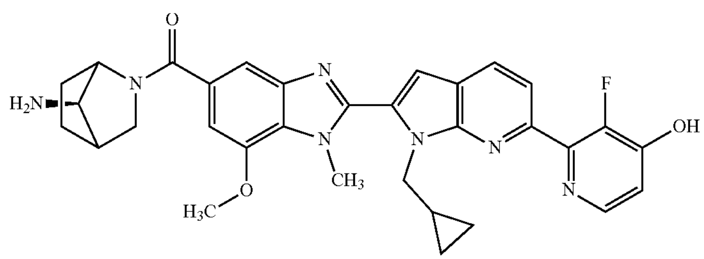 [SMILES: COc1cc(C(=O)N2CC3CCC2[C@@H]3N)cc2nc(-c3cc4ccc(-c5nccc(O)c5F)nc4n3CC3CC3)n(C)c12] | 2-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-3-fluoropyridin-4-ol | 582.1 | 1 | 1.11 |
| 721. | 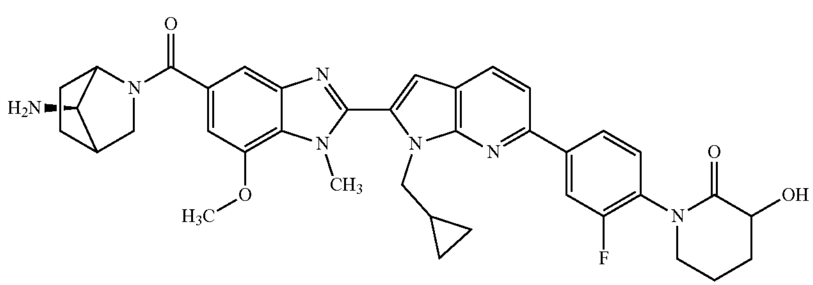 [SMILES: COc1cc(C(=O)N2CC3CCC2[C@@H]3N)cc2nc(-c3cc4ccc(-c5ccc(N6CCCC(O)C6=O)c(F)c5)nc4n3CC3CC3)n(C)c12] | 1-[4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-3-fluorophenyl]-3-hydroxypiperidin-2-one (mixture of diastereomers) | 678.3 | 2 | 1.49 |

| # | Structure | Name | Obs. MS Ion | HPLC Method ID | RT |
|---|---|---|---|---|---|
| 722. | 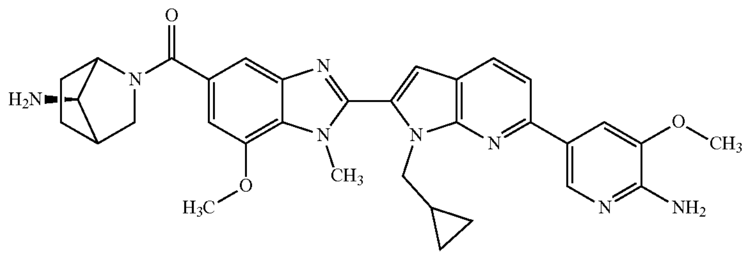 [SMILES: COc1cc(-c2ccc3cc(-c4nc5cc(C(=O)N6CC7CCC6[C@@H]7N)cc(OC)c5n4C)n(CC4CC4)c3n2)cnc1N] | (7R)-2-{2-[6-(6-amino-5-methoxypyridin-3-yl)-1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 593.3 | 1 | 1.58 |
| 723. | 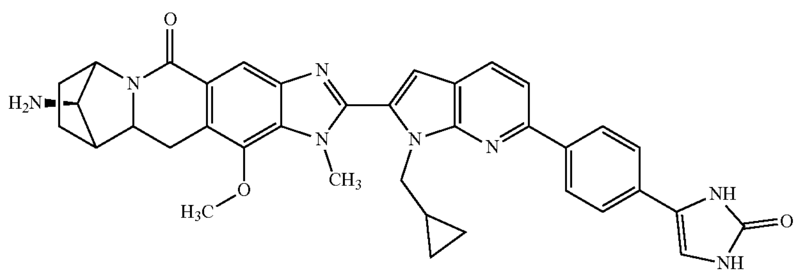 [SMILES: COc1c2c(cc3nc(-c4cc5ccc(-c6ccc(-c7c[nH]c(=O)[nH]7)cc6)nc5n4CC4CC4)n(C)c13)C(=O)N1C(C2)C2CCC1[C@@H]2N] | 4-[4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]-2,3-dihydro-1H-imidazol-2-one | 629.2 | 2 | 1.21 |
| 724. | 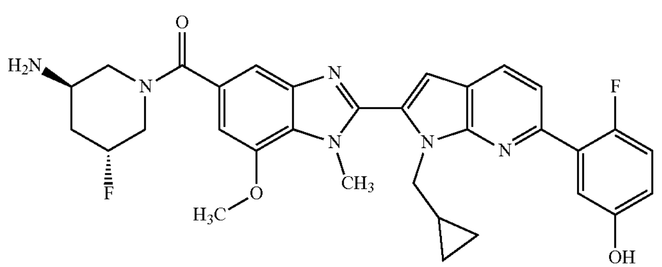 [SMILES: COc1cc(C(=O)N2C[C@H](N)C[C@@H](F)C2)cc2nc(-c3cc4ccc(-c5cc(O)ccc5F)nc4n3CC3CC3)n(C)c12] | 3-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-4-fluorophenol | 293.9 | 2 | 1.53 |

| # | Structure | Name | Obs. MS Ion | HPLC Method ID | RT |
|---|---|---|---|---|---|
| 725. | 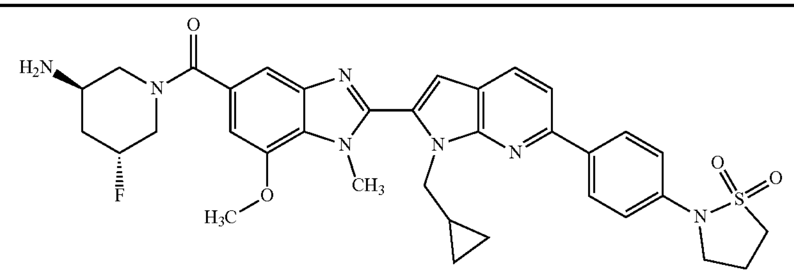 | ((3R,5R)-3-amino-5-fluoropiperidin-1-yl)(2-(1-(cyclopropylmethyl)-6-(4-(1,1-dioxidoisothiazolidin-2-yl)phenyl)-1H-pyrrolo[2,3-b]pyridin-2-yl)-7-methoxy-1-methyl-1H-benzo[d]imidazol-5-yl)methanone | 672.3 | 1 | 1.56 |
| 726. | 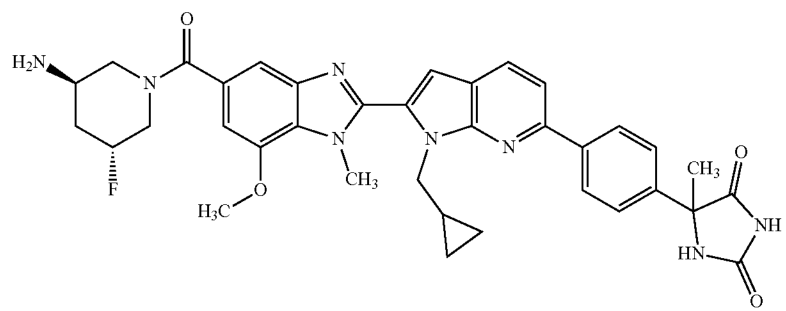 [SMILES: COc1cc(C(=O)N2C[C@H](N)C[C@@H](F)C2)cc2nc(-c3cc4ccc(-c5ccc(C6(C)NC(=O)NC6=O)cc5)nc4n3CC3CC3)n(C)c12] | 5-[4-(2-{5-[((3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)phenyl]-5-methylimidazolidine-2,4-dione | 665 | 2 | 1.38 |
| 727. | 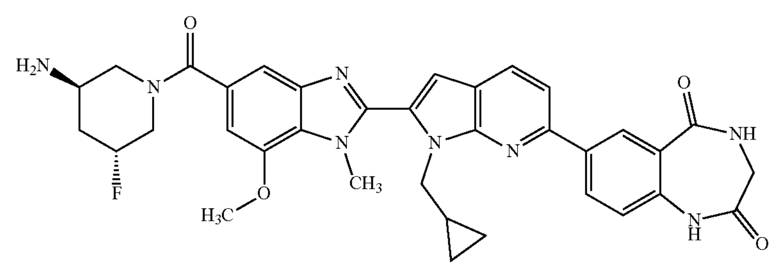 [SMILES: COc1cc(C(=O)N2C[C@H](N)C[C@@H](F)C2)cc2nc(-c3cc4ccc(-c5ccc6c(c5)C(=O)NCC(=O)N6)nc4n3CC3CC3)n(C)c12] | 7-(2-{5-[((3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2,3,4,5-tetrahydro-1H-1,4-benzodiazepine-2,5-dione | 651.1 | 2 | 1.18 |

| # | Structure | Name | Obs. MS Ion | HPLC Method ID | RT |
|---|---|---|---|---|---|
| 728. | 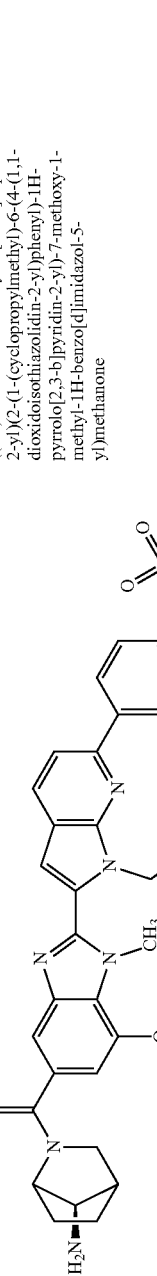 | ((7R)-7-amino-2-azabicyclo[2.2.1]heptan-2-yl)(2-(1-(cyclopropylmethyl)-6-(4-(1,1-dioxidoisothiazolidin-2-yl)phenyl)-1H-pyrrolo[2,3-b]pyridin-2-yl)-7-methoxy-1-methyl-1H-benzo[d]imidazol-5-yl)methanone | 666.2 | 1 | 1.67 |
| 729. | 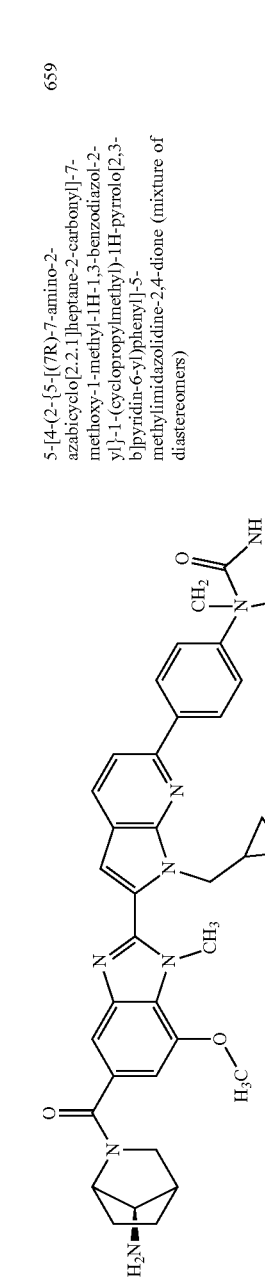 | 5-[4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]-5-methylimidazolidine-2,4-dione (mixture of diastereomers) | 659 | 1 | 1.53 |
| 730. | 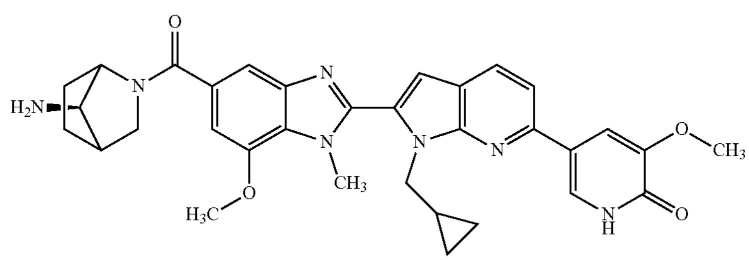 [SMILES: COc1cc(-c2ccc3cc(-c4nc5cc(C(=O)N6CC7CCC6[C@@H]7N)cc(OC)c5n4C)n(CC4CC4)c3n2)c[nH]c1=O] | 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-3-methoxy-1,2-dihydropyridin-2-one | 594.2 | 2 | 1.2 |

| # | Structure | Name | Obs. MS Ion | HPLC Method ID | RT |
|---|---|---|---|---|---|
| 731. | 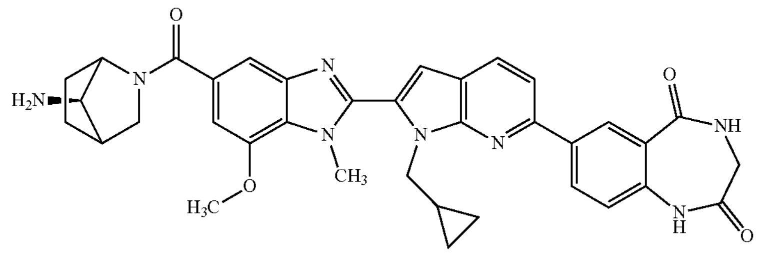 [SMILES: COc1cc(C(=O)N2CC3CCC2[C@@H]3N)cc2nc(-c3cc4ccc(-c5ccc6c(c5)C(=O)NCC(=O)N6)nc4n3CC3CC3)n(C)c12] | 7-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2,3,4,5-tetrahydro-1H-1,4-benzodiazepine-2,5-dione | 645.2 | 2 | 1.24 |
| 732. | 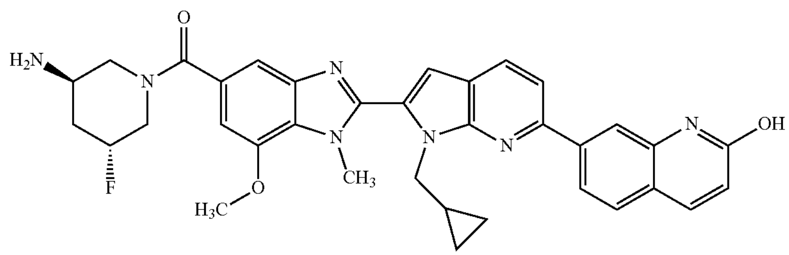 [SMILES: COc1cc(C(=O)N2C[C@H](N)C[C@@H](F)C2)cc2nc(-c3cc4ccc(-c5ccc6ccc(O)nc6c5)nc4n3CC3CC3)n(C)c12] | 7-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)quinolin-2-ol | 620.18 | 2 | 1.34 |
| 733. | 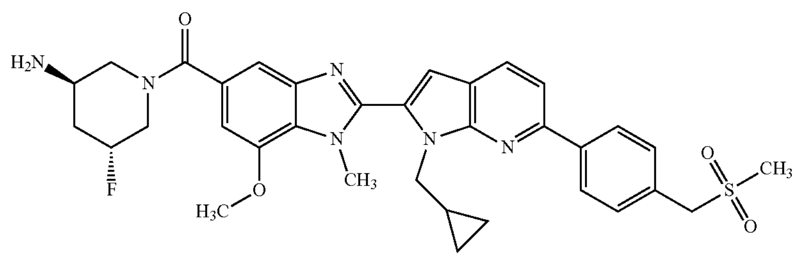 [SMILES: COc1cc(C(=O)N2C[C@H](N)C[C@@H](F)C2)cc2nc(-c3cc4ccc(-c5ccc(CS(C)(=O)=O)cc5)nc4n3CC3CC3)n(C)c12] | (3R,5R)-1-{2-[1-(cyclopropylmethyl)-6-[4-(methanesulfonylmethyl)phenyl]-1H-pyrrolo[2,3-b]pyridin-2-yl]-7-methoxy-1-methyl-1H-1,3-benzodiazole-5-carbonyl}-5-fluoropiperidin-3-amine | 645.2 | 2 | 1.52 |
| 734. | 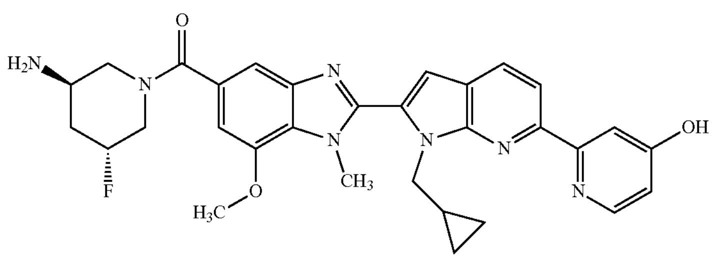 | 2-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)pyridin-4-ol | 570.2 | 2 | 1.09 |

| # | Structure | Name | Obs. MS Ion | HPLC Method ID | RT |
|---|---|---|---|---|---|
| 735. | 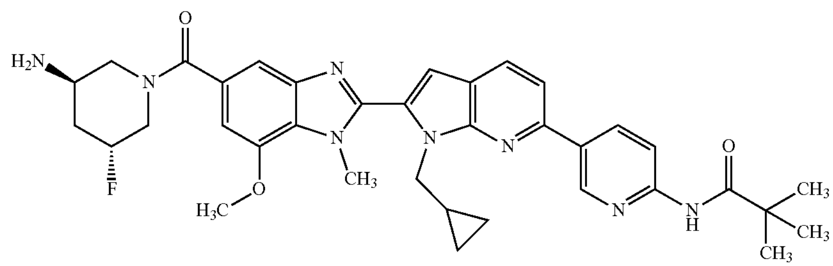 [SMILES: COc1cc(C(=O)N2C[C@H](N)C[C@@H](F)C2)cc2nc(-c3cc4ccc(-c5ccc(NC(=O)C(C)(C)C)nc5)nc4n3CC3CC3)n(C)c12] | N-[5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)pyridin-2-yl]-2,2-dimethylpropanamide | 653.4 | 1 | 1.86 |
| 736. | 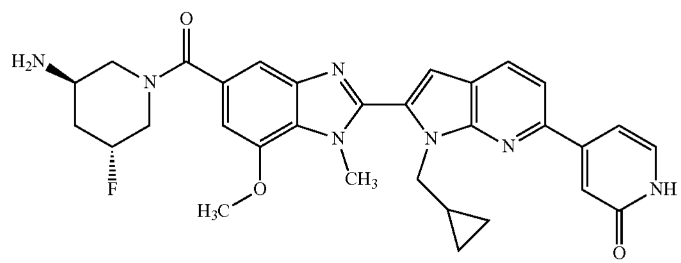 [SMILES: COc1cc(C(=O)N2C[C@H](N)C[C@@H](F)C2)cc2nc(-c3cc4ccc(-c5cc[nH]c(=O)c5)nc4n3CC3CC3)n(C)c12] | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-1,2-dihydropyridin-2-one | 570.1 | 2 | 1.18 |
| 737. | 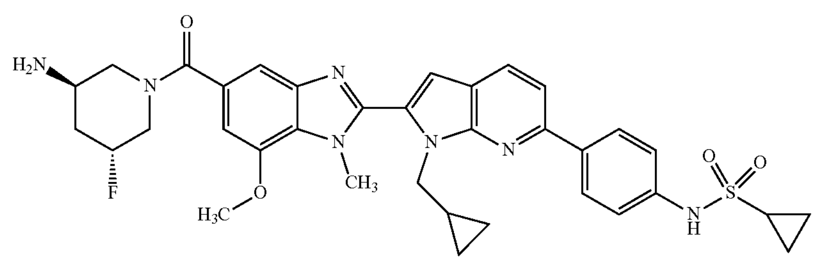 [SMILES: COc1cc(C(=O)N2C[C@H](N)C[C@@H](F)C2)cc2nc(-c3cc4ccc(-c5ccc(NS(=O)(=O)C6CC6)cc5)nc4n3CC3CC3)n(C)c12] | N-[4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)phenyl]cyclopropanesulfonamide | 672.2 | 2 | 1.58 |

| # | Structure | Name | Obs. MS Ion | HPLC Method ID | RT |
|---|---|---|---|---|---|
| 738. | 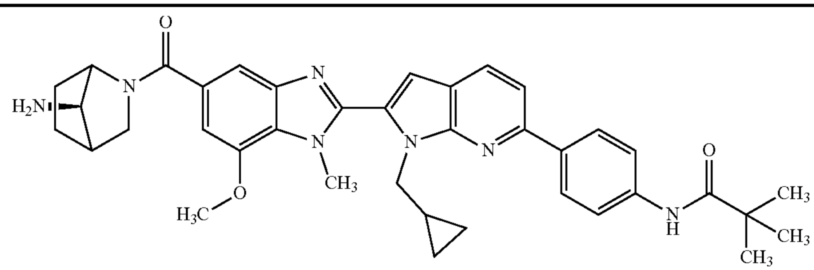 | N-[4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]-2,2-dimethylpropanamide | 646 | 2 | 1.69 |
| 739. | 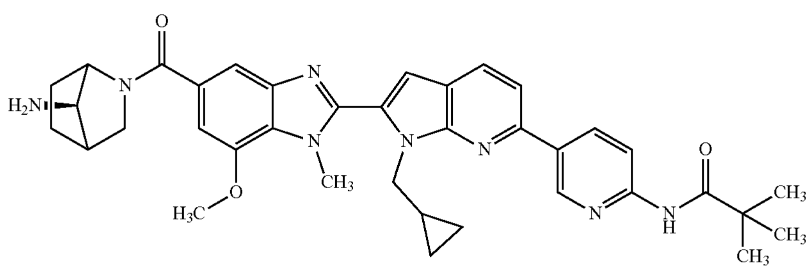 [SMILES: COc1cc(C(=O)N2CC3CCC2[C@@H]3N)cc2nc(-c3cc4ccc(-c5ccc(NC(=O)C(C)(C)C)cc5)nc4n3CC3CC3)n(C)c12] | N-[5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)pyridin-2-yl]-2,2-dimethylpropanamide | 647 | 1 | 2.02 |
| 740. | 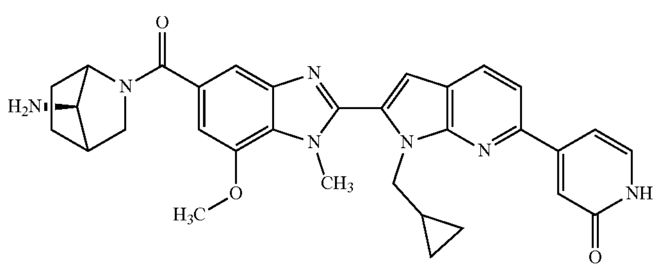 [SMILES: COc1cc(C(=O)N2CC3CCC2[C@@H]3N)cc2nc(-c3cc4ccc(-c5cc[nH]c(=O)c5)nc4n3CC3CC3)n(C)c12] | 4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1,2-dihydropyridin-2-one | 564.2 | 1 | 1.21 |

| # | Structure | Name | Obs. MS Ion | HPLC Method ID | RT |
|---|---|---|---|---|---|
| 741. | 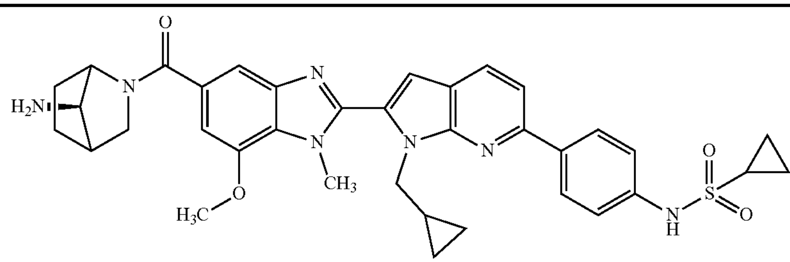 | N-[4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]cyclopropanesulfonamide | 666 | 1 | 1.82 |
| 742. | 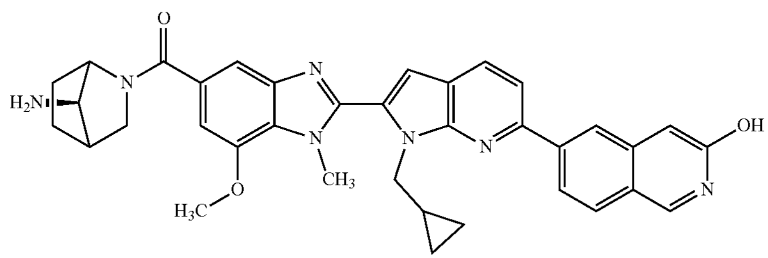 [SMILES: COc1cc(C(=O)N2CC3CCC2[C@@H]3N)cc2nc(-c3cc4ccc(-c5ccc6cnc(O)cc6c5)nc4n3CC3CC3)n(C)c12] | 6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)isoquinolin-3-ol | 614.2 | 1 | 1.47 |
| 743. | 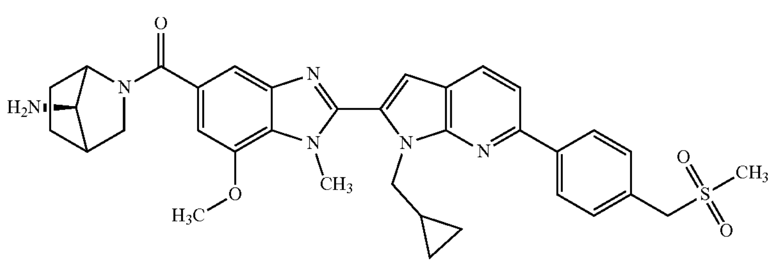 [SMILES: COc1cc(C(=O)N2CC3CCC2[C@@H]3N)cc2nc(-c3cc4ccc(-c5ccc(CS(C)(=O)=O)cc5)nc4n3CC3CC3)n(C)c12] | (7R)-2-{2-[1-(cyclopropylmethyl)-6-[4-(methanesulfonylmethyl)phenyl]-1H-pyrrolo[2,3-b]pyridin-2-yl]-7-methoxy-1-methyl-1H-1,3-benzodiazole-5-carbonyl}-2-azabicyclo[2.2.1]heptan-7-amine | 639.2 | 2 | 1.45 |

| # | Structure | Name | Obs. MS Ion | HPLC Method ID | RT |
|---|---|---|---|---|---|
| 744. | 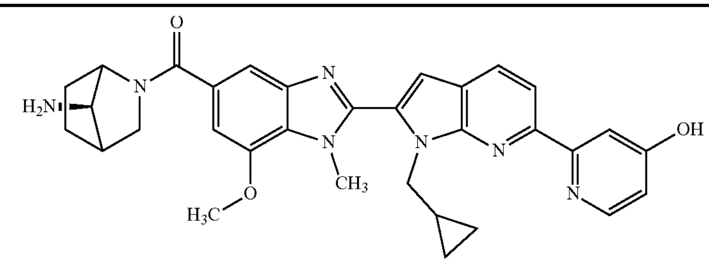 | 2-(2-(5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)pyridin-4-ol | 564 | 1 | 1.27 |
| 745. | 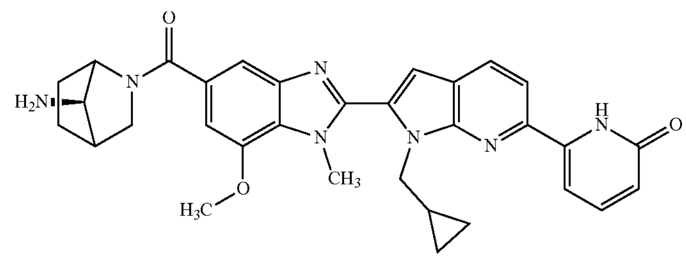 [SMILES: COc1cc(C(=O)N2CC3CCC2[C@@H]3N)cc2nc(-c3cc4ccc(-c5cccc(=O)[nH]5)nc4n3CC3CC3)n(C)c12] | 6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1,2-dihydropyridin-2-one | 564.2 | 1 | 1.44 |
| 746. | 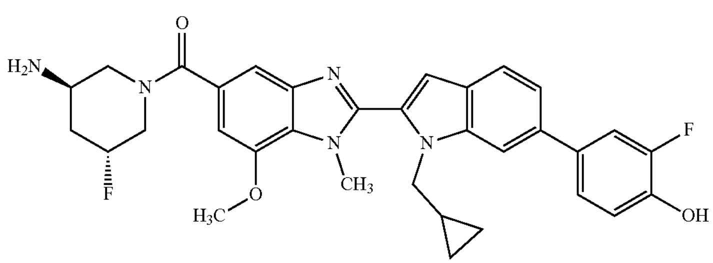 [SMILES: COc1cc(C(=O)N2C[C@H](N)C[C@@H](F)C2)cc2nc(-c3cc4ccc(-c5ccc(O)c(F)c5)cc4n3CC3CC3)n(C)c12] | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)-2-fluorophenol | 586.4 | 2 | 1.58 |

| # | Structure | Name | Obs. MS Ion | HPLC Method ID | RT |
|---|---|---|---|---|---|
| 747. | 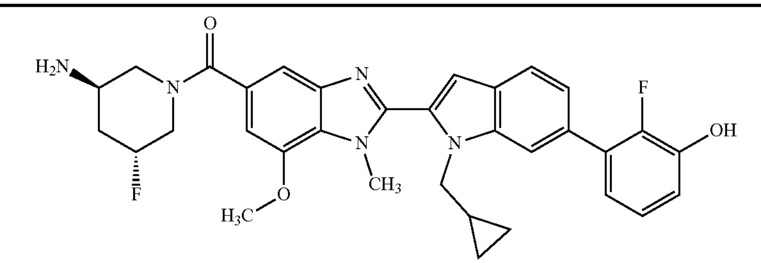 | 3-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)-2-fluorophenol | 586.2 | 2 | 1.47 |
| 748. | 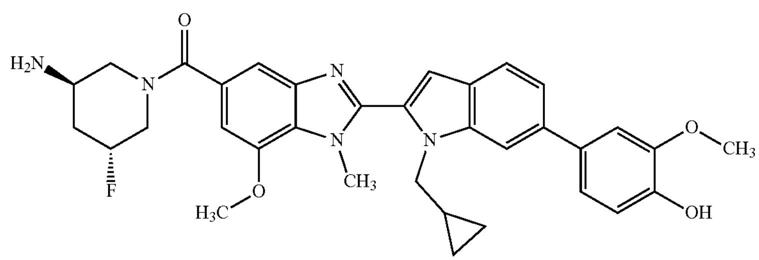 [SMILES: COc1cc(-c2ccc3cc(-c4nc5cc(C(=O)N6C[C@H](N)C[C@@H](F)C6)cc(OC)c5n4C)n(CC4CC4)c3c2)ccc1O] | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)-2-methoxyphenol | 598 | 1 | 1.65 |
| 749. | 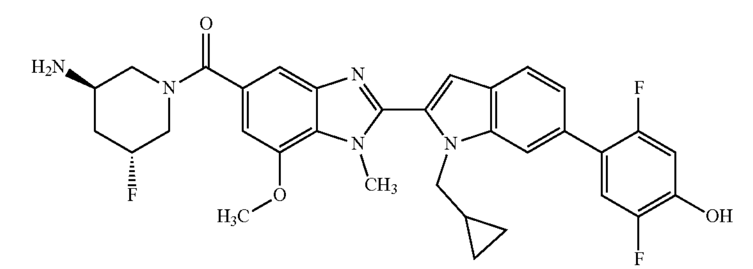 [SMILES: COc1cc(C(=O)N2C[C@H](N)C[C@@H](F)C2)cc2nc(-c3cc4ccc(-c5cc(F)c(O)cc5F)cc4n3CC3CC3)n(C)c12] | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)-2,5-difluorophenol | 604.2 | 1 | 1.75 |

-continued

| # | Structure | Name | Obs. MS Ion | HPLC Method ID | RT |
|---|---|---|---|---|---|
| 750. | 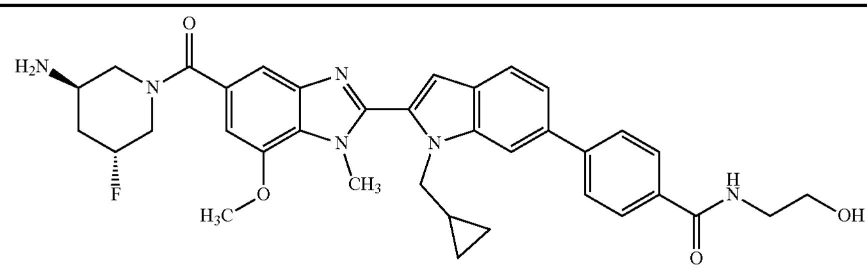 | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)-N-(2-hydroxyethyl)benzamide | 639.2 | 1 | 1.45 |
| 751. | 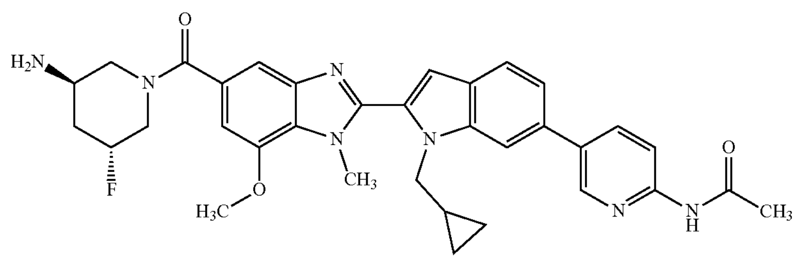 [SMILES: COc1cc(C(=O)N2C[C@H](N)C[C@@H](F)C2)cc2nc(-c3cc4ccc(-c5ccc(NC(C)=O)nc5)cc4n3CC3CC3)n(C)c12] | N-[5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)pyridin-2-yl]acetamide | 610.2 | 1 | 1.56 |
| 752. | 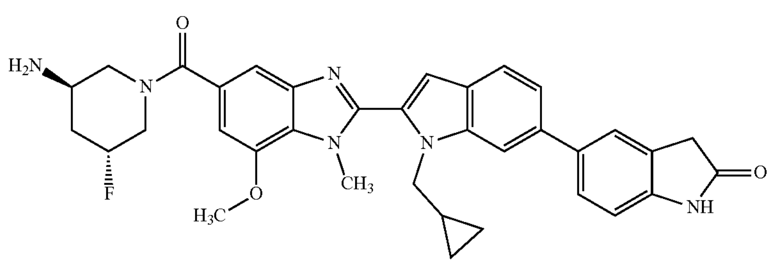 [SMILES: COc1cc(C(=O)N2C[C@H](N)C[C@@H](F)C2)cc2nc(-c3cc4ccc(-c5ccc6c(c5)CC(=O)N6)cc4n3CC3CC3)n(C)c12] | 2'-{5-[(3R,5R)-3-amino-5-fluoropiperidine-1-carbonyl]-7-methoxy-1-methyl-1H-1,3-benzodiazol-2-yl}-1'-(cyclopropylmethyl)-2,3-dihydro-1H,1'H-[5,6-biindole]-2-one | 607 | 2 | 1.38 |

| # | Structure | Name | Obs. MS Ion | HPLC Method ID | RT |
|---|---|---|---|---|---|
| 753. | 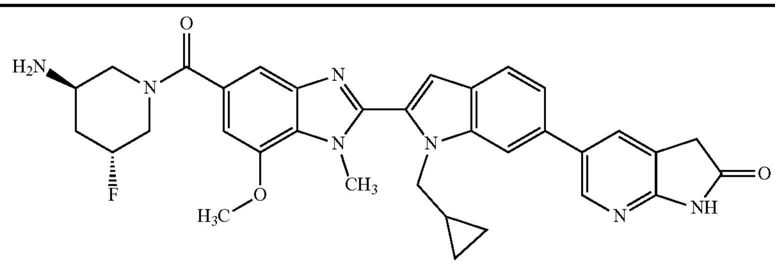 | 5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H,2H,3H-pyrrolo[2,3-b]pyridin-2-one | 608.1 | 1 | 1.53 |
| 754. | 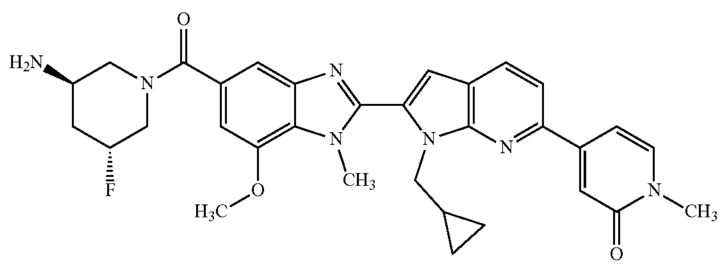 [SMILES: COc1cc(C(=O)N2C[C@H](N)C[C@@H](F)C2)cc2nc(-c3cc4ccc(-c5ccn(C)c(=O)c5)nc4n3CC3CC3)n(C)c12] | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)-1-methyl-1,2-dihydropyridin-2-one | 582.9 | 1 | 1.41 |
| 755. | 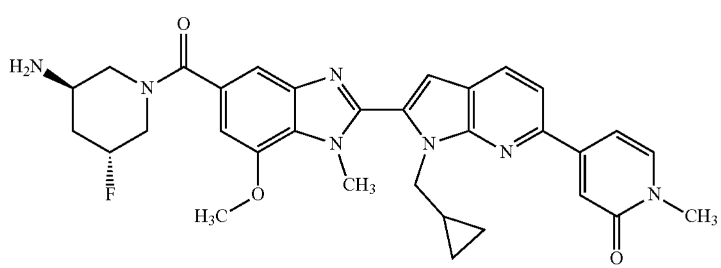 [SMILES: COc1cc(C(=O)N2C[C@H](N)C[C@@H](F)C2)cc2nc(-c3cc4ccc(-c5ccn(C)c(=O)c5)nc4n3CC3CC3)n(C)c12] | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-1-methyl-1,2-dihydropyridin-2-one | 584.2 | 2 | 1.31 |

| # | Structure | Name | Obs. MS Ion | HPLC Method ID | RT |
|---|---|---|---|---|---|
| 756. | 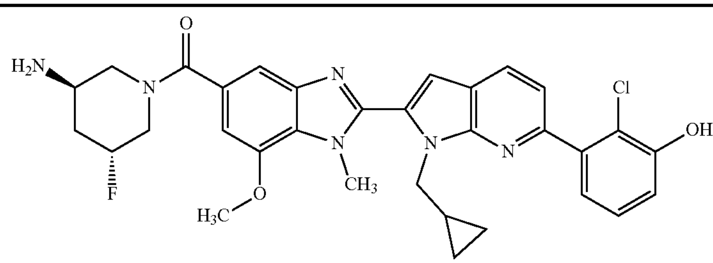 | 3-(2-{5-[(3R,5R)-3-amino-5-fluoropiperidine-1-carbonyl]-7-methoxy-1-methyl-1H-1,3-benzodiazol-2-yl]-1-(cyclopropylmethyl)-1H-pyrrolo[2,3-b]pyridin-6-yl)-2-chlorophenol | 603.2 | 1 | 1.7 |
| 757. | 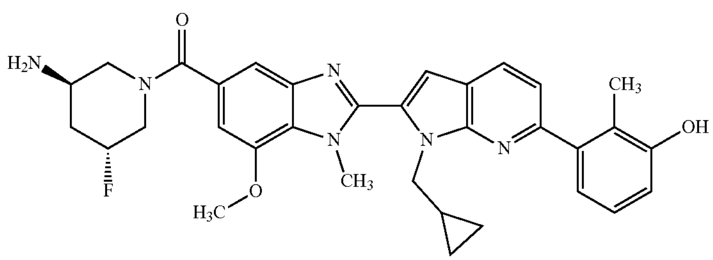 | 3-(2-{5-[(3R,5R)-3-amino-5-fluoropiperidine-1-carbonyl]-7-methoxy-1-methyl-1H-1,3-benzodiazol-2-yl]-1-(cyclopropylmethyl)-1H-pyrrolo[2,3-b]pyridin-6-yl)-2-methylphenol | 583 | 1 | 1.7 |
| 758. | 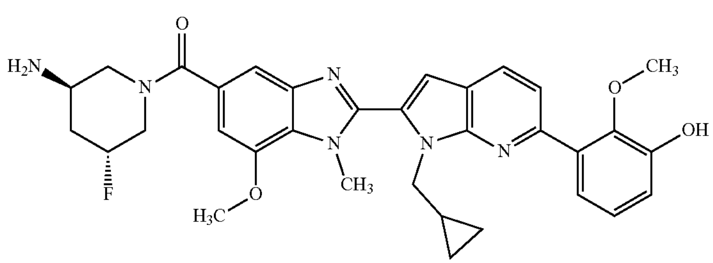 | 3-(2-{5-[(3R,5R)-3-amino-5-fluoropiperidine-1-carbonyl]-7-methoxy-1-methyl-1H-1,3-benzodiazol-2-yl]-1-(cyclopropylmethyl)-1H-pyrrolo[2,3-b]pyridin-6-yl)-2-methoxyphenol | 599.2 | 1 | 1.68 |

| # | Structure | Name | Obs. MS Ion | HPLC Method ID | RT |
|---|---|---|---|---|---|
| 759. | 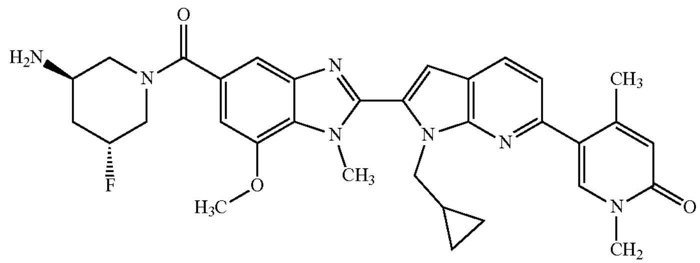 [SMILES: COc1cc(C(=O)N2C[C@H](N)C[C@@H](F)C2)cc2nc(-c3cc4ccc(-c5cn(C)c(=O)cc5C)nc4n3CC3CC3)n(C)c12] | 5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-1,4-dimethyl-1,2-dihydropyridin-2-one | 597.9 | 2 | 1.32 |
| 760. | 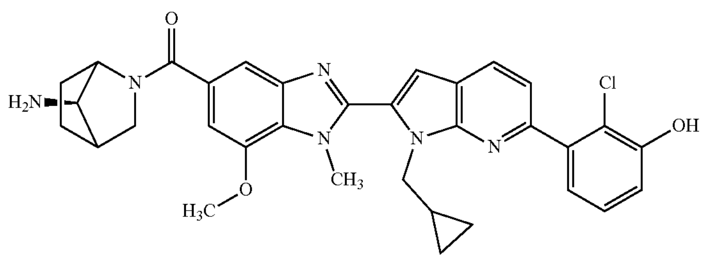 | 3-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-chlorophenol | 597.4 | 1 | 1.72 |
| 761. | 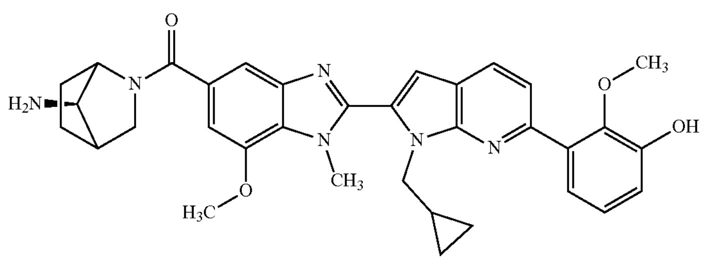 [SMILES: COc1c(O)cccc1-c1ccc2cc(-c3nc4cc(C(=O)N5CC6CCC5[C@@H]6N)cc(OC)c4n3C)n(CC3CC3)c2n1] | 3-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-methoxyphenol | 593.2 | 1 | 1.6 |

| # | Structure | Name | Obs. MS Ion | HPLC Method ID | RT |
|---|---|---|---|---|---|
| 762. | 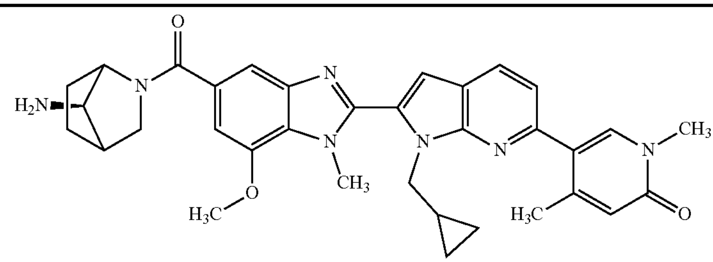 | 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1,4-dimethyl-1,2-dihydropyridin-2-one | 592 | 1 | 1.33 |
| 763. | 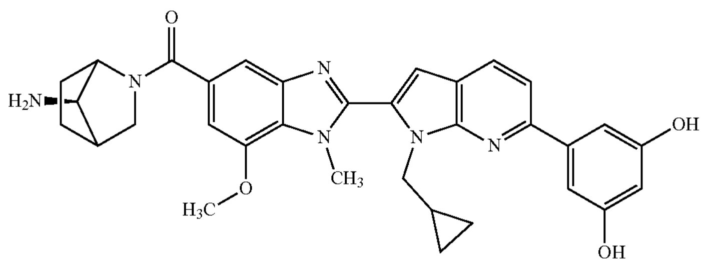 [SMILES: COc1cc(C(=O)N2CC3CCC2[C@@H]3N)cc2nc(-c3cc4ccc(-c5cc(O)cc(O)c5)nc4n3CC3CC3)n(C)c12] | 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)benzene-1,3-diol | 578.9 | 1 | 1.47 |
| 764. | 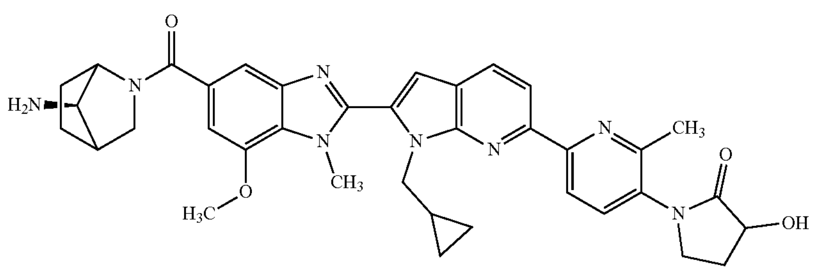 [SMILES: COc1cc(C(=O)N2CC3CCC2[C@@H]3N)cc2nc(-c3cc4ccc(-c5ccc(N6CCC(O)C6=O)c(C)n5)nc4n3CC3CC3)n(C)c12] | 1-[6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-methylpyridin-3-yl]-3-hydroxypyrrolidin-2-one | 661.3 | 1 | 1.51 |

| # | Structure | Name | Obs. MS Ion | HPLC Method ID | RT |
|---|---|---|---|---|---|
| 765. | 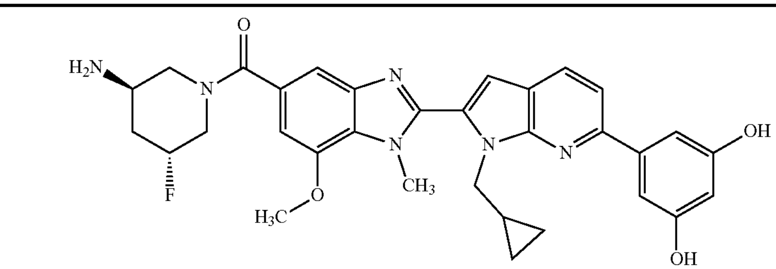 | 5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)benzene-1,3-diol | 585.2 | 1 | 1.42 |
| 766. | 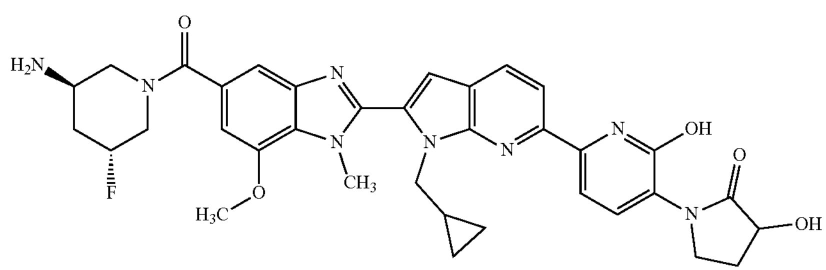 [SMILES: COc1cc(C(=O)N2C[C@H](N)C[C@@H](F)C2)cc2nc(-c3cc4ccc(-c5ccc(N6CCC(O)C6=O)c(O)n5)nc4n3CC3CC3)n(C)c12] | 1-[6-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-methylpyridin-3-yl]-3-hydroxypyrrolidin-2-one | 667.2 | 1 | 1.37 |
| 767. | 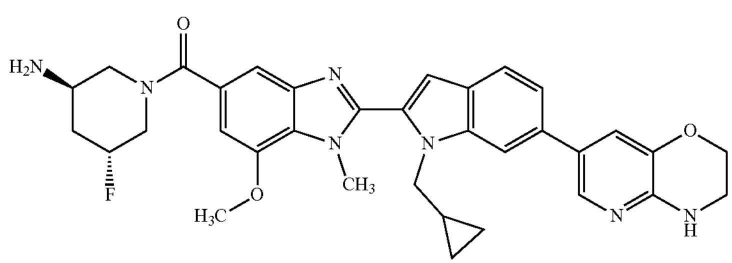 [SMILES: COc1cc(C(=O)N2C[C@H](N)C[C@@H](F)C2)cc2nc(-c3cc4ccc(-c5cnc6c(c5)OCCN6)cc4n3CC3CC3)n(C)c12] | (3R,5R)-1-{2-[1-(cyclopropylmethyl)-6-(2H,3H,4H-pyrido[3,2-b][1,4]oxazin-7-yl)-1H-indol-2-yl]-7-methoxy-1-methyl-1H-1,3-benzodiazole-5-carbonyl}-5-fluoropiperidin-3-amine | 610 | 2 | 1.23 |

| # | Structure | Name | Obs. MS Ion | HPLC Method ID | RT |
|---|---|---|---|---|---|
| 768. | 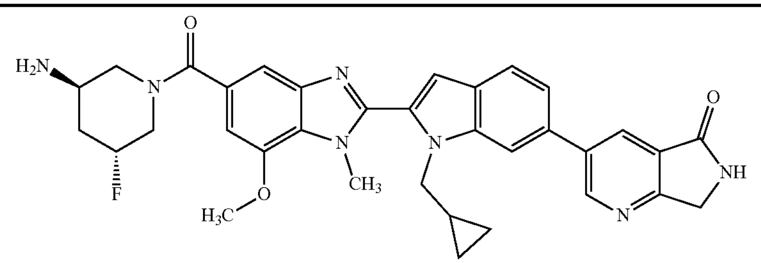 | 3-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)-5H,6H,7H-pyrrolo[3,4-b]pyridin-5-one | 608.1 | 1 | 1.47 |
| 769. | 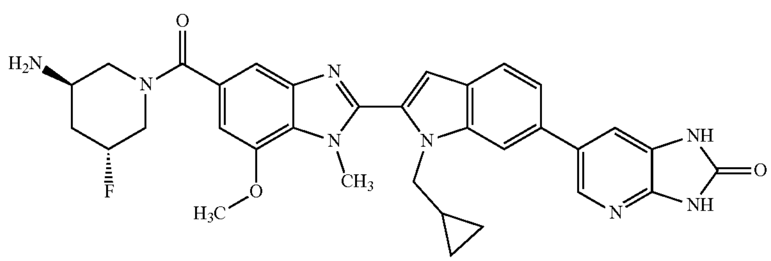 [SMILES: COc1cc(C(=O)N2C[C@H](N)C[C@@H](F)C2)cc2nc(-c3cc4ccc(-c5cnc6[nH]c(=O)[nH]c6c5)cc4n3CC3CC3)n(C)c12] | 6-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)-1H,2H,3H-imidazo[4,5-b]pyridin-2-one | 608.9 | 2 | 1.19 |
| 770. | 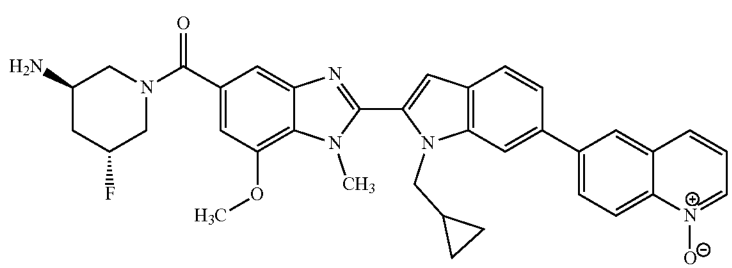 [SMILES: COc1cc(C(=O)N2C[C@H](N)C[C@@H](F)C2)cc2nc(-c3cc4ccc(-c5ccc6c(ccc[n+]6[O-])c5)cc4n3CC3CC3)n(C)c12] | 6-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)quinolin-1-ium-1-olate | 619.2 | 1 | 1.49 |

| # | Structure | Name | Obs. MS Ion | HPLC Method ID | RT |
|---|---|---|---|---|---|
| 771. | 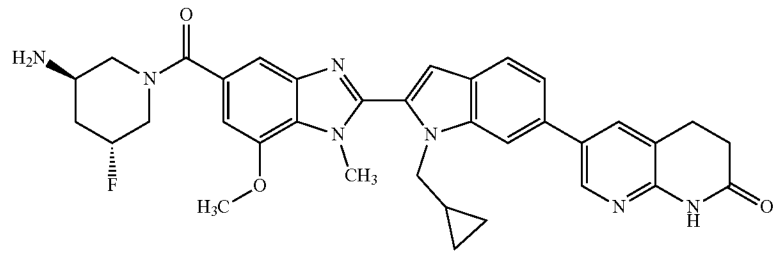 [SMILES: COc1cc(C(=O)N2C[C@H](N)C[C@@H](F)C2)cc2nc(-c3cc4ccc(-c5cnc6c(c5)CCC(=O)N6)cc4n3CC3CC3)n(C)c12] | 6-(2-{5-[((3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)-1,2,3,4-tetrahydro-1,8-naphthyridin-2-one | 622.2 | 2 | 1.35 |
| 772. | 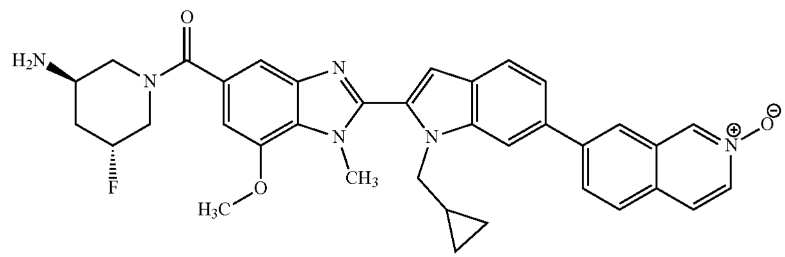 [SMILES: COc1cc(C(=O)N2C[C@H](N)C[C@@H](F)C2)cc2nc(-c3cc4ccc(-c5ccc6cc[n+]([O-])cc6c5)cc4n3CC3CC3)n(C)c12] | 7-(2-{5-[((3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)isoquinolin-2-ium-2-olate | 619.2 | 1 | 1.47 |
| 773. | 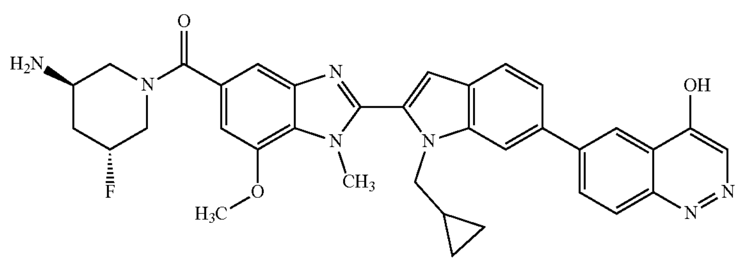 [SMILES: COc1cc(C(=O)N2C[C@H](N)C[C@@H](F)C2)cc2nc(-c3cc4ccc(-c5ccc6nncc(O)c6c5)cc4n3CC3CC3)n(C)c12] | 6-(2-{5-[((3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)cinnolin-4-ol | 620 | 1 | 1.38 |

-continued

| # | Structure | Name | Obs. MS Ion | HPLC Method ID | RT |
|---|---|---|---|---|---|
| 774. | 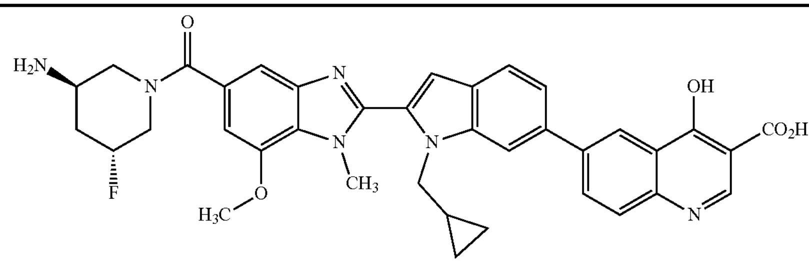 | 6-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)-4-hydroxyquinoline-3-carboxylic acid | 663.2 | 2 | 1.41 |
| 775. | 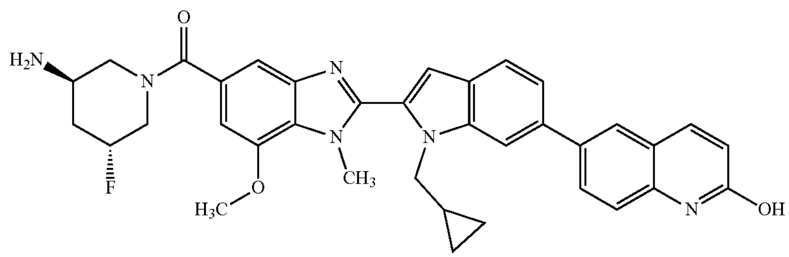 [SMILES: COc1cc(C(=O)N2C[C@H](N)C[C@@H](F)C2)cc2nc(-c3cc4ccc(-c5ccc6nc(O)ccc6c5)cc4n3CC3CC3)n(C)c12] | 6-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)quinolin-2-ol | 619.2 | 1 | 1.55 |
| 776. | 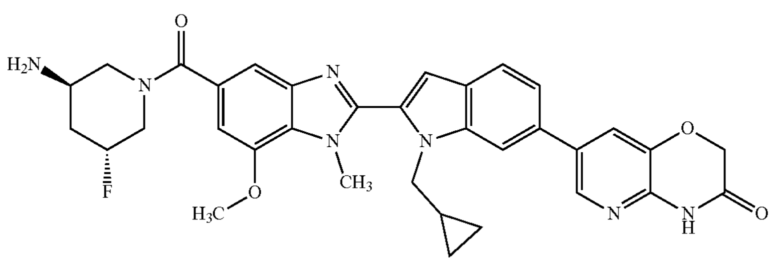 [SMILES: COc1cc(C(=O)N2C[C@H](N)C[C@@H](F)C2)cc2nc(-c3cc4ccc(-c5cnc6c(c5)OCC(=O)N6)cc4n3CC3CC3)n(C)c12] | 7-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)-2H,3H,4H-pyrido[3,2-b][1,4]oxazin-3-one | 624 | 2 | 1.41 |

| # | Structure | Name | Obs. MS Ion | HPLC Method ID | RT |
|---|---|---|---|---|---|
| 777. | 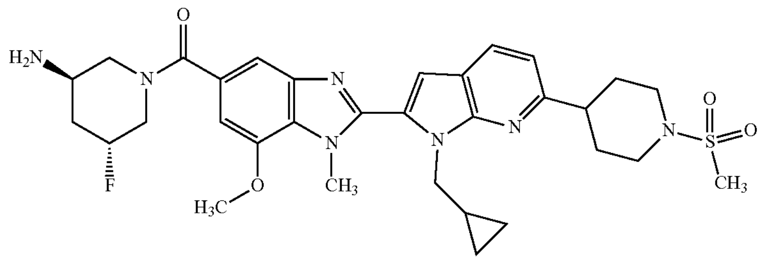 [SMILES: COc1cc(C(=O)N2C[C@H](N)C[C@@H](F)C2)cc2nc(-c3cc4ccc(C5CCN(S(C)(=O)=O)CC5)nc4n3CC3CC3)n(C)c12] | (3R,5R)-1-(2-[1-(cyclopropylmethyl)-6-(1-methanesulfonylpiperidin-4-yl)-1H-pyrrolo[2,3-b]pyridin-2-yl]-7-methoxy-1-methyl-1H-1,3-benzodiazole-5-carbonyl]-5-fluoropiperidin-3-amine | 638.2 | 2 | 1.53 |
| 778. | 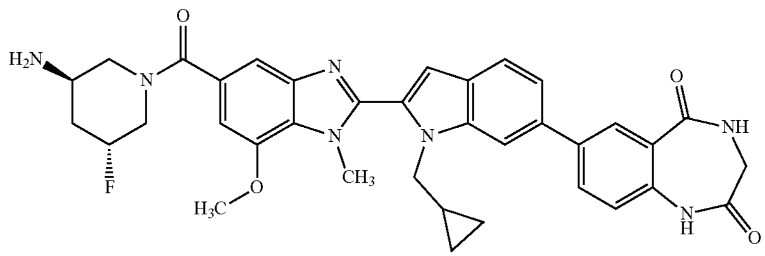 [SMILES: COc1cc(C(=O)N2C[C@H](N)C[C@@H](F)C2)cc2nc(-c3cc4ccc(-c5ccc6c(c5)C(=O)NCC(=O)N6)cc4n3CC3CC3)n(C)c12] | 7-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)-2,3,4,5-tetrahydro-1H-1,4-benzodiazepine-2,5-dione | 649.9 | 1 | 1.38 |
| 779. | 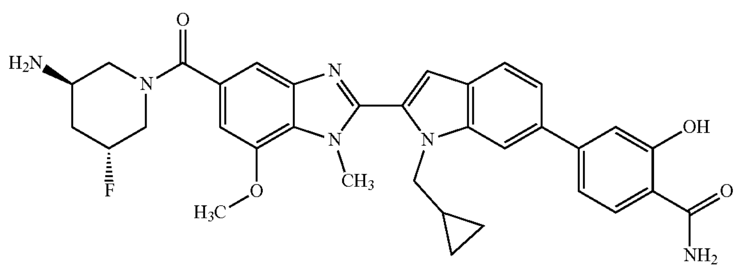 [SMILES: COc1cc(C(=O)N2C[C@H](N)C[C@@H](F)C2)cc2nc(-c3cc4ccc(-c5ccc(C(N)=O)c(O)c5)cc4n3CC3CC3)n(C)c12] | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)-2-hydroxybenzamide | 611.2 | 1 | 1.45 |

| # | Structure | Name | Obs. MS Ion | HPLC Method ID | RT |
|---|---|---|---|---|---|
| 780. | 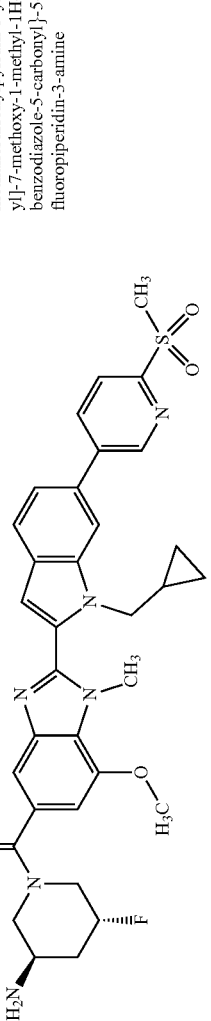 | (3R,5R)-1-{2-[1-(cyclopropylmethyl)-6-(6-methanesulfonylpyridin-3-yl)-1H-indol-2-yl]-7-methoxy-1-methyl-1H-1,3-benzodiazole-5-carbonyl}-5-fluoropiperidin-3-amine | 631.2 | 1 | 1.6 |
| 781. | 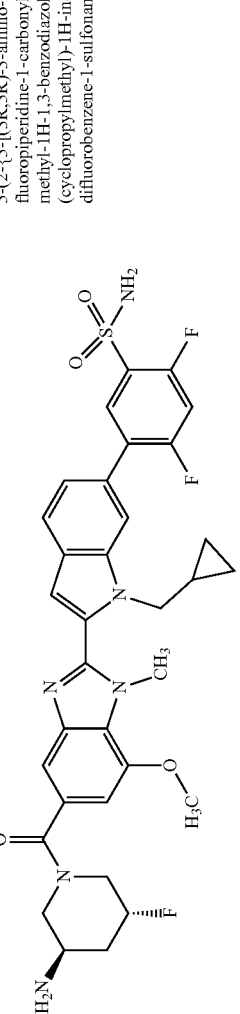 | 5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)-2,4-difluorobenzene-1-sulfonamide | 667.2 | 1 | 1.66 |
| 782. | 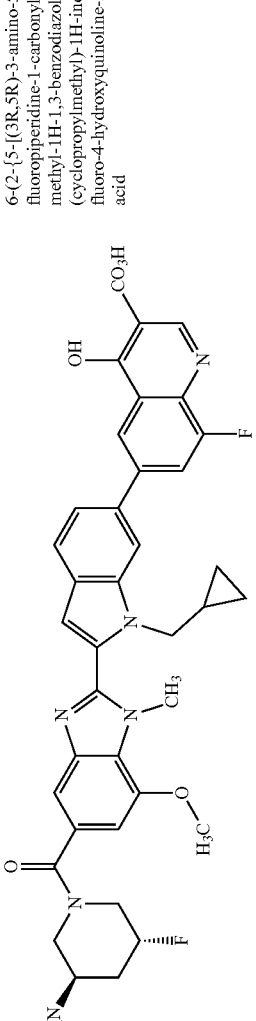 | 6-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)-8-fluoro-4-hydroxyquinoline-3-carboxylic acid | 680.92 | 2 | 1.47 |

| # | Structure | Name | Obs. MS Ion | HPLC Method ID | RT |
|---|---|---|---|---|---|
| 783. | 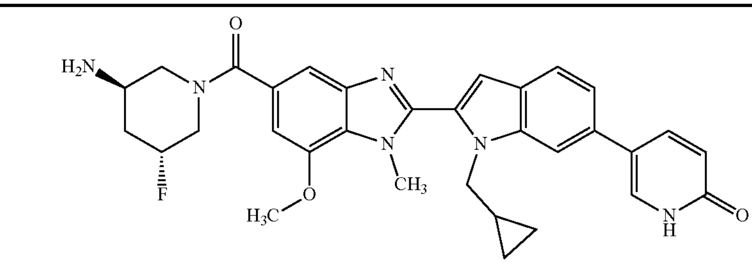 | 5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)-1,2-dihydropyridin-2-one | 569.2 | 2 | 1.2 |
| 784. | 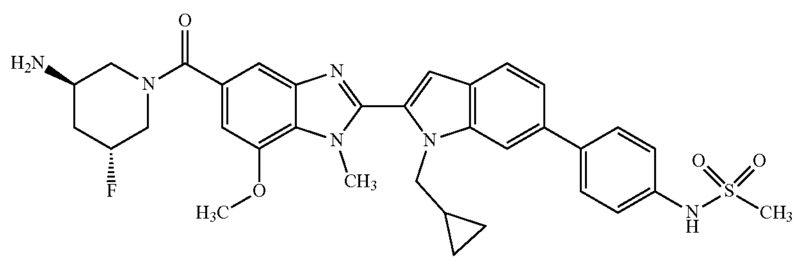 [SMILES: COc1cc(C(=O)N2C[C@H](N)C[C@@H](F)C2)cc2nc(-c3cc4ccc(-c5ccc(NS(C)(=O)=O)cc5)cc4n3CC3CC3)n(C)c12] | N-[4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)phenyl]methanesulfonamide | 645.2 | 1 | 1.65 |
| 785. | 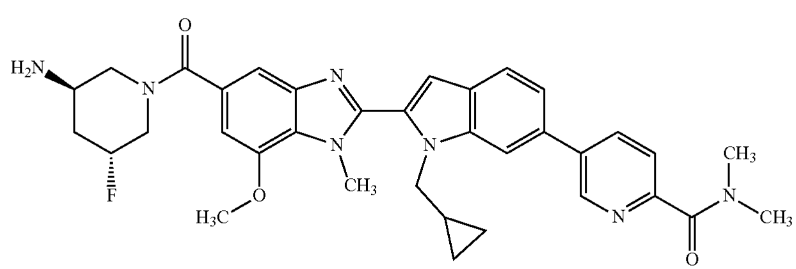 [SMILES: COc1cc(C(=O)N2C[C@H](N)C[C@@H](F)C2)cc2nc(-c3cc4ccc(-c5ccc(C(=O)N(C)C)nc5)cc4n3CC3CC3)n(C)c12] | 5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)-N,N-dimethylpyridine-2-carboxamide | 624.2 | 2 | 1.3 |

| # | Structure | Name | Obs. MS Ion | HPLC Method ID | RT |
|---|---|---|---|---|---|
| 786. | 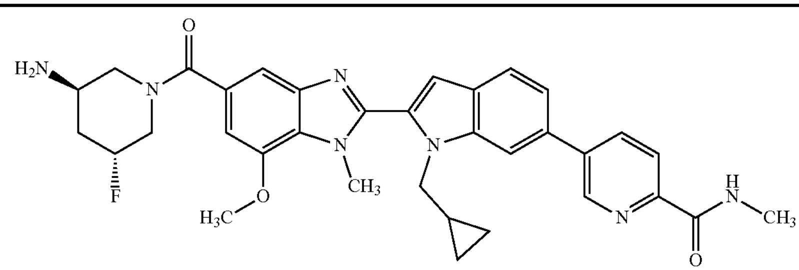 | 5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)-N-methylpyridine-2-carboxamide | 610.2 | 1 | 1.61 |
| 787. | 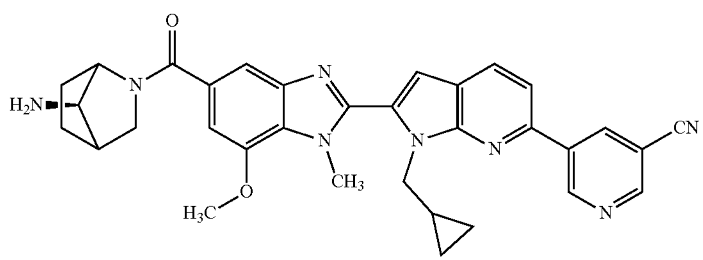 [SMILES: COc1cc(C(=O)N2CC3CCC2[C@@H]3N)cc2nc(-c3cc4ccc(-c5cncc(C#N)c5)nc4n3CC3CC3)n(C)c12] | 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)pyridine-3-carbonitrile | 573 | 2 | 1.53 |
| 788. | 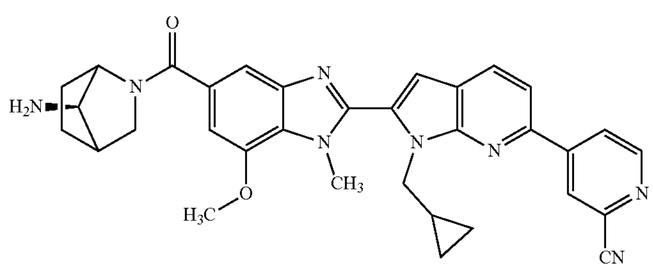 [SMILES: COc1cc(C(=O)N2CC3CCC2[C@@H]3N)cc2nc(-c3cc4ccc(-c5ccnc(C#N)c5)nc4n3CC3CC3)n(C)c12] | 4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)pyridine-2-carbonitrile | 573.2 | 1 | 1.79 |

| # | Structure | Name | Obs. MS Ion | HPLC Method ID | RT |
|---|---|---|---|---|---|
| 789. | 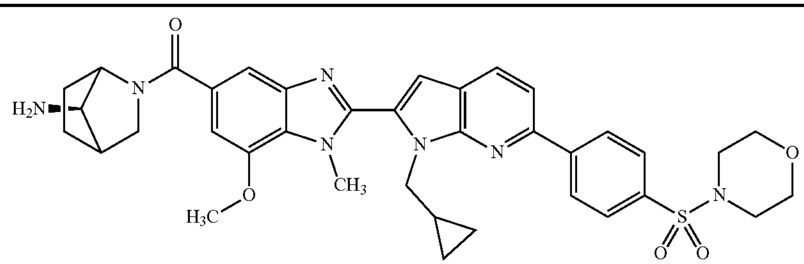 | (7R)-2-{2-[1-(cyclopropylmethyl)-6-[4-(morpholine-4-sulfonyl)phenyl]-1H-pyrrolo[2,3-b]pyridin-2-yl]-7-methoxy-1-methyl-1H-1,3-benzodiazole-5-carbonyl}-2-azabicyclo[2.2.1]heptan-7-amine | 696.2 | 1 | 1.82 |
| 790. | 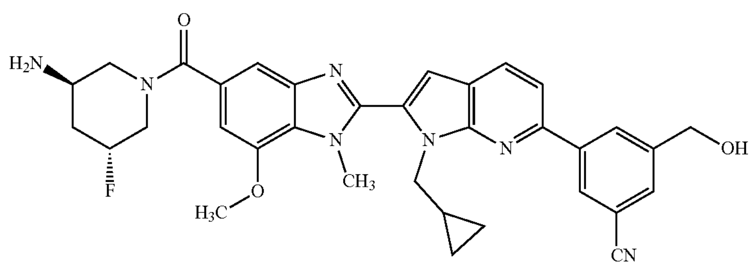 [SMILES: COc1cc(C(=O)N2C[C@H](N)C[C@@H](F)C2)cc2nc(-c3cc4ccc(-c5cc(C#N)cc(CO)c5)nc4n3CC3CC3)n(C)c12] | 3-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-5-(hydroxymethyl)benzonitrile | 608.2 | 2 | 1.54 |
| 791. | 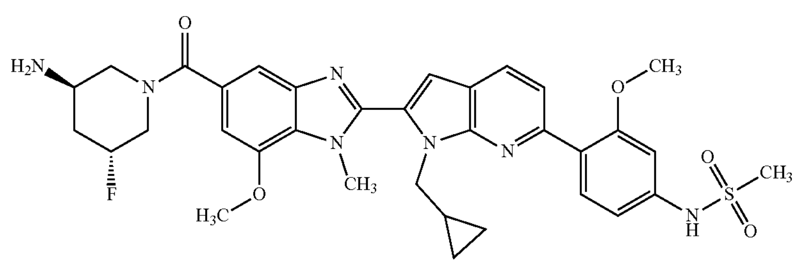 [SMILES: COc1cc(NS(C)(=O)=O)ccc1-c1ccc2cc(-c3nc4cc(C(=O)N5C[C@H](N)C[C@@H](F)C5)cc(OC)c4n3C)n(CC3CC3)c2n1] | N-[4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-3-methoxyphenyl]methanesulfonamide | 676.4 | 2 | 1.46 |

| # | Structure | Name | Obs. MS Ion | HPLC Method ID | RT |
|---|---|---|---|---|---|
| 792. | 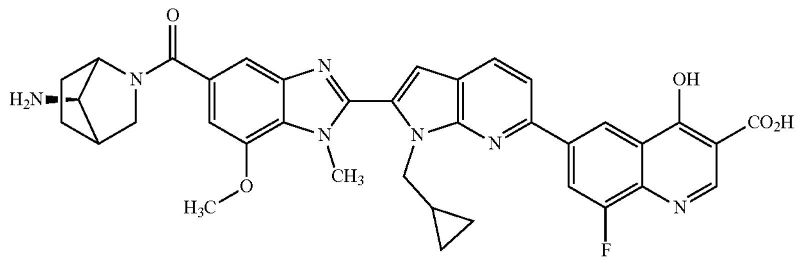 [SMILES: COc1cc(C(=O)N2CC3CCC2[C@@H]3N)cc2nc(-c3cc4ccc(-c5cc(F)c6ncc(C(=O)O)c(O)c6c5)nc4n3CC3CC3)n(C)c12] | 6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-8-fluoro-4-hydroxyquinoline-3-carboxylic acid | 676.2 | 2 | 1.48 |
| 793. | 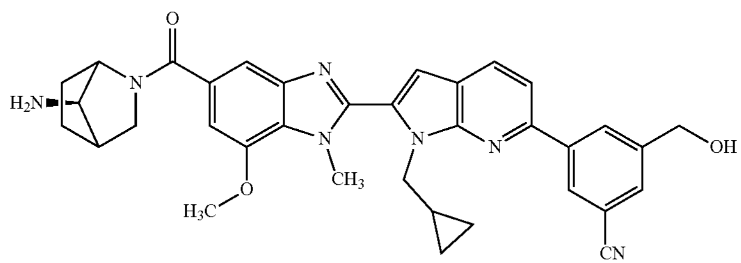 [SMILES: COc1cc(C(=O)N2CC3CCC2[C@@H]3N)cc2nc(-c3cc4ccc(-c5cc(C#N)cc(CO)c5)nc4n3CC3CC3)n(C)c12] | 3-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-5-(hydroxymethyl)benzonitrile | 601.9 | 1 | 1.67 |
| 794. | 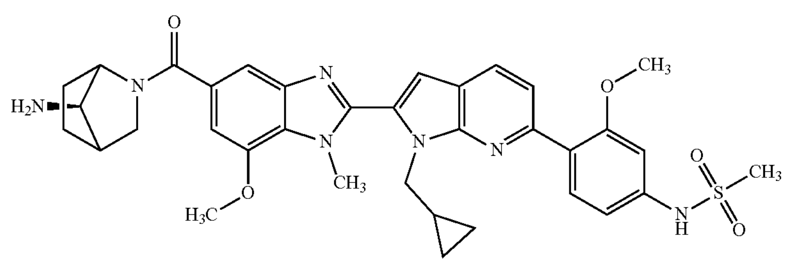 [SMILES: COc1cc(NS(C)(=O)=O)ccc1-c1ccc2cc(-c3nc4cc(C(=O)N5CC6CCC5[C@@H]6N)cc(OC)c4n3C)n(CC3CC3)c2n1] | N-[4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-3-methoxyphenyl]methanesulfonamide | 670.2 | 2 | 1.44 |

| # | Structure | Name | Obs. MS Ion | HPLC Method ID | RT |
|---|---|---|---|---|---|
| 795. | 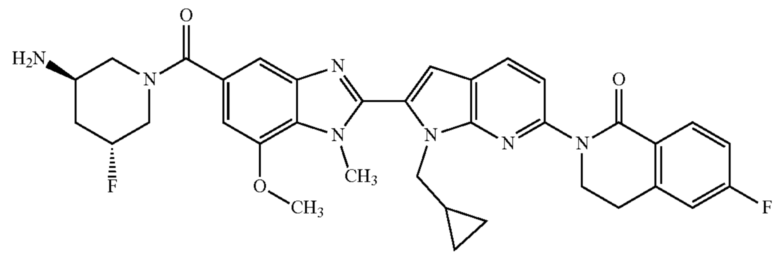 [SMILES: COc1cc(C(=O)N2C[C@H](N)C[C@@H](F)C2)cc2nc(-c3cc4ccc(N5CCc6cc(F)ccc6C5=O)nc4n3CC3CC3)n(C)c12] | 2-(2-{5-[(3R,5R)-3-amino-5-fluoropiperidine-1-carbonyl]-7-methoxy-1-methyl-1H-1,3-benzodiazol-2-yl}-1-(cyclopropylmethyl)-6-fluoro-1H-pyrrolo[2,3-b]pyridin-6-yl)-6-fluoro-1,2,3,4-tetrahydroisoquinolin-1-one | 640 | 2 | 1.73 |
| 796. | 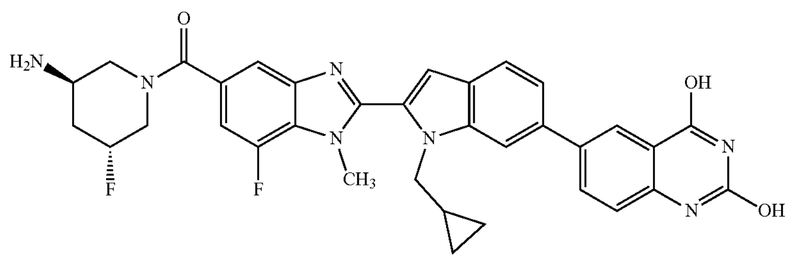 [SMILES: Cn1c(-c2cc3ccc(-c4ccc5nc(O)nc(O)c5c4)cc3n2CC2CC2)nc2cc(C(=O)N3C[C@H](N)C[C@@H](F)C3)cc(F)c21] | 6-(2-{5-[(3R,5R)-3-amino-5-fluoropiperidine-1-carbonyl]-7-fluoro-1-methyl-1H-1,3-benzodiazol-2-yl}-1-(cyclopropylmethyl)-1H-indol-6-yl)quinazoline-2,4-diol | 625.4 | 2 | 1.26 |
| 797. | 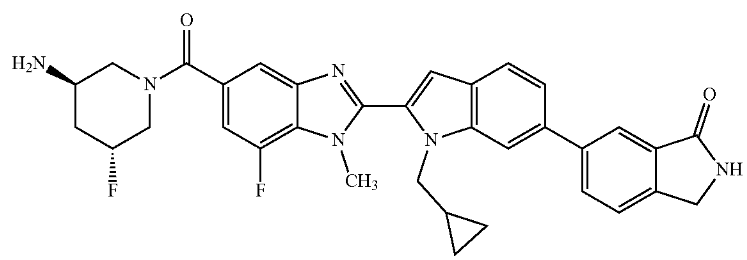 [SMILES: Cn1c(-c2cc3ccc(-c4ccc5c(c4)C(=O)NC5)cc3n2CC2CC2)nc2cc(C(=O)N3C[C@H](N)C[C@@H](F)C3)cc(F)c21] | 6-(2-{5-[(3R,5R)-3-amino-5-fluoropiperidine-1-carbonyl]-7-fluoro-1-methyl-1H-1,3-benzodiazol-2-yl}-1-(cyclopropylmethyl)-1H-indol-6-yl)-2,3-dihydro-1H-isoindol-1-one | 596.2 | 1 | 1.52 |

| # | Structure | Name | Obs. MS Ion | HPLC Method ID | RT |
|---|---|---|---|---|---|
| 798. | 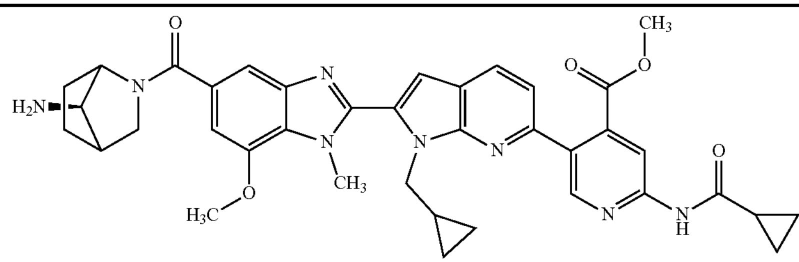 | methyl 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-cyclopropaneamidopyridine-4-carboxylate | 689.2 | 1 | 1.64 |
| 799. | 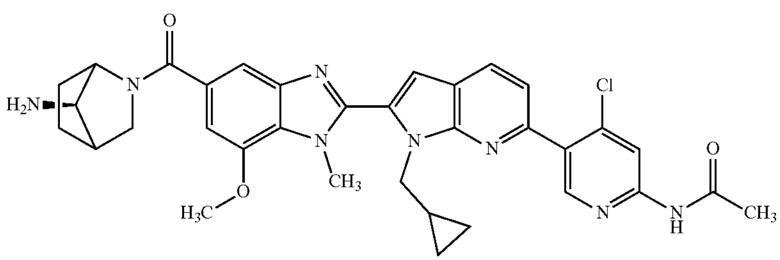 [SMILES: COc1cc(C(=O)N2CC3CCC2[C@@H]3N)cc2nc(-c3cc4ccc(-c5cnc(NC(C)=O)cc5Cl)nc4n3CC3CC3)n(C)c12] | N-[5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-4-chloropyridin-2-yl]acetamide | 639.1 | 1 | 1.73 |
| 800. | 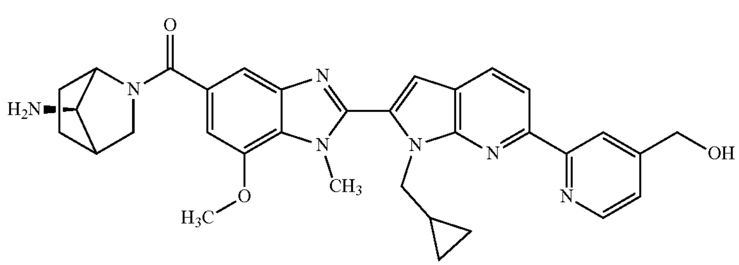 [SMILES: COc1cc(C(=O)N2CC3CCC2[C@@H]3N)cc2nc(-c3cc4ccc(-c5cc(CO)ccn5)nc4n3CC3CC3)n(C)c12] | [2-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)pyridin-4-yl]methanol | 578.2 | 1 | 1.52 |

| # | Structure | Name | Obs. MS Ion | HPLC Method ID | RT |
|---|---|---|---|---|---|
| 801. | 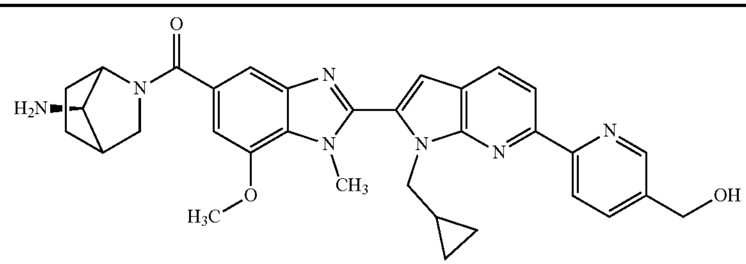 | [6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl]pyridin-3-yl]methanol | 578 | 2 | 1.08 |
| 802. | 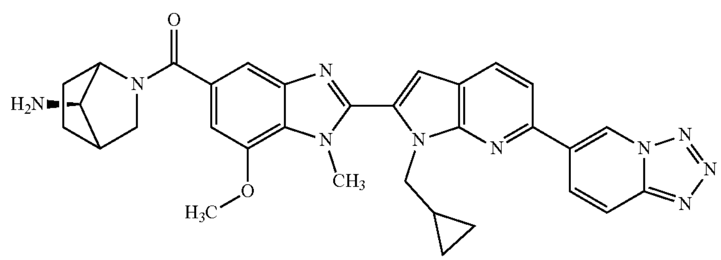 [SMILES: COc1cc(C(=O)N2CC3CCC2[C@@H]3N)cc2nc(-c3cc4ccc(-c5ccc6nnnn6c5)nc4n3CC3CC3)n(C)c12] | (7R)-2-{2-[1-(cyclopropylmethyl)-6-{[1,2,3,4]tetrazolo[1,5-a]pyridin-6-yl]}-1H-pyrrolo[2,3-b]pyridin-2-yl]-7-methoxy-1-methyl-1H-1,3-benzodiazole-5-carbonyl}-2-azabicyclo[2.2.1]heptan-7-amine | 589.2 | 1 | 1.54 |
| 803. | 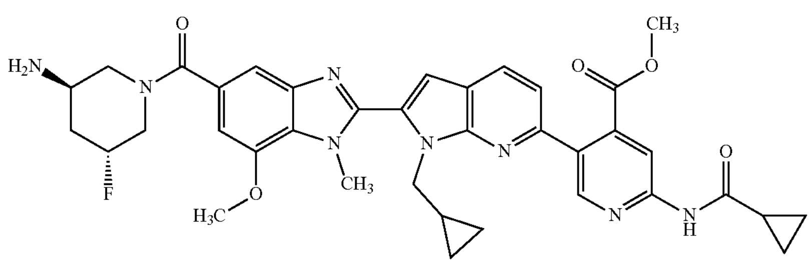 [SMILES: COC(=O)c1cc(NC(=O)C2CC2)ncc1-c1ccc2cc(-c3nc4cc(C(=O)N5C[C@H](N)C[C@@H](F)C5)cc(OC)c4n3C)n(CC3CC3)c2n1] | methyl 5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-cyclopropaneamidopyridine-4-carboxylate | 695.2 | 1 | 1.71 |

| # | Structure | Name | Obs. MS Ion | HPLC Method ID | RT |
|---|---|---|---|---|---|
| 804. | 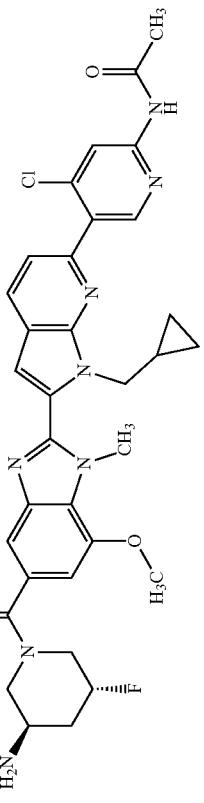 | N-[5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-4-chloropyridin-2-yl]acetamide | 645.2 | 2 | 1.52 |
| 805. | 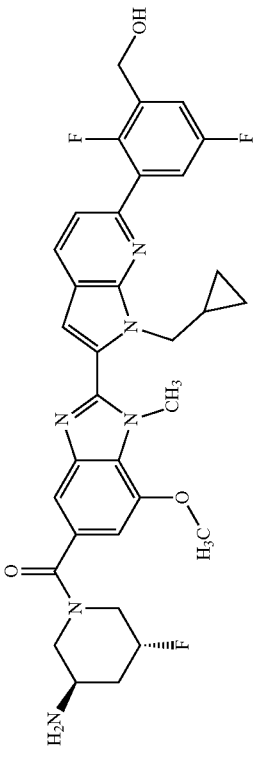 | [3-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2,5-difluorophenyl]methanol | 619 | 1 | 1.61 |
| 806. | 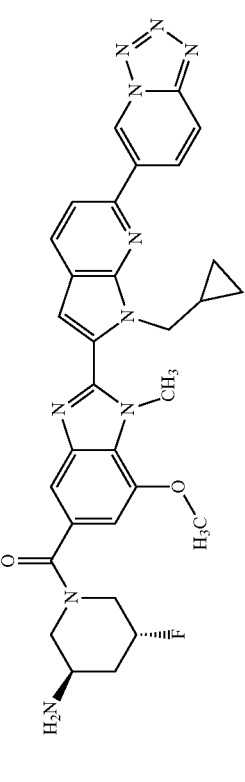 | (3R,5R)-1-{2-[1-(cyclopropylmethyl)-6-{[1,2,3,4]tetrazolo[1,5-a]pyridin-6-yl}-1H-pyrrolo[2,3-b]pyridin-2-yl]-7-methoxy-1-methyl-1H-1,3-benzodiazole-5-carbonyl}-5-fluoropiperidin-3-amine | 595 | 2 | 1.44 |

-continued

| # | Structure | Name | Obs. MS Ion | HPLC Method ID | RT |
|---|---|---|---|---|---|
| 807. | 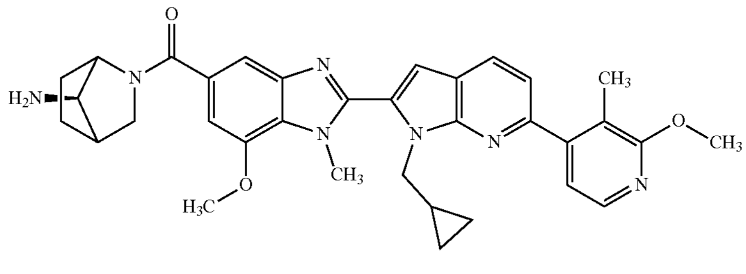 [SMILES: COc1nccc(-c2ccc3cc(-c4nc5cc(C(=O)N6CC7CCC6[C@@H]7N)cc(OC)c5n4C)n(CC4CC4)c3n2)c1C] | (7R)-2-{2-[1-(cyclopropylmethyl)-6-(2-methoxy-3-methylpyridin-4-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 592.1 | 2 | 1.74 |
| 808. | 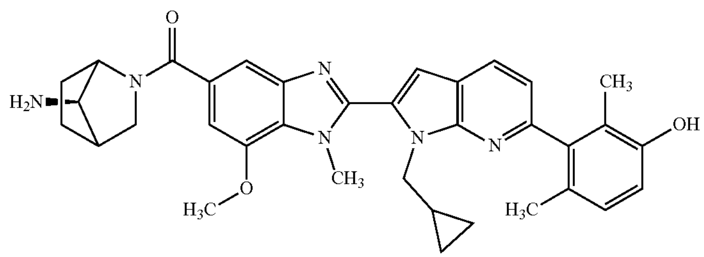 [SMILES: COc1cc(C(=O)N2CC3CCC2[C@@H]3N)cc2nc(-c3cc4ccc(-c5c(C)ccc(O)c5C)nc4n3CC3CC3)n(C)c12] | 3-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2,4-dimethylphenol | 591.2 | 1 | 1.7 |
| 809. | 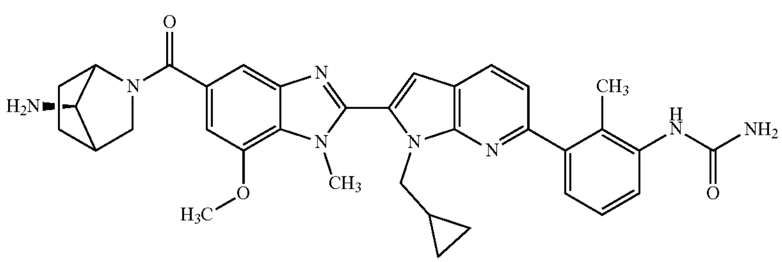 [SMILES: COc1cc(C(=O)N2CC3CCC2[C@@H]3N)cc2nc(-c3cc4ccc(-c5cccc(NC(N)=O)c5C)nc4n3CC3CC3)n(C)c12] | [3-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-methylphenyl]urea | 619.1 | 2 | 1.38 |

| # | Structure | Name | Obs. MS Ion | HPLC Method ID | RT |
|---|---|---|---|---|---|
| 810. | 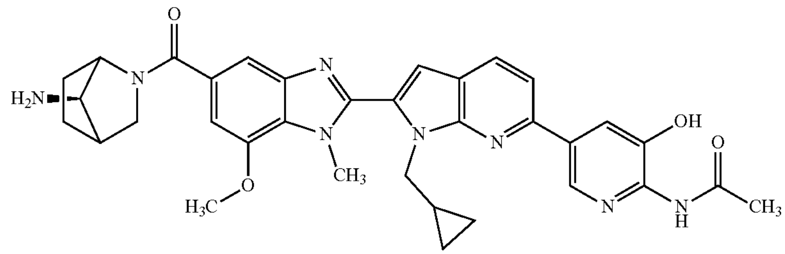 [SMILES: COc1cc(C(=O)N2CC3CCC2[C@@H]3N)cc2nc(-c3cc4ccc(-c5cnc(NC(C)=O)c(O)c5)nc4n3CC3CC3)n(C)c12] | N-[5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-3-hydroxypyridin-2-yl]acetamide | 621.2 | 1 | 1.58 |
| 811. | 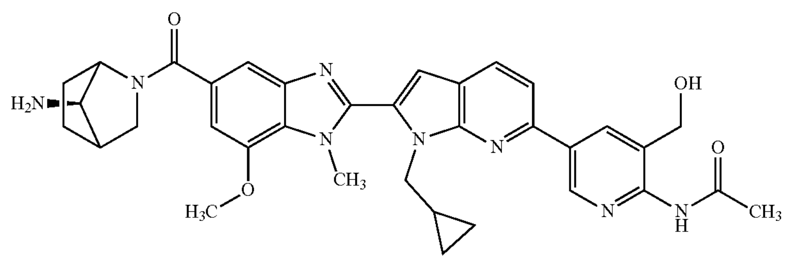 [SMILES: COc1cc(C(=O)N2CC3CCC2[C@@H]3N)cc2nc(-c3cc4ccc(-c5cnc(NC(C)=O)c(CO)c5)nc4n3CC3CC3)n(C)c12] | N-[5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-3-(hydroxymethyl)pyridin-2-yl]acetamide | 635.2 | 1 | 1.6 |
| 812. | 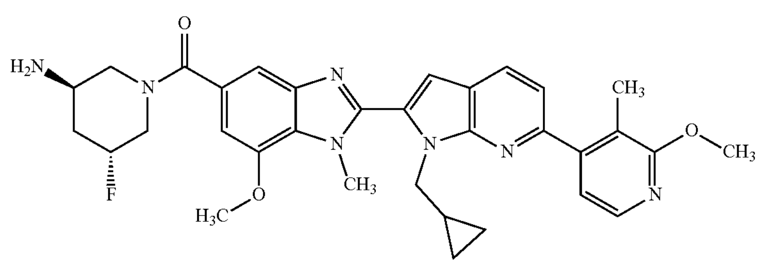 [SMILES: COc1nccc(-c2ccc3cc(-c4nc5cc(C(=O)N6C[C@H](N)C[C@@H](F)C6)cc(OC)c5n4C)n(CC4CC4)c3n2)c1C] | (3R,5R)-1-{2-[1-(cyclopropylmethyl)-6-(2-methoxy-3-methylpyridin-4-yl)-1H-pyrrolo[2,3-b]pyridin-2-yl]-7-methoxy-1-methyl-1H-1,3-benzodiazole-5-carbonyl}-5-fluoropiperidin-3-amine | 598.1 | 1 | 1.9 |

| # | Structure | Name | Obs. MS Ion | HPLC Method ID | RT |
|---|---|---|---|---|---|
| 813. | 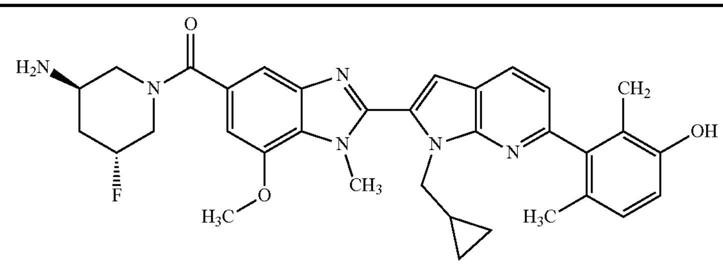 | 3-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2,4-dimethylphenol | 597.2 | 1 | 1.68 |
| 814. | 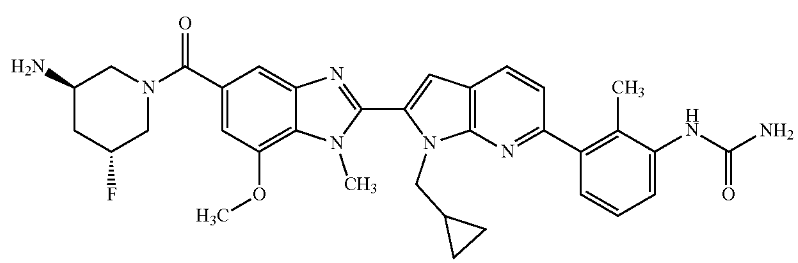 [SMILES: COc1cc(C(=O)N2C[C@H](N)C[C@@H](F)C2)cc2nc(-c3cc4ccc(-c5cccc(NC(N)=O)c5C)nc4n3CC3CC3)n(C)c12] | [3-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-methylphenyl]urea | 625.2 | 1 | 1.43 |
| 815. | 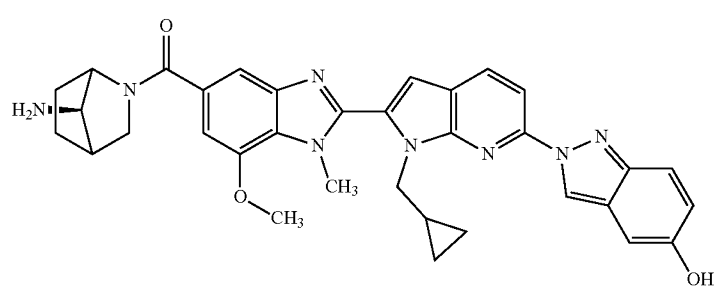 [SMILES: COc1cc(C(=O)N2CC3CCC2[C@@H]3N)cc2nc(-c3cc4ccc(-n5cc6cc(O)ccc6n5)nc4n3CC3CC3)n(C)c12] | 2-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2H-indazol-5-ol | 603.2 | 1 | 1.67 |

| # | Structure | Name | Obs. MS Ion | HPLC Method ID | RT |
|---|---|---|---|---|---|
| 816. | 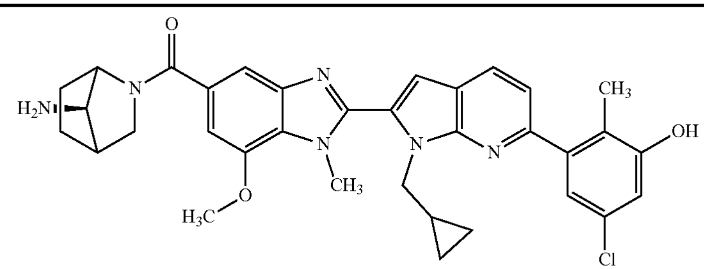 | 3-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-5-chloro-2-methylphenol | 611.2 | 1 | 1.93 |
| 817. | 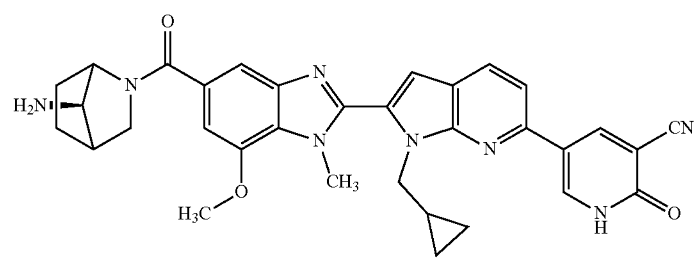 [SMILES: COc1cc(C(=O)N2CC3CCC2[C@@H]3N)cc2nc(-c3cc4ccc(-c5c[nH]c(=O)c(C#N)c5)nc4n3CC3CC3)n(C)c12] | 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-oxo-1,2-dihydropyridine-3-carbonitrile | 589.2 | 1 | 1.45 |
| 818. | 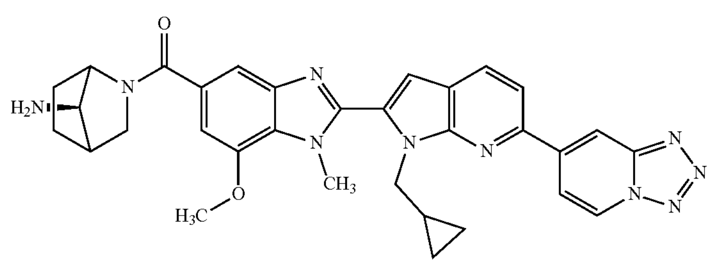 [SMILES: COc1cc(C(=O)N2CC3CCC2[C@@H]3N)cc2nc(-c3cc4ccc(-c5ccn6nnnc6c5)nc4n3CC3CC3)n(C)c12] | (7R)-2-{2-1-(cyclopropylmethyl)-6-{[1,2,3,4]tetrazolo[1,5-a]pyridin-7-yl]-1H-pyrrolo[2,3-b]pyridin-2-yl]-7-methoxy-1-methyl-1H-1,3-benzodiazole-5-carbonyl}-2-azabicyclo[2.2.1]heptan-7-amine | 588.9 | 1 | 1.63 |

| # | Structure | Name | Obs. MS Ion | HPLC Method ID | RT |
|---|---|---|---|---|---|
| 819. | 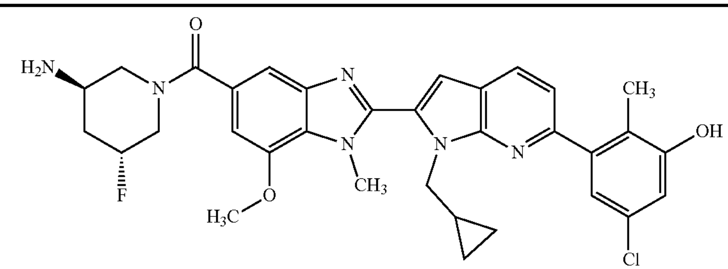 | 3-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-5-chloro-2-methylphenol | 616.9 | 1 | 1.9 |
| 820. | 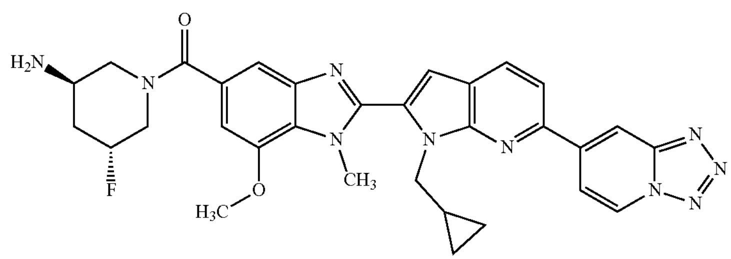 [SMILES: COc1cc(C(=O)N2C[C@H](N)C[C@@H](F)C2)cc2nc(-c3cc4ccc(-c5ccn6nnnc6c5)nc4n3CC3CC3)n(C)c12] | (3R,5R)-1-{2-[1-(cyclopropylmethyl)-6-{[1,2,3,4]tetrazolo[1,5-a]pyridin-7-yl}-1H-pyrrolo[2,3-b]pyridin-2-yl]-7-methoxy-1-methyl-1H-1,3-benzodiazole-5-carbonyl}-5-fluoropiperidin-3-amine | 595.2 | 1 | 1.6 |
| 821. | 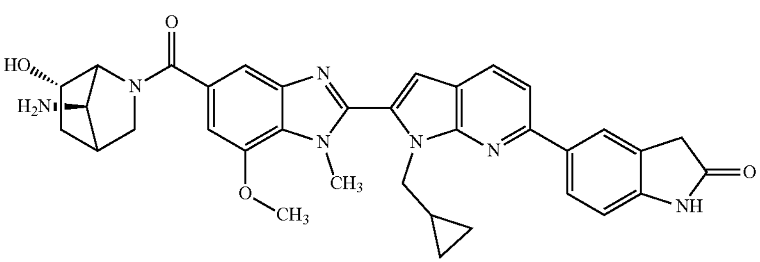 [SMILES: COc1cc(C(=O)N2CC3C[C@H](O)C2[C@@H]3N)cc2nc(-c3cc4ccc(-c5ccc6c(c5)CC(=O)N6)nc4n3CC3CC3)n(C)c12] | 5-(2-{5-[(6S,7R)-7-amino-6-hydroxy-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2,3-dihydro-1H-indol-2-one | 618.4 | 2 | 1.25 |

| # | Structure | Name | Obs. MS Ion | HPLC Method ID | RT |
|---|---|---|---|---|---|
| 822. | 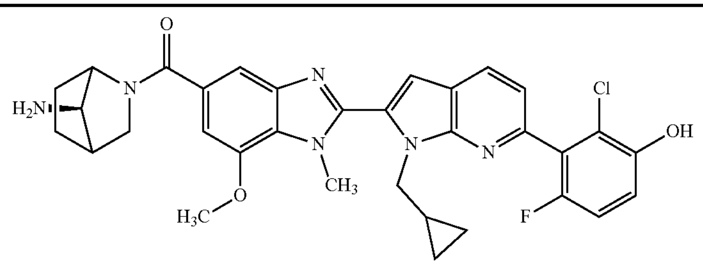 | 3-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-chloro-4-fluorophenol | 615.2 | 1 | 1.64 |
| 823. | 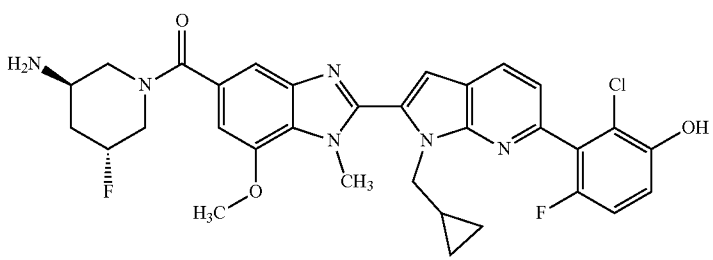 [SMILES: COc1cc(C(=O)N2C[C@H](N)C[C@@H](F)C2)cc2nc(-c3cc4ccc(-c5c(F)ccc(O)c5Cl)nc4n3CC3CC3)n(C)c12] | 3-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-chloro-4-fluorophenol | 621.4 | 1 | 1.62 |
| 824. | 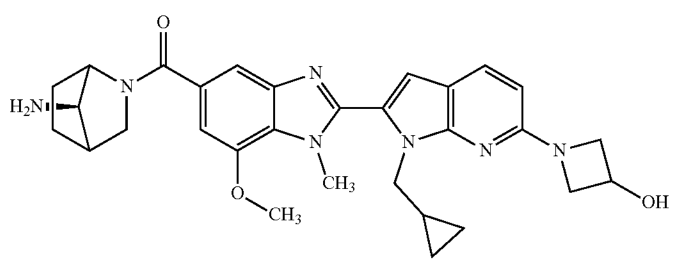 [SMILES: COc1cc(C(=O)N2CC3CCC2[C@@H]3N)cc2nc(-c3cc4ccc(N5CC(O)C5)nc4n3CC3CC3)n(C)c12] | 1-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)azetidin-3-ol | 542.1 | 1 | 1.34 |

| # | Structure | Name | Obs. MS Ion | HPLC Method ID | RT |
|---|---|---|---|---|---|
| 825. | 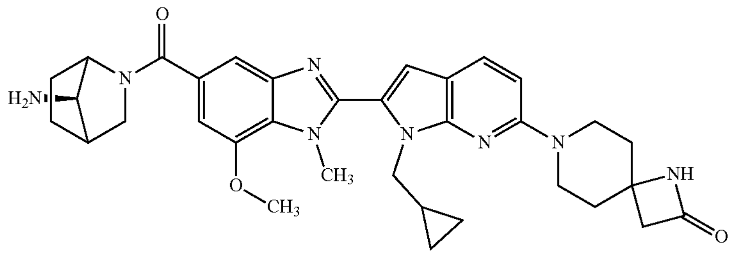 [SMILES: COc1cc(C(=O)N2CC3CCC2[C@@H]3N)cc2nc(-c3cc4ccc(N5CCC6(CC5)CC(=O)N6)nc4n3CC3CC3)n(C)c12] | 7-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1,7-diazaspiro[3.5]nonan-2-one | 609.3 | 2 | 1 |
| 826. | 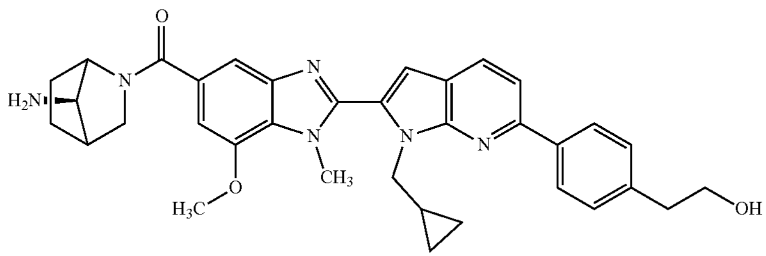 [SMILES: COc1cc(C(=O)N2CC3CCC2[C@@H]3N)cc2nc(-c3cc4ccc(-c5ccc(CCO)cc5)nc4n3CC3CC3)n(C)c12] | 2-[4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]ethan-1-ol | 591 | 1 | 1.68 |
| 827. | 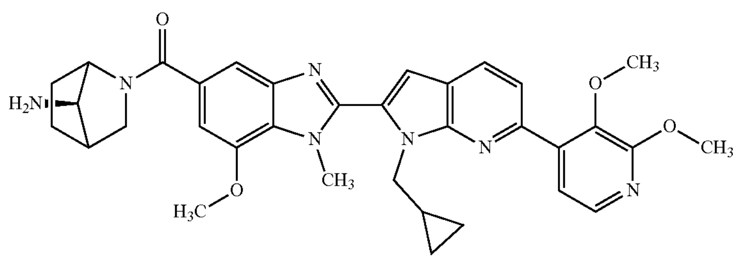 [SMILES: COc1nccc(-c2ccc3cc(-c4nc5cc(C(=O)N6CC7CCC6[C@@H]7N)cc(OC)c5n4C)n(CC4CC4)c3n2)c1OC] | (7R)-2-{2-[1-(cyclopropylmethyl)-6-(2,3-dimethoxypyridin-4-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 608 | 2 | 1.64 |

| # | Structure | Name | Obs. MS Ion | HPLC Method ID | RT |
|---|---|---|---|---|---|
| 828. | 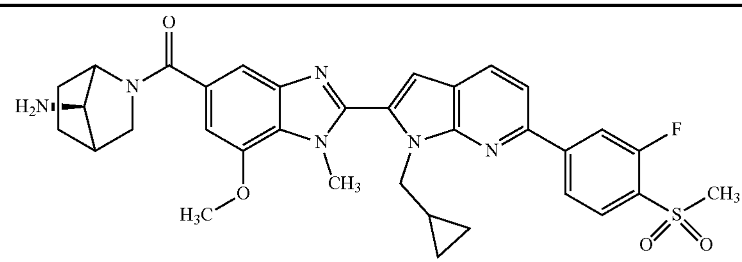 | (7R)-2-{2-[1-(cyclopropylmethyl)-6-(3-fluoro-4-methanesulfonylphenyl)-1H-pyrrolo[2,3-b]pyridin-2-yl]-7-methoxy-1-methyl-1H-1,3-benzodiazole-5-carbonyl]-2-azabicyclo[2.2.1]heptan-7-amine | 643.1 | 2 | 1.45 |
| 829. | 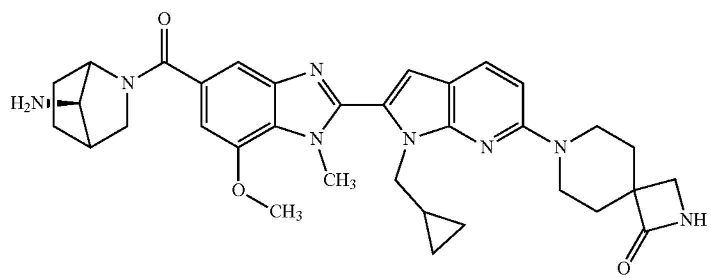 [SMILES: COc1cc(C(=O)N2CC3CCC2[C@@H]3N)cc2nc(-c3cc4ccc(N5CCC6(CC5)CNC6=O)nc4n3CC3CC3)n(C)c12] | 7-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2,7-diazaspiro[3.5]nonan-1-one | 609.2 | 1 | 1.12 |
| 830. | 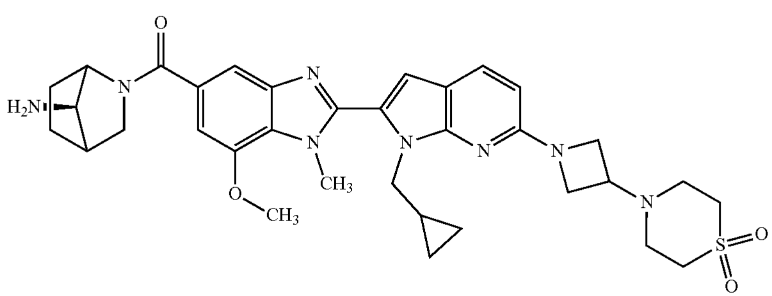 [SMILES: COc1cc(C(=O)N2CC3CCC2[C@@H]3N)cc2nc(-c3cc4ccc(N5CC(N6CCS(=O)(=O)CC6)C5)nc4n3CC3CC3)n(C)c12] | ((7R)-7-amino-2-azabicyclo[2.2.1]heptan-2-yl)(2-(1-(cyclopropylmethyl)-6-(3-(1,1-dioxidothiomorpholino)azetidin-1-yl)-1H-pyrrolo[2,3-b]pyridin-2-yl)-7-methoxy-1-methyl-1H-benzo[d]imidazol-5-yl)methanone | 659.4 | 1 | 1.58 |

| # | Structure | Name | Obs. MS Ion | HPLC Method ID | RT |
|---|---|---|---|---|---|
| 831. | 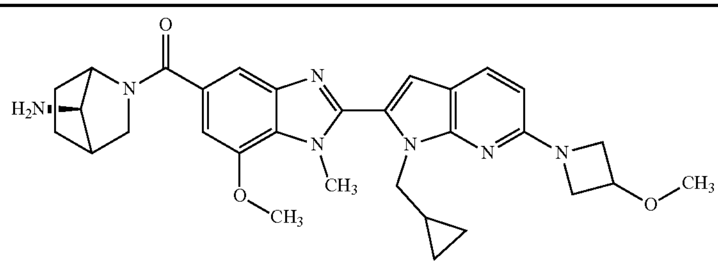 | (7R)-2-{2-[1-(cyclopropylmethyl)-6-(3-methoxyazetidin-1-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 556.2 | 2 | 1.37 |
| 832. | 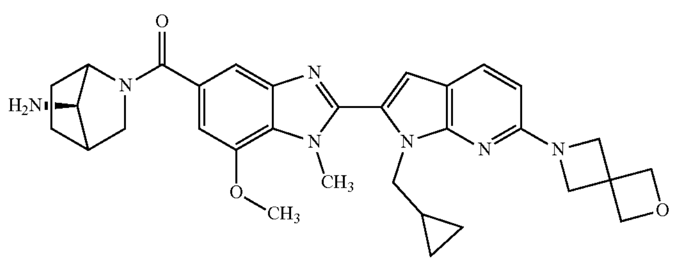 [SMILES: COc1cc(C(=O)N2CC3CCC2[C@@H]3N)cc2nc(-c3cc4ccc(N5CC6(COC6)C5)nc4n3CC3CC3)n(C)c12] | (7R)-2-{2-[1-(cyclopropylmethyl)-6-{2-oxa-6-azaspiro[3.3]heptan-6-yl}-1H-pyrrolo[2,3-b]pyridin-2-yl]-7-methoxy-1-methyl-1H-1,3-benzodiazole-5-carbonyl}-2-azabicyclo[2.2.1]heptan-7-amine | 568.1 | 1 | 1.51 |
| 833. | 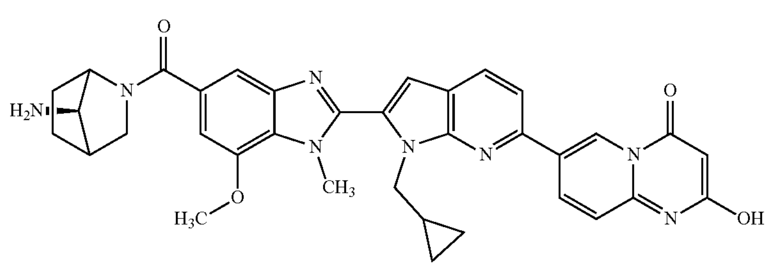 [SMILES: COc1cc(C(=O)N2CC3CCC2[C@@H]3N)cc2nc(-c3cc4ccc(-c5ccc6nc(O)cc(=O)n6c5)nc4n3CC3CC3)n(C)c12] | 7-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-hydroxy-4H-pyrido[1,2-a]pyrimidin-4-one | 630.9 | 1 | 1.3 |

| # | Structure | Name | Obs. MS Ion | HPLC Method ID | RT |
|---|---|---|---|---|---|
| 834. | 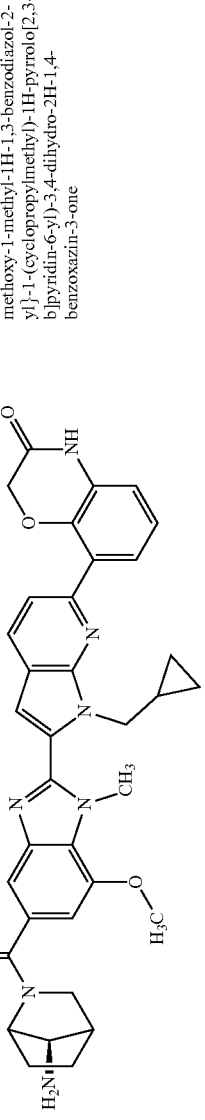 | 8-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-3,4-dihydro-2H-1,4-benzoxazin-3-one | 618 | 1 | 1.58 |
| 835. | 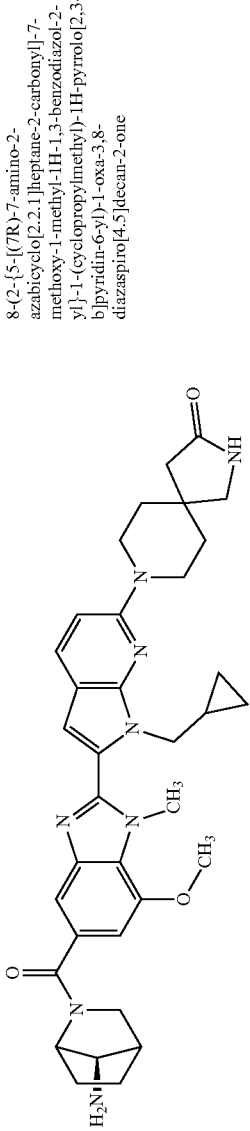 | 8-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1-oxa-3,8-diazaspiro[4.5]decan-2-one | 625.3 | 1 | 1.13 |
| 836. | 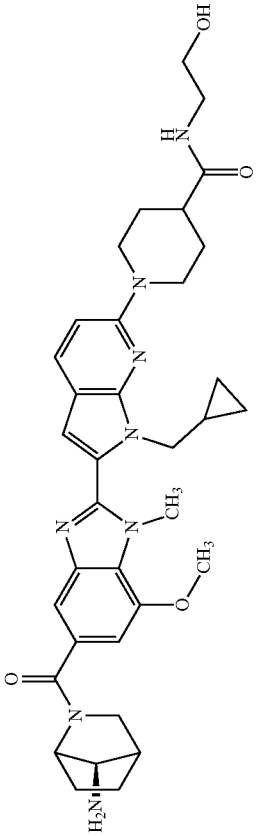 | 1-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-N-(2-hydroxyethyl)piperidine-4-carboxamide | 641 | 1 | 1.28 |

| # | Structure | Name | Obs. MS Ion | HPLC Method ID | RT |
|---|---|---|---|---|---|
| 837. | 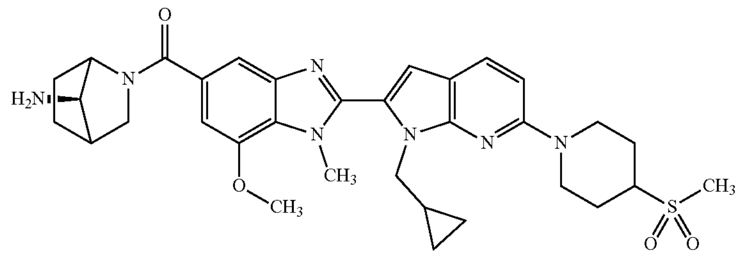 [SMILES: COc1cc(C(=O)N2CC3CCC2[C@@H]3N)cc2nc(-c3cc4ccc(N5CCC(S(C)(=O)=O)CC5)nc4n3CC3CC3)n(C)c12] | (7R)-2-{2-[1-(cyclopropylmethyl)-6-(4-methanesulfonyl)piperidin-1-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 632.2 | 2 | 1.32 |
| 838. | 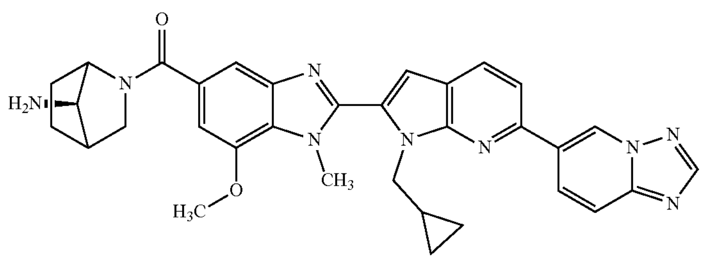 [SMILES: COc1cc(C(=O)N2CC3CCC2[C@@H]3N)cc2nc(-c3cc4ccc(-c5ccc6ncnn6c5)nc4n3CC3CC3)n(C)c12] | (7R)-2-{2-[1-(cyclopropylmethyl)-6-{[1,2,4]triazolo[1,5-a]pyridin-6-yl}-1H-pyrrolo[2,3-b]pyridin-2-yl]-7-methoxy-1-methyl-1H-1,3-benzodiazole-5-carbonyl}-2-azabicyclo[2.2.1]heptan-7-amine | 588 | 2 | 1.4 |
| 839. | 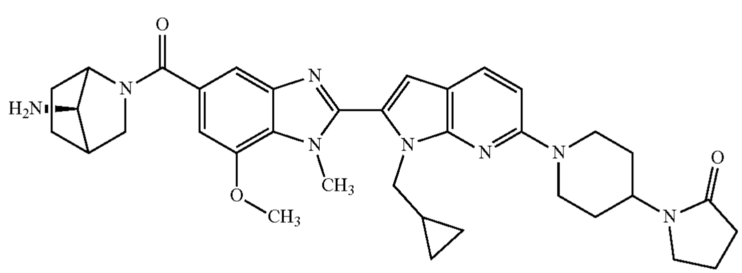 [SMILES: COc1cc(C(=O)N2CC3CCC2[C@@H]3N)cc2nc(-c3cc4ccc(N5CCC(N6CCCC6=O)CC5)nc4n3CC3CC3)n(C)c12] | 1-[1-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)piperidin-4-yl]pyrrolidin-2-one | 319.1 | 2 | 1.4 |

| # | Structure | Name | Obs. MS Ion | HPLC Method ID | RT |
|---|---|---|---|---|---|
| 840. | 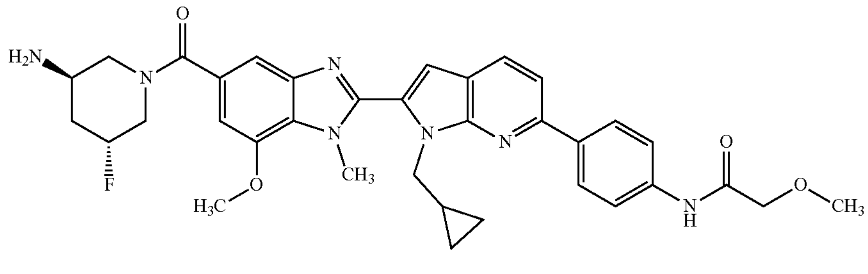 [SMILES: COCC(=O)Nc1ccc(-c2ccc3cc(-c4nc5cc(C(=O)N6C[C@H](N)C[C@@H](F)C6)cc(OC)c5n4C)n(CC4CC4)c3n2)cc1] | N-[4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)phenyl]-2-methoxyacetamide | 640 | 1 | 1.71 |
| 841. | 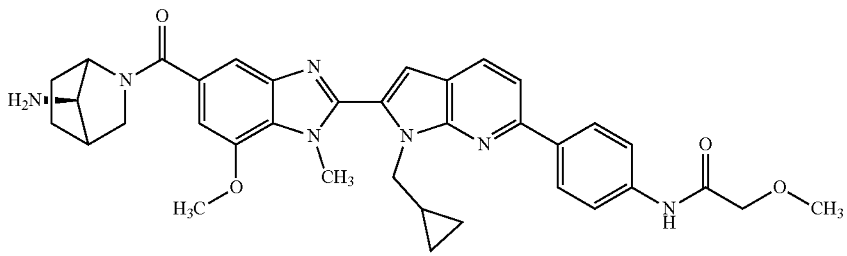 [SMILES: COCC(=O)Nc1ccc(-c2ccc3cc(-c4nc5cc(C(=O)N6CC7CCC6[C@@H]7N)cc(OC)c5n4C)n(CC4CC4)c3n2)cc1] | N-[4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]-2-methoxyacetamide | 634.3 | 1 | 1.64 |
| 842. | 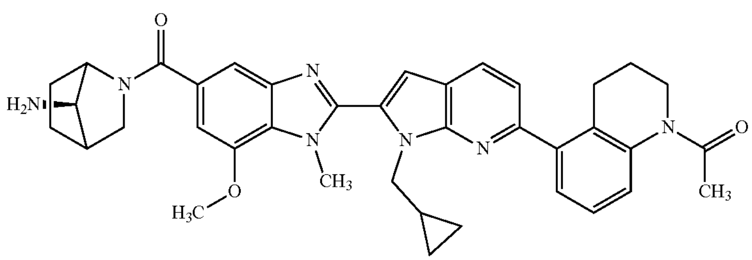 [SMILES: COc1cc(C(=O)N2CC3CCC2[C@@H]3N)cc2nc(-c3cc4ccc(-c5cccc6c5CCCN6C(C)=O)nc4n3CC3CC3)n(C)c12] | 1-[5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1,2,3,4-tetrahydroquinolin-1-yl]ethan-1-one | 644.1 | 2 | 1.62 |

| # | Structure | Name | Obs. MS Ion | HPLC Method ID | RT |
|---|---|---|---|---|---|
| 843. | 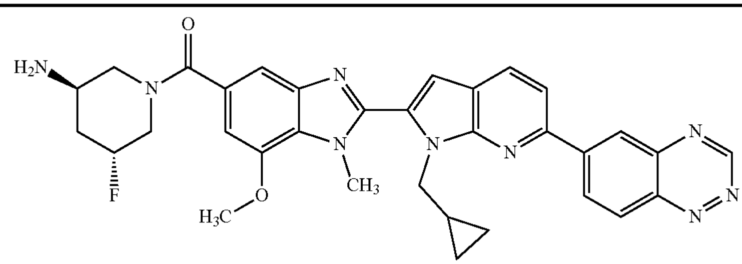 | (3R,5R)-1-{2-[6-(1,2,4-benzotriazin-6-yl)-1-(cyclopropylmethyl)-1H-pyrrolo[2,3-b]pyridin-2-yl]-7-methoxy-1-methyl-1H-1,3-benzodiazole-5-carbonyl}-5-fluoropiperidin-3-amine | 606.3 | 1 | 1.66 |
| 844. | 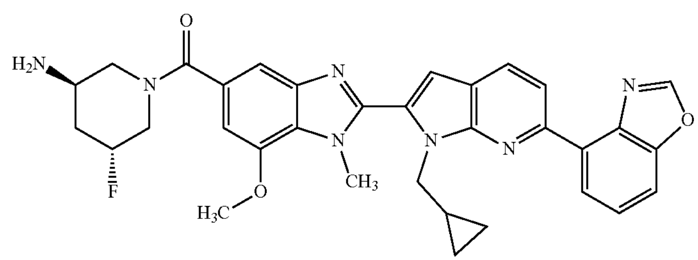 [SMILES: COc1cc(C(=O)N2C[C@H](N)C[C@@H](F)C2)cc2nc(-c3cc4ccc(-c5cccc6ocnc56)nc4n3CC3CC3)n(C)c12] | (3R,5R)-1-{2-[6-(1,3-benzoxazol-4-yl)-1-(cyclopropylmethyl)-1H-pyrrolo[2,3-b]pyridin-2-yl]-7-methoxy-1-methyl-1H-1,3-benzodiazole-5-carbonyl}-5-fluoropiperidin-3-amine | 594.1 | 2 | 1.71 |
| 845. | 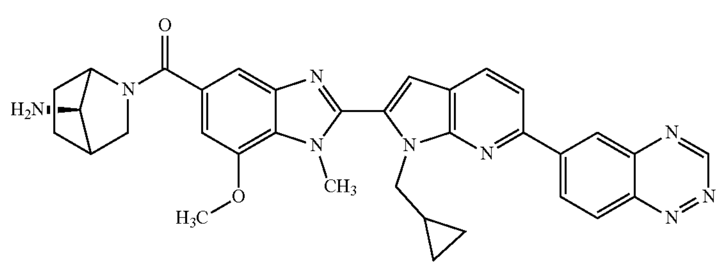 [SMILES: COc1cc(C(=O)N2CC3CCC2[C@@H]3N)cc2nc(-c3cc4ccc(-c5ccc6nncnc6c5)nc4n3CC3CC3)n(C)c12] | (7R)-2-{2-[6-(1,2,4-benzotriazin-6-yl)-1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 600.1 | 1 | 1.69 |

| # | Structure | Name | Obs. MS Ion | HPLC Method ID | RT |
|---|---|---|---|---|---|
| 846. | 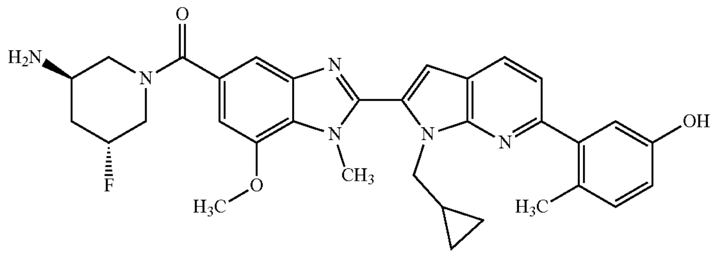 [SMILES: COc1cc(C(=O)N2C[C@H](N)C[C@@H](F)C2)cc2nc(-c3cc4ccc(-c5cc(O)ccc5C)nc4n3CC3CC3)n(C)c12] | 3-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-4-methylphenol | 583.1 | 1 | 1.6 |
| 847. | 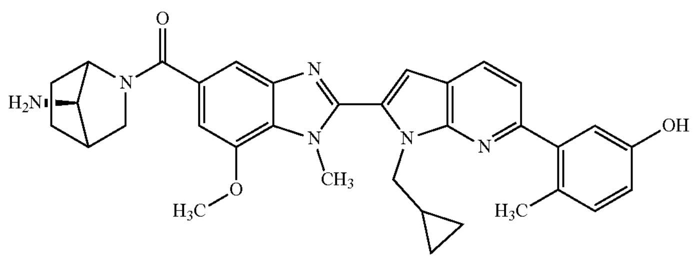 [SMILES: COc1cc(C(=O)N2CC3CCC2[C@@H]3N)cc2nc(-c3cc4ccc(-c5cc(O)ccc5C)nc4n3CC3CC3)n(C)c12] | 3-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-4-methylphenol | 577.1 | 1 | 1.83 |
| 848. | 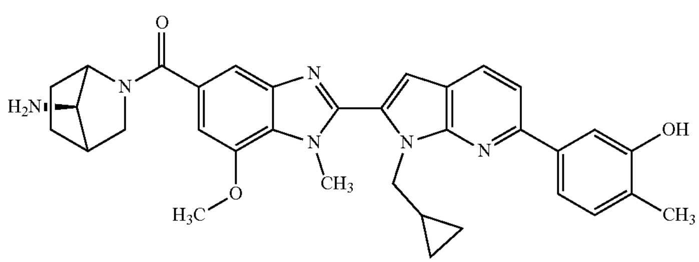 [SMILES: COc1cc(C(=O)N2CC3CCC2[C@@H]3N)cc2nc(-c3cc4ccc(-c5ccc(C)c(O)c5)nc4n3CC3CC3)n(C)c12] | 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-methylphenol | 577 | 2 | 1.71 |

| # | Structure | Name | Obs. MS Ion | HPLC Method ID | RT |
|---|---|---|---|---|---|
| 849. | 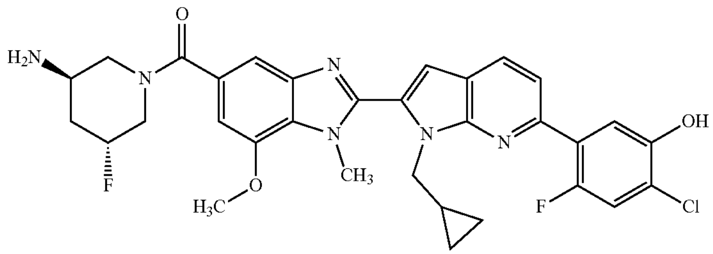 [SMILES: COc1cc(C(=O)N2C[C@H](N)C[C@@H](F)C2)cc2nc(-c3cc4ccc(-c5cc(O)c(Cl)cc5F)nc4n3CC3CC3)n(C)c12] | 5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-chloro-4-fluorophenol | 620.9 | 1 | 1.99 |
| 850. | 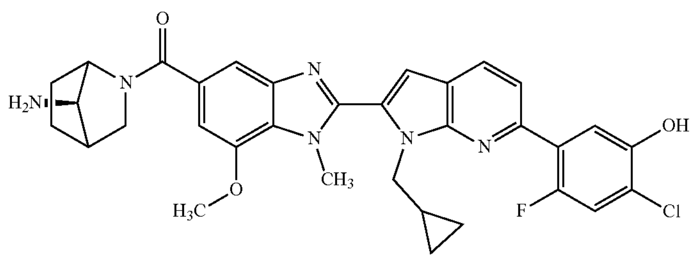 [SMILES: COc1cc(C(=O)N2CC3CCC2[C@@H]3N)cc2nc(-c3cc4ccc(-c5cc(O)c(Cl)cc5F)nc4n3CC3CC3)n(C)c12] | 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-chloro-4-fluorophenol | 615.3 | 2 | 1.71 |
| 851. | 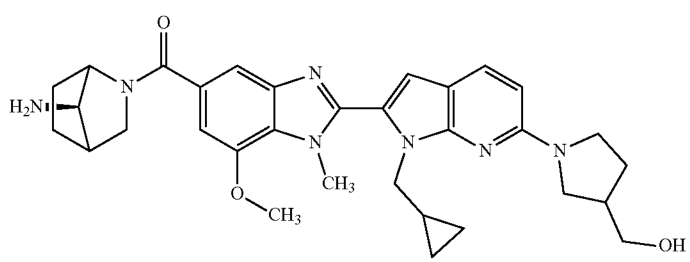 [SMILES: COc1cc(C(=O)N2CC3CCC2[C@@H]3N)cc2nc(-c3cc4ccc(N5CCC(CO)C5)nc4n3CC3CC3)n(C)c12] | [1-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)pyrrolidin-3-yl]methanol (mixture of diastereomers) | 570.9 | 1 | 1.63 |

| # | Structure | Name | Obs. MS Ion | HPLC Method ID | RT |
|---|---|---|---|---|---|
| 852. | 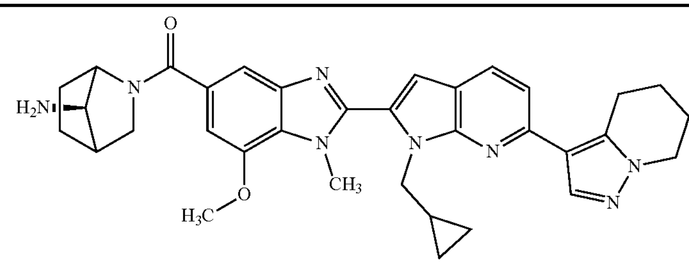 | (7R)-2-{2-[1-(cyclopropylmethyl)-6-{4H,5H,6H,7H-pyrazolo[1,5-a]pyridin-3-yl}-1H-pyrrolo[2,3-b]pyridin-2-yl]-7-methoxy-1-methyl-1H-1,3-benzodiazole-5-carbonyl}-2-azabicyclo[2.2.1]heptan-7-amine | 591 | 2 | 1.39 |
| 853. | 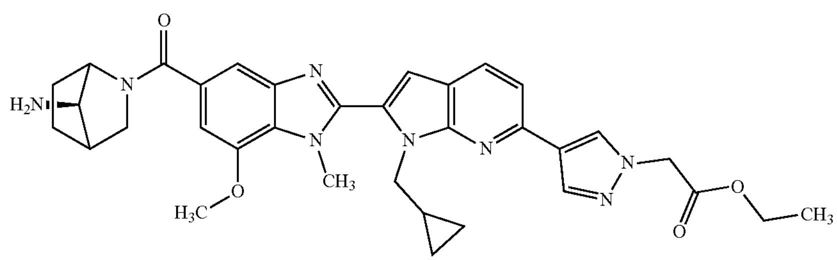 [SMILES: CCOC(=O)Cn1cc(-c2ccc3cc(-c4nc5cc(C(=O)N6CC7CCC6[C@@H]7N)cc(OC)c5n4C)n(CC4CC4)c3n2)cn1] | ethyl 2-[4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1H-pyrazol-1-yl]acetate | 623.1 | 1 | 1.69 |
| 854. | 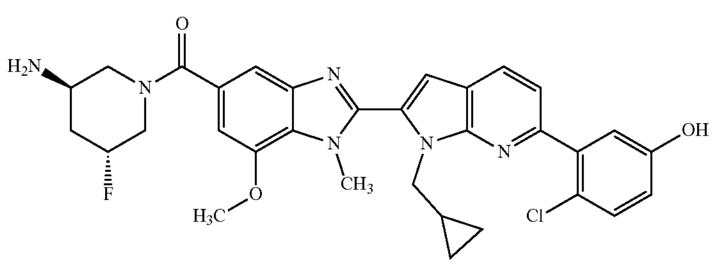 [SMILES: COc1cc(C(=O)N2C[C@H](N)C[C@@H](F)C2)cc2nc(-c3cc4ccc(-c5cc(O)ccc5Cl)nc4n3CC3CC3)n(C)c12] | 3-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-4-chlorophenol | 603.3 | 1 | 1.78 |

| # | Structure | Name | Obs. MS Ion | HPLC Method ID | RT |
|---|---|---|---|---|---|
| 855. | 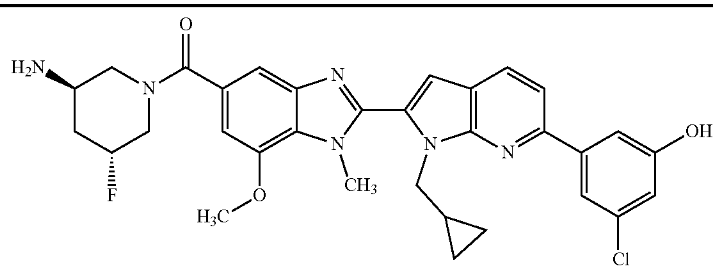 | 3-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-5-chlorophenol | 603.1 | 2 | 1.65 |
| 856. | 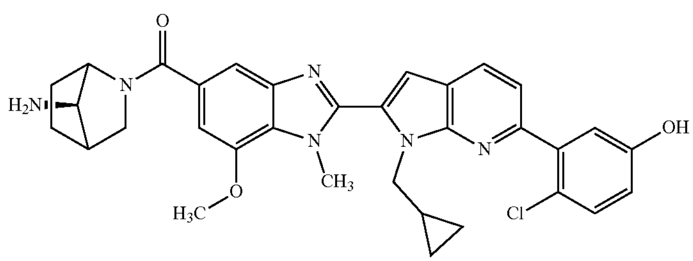 [SMILES: COc1cc(C(=O)N2CC3CCC2[C@@H]3N)cc2nc(-c3cc4ccc(-c5cc(O)ccc5Cl)nc4n3CC3CC3)n(C)c12] | 3-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-4-chlorophenol | 597.4 | 1 | 1.83 |
| 857. | 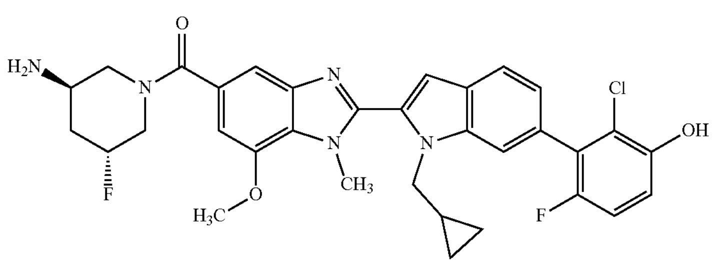 [SMILES: COc1cc(C(=O)N2C[C@H](N)C[C@@H](F)C2)cc2nc(-c3cc4ccc(-c5c(F)ccc(O)c5Cl)cc4n3CC3CC3)n(C)c12] | 3-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)-2-chloro-4-fluorophenol | 620.4 | 1 | 1.77 |

| # | Structure | Name | Obs. MS Ion | HPLC Method ID | RT |
|---|---|---|---|---|---|
| 858. | 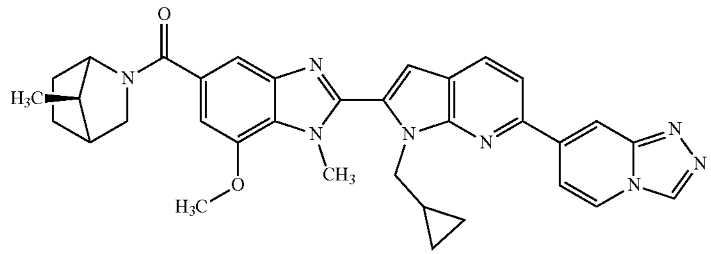 [SMILES: COc1cc(C(=O)N2CC3CCC2[C@@H]3C)cc2nc(-c3cc4ccc(-c5ccn6cnnc6c5)nc4n3CC3CC3)n(C)c12] | (7R)-2-{2-[1-(cyclopropylmethyl)-6-{[1,2,4]triazolo[4,3-a]pyridin-7-yl]}-1H-pyrrolo[2,3-b]pyridin-2-yl]-7-methoxy-1-methyl-1H-1,3-benzodiazole-5-carbonyl}-2-azabicyclo[2.2.1]heptan-7-amine | 588.4 | 2 | 1.19 |
| 859. | 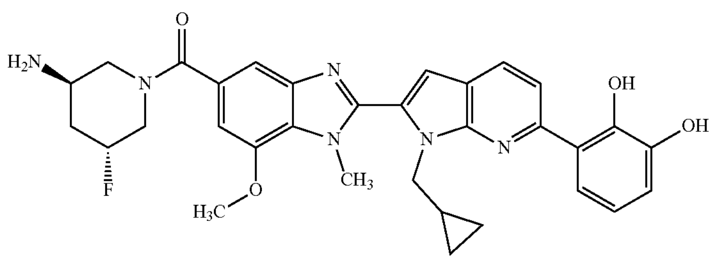 | 2-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-6-hydroxybenzonitrile | 594.1 | 1 | 1.56 |
| 860. | 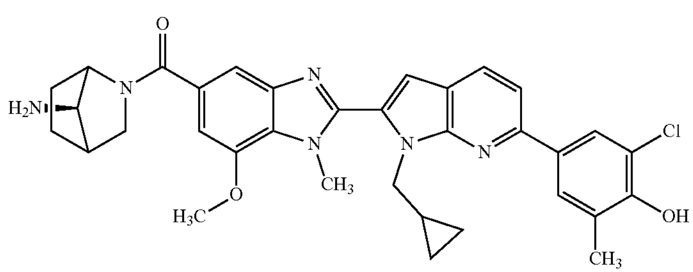 [SMILES: COc1cc(C(=O)N2CC3CCC2[C@@H]3N)cc2nc(-c3cc4ccc(-c5cc(C)c(O)c(Cl)c5)nc4n3CC3CC3)n(C)c12] | 4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-chloro-6-methylphenol | 611.1 | 2 | 1.73 |

| # | Structure | Name | Obs. MS Ion | HPLC Method ID | RT |
|---|---|---|---|---|---|
| 861. | 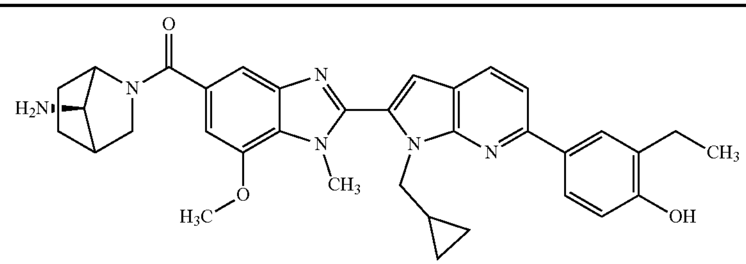 | 4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-ethylphenol | 591 | 2 | 1.65 |
| 862. | 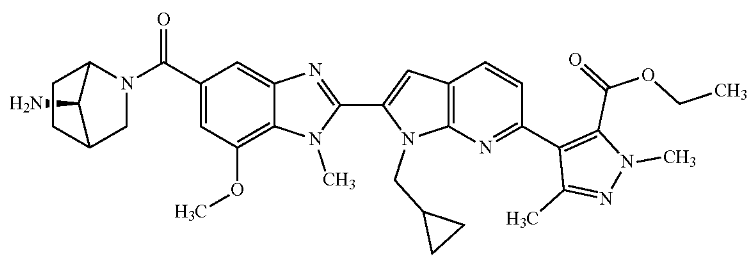 [SMILES: CCOC(=O)c1c(-c2ccc3cc(-c4nc5cc(C(=O)N6CC7CCC6[C@@H]7N)cc(OC)c5n4C)n(CC4CC4)c3n2)c(C)nn1C] | ethyl 4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1,3-dimethyl-1H-pyrazole-5-carboxylate | 637.1 | 2 | 1.61 |
| 863. | 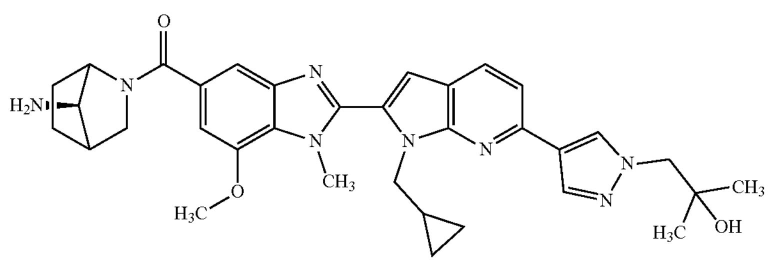 [SMILES: COc1cc(C(=O)N2CC3CCC2[C@@H]3N)cc2nc(-c3cc4ccc(-c5cnn(CC(C)(C)O)c5)nc4n3CC3CC3)n(C)c12] | 1-[4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1H-pyrazol-1-yl]-2-methylpropan-2-ol | 609.2 | 1 | 1.54 |

| # | Structure | Name | Obs. MS Ion | HPLC Method ID | RT |
|---|---|---|---|---|---|
| 864. | 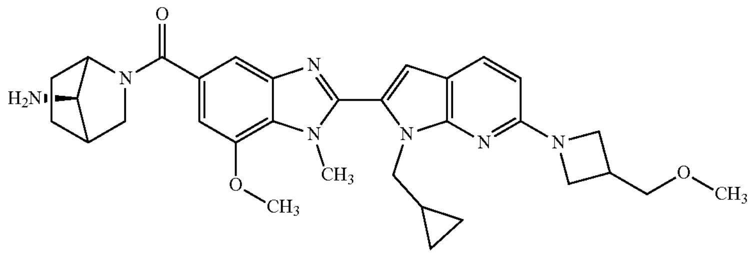 [SMILES: COCC1CN(c2ccc3cc(-c4nc5cc(C(=O)N6CC7CCC6[C@@H]7N)cc(OC)c5n4C)n(CC4CC4)c3n2)C1] | (7R)-2-{2-[1-(cyclopropylmethyl)-6-[3-(methoxymethyl)azetidin-1-yl]-1H-pyrrolo[2,3-b]pyridin-2-yl]-7-methoxy-1-methyl-1H-1,3-benzodiazole-5-carbonyl]-2-azabicyclo[2.2.1]heptan-7-amine | 570.1 | 1 | 1.86 |
| 865. | 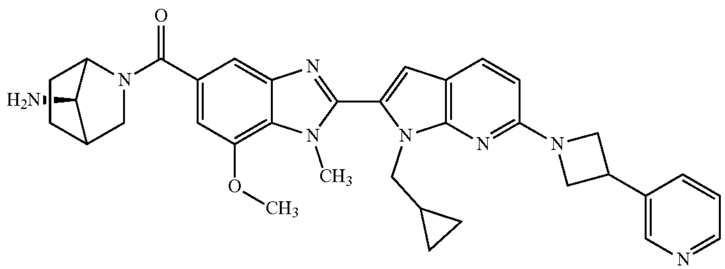 [SMILES: COc1cc(C(=O)N2CC3CCC2[C@@H]3N)cc2nc(-c3cc4ccc(N5CC(c6cccnc6)C5)nc4n3CC3CC3)n(C)c12] | (7R)-2-{2-[1-(cyclopropylmethyl)-6-[3-(pyridin-3-yl)azetidin-1-yl]-1H-pyrrolo[2,3-b]pyridin-2-yl]-7-methoxy-1-methyl-1H-1,3-benzodiazole-5-carbonyl]-2-azabicyclo[2.2.1]heptan-7-amine | 603.1 | 2 | 1.15 |
| 866. | 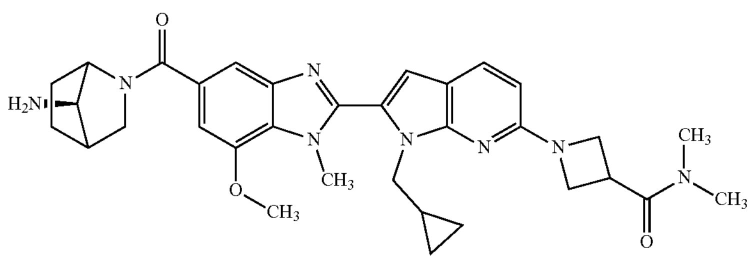 [SMILES: COc1cc(C(=O)N2CC3CCC2[C@@H]3N)cc2nc(-c3cc4ccc(N5CC(C(=O)N(C)C)C5)nc4n3CC3CC3)n(C)c12] | 1-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-N,N-dimethylazetidine-3-carboxamide | 597.2 | 1 | 1.59 |

| # | Structure | Name | Obs. MS Ion | HPLC Method ID | RT |
|---|---|---|---|---|---|
| 867. | 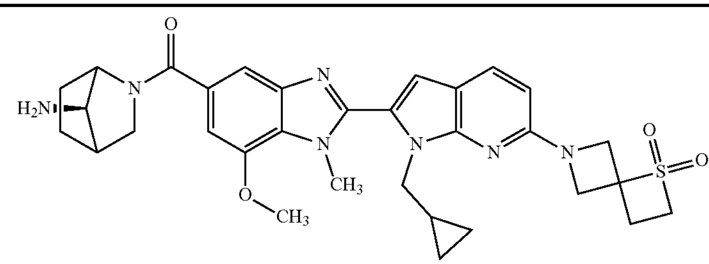 | ((7R)-7-amino-2-azabicyclo[2.2.1]heptan-2-yl)(2-(1-(cyclopropylmethyl)-6-(1,1-dioxido-1-thia-6-azaspiro[3.3]heptan-6-yl)-1H-pyrrolo[2,3-b]pyridin-2-yl)-7-methoxy-1-methyl-1H-benzo[d]imidazol-5-yl)methanone | 616 | 2 | 1.35 |
| 868. | 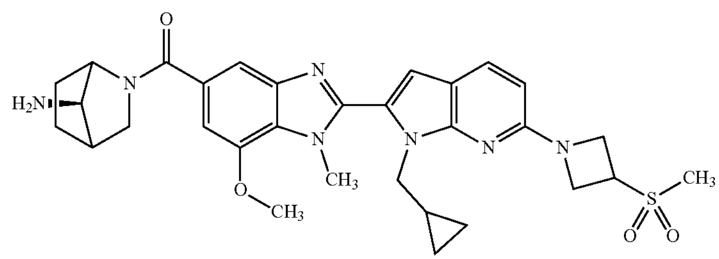 [SMILES: COc1cc(C(=O)N2CC3CCC2[C@@H]3N)cc2nc(-c3cc4ccc(N5CC(S(C)(=O)=O)C5)nc4n3CC3CC3)n(C)c12] | (7R)-2-{2-[1-(cyclopropylmethyl)-6-(3-methanesulfonylazetidin-1-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 604.1 | 1 | 1.51 |
| 869. | 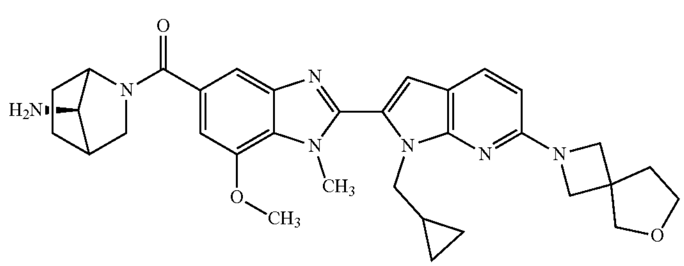 [SMILES: COc1cc(C(=O)N2CC3CCC2[C@@H]3N)cc2nc(-c3cc4ccc(N5CC6(CCOC6)C5)nc4n3CC3CC3)n(C)c12] | (7R)-2-{2-[1-(cyclopropylmethyl)-6-{6-oxa-2-azaspiro[3.4]octan-2-yl}-1H-pyrrolo[2,3-b]pyridin-2-yl]-7-methoxy-1-methyl-1H-1,3-benzodiazole-5-carbonyl}-2-azabicyclo[2.2.1]heptan-7-amine | 582 | 2 | 1.43 |

| # | Structure | Name | Obs. MS Ion | HPLC Method ID | RT |
|---|---|---|---|---|---|
| 870. | 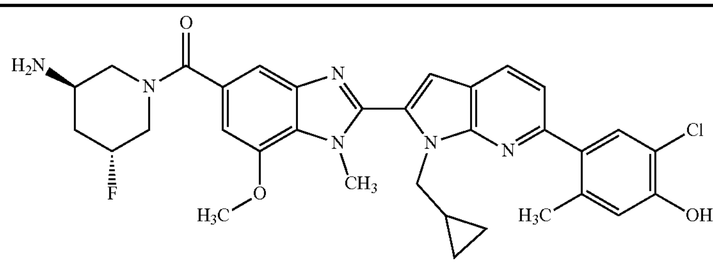 | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-chloro-5-methylphenol | 617 | 1 | 1.83 |
| 871. | 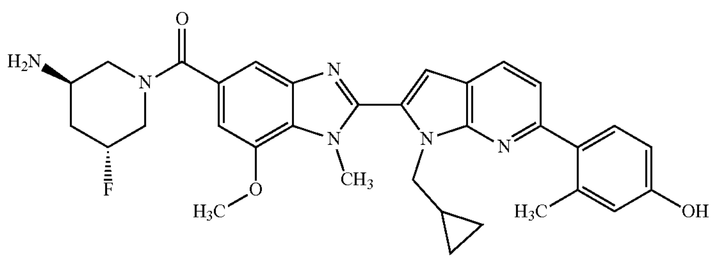 [SMILES: COc1cc(C(=O)N2C[C@H](N)C[C@@H](F)C2)cc2nc(-c3cc4ccc(-c5ccc(O)cc5C)nc4n3CC3CC3)n(C)c12] | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-3-methylphenol | 583.1 | 2 | 1.58 |
| 872. | 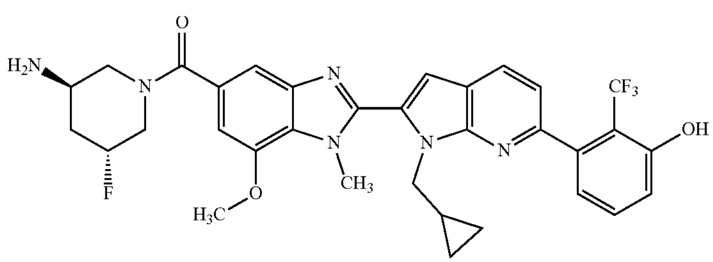 [SMILES: COc1cc(C(=O)N2C[C@H](N)C[C@@H](F)C2)cc2nc(-c3cc4ccc(-c5cccc(O)c5C(F)(F)F)nc4n3CC3CC3)n(C)c12] | 3-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-(trifluoromethyl)phenol | 637.3 | 1 | 1.71 |

| # | Structure | Name | Obs. MS Ion | HPLC Method ID | RT |
|---|---|---|---|---|---|
| 873. | 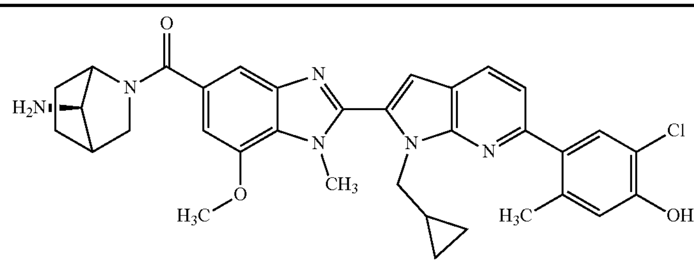 | 4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-chloro-5-methylphenol | 611.3 | 2 | 1.66 |
| 874. | 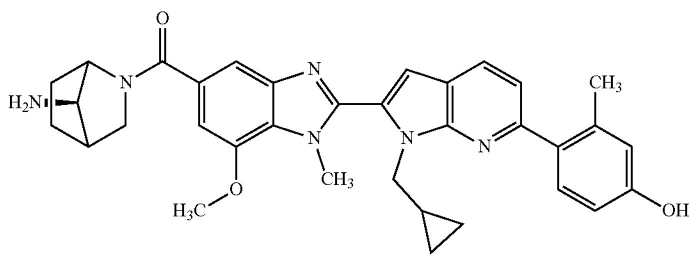 [SMILES: COc1cc(C(=O)N2CC3CCC2[C@@H]3N)cc2nc(-c3cc4ccc(-c5ccc(O)cc5C)nc4n3CC3CC3)n(C)c12] | 4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-3-methylphenol | 577.2 | 1 | 1.74 |
| 875. | 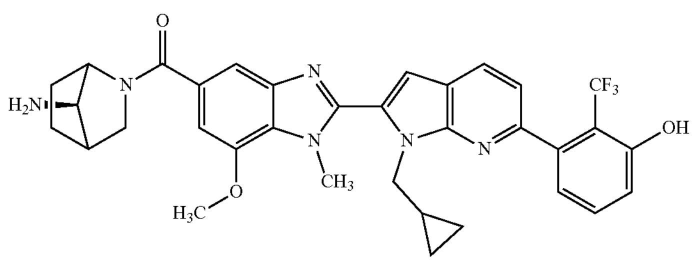 [SMILES: COc1cc(C(=O)N2CC3CCC2[C@@H]3N)cc2nc(-c3cc4ccc(-c5cccc(O)c5C(F)(F)F)nc4n3CC3CC3)n(C)c12] | 3-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-(trifluoromethyl)phenol | 631.2 | 1 | 1.8 |
| 876. | 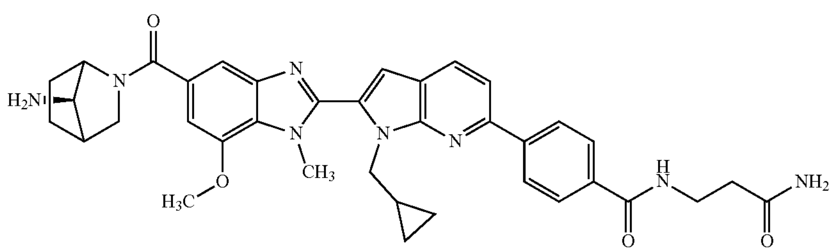 [SMILES: COc1cc(C(=O)N2CC3CCC2[C@@H]3N)cc2nc(-c3cc4ccc(-c5ccc(C(=O)NCCC(N)=O)cc5)nc4n3CC3CC3)n(C)c12] | 3-{[4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]formamido}propanamide | 661.1 | 2 | 1.3 |

| # | Structure | Name | Obs. MS Ion | HPLC Method ID | RT |
|---|---|---|---|---|---|
| 877. | 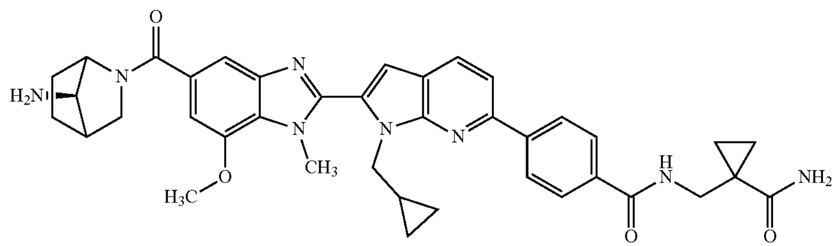 [SMILES: COc1cc(C(=O)N2CC3CCC2[C@@H]3N)cc2nc(-c3cc4ccc(-c5ccc(C(=O)NCC6(C(N)=O)CC6)cc5)nc4n3CC3CC3)n(C)c12] | 4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-N-[(1-carbamoylcyclopropyl)methyl]benzamide | 687.2 | 2 | 1.4 |
| 878. | 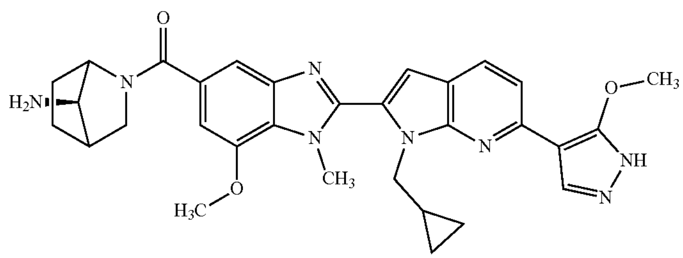 [SMILES: COc1[nH]ncc1-c1ccc2cc(-c3nc4cc(C(=O)N5CC6CCC5[C@@H]6N)cc(OC)c4n3C)n(CC3CC3)c2n1] | (7R)-2-{2-[1-(cyclopropylmethyl)-6-(5-methoxy-1H-pyrazol-4-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 567.3 | 1 | 1.62 |
| 879. | 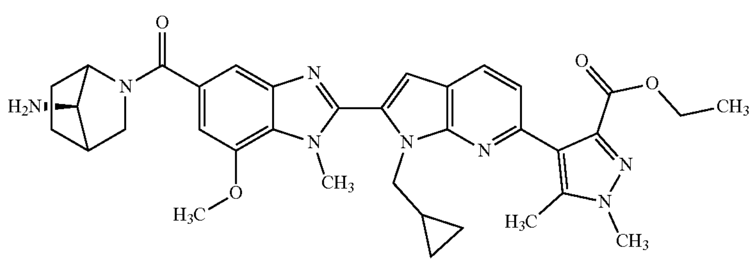 [SMILES: CCOC(=O)c1nn(C)c(C)c1-c1ccc2cc(-c3nc4cc(C(=O)N5CC6CCC5[C@@H]6N)cc(OC)c4n3C)n(CC3CC3)c2n1] | ethyl 4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1,5-dimethyl-1H-pyrazole-3-carboxylate | 637.4 | 1 | 1.69 |

| # | Structure | Name | Obs. MS Ion | HPLC Method ID | RT |
|---|---|---|---|---|---|
| 880. | 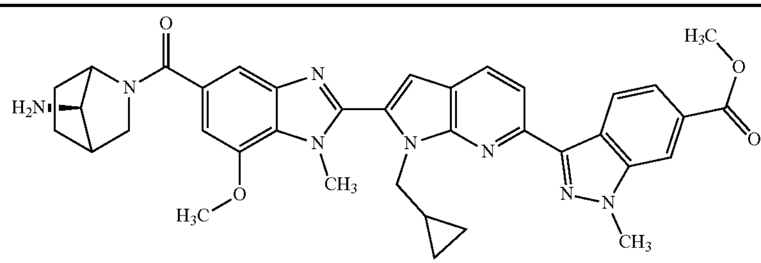 | methyl 3-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1-methyl-1H-indazole-6-carboxylate | 659.1 | 1 | 1.97 |
| 881. | 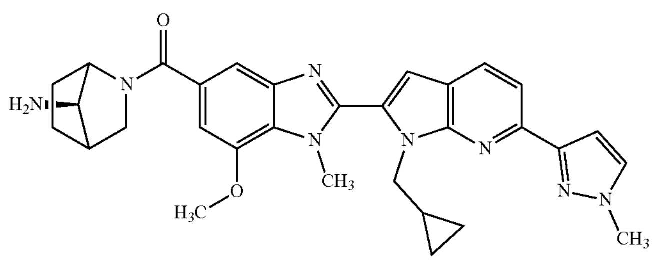 [SMILES: COc1cc(C(=O)N2CC3CCC2[C@@H]3N)cc2nc(-c3cc4ccc(-c5ccn(C)n5)nc4n3CC3CC3)n(C)c12] | (7R)-2-{2-[1-(cyclopropylmethyl)-6-(1-methyl-1H-pyrazol-3-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 551 | 1 | 1.67 |
| 882. | 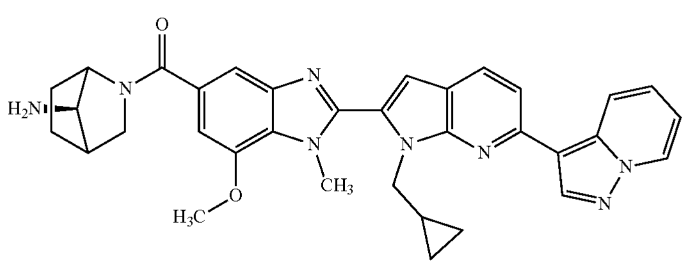 [SMILES: COc1cc(C(=O)N2CC3CCC2[C@@H]3N)cc2nc(-c3cc4ccc(-c5cnn6ccccc56)nc4n3CC3CC3)n(C)c12] | (7R)-2-{2-[1-(cyclopropylmethyl)-6-{pyrazolo[1,5-a]pyridin-3-yl}-1H-pyrrolo[2,3-b]pyridin-2-yl]-7-methoxy-1-methyl-1H-1,3-benzodiazole-5-carbonyl}-2-azabicyclo[2.2.1]heptan-7-amine | 587.1 | 2 | 1.62 |

| # | Structure | Name | Obs. MS Ion | HPLC Method ID | RT |
|---|---|---|---|---|---|
| 883. | 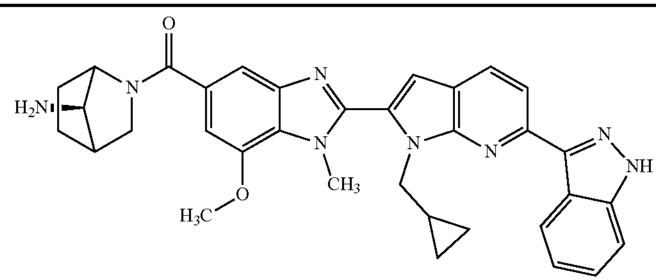 | (7R)-2-{2-[1-(cyclopropylmethyl)-6-(1H-indazol-3-yl)-1H-pyrrolo[2,3-b]pyridin-2-yl]-7-methoxy-1H-1,3-benzodiazole-5-carbonyl}-2-azabicyclo[2.2.1]heptan-7-amine | 587.3 | 1 | 1.75 |
| 884. | 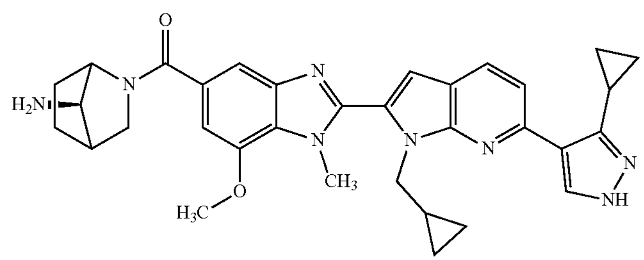 [SMILES: COc1cc(C(=O)N2CC3CCC2[C@@H]3N)cc2nc(-c3cc4ccc(-c5c[nH]nc5C5CC5)nc4n3CC3CC3)n(C)c12] | (7R)-2-{2-[6-(3-cyclopropyl-1H-pyrazol-4-yl)-1-(cyclopropylmethyl)-1H-pyrrolo[2,3-b]pyridin-2-yl]-7-methoxy-1H-1,3-benzodiazole-5-carbonyl}-2-azabicyclo[2.2.1]heptan-7-amine | 577 | 2 | 1.28 |
| 885. | 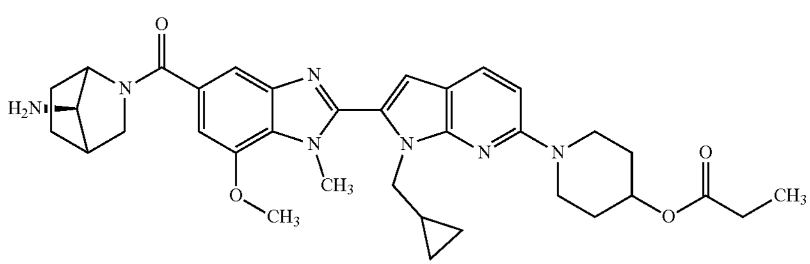 [SMILES: CCC(=O)OC1CCN(c2ccc3cc(-c4nc5cc(C(=O)N6CC7CCC6[C@@H]7N)cc(OC)c5n4C)n(CC4CC4)c3n2)CC1] | methyl 2-[1-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)piperidin-4-yl]acetate | 626.2 | 1 | 1.98 |

| # | Structure | Name | Obs. MS Ion | HPLC Method ID | RT |
|---|---|---|---|---|---|
| 886. | 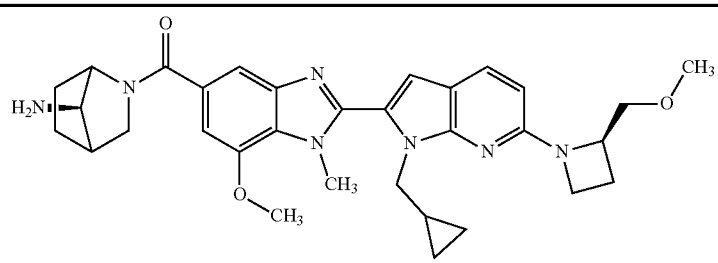 | (7R)-2-{2-[1-(cyclopropylmethyl)-6-[(2R)-2-(methoxymethyl)azetidin-1-yl]-1H-pyrrolo[2,3-b]pyridin-2-yl]-7-methoxy-1-methyl-1H-1,3-benzodiazole-5-carbonyl]-2-azabicyclo[2.2.1]heptan-7-amine | 570.2 | 2 | 1.44 |
| 887. | 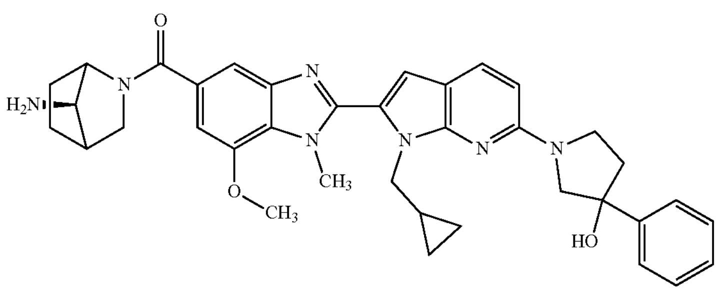 [SMILES: COc1cc(C(=O)N2CC3CCC2[C@@H]3N)cc2nc(-c3cc4ccc(N5CCC(O)(c6ccccc6)C5)nc4n3CC3CC3)n(C)c12] | 1-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-3-phenylpyrrolidin-3-ol (mixture of diastereomers) | 632.2 | 2 | 1.62 |
| 888. | 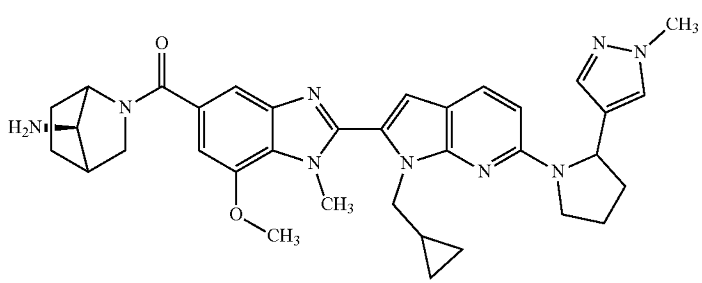 [SMILES: COc1cc(C(=O)N2CC3CCC2[C@@H]3N)cc2nc(-c3cc4ccc(N5CCCC5c5cnn(C)c5)nc4n3CC3CC3)n(C)c12] | (7R)-2-{2-[1-(cyclopropylmethyl)-6-[2-(1-methyl-1H-pyrazol-4-yl)pyrrolidin-1-yl]-1H-pyrrolo[2,3-b]pyridin-2-yl]-7-methoxy-1-methyl-1H-1,3-benzodiazole-5-carbonyl}-2-azabicyclo[2.2.1]heptan-7-amine (mixture of diastereomers) | 620.2 | 2 | 1.51 |

| # | Structure | Name | Obs. MS Ion | HPLC Method ID | RT |
|---|---|---|---|---|---|
| 889. | 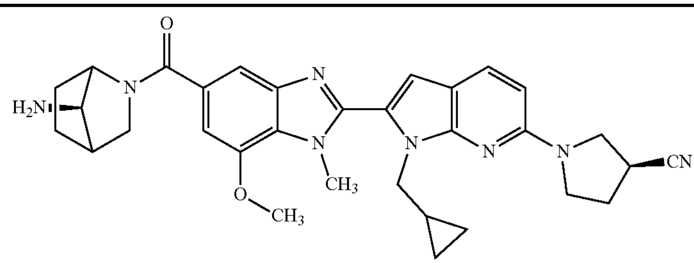 | (3S)-1-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)pyrrolidine-3-carbonitrile | 565.1 | 1 | 1.62 |
| 890. | 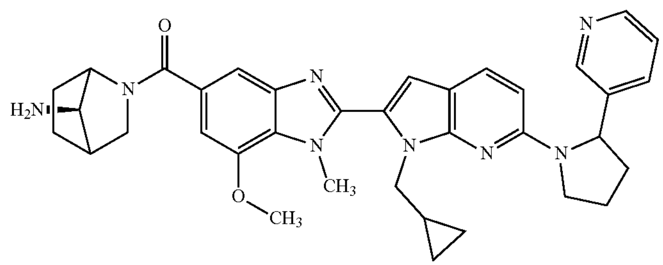 [SMILES: COc1cc(C(=O)N2CC3CCC2[C@@H]3N)cc2nc(-c3cc4ccc(N5CCCC5c5cccnc5)nc4n3CC3CC3)n(C)c12] | (7R)-2-{2-[1-(cyclopropylmethyl)-6-[2-(pyridin-3-yl)pyrrolidin-1-yl]-1H-pyrrolo[2,3-b]pyridin-2-yl]-7-methoxy-1-methyl-1H-1,3-benzodiazole-5-carbonyl}-2-azabicyclo[2.2.1]heptan-7-amine (mixture of diastereomers) | 617.2 | 2 | 1.27 |
| 891. | 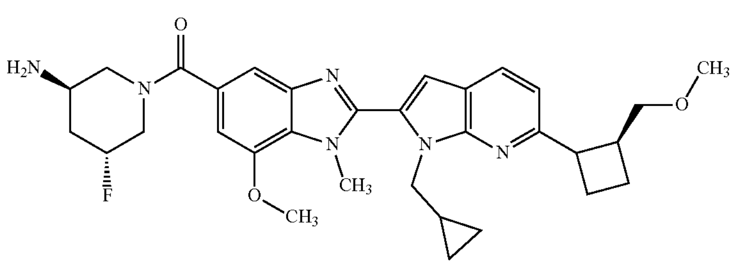 [SMILES: COC[C@H]1CCC1c1ccc2cc(-c3nc4cc(C(=O)N5C[C@H](N)C[C@@H](F)C5)cc(OC)c4n3C)n(CC3CC3)c2n1] | (3R,5R)-1-{2-[1-(cyclopropylmethyl)-6-[(2R)-2-(methoxymethyl)azetidin-1-yl]-1H-pyrrolo[2,3-b]pyridin-2-yl]-7-methoxy-1-methyl-1H-1,3-benzodiazole-5-carbonyl}-5-fluoropiperidin-3-amine | 576.2 | 1 | 1.84 |

| # | Structure | Name | Obs. MS Ion | HPLC Method ID | RT |
|---|---|---|---|---|---|
| 892. | 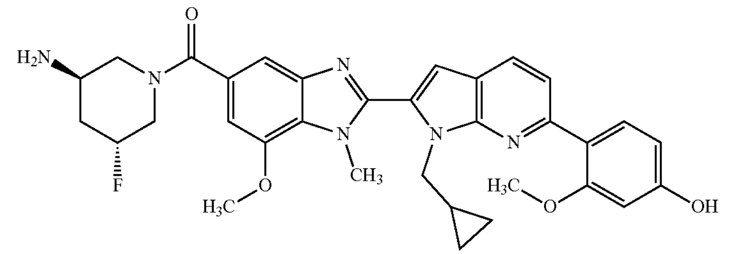 [SMILES: COc1cc(O)ccc1-c1ccc2cc(-c3nc4cc(C(=O)N5C[C@H](N)C[C@@H](F)C5)cc(OC)c4n3C)n(CC3CC3)c2n1] | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-3-methoxyphenol | 599.1 | 1 | 1.63 |
| 893. | 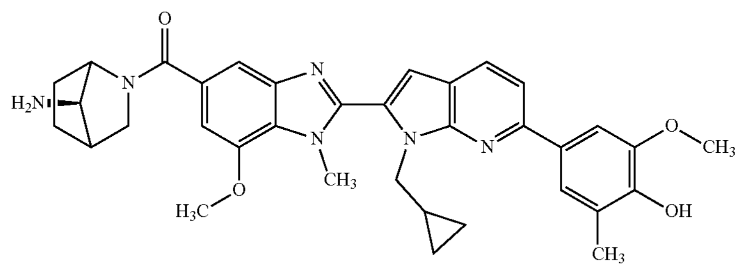 [SMILES: COc1cc(-c2ccc3cc(-c4nc5cc(C(=O)N6CC7CCC6[C@@H]7N)cc(OC)c5n4C)n(CC4CC4)c3n2)cc(C)c1O] | 4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-methoxy-6-methylphenol | 607.3 | 2 | 1.66 |
| 894. | 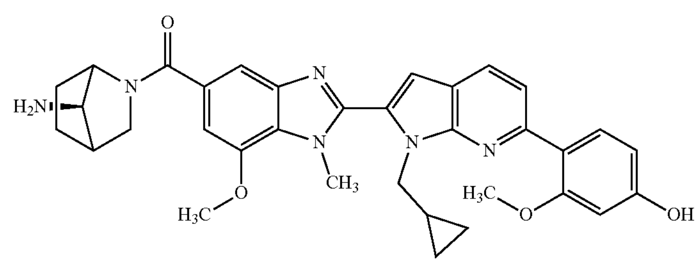 [SMILES: COc1cc(O)ccc1-c1ccc2cc(-c3nc4cc(C(=O)N5CC6CCC5[C@@H]6N)cc(OC)c4n3C)n(CC3CC3)c2n1] | 4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-3-methoxyphenol | 593 | 1 | 1.69 |

| # | Structure | Name | Obs. MS Ion | HPLC Method ID | RT |
|---|---|---|---|---|---|
| 895. | 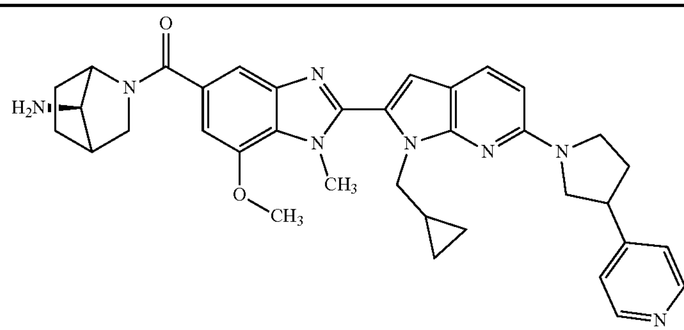 | (7R)-2-{2-[1-(cyclopropylmethyl)-6-[3-(pyridin-4-yl)pyrrolidin-1-yl]-1H-pyrrolo[2,3-b]pyridin-2-yl]-7-methoxy-1H-1,3-benzodiazole-5-carbonyl]-2-azabicyclo[2.2.1]heptan-7-amine (mixture of diastereomers) | 617.2 | 2 | 1.07 |
| 896. | 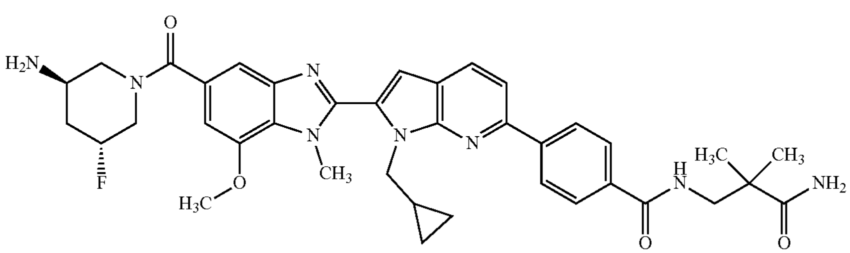 [SMILES: COc1cc(C(=O)N2C[C@H](N)C[C@@H](F)C2)cc2nc(-c3cc4ccc(-c5ccc(C(=O)NCC(C)(C)C(N)=O)cc5)nc4n3CC3CC3)n(C)c12] | 3-{[4-(2-{5-[(3R,5R)-3-amino-5-fluoropiperidine-1-carbonyl]-7-methoxy-1-methyl-1H-1,3-benzodiazol-2-yl]-1-(cyclopropylmethyl)-1H-pyrrolo[2,3-b]pyridin-6-yl}phenyl]formamido}-2,2-dimethylpropanamide | 695 | 1 | 1.49 |
| 897. | 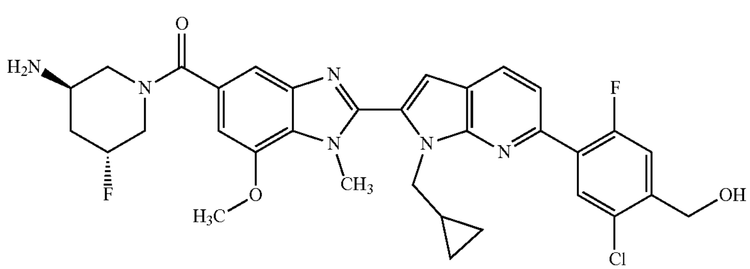 [SMILES: COc1cc(C(=O)N2C[C@H](N)C[C@@H](F)C2)cc2nc(-c3cc4ccc(-c5cc(Cl)c(CO)cc5F)nc4n3CC3CC3)n(C)c12] | [4-(2-{5-[(3R,5R)-3-amino-5-fluoropiperidine-1-carbonyl]-7-methoxy-1-methyl-1H-1,3-benzodiazol-2-yl]-1-(cyclopropylmethyl)-1H-pyrrolo[2,3-b]pyridin-6-yl)-2-chloro-5-fluorophenyl]methanol | 635.1 | 2 | 1.61 |

| # | Structure | Name | Obs. MS Ion | HPLC Method ID | RT |
|---|---|---|---|---|---|
| 898. | 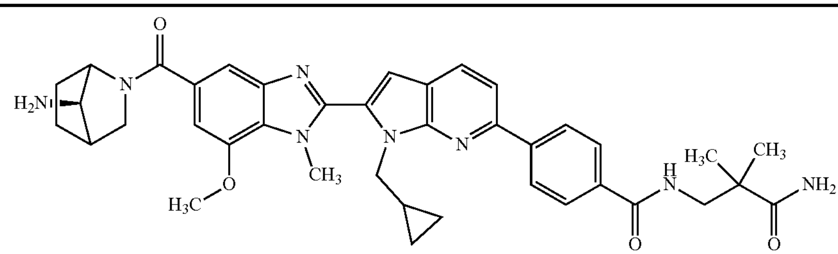 | 3-[{4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]formamido]-2,2-dimethylpropanamide | 689.2 | 1 | 1.61 |
| 899. | 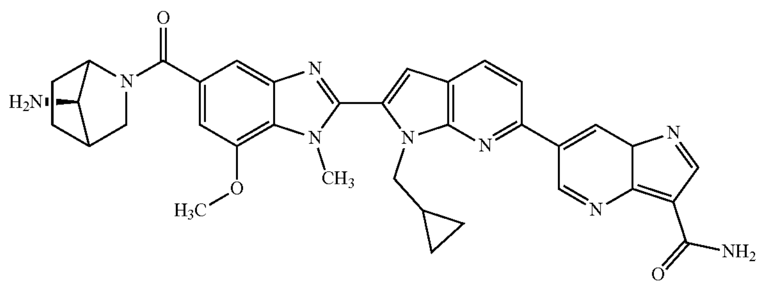 [SMILES: COc1cc(C(=O)N2CC3CCC2[C@@H]3N)cc2nc(-c3cc4ccc(C5=CC6N=CC(C(N)=O)=C6N=C5)nc4n3CC3CC3)n(C)c12] | 6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-7aH-pyrrolo[3,2-b]pyridine-3-carboxamide | 629.9 | 1 | 1.41 |
| 900. | 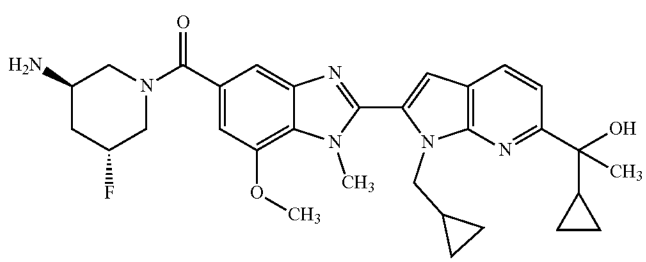 [SMILES: COc1cc(C(=O)N2C[C@H](N)C[C@@H](F)C2)cc2nc(-c3cc4ccc(C(C)(O)C5CC5)nc4n3CC3CC3)n(C)c12] | 1-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-1-cyclopropylethan-1-ol (mixture of diastereomers) | 561.2 | 2 | 1.67 |

-continued

| # | Structure | Name | Obs. MS Ion | HPLC Method ID | RT |
|---|---|---|---|---|---|
| 901. | 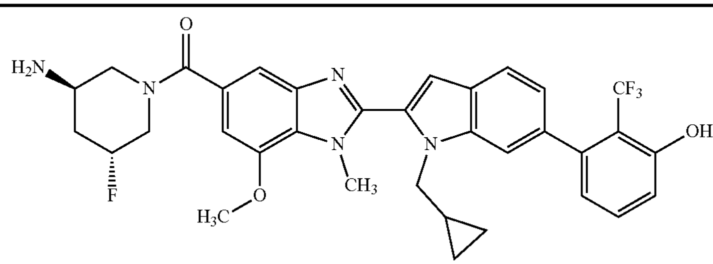 | 3-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)-2-(trifluoromethyl)phenol | 636.3 | 1 | 1.79 |
| 902. | 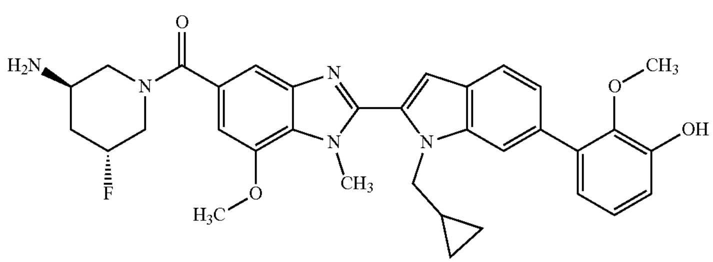 [SMILES: COc1c(O)cccc1-c1ccc2cc(-c3nc4cc(C(=O)N5C[C@H](N)C[C@@H](F)C5)cc(OC)c4n3C)n(CC3CC3)c2c1] | 3-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)-2-methoxyphenol | 598.1 | 2 | 1.6 |
| 903. | 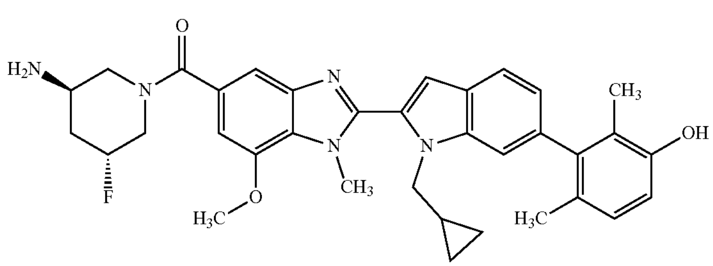 [SMILES: COc1cc(C(=O)N2C[C@H](N)C[C@@H](F)C2)cc2nc(-c3cc4ccc(-c5c(C)ccc(O)c5C)cc4n3CC3CC3)n(C)c12] | 3-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)-2,4-dimethylphenol | 596.1 | 1 | 1.87 |

| # | Structure | Name | Obs. MS Ion | HPLC Method ID | RT |
|---|---|---|---|---|---|
| 904. | 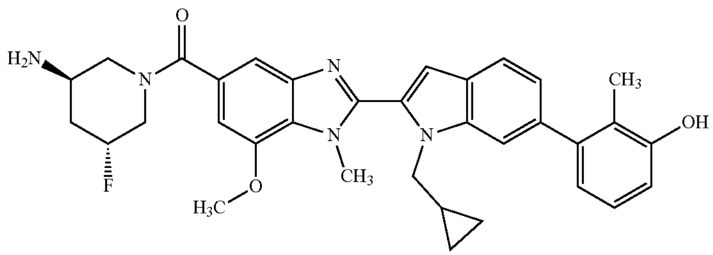 | 3-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)-2-methylphenol | 582.1 | 2 | 1.59 |
| 905. | 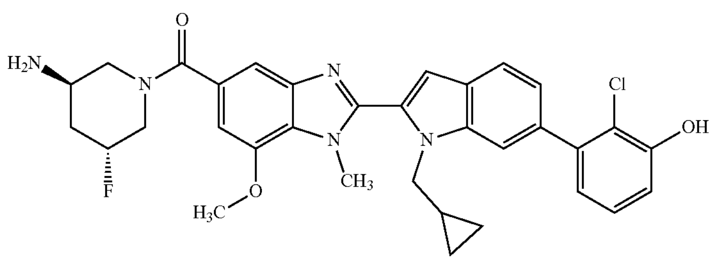 | 3-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)-2-chlorophenol | 602.1 | 2 | 1.65 |
| 906. | 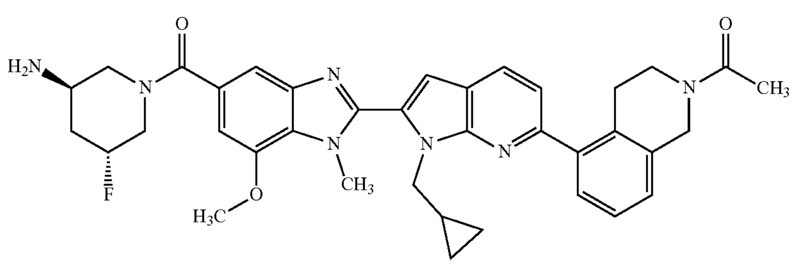 [SMILES: COc1cc(C(=O)N2C[C@H](N)C[C@@H](F)C2)cc2nc(-c3cc4ccc(-c5cccc6c5CCN(C(C)=O)C6)nc4n3CC3CC3)n(C)c12] | 1-[5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-1,2,3,4-tetrahydroisoquinolin-2-yl]ethan-1-one | 650.2 | 1 | 1.76 |

| # | Structure | Name | Obs. MS Ion | HPLC Method ID | RT |
|---|---|---|---|---|---|
| 907. | 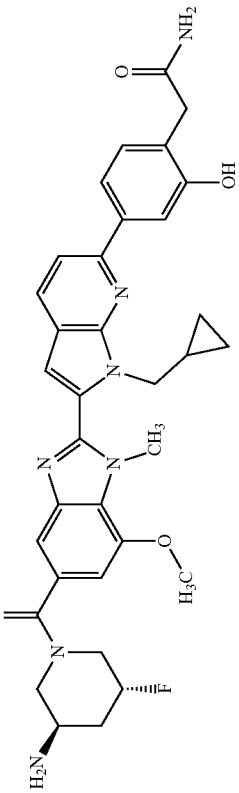 | 2-[4-(2-{5-[(3R,5R)-3-amino-5-fluoropiperidine-1-carbonyl]-7-methoxy-1-methyl-1H-1,3-benzodiazol-2-yl]-1-(cyclopropylmethyl)-1H-pyrrolo[2,3-b]pyridin-6-yl)-2-hydroxyphenyl]acetamide | 625.9 | 1 | 1.49 |
| 908. | 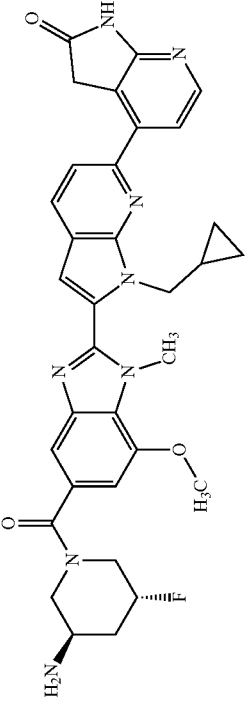 | 4-(2-{5-[(3R,5R)-3-amino-5-fluoropiperidine-1-carbonyl]-7-methoxy-1-methyl-1H-1,3-benzodiazol-2-yl]-1-(cyclopropylmethyl)-1H-pyrrolo[2,3-b]pyridin-6-yl)-1H,2H,3H-pyrrolo[2,3-b]pyridin-2-one | 609.1 | 1 | 1.49 |
| 909. | 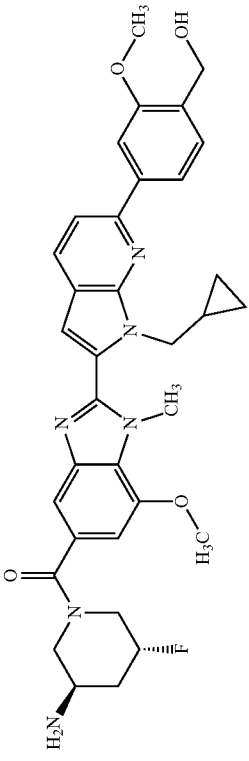 | [4-(2-{5-[(3R,5R)-3-amino-5-fluoropiperidine-1-carbonyl]-7-methoxy-1-methyl-1H-1,3-benzodiazol-2-yl]-1-(cyclopropylmethyl)-1H-pyrrolo[2,3-b]pyridin-6-yl)-2-methoxyphenyl]methanol | 613.3 | 2 | 1.43 |

| # | Structure | Name | Obs. MS Ion | HPLC Method ID | RT |
|---|---|---|---|---|---|
| 910. | 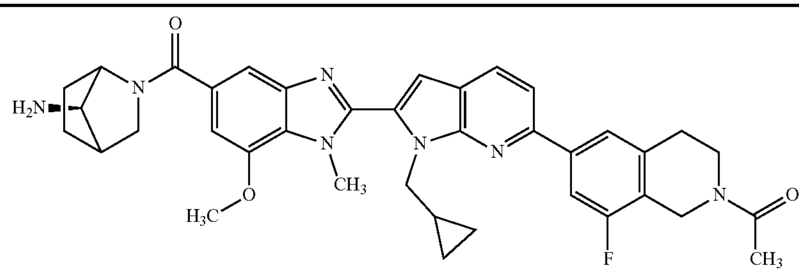 | 1-[6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-8-fluoro-1,2,3,4-tetrahydroisoquinolin-2-yl]ethan-1-one | 662.1 | 2 | 1.52 |
| 911. | 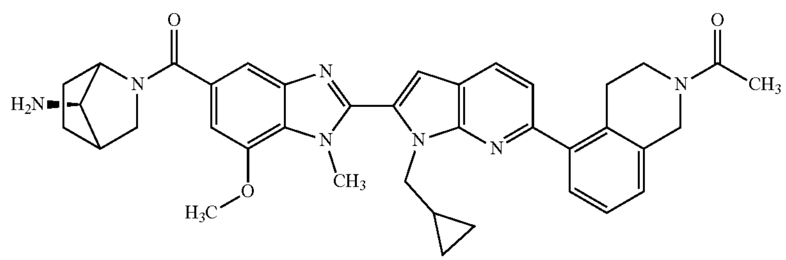 [SMILES: COc1cc(C(=O)N2CC3CCC2[C@@H]3N)cc2nc(-c3cc4ccc(-c5cccc6c5CCN(C(C)=O)C6)nc4n3CC3CC3)n(C)c12] | 1-[5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1,2,3,4-tetrahydroisoquinolin-2-yl]ethan-1-one | 644 | 1 | 1.73 |
| 912. | 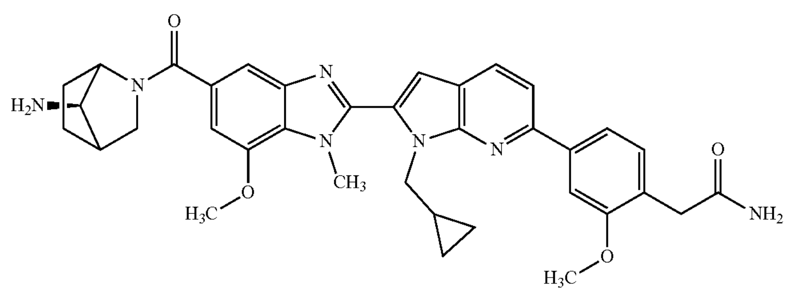 [SMILES: COc1cc(-c2ccc3cc(-c4nc5cc(C(=O)N6CC7CCC6[C@@H]7N)cc(OC)c5n4C)n(CC4CC4)c3n2)ccc1CC(N)=O] | 2-[4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-methoxyphenyl]acetamide | 633.9 | 1 | 1.6 |

| # | Structure | Name | Obs. MS Ion | HPLC Method ID | RT |
|---|---|---|---|---|---|
| 913. | 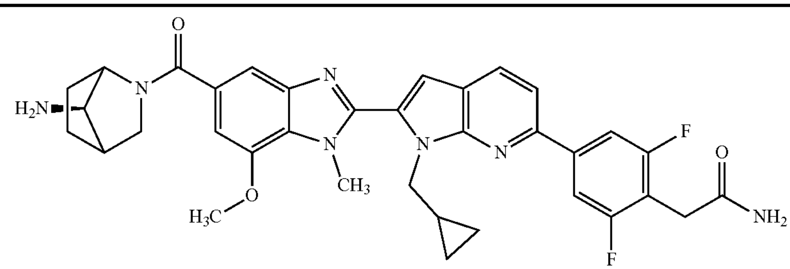 | 2-[4-(2-{5-[(7R)-7-amino-2-azabicyclo[2.2.1]heptane-2-carbonyl]-7-methoxy-1H-1,3-benzodiazol-2-yl}-1-(cyclopropylmethyl)-1H-pyrrolo[2,3-b]pyridin-6-yl)-2,6-difluorophenyl]acetamide | 640.2 | 1 | 1.64 |
| 914. | 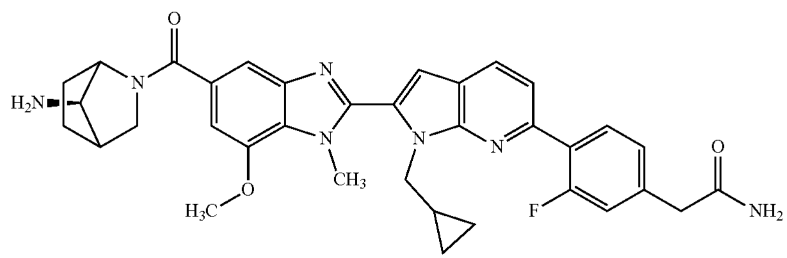 [SMILES: COc1cc(C(=O)N2CC3CCC2[C@@H]3N)cc2nc(-c3cc4ccc(-c5ccc(CC(N)=O)cc5F)nc4n3CC3CC3)n(C)c12] | 2-[4-(2-{5-[(7R)-7-amino-2-azabicyclo[2.2.1]heptane-2-carbonyl]-7-methoxy-1H-1,3-benzodiazol-2-yl}-1-(cyclopropylmethyl)-1H-pyrrolo[2,3-b]pyridin-6-yl)-3-fluorophenyl]acetamide | 622.2 | 2 | 1.27 |
| 915. | 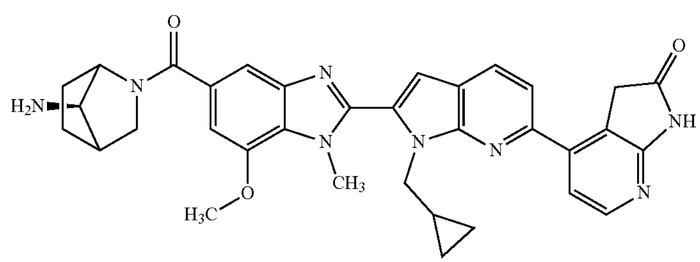 [SMILES: COc1cc(C(=O)N2CC3CCC2[C@@H]3N)cc2nc(-c3cc4ccc(-c5ccnc6c5CC(=O)N6)nc4n3CC3CC3)n(C)c12] | 4-(2-{5-[(7R)-7-amino-2-azabicyclo[2.2.1]heptane-2-carbonyl]-7-methoxy-1H-1,3-benzodiazol-2-yl}-1-(cyclopropylmethyl)-1H-pyrrolo[2,3-b]pyridin-6-yl)-1H,2H,3H-pyrrolo[2,3-b]pyridin-2-one | 603.3 | 1 | 1.56 |

| # | Structure | Name | Obs. MS Ion | HPLC Method ID | RT |
|---|---|---|---|---|---|
| 916. | 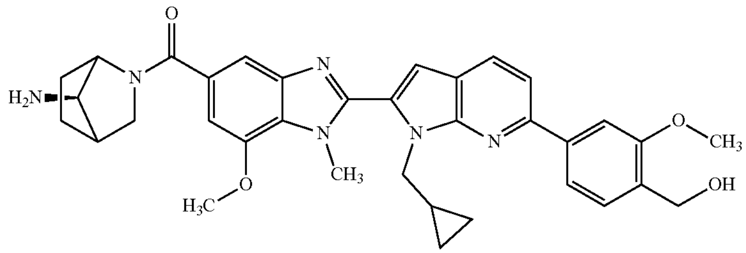 [SMILES: COc1cc(-c2ccc3cc(-c4nc5cc(C(=O)N6CC7CCC6[C@@H]7N)cc(OC)c5n4C)n(CC4CC4)c3n2)ccc1CO] | [4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-methoxyphenyl]methanol | 1213.3 | 1 | 1.63 |
| 917. | 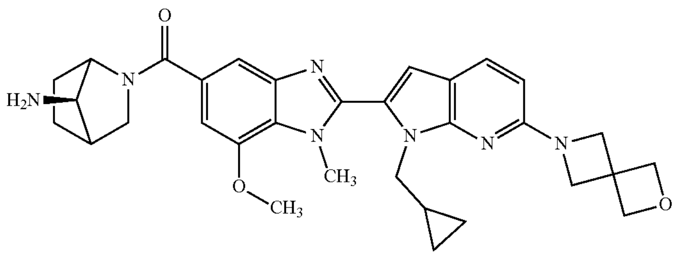 [SMILES: COc1cc(C(=O)N2CC3CCC2[C@@H]3N)cc2nc(-c3cc4ccc(N5CC6(COC6)C5)nc4n3CC3CC3)n(C)c12] | (7R)-2-{2-[1-(cyclopropylmethyl)-6-{2-oxa-6-azaspiro[3.3]heptan-6-yl}-1H-indol-2-yl]-7-methoxy-1-methyl-1H-1,3-benzodiazole-5-carbonyl}-2-azabicyclo[2.2.1]heptan-7-amine | 567 | 2 | 1.15 |
| 918. | 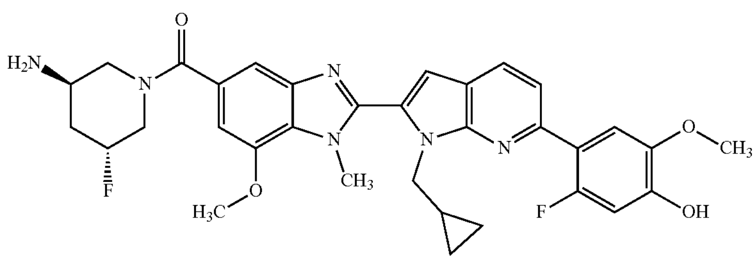 [SMILES: COc1cc(-c2ccc3cc(-c4nc5cc(C(=O)N6C[C@H](N)C[C@@H](F)C6)cc(OC)c5n4C)n(CC4CC4)c3n2)c(F)cc1O] | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-5-fluoro-2-methoxyphenol | 617.2 | 1 | 1.8 |

| # | Structure | Name | Obs. MS Ion | HPLC Method ID | RT |
|---|---|---|---|---|---|
| 919. | 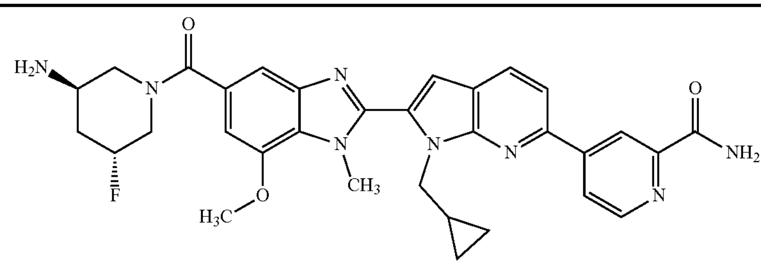 | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)pyridine-2-carboxamide | 597.2 | 1 | 1.53 |
| 920. | 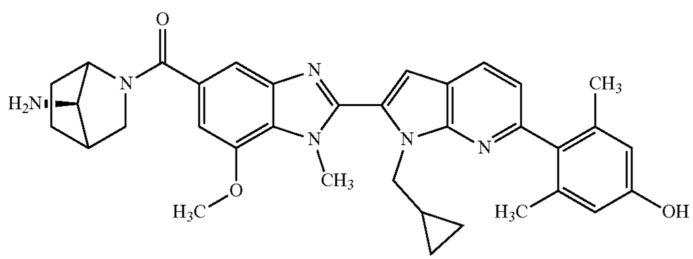 [SMILES: COc1cc(C(=O)N2CC3CCC2[C@@H]3N)cc2nc(-c3cc4ccc(-c5c(C)cc(O)cc5C)nc4n3CC3CC3)n(C)c12] | 4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-3,5-dimethylphenol | 591 | 1 | 1.72 |
| 921. | 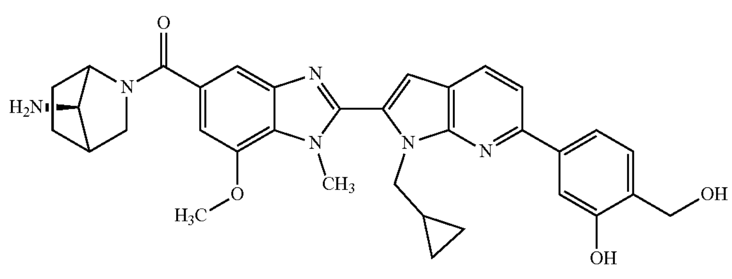 [SMILES: COc1cc(C(=O)N2CC3CCC2[C@@H]3N)cc2nc(-c3cc4ccc(-c5ccc(CO)c(O)c5)nc4n3CC3CC3)n(C)c12] | [4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-methylphenyl]methanol | 591.1 | 1 | 1.82 |

| # | Structure | Name | Obs. MS Ion | HPLC Method ID | RT |
|---|---|---|---|---|---|
| 922. | 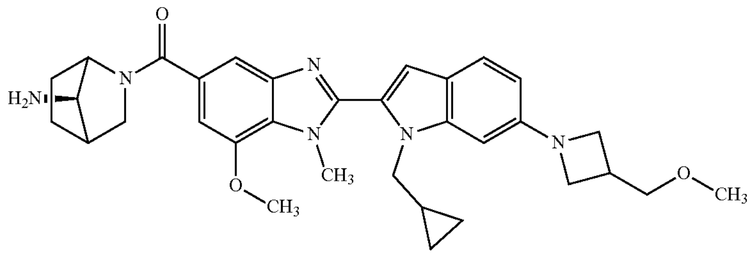 [SMILES: COCC1CN(c2ccc3cc(-c4nc5cc(C(=O)N6CC7CCC6[C@@H]7N)cc(OC)c5n4C)n(CC4CC4)c3c2)C1] | (7R)-2-{2-[1-(cyclopropylmethyl)-6-[3-(methoxymethyl)azetidin-1-yl]-1H-indol-2-yl]-7-methoxy-1-methyl-1H-1,3-benzodiazole-5-carbonyl}-2-azabicyclo[2.2.1]heptan-7-amine | 569.2 | 2 | 1.36 |
| 923. | 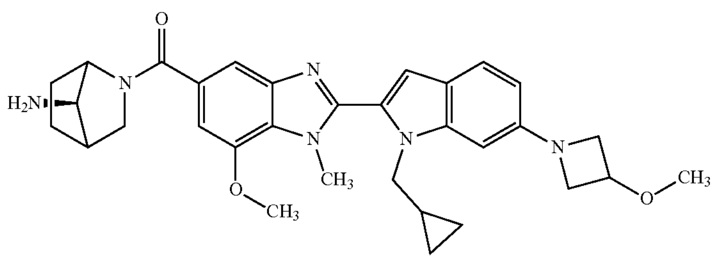 | (7R)-2-{2-[1-(cyclopropylmethyl)-6-(3-methoxyazetidin-1-yl)-1H-indol-2-yl]-7-methoxy-1-methyl-1H-1,3-benzodiazole-5-carbonyl}-2-azabicyclo[2.2.1]heptan-7-amine | 555.2 | 2 | 1.22 |
| 924. | 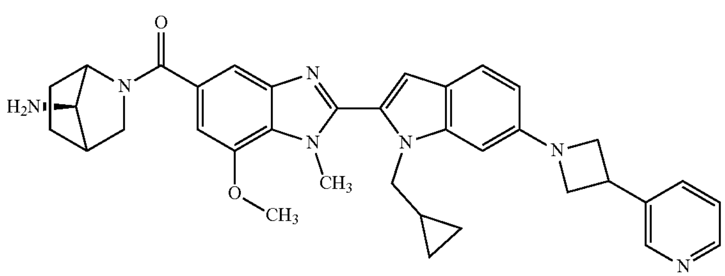 [SMILES: COc1cc(C(=O)N2CC3CCC2[C@@H]3N)cc2nc(-c3cc4ccc(N5CC(c6cccnc6)C5)cc4n3CC3CC3)n(C)c12] | (7R)-2-{2-[1-(cyclopropylmethyl)-6-[3-(pyridin-3-yl)azetidin-1-yl]-1H-indol-2-yl]-7-methoxy-1-methyl-1H-1,3-benzodiazole-5-carbonyl}-2-azabicyclo[2.2.1]heptan-7-amine | 602.2 | 1 | 1.69 |

| # | Structure | Name | Obs. MS Ion | HPLC Method ID | RT |
|---|---|---|---|---|---|
| 925. | 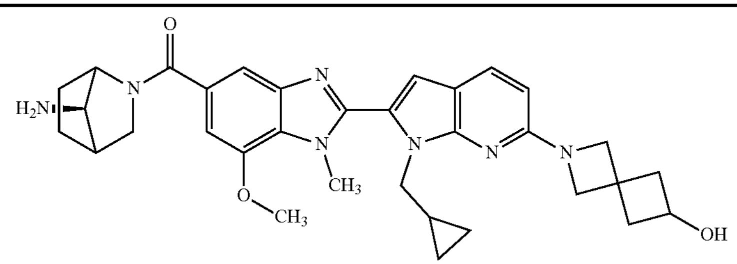 | 2-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-azaspiro[3.3]heptan-6-ol | 582.1 | 1 | 1.63 |
| 926. | 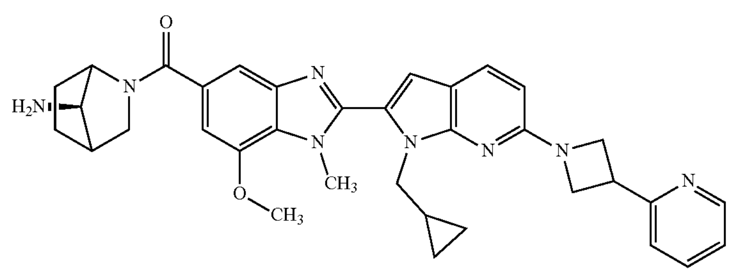 [SMILES: COc1cc(C(=O)N2CC3CCC2[C@@H]3N)cc2nc(-c3cc4ccc(N5CC(c6ccccn6)C5)nc4n3CC3CC3)n(C)c12] | (7R)-2-{2-[1-(cyclopropylmethyl)-6-[3-(pyridin-2-yl)azetidin-1-yl]-1H-pyrrolo[2,3-b]pyridin-2-yl]-7-methoxy-1-methyl-1H-1,3-benzodiazole-5-carbonyl}-2-azabicyclo[2.2.1]heptan-7-amine | 603.1 | 2 | 1.2 |
| 927. | 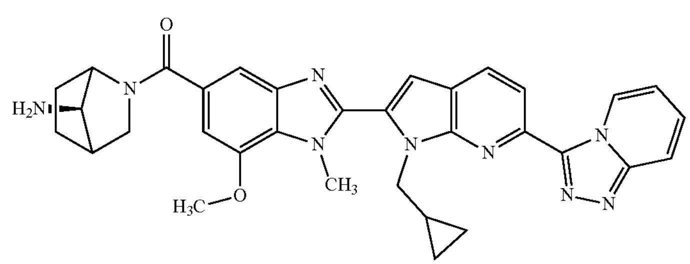 [SMILES: COc1cc(C(=O)N2CC3CCC2[C@@H]3N)cc2nc(-c3cc4ccc(-c5nnc6ccccn56)nc4n3CC3CC3)n(C)c12] | (7R)-2-{2-[1-(cyclopropylmethyl)-6-{[1,2,4]triazolo[4,3-a]pyridin-3-yl}-1H-pyrrolo[2,3-b]pyridin-2-yl]-7-methoxy-1-methyl-1H-1,3-benzodiazole-5-carbonyl}-2-azabicyclo[2.2.1]heptan-7-amine | 588.3 | 1 | 1.49 |

| # | Structure | Name | Obs. MS Ion | HPLC Method ID | RT |
|---|---|---|---|---|---|
| 928. | 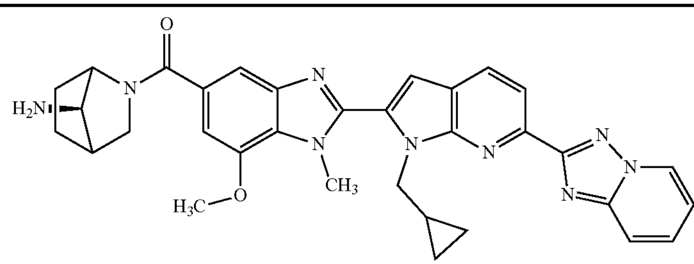 | (7R)-2-{2-[1-(cyclopropylmethyl)-6-{[1,2,4]triazolo[1,5-a]pyridin-2-yl}-1H-pyrrolo[2,3-b]pyridin-2-yl]-7-methoxy-1-methyl-1H-1,3-benzodiazole-5-carbonyl}-2-azabicyclo[2.2.1]heptan-7-amine | 587.9 | 2 | 1.41 |
| 929. | 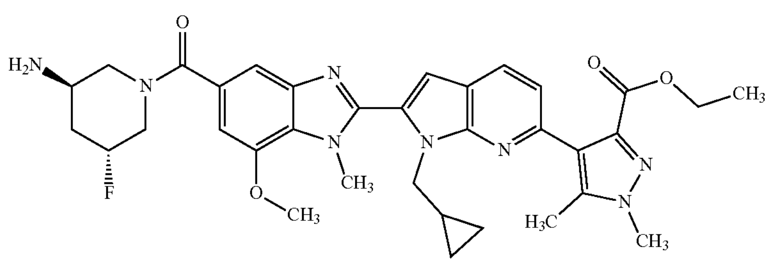 [SMILES: CCOC(=O)c1nn(C)c(C)c1-c1ccc2cc(-c3nc4cc(C(=O)N5C[C@H](N)C[C@@H](F)C5)cc(OC)c4n3C)n(CC3CC3)c2n1] | ethyl 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-1,5-dimethyl-1H-pyrazole-3-carboxylate | 643.2 | 1 | 1.44 |
| 930. | 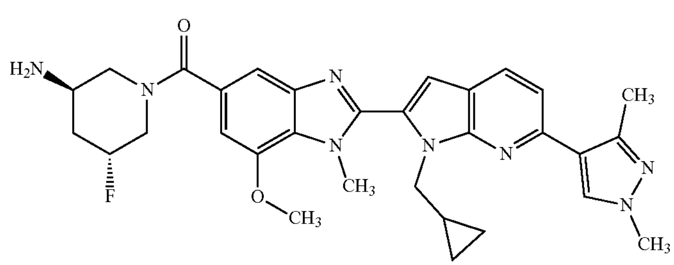 [SMILES: COc1cc(C(=O)N2C[C@H](N)C[C@@H](F)C2)cc2nc(-c3cc4ccc(-c5cn(C)nc5C)nc4n3CC3CC3)n(C)c12] | (3R,5R)-1-{2-[1-(cyclopropylmethyl)-6-(1,3-dimethyl-1H-pyrazol-4-yl)-1H-pyrrolo[2,3-b]pyridin-2-yl]-7-methoxy-1-methyl-1H-1,3-benzodiazole-5-carbonyl}-5-fluoropiperidin-3-amine | 571.2 | 1 | 1.63 |

-continued

| # | Structure | Name | Obs. MS Ion | HPLC Method ID | RT |
|---|---|---|---|---|---|
| 931. | 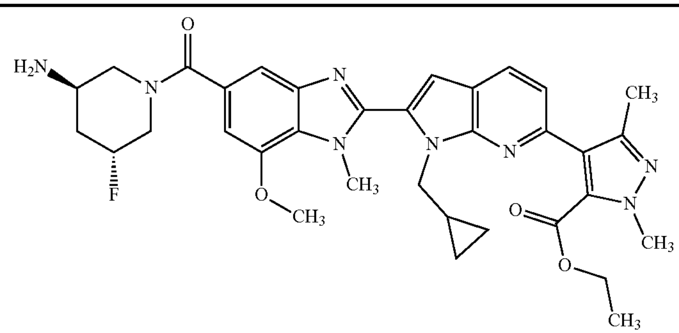 | ethyl 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-1,3-dimethyl-1H-pyrazole-5-carboxylate | 643.2 | 1 | 1.69 |
| 932. | 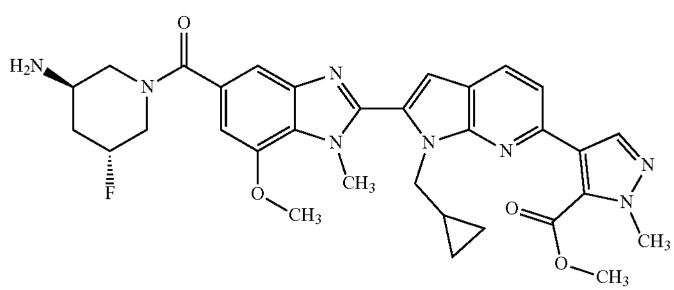 [SMILES: COC(=O)c1c(-c2ccc3cc(-c4nc5cc(C(=O)N6C[C@H](N)C[C@@H](F)C6)cc(OC)c5n4C)n(CC4CC4)c3n2)cnn1C] | methyl 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-1-methyl-1H-pyrazole-5-carboxylate | 615.4 | 2 | 1.53 |
| 933. | 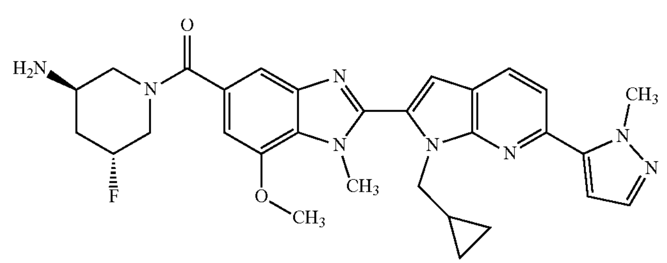 [SMILES: COc1cc(C(=O)N2C[C@H](N)C[C@@H](F)C2)cc2nc(-c3cc4ccc(-c5ccnn5C)nc4n3CC3CC3)n(C)c12] | (3R,5R)-1-{2-[1-(cyclopropylmethyl)-6-(1-methyl-1H-pyrazol-5-yl)-1H-pyrrolo[2,3-b]pyridin-2-yl]-7-methoxy-1-methyl-1H-1,3-benzodiazole-5-carbonyl}-5-fluoropiperidin-3-amine | 557.2 | 1 | 1.69 |

| # | Structure | Name | Obs. MS Ion | HPLC Method ID | RT |
|---|---|---|---|---|---|
| 934. | 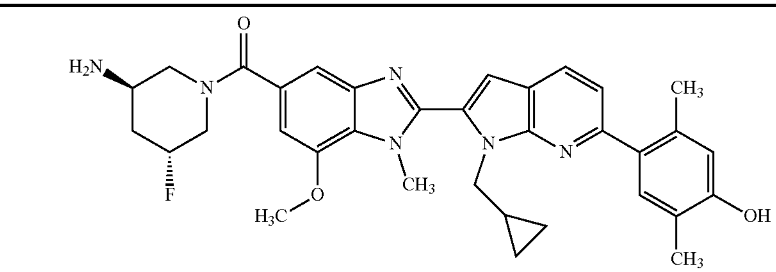 | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2,5-dimethylphenol | 597.2 | 1 | 1.62 |
| 935. | 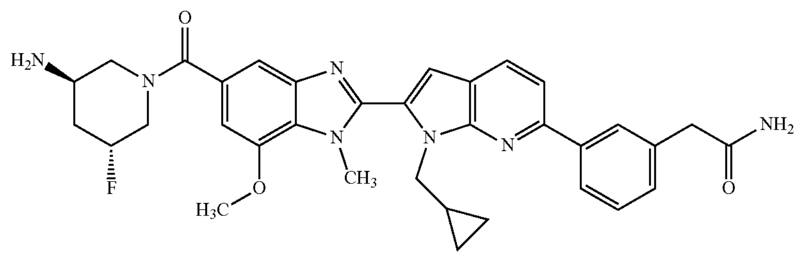 [SMILES: COc1cc(C(=O)N2C[C@H](N)C[C@@H](F)C2)cc2nc(-c3cc4ccc(-c5cccc(CC(N)=O)c5)nc4n3CC3CC3)n(C)c12] | 2-[3-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)phenyl]acetamide | 610.4 | 2 | 1.41 |
| 936. | 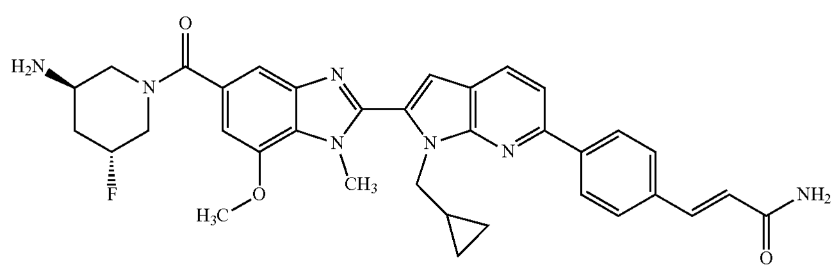 [SMILES: COc1cc(C(=O)N2C[C@H](N)C[C@@H](F)C2)cc2nc(-c3cc4ccc(-c5ccc(/C=C/C(N)=O)cc5)nc4n3CC3CC3)n(C)c12] | (2E)-3-[4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)phenyl]prop-2-enamide | 622.1 | 1 | 1.57 |

| # | Structure | Name | Obs. MS Ion | HPLC Method ID | RT |
|---|---|---|---|---|---|
| 937. | 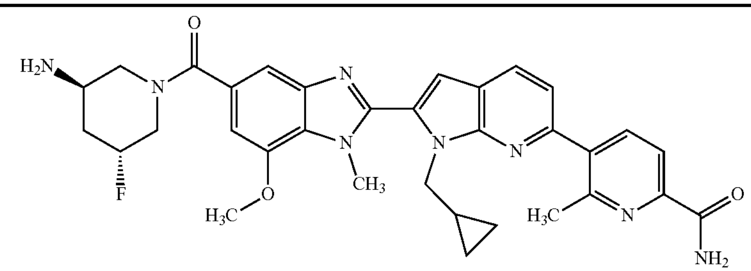 | 5-(2-{5-[(3R,5R)-3-amino-5-fluoropiperidine-1-carbonyl]-7-methoxy-1-methyl-1H-1,3-benzodiazol-2-yl]-1-(cyclopropylmethyl)-1H-pyrrolo[2,3-b]pyridin-6-yl)-6-methylpyridine-2-carboxamide | 611.2 | 1 | 1.55 |
| 938. | 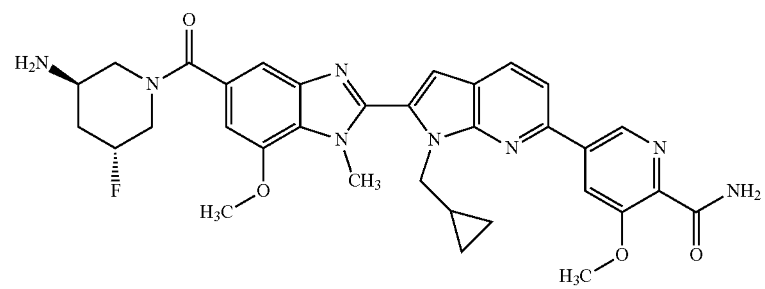 | 5-(2-{5-[(3R,5R)-3-amino-5-fluoropiperidine-1-carbonyl]-7-methoxy-1-methyl-1H-1,3-benzodiazol-2-yl]-1-(cyclopropylmethyl)-1H-pyrrolo[2,3-b]pyridin-6-yl)-3-methoxypyridine-2-carboxamide | 626.9 | 1 | 1.48 |
| 939. | 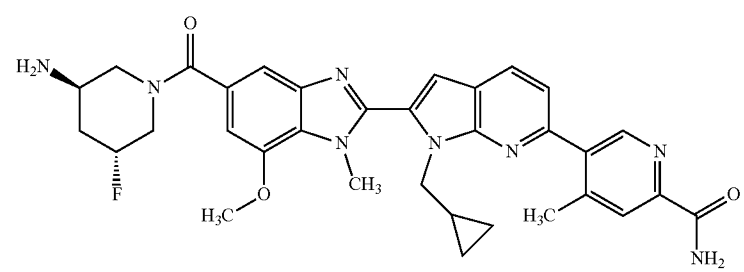 [SMILES: COc1cc(C(=O)N2C[C@H](N)C[C@@H](F)C2)cc2nc(-c3cc4ccc(-c5ccc(C(N)=O)nc5C)nc4n3CC3CC3)n(C)c12] | 5-(2-{5-[(3R,5R)-3-amino-5-fluoropiperidine-1-carbonyl]-7-methoxy-1-methyl-1H-1,3-benzodiazol-2-yl]-1-(cyclopropylmethyl)-1H-pyrrolo[2,3-b]pyridin-6-yl)-4-methylpyridine-2-carboxamide | 611.3 | 1 | 1.4 |

| # | Structure | Name | Obs. MS Ion | HPLC Method ID | RT |
|---|---|---|---|---|---|
| 940. | 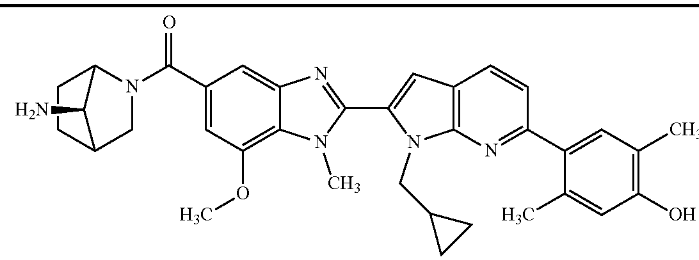 | 4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2,5-dimethylphenol | 591.3 | 1 | 1.75 |
| 941. | 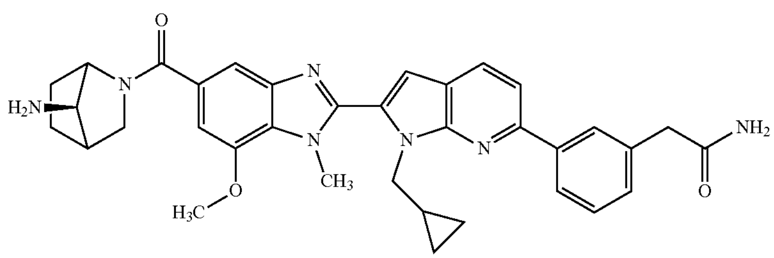 [SMILES: COc1cc(C(=O)N2CC3CCC2[C@@H]3N)cc2nc(-c3cc4ccc(-c5cccc(CC(N)=O)c5)nc4n3CC3CC3)n(C)c12] | 2-[3-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]acetamide | 604.2 | 1 | 1.41 |
| 942. | 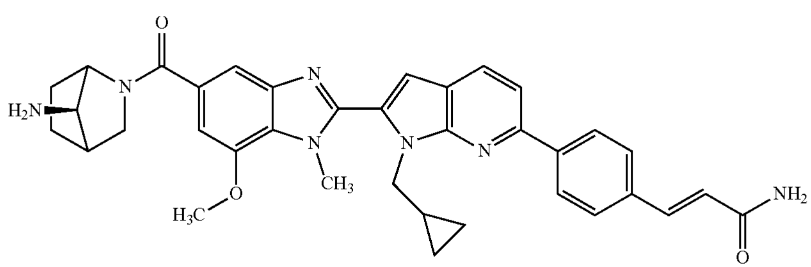 [SMILES: COc1cc(C(=O)N2CC3CCC2[C@@H]3N)cc2nc(-c3cc4ccc(-c5ccc(/C=C/C(N)=O)cc5)nc4n3CC3CC3)n(C)c12] | (2E)-3-[4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]prop-2-enamide | 616.1 | 1 | 1.6 |

| # | Structure | Name | Obs. MS Ion | HPLC Method ID | RT |
|---|---|---|---|---|---|
| 943. | 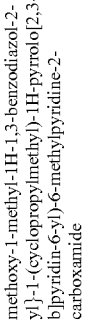 | 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-6-methylpyridine-2-carboxamide | 605.3 | 1 | 1.58 |
| 944. | 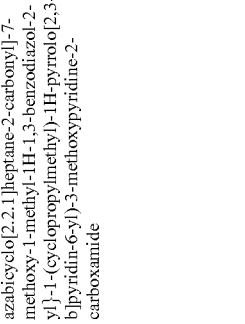 | 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-3-methoxypyridine-2-carboxamide | 621.2 | 1 | 1.51 |
| 945. | 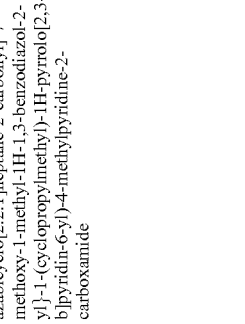 | 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-4-methylpyridine-2-carboxamide | 605.2 | 1 | 1.43 |

| # | Structure | Name | Obs. MS Ion | HPLC Method ID | RT |
|---|---|---|---|---|---|
| 946. | 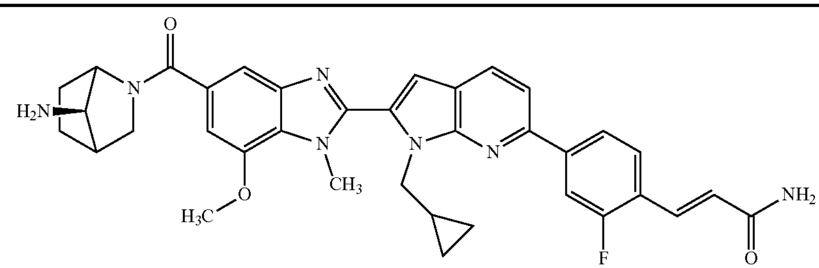 | (2E)-3-[4-(2-{5-[((7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-fluorophenyl]prop-2-enamide | 634 | 1 | 1.69 |
| 947. | 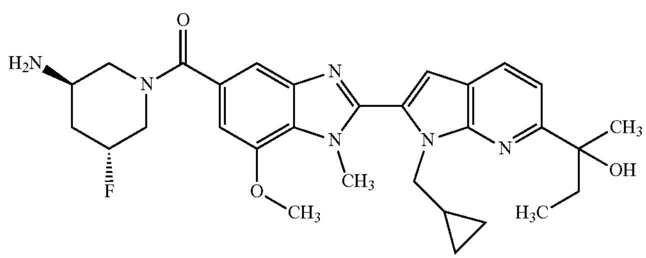 [SMILES: CCC(C)(O)c1ccc2cc(-c3nc4cc(C(=O)N5C[C@H](N)C[C@@H](F)C5)cc(OC)c4n3C)n(CC3CC3)c2n1] | 2-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)butan-2-ol (mixture of diastereomers) | 549 | 2 | 1.55 |
| 948. | 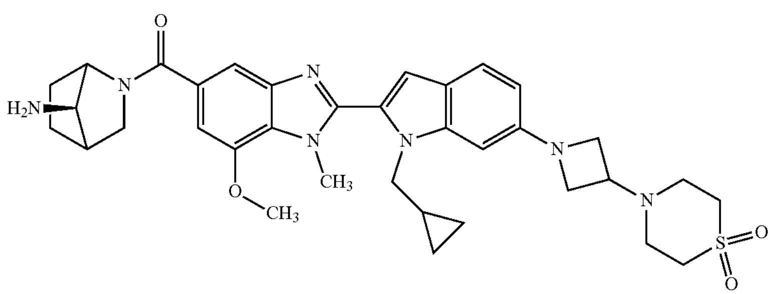 [SMILES: COc1cc(C(=O)N2CC3CCC2[C@@H]3N)cc2nc(-c3cc4ccc(N5CC(N6CCS(=O)(=O)CC6)C5)cc4n3CC3CC3)n(C)c12] | ((7R)-7-amino-2-azabicyclo[2.2.1]heptan-2-yl)(2-(1-(cyclopropylmethyl)-6-(3-(1,1-dioxidothiomorpholino)azetidin-1-yl)-1H-indol-2-yl)-7-methoxy-1-methyl-1H-benzo[d]imidazol-5-yl)methanone | 658.1 | 1 | 1.44 |

| # | Structure | Name | Obs. MS Ion | HPLC Method ID | RT |
|---|---|---|---|---|---|
| 949. | 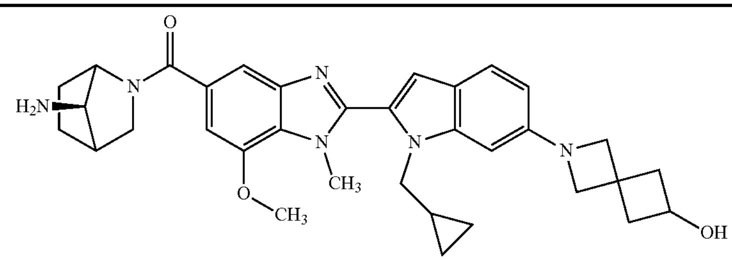 | 2-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-2-azaspiro[3.3]heptan-6-ol | 581.2 | 2 | 1.15 |
| 950. | 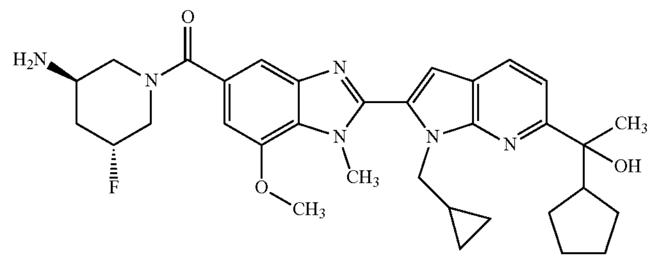 [SMILES: COc1cc(C(=O)N2C[C@H](N)C[C@@H](F)C2)cc2nc(-c3cc4ccc(C(C)(O)C5CCCC5)nc4n3CC3CC3)n(C)c12] | 1-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-1-cyclopentylethan-1-ol (mixture of diastereomers) | 589.4 | 3 | 0.78 |
| 951. | 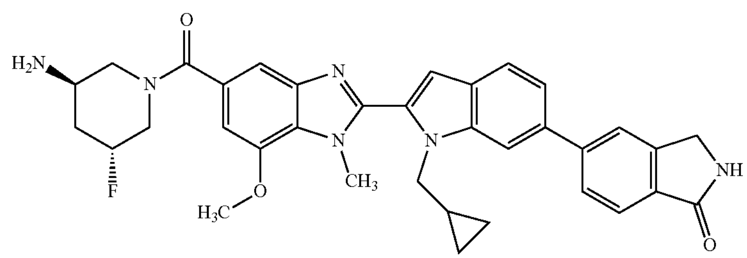 [SMILES: COc1cc(C(=O)N2C[C@H](N)C[C@@H](F)C2)cc2nc(-c3cc4ccc(-c5ccc6c(c5)CNC6=O)cc4n3CC3CC3)n(C)c12] | 5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)-2,3-dihydro-1H-isoindol-1-one | 607.1 | 1 | 1.38 |
| 952. | 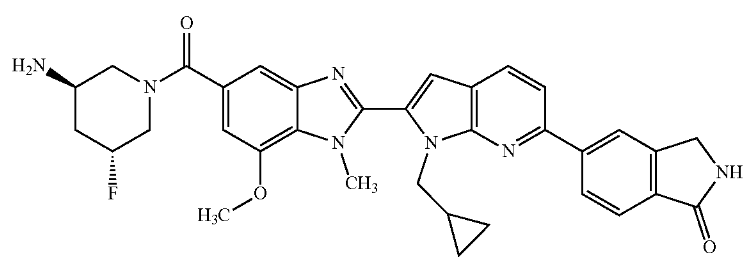 [SMILES: COc1cc(C(=O)N2C[C@H](N)C[C@@H](F)C2)cc2nc(-c3cc4ccc(-c5ccc6c(c5)CNC6=O)nc4n3CC3CC3)n(C)c12] | 5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2,3-dihydro-1H-isoindol-1-one | 608.1 | 1 | 1.56 |

| # | Structure | Name | Obs. MS Ion | HPLC Method ID | RT |
|---|---|---|---|---|---|
| 953. | 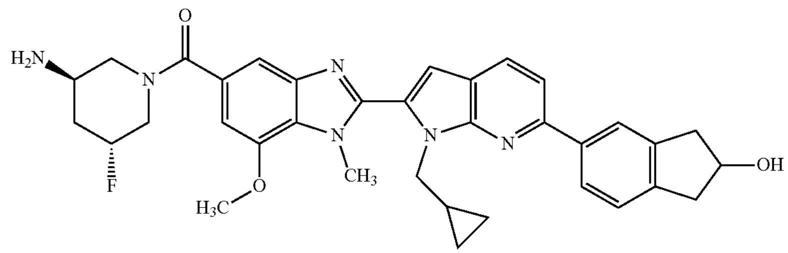 [SMILES: COc1cc(C(=O)N2C[C@H](N)C[C@@H](F)C2)cc2nc(-c3cc4ccc(-c5ccc6c(c5)CC(O)C6)nc4n3CC3CC3)n(C)c12] | 5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2,3-dihydro-1H-inden-2-ol (mixture of diastereomers) | 609.1 | 1 | 1.64 |
| 954. | 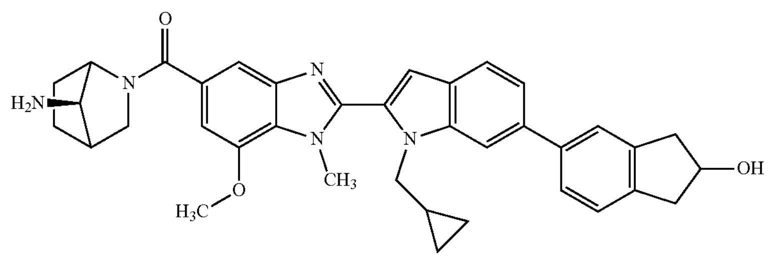 [SMILES: COc1cc(C(=O)N2CC3CCC2[C@@H]3N)cc2nc(-c3cc4ccc(-c5ccc6c(c5)CC(O)C6)cc4n3CC3CC3)n(C)c12] | 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2,3-dihydro-1H-inden-2-ol (mixture of diastereomers) | 603.2 | 2 | 1.59 |
| 955. | 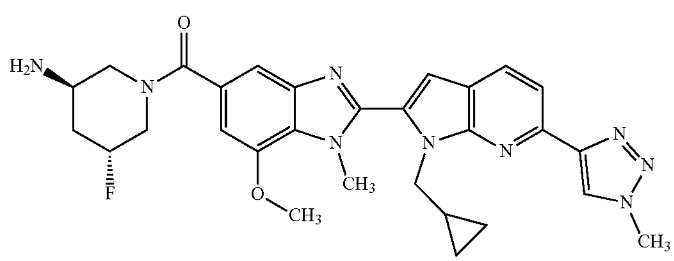 [SMILES: COc1cc(C(=O)N2C[C@H](N)C[C@@H](F)C2)cc2nc(-c3cc4ccc(-c5cn(C)nn5)nc4n3CC3CC3)n(C)c12] | (3R,5R)-1-{2-[1-(cyclopropylmethyl)-6-(1-methyl-1H-1,2,3-triazol-4-yl)-1H-pyrrolo[2,3-b]pyridin-2-yl]-7-methoxy-1-methyl-1H-1,3-benzodiazole-5-carbonyl}-5-fluoropiperidin-3-amine | 558.3 | 1 | 1.45 |

| # | Structure | Name | Obs. MS Ion | HPLC Method ID | RT |
|---|---|---|---|---|---|
| 956. | 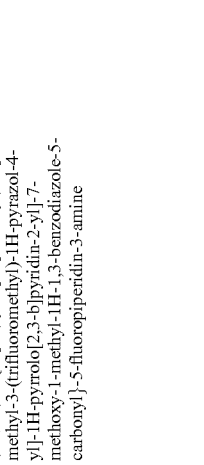 | (3R,5R)-1-{2-[1-(cyclopropylmethyl)-6-[1-methyl-3-(trifluoromethyl)-1H-pyrazol-4-yl]-1H-pyrrolo[2,3-b]pyridin-2-yl]-7-methoxy-1-methyl-1H-1,3-benzodiazole-5-carbonyl}-5-fluoropiperidin-3-amine | 625.3 | 2 | 1.55 |
| 957. | 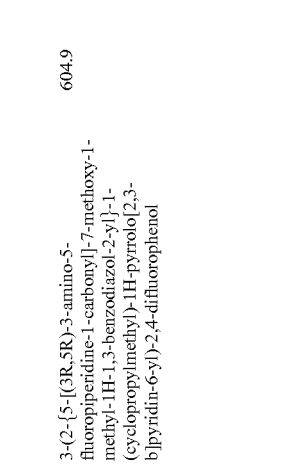 | 3-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2,4-difluorophenol | 604.9 | 1 | 1.57 |
| 958. | 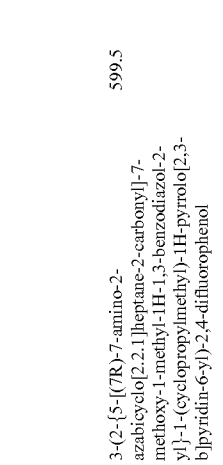 | 3-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2,4-difluorophenol | 599.5 | 1 | 1.54 |

| # | Structure | Name | Obs. MS Ion | HPLC Method ID | RT |
|---|---|---|---|---|---|
| 959. | 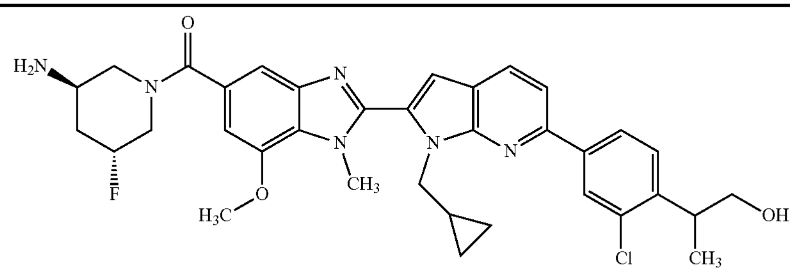 | 2-[4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-chlorophenyl]propan-1-ol (mixture of diastereomers) | 645.5 | 1 | 1.88 |
| 960. | 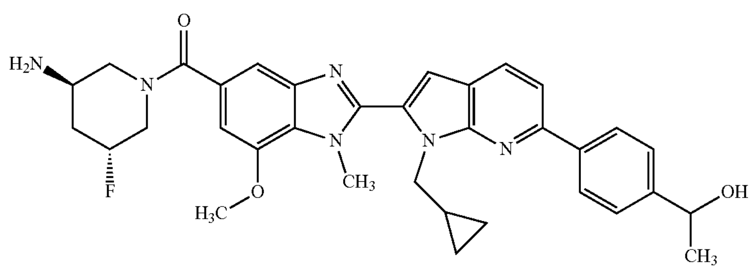 [SMILES: COc1cc(C(=O)N2C[C@H](N)C[C@@H](F)C2)cc2nc(-c3cc4ccc(-c5ccc(C(C)O)cc5)nc4n3CC3CC3)n(C)c12] | 1-[4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)phenyl]ethan-1-ol (mixture of diastereomers) | 597.5 | 2 | 1.46 |
| 961. | 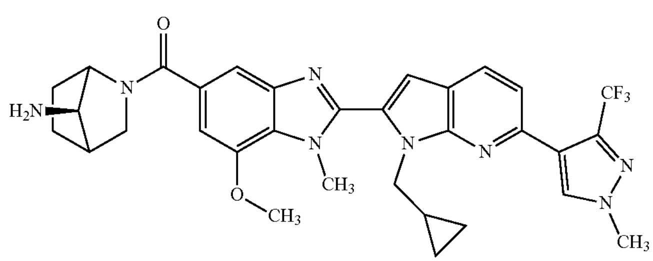 [SMILES: COc1cc(C(=O)N2CC3CCC2[C@@H]3N)cc2nc(-c3cc4ccc(-c5cn(C)nc5C(F)(F)F)nc4n3CC3CC3)n(C)c12] | (7R)-2-{2-[1-(cyclopropylmethyl)-6-[1-methyl-3-(trifluoromethyl)-1H-pyrazol-4-yl]-1H-pyrrolo[2,3-b]pyridin-2-yl]-7-methoxy-1-methyl-1H-1,3-benzodiazole-5-carbonyl}-2-azabicyclo[2.2.1]heptan-7-amine | 618.9 | 2 | 1.67 |

| # | Structure | Name | Obs. MS Ion | HPLC Method ID | RT |
|---|---|---|---|---|---|
| 962. | 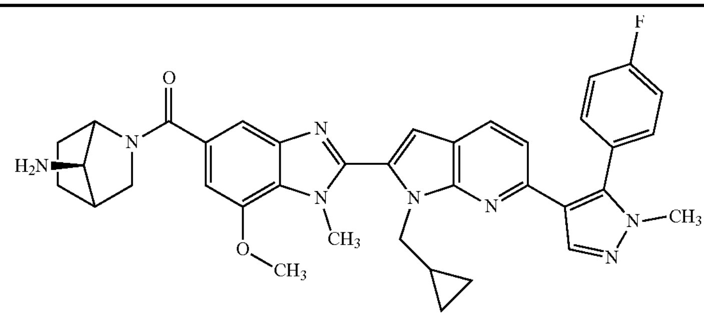 | (7R)-2-{2-[1-(cyclopropylmethyl)-6-[5-(4-fluorophenyl)-1-methyl-1H-pyrazol-4-yl]-1H-pyrrolo[2,3-b]pyridin-2-yl]-7-methoxy-1-methyl-1H-1,3-benzodiazole-5-carbonyl]-2-azabicyclo[2.2.1]heptan-7-amine | 645.3 | 2 | 1.68 |
| 963. | 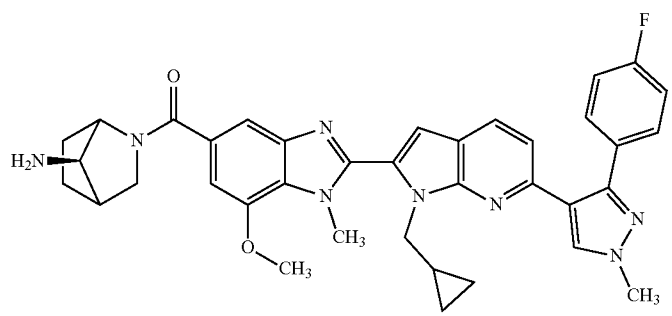 [SMILES: COc1cc(C(=O)N2CC3CCC2[C@@H]3N)cc2nc(-c3cc4ccc(-c5cn(C)nc5-c5ccc(F)cc5)nc4n3CC3CC3)n(C)c12] | (7R)-2-{2-[1-(cyclopropylmethyl)-6-[3-(4-fluorophenyl)-1-methyl-1H-pyrazol-4-yl]-1H-pyrrolo[2,3-b]pyridin-2-yl]-7-methoxy-1-methyl-1H-1,3-benzodiazole-5-carbonyl]-2-azabicyclo[2.2.1]heptan-7-amine | 645 | 1 | 1.8 |
| 964. | 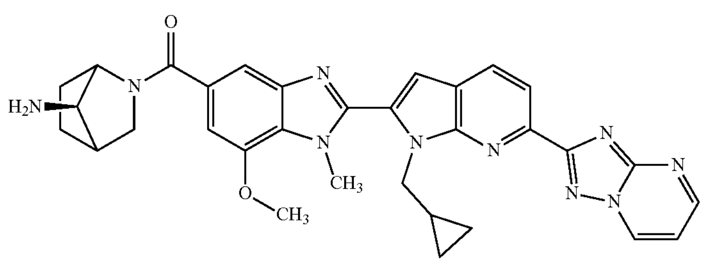 [SMILES: COc1cc(C(=O)N2CC3CCC2[C@@H]3N)cc2nc(-c3cc4ccc(-c5nc6ncccn6n5)nc4n3CC3CC3)n(C)c12] | (7R)-2-{2-1-(cyclopropylmethyl)-6-{[1,2,4]triazolo[1,5-a]pyrimidin-2-yl}-1H-pyrrolo[2,3-b]pyridin-2-yl]-7-methoxy-1-methyl-1H-1,3-benzodiazole-5-carbonyl]-2-azabicyclo[2.2.1]heptan-7-amine | 589.1 | 2 | 1.32 |

-continued

| # | Structure | Name | Obs. MS Ion | HPLC Method ID | RT |
|---|---|---|---|---|---|
| 965. | 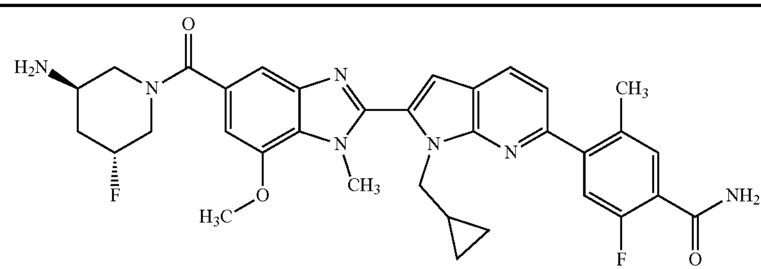 | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-fluoro-5-methylbenzamide | 628.1 | 2 | 1.33 |
| 966. | 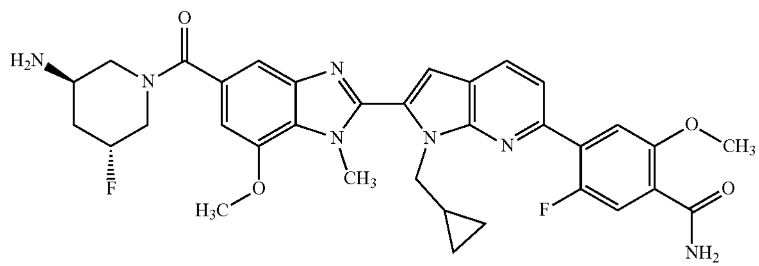 [SMILES: COc1cc(-c2ccc3cc(-c4nc5cc(C(=O)N6C[C@H](N)C[C@@H](F)C6)cc(OC)c5n4C)n(CC4CC4)c3n2)c(F)cc1C(N)=O] | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-5-fluoro-2-methoxybenzamide | 644 | 1 | 1.52 |
| 967. | 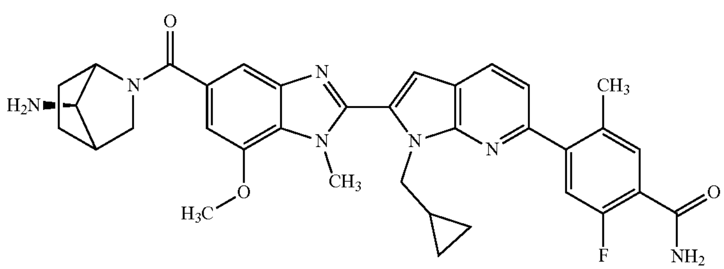 | 4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-fluoro-5-methylbenzamide | 622.1 | 2 | 1.31 |

| # | Structure | Name | Obs. MS Ion | HPLC Method ID | RT |
|---|---|---|---|---|---|
| 968. | 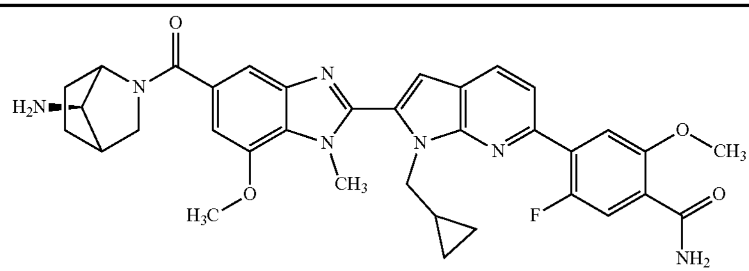 | 4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-5-fluoro-2-methoxybenzamide | 638.2 | 2 | 1.36 |
| 969. | 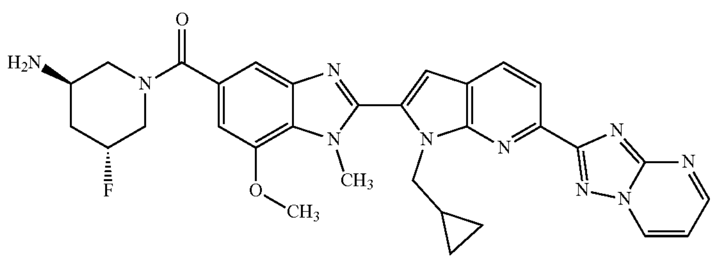 [SMILES: COc1cc(C(=O)N2C[C@H](N)C[C@@H](F)C2)cc2nc(-c3cc4ccc(-c5nc6ncccn6n5)nc4n3CC3CC3)n(C)c12] | (3R,5R)-1-{2-[1-(cyclopropylmethyl)-6-{[1,2,4]triazolo[1,5-a]pyrimidin-2-yl}-1H-pyrrolo[2,3-b]pyridin-2-yl]-7-methoxy-1-methyl-1H-1,3-benzodiazole-5-carbonyl}-5-fluoropiperidin-3-amine | 595.5 | 1 | 1.26 |
| 970. | 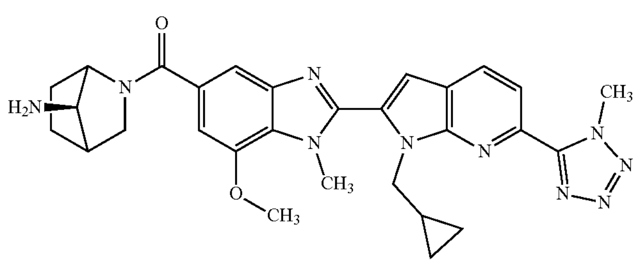 [SMILES: COc1cc(C(=O)N2CC3CCC2[C@@H]3N)cc2nc(-c3cc4ccc(-c5nnnn5C)nc4n3CC3CC3)n(C)c12] | (7R)-2-{2-[1-(cyclopropylmethyl)-6-(1-methyl-1H-1,2,3,4-tetrazol-5-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine | 553.3 | 1 | 1.44 |

| # | Structure | Name | Obs. MS Ion | HPLC Method ID | RT |
|---|---|---|---|---|---|
| 971. | 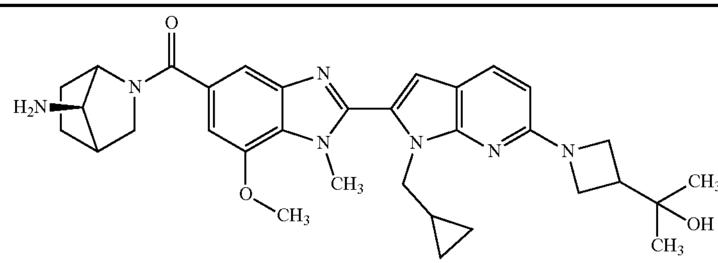 | 2-[1-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl]azetidin-3-yl]propan-2-ol | 584.2 | 1 | 1.75 |
| 972. | 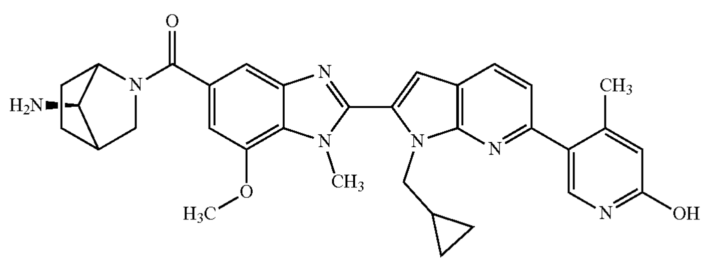 [SMILES: COc1cc(C(=O)N2CC3CCC2[C@@H]3N)cc2nc(-c3cc4ccc(-c5cnc(O)cc5C)nc4n3CC3CC3)n(C)c12] | 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-4-methylpyridine-2-carbonitrile | 587.1 | 1 | 1.89 |
| 973. | 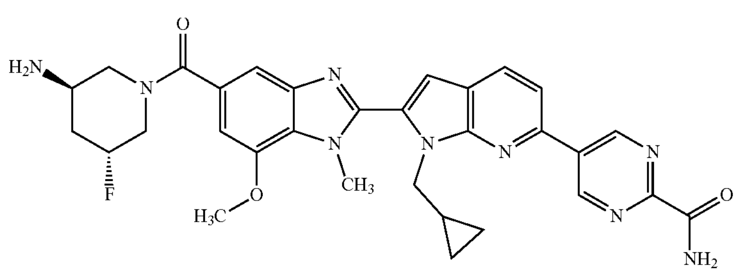 [SMILES: COc1cc(C(=O)N2C[C@H](N)C[C@@H](F)C2)cc2nc(-c3cc4ccc(-c5cnc(C(N)=O)nc5)nc4n3CC3CC3)n(C)c12] | 5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)pyrimidine-2-carboxamide | 598.1 | 2 | 1.09 |

| # | Structure | Name | Obs. MS Ion | HPLC Method ID | RT |
|---|---|---|---|---|---|
| 974. | 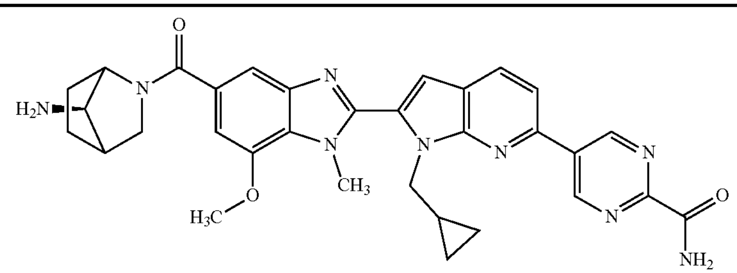 | 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)pyrimidine-2-carboxamide | 592.2 | 1 | 1.22 |
| 975. | 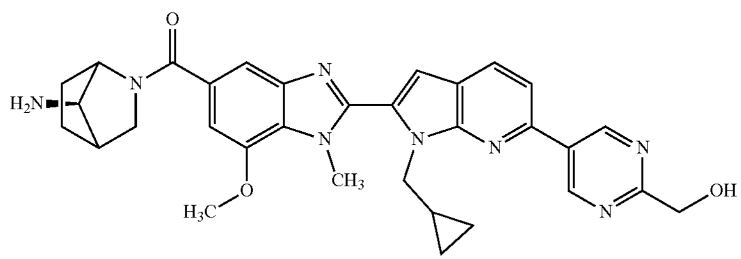 [SMILES: COc1cc(C(=O)N2CC3CCC2[C@@H]3N)cc2nc(-c3cc4ccc(-c5cnc(CO)nc5)nc4n3CC3CC3)n(C)c12] | [5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)pyrimidin-2-yl]methanol | 579.1 | 1 | 1.26 |
| 976. | 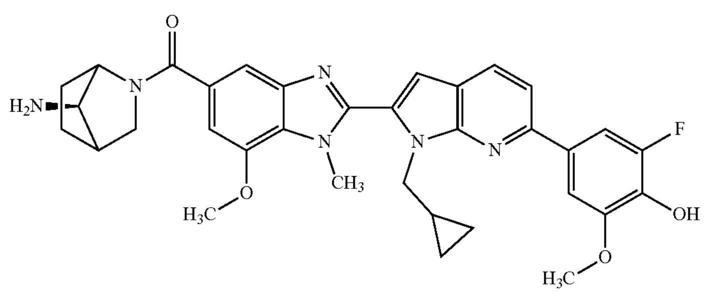 | 4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-fluoro-6-methoxyphenol | 611 | 2 | 1.42 |

| # | Structure | Name | Obs. MS Ion | HPLC Method ID | RT |
|---|---|---|---|---|---|
| 977. | 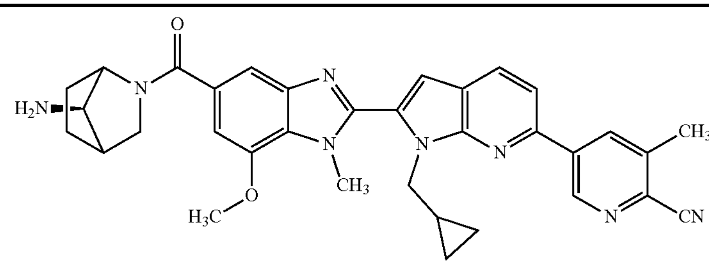 | 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-3-methylpyridine-2-carbonitrile | 587.2 | 1 | 1.65 |
| 978. | 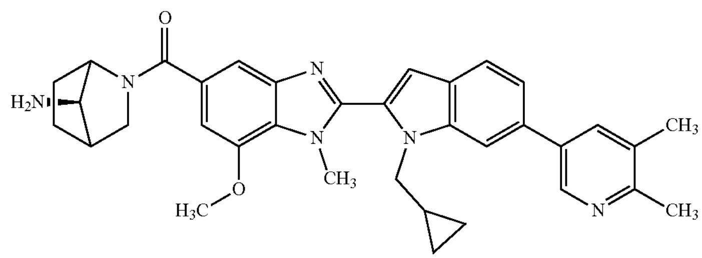 | 2-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-1,1,1-trifluoropropan-2-ol (first isomer off preparative HPLC) | 582.1 | 1 | 1.84 |
| 979. | 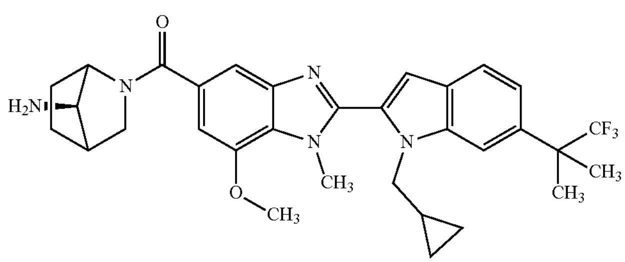 [SMILES: COc1cc(C(=O)N2CC3CCC2[C@@H]3N)cc2nc(-c3cc4ccc(C(C)(C)C(F)(F)F)cc4n3CC3CC3)n(C)c12] | 2-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-1,1,1-trifluoropropan-2-ol (second isomer off preparative HPLC) | 582.3 | 2 | 1.5 |

| # | Structure | Name | Obs. MS Ion | HPLC Method ID | RT |
|---|---|---|---|---|---|
| 980. | 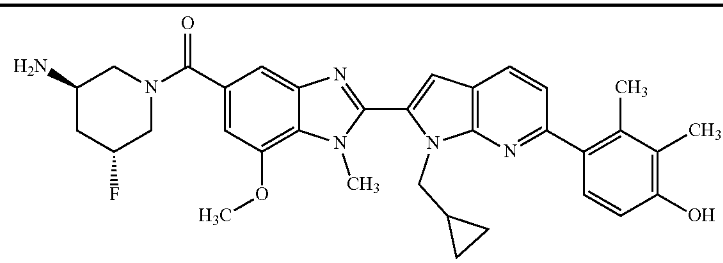 | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2,3-dimethylphenol | 597.2 | 1 | 1.9 |
| 981. | 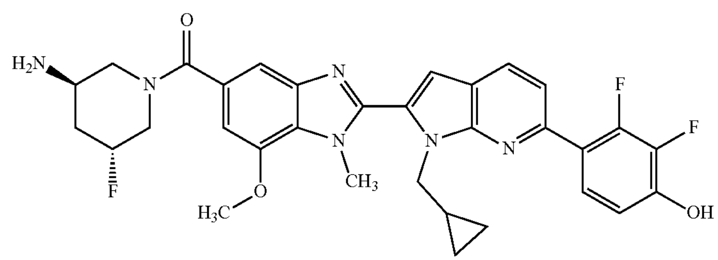 [SMILES: COc1cc(C(=O)N2C[C@H](N)C[C@@H](F)C2)cc2nc(-c3cc4ccc(-c5ccc(O)c(F)c5F)nc4n3CC3CC3)n(C)c12] | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2,3-difluorophenol | 604.9 | 2 | 1.51 |
| 982. | 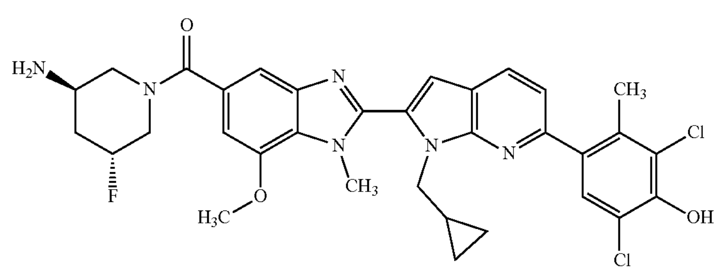 [SMILES: COc1cc(C(=O)N2C[C@H](N)C[C@@H](F)C2)cc2nc(-c3cc4ccc(-c5cc(Cl)c(O)c(Cl)c5C)nc4n3CC3CC3)n(C)c12] | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2,6-dichloro-3-methylphenol | 651.1 | 1 | 1.89 |

| # | Structure | Name | Obs. MS Ion | HPLC Method ID | RT |
|---|---|---|---|---|---|
| 983. | 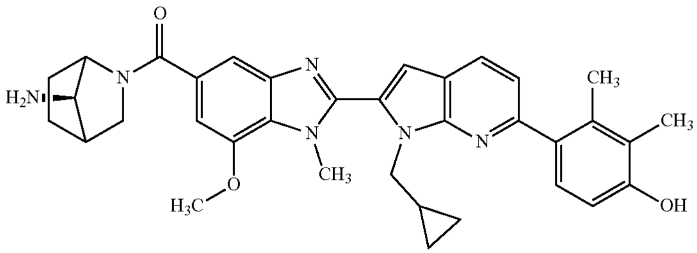 [SMILES: COc1cc(C(=O)N2CC3CCC2[C@@H]3N)cc2nc(-c3cc4ccc(-c5ccc(O)c(C)c5C)nc4n3CC3CC3)n(C)c12] | 4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2,3-dimethylphenol | 591.1 | 2 | 1.58 |
| 984. | 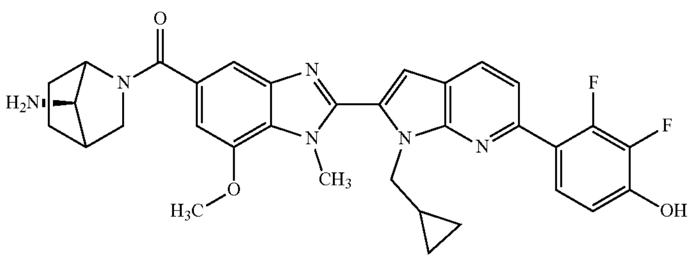 [SMILES: COc1cc(C(=O)N2CC3CCC2[C@@H]3N)cc2nc(-c3cc4ccc(-c5ccc(O)c(F)c5F)nc4n3CC3CC3)n(C)c12] | 4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2,3-difluorophenol | 599.3 | 2 | 1.48 |
| 985. | 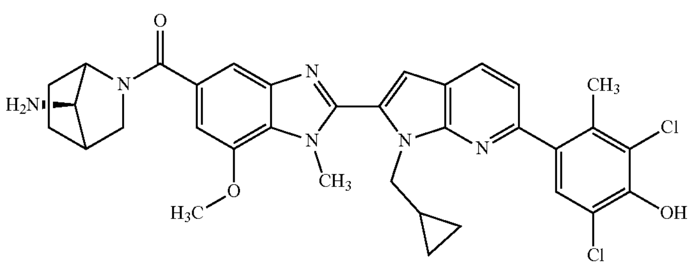 [SMILES: COc1cc(C(=O)N2CC3CCC2[C@@H]3N)cc2nc(-c3cc4ccc(-c5cc(Cl)c(O)c(Cl)c5C)nc4n3CC3CC3)n(C)c12] | 4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2,6-dichloro-3-methylphenol | 645.3 | 1 | 2.07 |

| # | Structure | Name | Obs. MS Ion | HPLC Method ID | RT |
|---|---|---|---|---|---|
| 986. | 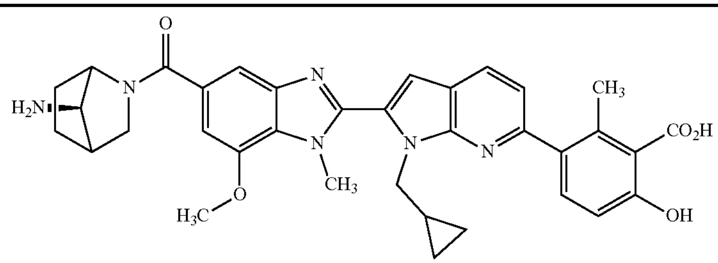 | 3-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-6-hydroxy-2-methylbenzoic acid | 621 | 1 | 1.29 |
| 987. | 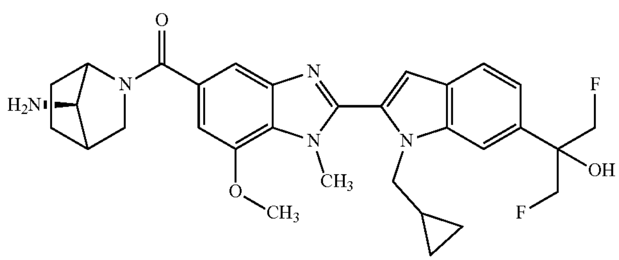 [SMILES: COc1cc(C(=O)N2CC3CCC2[C@@H]3N)cc2nc(-c3cc4ccc(C(O)(CF)CF)cc4n3CC3CC3)n(C)c12] | 2-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-1,3-difluoropropan-2-ol | 564.4 | 1 | 1.68 |
| 988. | 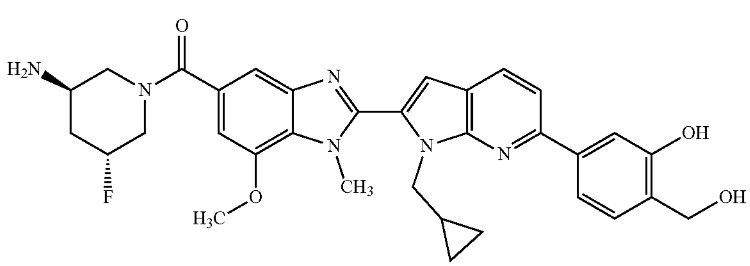 [SMILES: COc1cc(C(=O)N2C[C@H](N)C[C@@H](F)C2)cc2nc(-c3cc4ccc(-c5ccc(CO)c(O)c5)nc4n3CC3CC3)n(C)c12] | 5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-(hydroxymethyl)phenol | 598.9 | 1 | 1.36 |

| # | Structure | Name | Obs. MS Ion | HPLC Method ID | RT |
|---|---|---|---|---|---|
| 989. | 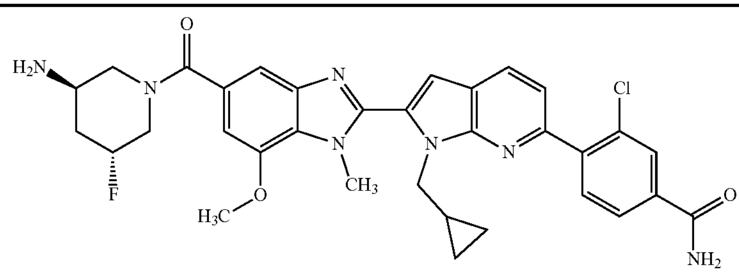 | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-3-chlorobenzamide | 630.3 | 1 | 1.31 |
| 990. | 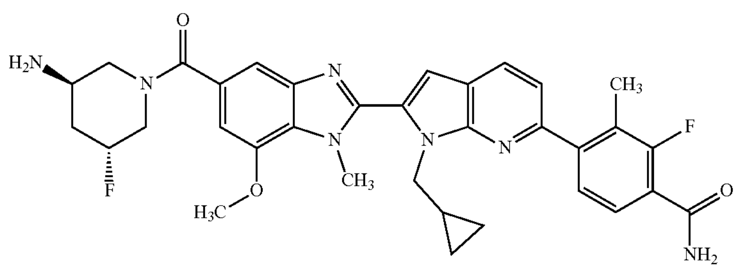 [SMILES: COc1cc(C(=O)N2C[C@H](N)C[C@@H](F)C2)cc2nc(-c3cc4ccc(-c5ccc(C(N)=O)c(F)c5C)nc4n3CC3CC3)n(C)c12] | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-fluoro-3-methylbenzamide | 628 | 1 | 1.32 |
| 991. | 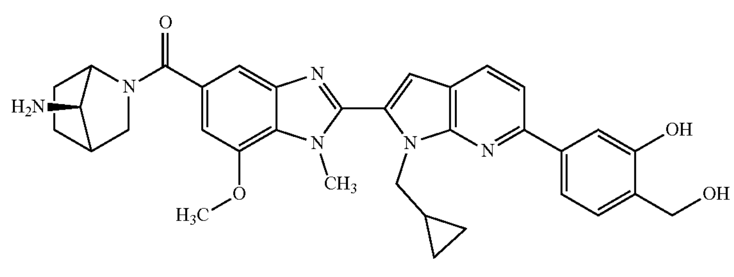 [SMILES: COc1cc(C(=O)N2CC3CCC2[C@@H]3N)cc2nc(-c3cc4ccc(-c5ccc(CO)c(O)c5)nc4n3CC3CC3)n(C)c12] | 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-(hydroxymethyl)phenol | 593.1 | 2 | 1.36 |

| # | Structure | Name | Obs. MS Ion | HPLC Method ID | RT |
|---|---|---|---|---|---|
| 992. | 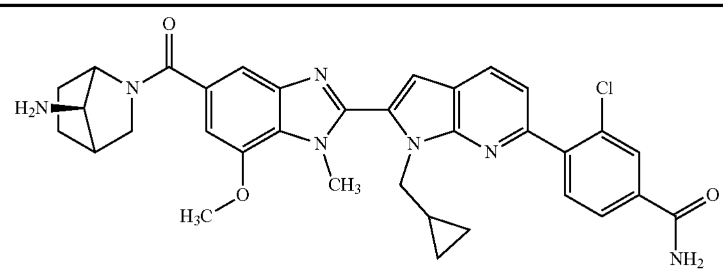 | 4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-3-chlorobenzamide | 624.4 | 1 | 1.29 |
| 993. | 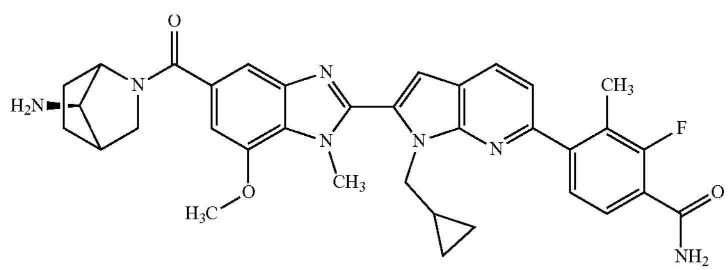 [SMILES: COc1cc(C(=O)N2CC3CCC2[C@@H]3N)cc2nc(-c3cc4ccc(-c5ccc(C(N)=O)c(F)c5C)nc4n3CC3CC3)n(C)c12] | 4-(2-{5-[(7R-(7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-fluoro-3-methylbenzamide | 622.2 | 2 | 1.48 |
| 994. | 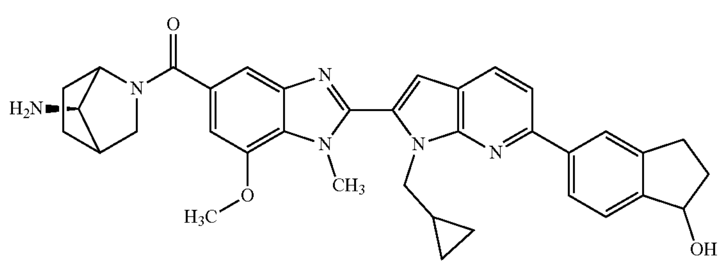 [SMILES: COc1cc(C(=O)N2CC3CCC2[C@@H]3N)cc2nc(-c3cc4ccc(-c5ccc6c(c5)CCC6O)nc4n3CC3CC3)n(C)c12] | 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2,3-dihydro-1H-inden-1-ol (mixture of diastereomers) | 603.2 | 1 | 1.69 |

| # | Structure | Name | Obs. MS Ion | HPLC Method ID | RT |
|---|---|---|---|---|---|
| 995. | 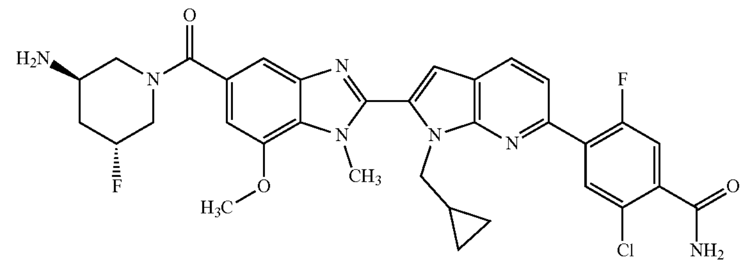 | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-chloro-5-fluorobenzamide | 648.1 | 1 | 1.7 |
| 996. | 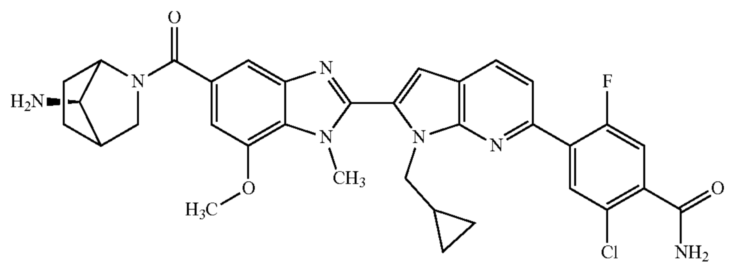 | 4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-chloro-5-fluorobenzamide | 642.2 | 1 | 1.74 |
| 997. | 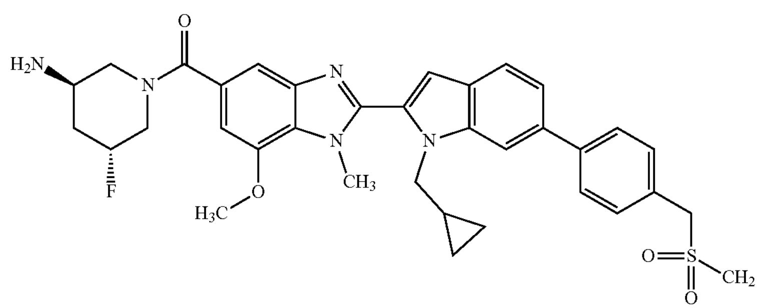 [SMILES: COc1cc(C(=O)N2C[C@H](N)C[C@@H](F)C2)cc2nc(-c3cc4ccc(-c5ccc(CS(C)(=O)=O)cc5)cc4n3CC3CC3)n(C)c12] | (3R,5R)-1-(2-[1-(cyclopropylmethyl)-6-[4-(methanesulfonylmethyl)phenyl]-1H-indol-2-yl]-7-methoxy-1-methyl-1H-1,3-benzodiazole-5-carbonyl)-5-fluoropiperidin-3-amine | 644 | 1 | 1.65 |

| # | Structure | Name | Obs. MS Ion | HPLC Method ID | RT |
|---|---|---|---|---|---|
| 998. | 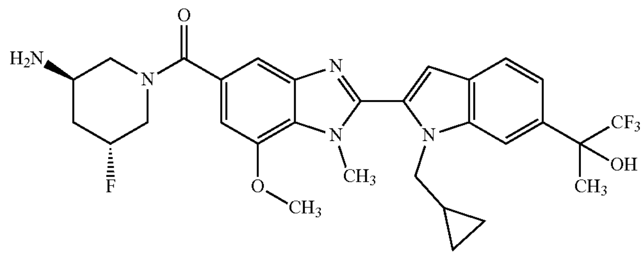 | 2-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)-1,1,1-trifluoropropan-2-ol (mixture of diastereomers) | 588 | 2 | 1.51 |
| 999. | 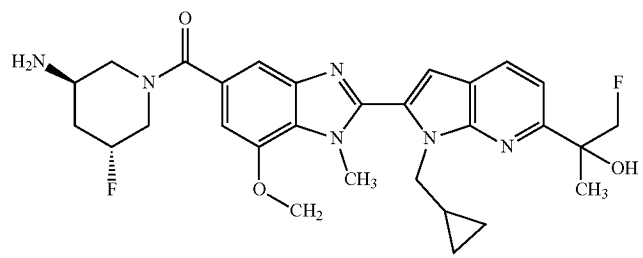 | 2-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-1-fluoropropan-2-ol (mixture of diastereomers) | 553.4 | 1 | 1.56 |
| 1000. | 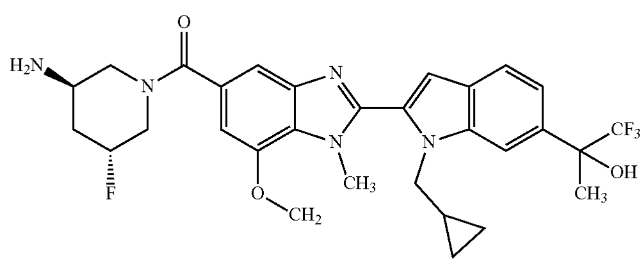 | 2-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)-1,1,1-trifluoropropan-2-ol (first isomer off preparative HPLC) | 588.2 | 1 | 1.71 |

-continued

| # | Structure | Name | Obs. MS Ion | HPLC Method ID | RT |
|---|---|---|---|---|---|
| 1001. | 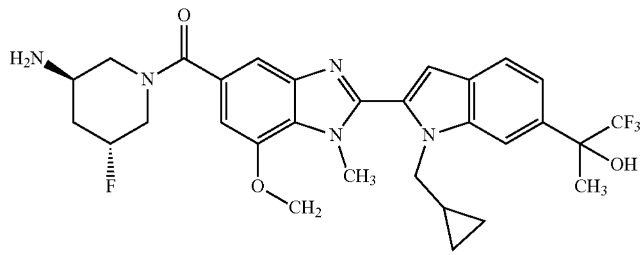 | 2-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)-1,1,1-trifluoropropan-2-ol (second isomer off preparative HPLC) | 588.3 | 2 | 1.51 |
| 1002. | 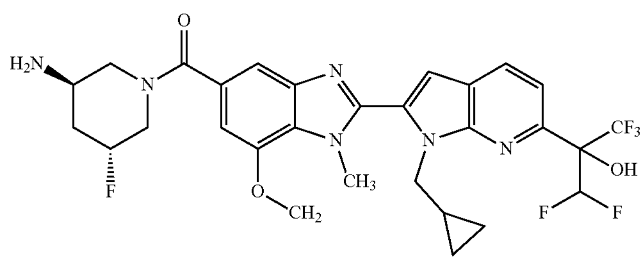 [SMILES: COc1cc(C(=O)N2C[C@H](N)C[C@@H](F)C2)cc2nc(-c3cc4ccc(C(O)(C(F)F)C(F)(F)F)nc4n3CC3CC3)n(C)c12] | 2-(2-{5-[(3R,5R)-3-amino-5-fluoropiperidine-1-carbonyl]-7-methoxy-1-methyl-1H-1,3-benzodiazol-2-yl}-1-(cyclopropylmethyl)pyrrolo[2,3-b]pyridin-6-yl)-1,1-difluoropropan-2-ol (mixture of diastereomers) | 571.3 | 1 | 1.63 |
| 1003. | 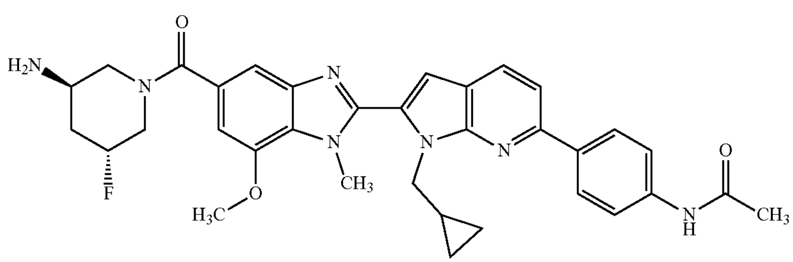 | N-[4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)phenyl]acetamide | 610.2 | 2 | 1.53 |

| # | Structure | Name | Obs. MS Ion | HPLC Method ID | RT |
|---|---|---|---|---|---|
| 1004. | 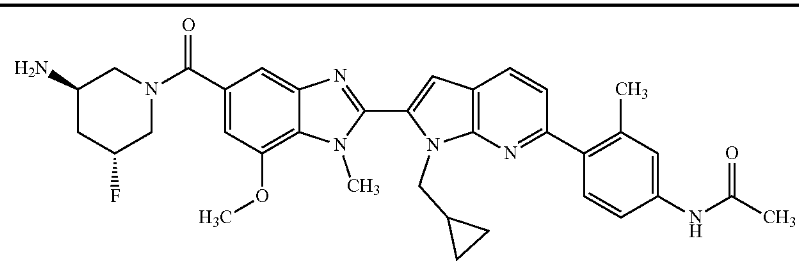 | N-[4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-3-methylphenyl]acetamide | 624.4 | 2 | 1.48 |
| 1005. | 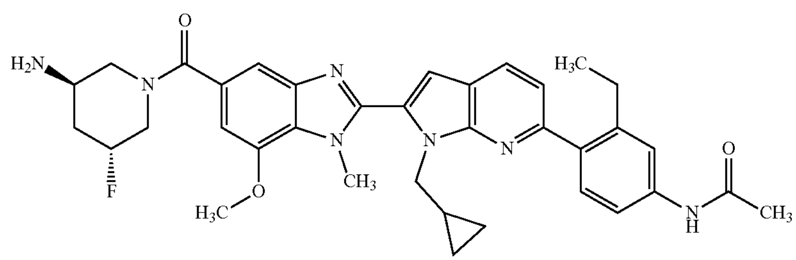 [SMILES: CCc1cc(NC(C)=O)ccc1-c1ccc2cc(-c3nc4cc(C(=O)N5C[C@H](N)C[C@@H](F)C5)cc(OC)c4n3C)n(CC3CC3)c2n1] | N-[4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-3-ethylphenyl]acetamide | 638.2 | 1 | 1.74 |
| 1006. | 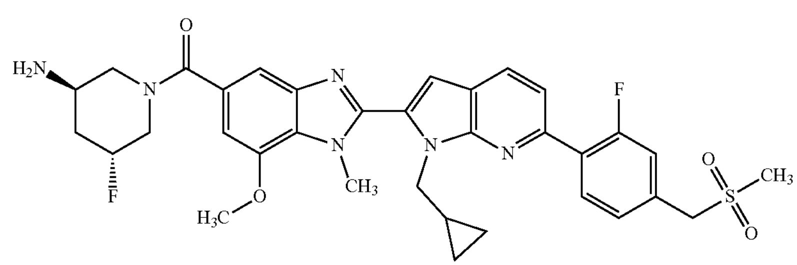 [SMILES: COc1cc(C(=O)N2C[C@H](N)C[C@@H](F)C2)cc2nc(-c3cc4ccc(-c5ccc(CS(C)(=O)=O)cc5F)nc4n3CC3CC3)n(C)c12] | (3R,5R)-1-{2-[1-(cyclopropylmethyl)-6-[2-fluoro-4-(methanesulfonylmethyl)phenyl]-1H-pyrrolo[2,3-b]pyridin-2-yl]-7-methoxy-1-methyl-1H-1,3-benzodiazole-5-carbonyl}-5-fluoropiperidin-3-amine | 663.2 | 1 | 1.66 |

| # | Structure | Name | Obs. MS Ion | HPLC Method ID | RT |
|---|---|---|---|---|---|
| 1007. | 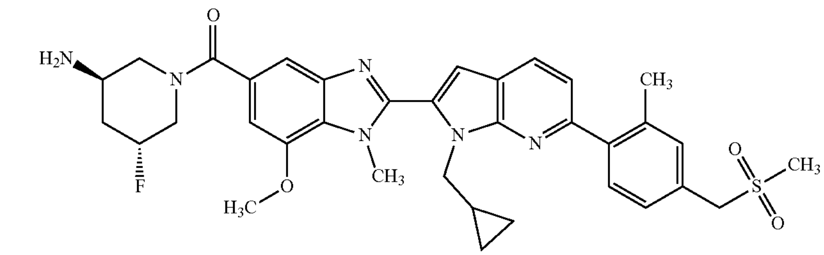 [SMILES: COc1cc(C(=O)N2C[C@H](N)C[C@@H](F)C2)cc2nc(-c3cc4ccc(-c5ccc(CS(C)(=O)=O)cc5C)nc4n3CC3CC3)n(C)c12] | (3R,5R)-1-{2-[1-(cyclopropylmethyl)-6-[4-(methanesulfonylmethyl)-2-methylphenyl]-1H-pyrrolo[2,3-b]pyridin-2-yl]-7-methoxy-1-methyl-1H-1,3-benzodiazole-5-carbonyl}-5-fluoropiperidin-3-amine | 659.1 | 1 | 1.73 |
| 1008. | 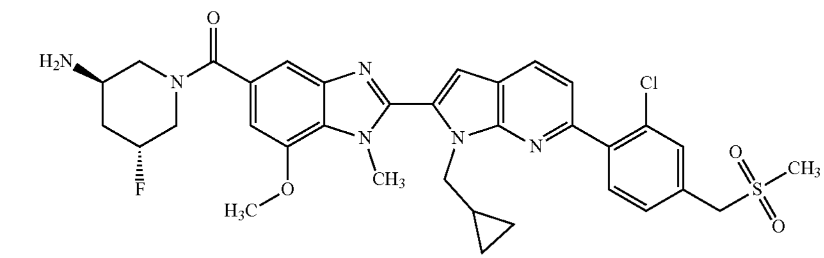 [SMILES: COc1cc(C(=O)N2C[C@H](N)C[C@@H](F)C2)cc2nc(-c3cc4ccc(-c5ccc(CS(C)(=O)=O)cc5Cl)nc4n3CC3CC3)n(C)c12] | (3R,5R)-1-(2-{6-[2-chloro-4-(methanesulfonylmethyl)phenyl]-1-(cyclopropylmethyl)-1H-pyrrolo[2,3-b]pyridin-2-yl}-7-methoxy-1-methyl-1H-1,3-benzodiazole-5-carbonyl)-5-fluoropiperidin-3-amine | 679.1 | 2 | 1.55 |
| 1009. | 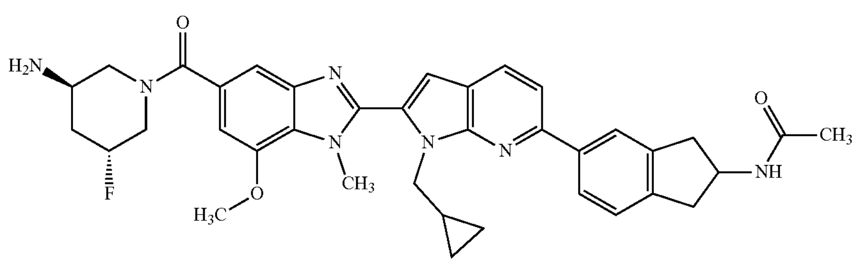 [SMILES: COc1cc(C(=O)N2C[C@H](N)C[C@@H](F)C2)cc2nc(-c3cc4ccc(-c5ccc6c(c5)CC(NC(C)=O)C6)nc4n3CC3CC3)n(C)c12] | N-[5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2,3-dihydro-1H-inden-2-yl]acetamide (mixture of diastereomers) | 650.1 | 2 | 1.5 |

| # | Structure | Name | Obs. MS Ion | HPLC Method ID | RT |
|---|---|---|---|---|---|
| 1010. | 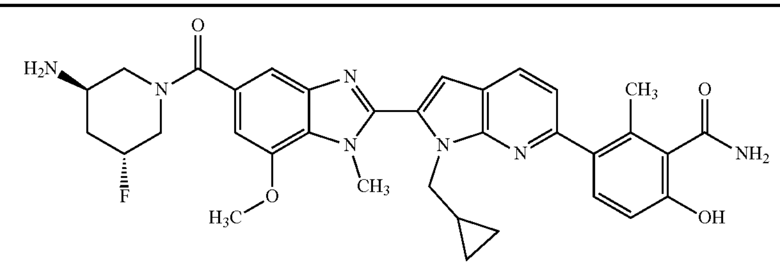 | 3-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-6-hydroxy-2-methylbenzamide | 626.2 | 1 | 1.37 |
| 1011. | 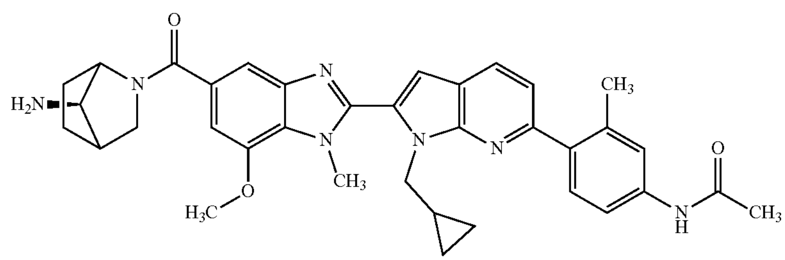 [SMILES: COc1cc(C(=O)N2CC3CCC2[C@@H]3N)cc2nc(-c3cc4ccc(-c5ccc(NC(C)=O)cc5C)nc4n3CC3CC3)n(C)c12] | N-[4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-3-methylphenyl]acetamide | 618.2 | 2 | 1.46 |
| 1012. | 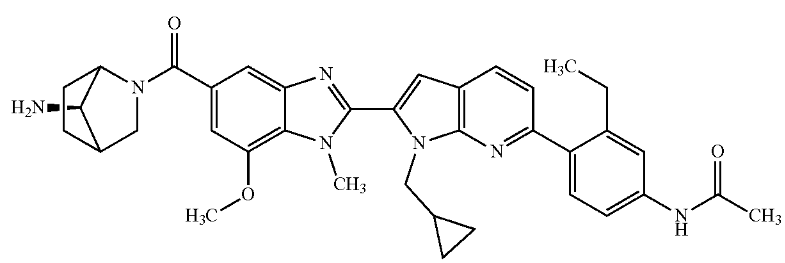 [SMILES: CCc1cc(NC(C)=O)ccc1-c1ccc2cc(-c3nc4cc(C(=O)N5CC6CCC5[C@@H]6N)cc(OC)c4n3C)n(CC3CC3)c2n1] | N-[4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-3-ethylphenyl]acetamide | 632.2 | 1 | 1.75 |

| # | Structure | Name | Obs. MS Ion | HPLC Method ID | RT |
|---|---|---|---|---|---|
| 1013. | 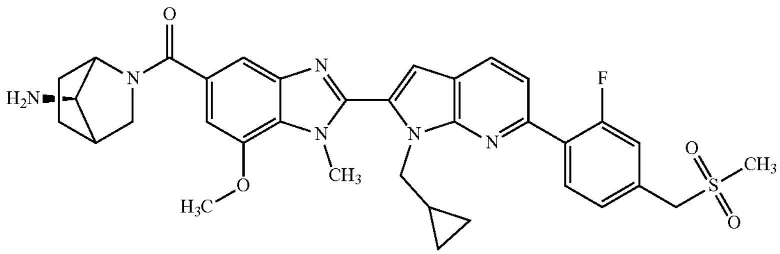 | (7R)-2-{2-[1-(cyclopropylmethyl)-6-[2-fluoro-4-(methanesulfonylmethyl)phenyl]-1H-pyrrolo[2,3-b]pyridin-2-yl]-7-methoxy-1-methyl-1H-1,3-benzodiazole-5-carbonyl}-2-azabicyclo[2.2.1]heptan-7-amine | 657.2 | 1 | 1.63 |
| 1014. | 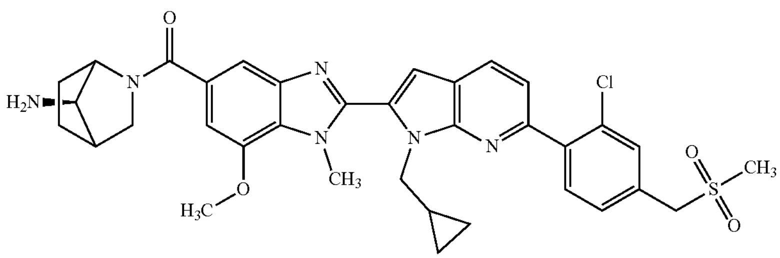 [SMILES: COc1cc(C(=O)N2CC3CCC2[C@@H]3N)cc2nc(-c3cc4ccc(-c5ccc(CS(C)(=O)=O)cc5F)nc4n3CC3CC3)n(C)c12] | (7R)-2-(2-{6-[2-chloro-4-(methanesulfonylmethyl)phenyl]-1-(cyclopropylmethyl)-1H-pyrrolo[2,3-b]pyridin-2-yl}-7-methoxy-1-methyl-1H-1,3-benzodiazole-5-carbonyl)-2-azabicyclo[2.2.1]heptan-7-amine | 673.1 | 1 | 1.65 |
| 1015. | 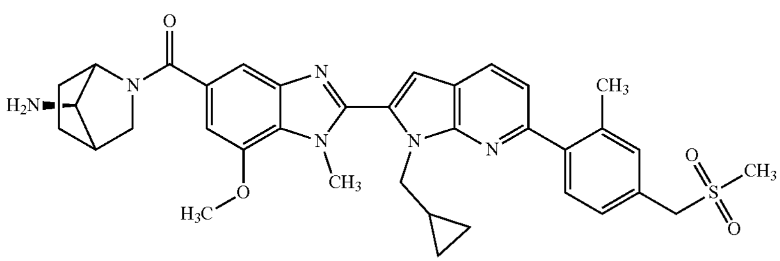 [SMILES: COc1cc(C(=O)N2CC3CCC2[C@@H]3N)cc2nc(-c3cc4ccc(-c5ccc(CS(C)(=O)=O)cc5C)nc4n3CC3CC3)n(C)c12] | (7R)-2-{2-[1-(cyclopropylmethyl)-6-[4-(methanesulfonylmethyl)-2-methylphenyl]-1H-pyrrolo[2,3-b]pyridin-2-yl]-7-methoxy-1-methyl-1H-1,3-benzodiazole-5-carbonyl}-2-azabicyclo[2.2.1]heptan-7-amine | 653.5 | 3 | 0.74 |

| # | Structure | Name | Obs. MS Ion | HPLC Method ID | RT |
|---|---|---|---|---|---|
| 1016. | 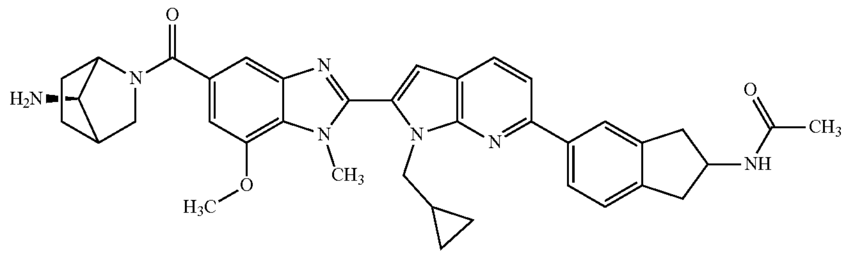 [SMILES: COc1cc(C(=O)N2CC3CCC2[C@@H]3N)cc2nc(-c3cc4ccc(-c5ccc6c(c5)CC(NC(C)=O)C6)nc4n3CC3CC3)n(C)c12] | N-[5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2,3-dihydro-1H-inden-2-yl]acetamide (mixture of diastereomers) | 644 | 2 | 1.49 |
| 1017. | 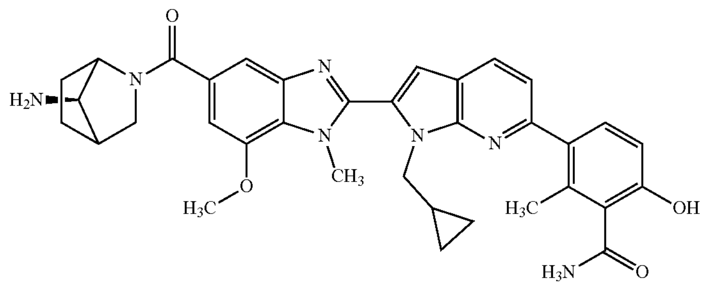 [SMILES: COc1cc(C(=O)N2CC3CCC2[C@@H]3N)cc2nc(-c3cc4ccc(-c5ccc(O)c(C(N)=O)c5C)nc4n3CC3CC3)n(C)c12] | 3-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-6-hydroxy-2-methylbenzamide | 620 | 1 | 1.37 |
| 1018. | 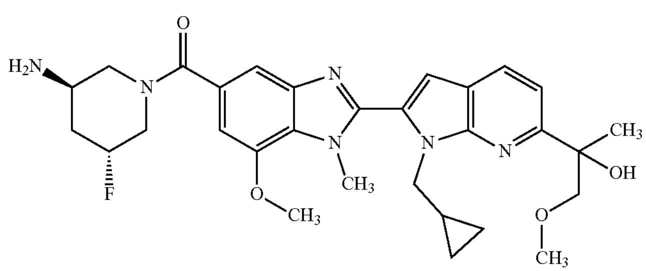 [SMILES: COCC(C)(O)c1ccc2cc(-c3nc4cc(C(=O)N5C[C@H](N)C[C@@H](F)C5)cc(OC)c4n3C)n(CC3CC3)c2n1] | 2-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-1-methoxypropan-2-ol (mixture of diastereomers) | 565 | 2 | 1.39 |

-continued

| # | Structure | Name | Obs. MS Ion | HPLC Method ID | RT |
|---|---|---|---|---|---|
| 1019. | 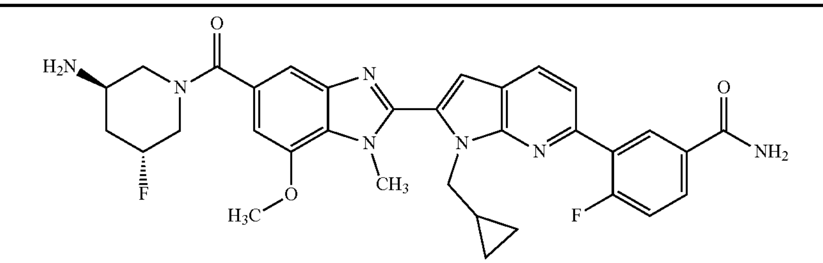 | 3-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-4-fluorobenzamide | 614.4 | 1 | 1.5 |
| 1020. | 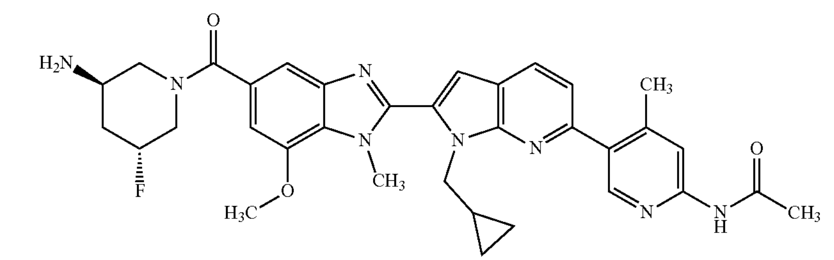 [SMILES: COc1cc(C(=O)N2C[C@H](N)C[C@@H](F)C2)cc2nc(-c3cc4ccc(-c5cnc(NC(C)=O)cc5C)nc4n3CC3CC3)n(C)c12] | N-[5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-4-methylpyridin-2-yl]acetamide | 625.2 | 2 | 1.3 |
| 1021. | 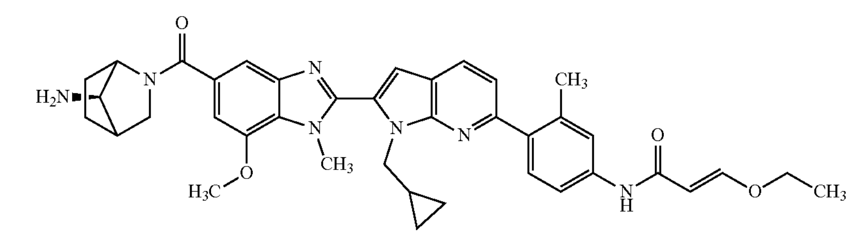 [SMILES: CCO/C=C/C(=O)Nc1ccc(-c2ccc3cc(-c4nc5cc(C(=O)N6CC7CCC6[C@@H]7N)cc(OC)c5n4C)n(CC4CC4)c3n2)c(C)c1] | (2E)-N-[4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-3-methylphenyl]-3-ethoxyprop-2-enamide | 672 | 1 | 1.87 |
| 1022. | 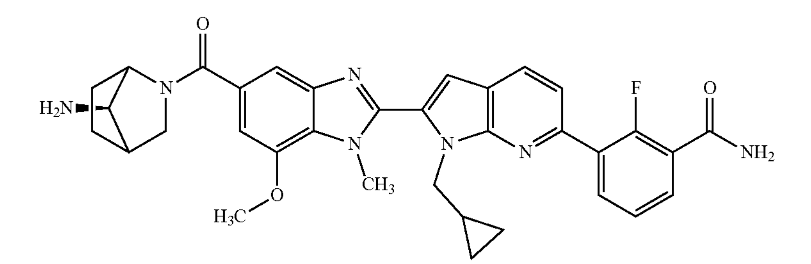 [SMILES: COc1cc(C(=O)N2CC3CCC2[C@@H]3N)cc2nc(-c3cc4ccc(-c5cccc(C(N)=O)c5F)nc4n3CC3CC3)n(C)c12] | 3-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-fluorobenzamide | 608.4 | 1 | 1.4 |

| # | Structure | Name | Obs. MS Ion | HPLC Method ID | RT |
|---|---|---|---|---|---|
| 1023. | 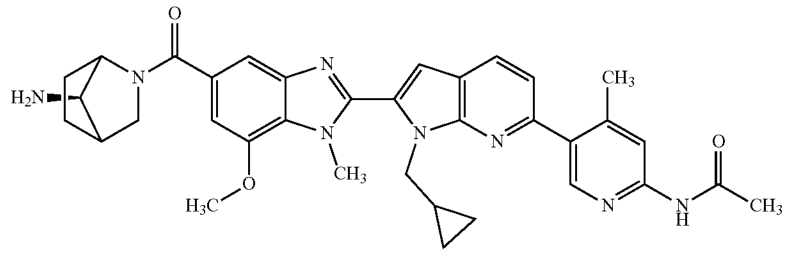 | N-[5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-4-methylpyridin-2-yl]acetamide | 618.9 | 2 | 1.37 |
| 1024. | 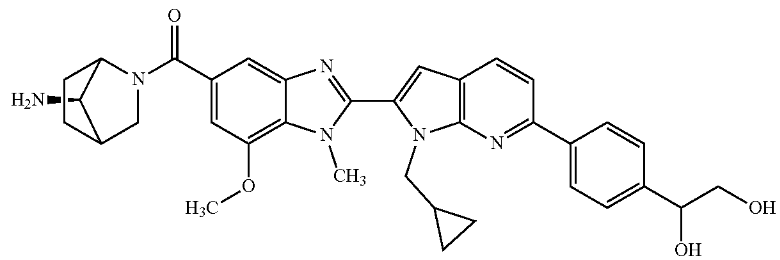 [SMILES: COc1cc(C(=O)N2CC3CCC2[C@@H]3N)cc2nc(-c3cc4ccc(-c5ccc(C(O)CO)cc5)nc4n3CC3CC3)n(C)c12] | 1-[4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]ethane-1,2-diol (mixture of diastereomers) | 607 | 1 | 1.49 |
| 1025. | 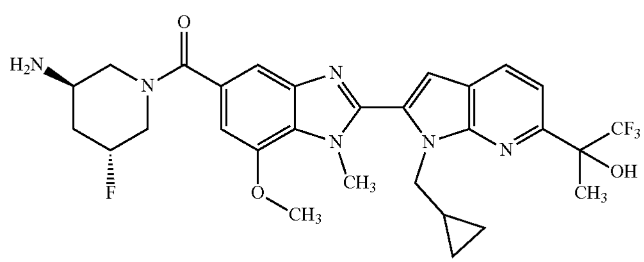 [SMILES: COc1cc(C(=O)N2C[C@H](N)C[C@@H](F)C2)cc2nc(-c3cc4ccc(C(C)(O)C(F)(F)F)nc4n3CC3CC3)n(C)c12] | 2-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-1,1,1-trifluoropropan-2-ol (first isomer off preparative HPLC) | 589.2 | 1 | 1.82 |

| # | Structure | Name | Obs. MS Ion | HPLC Method ID | RT |
|---|---|---|---|---|---|
| 1026. | 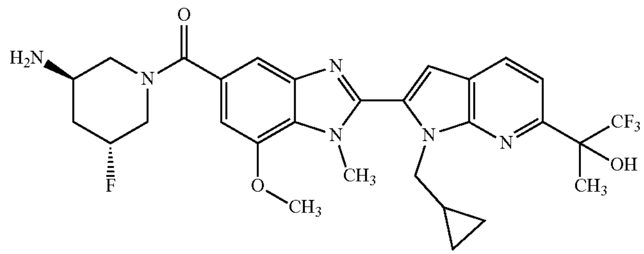 [SMILES: COc1cc(C(=O)N2C[C@H](N)C[C@@H](F)C2)cc2nc(-c3cc4ccc(C(C)(O)C(F)(F)F)nc4n3CC3CC3)n(C)c12] | 2-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-1,1,1-trifluoropropan-2-ol (second isomer off preparative HPLC) | 589.3 | 1 | 1.82 |
| 1027. | 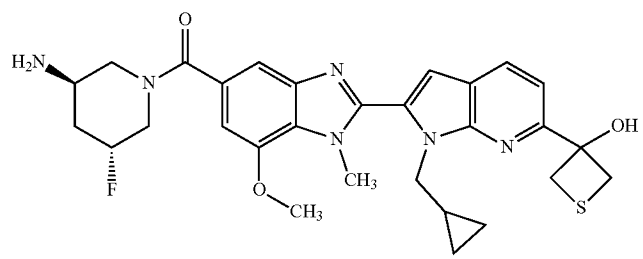 [SMILES: COc1cc(C(=O)N2C[C@H](N)C[C@@H](F)C2)cc2nc(-c3cc4ccc(C5(O)CSC5)nc4n3CC3CC3)n(C)c12] | 3-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)thietan-3-ol | 565.3 | 1 | 1.65 |
| 1028. | 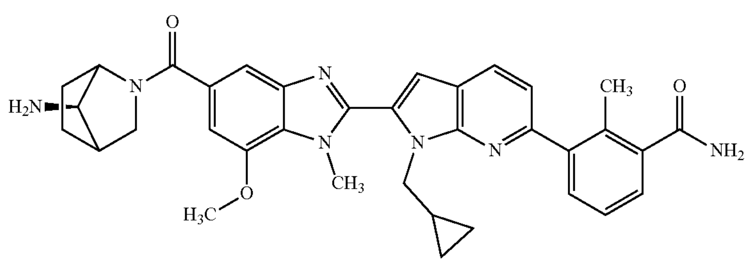 [SMILES: COc1cc(C(=O)N2CC3CCC2[C@@H]3N)cc2nc(-c3cc4ccc(-c5cccc(C(N)=O)c5C)nc4n3CC3CC3)n(C)c12] | 3-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-methylbenzamide | 604.2 | 1 | 1.5 |

| # | Structure | Name | Obs. MS Ion | HPLC Method ID | RT |
|---|---|---|---|---|---|
| 1029. | 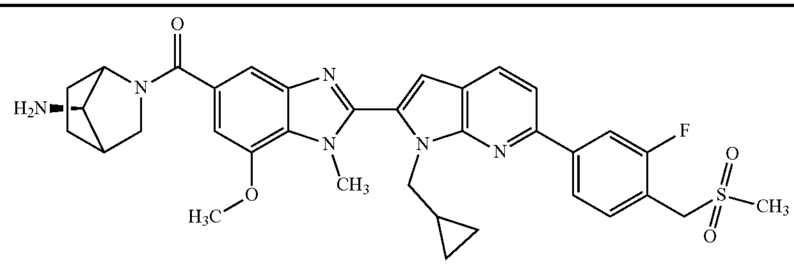 | (7R)-2-{2-[1-(cyclopropylmethyl)-6-[3-fluoro-4-(methanesulfonylmethyl)phenyl]-1H-pyrrolo[2,3-b]pyridin-2-yl]-7-methoxy-1-methyl-1H-1,3-benzodiazole-5-carbonyl}-2-azabicyclo[2.2.1]heptan-7-amine | 656.9 | 1 | 1.7 |
| 1030. | 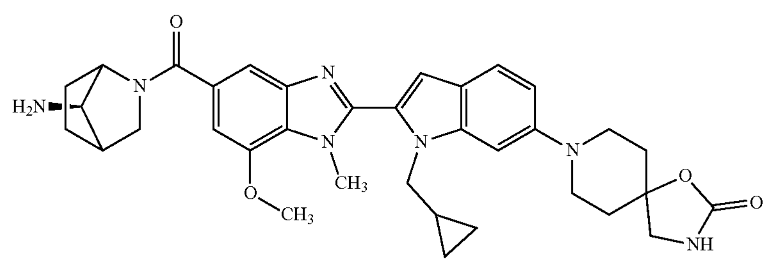 [SMILES: COc1cc(C(=O)N2CC3CCC2[C@@H]3N)cc2nc(-c3cc4ccc(N5CCC6(CC5)CNC(=O)O6)cc4n3CC3CC3)n(C)c12] | 8-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-1-oxa-3,8-diazaspiro[4.5]decan-2-one | 624.2 | 1 | 1.23 |
| 1031. | 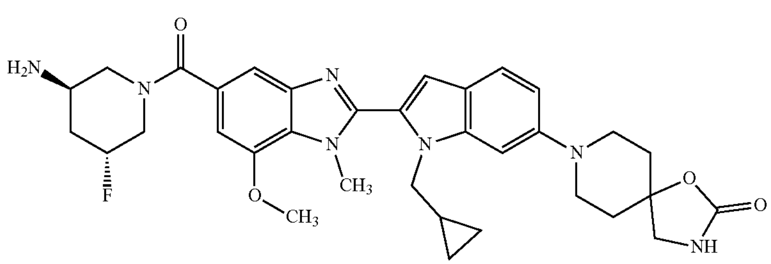 [SMILES: COc1cc(C(=O)N2C[C@H](N)C[C@@H](F)C2)cc2nc(-c3cc4ccc(N5CCC6(CC5)CNC(=O)O6)cc4n3CC3CC3)n(C)c12] | 8-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)-1-oxa-3,8-diazaspiro[4.5]decan-2-one | 630 | 1 | 1.28 |

| # | Structure | Name | Obs. MS Ion | HPLC Method ID | RT |
|---|---|---|---|---|---|
| 1032. | 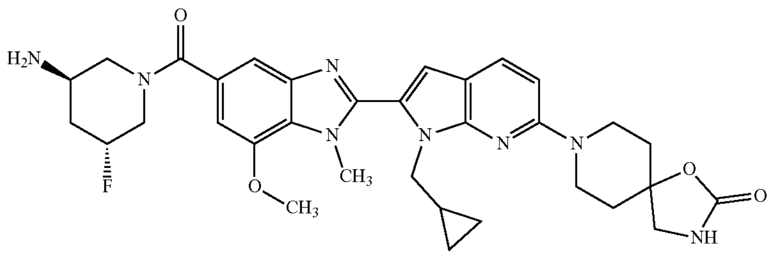 [SMILES: COc1cc(C(=O)N2C[C@H](N)C[C@@H](F)C2)cc2nc(-c3cc4ccc(N5CCC6(CC5)CNC(=O)O6)nc4n3CC3CC3)n(C)c12] | 8-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-1-oxa-3,8-diazaspiro[4.5]decan-2-one | 631.2 | 2 | 1.06 |
| 1033. | 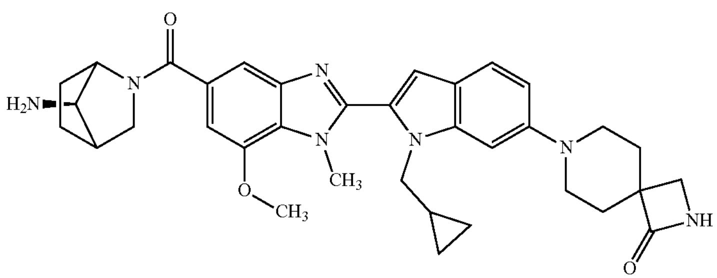 [SMILES: COc1cc(C(=O)N2CC3CCC2[C@@H]3N)cc2nc(-c3cc4ccc(N5CCC6(CC5)CNC6=O)cc4n3CC3CC3)n(C)c12] | 7-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-2,7-diazaspiro[3.5]nonan-1-one | 608 | 1 | 1.28 |
| 1034. | 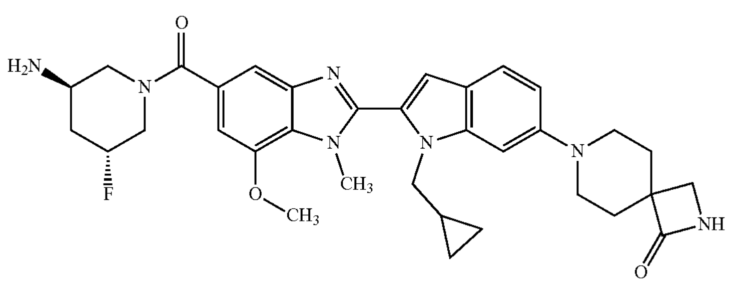 [SMILES: COc1cc(C(=O)N2C[C@H](N)C[C@@H](F)C2)cc2nc(-c3cc4ccc(N5CCC6(CC5)CNC6=O)cc4n3CC3CC3)n(C)c12] | 7-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)-2,7-diazaspiro[3.5]nonan-1-one | 614.2 | 1 | 1.24 |

-continued

| # | Structure | Name | Obs. MS Ion | HPLC Method ID | RT |
|---|---|---|---|---|---|
| 1035. | 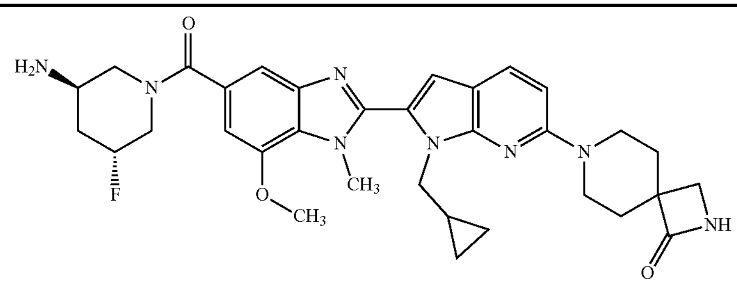 | 7-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2,7-diazaspiro[3.5]nonan-1-one | 615 | 1 | 1.25 |
| 1036. | 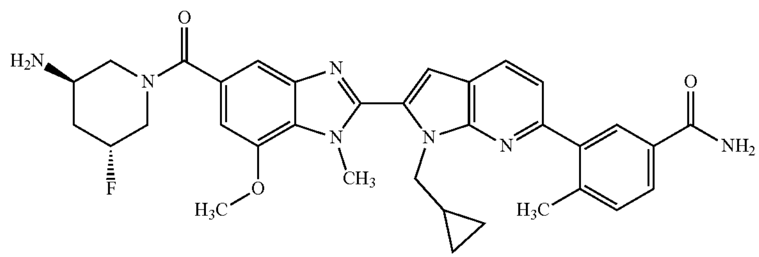 [SMILES: COc1cc(C(=O)N2C[C@H](N)C[C@@H](F)C2)cc2nc(-c3cc4ccc(-c5cc(C(N)=O)ccc5C)nc4n3CC3CC3)n(C)c12] | 3-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-4-methylbenzamide | 306 | 2 | 1.34 |
| 1037. | 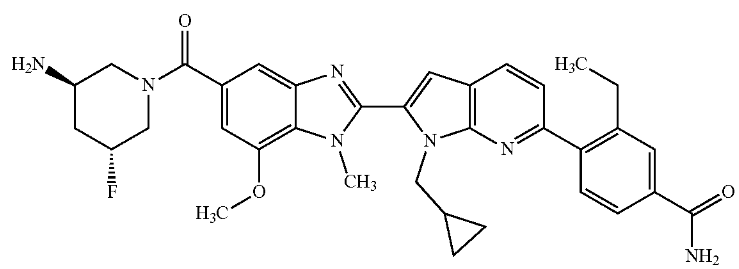 [SMILES: CCc1cc(C(N)=O)ccc1-c1ccc2cc(-c3nc4cc(C(=O)N5C[C@H](N)C[C@@H](F)C5)cc(OC)c4n3C)n(CC3CC3)c2n1] | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-3-ethylbenzamide | 624.2 | 1 | 1.55 |

| # | Structure | Name | Obs. MS Ion | HPLC Method ID | RT |
|---|---|---|---|---|---|
| 1038. | 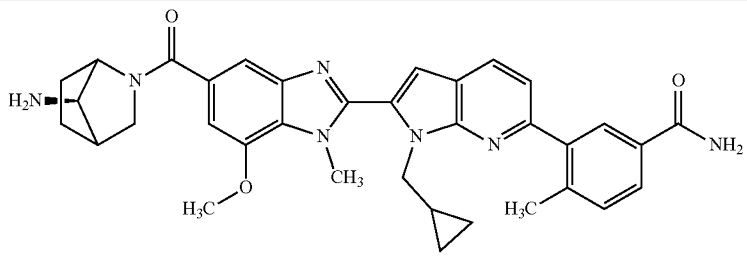 [SMILES: COc1cc(C(=O)N2CC3CCC2[C@@H]3N)cc2nc(-c3cc4ccc(-c5cc(C(N)=O)ccc5C)nc4n3CC3CC3)n(C)c12] | 3-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-4-methylbenzamide | 604.2 | 1 | 1.34 |
| 1039. | 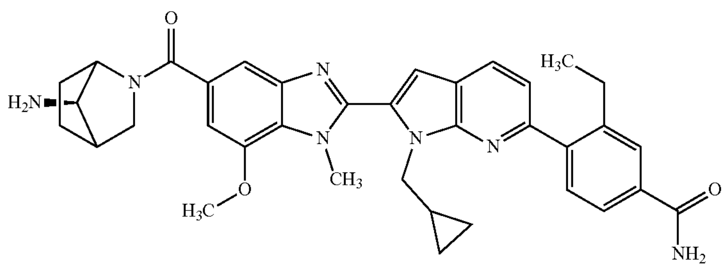 [SMILES: CCc1cc(C(N)=O)ccc1-c1ccc2cc(-c3nc4cc(C(=O)N5CC6CCC5[C@@H]6N)cc(OC)c4n3C)n(CC3CC3)c2n1] | 4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-3-ethylbenzamide | 618.1 | 2 | 1.42 |
| 1040. | 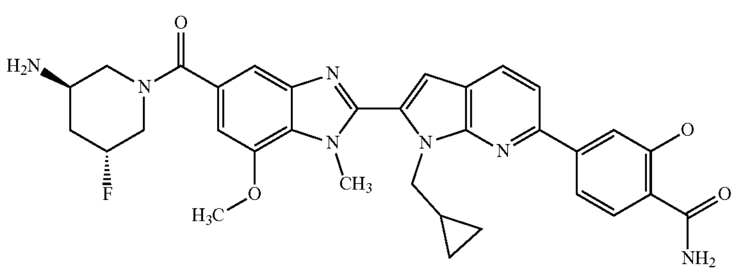 [SMILES: COc1cc(C(=O)N2C[C@H](N)C[C@@H](F)C2)cc2nc(-c3cc4ccc(-c5ccc(C(N)=O)c(O)c5)nc4n3CC3CC3)n(C)c12] | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-chlorobenzamide | 630.2 | 1 | 1.47 |

| # | Structure | Name | Obs. MS Ion | HPLC Method ID | RT |
|---|---|---|---|---|---|
| 1041. | 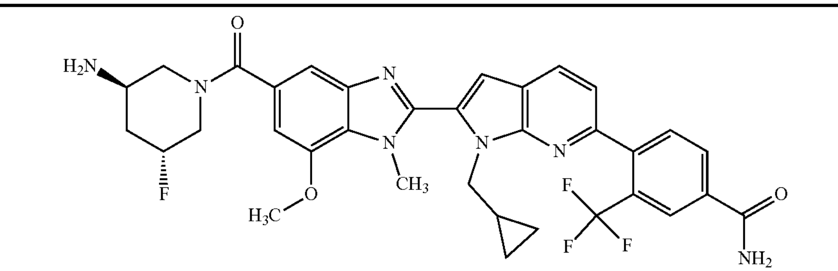 | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-3-(trifluoromethyl)benzamide | 664.4 | 1 | 1.66 |
| 1042. | 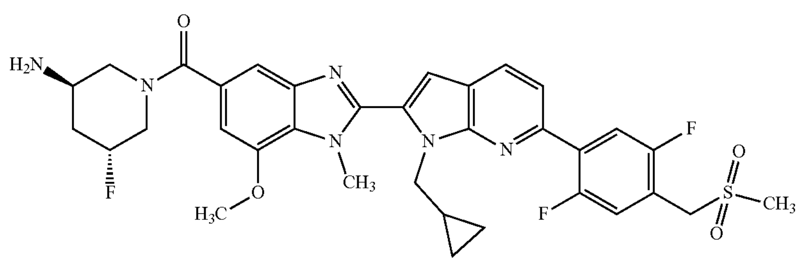 [SMILES: COc1cc(C(=O)N2C[C@H](N)C[C@@H](F)C2)cc2nc(-c3cc4ccc(-c5cc(F)c(CS(C)(=O)=O)cc5F)nc4n3CC3CC3)n(C)c12] | (3R,5R)-1-{2-[1-(cyclopropylmethyl)-6-[2,5-difluoro-4-(methanesulfonylmethyl)phenyl]-1H-pyrrolo[2,3-b]pyridin-2-yl]-7-methoxy-1-methyl-1H-1,3-benzodiazole-5-carbonyl}-5-fluoropiperidin-3-amine | 681.1 | 1 | 1.79 |
| 1043. | 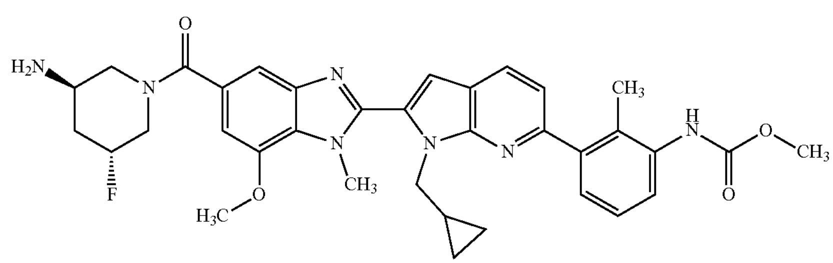 [SMILES: COC(=O)Nc1cccc(-c2ccc3cc(-c4nc5cc(C(=O)N6C[C@H](N)C[C@@H](F)C6)cc(OC)c5n4C)n(CC4CC4)c3n2)c1C] | methyl N-[3-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-methylphenyl]carbamate | 640.3 | 2 | 1.77 |

| # | Structure | Name | Obs. MS Ion | HPLC Method ID | RT |
|---|---|---|---|---|---|
| 1044. | 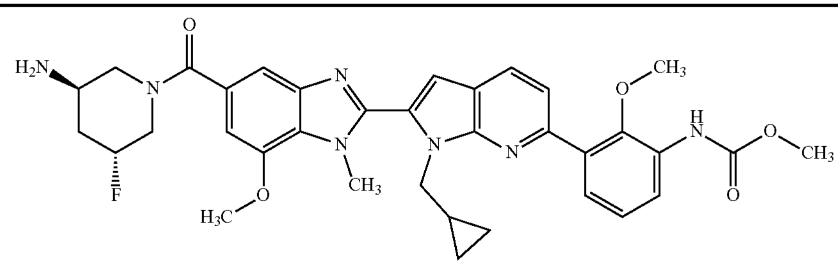 | methyl N-[3-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-2-methoxyphenyl]carbamate | 656.1 | 1 | 1.86 |
| 1045. | 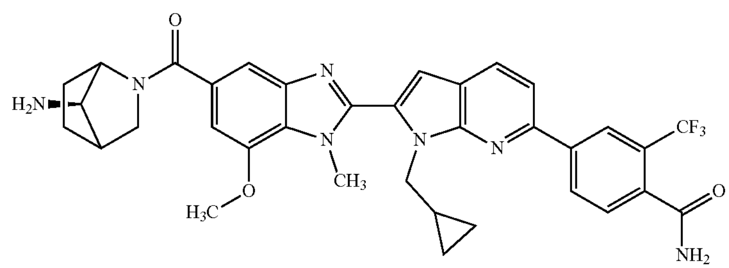 | 4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-(trifluoromethyl)benzamide | 657.9 | 1 | 1.64 |
| 1046. | 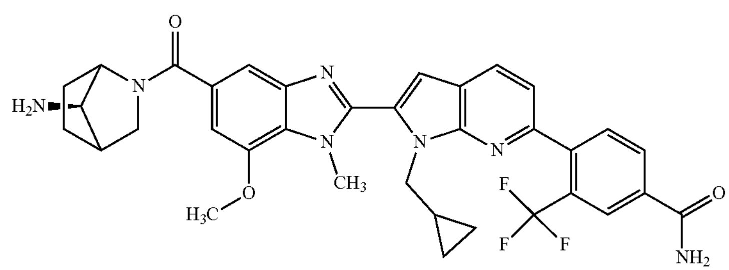 [SMILES: COc1cc(C(=O)N2CC3CCC2[C@@H]3N)cc2nc(-c3cc4ccc(-c5ccc(C(N)=O)cc5C(F)(F)F)nc4n3CC3CC3)n(C)c12] | 4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-3-(trifluoromethyl)benzamide | 658.4 | 1 | 1.61 |

| # | Structure | Name | Obs. MS Ion | HPLC Method ID | RT |
|---|---|---|---|---|---|
| 1047. | 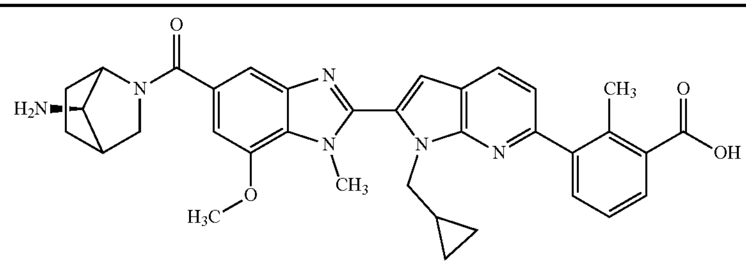 | 3-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-methylbenzoic acid | 605.1 | 1 | 1.32 |
| 1048. | 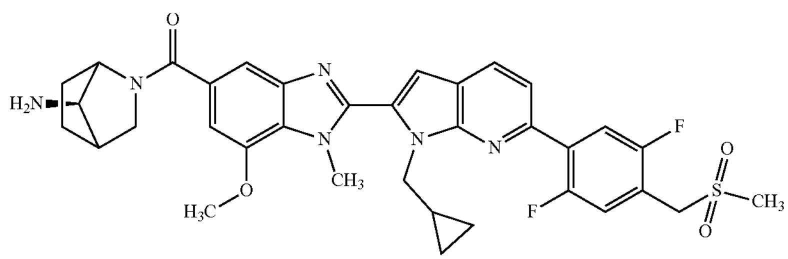 [SMILES: COc1cc(C(=O)N2CC3CCC2[C@@H]3N)cc2nc(-c3cc4ccc(-c5cc(F)c(CS(C)(=O)=O)cc5F)nc4n3CC3CC3)n(C)c12] | (7R)-2-{2-[1-(cyclopropylmethyl)-6-[2,5-difluoro-4-(methanesulfonylmethyl)phenyl]-1H-pyrrolo[2,3-b]pyridin-2-yl]-7-methoxy-1-methyl-1H-1,3-benzodiazole-5-carbonyl}-2-azabicyclo[2.2.1]heptan-7-amine | 675.3 | 2 | 1.53 |
| 1049. | 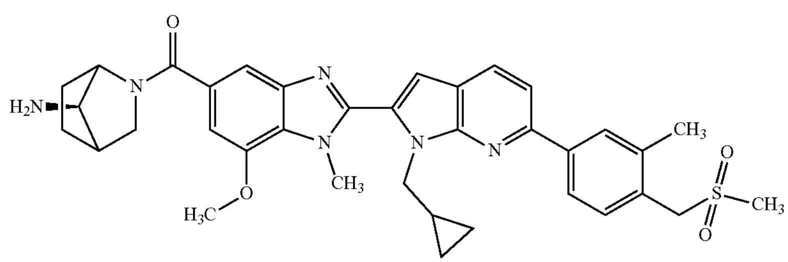 [SMILES: COc1cc(C(=O)N2CC3CCC2[C@@H]3N)cc2nc(-c3cc4ccc(-c5ccc(CS(C)(=O)=O)c(C)c5)nc4n3CC3CC3)n(C)c12] | (7R)-2-{2-[1-(cyclopropylmethyl)-6-[4-(methanesulfonylmethyl)-3-methylphenyl]-1H-pyrrolo[2,3-b]pyridin-2-yl]-7-methoxy-1-methyl-1H-1,3-benzodiazole-5-carbonyl}-2-azabicyclo[2.2.1]heptan-7-amine | 653.1 | 1 | 1.72 |

| # | Structure | Name | Obs. MS Ion | HPLC Method ID | RT |
|---|---|---|---|---|---|
| 1050. | 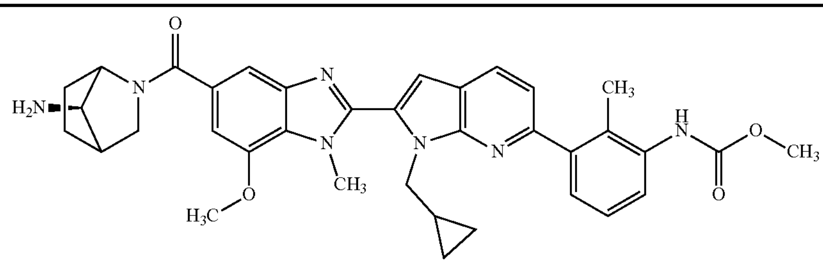 | methyl N-[3-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-methylphenyl]carbamate | 634.2 | 1 | 1.78 |
| 1051. | 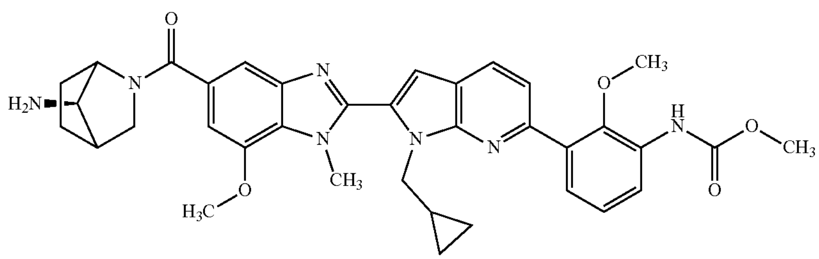 [SMILES: COC(=O)Nc1cccc(-c2ccc3cc(-c4nc5cc(C(=O)N6CC7CCC6[C@@H]7N)cc(OC)c5n4C)n(CC4CC4)c3n2)c1OC] | methyl N-[3-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-methoxyphenyl]carbamate | 650.4 | 2 | 1.65 |
| 1052. | 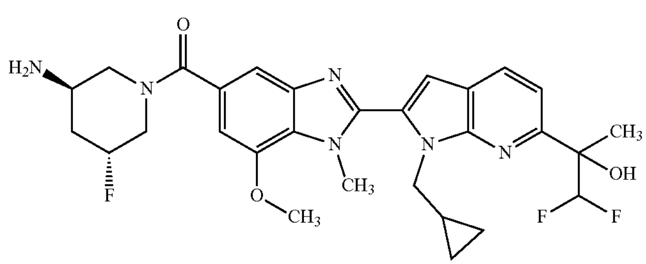 [SMILES: COc1cc(C(=O)N2C[C@H](N)C[C@@H](F)C2)cc2nc(-c3cc4ccc(C(C)(O)C(F)F)nc4n3CC3CC3)n(C)c12] | 2-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-1,1-difluoropropan-2-ol (first isomer off preparative HPLC) | 571.5 | 3 | 0.75 |

| # | Structure | Name | Obs. MS Ion | HPLC Method ID | RT |
|---|---|---|---|---|---|
| 1053. | 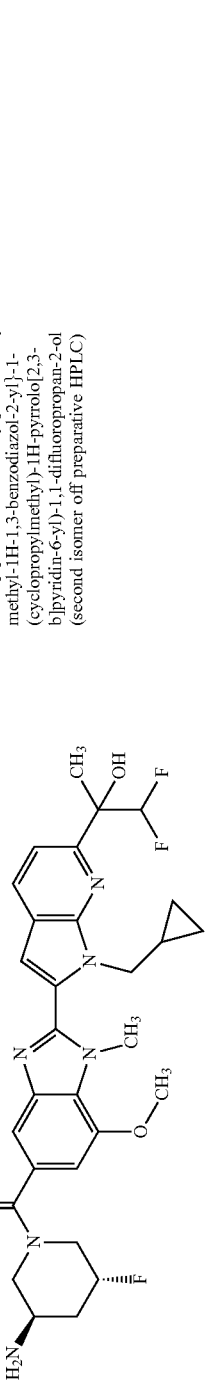 | 2-(2-{5-[((3R,5R)-3-amino-5-fluoropiperidine-1-carbonyl]-7-methoxy-1-methyl-1H-1,3-benzodiazol-2-yl]-1-(cyclopropylmethyl)-1H-pyrrolo[2,3-b]pyridin-6-yl)-1,1-difluoropropan-2-ol (second isomer off preparative HPLC) | 571.5 | 3 | 0.76 |
| 1054. | 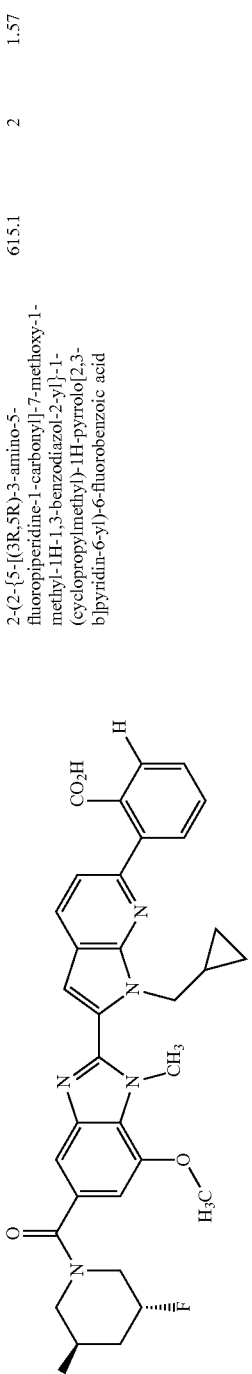 | 2-(2-{5-[((3R,5R)-3-amino-5-fluoropiperidine-1-carbonyl]-7-methoxy-1-methyl-1H-1,3-benzodiazol-2-yl]-1-(cyclopropylmethyl)-1H-pyrrolo[2,3-b]pyridin-6-yl)-6-fluorobenzoic acid | 615.1 | 2 | 1.57 |
| 1055. | 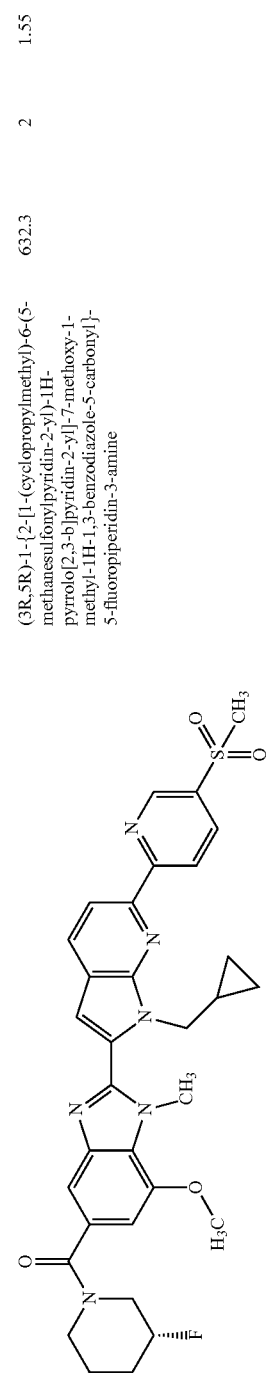 | (3R,5R)-1-{2-[1-(cyclopropylmethyl)-6-(5-methanesulfonylpyridin-2-yl)-1H-pyrrolo[2,3-b]pyridin-2-yl]-7-methoxy-1-methyl-1H-1,3-benzodiazole-5-carbonyl}-5-fluoropiperidin-3-amine | 632.3 | 2 | 1.55 |

| # | Structure | Name | Obs. MS Ion | HPLC Method ID | RT |
|---|---|---|---|---|---|
| 1056. | 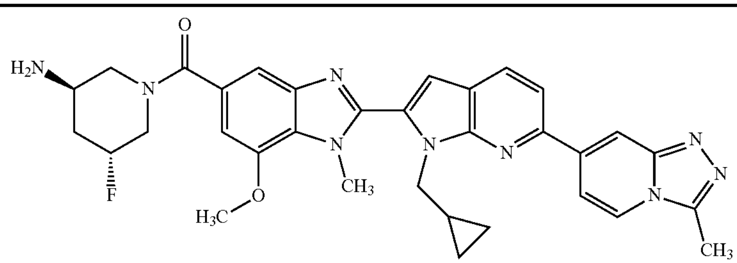 | (3R,5R)-1-{2-[1-(cyclopropylmethyl)-6-{3-methyl-[1,2,4]triazolo[4,3-a]pyridin-7-yl]-1H-pyrrolo[2,3-b]pyridin-2-yl]-7-methoxy-1-methyl-1H-1,3-benzodiazole-5-carbonyl}-5-fluoropiperidin-3-amine | 608.4 | 1 | 1.42 |
| 1057. | 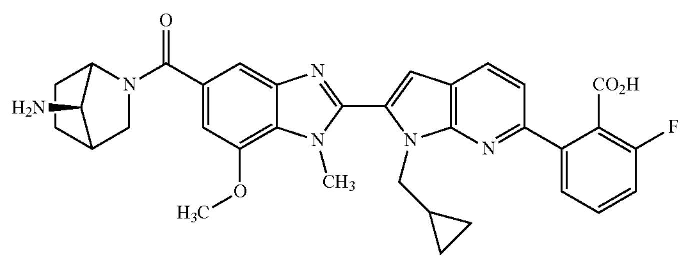 [SMILES: COc1cc(C(=O)N2CC3CCC2[C@@H]3N)cc2nc(-c3cc4ccc(-c5cccc(F)c5C(=O)O)nc4n3CC3CC3)n(C)c12] | 2-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-6-fluorobenzoic acid | 609.4 | 1 | 1.27 |
| 1058. | 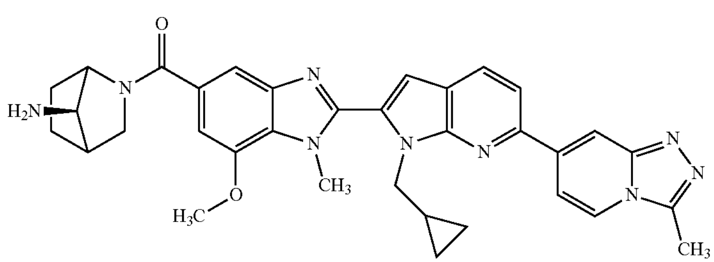 [SMILES: COc1cc(C(=O)N2CC3CCC2[C@@H]3N)cc2nc(-c3cc4ccc(-c5ccn6c(C)nnc6c5)nc4n3CC3CC3)n(C)c12] | (7R)-2-{2-[1-(cyclopropylmethyl)-6-{3-methyl-[1,2,4]triazolo[4,3-a]pyridin-7-yl]-1H-pyrrolo[2,3-b]pyridin-2-yl]-7-methoxy-1-methyl-1H-1,3-benzodiazole-5-carbonyl}-2-azabicyclo[2.2.1]heptan-7-amine | 602.4 | 1 | 1.45 |

| # | Structure | Name | Obs. MS Ion | HPLC Method ID | RT |
|---|---|---|---|---|---|
| 1059. | 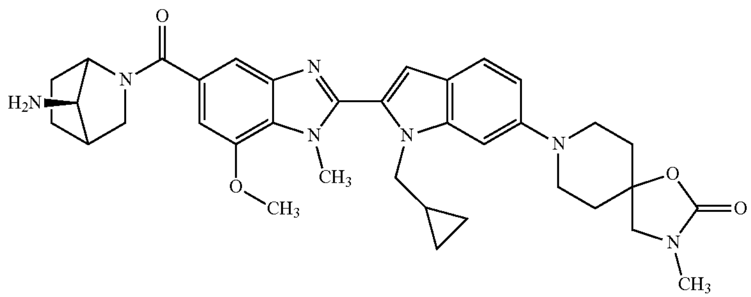 [SMILES: COc1cc(C(=O)N2CC3CCC2[C@@H]3N)cc2nc(-c3cc4ccc(N5CCC6(CC5)CN(C)C(=O)O6)cc4n3CC3CC3)n(C)c12] | 8-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-3-methyl-1-oxa-3,8-diazaspiro[4.5]decan-2-one | 638.2 | 1 | 1.59 |
| 1060. | 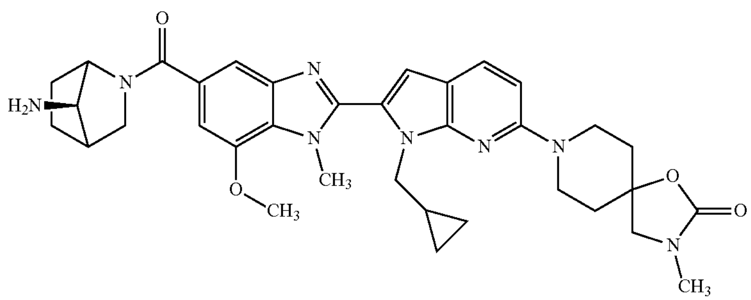 [SMILES: COc1cc(C(=O)N2CC3CCC2[C@@H]3N)cc2nc(-c3cc4ccc(N5CCC6(CC5)CN(C)C(=O)O6)nc4n3CC3CC3)n(C)c12] | 8-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-3-methyl-1-oxa-3,8-diazaspiro[4.5]decan-2-one | 639.2 | 2 | 1.38 |
| 1061. | 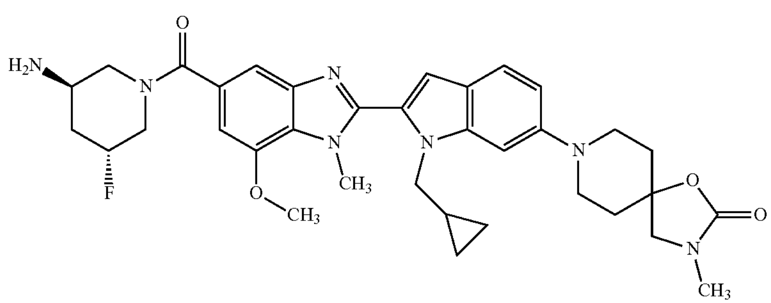 [SMILES: COc1cc(C(=O)N2C[C@H](N)C[C@@H](F)C2)cc2nc(-c3cc4ccc(N5CCC6(CC5)CN(C)C(=O)O6)cc4n3CC3CC3)n(C)c12] | 8-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)-3-methyl-1-oxa-3,8-diazaspiro[4.5]decan-2-one | 644.1 | 1 | 1.56 |

| # | Structure | Name | Obs. MS Ion | HPLC Method ID | RT |
|---|---|---|---|---|---|
| 1062. | 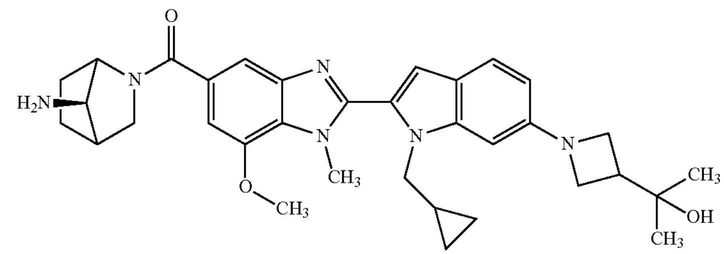 [SMILES: COc1cc(C(=O)N2CC3CCC2[C@@H]3N)cc2nc(-c3cc4ccc(N5CC(C(C)(C)O)C5)cc4n3CC3CC3)n(C)c12] | 2-1-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl]azetidin-3-yl]propan-2-ol | 583.2 | 1 | 1.7 |
| 1063. | 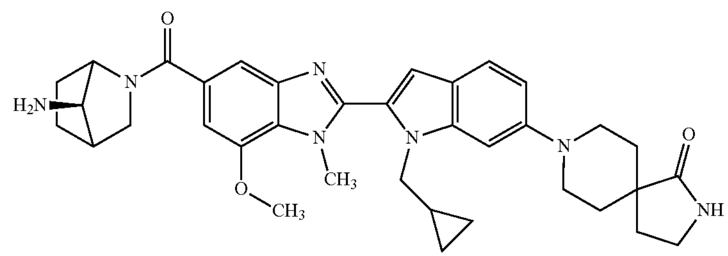 [SMILES: COc1cc(C(=O)N2CC3CCC2[C@@H]3N)cc2nc(-c3cc4ccc(N5CCC6(CCNC6=O)CC5)cc4n3CC3CC3)n(C)c12] | 8-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-2,8-diazaspiro[4.5]decan-1-one | 622.1 | 1 | 1.29 |
| 1064. | 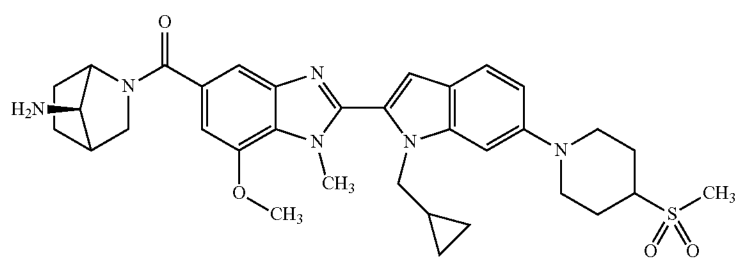 [SMILES: COc1cc(C(=O)N2CC3CCC2[C@@H]3N)cc2nc(-c3cc4ccc(N5CCC(S(C)(=O)=O)CC5)cc4n3CC3CC3)n(C)c12] | (7R)-2-{2-[1-(cyclopropylmethyl)-6-(4-methanesulfonylpiperidin-1-yl)-1H-indol-2-yl]-7-methoxy-1-methyl-1H-1,3-benzodiazole-5-carbonyl}-2-azabicyclo[2.2.1]heptan-7-amine | 631.1 | 1 | 1.52 |

| # | Structure | Name | Obs. MS Ion | HPLC Method ID | RT |
|---|---|---|---|---|---|
| 1065. | 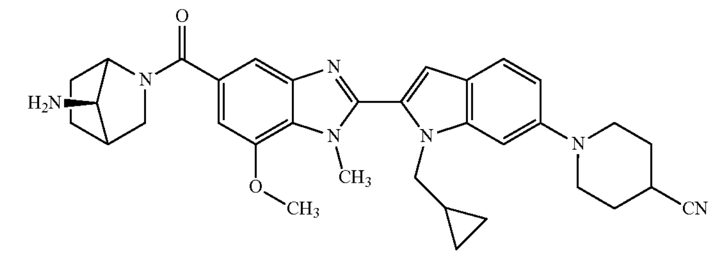 [SMILES: COc1cc(C(=O)N2CC3CCC2[C@@H]3N)cc2nc(-c3cc4ccc(N5CCC(C#N)CC5)cc4n3CC3CC3)n(C)c12] | 1-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)piperidine-4-carbonitrile | 578.2 | 1 | 1.73 |
| 1066. | 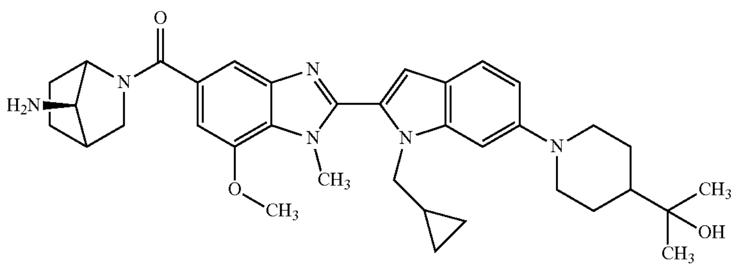 [SMILES: COc1cc(C(=O)N2CC3CCC2[C@@H]3N)cc2nc(-c3cc4ccc(N5CCC(C(C)(C)O)CC5)cc4n3CC3CC3)n(C)c12] | 2-[1-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)piperidin-4-yl]propan-2-ol | 611.2 | 2 | 1.18 |
| 1067. | 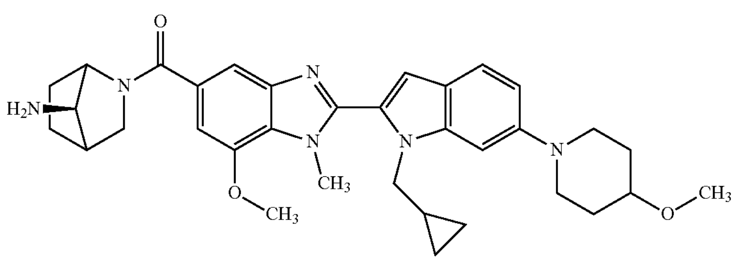 [SMILES: COc1cc(C(=O)N2CC3CCC2[C@@H]3N)cc2nc(-c3cc4ccc(N5CCC(OC)CC5)cc4n3CC3CC3)n(C)c12] | (7R)-2-{2-[1-(cyclopropylmethyl)-6-(4-methoxypiperidin-1-yl)-1H-indol-2-yl]-7-methoxy-1-methyl-1H-1,3-benzodiazole-5-carbonyl}-2-azabicyclo[2.2.1]heptan-7-amine | 583.2 | 1 | 1.8 |

| # | Structure | Name | Obs. MS Ion | HPLC Method ID | RT |
|---|---|---|---|---|---|
| 1068. | 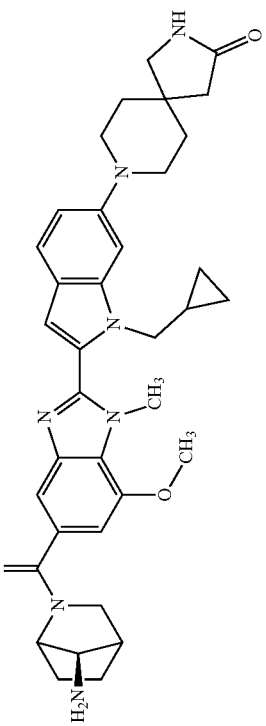 | 8-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-indol-6-yl)-2,8-diazaspiro[4.5]decan-3-one | 622.2 | 1 | 1.21 |
| 1069. | 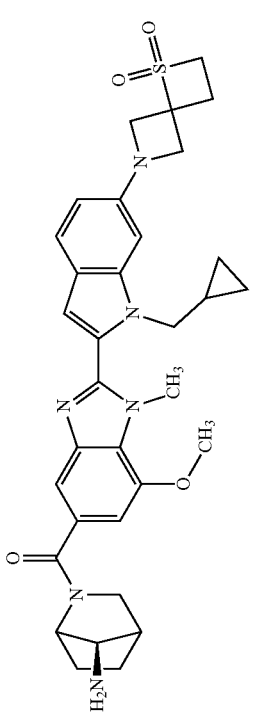 | ((7R)-7-amino-2-azabicyclo[2.2.1]heptan-2-yl)(2-(1-(cyclopropylmethyl)-6-(1,1-dioxido-1-thia-6-azaspiro[3.3]heptan-6-yl)-1H-indol-2-yl)-7-methoxy-1-methyl-1H-benzo[d]imidazol-5-yl)methanone | 615.3 | 1 | 1.59 |
| 1070. | 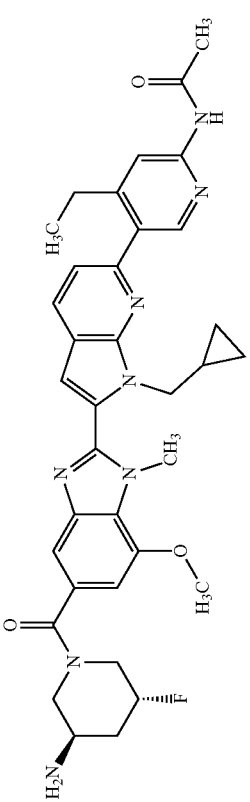 | N-[5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-4-ethylpyridin-2-yl]acetamide | 639.3 | 1 | 1.7 |

| # | Structure | Name | Obs. MS Ion | HPLC Method ID | RT |
|---|---|---|---|---|---|
| 1071. | 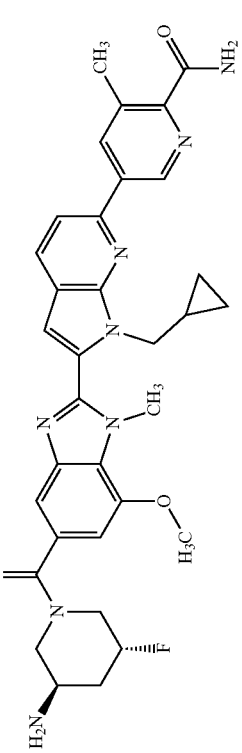 | 5-(2-{5-[(3R,5R)-3-amino-5-fluoropiperidine-1-carbonyl]-7-methoxy-1-methyl-1H-1,3-benzodiazol-2-yl]-1-(cyclopropylmethyl)-1H-pyrrolo[2,3-b]pyridin-6-yl})-3-methylpyridine-2-carboxamide | 611.1 | 1 | 1.53 |
| 1072. | 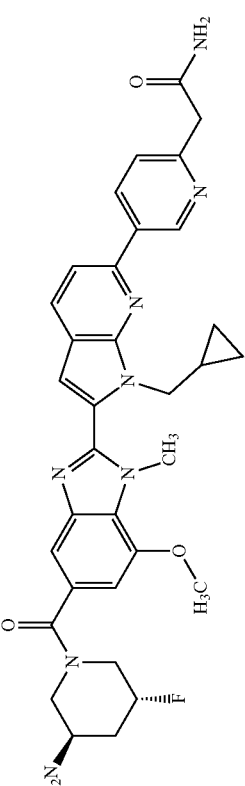 | 2-[5-(2-{5-[(3R,5R)-3-amino-5-fluoropiperidine-1-carbonyl]-7-methoxy-1-methyl-1H-1,3-benzodiazol-2-yl]-1-(cyclopropylmethyl)-1H-pyrrolo[2,3-b]pyridin-6-yl)pyridin-2-yl]acetamide | 611.4 | 1 | 1.16 |
| 1073. | 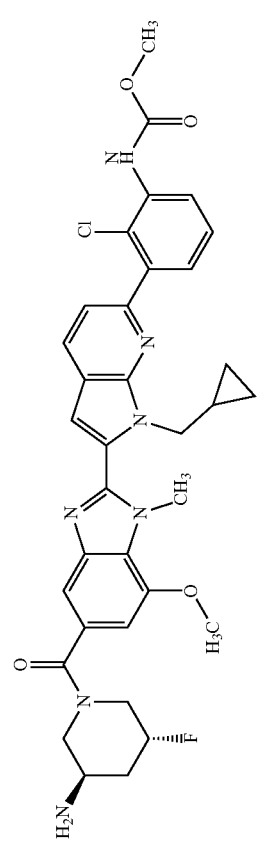 | methyl N-[3-(2-{5-[(3R,5R)-3-amino-5-fluoropiperidine-1-carbonyl]-7-methoxy-1-methyl-1H-1,3-benzodiazol-2-yl]-1-(cyclopropylmethyl)-1H-pyrrolo[2,3-b]pyridin-6-yl)-2-chlorophenyl]carbamate | 660.4 | 1 | 1.94 |

| # | Structure | Name | Obs. MS Ion | HPLC Method ID | RT |
|---|---|---|---|---|---|
| 1074. | 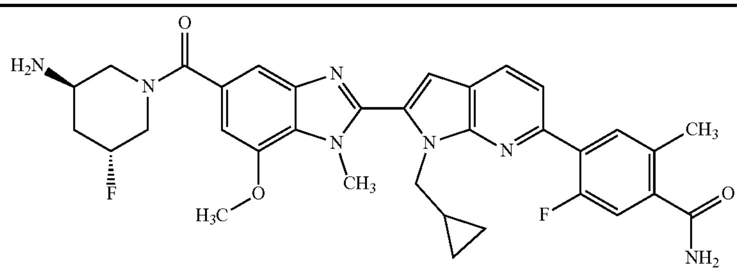 | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-5-fluoro-2-methylbenzamide | 628.2 | 1 | 1.59 |
| 1075. | 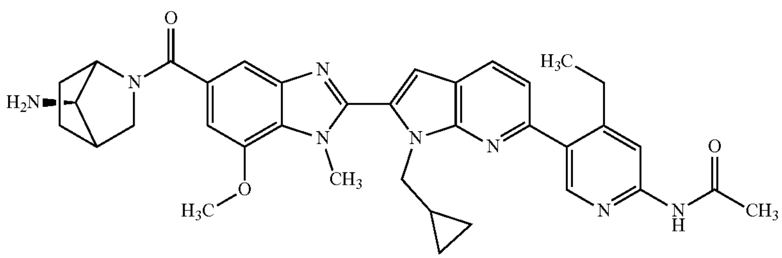 | N-[5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-4-ethylpyridin-2-yl]acetamide | 633.2 | 2 | 1.4 |
| 1076. | 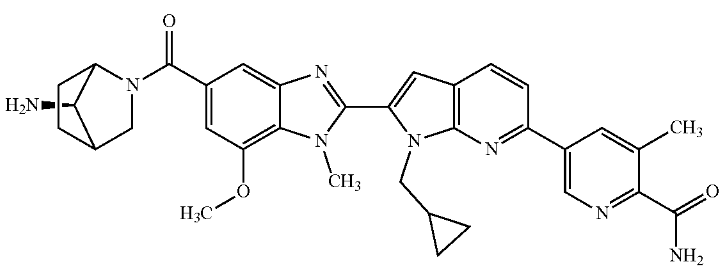 [SMILES: COc1cc(C(=O)N2CC3CCC2[C@@H]3N)cc2nc(-c3cc4ccc(-c5cnc(C(N)=O)c(C)c5)nc4n3CC3CC3)n(C)c12] | 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-3-methylpyridine-2-carboxamide | 605.1 | 1 | 1.56 |

| # | Structure | Name | Obs. MS Ion | HPLC Method ID | RT |
|---|---|---|---|---|---|
| 1077. | 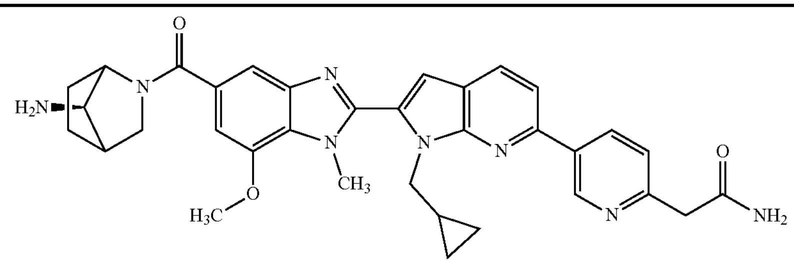 | 2-[5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)pyridin-2-yl]acetamide | 605.2 | 1 | 1.42 |
| 1078. | 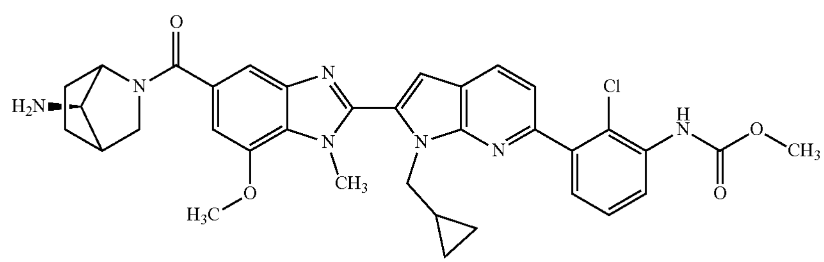 [SMILES: COC(=O)Nc1cccc(-c2ccc3cc(-c4nc5cc(C(=O)N6CC7CCC6[C@@H]7N)cc(OC)c5n4C)n(CC4CC4)c3n2)c1Cl] | methyl N-[3-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-2-chlorophenyl]carbamate | 654.1 | 1 | 1.97 |
| 1079. | 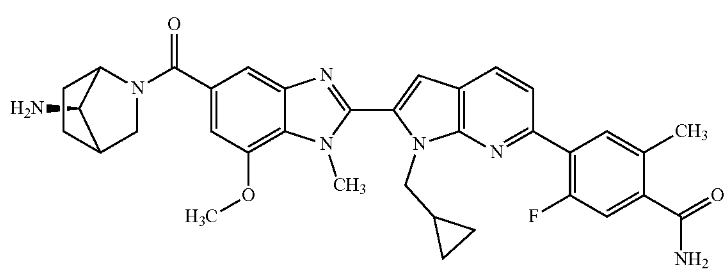 | 4-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-5-fluoro-2-methylbenzamide | 622.1 | 1 | 1.56 |

| # | Structure | Name | Obs. MS Ion | HPLC Method ID | RT |
|---|---|---|---|---|---|
| 1080. | 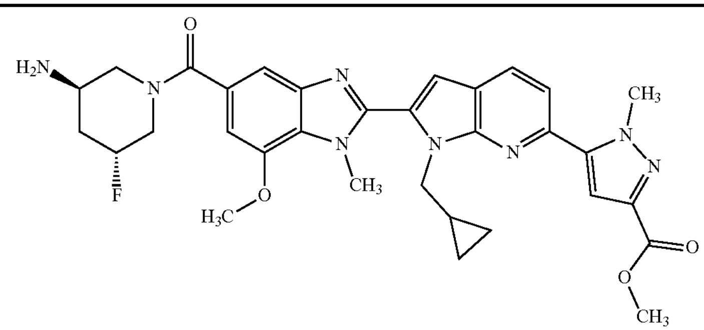 | methyl 5-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)-1-methyl-1H-pyrazole-3-carboxylate | 308.4 | 1 | 1.46 |
| 1081. | 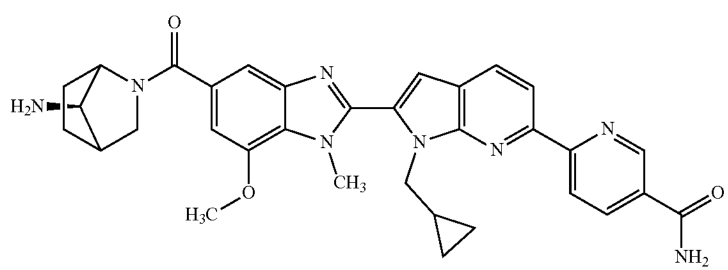 | 6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)pyridine-3-carboxamide | 591.5 | 1 | 1.08 |
| 1082. | 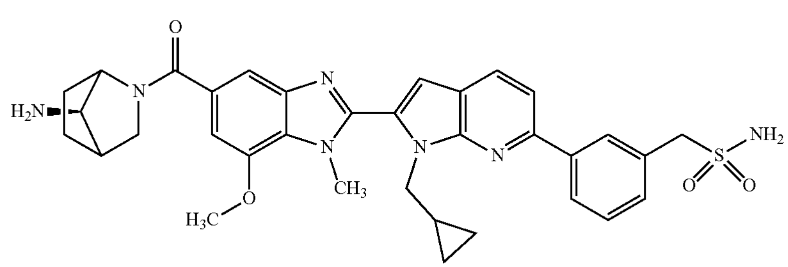 [SMILES: COc1cc(C(=O)N2CC3CCC2[C@@H]3N)cc2nc(-c3cc4ccc(-c5cccc(CS(N)(=O)=O)c5)nc4n3CC3CC3)n(C)c12] | [3-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]methanesulfonamide | 640.5 | 1 | 1.34 |

| # | Structure | Name | Obs. MS Ion | HPLC Method ID | RT |
|---|---|---|---|---|---|
| 1083. | 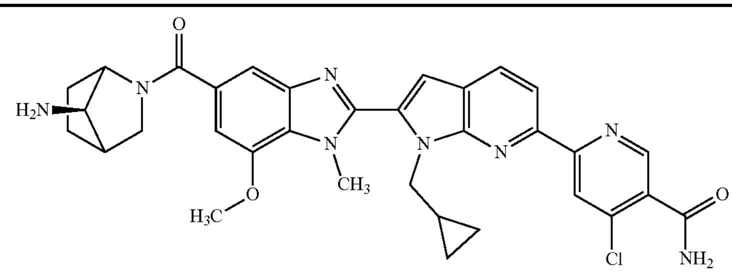 | 6-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-4-chloropyridine-3-carboxamide | 625 | 1 | 1.5 |
| 1084. | 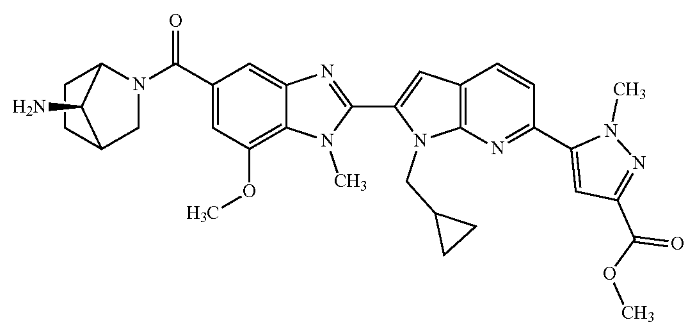 [SMILES: COC(=O)c1cc(-c2ccc3cc(-c4nc5cc(C(=O)N6CC7CCC6[C@@H]7N)cc(OC)c5n4C)n(CC4CC4)c3n2)n(C)n1] | methyl 5-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)-1-methyl-1H-pyrazole-3-carboxylate | 609.6 | 1 | 1.42 |
| 1085. | 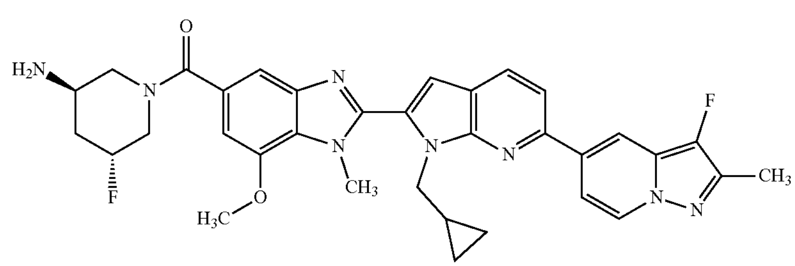 [SMILES: COc1cc(C(=O)N2C[C@H](N)C[C@@H](F)C2)cc2nc(-c3cc4ccc(-c5ccn6nc(C)c(F)c6c5)nc4n3CC3CC3)n(C)c12] | (3R,5R)-1-{2-[1-(cyclopropylmethyl)-6-{3-fluoro-2-methylpyrazolo[1,5-a]pyridin-5-yl}-1H-pyrrolo[2,3-b]pyridin-2-yl]-7-methoxy-1-methyl-1H-1,3-benzodiazole-5-carbonyl}-5-fluoropiperidin-3-amine | 625.2 | 1 | 2.02 |

| # | Structure | Name | Obs. MS Ion | HPLC Method ID | RT |
|---|---|---|---|---|---|
| 1086. | 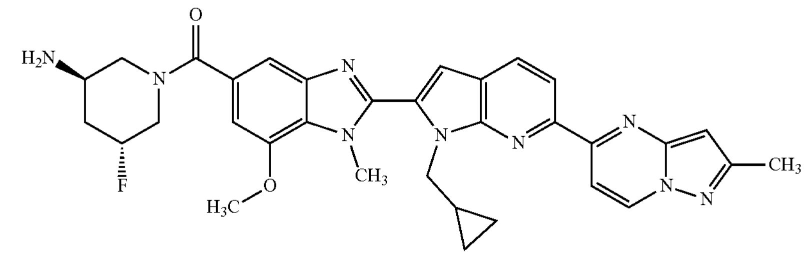 [SMILES: COc1cc(C(=O)N2C[C@H](N)C[C@@H](F)C2)cc2nc(-c3cc4ccc(-c5ccn6nc(C)cc6n5)nc4n3CC3CC3)n(C)c12] | (3R,5R)-1-{2-[1-(cyclopropylmethyl)-6-{2-methylpyrazolo[1,5-a]pyrimidin-5-yl}-1H-pyrrolo[2,3-b]pyridin-2-yl]-7-methoxy-1-methyl-1H-1,3-benzodiazole-5-carbonyl}-5-fluoropiperidin-3-amine | 608.2 | 1 | 1.85 |
| 1087. | 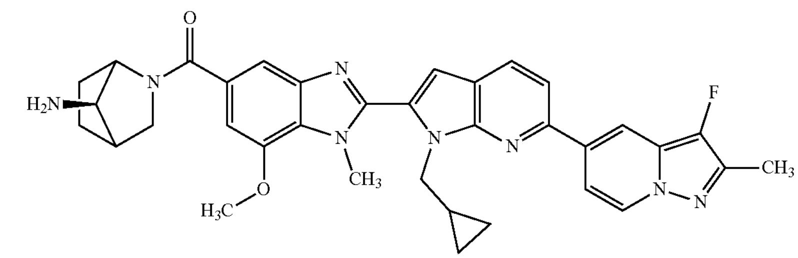 [SMILES: COc1cc(C(=O)N2CC3CCC2[C@@H]3N)cc2nc(-c3cc4ccc(-c5ccn6nc(C)c(F)c6c5)nc4n3CC3CC3)n(C)c12] | (7R)-2-(2-[1-(cyclopropylmethyl)-6-{3-fluoro-2-methylpyrazolo[1,5-a]pyridin-5-yl}-1H-pyrrolo[2,3-b]pyridin-2-yl]-7-methoxy-1-methyl-1H-1,3-benzodiazole-5-carbonyl}-2-azabicyclo[2.2.1]heptan-7-amine | 619.2 | 1 | 2.06 |
| 1088. | 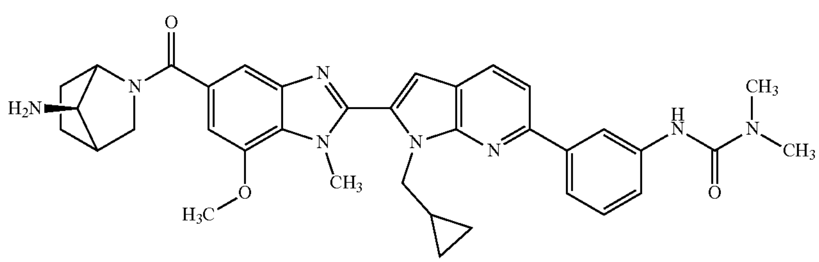 [SMILES: COc1cc(C(=O)N2CC3CCC2[C@@H]3N)cc2nc(-c3cc4ccc(-c5cccc(NC(=O)N(C)C)c5)nc4n3CC3CC3)n(C)c12] | 1-[3-(2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)phenyl]-3,3-dimethylurea | 633.3 | 1 | 1.49 |

| # | Structure | Name | Obs. MS Ion | HPLC Method ID | RT |
|---|---|---|---|---|---|
| 1089. | 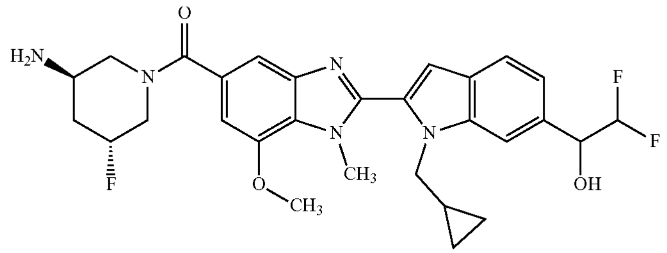 [SMILES: COc1cc(C(=O)N2C[C@H](N)C[C@@H](F)C2)cc2nc(-c3cc4ccc(C(O)C(F)F)cc4n3CC3CC3)n(C)c12] | 1-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-indol-6-yl)-2,2-difluoroethan-1-ol (mixture of diastereomers) | 556.3 | 3 | 0.74 |
| 1090. | 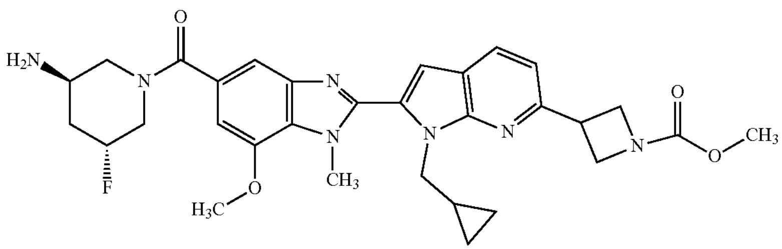 [SMILES: COC(=O)N1CC(c2ccc3cc(-c4nc5cc(C(=O)N6C[C@H](N)C[C@@H](F)C6)cc(OC)c5n4C)n(CC4CC4)c3n2)C1] | methyl 3-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)azetidine-1-carboxylate | 590.2 | 1 | 1.62 |
| 1091. | 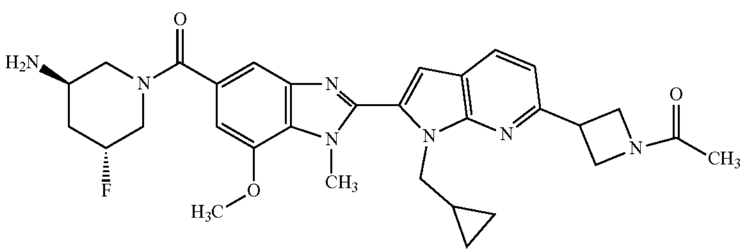 [SMILES: COc1cc(C(=O)N2C[C@H](N)C[C@@H](F)C2)cc2nc(-c3cc4ccc(C5CN(C(C)=O)C5)nc4n3CC3CC3)n(C)c12] | 1-[3-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)azetidin-1-yl]ethan-1-one | 574.2 | 1 | 1.4 |
| 1092. | 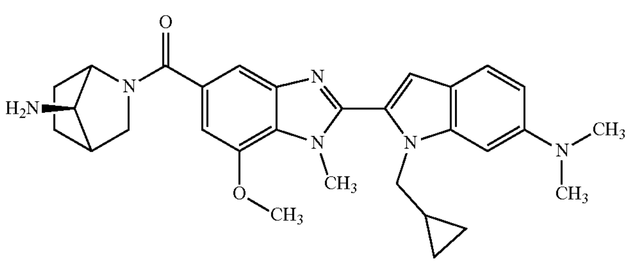 [SMILES: COc1cc(C(=O)N2CC3CCC2[C@@H]3N)cc2nc(-c3cc4ccc(N(C)C)cc4n3CC3CC3)n(C)c12] | 2-{5-[(7R)-7-amino-2-azabicyclo[2.2.1]heptane-2-carbonyl]-7-methoxy-1-methyl-1H-1,3-benzodiazol-2-yl}-1-(cyclopropylmethyl)-N,N-dimethyl-1H-indol-6-amine | 513.3 | 3 | 0.57 |

| # | Structure | Name | Obs. MS Ion | HPLC Method ID | RT |
|---|---|---|---|---|---|
| 1093. | 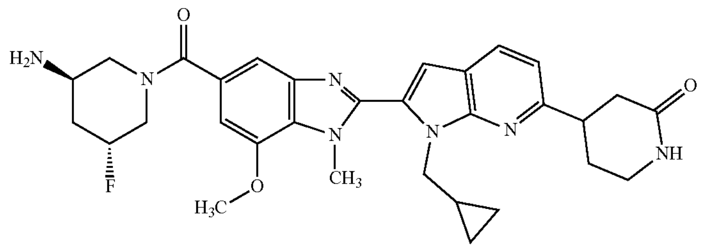 [SMILES: COc1cc(C(=O)N2C[C@H](N)C[C@@H](F)C2)cc2nc(-c3cc4ccc(C5CCNC(=O)C5)nc4n3CC3CC3)n(C)c12] | 4-(2-{5-[(3R,5R)-3-amino-5-fluoropiperidine-1-carbonyl]-7-methoxy-1-methyl-1H-1,3-benzodiazol-2-yl}-1-(cyclopropylmethyl)-1H-pyrrolo[2,3-b]pyridin-6-yl)piperidin-2-one (mixture of diastereomers) | 574.3 | 1 | 1.4 |
| 1094. | 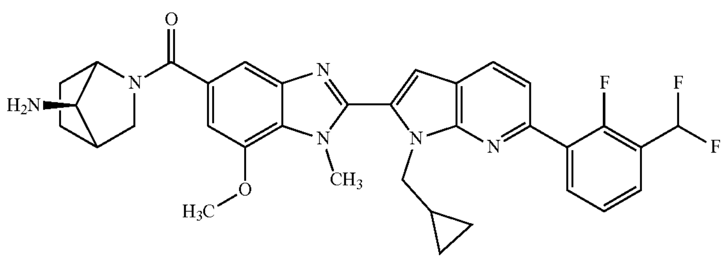 [SMILES: COc1cc(C(=O)N2CC3CCC2[C@@H]3N)cc2nc(-c3cc4ccc(-c5cccc(C(F)F)c5F)nc4n3CC3CC3)n(C)c12] | (7R)-2-{2-[1-(cyclopropylmethyl)-6-[3-(difluoromethyl)-2-fluorophenyl]-1H-pyrrolo[2,3-b]pyridin-2-yl]-7-methoxy-1-methyl-1H-1,3-benzodiazole-5-carbonyl}-2-azabicyclo[2.2.1]heptan-7-amine | 615.2 | 1 | 2.17 |
| 1095. | 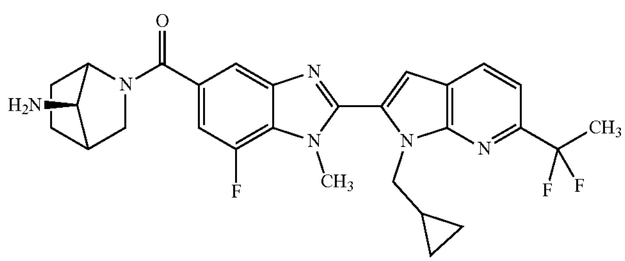 [SMILES: Cn1c(-c2cc3ccc(C(C)(F)F)nc3n2CC2CC2)nc2cc(C(=O)N3CC4CCC3[C@@H]4N)cc(F)c21] | (7R)-2-{2-[1-(cyclopropylmethyl)-6-(1,1-difluoroethyl)-1H-pyrrolo[2,3-b]pyridin-2-yl]-7-fluoro-1-methyl-1H-1,3-benzodiazole-5-carbonyl}-2-azabicyclo[2.2.1]heptan-7-amine | 523.5 | 3 | 0.85 |

| # | Structure | Name | Obs. MS Ion | HPLC Method ID | RT |
|---|---|---|---|---|---|
| 1096. | 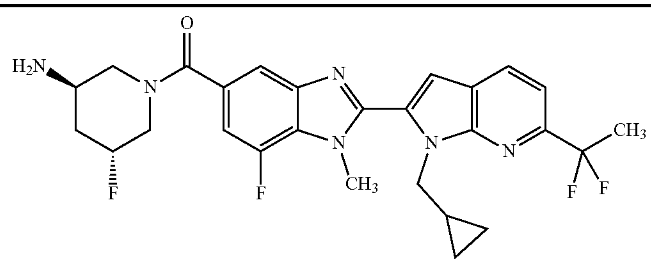 | (3R,5R)-1-{2-[1-(cyclopropylmethyl)-6-(1,1-difluoroethyl)-1H-pyrrolo[2,3-b]pyridin-2-yl]-7-fluoro-1-methyl-1H-1,3-benzodiazole-5-carbonyl}-5-fluoropiperidin-3-amine | 529.5 | 3 | 0.86 |
| 1097. | 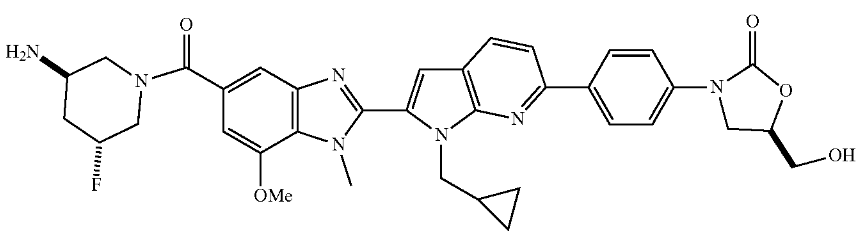 [SMILES: COc1cc(C(=O)N2C[C@H](N)C[C@@H](F)C2)cc2nc(-c3cc4ccc(-c5ccc(N6C[C@H](CO)OC6=O)cc5)nc4n3CC3CC3)n(C)c12] | (R)-3-(4-(2-(5-((3R,5R)-3-amino-5-fluoropiperidine-1-carbonyl)-7-methoxy-1-methyl-1H-benzo[d]imidazol-2-yl)-1-(cyclopropylmethyl)-1H-pyrrolo[2,3-b]pyridin-6-yl)phenyl)-5-(hydroxymethyl)oxazolidin-2-one | 668.2 | 2 | 1.45 |

Biological Assays

Compounds of the present invention were assayed as inhibitors of PAD4 using the assay protocol described below.

RFMS human PAD4 Functional Assay:

Compounds were solubilized in 100% DMSO to achieve a 10 mM compound concentration. Compound stock solutions were stored at RT. A series of dilutions were prepared in DMSO and mixed 8 times with 20 µL mixing volume. Final top concentration of compound in the assay is 50 µM. Final assay conditions were as follows:

Reaction volume: 26 µl
Assay buffer: 25 mM hepes, pH 7.5, 5 mM NaCl, 1 mM DTT, 0.2 mg/ml BSA, 0.01% CHAPS, 50 µM Calcium, and 5 µM TPEN
Final concentrations: 5 nM hPAD4 enzyme, 250 µM BAEE, and 0.5% DMSO
Total incubation time: 30 mins compound and enzyme preincubation at 37° C., 90 min enzyme/substrate reaction, 30 min reaction with phenyl glyoxal at 37° C.
Stop solution: 40 µl 5% TCA in ACN 0.13 µL of compound solution was added to 13 µL of 10 nM PAD4 in assay buffer. After 30 min 13 µl of 500 µM of BAEE was added in 25 mM hepes, pH 7.5, 5 mM NaCl, 1 mM DTT, 0.2 mg/ml BSA, 0.01% CHAPS, 50 µM Calcium, 5 µM TPEN was added and the reaction incubated for 90 min at 37° C. The enzymatic reaction was quenched by addition of 15 µl of 6.1N TCA, 100% Final Concentration is 20%, 35 µl of 8.5 mM phenyl glyoxal (final concentration 4 mM) is then added and the reaction is incubated for 30 min at 37° C.

After 30 minutes the plates are spun down to remove all precipitate. The enzyme reaction was quenched with an equal volume of methanol containing internal standard (modified citrulline). Samples were loaded onto the Rapid Fire RF300 system (Agilent) wherein they were first sipped for 1000 ms and then directly loaded to a C18 separations cartridge using a mixture of acetonitrile containing 0.01% formic acid for 3000 ms desalting. The flow rate of the mobile phase was 1.5 ml/min. Once the samples were eluted from the cartridge, a mobile phase of acetonitrile containing 0.01% formic acid was used to move the samples into the mass spectrometer for 4000 ms at a flow rate of 1.25 ml/min/Sciex API5500 triple quadrupole mass spectrometer (Applied Biosystems) equipped with ESI was used to analyze the peptidyl citrulline and internal standard ions.

MRM transition of product and internal standard were monitored at m/z 424.5 to 350.4 and m/z 293 to 247 respectively. The dwell time for each transition was set at 200 ms, and the ESI voltage was used at 5500 with a source temperature of 400° C. Extracted ion peaks for each transition were integrated using the Rapid Fire Integrator software. Peak area of analyte was normalized with internal standard).

For a given compound example, the Table below shows the human PAD4 (hPAD4) $IC_{50}$ in the rapid-fire mass spectrum (RFMS) assay.

TABLE 11

PAD4 Activity

| Cmpd # | hPAD4 RFMS $IC_{50}$ (µM) |
|---|---|
| 1. | 0.022 |
| 2. | 0.198 |
| 3. | 0.065 |
| 4. | 0.252 |

TABLE 11-continued

PAD4 Activity

| Cmpd # | hPAD4 RFMS $IC_{50}$ (µM) |
|---|---|
| 5. | 0.086 |
| 6. | 0.090 |
| 7. | 0.026 |
| 8. | 0.053 |
| 9. | 0.157 |
| 10. | 0.089 |
| 11. | 0.162 |
| 12. | 0.136 |
| 13. | 0.103 |
| 14. | 0.123 |
| 15. | 0.092 |
| 16. | 0.071 |
| 17. | 0.106 |
| 18. | 0.097 |
| 19. | 0.141 |
| 20. | 0.091 |
| 21. | 0.103 |
| 22. | 0.159 |
| 23. | 0.175 |
| 24. | 0.176 |
| 25. | 0.119 |
| 26. | 0.161 |
| 27. | 0.036 |
| 28. | 0.116 |
| 29. | 0.134 |
| 30. | 0.113 |
| 31. | 0.097 |
| 32. | 0.170 |
| 33. | 0.106 |
| 34. | 0.035 |
| 35. | 0.064 |
| 36. | 0.082 |
| 37. | 0.080 |
| 38. | 0.101 |
| 39. | 0.162 |
| 40. | 0.129 |
| 41. | 0.055 |
| 42. | 0.160 |
| 43. | 0.099 |
| 44. | 0.109 |
| 45. | 0.112 |
| 46. | 0.051 |
| 47. | 0.076 |
| 48. | 0.160 |
| 49. | 0.090 |
| 50. | 0.163 |
| 51. | 0.168 |
| 52. | 0.018 |
| 53. | 0.045 |
| 54. | 0.065 |
| 55. | 0.071 |
| 56. | 0.046 |
| 57. | 0.077 |
| 58. | 0.077 |
| 59. | 0.169 |
| 60. | 0.148 |
| 61. | 0.077 |
| 62. | 0.199 |
| 63. | 0.059 |
| 64. | 0.056 |
| 65. | 0.020 |
| 66. | 0.020 |
| 67. | 0.054 |
| 68. | 0.077 |
| 69. | 0.091 |
| 70. | 0.032 |
| 71. | 0.125 |
| 72. | 0.102 |
| 73. | 0.107 |
| 74. | 0.051 |
| 75. | 0.050 |
| 76. | 0.143 |
| 77. | 0.141 |
| 78. | 0.125 |
| 79. | 0.122 |

TABLE 11-continued

PAD4 Activity

| Cmpd # | hPAD4 RFMS IC$_{50}$ (μM) |
|---|---|
| 80. | 0.055 |
| 81. | 0.137 |
| 82. | 0.091 |
| 83. | 0.099 |
| 84. | 0.123 |
| 85. | 0.097 |
| 86. | 0.178 |
| 87. | 0.049 |
| 88. | 0.030 |
| 89. | 0.019 |
| 90. | 0.128 |
| 91. | 0.109 |
| 92. | 0.099 |
| 93. | 0.112 |
| 94. | 0.075 |
| 95. | 0.116 |
| 96. | 0.010 |
| 97. | 0.049 |
| 98. | 0.035 |
| 99. | 0.112 |
| 100. | 0.053 |
| 101. | 0.110 |
| 102. | 0.120 |
| 103. | 0.106 |
| 104. | 0.064 |
| 105. | 0.015 |
| 106. | 0.055 |
| 107. | 0.042 |
| 108. | 0.067 |
| 109. | 0.039 |
| 110. | 0.034 |
| 111. | 0.028 |
| 112. | 0.058 |
| 113. | 0.083 |
| 114. | 0.030 |
| 115. | 0.053 |
| 116. | 0.058 |
| 117. | 0.074 |
| 118. | 0.041 |
| 119. | 0.033 |
| 120. | 0.080 |
| 121. | 0.110 |
| 122. | 0.077 |
| 123. | 0.018 |
| 124. | 0.041 |
| 125. | 0.102 |
| 126. | 0.148 |
| 127. | 0.046 |
| 128. | 0.050 |
| 129. | 0.016 |
| 130. | 0.035 |
| 131. | 0.093 |
| 132. | 0.113 |
| 133. | 0.032 |
| 134. | 0.143 |
| 135. | 0.161 |
| 136. | 0.066 |
| 137. | 0.188 |
| 138. | 0.073 |
| 139. | 0.044 |
| 140. | 0.027 |
| 141. | 0.136 |
| 142. | 0.044 |
| 143. | 0.024 |
| 144. | 0.069 |
| 145. | 0.023 |
| 146. | 0.148 |
| 147. | 0.022 |
| 148. | 0.149 |
| 149. | 0.097 |
| 150. | 0.028 |
| 151. | 0.058 |
| 152. | 0.013 |
| 153. | 0.191 |
| 154. | 0.069 |
| 155. | 0.068 |
| 156. | 0.154 |
| 157. | 0.139 |
| 158. | 0.143 |
| 159. | 0.181 |
| 160. | 0.163 |
| 161. | 0.025 |
| 162. | 0.056 |
| 163. | 0.146 |
| 164. | 0.092 |
| 165. | 0.112 |
| 166. | 0.060 |
| 167. | 0.039 |
| 168. | 0.025 |
| 169. | 0.081 |
| 170. | 0.155 |
| 171. | 0.181 |
| 172. | 0.063 |
| 173. | 0.142 |
| 174. | 0.148 |
| 175. | 0.076 |
| 176. | 0.088 |
| 177. | 0.039 |
| 178. | 0.094 |
| 179. | 0.066 |
| 180. | 0.092 |
| 181. | 0.065 |
| 182. | 0.060 |
| 183. | 0.048 |
| 184. | 0.037 |
| 185. | 0.058 |
| 186. | 0.083 |
| 187. | 0.047 |
| 188. | 0.060 |
| 189. | 0.084 |
| 190. | 0.017 |
| 191. | 0.064 |
| 192. | 0.083 |
| 193. | 0.027 |
| 194. | 0.032 |
| 195. | 0.174 |
| 196. | 0.094 |
| 197. | 0.047 |
| 198. | 0.039 |
| 199. | 0.092 |
| 200. | 0.012 |
| 201. | 0.037 |
| 202. | 0.053 |
| 203. | 0.077 |
| 204. | 0.095 |
| 205. | 0.058 |
| 206. | 0.015 |
| 207. | 0.122 |
| 208. | 0.062 |
| 209. | 0.052 |
| 210. | 0.032 |
| 211. | 0.017 |
| 212. | 0.060 |
| 213. | 0.040 |
| 214. | 0.036 |
| 215. | 0.016 |
| 216. | 0.047 |
| 217. | 0.018 |
| 218. | 0.113 |
| 219. | 0.086 |
| 220. | 0.021 |
| 221. | 0.036 |
| 222. | 0.022 |
| 223. | 0.030 |
| 224. | 0.058 |
| 225. | 0.086 |
| 226. | 0.060 |
| 227. | 0.181 |
| 228. | 0.121 |
| 229. | 0.155 |

TABLE 11-continued

PAD4 Activity

| Cmpd # | hPAD4 RFMS IC$_{50}$ (μM) |
|---|---|
| 230. | 0.026 |
| 231. | 0.025 |
| 232. | 0.072 |
| 233. | 0.078 |
| 234. | 0.146 |
| 235. | 0.046 |
| 236. | 0.051 |
| 237. | 0.054 |
| 238. | 0.058 |
| 239. | 0.145 |
| 240. | 0.068 |
| 241. | 0.083 |
| 242. | 0.026 |
| 243. | 0.022 |
| 244. | 0.132 |
| 245. | 0.030 |
| 246. | 0.050 |
| 247. | 0.130 |
| 248. | 0.118 |
| 249. | 0.137 |
| 250. | 0.030 |
| 251. | 0.048 |
| 252. | 0.139 |
| 253. | 0.186 |
| 254. | 0.116 |
| 255. | 0.057 |
| 256. | 0.119 |
| 257. | 0.110 |
| 258. | 0.125 |
| 259. | 0.034 |
| 260. | 0.107 |
| 261. | 0.046 |
| 262. | 0.070 |
| 263. | 0.095 |
| 264. | 0.034 |
| 265. | 0.059 |
| 266. | 0.165 |
| 267. | 0.042 |
| 268. | 0.059 |
| 269. | 0.151 |
| 270. | 0.151 |
| 271. | 0.037 |
| 272. | 0.095 |
| 273. | 0.051 |
| 274. | 0.070 |
| 275. | 0.112 |
| 276. | 0.036 |
| 277. | 0.186 |
| 278. | 0.032 |
| 279. | 0.098 |
| 280. | 0.053 |
| 281. | 0.131 |
| 282. | 0.156 |
| 283. | 0.077 |
| 284. | 0.110 |
| 285. | 0.186 |
| 286. | 0.161 |
| 287. | 0.063 |
| 288. | 0.150 |
| 289. | 0.048 |
| 290. | 0.028 |
| 291. | 0.123 |
| 292. | 0.049 |
| 293. | 0.051 |
| 294. | 0.166 |
| 295. | 0.045 |
| 296. | 0.039 |
| 297. | 0.034 |
| 298. | 0.085 |
| 299. | 0.061 |
| 300. | 0.157 |
| 301. | 0.097 |
| 302. | 0.095 |
| 303. | 0.110 |
| 304. | 0.167 |
| 305. | 0.060 |
| 306. | 0.033 |
| 307. | 0.096 |
| 308. | 0.162 |
| 309. | 0.115 |
| 310. | 0.099 |
| 311. | 0.112 |
| 312. | 0.188 |
| 313. | 0.122 |
| 314. | 0.107 |
| 315. | 0.065 |
| 316. | 0.103 |
| 317. | 0.113 |
| 318. | 0.107 |
| 319. | 0.123 |
| 320. | 0.042 |
| 321. | 0.029 |
| 322. | 0.188 |
| 323. | 0.066 |
| 324. | 0.040 |
| 325. | 0.091 |
| 326. | 0.042 |
| 327. | 0.022 |
| 328. | 0.127 |
| 329. | 0.037 |
| 330. | 0.039 |
| 331. | 0.062 |
| 332. | 0.030 |
| 333. | 0.046 |
| 334. | 0.057 |
| 335. | 0.017 |
| 336. | 0.064 |
| 337. | 0.062 |
| 338. | 0.038 |
| 339. | 0.031 |
| 340. | 0.042 |
| 341. | 0.033 |
| 342. | 0.035 |
| 343. | 0.061 |
| 344. | 0.040 |
| 345. | 0.024 |
| 346. | 0.087 |
| 347. | 0.124 |
| 348. | 0.141 |
| 349. | 0.059 |
| 350. | 0.092 |
| 351. | 0.179 |
| 352. | 0.028 |
| 353. | 0.029 |
| 354. | 0.192 |
| 355. | 0.073 |
| 356. | 0.023 |
| 357. | 0.019 |
| 358. | 0.019 |
| 359. | 0.023 |
| 360. | 0.016 |
| 361. | 0.079 |
| 362. | 0.052 |
| 363. | 0.104 |
| 364. | 0.013 |
| 365. | 0.034 |
| 366. | 0.027 |
| 367. | 0.013 |
| 368. | 0.038 |
| 369. | 0.021 |
| 370. | 0.146 |
| 371. | 0.034 |
| 372. | 0.136 |
| 373. | 0.073 |
| 374. | 0.062 |
| 375. | 0.013 |
| 376. | 0.066 |
| 377. | 0.069 |
| 378. | 0.059 |
| 379. | 0.027 |

TABLE 11-continued

PAD4 Activity

| Cmpd # | hPAD4 RFMS IC$_{50}$ (µM) |
|---|---|
| 380. | 0.107 |
| 381. | 0.148 |
| 382. | 0.176 |
| 383. | 0.199 |
| 384. | 0.128 |
| 385. | 0.189 |
| 386. | 0.052 |
| 387. | 0.011 |
| 388. | 0.013 |
| 389. | 0.101 |
| 390. | 0.024 |
| 391. | 0.144 |
| 392. | 0.009 |
| 393. | 0.011 |
| 394. | 0.052 |
| 395. | 0.012 |
| 396. | 0.025 |
| 397. | 0.278 |
| 398. | 0.236 |
| 399. | 0.771 |
| 400. | 0.209 |
| 401. | 0.331 |
| 402. | 0.638 |
| 403. | 0.335 |
| 404. | 0.252 |
| 405. | 0.209 |
| 406. | 0.222 |
| 407. | 0.088 |
| 408. | 0.079 |
| 409. | 0.151 |
| 410. | 0.161 |
| 411. | 0.083 |
| 412. | 0.155 |
| 413. | 0.095 |
| 414. | 0.122 |
| 415. | 0.050 |
| 416. | 0.168 |
| 417. | 0.034 |
| 418. | 0.165 |
| 419. | 0.042 |
| 420. | 0.045 |
| 421. | 0.023 |
| 422. | 0.105 |
| 423. | 0.089 |
| 424. | 0.070 |
| 425. | 0.069 |
| 426. | 0.051 |
| 427. | 0.089 |
| 428. | 0.143 |
| 429. | 0.079 |
| 430. | 0.090 |
| 431. | 0.037 |
| 432. | 0.047 |
| 433. | 0.052 |
| 434. | 0.043 |
| 435. | 0.041 |
| 436. | 0.049 |
| 437. | 0.098 |
| 438. | 0.153 |
| 439. | 0.141 |
| 440. | 0.095 |
| 441. | 0.099 |
| 442. | 0.086 |
| 443. | 0.110 |
| 444. | 0.281 |
| 445. | 0.034 |
| 446. | 0.039 |
| 447. | 0.027 |
| 448. | 0.075 |
| 449. | 0.116 |
| 450. | 0.021 |
| 451. | 0.145 |
| 452. | 0.157 |
| 453. | 0.051 |
| 454. | 0.102 |
| 455. | 0.135 |
| 456. | 0.061 |
| 457. | 0.060 |
| 458. | 0.113 |
| 459. | 0.030 |
| 460. | 0.038 |
| 461. | 0.139 |
| 462. | 0.031 |
| 463. | 0.076 |
| 464. | 0.057 |
| 465. | 0.016 |
| 466. | 0.028 |
| 467. | 0.061 |
| 468. | 0.028 |
| 469. | 0.123 |
| 470. | 0.012 |
| 471. | 0.031 |
| 472. | 0.072 |
| 473. | 0.005 |
| 474. | 0.023 |
| 475. | 0.018 |
| 476. | 0.013 |
| 477. | 0.034 |
| 478. | 0.022 |
| 479. | 0.116 |
| 480. | 0.014 |
| 481. | 0.043 |
| 482. | 0.020 |
| 483. | 0.028 |
| 484. | 0.025 |
| 485. | 0.101 |
| 486. | 0.031 |
| 487. | 0.184 |
| 488. | 0.082 |
| 489. | 0.058 |
| 490. | 0.038 |
| 491. | 0.156 |
| 492. | 0.048 |
| 493. | 0.016 |
| 494. | 0.050 |
| 495. | 0.030 |
| 496. | 0.044 |
| 497. | 0.033 |
| 498. | 0.046 |
| 499. | 0.046 |
| 500. | 0.032 |
| 501. | 0.066 |
| 502. | 0.058 |
| 503. | 0.026 |
| 504. | 0.174 |
| 505. | 0.019 |
| 506. | 0.032 |
| 507. | 0.032 |
| 508. | 0.049 |
| 509. | 0.073 |
| 510. | 0.044 |
| 511. | 0.042 |
| 512. | 0.045 |
| 513. | 0.026 |
| 514. | 0.041 |
| 515. | 0.047 |
| 516. | 0.199 |
| 517. | 0.042 |
| 518. | 0.115 |
| 519. | 0.063 |
| 520. | 0.103 |
| 521. | 0.112 |
| 522. | 0.029 |
| 523. | 0.071 |
| 524. | 0.027 |
| 525. | 0.063 |
| 526. | 0.047 |
| 527. | 0.118 |
| 528. | 0.052 |
| 529. | 0.054 |

TABLE 11-continued

PAD4 Activity

| Cmpd # | hPAD4 RFMS IC$_{50}$ (μM) |
|---|---|
| 530. | 4.075 |
| 531. | 0.102 |
| 532. | 0.048 |
| 533. | 0.034 |
| 534. | 0.194 |
| 535. | 0.107 |
| 536. | 0.168 |
| 537. | 0.076 |
| 538. | 0.191 |
| 539. | 0.043 |
| 540. | 0.054 |
| 541. | 0.055 |
| 542. | 0.049 |
| 543. | 0.072 |
| 544. | 0.087 |
| 545. | 0.045 |
| 546. | 0.064 |
| 547. | 0.154 |
| 548. | 0.107 |
| 549. | 0.057 |
| 550. | 0.052 |
| 551. | 0.031 |
| 552. | 0.025 |
| 553. | 0.051 |
| 554 | 0.150 |
| 555. | 0.132 |
| 556. | 0.029 |
| 557. | 1.270 |
| 558. | 0.112 |
| 559. | 0.065 |
| 560. | 0.192 |
| 561. | 0.097 |
| 562. | 0.074 |
| 563. | 0.026 |
| 564. | 0.021 |
| 565. | 0.049 |
| 566. | 0.051 |
| 567. | 0.081 |
| 568. | 0.138 |
| 569. | 0.157 |
| 570. | 0.018 |
| 571. | 0.058 |
| 572. | 0.070 |
| 573. | 0.074 |
| 574. | 0.180 |
| 575. | 0.055 |
| 576. | 0.064 |
| 577. | 0.024 |
| 578. | 0.083 |
| 579. | 0.175 |
| 580. | 0.053 |
| 581. | 0.167 |
| 582. | 0.046 |
| 583. | 0.137 |
| 584. | 0.094 |
| 585. | 0.061 |
| 586. | 0.184 |
| 587. | 0.169 |
| 588. | 0.243 |
| 589. | 0.181 |
| 590. | 0.101 |
| 591. | 0.192 |
| 592. | 0.140 |
| 593. | 0.113 |
| 594. | 0.137 |
| 595. | 0.189 |
| 596. | 0.025 |
| 597. | 0.175 |
| 598. | 0.107 |
| 599. | 0.059 |
| 600. | 0.124 |
| 601. | 0.172 |
| 602. | 0.020 |
| 603. | 0.055 |
| 604. | 0.081 |
| 605. | 0.018 |
| 606. | 0.026 |
| 607. | 0.021 |
| 608. | 0.045 |
| 609. | 0.054 |
| 610. | 0.033 |
| 611. | 0.050 |
| 612. | 0.062 |
| 613. | 0.028 |
| 614. | 0.104 |
| 615. | 0.054 |
| 616. | 0.089 |
| 617. | 0.132 |
| 618. | 0.029 |
| 619. | 0.072 |
| 620. | 0.048 |
| 621. | 0.105 |
| 622. | 0.138 |
| 623. | 0.142 |
| 624. | 0.082 |
| 625. | 0.059 |
| 626. | 0.037 |
| 627. | 0.176 |
| 628. | 0.059 |
| 629. | 0.075 |
| 630. | 0.031 |
| 631. | 0.087 |
| 632. | 0.115 |
| 633. | 0.073 |
| 634. | 0.063 |
| 635. | 0.035 |
| 636. | 0.021 |
| 637. | 0.162 |
| 638. | 0.020 |
| 639. | 0.192 |
| 640. | 0.129 |
| 641. | 0.022 |
| 642. | 0.033 |
| 643. | 0.081 |
| 644. | 0.083 |
| 645. | 0.063 |
| 646. | 0.123 |
| 647. | 0.157 |
| 648. | 0.040 |
| 649. | 0.075 |
| 650. | 0.049 |
| 651. | 0.088 |
| 652. | 0.124 |
| 653. | 0.162 |
| 654. | 0.177 |
| 655. | 0.158 |
| 656. | 0.043 |
| 657. | 0.132 |
| 658. | 0.047 |
| 659. | 0.039 |
| 660. | 0.036 |
| 661. | 0.195 |
| 662. | 0.118 |
| 663. | 0.167 |
| 664. | 0.489 |
| 665. | 0.151 |
| 666. | 0.162 |
| 667. | 0.149 |
| 668. | 0.141 |
| 669. | 0.165 |
| 670. | 0.147 |
| 671. | 0.159 |
| 672. | 0.086 |
| 673. | 0.039 |
| 674. | 0.140 |
| 675. | 0.028 |
| 676. | 0.330 |
| 677. | 0.108 |
| 678. | 0.147 |
| 679. | 0.102 |

TABLE 11-continued

PAD4 Activity

| Cmpd # | hPAD4 RFMS IC$_{50}$ (μM) |
|---|---|
| 680. | 0.164 |
| 681. | 0.075 |
| 682. | 0.068 |
| 683. | 0.173 |
| 684. | 0.070 |
| 685. | 0.132 |
| 686. | 0.071 |
| 687. | 0.041 |
| 688. | 0.044 |
| 689. | 0.044 |
| 690. | 0.048 |
| 691. | 0.039 |
| 692. | 0.137 |
| 693. | 0.027 |
| 694. | 0.144 |
| 695. | 0.031 |
| 696. | 0.023 |
| 697. | 0.153 |
| 698. | 0.094 |
| 699. | 0.015 |
| 700. | 0.143 |
| 701. | 0.025 |
| 702. | 0.037 |
| 703. | 0.034 |
| 704. | 0.056 |
| 705. | 0.129 |
| 706. | 0.035 |
| 707. | 0.022 |
| 708. | 0.108 |
| 709. | 0.154 |
| 710. | 0.113 |
| 711. | 0.068 |
| 712. | 0.045 |
| 713. | 0.147 |
| 714. | 0.050 |
| 715. | 0.037 |
| 716. | 0.074 |
| 717. | 0.041 |
| 718. | 0.024 |
| 719. | 0.033 |
| 720. | 0.092 |
| 721. | 0.035 |
| 722. | 0.163 |
| 723. | 0.019 |
| 724. | 0.777 |
| 725. | 0.070 |
| 726. | 0.149 |
| 727. | 0.032 |
| 728. | 0.035 |
| 729. | 0.126 |
| 730. | 0.185 |
| 731. | 0.006 |
| 732. | 0.031 |
| 733. | 0.294 |
| 734. | 0.134 |
| 735. | 0.124 |
| 736. | 0.079 |
| 737. | 0.108 |
| 738. | 0.043 |
| 739. | 0.136 |
| 740. | 0.040 |
| 741. | 0.056 |
| 742. | 0.108 |
| 743. | 0.052 |
| 744. | 0.153 |
| 745. | 0.019 |
| 746. | 0.175 |
| 747. | 0.067 |
| 748. | 1.443 |
| 749. | 0.076 |
| 750. | 0.045 |
| 751. | 0.036 |
| 752. | 0.063 |
| 753. | 0.026 |
| 754. | 0.038 |
| 755. | 0.143 |
| 756. | 0.033 |
| 757. | 0.043 |
| 758. | 0.036 |
| 759. | 0.106 |
| 760. | 0.040 |
| 761. | 0.096 |
| 762. | 0.048 |
| 763. | 0.054 |
| 764. | 0.108 |
| 765. | 0.173 |
| 766. | 0.175 |
| 767. | 0.032 |
| 768. | 0.019 |
| 769. | 0.036 |
| 770. | 0.068 |
| 771. | 0.060 |
| 772. | 0.096 |
| 773. | 0.051 |
| 774. | 0.103 |
| 775. | 0.046 |
| 776. | 0.016 |
| 777. | 0.071 |
| 778. | 0.023 |
| 779. | 0.072 |
| 780. | 0.089 |
| 781. | 0.083 |
| 782. | 0.180 |
| 783. | 0.118 |
| 784. | 0.111 |
| 785. | 0.088 |
| 786. | 0.032 |
| 787. | 0.080 |
| 788. | 0.078 |
| 789. | 0.148 |
| 790. | 0.112 |
| 791. | 0.086 |
| 792. | 0.115 |
| 793. | 0.037 |
| 794. | 0.064 |
| 795. | 0.105 |
| 796. | 2.444 |
| 797. | 0.114 |
| 798. | 0.117 |
| 799. | 0.076 |
| 800. | 0.188 |
| 801. | 0.083 |
| 802. | 0.092 |
| 803. | 0.159 |
| 804. | 0.188 |
| 805. | 0.452 |
| 806. | 0.109 |
| 807. | 0.120 |
| 808. | 0.105 |
| 809. | 0.050 |
| 810. | 0.050 |
| 811. | 0.138 |
| 812. | 0.280 |
| 813. | 0.101 |
| 814. | 0.064 |
| 815. | 0.090 |
| 816. | 0.422 |
| 817. | 0.081 |
| 818. | 0.062 |
| 819. | 0.272 |
| 820. | 0.107 |
| 821. | 0.753 |
| 822. | 0.093 |
| 823. | 0.038 |
| 824. | 0.393 |
| 825. | 0.060 |
| 826. | 0.480 |
| 827. | 0.445 |
| 828. | 0.155 |
| 829. | 0.164 |

TABLE 11-continued

PAD4 Activity

| Cmpd # | hPAD4 RFMS IC$_{50}$ (μM) |
|---|---|
| 830. | 3.551 |
| 831. | 0.647 |
| 832. | 0.241 |
| 833. | 0.184 |
| 834. | 0.060 |
| 835. | 0.103 |
| 836. | 0.132 |
| 837. | 0.685 |
| 838. | 0.024 |
| 839. | 0.652 |
| 840. | 1.549 |
| 841. | 0.943 |
| 842. | 0.037 |
| 843. | 0.036 |
| 844. | 1.821 |
| 845. | 0.054 |
| 846. | 0.653 |
| 847. | 0.130 |
| 848. | 2.061 |
| 849. | 0.564 |
| 850. | 2.222 |
| 851. | 0.038 |
| 852. | 0.518 |
| 853. | 0.009 |
| 854. | 0.074 |
| 855. | 0.195 |
| 856. | 0.309 |
| 857. | 0.096 |
| 858. | 0.149 |
| 859. | 0.017 |
| 860. | 0.467 |
| 861. | 4.562 |
| 862. | 0.451 |
| 863. | 3.849 |
| 864. | 1.441 |
| 865. | 0.564 |
| 866. | 1.622 |
| 867. | 1.347 |
| 868. | 1.401 |
| 869. | 1.032 |
| 870. | 0.238 |
| 871. | 0.206 |
| 872. | 0.162 |
| 873. | 0.262 |
| 874. | 0.478 |
| 875. | 0.239 |
| 876. | 0.658 |
| 877. | 0.564 |
| 878. | 0.141 |
| 879. | 0.357 |
| 880. | 1.000 |
| 881. | 0.539 |
| 882. | 0.064 |
| 883. | 0.049 |
| 884. | 0.587 |
| 885. | 0.110 |
| 886. | 0.264 |
| 887. | 0.197 |
| 888. | 0.085 |
| 889. | 0.130 |
| 890. | 0.113 |
| 891. | 0.272 |
| 892. | 0.635 |
| 893. | 0.258 |
| 894. | 0.047 |
| 895. | 0.034 |
| 896. | 0.151 |
| 897. | 0.317 |
| 898. | 0.447 |
| 899. | 0.729 |
| 900. | 2.367 |
| 901. | 1.208 |
| 902. | 0.281 |
| 903. | 0.917 |
| 904. | 0.824 |
| 905. | 0.659 |
| 906. | 0.045 |
| 907. | 0.124 |
| 908. | 0.024 |
| 909. | 0.244 |
| 910. | 0.080 |
| 911. | 0.633 |
| 912. | 1.363 |
| 913. | 0.256 |
| 914. | 0.130 |
| 915. | 0.039 |
| 916. | 0.441 |
| 917. | 3.020 |
| 918. | 1.145 |
| 919. | 0.085 |
| 920. | 0.330 |
| 921. | 0.086 |
| 922. | 0.126 |
| 923. | 0.265 |
| 924. | 1.784 |
| 925. | 0.677 |
| 926. | 0.059 |
| 927. | 0.019 |
| 928. | 0.116 |
| 929. | 0.036 |
| 930. | 0.162 |
| 931. | 0.069 |
| 932. | 0.113 |
| 933. | 0.043 |
| 934. | 0.064 |
| 935. | 0.144 |
| 936. | 0.069 |
| 937. | 0.046 |
| 938. | 0.040 |
| 939. | 0.074 |
| 940. | 0.053 |
| 941. | 0.035 |
| 942. | 0.038 |
| 943. | 0.012 |
| 944. | 0.054 |
| 945. | 0.054 |
| 946. | 0.076 |
| 947. | 0.033 |
| 948. | 0.178 |
| 949. | 0.443 |
| 950. | 0.025 |
| 951. | 0.047 |
| 952. | 0.054 |
| 953. | 0.242 |
| 954. | 0.194 |
| 955. | 0.134 |
| 956. | 0.134 |
| 957. | 0.201 |
| 958. | 0.221 |
| 959. | 0.168 |
| 960. | 0.298 |
| 961. | 0.040 |
| 962. | 0.180 |
| 963. | 0.092 |
| 964. | 0.091 |
| 965. | 0.084 |
| 966. | 0.182 |
| 967. | 0.104 |
| 968. | 0.199 |
| 969. | 0.130 |
| 970. | 0.198 |
| 971. | 0.398 |
| 972. | 0.127 |
| 973. | 0.184 |
| 974. | 0.043 |
| 975. | 0.239 |
| 976. | 0.333 |
| 977. | 0.106 |
| 978. | 0.007 |
| 979. | 0.045 |

TABLE 11-continued

PAD4 Activity

| Cmpd # | hPAD4 RFMS IC$_{50}$ (μM) |
|---|---|
| 980. | 0.024 |
| 981. | 0.063 |
| 982. | 0.170 |
| 983. | 0.040 |
| 984. | 0.063 |
| 985. | 0.133 |
| 986. | 0.043 |
| 987. | 0.034 |
| 988. | 0.113 |
| 989. | 0.044 |
| 990. | 0.057 |
| 991. | 0.084 |
| 992. | 0.069 |
| 993. | 0.147 |
| 994. | 0.199 |
| 995. | 0.102 |
| 996. | 0.031 |
| 997. | 0.132 |
| 998. | 0.042 |
| 999. | 0.194 |
| 1000. | 0.035 |
| 1001. | 0.042 |
| 1002. | 0.043 |
| 1003. | 0.036 |
| 1004. | 0.042 |
| 1005. | 0.194 |
| 1006. | 0.083 |
| 1007. | 0.066 |
| 1008. | 0.055 |
| 1009. | 0.182 |
| 1010. | 0.084 |
| 1011. | 0.052 |
| 1012. | 0.238 |
| 1013. | 0.061 |
| 1014. | 0.029 |
| 1015. | 0.025 |
| 1016. | 0.111 |
| 1017. | 0.036 |
| 1018. | 0.110 |
| 1019. | 0.037 |
| 1020. | 0.593 |
| 1021. | 0.158 |
| 1022. | 0.024 |
| 1023. | 0.362 |
| 1024. | 1.133 |
| 1025. | 0.149 |
| 1026. | 0.302 |
| 1027. | 0.228 |
| 1028. | 0.066 |
| 1029. | 0.741 |
| 1030. | 0.047 |
| 1031. | 0.062 |
| 1032. | 0.034 |
| 1033. | 0.086 |
| 1034. | 0.141 |
| 1035. | 0.086 |
| 1036. | 0.066 |
| 1037. | 0.031 |
| 1038. | 0.035 |
| 1039. | 0.148 |
| 1040. | 0.065 |
| 1041. | 0.045 |
| 1042. | 0.207 |
| 1043. | 0.076 |
| 1044. | 0.109 |
| 1045. | 0.135 |
| 1046. | 0.038 |
| 1047. | 0.102 |
| 1048. | 0.110 |
| 1049. | 0.111 |
| 1050. | 0.043 |
| 1051. | 0.093 |
| 1052. | 0.062 |
| 1053. | 0.015 |
| 1054. | 0.117 |
| 1055. | 0.070 |
| 1056. | 0.038 |
| 1057. | 0.133 |
| 1058. | 0.047 |
| 1059. | 0.068 |
| 1060. | 0.059 |
| 1061. | 0.124 |
| 1062. | 0.538 |
| 1063. | 0.077 |
| 1064. | 0.045 |
| 1065. | 0.015 |
| 1066. | 0.058 |
| 1067. | 0.051 |
| 1068. | 0.093 |
| 1069. | 0.006 |
| 1070. | 0.072 |
| 1071. | 0.162 |
| 1072. | 0.128 |
| 1073. | 0.073 |
| 1074. | 0.052 |
| 1075. | 0.043 |
| 1076. | 0.052 |
| 1077. | 0.146 |
| 1078. | 0.058 |
| 1079. | 0.021 |
| 1080. | 0.102 |
| 1081. | 0.104 |
| 1082. | 0.113 |
| 1083. | 0.199 |
| 1084. | 0.064 |
| 1085. | 0.043 |
| 1086. | 0.102 |
| 1087. | 0.061 |
| 1088. | 0.151 |
| 1089. | 0.057 |
| 1090. | 0.032 |
| 1091. | 0.136 |
| 1092. | 0.195 |
| 1093. | 0.111 |
| 1094. | 0.148 |
| 1095. | 0.024 |
| 1096. | 0.066 |
| 1097. | 0.020 |

What is claimed is:

1. A compound of Formula (I):

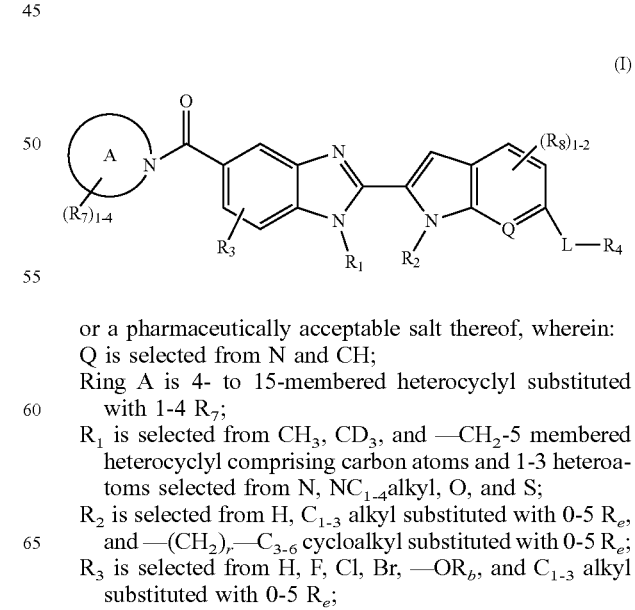

or a pharmaceutically acceptable salt thereof, wherein:

Q is selected from N and CH;

Ring A is 4- to 15-membered heterocyclyl substituted with 1-4 $R_7$;

$R_1$ is selected from $CH_3$, $CD_3$, and —$CH_2$-5 membered heterocyclyl comprising carbon atoms and 1-3 heteroatoms selected from N, $NC_{1-4}$alkyl, O, and S;

$R_2$ is selected from H, $C_{1-3}$ alkyl substituted with 0-5 $R_e$, and —$(CH_2)_r$—$C_{3-6}$ cycloalkyl substituted with 0-5 $R_e$;

$R_3$ is selected from H, F, Cl, Br, —$OR_b$, and $C_{1-3}$ alkyl substituted with 0-5 $R_e$;

L is absent or selected from —NR$_d$—, —O—, —C(=O)NR$_d$—, and —S(O)$_p$—;

R$_4$ is selected from —(CH$_2$)$_r$-aryl substituted with 1-7 R$_5$, —(CH$_2$)$_r$—C$_{3-12}$ cycloalkyl (substituted with 1-2 OR$_b$, C(=O)OR$_b$, —C(=O)NR$_a$R$_a$, —NR$_a$C(=O)R$_b$), —(CH$_2$)$_r$-heterocyclyl comprising carbon atoms and 1-3 heteroatoms selected from N, NR$_6$, O, and S and substituted with 1-7 R$_5$;

R$_5$, at each occurrence, is independently selected from H, F, Cl, Br, CN, =O, nitro, C$_{1-4}$alkyl substituted with 0-5 R$_e$, C$_{2-4}$alkenyl substituted with 0-5 R$_e$, C$_{2-4}$alkynyl substituted with 0-5 R$_e$, —(CHR$_d$)$_r$OR$_b$, —(CHR$_d$)$_r$S(O)$_p$R$_c$, —(CHR$_d$)$_r$S(O)$_p$NR$_a$R$_a$, —(CHR$_d$)$_r$NR$_a$S(O)$_p$R$_c$, —(CHR$_d$)$_r$NR$_a$R$_a$, —(CHR$_d$)$_r$NR$_a$C(=O)R$_b$, —(CHR$_d$)$_r$NR$_a$C(=O)OR$_b$, —(CHR$_d$)$_r$NR$_a$C(=O)NR$_a$R$_a$, —(CHR$_d$)$_r$C(=O)R$_b$, —(CHR$_d$)$_r$C(=O)OR$_b$, —(CHR$_d$)$_r$C(=O)NR$_a$R$_a$, —(CHR$_d$)$_r$OC(=O)R$_b$, —(CHR$_d$)$_r$OC(=O)OR$_b$, —(CHR$_d$)$_r$O(CH$_2$)$_r$C(=O)NR$_a$R$_a$, C$_{3-6}$cycloalkyl substituted with 0-4 R$_e$, aryl substituted with 0-4 R$_e$, and heterocyclyl substituted with 0-4 R$_e$;

R$_6$ is selected from H, C$_{1-3}$alkyl substituted with 0-4 R$_e$, —S(O)$_p$R$_c$, —(CH$_2$)$_r$C(=O)R$_b$, —(CH$_2$)$_r$C(=O)OR$_b$, —(CH$_2$)$_r$C(=O)(CH$_2$)$_r$NR$_a$R$_a$, —C(=O)(CH$_2$)$_r$NR$_a$C(=O)OR$_b$, —S(O)$_p$NR$_a$R$_a$, —(CH$_2$)$_r$—C$_{3-6}$cycloalkyl substituted with 0-4 R$_e$, —(CH$_2$)$_r$-aryl substituted with 0-4 R$_e$, and —(CH$_2$)$_r$-heterocyclyl substituted with 0-4 R$_e$;

R$_7$ is selected from H, F, Cl, CN, C$_{1-3}$ alkyl, =N—OR$_b$, —(CH$_2$)OR$_b$, —(CH$_2$)$_r$NR$_a$R$_a$, —NR$_a$C(=NH)C$_{1-3}$alkyl, —NR$_a$C(=O)OR$_b$, carbocyclyl, and heterocyclyl; alternatively, two R$_7$ groups are taken together to form carbocyclyl or heterocyclyl;

R$_8$, at each occurrence, is independently selected from H, F, Cl, Br, and C$_{1-4}$alkyl substituted with 0-5 R$_e$;

R$_a$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$ alkynyl substituted with 0-5 R$_e$, —(CH$_2$)$_r$—C$_{3-6}$ carbocyclyl substituted with 0-5 R$_e$, and —(CH$_2$)$_r$-heterocyclyl substituted with 0-5 R$_e$;

R$_d$, at each occurrence, is independently selected from H, C$_{1-6}$ alkyl substituted with 0-5 R$_e$, and OH;

R$_e$, at each occurrence, is independently selected from C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, —(CH$_2$)$_r$-aryl, —(CH$_2$)$_r$-heterocyclyl, Si(C$_{1-4}$alkyl)$_3$, F, Cl, Br, CN, NO$_2$, =O, CO$_2$H, —(CH$_2$)$_r$OR$_f$, S(O)$_p$R$_f$, C(=O)NR$_f$R$_f$, S(O)$_p$NR$_f$R$_f$, and —(CH$_2$)$_r$NR$_f$R$_f$;

R$_f$, at each occurrence, is independently selected from H, F, Cl, Br, CN, OH, C$_{1-5}$ alkyl optionally substituted with OH, C$_{2-5}$ alkenyl, C$_{2-5}$ alkynyl, C$_{3-6}$ cycloalkyl, and phenyl, or R$_f$ and R$_f$ together with the nitrogen atom to which they are both attached form a heterocyclic ring optionally substituted with C$_{1-4}$alkyl;

p, at each occurrence, is independently selected from zero, 1, and 2;

r, at each occurrence, is independently selected from zero, 1, 2, 3, and 4;

provided:

(1) when L is absent, R$_4$ is not

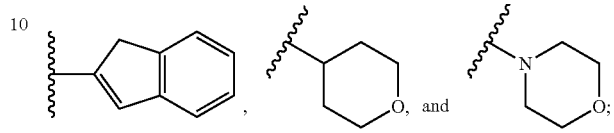

(2) when L is —NR$_d$—, R$_4$ is not

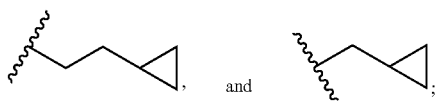 [SMILES: *CCC1CC1 ; *CC1CC1]

and (3) when L is —O—, R$_4$ is not C$_{3-6}$ cycloalkyl.

2. The compound according to claim 1 or a pharmaceutically acceptable salt thereof, wherein:

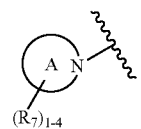

is selected from

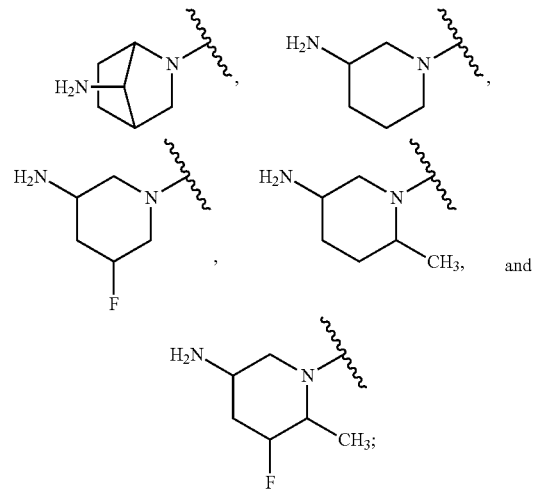

R$_1$ is selected from CH$_3$ and CD$_3$;

R$_2$ is selected from methyl, ethyl and —CH$_2$-cyclopropyl substituted with 0-3 R$_e$;

R$_3$ is selected from H, F, Cl, Br, and —OC$_{1-4}$ alkyl;

L is absent or selected from —NR$_d$—, —O—, —C(=O)NH—, —S—, and —S(O)$_2$—;

R<sub>4</sub> is selected from
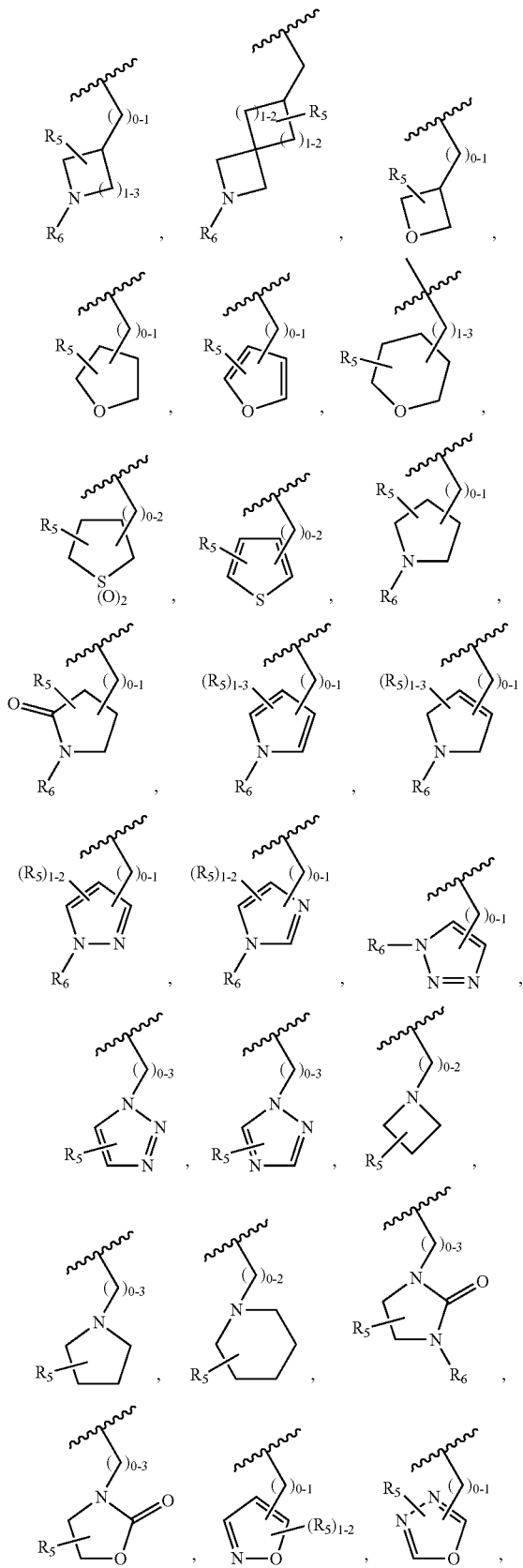
-continued
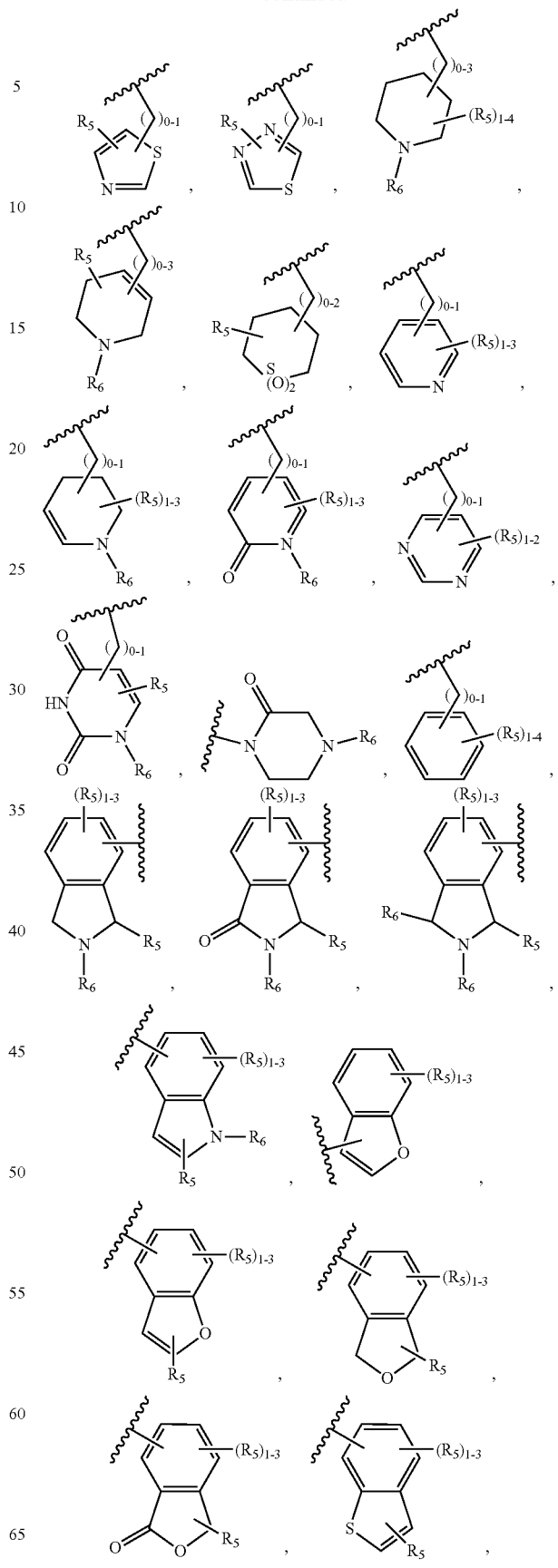

803
-continued
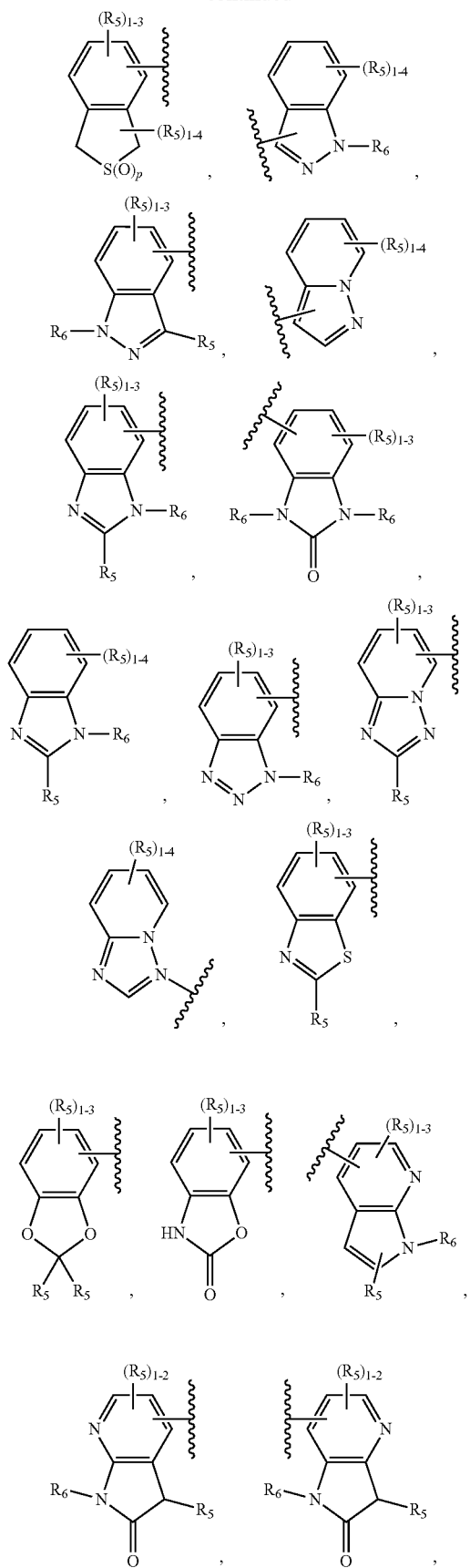
804
-continued
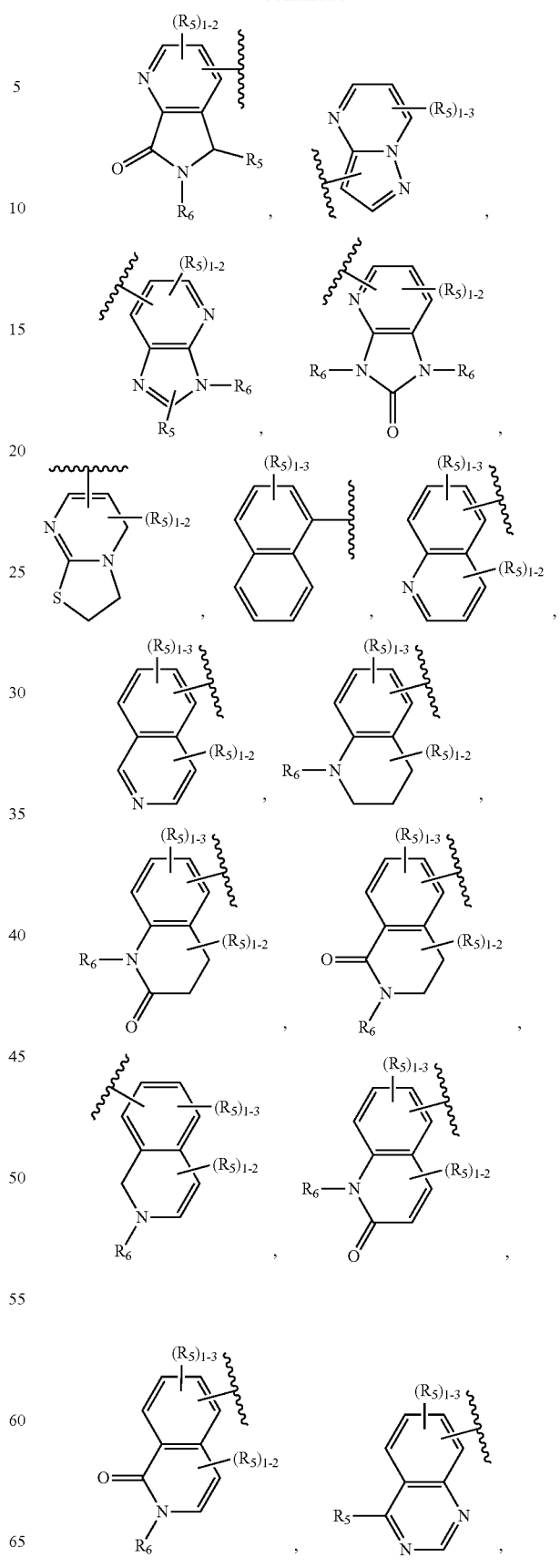

805

-continued

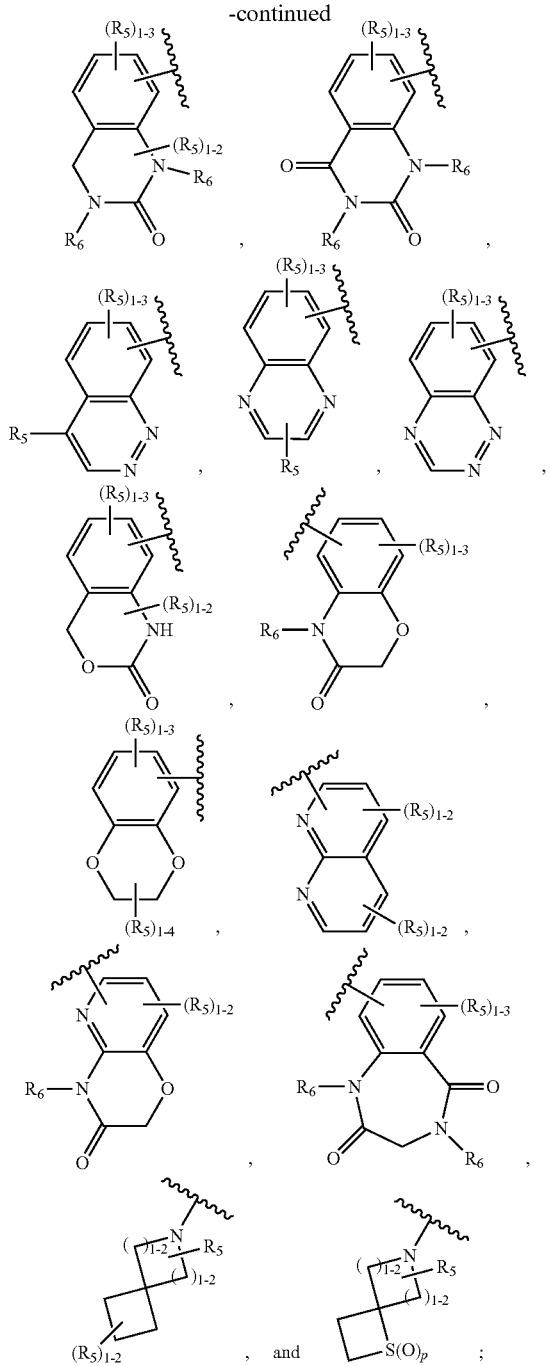

$R_5$, at each occurrence, is independently selected from H, F, Cl, Br, CN, =O, $C_{1-4}$alkyl substituted with 0-5 $R_e$, $C_{2-4}$alkenyl, $C_{2-4}$alkynyl, —(CHR$_d$)$_r$OR$_b$, —(CH$_2$)$_r$S(O)$_p$R$_c$, —(CH$_2$)$_r$S(O)$_p$NR$_a$R$_a$, —(CH$_2$)$_r$NR$_a$S(O)$_p$R$_c$, —(CH$_2$)$_r$NR$_a$R$_a$, —(CH$_2$)$_r$NR$_a$C(=O)R$_b$, —(CH$_2$)$_r$NR$_a$C(=O)OR$_b$, —(CH$_2$)$_r$NR$_a$C(=O)NR$_a$R$_a$, —(CH$_2$)$_r$C(=O)R$_b$, —(CH$_2$)$_r$C(=O)OR$_b$, —(CHR$_d$)$_r$C(=O)NR$_a$R$_a$, —(CH$_2$)$_r$OC(=O)R$_b$, —(CH$_2$)$_r$OC(=O)OR$_b$, —(CH$_2$)$_r$O(CH$_2$)$_r$C(=O)NR$_a$R$_a$, $C_{3-6}$cycloalkyl substituted with 0-4 $R_e$, aryl substituted with 0-4 $R_e$, and heterocyclyl substituted with 0-4 $R_e$;

$R_6$, at each occurrence, is independently selected from H, $C_{1-3}$alkyl substituted with 0-4 $R_e$, —S(O)$_p$R$_c$,

806

—C(=O)R$_b$, —(CH$_2$)$_r$C(=O)OR$_b$, —(CH$_2$)$_r$C(=O)(CH$_2$)$_r$NR$_a$R$_a$, —C(=O)(CH$_2$)$_r$NR$_a$C(=O)R$_b$, —S(O)$_p$NR$_a$R$_a$, —(CH$_2$)$_r$-aryl substituted with 0-4 $R_e$, and —(CH$_2$)$_r$-heterocyclyl substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$ alkynyl substituted with 0-5 $R_e$, —(CH$_2$)$_r$—$C_{3-6}$ carbocyclyl substituted with 0-5 $R_e$, and —(CH$_2$)$_r$-heterocyclyl substituted with 0-5 $R_e$;

$R_d$, at each occurrence, is independently selected from H, $C_{1-6}$ alkyl substituted with 0-5 $R_e$, and OH;

$R_e$, at each occurrence, is independently selected from $C_{1-6}$ alkyl substituted with 0-5 $R_f$, $C_{2-6}$ alkenyl, $C_{2-6}$ alkynyl, —(CH$_2$)$_r$—$C_{3-6}$ cycloalkyl, —(CH$_2$)$_r$-aryl, —(CH$_2$)$_r$-heterocyclyl, F, Cl, Br, CN, NO$_2$, =O, —NH$_2$, —NHC$_{1-4}$alkyl, —N(C$_{1-4}$alkyl)$_2$, —C(=O)OH, —C(=O)OC$_{1-4}$alkyl, —(CH$_2$)$_r$OH, and —(CH$_2$)$_r$OC$_{1-4}$alkyl;

$R_f$, at each occurrence, is independently selected from H, F, Cl, Br, CN, OH, $C_{1-5}$ alkyl optionally substituted with OH, $C_{3-6}$ cycloalkyl, and phenyl;

p, at each occurrence, is independently selected from zero, 1, and 2; and r, at each occurrence, is independently selected from zero, 1, 2, 3, and 4.

3. The compound according to claim 2 of Formula (II):

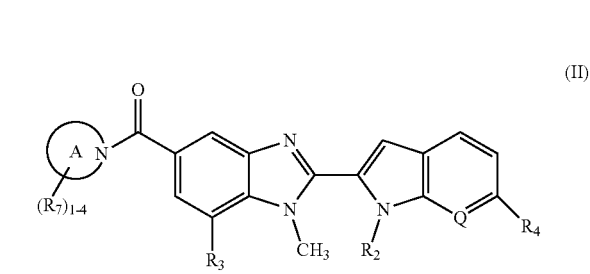

(II)

or a pharmaceutically acceptable salt thereof, wherein:

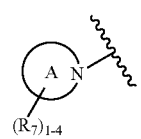

is selected from
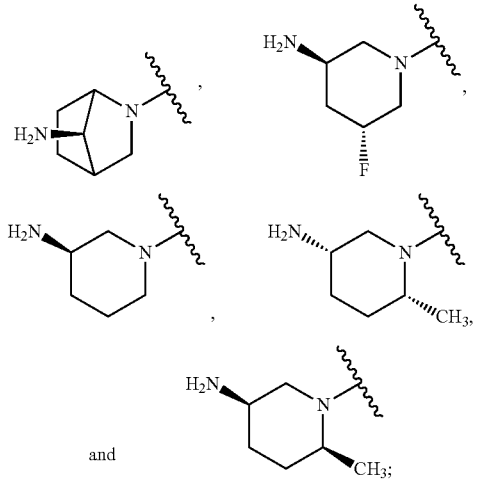
R$_2$ is selected from CH$_3$, CH$_2$CH$_3$ and —CH$_2$-cyclopropyl substituted with 0-2 F, Cl, and CH$_3$;
R$_3$ is selected from H, F, and —OC$_{1-4}$ alkyl;
R$_4$ is selected from
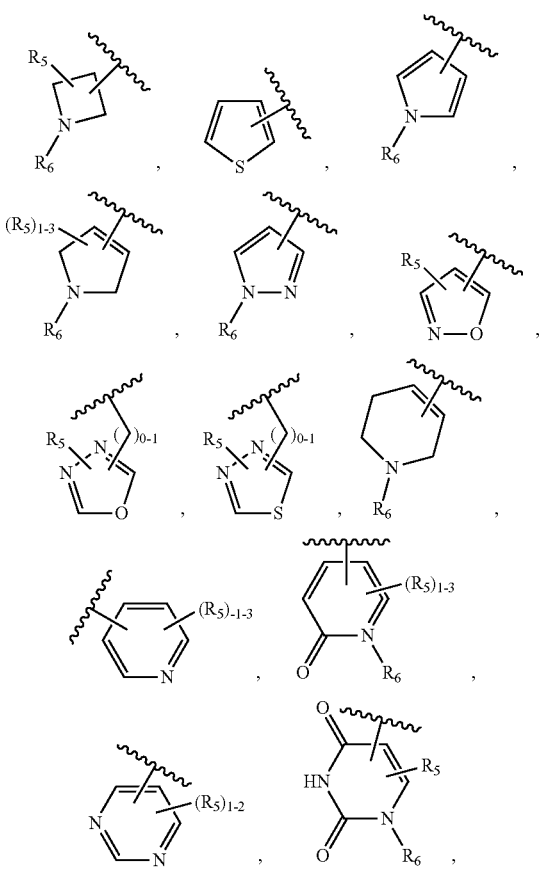
-continued
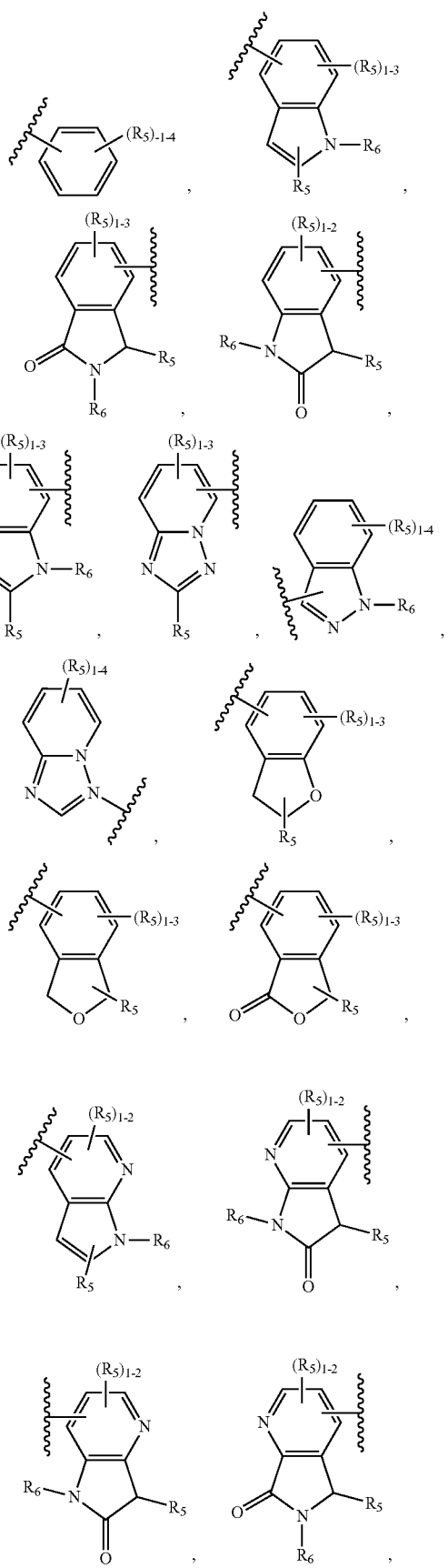

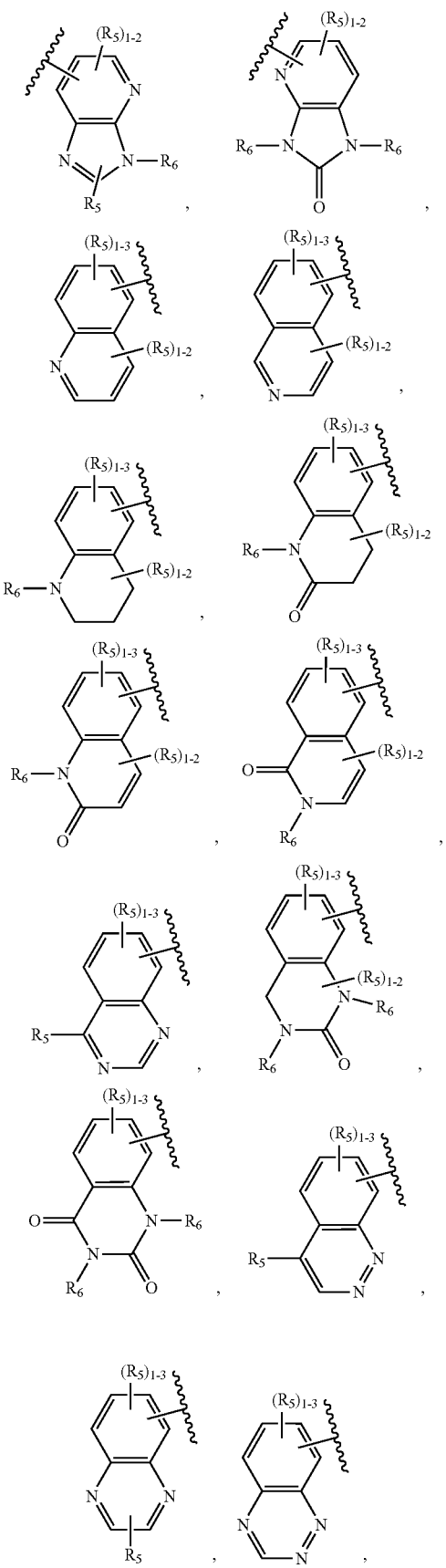

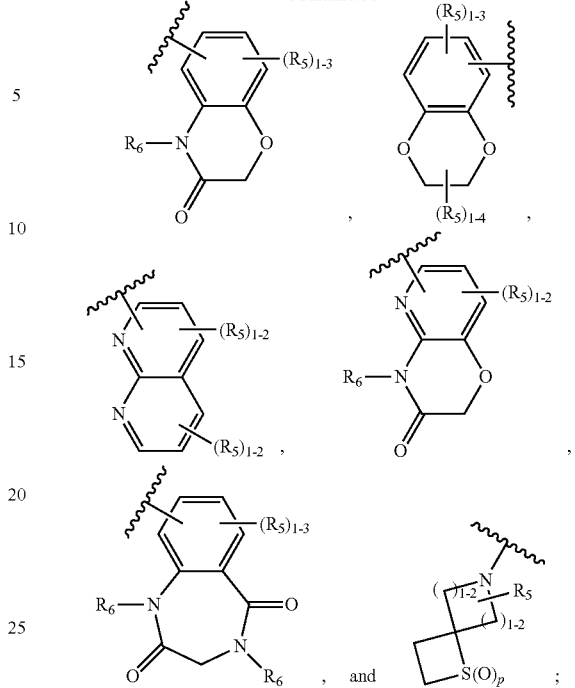

R₅, at each occurrence, is independently selected from H, F, Cl, Br, CN, =O, $C_{1-4}$alkyl substituted with 0-4 $R_e$, —(CHR$_d$)$_r$OR$_b$, —(CH$_2$)$_r$ S(O)$_p$R$_c$, —S(O)$_p$NR$_a$R$_a$, —(CH$_2$)$_r$NR$_a$S(O)$_p$R$_c$, —(CH$_2$)$_r$NR$_a$R$_a$, —(CH$_2$)$_r$N-R$_a$C(=O)R$_b$, —NR$_a$C(=O)OR$_b$, —NR$_a$C(=O)NR$_a$R$_a$, —(CH$_2$)$_r$C(=O)R$_b$, —(CH$_2$)$_r$C(=O)OR$_b$, —(CHR$_d$)$_r$C(=O)NR$_a$R$_a$, —(CH$_2$)$_r$OC(=O)R$_b$, —(CH$_2$)$_r$OC(=O)OR$_b$, —(CH$_2$)$_r$ O(CH$_2$)$_r$C(=O) NR$_a$R$_a$, $C_{3-6}$cycloalkyl substituted with 0-4 $R_e$, aryl substituted with 0-4 $R_e$, and heterocyclyl substituted with 0-4 $R_e$;

R₆, at each occurrence, is independently selected from H, $C_{1-3}$alkyl substituted with 0-4 $R_e$, —S(O)$_p$R$_c$, —C(=O)R$_b$, —(CH$_2$)$_r$C(=O)OR$_b$, —(CH$_2$)$_r$C(=O) NR$_a$R$_a$, —C(=O)(CH$_2$)$_r$NR$_a$C(=O)R$_b$, —S(O)$_p$ NR$_a$R$_a$, aryl substituted with 0-4 $R_e$, and heterocyclyl substituted with 0-4 $R_e$;

R$_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$; or R$_a$ and R$_a$ together with the nitrogen atom to which they are both attached form a heterocyclic ring substituted with 0-5 $R_e$;

R$_b$, at each occurrence, is independently selected from H, $C_{1-6}$ alkyl substituted with 0-5 $R_e$, $C_{2-6}$ alkenyl substituted with 0-5 $R_e$, —(CH$_2$)$_r$—$C_{2-6}$ alkynyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$;

R$_c$, at each occurrence, is independently selected from $C_{1-6}$ alkyl substituted with 0-5 $R_e$, $C_{2-6}$alkenyl substituted with 0-5 $R_e$, $C_{2-6}$ alkynyl substituted with 0-5 $R_e$, —(CH$_2$)$_r$—$C_{3-6}$ carbocyclyl substituted with 0-5 $R_e$, and —(CH$_2$)$_r$-heterocyclyl substituted with 0-5 $R_e$;

R$_d$, at each occurrence, is independently selected from H and $C_{1-6}$ alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$-aryl, —$(CH_2)_r$-heterocyclyl, F, Cl, Br, CN, $NO_2$, =O, —$NH_2$, —$NHC_{1-4}$alkyl, —$N(C_{1-4}$alkyl$)_2$, —C(=O)OH, —C(=O)O$C_{1-4}$alkyl, —$(CH_2)_r$OH, and —$(CH_2)_r$O$C_{1-4}$alkyl;

$R_f$, at each occurrence, is independently selected from H, F, Cl, Br, CN, OH, $C_{1-5}$ alkyl optionally substituted with OH, $C_{3-6}$ cycloalkyl, and phenyl;

p, at each occurrence, is independently selected from zero, 1, and 2; and r, at each occurrence, is independently selected from zero, 1, 2, 3, and 4.

4. The compound according to claim 3 of Formula (III):

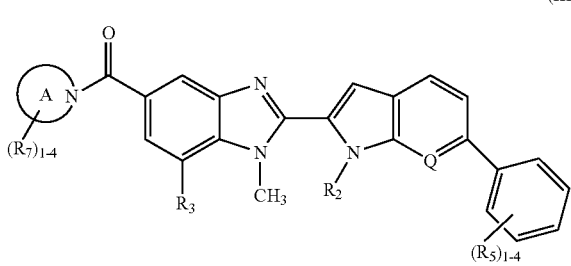

(III)

or a pharmaceutically acceptable salt thereof, wherein:

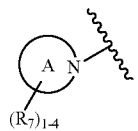

is selected from

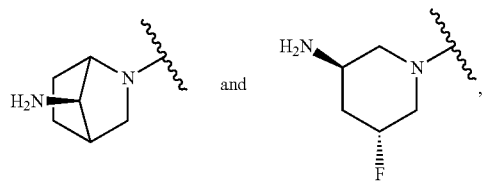 [SMILES: *N1CC2CCC1[C@@H]2N ; *N1C[C@H](N)C[C@@H](F)C1]

$R_2$ is —$CH_2$-cyclopropyl;
$R_3$ is —$OC_{1-4}$ alkyl;
$R_5$, at each occurrence, is independently selected from H, F, Cl, Br, CN, $C_{1-4}$alkyl substituted with 0-4 $R_e$, —$(CHR_d)_rOR_b$, —$(CH_2)_rS(O)_pR_c$, —$S(O)_pNR_aR_a$, —$(CH_2)_rNHS(O)_pR_c$, —$(CH_2)_rNR_aR_a$, —$(CH_2)_rNHC(=O)R_b$, —$NHC(=O)OR_b$, —$(CHR_d)_rC(=O)NR_aR_a$, —$(CH_2)_rC(=O)OR_b$, —$OC(=O)OR_b$, —$O(CH_2)_{0-1}C(=O)NR_aR_a$, $C_{3-6}$cycloalkyl substituted with 0-4 $R_e$, aryl substituted with 0-4 $R_e$, and heterocyclyl substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, —$(CH_2)_r$—$C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$ alkynyl substituted with 0-5 $R_e$, —$(CH_2)_r$—$C_{3-6}$ carbocyclyl substituted with 0-5 $R_e$, and —$(CH_2)_r$-heterocyclyl substituted with 0-5 $R_e$;

$R_d$, at each occurrence, is independently selected from H, $C_{1-4}$ alkyl, and OH;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$-aryl, —$(CH_2)_r$-heterocyclyl, F, Cl, Br, CN, $NO_2$, =O, —$NH_2$, —$NHC_{1-4}$alkyl, —$N(C_{1-4}$alkyl$)_2$, —C(=O)OH, —C(=O)O$C_{1-4}$alkyl, —$(CH_2)_r$OH, —$(CH_2)_r$O$C_{1-4}$alkyl, and $SO_2C_{1-4}$alkyl;

$R_f$, at each occurrence, is independently selected from H, F, Cl, Br, CN, OH, $C_{1-5}$ alkyl optionally substituted with OH, $C_{3-6}$ cycloalkyl, and phenyl;

p, at each occurrence, is independently selected from zero, 1, and 2; and r, at each occurrence, is independently selected from zero, 1, 2, 3, and 4.

5. The compound according to claim 4, or a pharmaceutically acceptable salt thereof, wherein:

$R_3$ is —$OCH_3$;

$R_5$, at each occurrence, is independently selected from H, F, Cl, Br, CN, $C_{1-4}$alkyl, —$(CH_2)_{0-1}OR_b$, —$S(O)_2NH_2$, —$NHS(O)_2C_{1-3}$ alkyl, —$NHS(O)_2C_{2-4}$alkenyl, —$NHC(=O)R_b$, —$C(=O)NH_2$ and heterocyclyl selected from

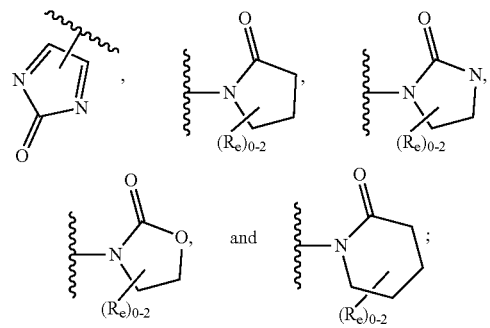

$R_b$, at each occurrence, is independently selected from H and $C_{1-6}$ alkyl substituted with 0-5 $R_e$, $R_e$, at each occurrence, is independently selected from $C_{1-6}$ alkyl, F, Cl, Br, CN, $NO_2$, =O, —$NH_2$, —$NHC_{1-4}$alkyl, —$N(C_{1-4}$alkyl$)_2$, —C(=O)OH, —C(=O)O$C_{1-4}$alkyl, —$(CH_2)_r$OH, —$(CH_2)$O$C_{1-4}$alkyl, and $SO_2C_{1-4}$alkyl; and r, at each occurrence, is independently selected from zero and 1.

6. The compound according to claim 3 or a pharmaceutically acceptable salt thereof, wherein:

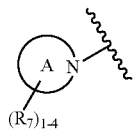

is selected from and

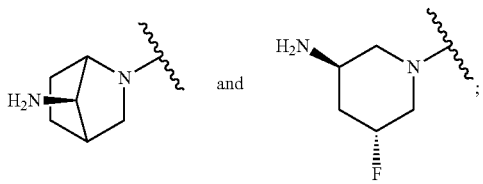 [SMILES: *N1CC2CCC1[C@@H]2N ; *N1C[C@H](N)C[C@@H](F)C1]

$R_2$ is —$CH_2$-cyclopropyl;
$R_3$ is —$OC_{1-4}$ alkyl;
$R_4$ is selected from

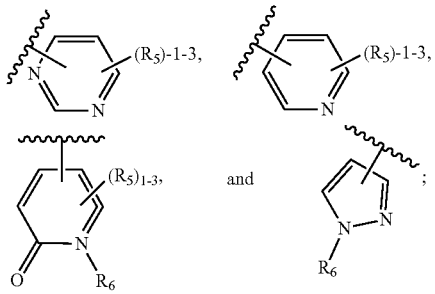

$R_5$, at each occurrence, is independently selected from H, F, Cl, Br, CN, $C_{1-4}$alkyl substituted with 0-4 $R_e$, —$(CH_2)_r OR_b$, —$S(O)_p R_c$, —$S(O)_p NR_a R_a$, —$(CH_2)_r NR_a S(O)_p R_c$, —$(CH_2)_r NR_a R_a$, —$(CH_2)_r N R_a C(=O)R_b$, —$NR_a C(=O)OR_b$, —$NR_a C(=O)NR_a R_a$, —$(CH_2)_r C(=O)R_b$, —$(CH_2)_r C(=O)OR_b$, —$(CH_2)_r C(=O)NR_a R_a$, —$(CH_2 OC(=O)R_b$, $C_{3-6}$cycloalkyl substituted with 0-4 $R_e$, aryl substituted with 0-4 $R_e$, and heterocyclyl substituted with 0-4 $R_e$;
$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;
$R_b$, at each occurrence, is independently selected from H, $C_{1-6}$ alkyl substituted with 0-5 $R_e$, $C_{2-6}$ alkenyl substituted with 0-5 $R_e$, —$(CH_2)_r$—$C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;
$R_c$, at each occurrence, is independently selected from $C_{1-6}$ alkyl substituted with 0-5 $R_e$, $C_{2-6}$alkenyl substituted with 0-5 $R_e$, $C_{2-6}$ alkynyl substituted with 0-5 $R_e$, —$(CH_2)_r$—$C_{3-6}$ carbocyclyl substituted with 0-5 $R_e$, and —$(CH_2)_r$-heterocyclyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$-aryl, F, Cl, Br, CN, $NO_2$, =O, —$NH_2$, —$NHC_{1-4}$alkyl, —$N(C_{1-4}$alkyl$)_2$, —$C(=O)OH$, —$C(=O)OC_{1-4}$alkyl, —$(CH_2)_r OH$, and —$(CH_2)_r OC_{1-4}$alkyl;
$R_f$, at each occurrence, is independently selected from H, F, Cl, Br, CN, OH, $C_{1-5}$ alkyl optionally substituted with OH, $C_{3-6}$ cycloalkyl, and phenyl;
p, at each occurrence, is independently selected from zero, 1, and 2; and
r, at each occurrence, is independently selected from zero, 1, 2, 3, and 4.

7. The compound according to claim 6, or a pharmaceutically acceptable salt thereof, wherein:

$R_3$ is —$OCH_3$;
$R_5$, at each occurrence, is independently selected from H, F, Cl, Br, $C_{1-4}$alkyl, —OH, —$OC_{1-3}$alkyl, —$NHS(O)_2 C_{2-4}$alkenyl, $NHC(=O)OC_{1-4}$ alkyl, $C(=O)NH_2$, $C(=O)NHC_{1-4}$alkyl, and heterocyclyl selected from

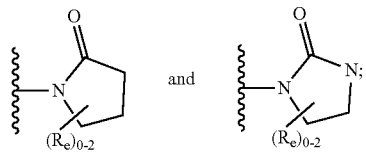

and $R_e$, at each occurrence, is independently selected from $C_{1-6}$ alkyl, F, Cl, Br, CN, $NO_2$, =O, —$NH_2$, —$NHC_{1-4}$alkyl, —$N(C_{1-4}$alkyl$)_2$, —$C(=O)OH$, —$C(=O)OC_{1-4}$alkyl, —$(CH_2)_r OH$, —$(CH_2)OC_{1-4}$alkyl, and $SO_2 C_{1-4}$alkyl.

8. The compound according to claim 3 or a pharmaceutically acceptable salt thereof, wherein:

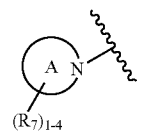

is selected from

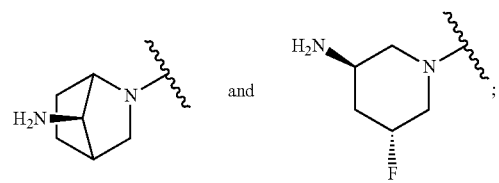 [SMILES: *N1CC2CCC1[C@@H]2N ; *N1C[C@H](N)C[C@@H](F)C1]

R₂ is —CH₂-cyclopropyl;
R₃ is —OC₁₋₄ alkyl;
R₄ is selected from

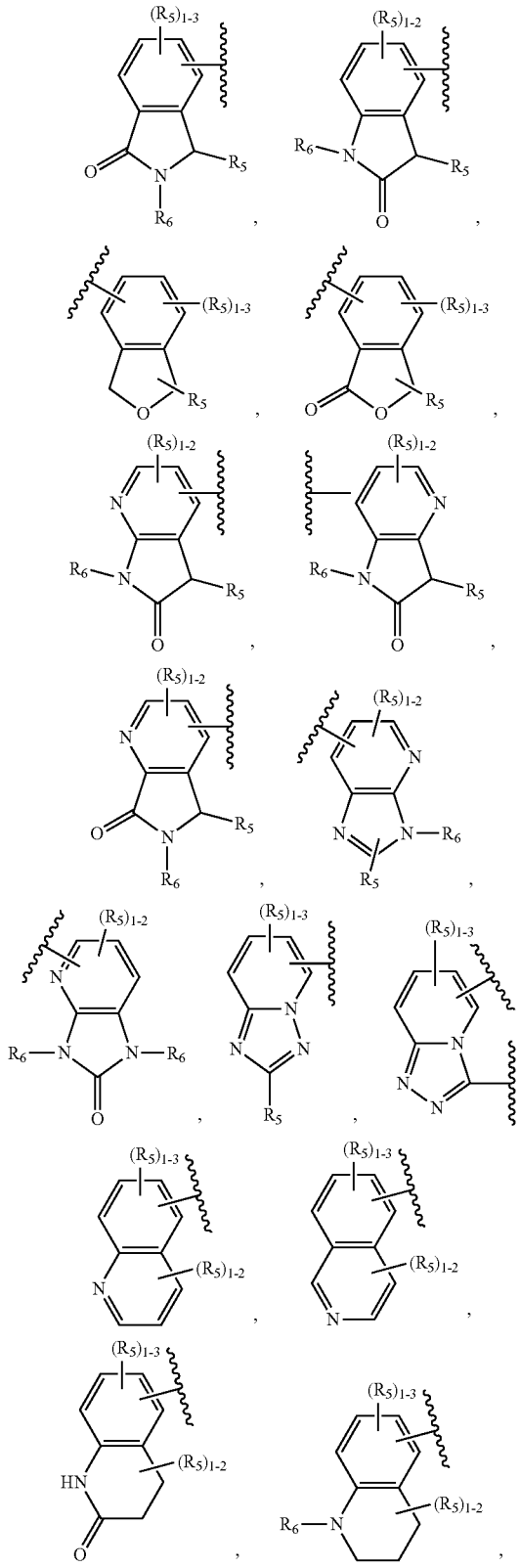

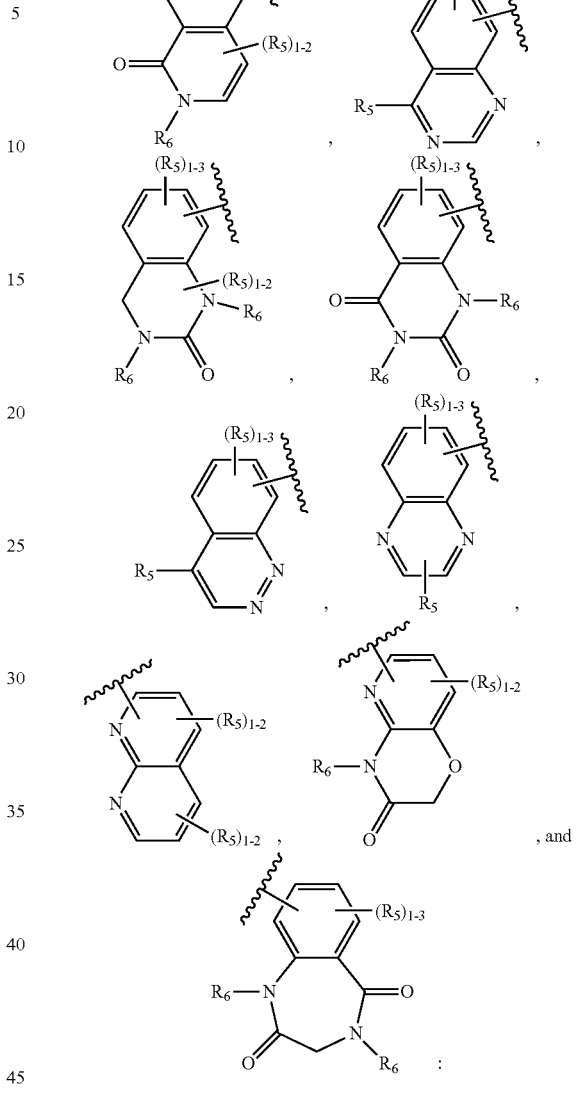

R₅, at each occurrence, is independently selected from H, F, Cl, Br, CN C₁₋₄alkyl, —OR$_b$, —S(O)$_p$R$_c$ —(CH₂)$_r$NR$_a$S(O)$_p$R$_c$, —(CH₂)$_r$NR$_a$R$_a$, —(CH₂)$_r$N-R$_a$C(=O)R$_b$, —NR$_a$C(=O)OR$_b$, —C(=O)OR$_b$, C(=O)NR$_a$R$_a$, C₃₋₆cycloalkyl substituted with 0-4 R$_e$, aryl substituted with 0-4 R$_e$, and heterocyclyl substituted with 0-4 R$_e$;

R₆, at each occurrence, is independently selected from H, C₁₋₃alkyl substituted with 0-4 R$_e$, —S(O)$_p$R$_c$, —C(=O)R$_b$, —C(=O)OR$_b$, —(CH₂)$_r$—C(=O) NR$_a$R$_a$, —C(=O)CH₂)$_r$NR$_a$C(=O)R$_b$, —S(O)$_p$ NR$_a$R$_a$, aryl substituted with 0-4 R$_e$, and heterocyclyl substituted with 0-4 R$_e$;

R$_a$, at each occurrence, is independently selected from H, C₁₋₆ alkyl substituted with 0-5 R$_e$, C₂₋₆ alkenyl substituted with 0-5 R$_e$, C₂₋₆ alkynyl substituted with 0-5 R$_e$, —(CH₂)$_r$—C₃₋₁₀carbocyclyl substituted with 0-5 R$_e$, and —(CH₂)$_r$-heterocyclyl substituted with 0-5 R$_e$; or R$_a$ and R$_a$ together with the nitrogen atom to which they are both attached form a heterocyclic ring substituted with 0-5 R$_e$;

$R_b$, at each occurrence, is independently selected from H, $C_{1-6}$ alkyl substituted with 0-5 $R_e$, $C_{2-6}$ alkenyl substituted with 0-5 $R_e$, —$(CH_2)_r$—$C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-6}$ carbocyclyl substituted with 0-5 $R_e$, and —$(CH_2)_r$-heterocyclyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$-aryl, F, Cl, Br, CN, $NO_2$, =O, —$NH_2$, —$NHC_{1-4}$alkyl, —$N(C_{1-4}$alkyl$)_2$, —C(=O)OH, —C(=O)O$C_{1-4}$alkyl, —$(CH_2)_r$OH, and —$(CH_2)_r$O$C_{1-4}$alkyl;

$R_f$, at each occurrence, is independently selected from H, F, Cl, Br, CN, OH, $C_{1-5}$ alkyl optionally substituted with OH, $C_{3-6}$ cycloalkyl, and phenyl;

p, at each occurrence, is independently selected from zero, 1, and 2; and r, at each occurrence, is independently selected from zero, 1, 2, 3, and 4.

9. The compound according to claim 8, or a pharmaceutically acceptable salt thereof, wherein:

$R_4$ is selected from

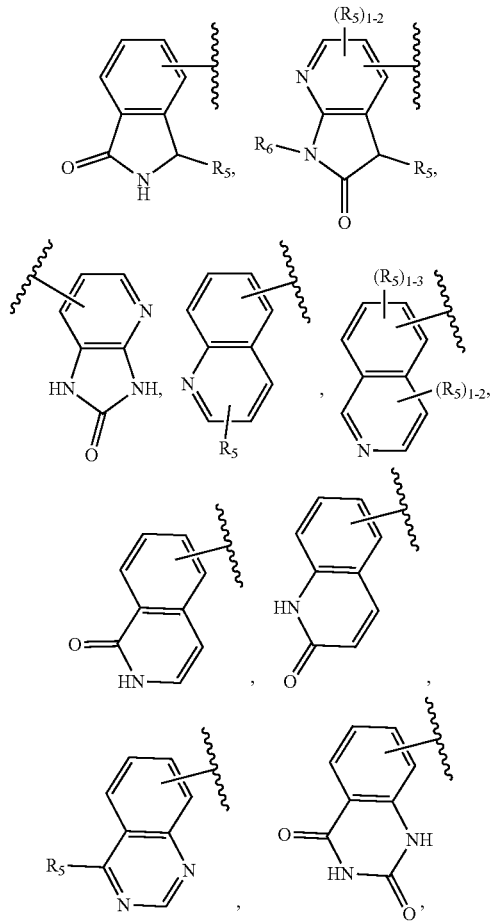

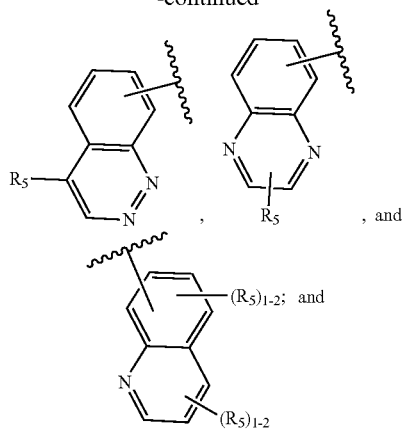

$R_5$, at each occurrence, is independently selected from H, F, Cl, Br, $C_{1-4}$alkyl, OH, and —C(=O)OH.

10. The compound according to claim 2 of Formula (IV):

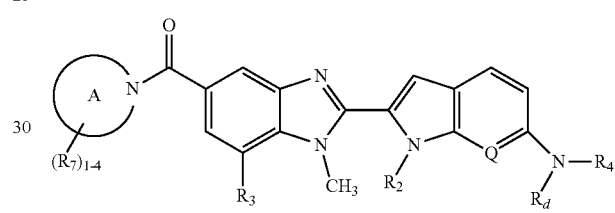

(IV)

or a pharmaceutically acceptable salt thereof, wherein:

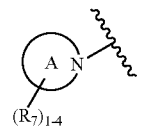

is selected from

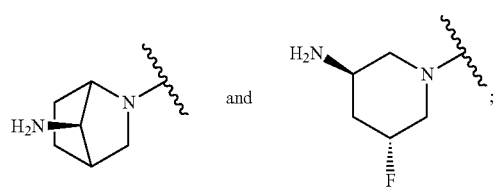 [SMILES: *N1CC2CCC1[C@@H]2N ; *N1C[C@H](N)C[C@@H](F)C1]

$R_2$ is selected from $CH_3$ and —$CH_2$-cyclopropyl;
$R_3$ is selected from H, F, and —O$C_{1-4}$ alkyl;
$R_4$ is selected from

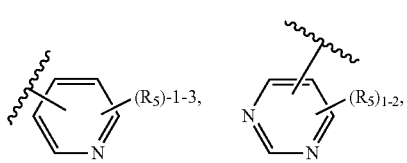

-continued

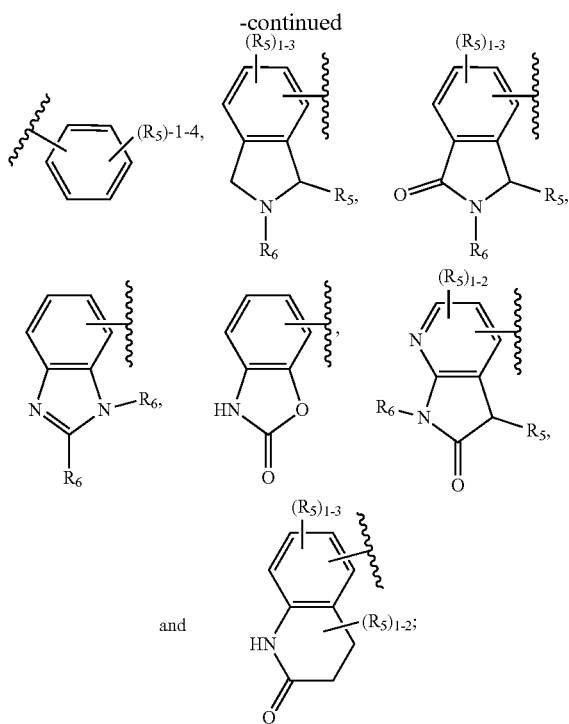

and

R₅, at each occurrence, is independently selected from H, F, Cl, Br, CN, C₁₋₄alkyl, —(CH₂)ᵣORᵦ, —NRₐS(O)ₚRc, —NRₐRₐ, —NRₐC(=O)Rᵦ, —NRₐC(=O)ORᵦ, —C(=O)ORᵦ, —C(=O)NRₐRₐ, —NRₐC(=O)NRₐRₐ, C₃₋₆cycloalkyl substituted with 0-4 Rₑ, aryl substituted with 0-4 Rₑ, and heterocyclyl substituted with 0-4 Rₑ;

R₆, at each occurrence, is independently selected from H and C₁₋₃alkyl;

Rₐ, at each occurrence, is independently selected from H, C₁₋₆ alkyl substituted with 0-5 Rₑ, C₂₋₆ alkenyl substituted with 0-5 Rₑ, C₂₋₆ alkynyl substituted with 0-5 Rₑ, —(CH₂)ᵣ—C₃₋₁₀carbocyclyl substituted with 0-5 Rₑ, and —(CH₂)ᵣ-heterocyclyl substituted with 0-5 Rₑ;

Rᵦ, at each occurrence, is independently selected from H, C₁₋₆ alkyl substituted with 0-5 Rₑ, C₂₋₆ alkenyl substituted with 0-5 Rₑ, C₂₋₆ alkynyl substituted with 0-5 Rₑ, —(CH₂)ᵣ—C₃₋₁₀carbocyclyl substituted with 0-5 Rₑ, and —(CH₂)ᵣ-heterocyclyl substituted with 0-5 Rₑ;

Rc, at each occurrence, is independently selected from C₁₋₆ alkyl substituted with 0-5 Rₑ, C₂₋₆alkenyl substituted with 0-5 Rₑ, C₂₋₆ alkynyl substituted with 0-5 Rₑ, —(CH₂)ᵣ—C₃₋₆ carbocyclyl substituted with 0-5 Rₑ, and —(CH₂)ᵣ-heterocyclyl substituted with 0-5 Rₑ;

Rₐ, at each occurrence, is independently selected from H and C₁₋₃ alkyl;

Rₑ, at each occurrence, is independently selected from C₁₋₆ alkyl substituted with 0-5 Rf, C₂₋₆ alkenyl, C₂₋₆ alkynyl, —(CH₂)ᵣ—C₃₋₆ cycloalkyl, —(CH₂)ᵣ-aryl, F, Cl, Br, CN, NO₂, =O, N(C₁₋₄alkyl)₂, —C(=O)OH, —C(=O)OC₁₋₄alkyl, —(CH₂)ᵣOH, and —(CH₂)OC₁₋₄alkyl;

Rf, at each occurrence, is independently selected from H, F, Cl, Br, CN, OH, C₁₋₅ alkyl optionally substituted with OH, C₃₋₆ cycloalkyl, and phenyl;

p, at each occurrence, is independently selected from zero, 1, and 2; and r, at each occurrence, is independently selected from zero, 1, 2, 3, and 4.

11. The compound according to claim 10, or a pharmaceutically acceptable salt thereof, wherein:
R₂ is CH₂-cyclopropyl;
R₃ is —OCH₃;
R₄ is

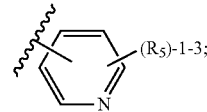

R₅, at each occurrence, is independently selected from H, F, Cl, Br, C₁₋₄alkyl, and —(CH₂)₀₋₁OH; and
Rₐ is H.

12. The compound according to claim 2 or a pharmaceutically acceptable salt thereof, wherein:
L is —C(=O)NH—;
R₂ is —CH₂-cyclopropyl;
R₃ is —OC₁₋₄ alkyl;
R₄ is selected from

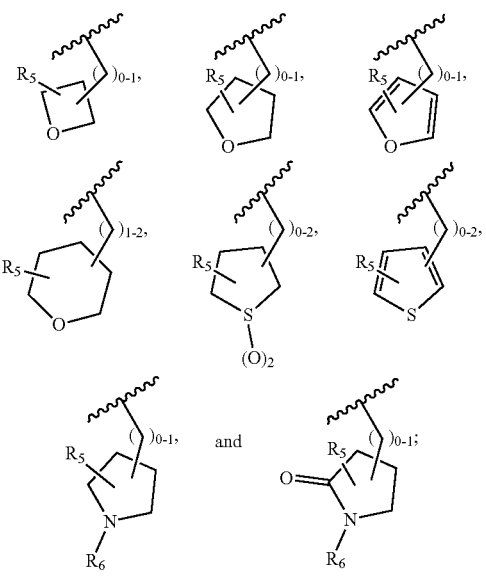

R₅, at each occurrence, is independently selected from H, F, Cl, Br, C₁₋₄alkyl, —OH, and —CN; and
R₆, at each occurrence, is independently selected from H and C₁₋₃alkyl.

13. The compound according to claim 2 or a pharmaceutically acceptable salt thereof, wherein:
L is —O—;
R₂ is —CH₂-cyclopropyl;
R₃ is —OC₁₋₄alkyl;
R₄ is selected from

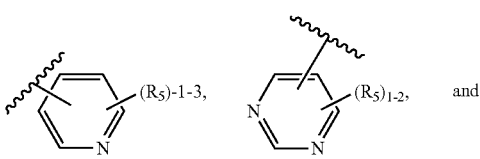

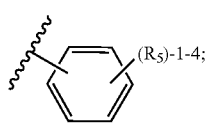

and

R₅, at each occurrence, is independently selected from H, F, Cl, Br, C₁₋₄alkyl, —OH, and —CN.

14. The compound according to claim 2 of Formula (VI):

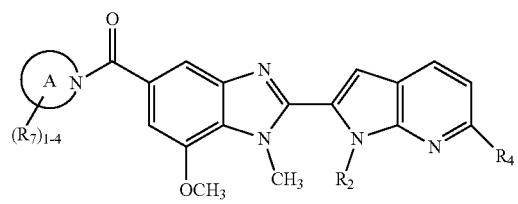

(VI)

or a pharmaceutically acceptable salt thereof, wherein:

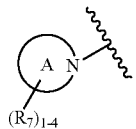

is selected from

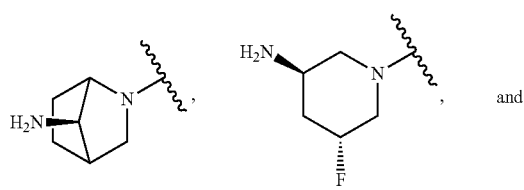

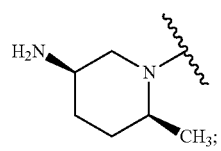

R₂ is —CH₂-cyclopropyl;
R₄ is selected from

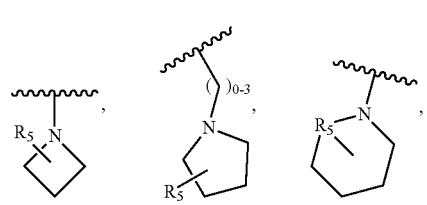

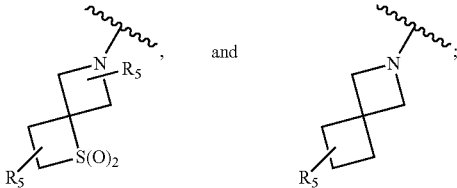

and

R₅ is selected from H, OH, CH₂OH, and —C(CH₃)₂OH.

15. The compound according to claim 2 of Formula (VII):

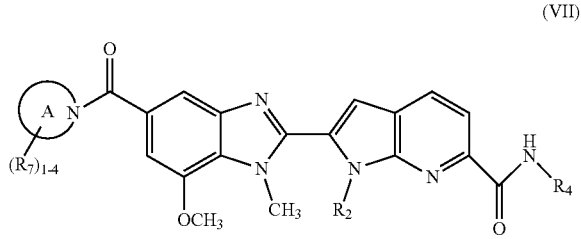

(VII)

or a pharmaceutically acceptable salt thereof:

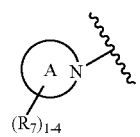

is selected from

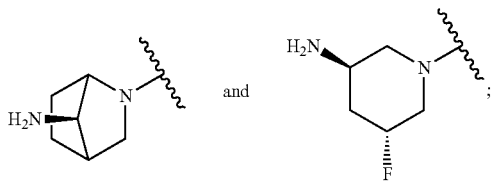 [SMILES: *N1CC2CCC1[C@@H]2N ; *N1C[C@H](N)C[C@@H](F)C1]

R₂ is —CH₂-cyclopropyl;
R₄ is selected from

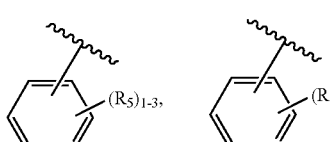
and
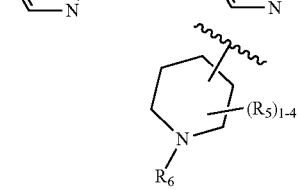

R₅, at each occurrence, is independently selected from F, Cl, C₁₋₄alkyl, —(CH₂ORᵦ, —S(O)₂NRₐRₐ, —NRₐS(O)₂R_c, and —C(=O)NRₐRₐ;

$R_6$, at each occurrence, is independently selected from H and $C_{1-3}$alkyl;

$R_a$, at each occurrence, is independently selected from H and $C_{1-4}$ alkyl substituted with 0-5 $R_e$;

$R_b$, at each occurrence, is independently selected from H and $C_{1-4}$ alkyl substituted with 0-5 $R_e$, $R_c$, at each occurrence, is independently $C_{1-4}$ alkyl substituted with 0-5 $R_e$;

$R_e$, at each occurrence, is independently selected from F, Cl, Br, —OH, and —$OC_{1-4}$alkyl;

r, at each occurrence, is independently selected from zero, 1, and 2.

16. A pharmaceutical composition comprising the compound according to claim 1 and a pharmaceutically acceptable carrier, adjuvant, or vehicle.

17. The composition according to claim 16, in combination with an additional therapeutic agent.

18. A method of inhibiting PAD4 in a subject or in a biological sample comprising the step of contacting the PAD4 with a compound according to claim 1.

* * * * *